US012590084B2

(12) United States Patent
Wagner et al.

(10) Patent No.: US 12,590,084 B2
(45) Date of Patent: Mar. 31, 2026

(54) OXADIAZOLE HDAC6 INHIBITORS AND USES THEREOF

(71) Applicant: Eikonizo Therapeutics, Inc., Cambridge, MA (US)

(72) Inventors: Florence Fevrier Wagner, Ashland, MA (US); Thomas Edward Richardson, Cary, NC (US)

(73) Assignee: Eikonizo Therapeutics, Inc., Cambridge, MA (US)

(*) Notice: Subject to any disclaimer, the term of this patent is extended or adjusted under 35 U.S.C. 154(b) by 236 days.

(21) Appl. No.: 18/132,216

(22) Filed: Apr. 7, 2023

(65) Prior Publication Data

US 2023/0322747 A1 Oct. 12, 2023

Related U.S. Application Data

(60) Provisional application No. 63/329,143, filed on Apr. 8, 2022.

(51) Int. Cl.

| | |
|---|---|
| ***C07D 413/04*** | (2006.01) |
| ***A61K 31/4439*** | (2006.01) |
| ***A61K 31/444*** | (2006.01) |
| ***A61K 31/4709*** | (2006.01) |
| ***A61K 31/4725*** | (2006.01) |
| ***A61K 31/498*** | (2006.01) |
| ***A61K 31/4985*** | (2006.01) |
| ***A61K 31/501*** | (2006.01) |
| ***A61K 31/506*** | (2006.01) |
| ***A61K 31/517*** | (2006.01) |
| ***A61K 31/519*** | (2006.01) |
| ***A61K 31/5377*** | (2006.01) |
| ***A61K 31/5386*** | (2006.01) |
| ***C07D 413/14*** | (2006.01) |
| ***C07D 471/04*** | (2006.01) |
| ***C07D 487/04*** | (2006.01) |
| ***C07D 498/04*** | (2006.01) |
| ***C07D 498/08*** | (2006.01) |

(52) U.S. Cl.

CPC ........ *C07D 413/04* (2013.01); *A61K 31/4439* (2013.01); *A61K 31/444* (2013.01); *A61K 31/4709* (2013.01); *A61K 31/4725* (2013.01); *A61K 31/498* (2013.01); *A61K 31/4985* (2013.01); *A61K 31/501* (2013.01); *A61K 31/506* (2013.01); *A61K 31/517* (2013.01); *A61K 31/519* (2013.01); *A61K 31/5377* (2013.01); *A61K 31/5386* (2013.01); *C07D 413/14* (2013.01); *C07D 471/04* (2013.01); *C07D 487/04* (2013.01); *C07D 498/04* (2013.01); *C07D 498/08* (2013.01)

(58) Field of Classification Search

CPC .. C07D 413/04; C07D 413/14; C07D 471/04; C07D 487/04

USPC ........................................................ 544/333

See application file for complete search history.

(56) References Cited

U.S. PATENT DOCUMENTS

| | | | |
|---|---|---|---|
| 4,205,085 | A | 5/1980 | Shepherd |
| 5,231,097 | A | 7/1993 | Klausener et al. |
| 5,272,158 | A | 12/1993 | Hartman et al. |
| 5,686,018 | A | 11/1997 | Demus et al. |
| 5,728,844 | A | 3/1998 | Muller et al. |
| 5,728,845 | A | 3/1998 | Muller et al. |
| 8,778,931 | B2 | 7/2014 | Gould |
| 9,096,518 | B2 | 8/2015 | Blackburn et al. |
| 9,145,405 | B2 | 9/2015 | Luo et al. |
| 9,650,379 | B2 | 5/2017 | Lee et al. |
| 10,272,084 | B2 | 4/2019 | Kavelaars et al. |
| 10,357,493 | B2 | 7/2019 | Yates |
| 10,774,179 | B2 | 9/2020 | Kember et al. |
| 11,066,396 | B2 | 7/2021 | Walji et al. |
| 11,938,134 | B2 | 3/2024 | Yates |
| 12,370,194 | B2 | 7/2025 | Yates et al. |
| 2005/0165015 | A1 | 7/2005 | Ncube et al. |
| 2006/0052599 | A1 | 3/2006 | Ishibashi et al. |
| 2006/0142321 | A1 | 6/2006 | Jover et al. |
| 2006/0142332 | A1 | 6/2006 | Torrens Jover et al. |
| 2008/0214603 | A1 | 9/2008 | Torrens Jover et al. |
| 2009/0036480 | A1 | 2/2009 | Torrens Jover et al. |
| 2009/0074717 | A1 | 3/2009 | Leivers et al. |
| 2009/0197880 | A1 | 8/2009 | Leivers et al. |
| 2009/0247757 | A1 | 10/2009 | Li et al. |
| 2010/0130499 | A1 | 5/2010 | Tafesse |

(Continued)

FOREIGN PATENT DOCUMENTS

| | | | |
|---|---|---|---|
| CN | 101573333 | A | 11/2009 |
| CN | 105884767 | A | 8/2016 |

(Continued)

OTHER PUBLICATIONS

Invitation to Pay Additional Fees mailed Sep. 24, 2020 for Application No. PCT/US2020/044148.
International Search Report and Written Opinion mailed Feb. 16, 2021 for Application No. PCT/US2020/044148.
International Preliminary Report on Patentability mailed Feb. 10, 2022 for Application No. PCT/US2020/044148.
International Search Report and Written Opinion mailed May 10, 2018 for Application No. PCT/US2018/021696.
International Preliminary Report on Patentability mailed Sep. 19, 2021 for Application No. PCT/US2018/021696.
Invitation to Pay Additional Fees mailed Apr. 29, 2022 for Application No. PCT/US2022/015129.

(Continued)

*Primary Examiner* — Jeffrey H Murray
*Assistant Examiner* — Grace Ching Hsu
(74) *Attorney, Agent, or Firm* — Wolf, Greenfield & Sacks, P.C.

(57) ABSTRACT

Provided herein are compounds that selectively inhibit HDAC6, a protein whose activity is associated with a variety of diseases (e.g., cancer, neurological disorders). Also provided are pharmaceutical compositions and kits comprising the compounds, and methods of treating HDAC6-related diseases and disorders (e.g., Alzheimer's disease, cancer) with the compounds in a subject, by administering the compounds and/or compositions described herein.

20 Claims, No Drawings

(56) References Cited

U.S. PATENT DOCUMENTS

| | | | |
|---|---|---|---|
| 2011/0039827 | A1 | 2/2011 | Blackburn et al. |
| 2011/0212969 | A1 | 9/2011 | Blackburn et al. |
| 2011/0251184 | A1 | 10/2011 | Blackburn et al. |
| 2011/0288117 | A1 | 11/2011 | Gould et al. |
| 2012/0040953 | A1 | 2/2012 | Barba et al. |
| 2012/0094997 | A1 | 4/2012 | England et al. |
| 2012/0202834 | A1 | 8/2012 | Aspnes et al. |
| 2014/0275093 | A1 | 9/2014 | Blackburn et al. |
| 2014/0329825 | A1 | 11/2014 | Hebach et al. |
| 2015/0197497 | A1 | 7/2015 | Abeywickrama et al. |
| 2015/0359794 | A1 | 12/2015 | Benz et al. |
| 2016/0039789 | A1 | 2/2016 | England et al. |
| 2017/0096405 | A1 | 4/2017 | Song et al. |
| 2017/0183325 | A1 | 6/2017 | Chen et al. |
| 2017/0313698 | A1 | 11/2017 | Shuttleworth et al. |
| 2017/0349540 | A1 | 12/2017 | Hooker et al. |
| 2018/0215743 | A1 | 8/2018 | Lee et al. |
| 2018/0256572 | A1 | 9/2018 | Yates |
| 2018/0273495 | A1 | 9/2018 | Kim et al. |
| 2019/0077786 | A1 | 3/2019 | Ueng et al. |
| 2019/0135799 | A1 | 5/2019 | Ito et al. |
| 2020/0171028 | A1 | 6/2020 | Yates |
| 2021/0188831 | A1 | 6/2021 | Lee et al. |
| 2022/0041584 | A1 | 2/2022 | Piscopio et al. |
| 2022/0088018 | A1 | 3/2022 | Yates |
| 2022/0098180 | A1 | 3/2022 | Ito et al. |
| 2022/0144815 | A1 | 5/2022 | Brunet et al. |
| 2022/0251043 | A1 | 8/2022 | Pan et al. |
| 2022/0281814 | A1 | 9/2022 | Wagner et al. |
| 2023/0322747 | A1 | 10/2023 | Wagner |
| 2024/0307391 | A1 | 9/2024 | Yates |
| 2025/0230166 | A1 | 7/2025 | Wagner |
| 2025/0250263 | A1 | 8/2025 | Wagner et al. |

FOREIGN PATENT DOCUMENTS

| | | | |
|---|---|---|---|
| CN | 108976223 | A | 12/2018 |
| CN | 109651357 | A | 4/2019 |
| CN | 110950860 | A | 4/2020 |
| CN | 112794860 | A | 5/2021 |
| DE | 3929233 | A1 | 3/1991 |
| DE | 4029466 | A1 | 3/1991 |
| DE | 4307243 | A1 | 10/1993 |
| DE | 10312963 | A1 | 10/2004 |
| EP | 540334 | A1 | 5/1993 |
| EP | 625513 | A1 | 11/1994 |
| EP | 2624832 | B1 | 9/2017 |
| JP | S58-170780 | A | 10/1983 |
| JP | H04-272989 | A | 9/1992 |
| JP | H07-206829 | A | 8/1995 |
| JP | H10-251255 | A | 9/1998 |
| JP | 2002-305083 | A | 10/2002 |
| JP | 2011-8205 | A | 1/2011 |
| JP | 2011-148714 | A | 8/2011 |
| JP | 2013-542994 | A | 11/2013 |
| JP | 2017-190296 | A | 10/2017 |
| WO | WO 1995/11228 | A1 | 4/1995 |
| WO | WO 1997/040017 | A2 | 10/1997 |
| WO | WO 1998/45268 | A1 | 10/1998 |
| WO | WO 1999/019419 | A1 | 4/1999 |
| WO | WO 2000/015637 | A1 | 3/2000 |
| WO | WO 2000/068230 | A1 | 11/2000 |
| WO | WO 2001/072712 | A1 | 10/2001 |
| WO | WO 2001/085695 | A1 | 11/2001 |
| WO | WO 2002/002530 | A1 | 1/2002 |
| WO | WO 2002/026696 | A1 | 4/2002 |
| WO | WO 2002/026703 | A1 | 4/2002 |
| WO | WO 2002/030879 | A2 | 4/2002 |
| WO | WO 2002/098426 | A1 | 12/2002 |
| WO | WO 2003/024448 | A2 | 3/2003 |
| WO | WO 2003/041641 | A2 | 5/2003 |
| WO | WO 2003/074038 | A1 | 9/2003 |
| WO | WO 2003/082288 | A1 | 10/2003 |
| WO | WO 2004/065354 | A1 | 8/2004 |
| WO | WO 2004/069823 | A1 | 8/2004 |
| WO | WO 2004/076386 | A2 | 9/2004 |
| WO | WO 2004/082638 | A2 | 9/2004 |
| WO | WO 2004/098609 | A1 | 11/2004 |
| WO | WO 2005/000300 | A1 | 1/2005 |
| WO | WO 2005/020921 | A2 | 3/2005 |
| WO | WO 2005/051300 | A2 | 6/2005 |
| WO | WO 2005/065681 | A2 | 7/2005 |
| WO | WO 2005/066151 | A2 | 7/2005 |
| WO | WO 2005/092899 | A1 | 10/2005 |
| WO | WO 2006/018308 | A1 | 2/2006 |
| WO | WO 2006/018309 | A1 | 2/2006 |
| WO | WO 2006/044958 | A1 | 4/2006 |
| WO | WO 2006/065842 | A2 | 6/2006 |
| WO | WO 2006/066133 | A2 | 6/2006 |
| WO | WO 2006/084186 | A2 | 8/2006 |
| WO | WO 2006/087309 | A1 | 8/2006 |
| WO | WO 2007/003604 | A2 | 1/2007 |
| WO | WO 2007/011626 | A2 | 1/2007 |
| WO | WO 2007/029035 | A2 | 3/2007 |
| WO | WO 2007/056593 | A2 | 5/2007 |
| WO | WO 2007/084390 | A2 | 7/2007 |
| WO | WO 2007/084455 | A1 | 7/2007 |
| WO | WO 2007/093827 | A1 | 8/2007 |
| WO | WO 2007/098608 | A1 | 9/2007 |
| WO | WO 2007/115408 | A1 | 10/2007 |
| WO | WO 2008/016123 | A1 | 2/2008 |
| WO | WO 2008/060721 | A1 | 5/2008 |
| WO | WO 2008/064265 | A2 | 5/2008 |
| WO | WO 2008/074132 | A1 | 6/2008 |
| WO | WO 2008/097428 | A2 | 8/2008 |
| WO | WO 2008/128335 | A1 | 10/2008 |
| WO | WO 2009/011787 | A1 | 1/2009 |
| WO | WO 2009/011876 | A1 | 1/2009 |
| WO | WO 2009/027349 | A2 | 3/2009 |
| WO | WO 2009/079011 | A1 | 6/2009 |
| WO | WO 2009/129036 | A1 | 10/2009 |
| WO | WO 2009/129335 | A2 | 10/2009 |
| WO | WO 2009/137462 | A2 | 11/2009 |
| WO | WO 2010/028192 | A1 | 3/2010 |
| WO | WO 2010/033906 | A2 | 3/2010 |
| WO | WO 2010/043953 | A2 | 4/2010 |
| WO | WO 2010/054278 | A2 | 5/2010 |
| WO | WO 2010/075551 | A1 | 7/2010 |
| WO | WO 2010/078449 | A2 | 7/2010 |
| WO | WO 2010/081145 | A1 | 7/2010 |
| WO | WO 2010/083141 | A1 | 7/2010 |
| WO | WO 2010/086311 | A1 | 8/2010 |
| WO | WO 2010/088414 | A2 | 8/2010 |
| WO | WO 2010/122151 | A1 | 10/2010 |
| WO | WO 2010/139966 | A1 | 12/2010 |
| WO | WO 2010/151318 | A1 | 12/2010 |
| WO | WO 2011/002520 | A2 | 1/2011 |
| WO | WO 2011/038185 | A2 | 3/2011 |
| WO | WO 2011/058582 | A1 | 5/2011 |
| WO | WO 2011/088181 | A1 | 7/2011 |
| WO | WO 2011/088187 | A1 | 7/2011 |
| WO | WO 2011/088192 | A1 | 7/2011 |
| WO | WO 2011/106632 | A1 | 9/2011 |
| WO | WO 2011/133888 | A1 | 10/2011 |
| WO | WO 2011/133920 | A1 | 10/2011 |
| WO | WO 2011/137320 | A2 | 11/2011 |
| WO | WO 2011/154374 | A1 | 12/2011 |
| WO | WO 2011/154431 | A1 | 12/2011 |
| WO | WO 2012/012320 | A1 | 1/2012 |
| WO | WO 2012/027564 | A1 | 3/2012 |
| WO | WO 2012/038438 | A1 | 3/2012 |
| WO | WO 2012/045804 | A1 | 4/2012 |
| WO | WO 2012/047852 | A2 | 4/2012 |
| WO | WO 2012/068109 | A2 | 5/2012 |
| WO | WO 2012/076898 | A1 | 6/2012 |
| WO | WO 2012/085038 | A1 | 6/2012 |
| WO | WO 2012/088015 | A2 | 6/2012 |
| WO | WO 2012/103008 | A1 | 8/2012 |
| WO | WO 2012/117027 | A1 | 9/2012 |
| WO | WO 2012/120023 | A1 | 9/2012 |
| WO | WO 2012/123916 | A2 | 9/2012 |
| WO | WO 2012/136111 | A1 | 10/2012 |
| WO | WO 2012/157984 | A2 | 11/2012 |
| WO | WO 2012/158957 | A2 | 11/2012 |

(56) References Cited

FOREIGN PATENT DOCUMENTS

| | | | |
|---|---|---|---|
| WO | WO 2012/170867 | A1 | 12/2012 |
| WO | WO 2013/006408 | A1 | 1/2013 |
| WO | WO 2013/008162 | A1 | 1/2013 |
| WO | WO 2013/009810 | A1 | 1/2013 |
| WO | WO 2013/009812 | A1 | 1/2013 |
| WO | WO 2013/009827 | A1 | 1/2013 |
| WO | WO 2013/009830 | A1 | 1/2013 |
| WO | WO 2013/059582 | A2 | 4/2013 |
| WO | WO 2013/062344 | A1 | 5/2013 |
| WO | WO 2013/063549 | A1 | 5/2013 |
| WO | WO 2013/066831 | A1 | 5/2013 |
| WO | WO 2013/066832 | A1 | 5/2013 |
| WO | WO 2013/066833 | A1 | 5/2013 |
| WO | WO 2013/066834 | A1 | 5/2013 |
| WO | WO 2013/066835 | A2 | 5/2013 |
| WO | WO 2013/066836 | A1 | 5/2013 |
| WO | WO 2013/066838 | A1 | 5/2013 |
| WO | WO 2013/066839 | A2 | 5/2013 |
| WO | WO 2013/080120 | A1 | 6/2013 |
| WO | WO 2013/085890 | A1 | 6/2013 |
| WO | WO 2013/101600 | A1 | 7/2013 |
| WO | WO 2013/155262 | A2 | 10/2013 |
| WO | WO 2013/169574 | A2 | 11/2013 |
| WO | WO 2013/185353 | A1 | 12/2013 |
| WO | WO 2014/014900 | A1 | 1/2014 |
| WO | WO 2014/049107 | A1 | 4/2014 |
| WO | WO 2014/059306 | A1 | 4/2014 |
| WO | WO 2014/159210 | A1 | 10/2014 |
| WO | WO 2014/159214 | A1 | 10/2014 |
| WO | WO 2014/159218 | A1 | 10/2014 |
| WO | WO 2014/159224 | A1 | 10/2014 |
| WO | WO 2014/172191 | A1 | 10/2014 |
| WO | WO 2014/178606 | A1 | 11/2014 |
| WO | WO 2014/179528 | A2 | 11/2014 |
| WO | WO 2014/180984 | A1 | 11/2014 |
| WO | WO 2014/181137 | A1 | 11/2014 |
| WO | WO 2014/194280 | A2 | 12/2014 |
| WO | WO 2014/202827 | A1 | 12/2014 |
| WO | WO 2015/017546 | A1 | 2/2015 |
| WO | WO 2015/052160 | A1 | 4/2015 |
| WO | WO 2015/058106 | A1 | 4/2015 |
| WO | WO 2015/087151 | A1 | 6/2015 |
| WO | WO 2015/102426 | A1 | 7/2015 |
| WO | WO 2015/137750 | A1 | 9/2015 |
| WO | WO 2015/154064 | A2 | 10/2015 |
| WO | WO 2015/165960 | A1 | 11/2015 |
| WO | WO 2015/187542 | A1 | 12/2015 |
| WO | WO 2016/012485 | A1 | 1/2016 |
| WO | WO 2016/018795 | A1 | 2/2016 |
| WO | WO 2016/031815 | A1 | 3/2016 |
| WO | WO 2016/040223 | A1 | 3/2016 |
| WO | WO 2016/055786 | A1 | 4/2016 |
| WO | WO 2016/087257 | A1 | 6/2016 |
| WO | WO 2016/087265 | A1 | 6/2016 |
| WO | WO 2016/100619 | A2 | 6/2016 |
| WO | WO 2016/105518 | A1 | 6/2016 |
| WO | WO 2016/120182 | A1 | 8/2016 |
| WO | WO 2016/126721 | A1 | 8/2016 |
| WO | WO 2016/126722 | A1 | 8/2016 |
| WO | WO 2016/126724 | A1 | 8/2016 |
| WO | WO 2016/126725 | A1 | 8/2016 |
| WO | WO 2016/126726 | A1 | 8/2016 |
| WO | WO 2016/128541 | A1 | 8/2016 |
| WO | WO 2016/168598 | A1 | 10/2016 |
| WO | WO 2016/168660 | A1 | 10/2016 |
| WO | WO 2016/179550 | A1 | 11/2016 |
| WO | WO 2016/179554 | A1 | 11/2016 |
| WO | WO 2016/183331 | A1 | 11/2016 |
| WO | WO 2016/190630 | A1 | 12/2016 |
| WO | WO 2016/196771 | A1 | 12/2016 |
| WO | WO 2017/011323 | A1 | 1/2017 |
| WO | WO 2017/014321 | A1 | 1/2017 |
| WO | WO 2017/018803 | A1 | 2/2017 |
| WO | WO 2017/018804 | A1 | 2/2017 |
| WO | WO 2017/018805 | A1 | 2/2017 |
| WO | WO 2017/023133 | A2 | 2/2017 |
| WO | WO 2017/024009 | A1 | 2/2017 |
| WO | WO 2017/029514 | A1 | 2/2017 |
| WO | WO 2017/033946 | A1 | 3/2017 |
| WO | WO 2017/060854 | A1 | 4/2017 |
| WO | WO 2017/065473 | A1 | 4/2017 |
| WO | WO 2017/076757 | A1 | 5/2017 |
| WO | WO 2017/081310 | A1 | 5/2017 |
| WO | WO 2017/081311 | A1 | 5/2017 |
| WO | WO 2017/083368 | A1 | 5/2017 |
| WO | WO 2017/093019 | A1 | 6/2017 |
| WO | WO 2017/109044 | A1 | 6/2017 |
| WO | WO 2017/110861 | A1 | 6/2017 |
| WO | WO 2017/110862 | A1 | 6/2017 |
| WO | WO 2017/111152 | A1 | 6/2017 |
| WO | WO 2017/123568 | A2 | 7/2017 |
| WO | WO 2017/142883 | A1 | 8/2017 |
| WO | WO 2017/156350 | A1 | 9/2017 |
| WO | WO 2017/162834 | A1 | 9/2017 |
| WO | WO 2017/165256 | A1 | 9/2017 |
| WO | WO 2017/190109 | A1 | 11/2017 |
| WO | WO 2017/193030 | A1 | 11/2017 |
| WO | WO 2017/197046 | A1 | 11/2017 |
| WO | WO 2017/208032 | A1 | 12/2017 |
| WO | WO 2017/213252 | A1 | 12/2017 |
| WO | WO 2017/222950 | A1 | 12/2017 |
| WO | WO 2017/222951 | A1 | 12/2017 |
| WO | WO 2017/222952 | A1 | 12/2017 |
| WO | WO 2018/005192 | A1 | 1/2018 |
| WO | WO 2018/050656 | A2 | 3/2018 |
| WO | WO 2018/055135 | A1 | 3/2018 |
| WO | WO 2018/075959 | A1 | 4/2018 |
| WO | WO 2018/085170 | A1 | 5/2018 |
| WO | WO 2018/129533 | A1 | 7/2018 |
| WO | WO 2018/154466 | A1 | 8/2018 |
| WO | WO 2018/165520 | A1 | 9/2018 |
| WO | WO 2018/187553 | A1 | 10/2018 |
| WO | WO 2018/188962 | A1 | 10/2018 |
| WO | WO 2018/189340 | A1 | 10/2018 |
| WO | WO 2018/191360 | A1 | 10/2018 |
| WO | WO 2018/202491 | A1 | 11/2018 |
| WO | WO 2018/213364 | A1 | 11/2018 |
| WO | WO 2018/219356 | A1 | 12/2018 |
| WO | WO 2019/027054 | A1 | 2/2019 |
| WO | WO 2019/060210 | A1 | 3/2019 |
| WO | WO 2019/100735 | A1 | 5/2019 |
| WO | WO 2019/101709 | A1 | 5/2019 |
| WO | WO 2019/109046 | A1 | 6/2019 |
| WO | WO 2019/110663 | A1 | 6/2019 |
| WO | WO 2019/122323 | A1 | 6/2019 |
| WO | WO 2019/139921 | A1 | 7/2019 |
| WO | WO 2019/164222 | A1 | 8/2019 |
| WO | WO 2019/166824 | A1 | 9/2019 |
| WO | WO 2019/171234 | A1 | 9/2019 |
| WO | WO 2019/200238 | A1 | 10/2019 |
| WO | WO 2019/204550 | A1 | 10/2019 |
| WO | WO 2019/212927 | A1 | 11/2019 |
| WO | WO 2019/228289 | A1 | 12/2019 |
| WO | WO 2020/011816 | A1 | 1/2020 |
| WO | WO 2020/022794 | A1 | 1/2020 |
| WO | WO 2020/028150 | A1 | 2/2020 |
| WO | WO 2020/029908 | A1 | 2/2020 |
| WO | WO 2020/039028 | A1 | 2/2020 |
| WO | WO 2020/061112 | A1 | 3/2020 |
| WO | WO 2020/061118 | A1 | 3/2020 |
| WO | WO 2020/061216 | A1 | 3/2020 |
| WO | WO 2020/070610 | A1 | 4/2020 |
| WO | WO 2020/096916 | A2 | 5/2020 |
| WO | WO 2020/106119 | A1 | 5/2020 |
| WO | WO 2020/127974 | A1 | 6/2020 |
| WO | WO 2020/132561 | A1 | 6/2020 |
| WO | WO 2020/158762 | A1 | 8/2020 |
| WO | WO 2020/194272 | A1 | 10/2020 |
| WO | WO 2020/201773 | A1 | 10/2020 |
| WO | WO 2020/207941 | A1 | 10/2020 |
| WO | WO 2020/212479 | A1 | 10/2020 |
| WO | WO 2020/219650 | A1 | 10/2020 |
| WO | WO 2020/223136 | A1 | 11/2020 |
| WO | WO 2020/240492 | A1 | 12/2020 |

(56) References Cited

FOREIGN PATENT DOCUMENTS

| | | | |
|---|---|---|---|
| WO | WO 2020/240493 | A1 | 12/2020 |
| WO | WO 2020/245381 | A1 | 12/2020 |
| WO | WO 2020/254494 | A1 | 12/2020 |
| WO | WO 2020/264437 | A1 | 12/2020 |
| WO | WO 2021/021979 | A2 | 2/2021 |
| WO | WO 2021/022076 | A1 | 2/2021 |
| WO | WO 2021/046183 | A1 | 3/2021 |
| WO | WO 2021/048242 | A1 | 3/2021 |
| WO | WO 2021/057872 | A1 | 4/2021 |
| WO | WO 2021/060567 | A1 | 4/2021 |
| WO | WO 2021/067859 | A1 | 4/2021 |
| WO | WO 2021/092151 | A1 | 5/2021 |
| WO | WO 2021/092153 | A1 | 5/2021 |
| WO | WO 2021/092174 | A1 | 5/2021 |
| WO | WO 2021/127643 | A1 | 6/2021 |
| WO | WO 2021/133957 | A1 | 7/2021 |
| WO | WO 2021/172886 | A1 | 9/2021 |
| WO | WO 2021/172887 | A1 | 9/2021 |
| WO | WO 2021/208945 | A1 | 10/2021 |
| WO | WO 2021/210857 | A1 | 10/2021 |
| WO | WO 2021/236491 | A1 | 11/2021 |
| WO | WO 2021/244416 | A1 | 12/2021 |
| WO | WO 2021/263171 | A1 | 12/2021 |
| WO | WO 2022/013728 | A1 | 1/2022 |
| WO | WO 2022/029041 | A1 | 2/2022 |
| WO | WO 2022/049496 | A1 | 3/2022 |
| WO | WO 2022/081928 | A1 | 4/2022 |
| WO | WO 2022/133551 | A1 | 6/2022 |
| WO | WO 2022/174193 | A1 | 8/2022 |
| WO | WO 2022/187690 | A1 | 9/2022 |
| WO | WO 2022/197690 | A1 | 9/2022 |
| WO | WO 2022/215020 | A1 | 10/2022 |
| WO | WO 2022/216616 | A1 | 10/2022 |
| WO | WO 2022/226388 | A1 | 10/2022 |
| WO | WO 2022/235842 | A1 | 11/2022 |
| WO | WO 2023/081328 | A1 | 5/2023 |
| WO | WO 2023/097386 | A1 | 6/2023 |
| WO | WO 2023/118507 | A2 | 6/2023 |
| WO | WO 2023/154758 | A1 | 8/2023 |
| WO | WO 2023/195809 | A1 | 10/2023 |
| WO | WO 2023/198172 | A1 | 10/2023 |
| WO | WO 2024/013690 | A1 | 1/2024 |
| WO | WO 2024/017897 | A1 | 1/2024 |

OTHER PUBLICATIONS

International Search Report and Written Opinion mailed Jun. 24, 2022 for Application No. PCT/US2022/015129.

Invitation to Pay Additional Fees mailed Jun. 9, 2023 for Application No. PCT/US2023/017900.

[No Author Listed], 2-(Difluoromethyl)-5-[2-(4-fluorophenoxy)pyrimidin-5-yl]-1,3,4-oxadiazole. PubChem CID No. 162351258. Accessed May 25, 2023. Created Dec. 13, 2021. https://pubchem.ncbi.nlm.nih.gov/compound/162351258. 10 pages.

[No Author Listed], 2-(Phenoxymethyl)pyrimidine. PubChem CID No. 19371420. Accessed May 25, 2023. Created Dec. 4, 2017. https://pubchem.ncbi.nlm.nih.gov/compound/19371420. 11 pages.

[No Author Listed], Bringing NHA HDAC6 inhibitors to the clinic for cardiovascular and neurodegenerative disorders. Chong Kun Dang Pharmaceutical Corp. Nature Research Custom Media. Jun. 2022;B41.

[No Author Listed], Cancer Innovates, accelerating early cancer drug discovery. Cancer Innova. Feb. 2022. Accessed from <https://www-cancerinnova-com.translate.goog/en/cancer-innova-acelerando-el-descubrimiento-temprano-de-farmacos-en-cancer/?_x_tr_sl=auto&_x_tr_tl=en&_x_tr_hl=en&_x_tr_pto=wapp>. 10 pages.

[No Author Listed], CAS Registration No. 1332894-18-4. Registry (STN). Sep. 20, 2011. 1 page.

[No Author Listed], CAS Registration No. 1860746-44-6. Registry (STN). Feb. 5, 2016. 1 page.

[No Author Listed], CAS Registration No. 1875612-53-5. Registry (STN). Feb. 28, 2016. 1 page.

[No Author Listed], CAS Registration No. 73779-41-6. Registry (STN). Nov. 16, 1984. 1 page.

[No Author Listed], CAY10603: Catalog No. S7596; Synonyms: BML-281. Apr. 2015. 4 pages. Accessed Jul. 19, 2022 from <https://www.selleckchem.com/products/cay10603.html?gclid=CjwKCAjwoMSWBhAdEiwAVJ2ndv0I8KYzzn0XiWLIF5DRM50crFNHcVSDwVsA6XALwr0yzmIKn10muxoCgkcQAvD_BwE>.

[No Author Listed], HDAC: Inhibitory Selectivity. AdooQ Bioscience. 21 pages. Accessed May 18, 2022 from <https://www.adooq.com/epigenetics-histone-deacetylase-hdac.html?gclid=EAIaIQobChMI4K_CiJzk9AIVpQaICR2_rgPTEAMYASAAEgKHnvD_BWE>.

[No Author Listed], Augustine Therapeutics Showcase Presentation. Recorded at the 2022 Investival Showcase in London, England on Nov. 14, 2022. Accessed Feb. 7, 2023 from <https://www.youtube.com/watch?v=8wJXGd2CgQU>. Selected screenshots. 6 pages.

[No Author Listed], Jubilant Therapeutics Inc. receives Orphan Drug Designation for JBI-802 for Acute Myeloid Leukemia (AML) and Small Cell Lung Cancer (SCLC). Jubilant Therapeutics. Jan. 5, 2023. Accessed from <https://www.prnewswire.com/news-releases/jubilant-therapeutics-inc-receives-orphan-drug-designation-for-jbi-802-for-acute-myeloid-leukemia-aml-and-small-cell-lung-cancer-sclc-301714552.html>. 3 pages.

[No Author Listed], NCT03713892: CKD-504 in SAD and MAD in Healthy Korean and Caucasian Adult Male and Female Subjects. Last Update Posted Feb. 24, 2020. 6 pages. Accessed Feb. 7, 2023 from <https://clinicaltrials.gov/ct2/show/NCT03713892>.

[No Author Listed], NCT04746287: Evaluation of the Safety and Tolerability of CKD-510 in Healthy Subjects. Last Update Posted May 4, 2022. 8 pages. Accessed Feb. 7, 2023 from <https://clinicaltrials.gov/ct2/show/NCT04746287>.

[No Author Listed], NCT05526742: A Study to Evaluate the Relative Bioavailability of Formulations of CKD-510 and to Assess the Effect of Food on the CKD-510 Tablet Formulation in Healthy Subjects. Last Update Posted Sep. 8, 2022. 7 pages. Accessed Feb. 7, 2023 from <https://clinicaltrials.gov/ct2/show/NCT05526742>.

[No Author Listed], OnKure Expands Executive Team with the Addition of Chief Scientific Officer and Chief Development Officer. OnKure Therapeutics. Aug. 3, 2021. Accessed from <https://onkuretherapeutics.com/press-release/onkure-expands-executive-team-and-appoints-head-of-discovery-chief-financial-officer-and-general-counsel-2/>. 4 pages.

[No Author Listed], OnKure Therapeutics Appoints Jennifer R. Diamond, M.D., as Chief Medical Officer. OnKure Therapeutics. Oct. 14, 2021. Accessed from <https://onkuretherapeutics.com/year/2021/onkure-therapeutics-appoints-jennifer-r-diamond-m-d-as-chief-medical-officer/>. 3 pages.

[No Author Listed], Oryzon collaborates with the CMT Research Foundation in the US. Oryzon Press Release. Jul. 26, 2022. 2 pages.

[No Author Listed], Pharmacology review for belinostat. Center for Drug Evaluation and Research. Application No. 206256Orig1s000. May 22, 2014. 98 pages.

[No Author Listed], Pharmacology review for panobinostat. Center for Drug Evaluation and Research. Application No. 205353Orig1s000. Sep. 2, 2014. 125 pages.

[No Author Listed], Pharmacology review for vorinostat. Center for Drug Evaluation and Research. Application No. 21-991. Oct. 5, 2006. 106 pages.

[No Author Listed], Pipeline Program and Development Status. OnKure Therapeutics. May 13, 2021. Accessed from <https://web.archive.org/web/20210513123624/https:/onkuretherapeutics.com/pipeline/>. 2 pages.

[No Author Listed], Pipeline Program and Development Status. OnKure Therapeutics. Oct. 8, 2021. Accessed from <https://web.archive.org/web/20210513123624/https:/onkuretherapeutics.com/pipeline/>. 2 pages.

[No Author Listed], Precision oral medicines with enhanced therapeutic index. Jubilant Therapeutics. Corporate Presentation. Jan. 2023. 38 pages.

[No Author Listed], PubChem Substance Record for PubChem SID 227322283, SCHEMBL1075847. Accessed Sep. 21, 2020. 9 pages.

(56) References Cited

OTHER PUBLICATIONS

[No Author Listed], PubChem Substance Record for PubChem SID 274711921, 2-[5-(3-Nitrophenyl)furfuryl]-1,2,3,4-tetrahydroisoquinoline-7-carbohydroximic acid. Accessed Sep. 21, 2020. 8 pages.
[No Author Listed], Scaling New Heights in the Fight Against Heart Disease. Tenaya Therapeutics. Corporate Presentation. Sep. 2022. 38 pages.
[No Author Listed], Tenaya Therapeutics Announces TN-201 IND Clearance and Anticipated 2023 Milestones. GlobeNewswire. Jan. 9, 2023. Accessed from <https://www.globenewswire.com/news-release/2023/01/09/2585026/0/en/Tenaya-Therapeutics-Announces-TN-201-IND-Clearance-and-Anticipated-2023-Milestones.html>. 7 pages.
[No Author Listed], The basque-based company Quimatryx licenses a cancer drug for 92 million dollars. Basque Press. Jul. 29, 2022. Accessed from <https://basque.press/the-guipuzcoa-based-company-quimatryx-licenses-a-cancer-drug-for-92-million-dollars-la-empresa-guipuzcoana-quimatryx-licencia-un-farmaco-contra-el-cancer-por-92-millones-de-dolares/>. 5 pages.
[No Author Listed], The McQuade Center for Strategic Research and Development and Eikonizo Therapeutics Enter Agreement to Develop Treatments for Patients with Rare Diseases. Feb. 9, 2021.
Adalbert et al., Novel HDAC6 Inhibitors Increase Tubulin Acetylation and Rescue Axonal Transport of Mitochondria in a Model of Charcot-Marie-Tooth Type 2F. ACS Chem Neurosci. Feb. 5, 2020;11(3):258-267. doi: 10.1021/acschemneuro.9b00338. Epub Jan. 8, 2020.
Aleksandrova et al., Elaboration of the Effective Multi-Target Therapeutic Platform for the Treatment of Alzheimer's Disease Based on Novel Monoterpene-Derived Hydroxamic Acids. Int J Mol Sci. Jun. 4, 2023;24(11):9743. doi: 10.3390/ijms24119743.
Bae et al., CKD-506: A novel HDAC6-selective inhibitor that exerts therapeutic effects in a rodent model of multiple sclerosis. Sci Rep. Jul. 14, 2021;11(1):14466. doi: 10.1038/s41598-021-93232-6.
Bae et al., CKD-510, a novel non-hydroxamic acid histone deacetylase 6 (HDAC6) inhibitor for Charcot-Marie-Tooth disease type 1A. J Peripher Nerv Syst.2022;27(Suppl. 3):S4. Abstract Only.
Beshore et al., Redefining the Histone Deacetylase Inhibitor Pharmacophore: High Potency with No Zinc Cofactor Interaction. ACS Med Chem Lett. Mar. 7, 2021;12(4):540-547. doi: 10.1021/acsmedchemlett.1c00074.
Blackburn et al., Histone deacetylase inhibitors derived from 1,2,3,4-tetrahydropyrrolo[1,2-alpyrazine and related heterocycles selective for the HDAC6 isoform. Bioorg Med Chem Lett. Dec. 1, 2014;24(23):5450-4. doi: 10.1016/j.bmcl.2014.10.022.
Blackburn et al., Potent histone deacetylase inhibitors derived from 4-(aminomethyl)-N-hydroxybenzamide with high selectivity for the HDAC6 isoform. J Med Chem. Sep. 26, 2013;56(18):7201-11. doi: 10.1021/jm400385r. Epub Sep. 4, 2013.
Bondarev et al., Recent developments of HDAC inhibitors: Emerging indications and novel molecules. Br J Clin Pharmacol. 2021; 87( 12): 4577-4597. https://doi.org/10.1111/bcp.14889.
Chang et al., The Role of HDAC6 in Autophagy and NLRP3 Inflammasome. Front Immunol. Oct. 27, 2021;12:763831. doi: 10.3389/fimmu.2021.763831.
Choi et al., Acetylation changes tau interactome to degrade tau in Alzheimer's disease animal and organoid models. Aging Cell. Jan. 2020;19(1):e13081. doi: 10.1111/acel.13081. Epub Nov. 25, 2019.
Choi et al., CKD-506, a novel HDAC6-selective inhibitor, improves renal outcomes and survival in a mouse model of systemic lupus erythematosus. Sci Rep. Nov. 23, 2018;8(1):17297. doi: 10.1038/s41598-018-35602-1.
Cragin et al., A Novel Zinc Binding Group for HDAC6 Inhibition. FASEB J. May 2022;36 Suppl 1. doi: 10.1096/fasebj.2022.36.S1.R3604. Abstract Only.
Faridoon et al., Medicinal chemistry insights into non-hydroxamate HDAC6 selective inhibitors. Med Chem Res. Oct. 31, 2022;32(1):1-14. doi: 10.1007/s00044-022-02987-8.
Fazal et al., HDAC6 inhibition restores TDP-43 pathology and axonal transport defects in human motor neurons with TARDBP mutations. EMBO J. 2021;40:e106177.
Gaisina et al., Activation of Nrf2 and Hypoxic Adaptive Response Contribute to Neuroprotection Elicited by Phenylhydroxamic Acid Selective HDAC6 Inhibitors. ACS Chem Neurosci. May 16, 2018;9(5):894-900. doi: 10.1021/acschemneuro.7b00435. Epub Jan. 17, 2018.
Gajendran et al., Novel dual LSD1/HDAC6 inhibitor for the treatment of cancer. PLoS One. Jan. 3, 2023;18(1):e0279063. doi: 10.1371/journal.pone.0279063.
Guo et al., Design, synthesis and biological evaluation of brain penetrant benzazepine-based histone deacetylase 6 inhibitors for alleviating stroke-induced brain infarction. Eur J Med Chem. Jun. 5, 2021;218:113383. doi: 10.1016/j.ejmech.2021.113383. Epub Mar. 17, 2021.
Ha et al., A novel histone deacetylase 6 inhibitor improves myelination of Schwann cells in a model of Charcot-Marie-Tooth disease type 1A. Br J Pharmacol. Nov. 2020;177(22):5096-5113. doi: 10.1111/bph.15231. Epub Sep. 27, 2020.
Hendricks et al., In vivo PET imaging of histone deacetylases by 18F-suberoylanilide hydroxamic acid (18F-SAHA). J Med Chem. Aug. 11, 2011;54(15):5576-82. doi: 10.1021/jm200620f. Epub Jul. 18, 2011.
Hong et al., CKD-510, a novel selective HDAC6 inhibitor, is well-tolerated and increased acetyl-tubulin in healthy volunteers. J Peripher Nerv Syst.2022;27(Suppl. 3):S76-7. Abstract Only.
Hu et al., 3D-QSAR Studies of HDAC6 Inhibitors Using Docking-Based Alignment. Lett Drug Des Discov. Jul. 2017; 14(7):798-810. doi: 10.2174/1570180813666161028165151.
Hubbert et al., HDAC6 is a microtubule-associated deacetylase. Nature. May 23, 2002;417(6887):455-8. doi: 10.1038/417455a.
Jeong et al., Therapeutic Potential of CKD-504, a Novel Selective Histone Deacetylase 6 Inhibitor, in a Zebrafish Model of Neuromuscular Junction Disorders. Mol Cells. Apr. 30, 2022;45(4):231-242. doi: 10.14348/molcells.2022.5005.
Kattar, et al., Parallel medicinal chemistry approaches to selective HDAC1/HDAC2 inhibitor (SHI-1:2) optimization. Bioorg Med Chem Lett. Feb. 15, 2009;19(4):1168-72. doi: 10.1016/j.bmcl.2008.12.083. Epub Dec. 25, 2008.
Kim et al., HDAC6 inhibitor blocks amyloid beta-induced impairment of mitochondrial transport in hippocampal neurons. PLoS One. 2012;7(8):e42983. doi: 10.1371/journal.pone.0042983. Epub Aug. 22, 2012.
Kim et al., HDAC6 Inhibitors Rescued the Defective Axonal Mitochondrial Movement in Motor Neurons Derived from the Induced Pluripotent Stem Cells of Peripheral Neuropathy Patients with HSPB1 Mutation. Stem Cells Int. 2016;2016:9475981. doi: 10.1155/2016/9475981. Epub Dec. 26, 2016.
Kleinschek et al., Potent and Selective Non-hydroxamate Histone Deacetylase 8 Inhibitors. ChemMedChem. Dec. 6, 2016;11(23):2598-2606. doi: 10.1002/cmdc.201600528. Epub Nov. 9, 2016.
Kozikowski et al., Brain Penetrable Histone Deacetylase 6 Inhibitor SW-100 Ameliorates Memory and Learning Impairments in a Mouse Model of Fragile X Syndrome. ACS Chem Neurosci. Mar. 20, 2019;10(3):1679-1695. doi: 10.1021/acschemneuro.8b00600. Epub Dec. 14, 2018.
Kozikowski, A.P., Application for Federal Assistance for Study of the New HDAC6i SW-100 as a Treatment for Alzheimer's Disease and Other Tauopathies; Title: Study of the New HDAC6i SW-100 as a Treatment for Alzheimer's Disease and Other Tauopathies for StarWise Therapeutics LLC and University of South Florida. FOA: PAS17-065. Received Mar. 31, 2017. 62 pages.
Krukowski et al., HDAC6 inhibition effectively reverses chemotherapy-induced peripheral neuropathy. Pain. Jun. 2017;158(6):1126-1137. doi: 10.1097/j.pain.0000000000000893.
Lechner et al., Target deconvolution of HDAC pharmacopoeia reveals MBLAC2 as common off-target. Nat Chem Biol. Aug. 2022;18(8):812-820. doi: 10.1038/s41589-022-01015-5. Epub Apr. 28, 2022. Erratum in: Nat Chem Biol. Jul. 15, 2022.
Lee et al., Novel Histone Deacetylase 6 Inhibitor CKD-506 Inhibits NF-κB Signaling in Intestinal Epithelial Cells and Macrophages and

(56) References Cited

OTHER PUBLICATIONS

Ameliorates Acute and Chronic Murine Colitis. Inflamm Bowel Dis. May 12, 2020;26(6):852-862. doi: 10.1093/ibd/izz317.
Lee et al., Novel Histone Deacetylase 6 Inhibitor Confers Anti-inflammatory Effects and Enhances Gut Barrier Function. Gut Liver. Sep. 27, 2022. doi: 10.5009/gnl220159. Epub ahead of print.
Li et al., A Novel HDAC6 Inhibitor, CKD-504, is Effective in Treating Preclinical Models of Huntington's Disease. BMB Rep. Jan. 3, 2023:5747. Epub ahead of print.
Li et al., Abstract 4441: CS3003, an HDAC6-selective inhibitor, improves anti-PD-1 immune checkpoint blockade therapy efficacy. Proceedings of the Annual Meeting of the American Association for Cancer Research. Apr. 27-28, 2020 and Jun 22-24. Philadelphia, PA. Cancer Res 2020;80(16 Suppl). Poster. 1 page.
Lipczynska-Kochany et al., Mutagenicity of pyridine- and quinoline-carbohydroxamic acid derivatives. Mutat Res. Mar. 1984;135(3):139-48. doi: 10.1016/0165-1218(84)90114-9.
Liu et al., MiR-222-3p Inhibits Trophoblast Cell Migration and Alleviates Preeclampsia in Rats Through Inhibiting HDAC6 and Notch1 Signaling. Reprod Sci. Nov. 18, 2021. doi: 10.1007/s43032-021-00793-y. Epub ahead of print.
Mahmoud et al., Nimbolide inhibits 2D and 3D prostate cancer cells migration, affects microtubules and angiogenesis and suppresses B-RAF/p.ERK-mediated in vivo tumor growth. Phytomedicine. Jan. 2022;94:153826. doi: 10.1016/j.phymed.2021.153826. Epub Nov. 1, 2021.
Martin et al., Discovery of novel N-hydroxy-2-arylisoindoline-4-carboxamides as potent and selective inhibitors of HDAC11. Bioorg Med Chem Lett. Jul. 1, 2018;28(12):2143-2147. doi: 10.1016/j.bmcl.2018.05.021. Epub May 9, 2018.
McMahon, VEGF receptor signaling in tumor angiogenesis. The Oncologist. 2000;5(suppl 1):3-10.
Munakata et al., Mutagenicity of N-acylglycinohydroxamic acids and related compounds. J Pharmacobiodyn. Nov. 1980;3(11):557-61. doi: 10.1248/bpb1978.3.557.
Neidle, Cancer Drug Design and Discovery. Elsevier/Academic Press. 2008; 427-431.
Onishi et al., A novel orally active HDAC6 inhibitor T-518 shows a therapeutic potential for Alzheimer's disease and tauopathy in mice. Sci Rep. Jul. 29, 2021;11(1):15423. doi: 10.1038/s41598-021-94923-w.
Park et al., Therapeutic potential of CKD-506, a novel selective histone deacetylase 6 inhibitor, in a murine model of rheumatoid arthritis. Arthritis Res Ther. Jul. 25, 2020;22(1):176. doi: 10.1186/s13075-020-02258-0.
Pinedo et al., Translational Research: The Role of VEGF in Tumor Angiogenesis. The Oncologist. 2000;5(Suppl 1):1-2.
Rivieccio et al., HDAC6 is a target for protection and regeneration following injury in the nervous system. Proc Natl Acad Sci U S A. Nov. 17, 2009;106(46):19599-604. doi: 10.1073/pnas.0907935106. Epub Nov. 2, 2009.
Sandrone et al., Role of Fluorination in the Histone Deacetylase 6 (HDAC6) Selectivity of Benzohydroxamate-Based Inhibitors. ACS Med Chem Lett. Oct. 11, 2021;12(11):1810-1817. doi: 10.1021/acsmedchemlett.1c00425.
Selenica et al., Histone deacetylase 6 inhibition improves memory and reduces total tau levels in a mouse model of tau deposition. Alzheimers Res Ther. Feb. 27, 2014;6(1):12. doi: 10.1186/alzrt241.
Shen et al., A patent review of histone deacetylase 6 inhibitors in neurodegenerative diseases (2014-2019). Expert Opin Ther Pat. Feb. 2020;30(2):121-136. doi: 10.1080/13543776.2019.1708901. Epub Dec. 25, 2019.
Shen et al., A patent review of histone deacetylase 6 inhibitors in neurodegenerative diseases (2014-2019). Expert Opin Ther Pat. 2020;30(2):121-136. doi: 10.1080/13543776.2019.1708901.
Shen et al., Bicyclic-Capped Histone Deacetylase 6 Inhibitors with Improved Activity in a Model of Axonal Charcot-Marie-Tooth Disease. ACS Chem Neurosci. Feb. 17, 2016;7(2):240-58. doi: 10.1021/acschemneuro.5b00286. Epub Dec. 7, 2015.
Shen et al., Why Hydroxamates May Not Be the Best Histone Deacetylase Inhibitors—What Some May Have Forgotten or Would Rather Forget? ChemMedChem. Jan. 5, 2016;11(1):15-21. doi: 10.1002/cmdc.201500486. Epub Nov. 25, 2015.
Shidore et al., 3-Substituted 1-methyl-3-benzazepin-2-ones as 5-HT2C receptor agonists. RSC Adv. Oct. 19, 2015;5(111):91908-21. doi: 10.1039/C5RA17718A.
Shukla et al., Histone Deacetylases Inhibitors in Neurodegenerative Diseases, Neuroprotection and Neuronal Differentiation. Front Pharmacol. Apr. 24, 2020;11:537. doi: 10.3389/fphar.2020.00537.
Simoes-Pires et al., HDAC6 as a target for neurodegenerative diseases: what makes it different from the other HDACs? Mol Neurodegener. Jan. 29, 2013;8:7. doi: 10.1186/1750-1326-8-7.
Sixto-Lopez et al., silico design of HDAC6 inhibitors with neuroprotective effects. J Biomol Struct Dyn. Nov. 16, 2021:1-19. doi: 10.1080/07391102.2021.2001378. Epub ahead of print.
Wang et al., Mutagenicity and antibacterial activity of hydroxamic acids. Antimicrob Agents Chemother. Apr. 1977;11(4):753-5. doi: 10.1128/AAC.11.4.753.
Wang, C.Y., Mutagenicity of hydroxamic acids for *Salmonella typhimurium*. Mutat Res. Sep. 1977;56(1):7-12. doi: 10.1016/0027-5107(77)90235-4.
Watson et al., Aromatic C—F Interactions Influence Binding Mode of Inhibitors in HDAC6. FASEB J. May 2022;36 Suppl 1. doi: 10.1096/fasebj.2022.36.S1.R2257. Abstract Only.
Wei et al., Mutagenicity of some monoaromatic hydroxamic acids. Toxicol Lett. Jan. 1985;24(1):111-6. doi: 10.1016/0378-4274(85)90148-1.
Xu et al., Design, Synthesis, Bioactivity Evaluation, Crystal Structures, and In Silico Studies of New α-Amino Amide Derivatives as Potential Histone Deacetylase 6 Inhibitors. Molecules. May 22, 2022;27(10):3335. doi: 10.3390/molecules27103335.
Yang et al., Phenotypic screening with deep learning identifies HDAC6 inhibitors as cardioprotective in a BAG3 mouse model of dilated cardiomyopathy. Sci Transl Med. Jul. 6, 2022;14(652):1-15. doi: 10.1126/scitranslmed.abl5654. Supplementary Materials, 44 pages.
Zhang et al., Design, synthesis, and biological evaluation of novel histone deacetylase 6 selective inhibitors. J Saudi Chem Soc. May 2022;26(3):101450. doi: 10.1016/j.jscs.2022.101450.
Zhang et al., Tubastatin A/ACY-1215 improves cognition in Alzheimer's disease transgenic mice. J Alzheimers Dis. 2014;41(4):1193-205. doi: 10.3233/JAD-140066.
U.S. Appl. No. 18/443,509, filed Feb. 16, 2024, Yates.
U.S. Appl. No. 18/854,932, filed Oct. 7, 2024, Wagner.
U.S. Appl. No. 18/854,938, filed Oct. 7, 2024, Wagner et al.
PCT/US2023/017894, Oct. 17, 2024, International Preliminary Report on Patentability.
PCT/US2023/017900, Aug. 23, 2023, International Search Report and Written Opinion.
PCT/US2023/017900, Oct. 17, 2024, International Preliminary Report on Patentability.
International Preliminary Report on Patentability mailed Oct. 17, 2024 for Application No. PCT/US2023/017894.
International Search Report and Written Opinion mailed Aug. 23, 2023 for Application No. PCT/US2023/017900.
International Preliminary Report on Patentability mailed Oct. 17, 2024 for Application No. PCT/US2023/017900.
Buommino et al., Synergism of a Novel 1,2,4-oxadiazole-containing Derivative with Oxacillin against Methicillin-Resistant *Staphylococcus aureus*. Antibiotics (Basel). Oct. 16, 2021;10(10):1258. doi: 10.3390/antibiotics10101258.
Cakir et al., Histone deacetylase 6 inhibition restores leptin sensitivity and reduces obesity. Nat Metab. Jan. 2022;4(1):44-59. doi: 10.1038/s42255-021-00515-3. Epub Jan. 17, 2022. Author Manuscript, 51 pages.
James et al., Development of EKZ-102, a potent and selective CNS-penetrant HDAC6 inhibitor with the potential to benefit a broad population of people with ALS. Oct. 23, 2024. Eikonizo Therapeutics. Poster. 3 pages.
James et al., Development of EKZ-102, a highly selective CNS-penetrant small molecule HDAC6 inhibitor for improved axonal

(56) References Cited

OTHER PUBLICATIONS transport, proteostasis, and neuronal survival in the treatment of ALS. Eikonizo Therapeutics, Inc. Dec. 6, 2024. 1 page.
PCT/US2023/017894, Aug. 25, 2023, International Search Report and Written Opinion.
International Search Report and Written Opinion mailed Aug. 25, 2023 for Application No. PCT/US2023/017894.
[No Author Listed], 1,4-Dimethyl-7-(pyridin-2-ylmethoxy)indole-2-carboxylic acid. PubChem CID No. 140972344. Accessed May 25, 2023. Created Dec. 6, 2019. https://pubchem.ncbi.nlm.nih.gov/compound/140972344. 10 pages.
International Preliminary Report on Patentability mailed Aug. 17, 2023 for Application No. PCT/US2022/015129.

OXADIAZOLE HDAC6 INHIBITORS AND USES THEREOF

RELATED PATENT APPLICATION

This patent application claims priority under 35 U.S.C. 119(e) to U.S. Provisional Patent Application U.S. Ser. No. 63/329,143, filed Apr. 8, 2022, which is incorporated herein by reference in its entirety.

BACKGROUND

Histone deacetylases (HDACs) are divided into four classes based on sequence homology. HDAC6, a class IIb HDAC, is a cytoplasmic, microtubule-associated enzyme. HDAC6 has unique features among the HDAC paralogs. Unlike other HDACs, HDAC6 contains two deacetylase domains and a ubiquitin binding domain allowing HDAC6 to function in distinct cell signaling systems involving protein acetylation and ubiquitination, respectively. Importantly, it does not deacetylate histones. HDAC6 deacetylates tubulin, tau, Hsp90, cortactin, and other emerging targets. HDAC6 deacetylase function is involved in microtubule-based cargo transport, protein degradation/recycling and stress-induced glucocorticoid receptor signaling. HDAC6 deacetylase function is also involved in cell morphology, motility and migration, as well as cell growth and survival. In addition to deacetylase functions, HDAC6 forms complexes with partner proteins linked to ubiquitin-dependent functions, and influences protein aggregation, trafficking and degradation via the aggresome pathway. HDAC6 expression was shown to be elevated in postmortem brain samples from Alzheimer's disease patients. Small molecule compounds inhibiting HDAC6 are being developed as a potential therapy for Alzheimer's Disease patients.

SUMMARY

The cytosolic location, distinct substrates, and structure of HDAC6 are unique among the HDAC paralogs and HDAC6-selective treatment regimens show promise to avoid many of the side effects of first-generation pan-HDAC inhibitors. However, paralog selectivity is difficult to obtain. The present disclosure stems from the recognition that the unique structure and function of HDAC6, among the HDAC paralogs, provides an opportunity for the design of selective HDAC6 inhibitors. The present disclosure also recognizes that targeting HDAC6-mediated pathways may provide improved treatments for neurological disorders. In relation to neurodegeneration, HDAC6 (1) impairs microtubule function by deacetylating tubulin, which leads to defects in axonal and mitochondrial transport; (2) promotes tau aggregation by deacetylating tau, which leads to pathological tau phosphorylation and neurofibrillary tangle formation; and (3) prevents degradation of HSP90 client proteins, including misfolded tau, by deacetylating HSP90, which stabilizes the chaperone complex associated with protein refolding/recycling. Thus, the present disclosure provides brain-penetrant, selective HDAC6 inhibitors. These compounds provide new compositions and methods for the treatment of diseases associated with HDAC6 activity (e.g., neurological disorders, such as Alzheimer's disease and other tauopathies, amyotrophic lateral sclerosis, and cancer).

In one aspect, provided are compounds of Formula (I):

(I)

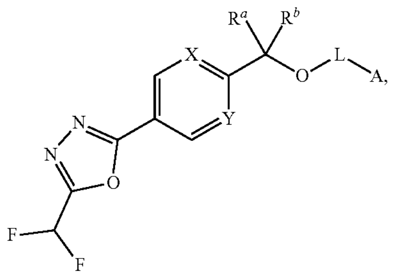

or a pharmaceutically acceptable salt thereof, wherein:

X is $CR^1$ or N, and Y is $CR^1$ or N, provided that at least one of X and Y is N;

$R^a$ and $R^b$ are each independently hydrogen or halogen;

L is a bond or $C_{1-4}$ alkylene optionally substituted with one or more halogen;

A is aryl, heteroaryl, carbocyclyl, or heterocyclyl, wherein A is optionally substituted with one or more substituents $R^2$;

$R^1$ is hydrogen or halogen; and each occurrence of $R^2$ is independently halogen, substituted or unsubstituted amino, substituted or unsubstituted amido, cyano, substituted or unsubstituted acyl, substituted or unsubstituted alkyl, substituted or unsubstituted alkenyl, substituted or unsubstituted alkynyl, substituted or unsubstituted heteroaliphatic, substituted or unsubstituted carbocyclyl, substituted or unsubstituted heterocyclyl, substituted or unsubstituted aryl, or substituted or unsubstituted heteroaryl; or two occurrences of $R^2$ are joined with their intervening atoms to form substituted or unsubstituted carbocyclyl, substituted or unsubstituted heterocyclyl, substituted or unsubstituted aryl, or substituted or unsubstituted heteroaryl.

In certain embodiments of the compounds of Formula (I): $R^a$ and $R^b$ are each independently hydrogen or fluorine; L is a bond or $—CH_2—$; $R^1$ is hydrogen or fluorine; A is a $C_6$ monocyclic aryl, a bicyclic ring comprising a $C_6$ aryl or 6-membered heteroaryl fused with a $C_6$ carbocyclyl or 6-membered heterocyclyl comprising a nitrogen, oxygen or sulfur heteroatom, a $C_{10}$ bicyclic aryl, a 5-6 membered monocyclic heteroaryl comprising one or more heteroatoms selected from nitrogen, oxygen and sulfur, a 9-10 membered bicyclic heteroaryl comprising one or more nitrogen or oxygen heteroatoms (e.g., a 5,6-bicyclic heteroaryl group or a 6,6-bicyclic heteroaryl group), a $C_{4-10}$ carbocyclyl (e.g., $C_{4-7}$ monocyclic carbocyclyl or $C_{4-7}$ bridged polycyclic ring system), or a 6-10 membered heterocyclyl (e.g., 6-7 membered monocyclic heterocyclyl ring having one or more nitrogen, oxygen or sulfur heteroatoms, or a fused or bridged 7-10 membered polycyclic ring system), wherein A is optionally substituted with one or more substituents $R^2$; and each $R^2$ is independently chlorine, fluorine, —CN, $—CH_2CN$, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom.

In certain embodiments of the compounds of Formula (I): $R^a$ and $R^b$ are each hydrogen; L is a bond; $R^1$ is hydrogen or fluorine; A is a $C_{5-6}$ monocyclic aryl substituted with one or more substituents $R^2$; and each $R^2$ is independently chloro, fluoro, —CN, $—CH_2CN$, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom.

In certain embodiments of the compounds of Formula (I): $R^a$ and $R^b$ are each independently hydrogen or fluorine; L is a bond; $R^1$ is hydrogen or fluorine; A is a 6,6-bicyclic aryl ring system, a 5,6-bicyclic heteroaryl ring system or a 6,6-bicyclic heteroaryl ring system, optionally substituted with one or more substituents $R^2$; and each $R^2$ is independently chlorine, fluorine, $C_{1-4}$ alkyl, or $C_{1-4}$ haloalkyl.

In certain embodiments of the compounds of Formula (I): $R^a$ and $R^b$ are each hydrogen; L is a bond; $R^1$ is hydrogen; A is a bicyclic ring comprising a $C_6$ aryl or 6-membered heteroaryl fused with a $C_6$ carbocyclyl or 6-membered heterocyclyl comprising a nitrogen, oxygen or sulfur heteroatom, wherein A is optionally substituted with one or more substituents $R^2$; and each $R^2$ is independently chlorine, fluorine, $C_{1-4}$ alkyl, or $C_{1-4}$ haloalkyl.

In certain embodiments of the compounds of Formula (I): $R^a$ and $R^b$ are each hydrogen; L is a bond or —$CH_2$—; $R^1$ is hydrogen or fluorine; A is a $C_{4-7}$ monocyclic carbocyclyl, a $C_{4-7}$ bridged polycyclic ring system, a 6-7 membered monocyclic heterocyclyl ring having one or more nitrogen, oxygen or sulfur heteroatoms, or a fused or bridged 7-10 membered polycyclic ring system, wherein A is optionally substituted with one or more substituents $R^2$; and each $R^2$ is independently chlorine, fluorine, —CN, —$CH_2CN$, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom.

In certain embodiments, the compounds of Formula (I) are compounds of Formula (I-a), (I-b), (I-c), (I-d), (I-e), (I-f), (I-f-1), (I-f-2), (I-g), (I-g-1), (I-g-2), (I-h), (I-h-1), (I-h-2), (I-i), (I-i-1), (I-i-2), (I-i-3), (I-i-5), (I-i-7), (I-j), (I-j-1), (I-j-2), (I-k), (I-k-1), or (I-k-2):

(I-a)

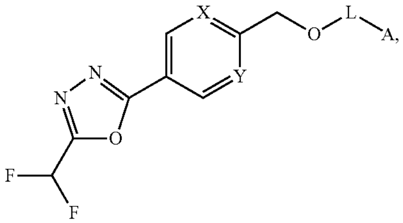

(I-b)

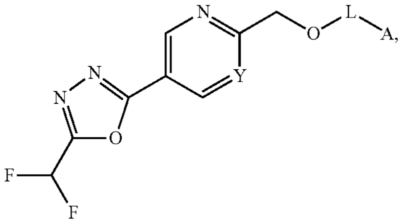

(I-c)

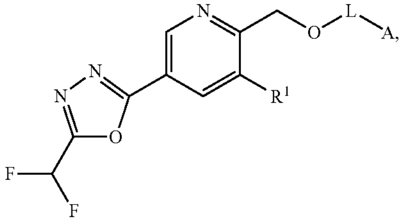

-continued (I-d)

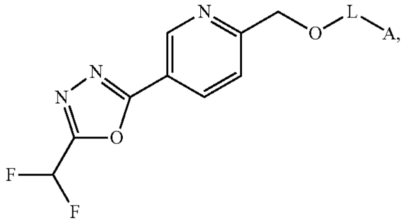

(I-e)

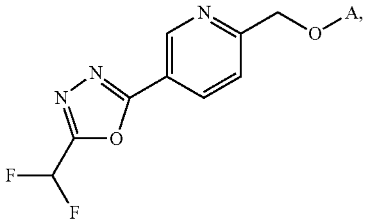

(I-f)

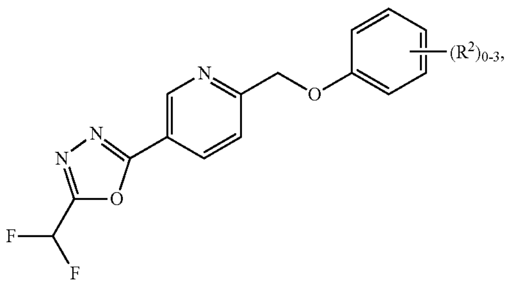

(I-f-1)

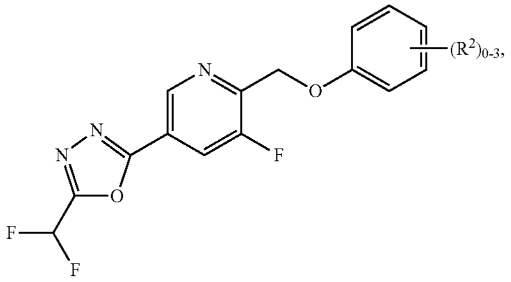

(I-f-2)

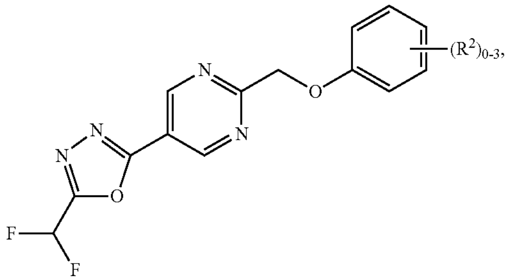

-continued
(I-g)
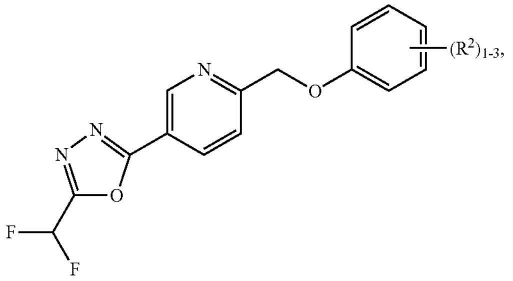
(I-g-1)
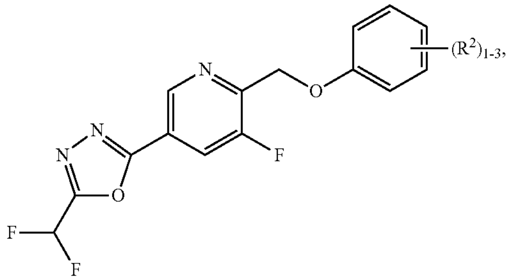
(I-g-2)
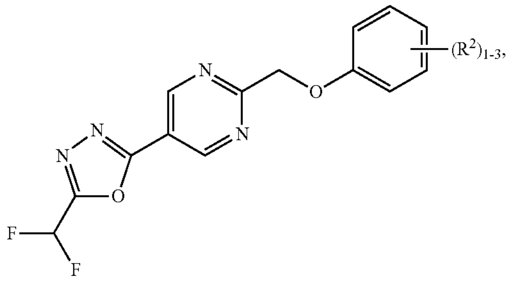
(I-h)
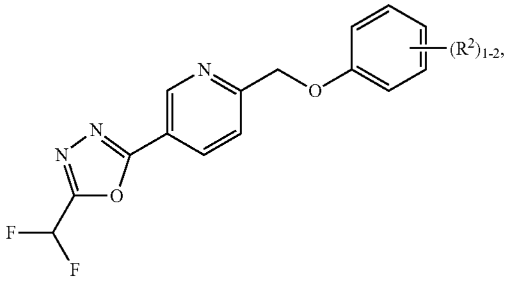
(I-h-1)
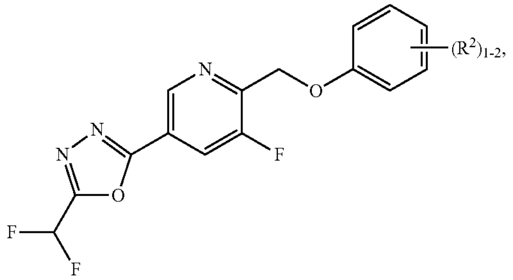
-continued
(I-h-2)
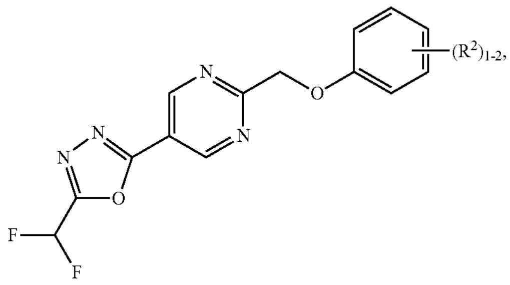
(I-i)
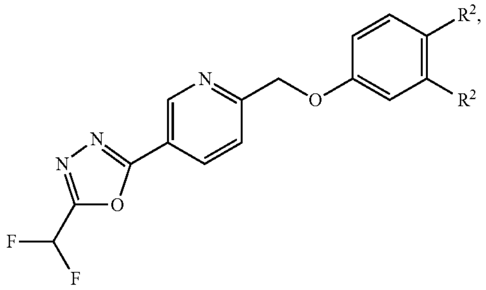
(I-i-1)
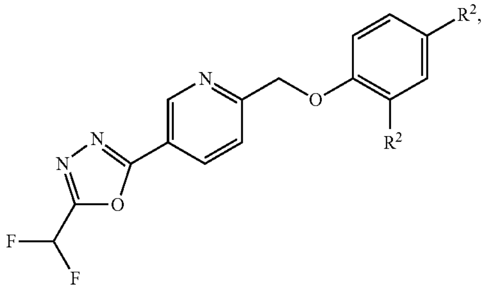
(I-i-3)
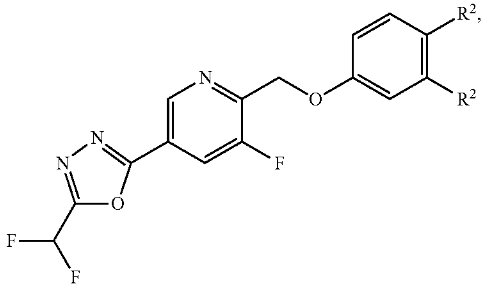
(I-i-4)
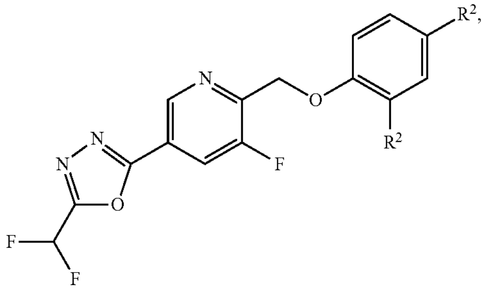

-continued (I-i-6)

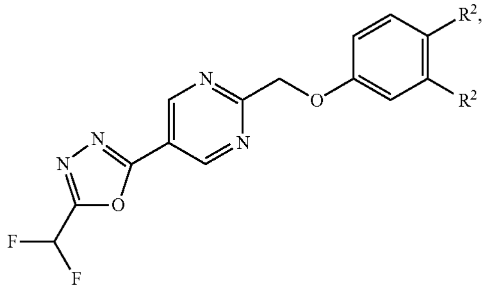

(I-i-7)

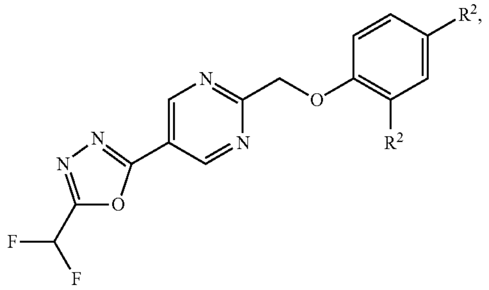

(I-j)

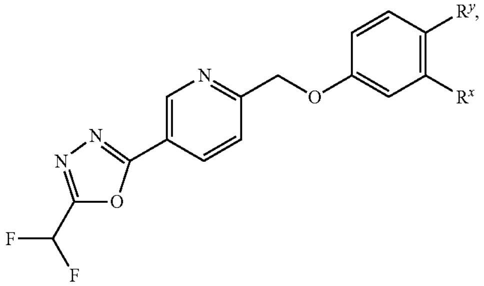

(I-j-1)

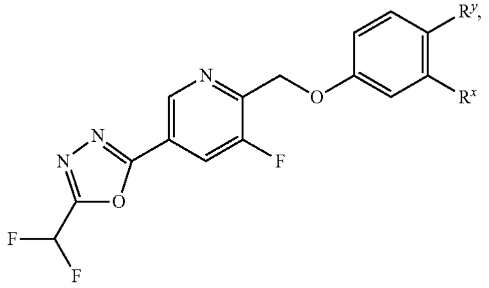

(I-j-2)

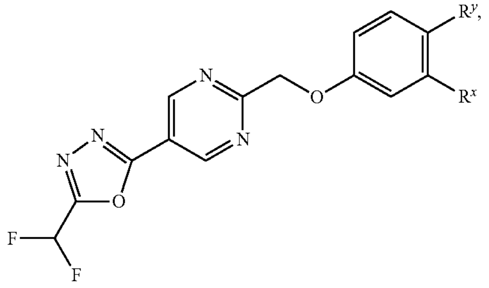

-continued (I-k)

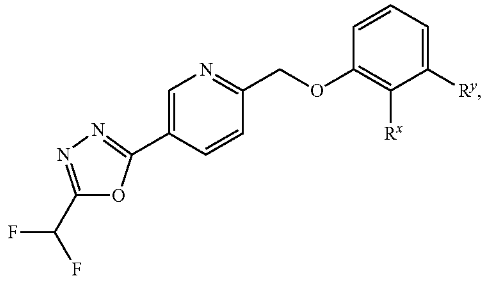

(I-k-1)

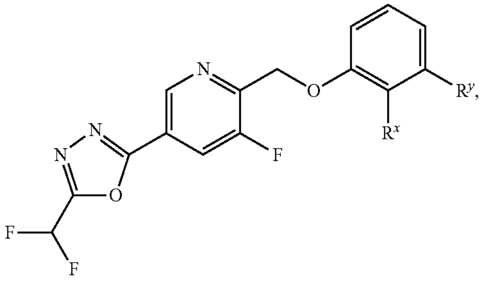

(I-k-2)

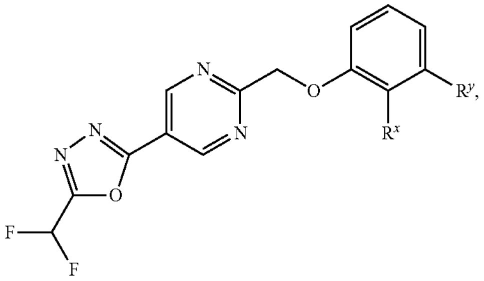

or pharmaceutically acceptable salts thereof, wherein X Y, L, A, $R^2$, $R^x$ and $R^y$ can be as defined herein with respect to Formula (I).

In another aspect, provided are pharmaceutical compositions comprising a compound of Formula (I), or a pharmaceutically acceptable salt thereof, and optionally a pharmaceutically acceptable excipient.

In another aspect, provided are methods of treating a neurological or peripheral disease or disorder in a subject in need thereof, the method comprising administering a compound of Formula (I), or a pharmaceutically acceptable salt thereof, or a pharmaceutical composition comprising a compound of Formula (I), to the subject.

In certain embodiments, the neurological disease or disorder being treated using a compound or composition described herein is a neurodegenerative, neurodevelopmental, neuropsychiatric, or neuropathy disease. In certain embodiments, the neurological disease or disorder is Alzheimer's disease, Fragile-X syndrome, Charcot-Marie-Tooth disease, Parkinson's disease, Huntington's disease, multiple sclerosis, amyotrophic lateral sclerosis, Rett Syndrome, major depressive disorder, chemotherapy-induced cognitive dysfunction, traumatic brain injury (TBI), chronic traumatic encephalopathy (CTE), brain cancer, or a tauopathy such as frontotemporal dementia, progressive supranuclear palsy, or corticobasal degeneration. In certain embodiments, the peripheral disease or disorder is chemotherapy-induced peripheral neuropathy, diabetic peripheral neuropathy, peripheral neuropathy, diabetic retinopathy, obesity, autosomal dominant polycystic kidney disease, cardiomyopathy, an auto-immune disease such as systemic lupus erythematosus (SLE), or cancer.

In another aspect, provided are methods of inhibiting the activity of HDAC6, the method comprising contacting HDAC6 with a compound of Formula (I), or a pharmaceutically acceptable salt thereof. In certain embodiments, inhibiting the activity of HDAC6 comprises selectively inhibiting the activity of HDAC6 over the activity of HDAC8. In certain embodiments, the HDAC6 is in a cell (e.g., a human cell). In certain embodiments, the inhibiting of the activity of HDAC6 takes place in vitro. In certain embodiments, the inhibiting of the activity of HDAC6 takes place in vivo.

In another aspect, provided are kits comprising a compound of Formula (I), or a pharmaceutically acceptable salt thereof, or a pharmaceutical composition comprising a compound of Formula (I), or a pharmaceutically acceptable salt thereof. In certain embodiments, the kits further comprise instructions for administration (e.g., human administration).

The details of certain embodiments of the invention are set forth in the Detailed Description of Certain Embodiments, as described below. Other features, objects, and advantages of the invention will be apparent from the Definitions, Examples, and Claims.

Definitions

Chemical Definitions

Definitions of specific functional groups and chemical terms are described in more detail below. The chemical elements are identified in accordance with the Periodic Table of the Elements, CAS version, *Handbook of Chemistry and Physics,* 75$^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March, *March's Advanced Organic Chemistry,* 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis,* 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., Enantiomers, Racemates and Resolutions (Wiley Interscience, New York, 1981); Wilen et al., Tetrahedron 33:2725 (1977); Eliel, E. L. Stereochemistry of Carbon Compounds (McGraw-Hill, NY, 1962); and Wilen, S. H., Tables of Resolving Agents and Optical Resolutions p. 268 (E. L. Eliel, Ed., Univ. of Notre Dame Press, Notre Dame, IN 1972). The invention additionally encompasses compounds as individual isomers substantially free of other isomers, and alternatively, as mixtures of various isomers.

In a formula,  is a single bond where the stereochemistry of the moieties immediately attached thereto is not specified,  is absent or a single bond, and  or  is a single or double bond.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{18}F$, or the replacement of $^{12}C$ with $^{13}C$ or $^{14}C$ are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., $-CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., $-CF_3$, Bn).

The term "haloalkyl" is a substituted alkyl group, wherein one or more of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). Examples of haloalkyl groups include —$CHF_2$, —$CH_2F$, —$CF_3$, —$CH_2CF_3$, —$CF_2CF_3$, —$CF_2CF_2CF_3$, —$CCl_3$, —$CFCl_2$, —$CF_2Cl$, and the like.

The term "alkoxy" refers to an alkyl group, as defined herein, appended to the parent molecular moiety through an oxygen atom. In some embodiments, the alkoxy moiety has 1 to 8 carbon atoms ("$C_{1-8}$ alkoxy"). In some embodiments, the alkoxy moiety has 1 to 6 carbon atoms ("$C_{1-6}$ alkoxy"). In some embodiments, the alkoxy moiety has 1 to 4 carbon atoms ("$C_{1-4}$ alkoxy"). In some embodiments, the alkoxy moiety has 1 to 3 carbon atoms ("$C_{1-3}$ alkoxy"). In some embodiments, the alkoxy moiety has 1 to 2 carbon atoms ("$C_{1-2}$ alkoxy"). Representative examples of alkoxy include, but are not limited to, methoxy, ethoxy, propoxy, 2-propoxy, butoxy and tert-butoxy.

The term "alkoxyalkyl" is a substituted alkyl group, wherein one or more of the hydrogen atoms are independently replaced by an alkoxy group, as defined herein. In some embodiments, the alkoxyalkyl moiety has 1 to 8 carbon atoms ("$C_{1-8}$ alkoxyalkyl"). In some embodiments, the alkoxyalkyl moiety has 1 to 6 carbon atoms ("$C_{1-6}$ alkoxyalkyl"). In some embodiments, the alkoxyalkyl moiety has 1 to 4 carbon atoms ("$C_{1-4}$ alkoxyalkyl"). In some embodiments, the alkoxyalkyl moiety has 1 to 3 carbon atoms ("$C_{1-3}$ alkoxyalkyl"). In some embodiments, the alkoxyalkyl moiety has 1 to 2 carbon atoms ("$C_{1-2}$ alkoxyalkyl").

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 20 carbon atoms and 1 or more heteroatoms within the parent chain ("hetero$C_{1-20}$ alkyl"). In some embodiments, a heteroalkyl group is a saturated group having 1 to 18 carbon atoms and 1 or more heteroatoms within the parent chain ("hetero$C_{1-18}$ alkyl"). In some embodiments, a heteroalkyl group is a saturated group having 1 to 16 carbon atoms and 1 or more heteroatoms within the parent chain ("hetero$C_{1-16}$ alkyl"). In some embodiments, a heteroalkyl group is a saturated group having 1 to 14 carbon atoms and 1 or more heteroatoms within the parent chain ("hetero$C_{1-14}$ alkyl"). In some embodiments, a heteroalkyl group is a saturated group having 1 to 12 carbon atoms and 1 or more heteroatoms within the parent chain ("hetero$C_{1-12}$ alkyl"). In some embodiments, a heteroalkyl group is a saturated group having 1 to 10 carbon atoms and 1 or more heteroatoms within the parent chain ("hetero$C_{1-10}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, the heteroalkyl group defined herein is a partially unsaturated group having 1 or more heteroatoms within the parent chain and at least one unsaturated carbon, such as a carbonyl group. For example, a heteroalkyl group may comprise an amide or ester functionality in its parent chain such that one or more carbon atoms are unsaturated carbonyl groups. Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-20}$ alkyl. In certain embodiments, the heteroalkyl group is an unsubstituted hetero$C_{1-10}$ alkyl. In certain embodiments, the heteroalkyl group is a substituted hetero$C_{1-20}$ alkyl. In certain embodiments, the heteroalkyl group is an unsubstituted hetero$C_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C═C double bond for which the stereochemistry is not specified (e.g., —CH═$CHCH_3$ or

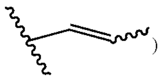

) may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl"). In some embodiments, a heteroalkenyl group has 2 to 8 carbon atoms, at least one double bond, and 1 or more heteroatoms within the parent chain ("hetero$C_{2-8}$ alkenyl"). In some embodiments, a heteroalkenyl group has 2 to 7 carbon atoms, at least one double bond, and 1 or more heteroatoms within the parent chain ("hetero$C_{2-7}$ alkenyl"). In some embodiments, a heteroalkenyl group has 2 to 6 carbon atoms, at least one double bond, and 1 or more heteroatoms within the parent chain ("hetero$C_{2-6}$ alkenyl"). In some embodiments, a heteroalkenyl group has 2 to 5 carbon atoms, at least one double bond, and 1 or 2 heteroatoms within the parent chain ("hetero$C_{2-5}$ alkenyl"). In some embodiments, a heteroalkenyl group has 2 to 4 carbon atoms, at least one double bond, and 1 or 2 heteroatoms within the parent chain ("hetero$C_{2-4}$ alkenyl"). In some embodiments, a heteroalkenyl group has 2 to 3 carbon atoms, at least one double bond, and 1 heteroatom within the parent chain ("hetero$C_{2-3}$ alkenyl"). In some embodiments, a heteroalkenyl group has 2 to 6 carbon atoms, at least one double bond, and 1 or 2 heteroatoms within the parent chain ("hetero$C_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted hetero$C_{2-10}$ alkenyl. In certain embodiments, the heteroalkenyl group is a substituted hetero$C_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("hetero$C_{2-10}$ alkynyl"). In some embodiments, a heteroalkynyl group has 2 to 9 carbon atoms, at least one triple bond, and 1 or more heteroatoms within the parent chain ("hetero$C_{2-9}$ alkynyl"). In some embodiments, a heteroalkynyl group has 2 to 8 carbon atoms, at least one triple bond, and 1 or more heteroatoms within the parent chain ("hetero$C_{2-8}$ alkynyl"). In some embodiments, a heteroalkynyl group has 2 to 7 carbon atoms, at least one triple bond, and 1 or more heteroatoms within the parent chain ("hetero$C_{2-7}$ alkynyl"). In some embodiments, a heteroalkynyl group has 2 to 6 carbon atoms, at least one triple bond, and 1 or more heteroatoms within the parent chain ("hetero$C_{2-6}$ alkynyl"). In some embodiments, a heteroalkynyl group has 2 to 5 carbon atoms, at least one triple bond, and 1 or 2 heteroatoms within the parent chain ("hetero$C_{2-5}$ alkynyl"). In some embodiments, a heteroalkynyl group has 2 to 4 carbon atoms, at least one triple bond, and 1 or 2 heteroatoms within the parent chain ("hetero$C_{2-4}$ alkynyl"). In some embodiments, a heteroalkynyl group has 2 to 3 carbon atoms, at least one triple bond, and 1 heteroatom within the parent chain ("hetero$C_{2-3}$ alkynyl"). In some embodiments, a heteroalkynyl group has 2 to 6 carbon atoms, at least one triple bond, and 1 or 2 heteroatoms within the parent chain ("hetero$C_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted hetero$C_{2-10}$ alkynyl. In certain embodiments, the heteroalkynyl group is a substituted hetero$C_{2-10}$ alkynyl.

The term "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 4 to 7 ring carbon atoms ("$C_{4-7}$ carbocyclyl"). In some embodiments, a carbocyclyl group has 4 to 8 ring carbon atoms ("$C_{4-8}$ carbocyclyl"). In some embodiments, a carbocyclyl group has 4 to 10 ring carbon atoms ("$C_{4-10}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 6-10 membered non-aromatic ring system having ring carbon atoms and 1-4 ring heteroatoms, wherein each heteroatom is independently selected from nitrogen, oxygen, and sulfur ("6-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]

pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl, and phenazinyl.

"Heteroaralkyl" is a subset of "alkyl" and refers to an alkyl group substituted by a heteroaryl group, wherein the point of attachment is on the alkyl moiety.

The term "polycyclic spiro ring system" refers to ring systems having two or more rings linked by one common atom. The common atom is known as a spiro atom. The ring systems may be fully carbocyclic (all carbon) or heterocyclic (having one or more non-carbon atom). A ring system is considered heterocyclic if the spiro atom or any atom in either ring are not carbon atoms.

The term "bridged ring system" refers to ring systems having two or more rings that contain a bridge—a single atom or an unbranched chain of atoms (or even just a valence bond) that connect two "bridgehead" atoms. The bridgehead atoms are defined as any atom that is not a hydrogen, and that is part of the skeletal framework of the molecule that is bonded to three or more other skeletal atoms. The ring systems may be fully carbocyclic (all carbon) or heterocyclic (having one or more non-carbon atoms). A ring system is considered heterocyclic if any atom is not a carbon atom.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl. As one further example, haloalkylene is the divalent moiety of haloalkyl (i.e., an alkylene group substituted with one or more halogens)

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —$NO_2$, —$N_3$, —$SO_2H$, —$SO_3H$, —OH, —$OR^{aa}$, —$ON(R^{bb})_2$, —$N(R^{bb})_2$, —$N(R^{bb})_3^+X^-$, —$N(OR^{cc})R^{bb}$, —SH, —$SR^{aa}$, —$SSR^{cc}$, —$C(=O)R^{aa}$, —$CO_2H$, —CHO, —$C(OR^{cc})_3$, —$CO_2R^{aa}$, —$OC(=O)R^{aa}$, —$OCO_2R^{aa}$, —$C(=O)N(R^{bb})_2$, —$OC(=O)N(R^{bb})_2$, —$NR^{bb}C(=O)R^{aa}$, —$NR^{bb}CO_2R^{aa}$, —$NR^{bb}C(=O)N(R^{bb})_2$, —$C(=NR^{bb})R^{aa}$, —$C(=NR^{bb})OR^{aa}$, —$OC(=NR^{bb})R^{aa}$, —$OC(=NR^{bb})OR^{aa}$, —$C(=NR^{bb})N(R^{bb})_2$, —$OC(=NR^{bb})N(R^{bb})_2$, —$NR^{bb}C(=NR^{bb})N(R^{bb})_2$, —$C(=O)NR^{bb}SO_2R^{aa}$, —$NR^{bb}SO_2R^{aa}$, —$SO_2N(R^{bb})_2$, —$SO_2R^{aa}$, —$SO_2OR^{aa}$, —$OSO_2R^{a}$, —$S(=O)R^{aa}$, —$OS(=O)R^{aa}$, —$Si(R^{aa})_3$, —$OSi(R^{aa})_3$—$C(=S)N(R^{bb})_2$, —$C(=O)SR^{aa}$, —$C(=S)SR^{aa}$, —$SC(=S)SR^{aa}$, —$SC(=O)SR^{aa}$, —$OC(=O)SR^{aa}$, —$SC(=O)OR^{aa}$, —$SC(=O)R^{aa}$, —$P(=O)(R^{aa})_2$, —$P(=O)(OR^{cc})_2$, —$OP(=O)(R^{aa})_2$, —$OP(=O)(OR^{cc})_2$, —$P(=O)(N(R^{bb})_2)_2$, —$OP(=O)(N(R^{bb})_2)_2$, —$NR^{bb}P(=O)(R^{aa})_2$, —$NR^{bb}P(=O)(OR^{cc})_2$, —$NR^{bb}P(=O)(N(R^{bb})_2)_2$, —$P(R^{cc})_2$, —$P(OR^{cc})_2$, —$P(R^{cc})_3^+X^-$, —$P(OR^{cc})_3^+X^-$, —$P(R^{cc})_4$, —$P(OR^{cc})_4$, —$OP(R^{cc})_2$, —$OP(R^{cc})_3^+X^-$, —$OP(OR^{cc})_2$, —$OP(OR^{cc})_3^+X^-$, —$OP(R^{cc})_4$, —$OP(OR^{cc})_4$, —$B(R^{aa})_2$, —$B(OR^{cc})_2$, —$BR^{aa}(OR^{cc})$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

or two geminal hydrogens on a carbon atom are replaced with the group =O, =S, =$NN(R^{bb})_2$, =$NNR^{bb}C(=O)R^{aa}$, =$NNR^{bb}C(=O)OR^{aa}$, =$NNR^{bb}S(=O)_2R^{aa}$, =$NR^{bb}$, or =$NOR^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —$OR^{aa}$, —$N(R^{cc})_2$, —CN, —$C(=O)R^{aa}$, —$C(=O)N(R^{cc})_2$, —$CO_2R^{aa}$, —$SO_2R^{aa}$, —$C(=NR^{cc})OR^{aa}$, —$C(=NR^{cc})N(R^{cc})_2$, —$SO_2N(R^{cc})_2$, —$SO_2R^{cc}$, —$SO_2OR^{cc}$, —$SOR^{aa}$, —$C(=S)N(R^{cc})_2$, —$C(=O)SR^{cc}$, —$C(=S)SR^{cc}$, —$P(=O)(R^{aa})_2$, —$P(=O)(OR^{cc})_2$, —$P(=O)(N(R^{cc})_2)_2$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —$NO_2$, —$N_3$, —$SO_2H$, —$SO_3H$, —OH, —$OR^{ee}$, —$ON(R^{ff})_2$, —$N(R^{ff})_2$, —$N(R^{ff})_3^+X^-$, —$N(OR^{ee})R^{ff}$, —SH, —$SR^{ee}$, —$SSR^{ee}$, —C(=O)$R^{ee}$, —$CO_2H$, —$CO_2R^{ee}$, —OC(=O)$R^{ee}$, —$OCO_2R^{ee}$, —C(=O)$N(R^{ff})_2$, —OC(=O)$N(R^{ff})_2$, —$NR^{ff}$C(=O)$R^{ee}$, —$NR^{ff}CO_2R^{ee}$, —$NR^{ff}$C(=O)$N(R^{ff})_2$, —C(=$NR^{ff}$)$OR^{ee}$, —OC(=$NR^{ff}$)$R^{ee}$, —OC(=$NR^{ff}$)$OR^{ee}$, —C(=$NR^{ff}$)$N(R^{ff})_2$, —OC(=$NR^{ff}$)$N(R^{ff})_2$, —$NR^{ff}$C(=$NR^{ff}$)$N(R^{ff})_2$, —$NR^{ff}SO_2R^{ee}$, —$SO_2N(R^{ff})_2$, —$SO_2R^{ee}$, —$SO_2OR^{ee}$, —$OSO_2R^{ee}$, —S(=O)$R^{ee}$, —$Si(R^{ee})_3$, —$OSi(R^{ee})_3$, —C(=S)$N(R^{ff})_2$, —C(=O)$SR^{ee}$, —C(=S)$SR^{ee}$, —SC(=S)$SR^{ee}$, —P(=O)$(OR^{ee})_2$, —P(=O)$(R^{ee})_2$, —OP(=O)$(R^{ee})_2$, —OP(=O)$(OR^{ee})_2$, $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form O or =S; wherein $X^-$ is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —$NO_2$, —$N_3$, —$SO_2H$, —$SO_3H$, —OH, —$OC_{1-6}$ alkyl, —$ON(C_{1-6}$ alkyl$)_2$, —$N(C_{1-6}$ alkyl$)_2$, —$N(C_{1-6}$ alkyl$)_3^+X^-$, —$NH(C_{1-6}$ alkyl$)_2^+X^-$, —$NH_2(C_{1-6}$alkyl$)^+X^-$, —$NH_3^+X^-$, —$N(OC_{1-6}$ alkyl$)(C_{1-6}$ alkyl), —N(OH)($C_{1-6}$ alkyl), —NH(OH), —SH, —$SC_{1-6}$ alkyl, —SS($C_{1-6}$ alkyl), —C(=O)($C_{1-6}$ alkyl), —$CO_2H$, —$CO_2(C_{1-6}$ alkyl), —OC(=O)($C_{1-6}$ alkyl), —$OCO_2(C_{1-6}$ alkyl), —C(=NH)N—C(=O)$(C_{1-6}$ alkyl$)_2$, —OC(=O)NH($C_{1-6}$alkyl), —NHC(=O)($C_{1-6}$ alkyl), —$N(C_{1-6}$ alkyl)C(=O)($C_{1-6}$ alkyl), —$NHCO_2(C_{1-6}$ alkyl), —NHC(=O)$N(C_{1-6}$ alkyl$)_2$, —NHC(=O)NH($C_{1-6}$ alkyl), —NHC(=O)$NH_2$, —C(=NH)O($C_{1-6}$ alkyl), —OC(=NH)($C_{1-6}$ alkyl), —OC(=NH)$OC_{1-6}$ alkyl, —C(=NH)$N(C_{1-6}$ alkyl$)_2$, —C(=NH)NH($C_{1-6}$ alkyl), —C(=NH)$NH_2$, —OC(=NH)$N(C_{1-6}$ alkyl$)_2$, —OC(=NH)NH($C_{1-6}$ alkyl), —OC(=NH)$NH_2$, —NHC(=NH)$N(C_{1-6}$ alkyl$)_2$, —NHC(=NH)$NH_2$, —$NHSO_2(C_{1-6}$ alkyl), —$SO_2N(C_{1-6}$ alkyl$)_2$, —$SO_2NH(C_{1-6}$ alkyl), —$SO_2NH_2$, —$SO_2(C_{1-6}$ alkyl), —$SO_2O(C_{1-6}$ alkyl), —$OSO_2(C_{1-6}$ alkyl), —SO($C_{1-6}$ alkyl), —$Si(C_{1-6}$ alkyl$)_3$, —$OSi(C_{1-6}$ alkyl$)_3$ —C(=S)$N(C_{1-6}$ alkyl$)_2$, C(=S)NH($C_{1-6}$ alkyl), C(=S)$NH_2$, —C(=O)S($C_{1-6}$ alkyl), —C(=S)$SC_{1-6}$ alkyl, —SC(=S)$SC_{1-6}$ alkyl, —P(=O)$(OC_{1-6}$ alkyl$)_2$, —P(=O)$(C_{1-6}$ alkyl$)_2$, —OP(=O)$(C_{1-6}$ alkyl$)_2$, —OP(=O)$(OC_{1-6}$ alkyl$)_2$, $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —$OR^{aa}$, —$ON(R^{bb})_2$, —OC(=O)$SR^{aa}$, —OC(=O)$R^{aa}$, —$OCO_2R^{aa}$, —OC(=O)$N(R^{bb})_2$, —OC(=$NR^{bb}$)$R^{aa}$, —OC(=$NR^{bb}$)$OR^{aa}$, —OC(=$NR^{bb}$)$N(R^{bb})_2$, —OS(=O)$R^{aa}$, —$OSO_2R^{aa}$, —$OSi(R^{aa})_3$, —$OP(R^{cc})_2$, —$OP(R^{cc})_3^+X^-$, —$OP(OR^{cc})_2$, —$OP(OR^{cc})_3^+X^-$, —OP(=O)$(R^{aa})_2$, —OP(=O)$(OR^{cc})_2$, and —OP(=O)$(N(R^{bb})_2)_2$, wherein $X^-$, $R^{aa}$, $R^{bb}$, and $R^{cc}$ are as defined herein.

The term "amino" refers to the group —$NH_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —$NH(R^{bb})$, —NHC(=O)$R^{aa}$, —$NHCO_2R^{aa}$, —NHC(=O)$N(R^{bb})_2$, —NHC(=$NR^{bb}$)$N(R^{bb})_2$, —$NHSO_2R^{aa}$, —NHP(=O)$(OR^{cc})_2$, and —NHP(=O)$(N(R^{bb})_2)_2$, wherein $R^{aa}$, $R^{bb}$ and $R^{cc}$ are as defined herein, and wherein $R^{bb}$ of the group —$NH(R^{bb})$ is not hydrogen.

The term "disubstituted amino" refers to an amino group wherein the nitrogen atom directly attached to the parent molecule is substituted with two groups other than hydrogen, and includes groups selected from —$N(R^{bb})_2$, —$NR^{bb}$C(=O)$R^{aa}$, —$NR^{bb}CO_2R^{aa}$, —$NR^{bb}$C(=O)$N(R^{bb})_2$, —$NR^{bb}$C(=$NR^{bb}$)$N(R^{bb})_2$, —$NR^{bb}SO_2R^{aa}$, —$NR^{bb}$P(=O)$(OR^{cc})_2$, and —$NR^{bb}$P(=O)$(N(R^{bb})_2)_2$, wherein $R^{aa}$, $R^{bb}$, and $R^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —$N(R^{bb})_3$ and —$N(R^{bb})_3^+X^-$, wherein $R^{bb}$ and $X^-$ are as defined herein.

The term "sulfonyl" refers to a group selected from —$SO_2N(R^{bb})_2$, —$SO_2R^{aa}$, and —$SO_2OR^{aa}$, wherein $R^{aa}$ and $R^{bb}$ are as defined herein.

The term "sulfinyl" refers to the group —S(=O)$R^{aa}$, wherein $R^{aa}$ is as defined herein.

The term "acyl" refers to a group having the general formula: —C(=O)$R^{X1}$, —C(=O)$OR^{X1}$, —C(=O)—O—C(=O)$R^{X1}$, —C(=O)$SR^{X1}$, —C(=O)$N(R^{X1})_2$, —C(=S)$R^{X1}$, —C(=S)$N(R^{X1})_2$, —C(=S)O($R^{X1}$), —C(=S)S($R^{X1}$), —C(=$NR^{X1}$)$R^{X1}$, —C(=$NR^{X1}$)$OR^{X1}$, —C(=$NR^{X1}$)$SR^{X1}$, or —C(=$NR^{X1}$)$N(R^{X1})_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken to give theher form a 5- to 6-membered heterocyclic ring. Exemplary acyl groups include aldehydes (—CHO), carboxylic acids (—$CO_2H$), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term “oxo” refers to the group ═O, and the term “thiooxo” refers to the group ═S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —$OR^{aa}$, —$N(R^{cc})_2$, —CN, —C(═O)$R^{aa}$, —C(═O)$N(R^{cc})_2$, —$CO_2R^{aa}$, —$SO_2R^{aa}$, —C(═$NR^{bb}$)$R^{aa}$, —C(═$NR^{cc}$)$OR^{aa}$, —C(═$NR^{cc}$)$N(R^{cc})_2$, —$SO_2N(R^{cc})_2$, —$SO_2R^{cc}$, —$SO_2OR^{cc}$, —$SOR^{aa}$, —C(═S)$N(R^{cc})_2$, —C(═O)$SR^{cc}$, —C(═S)$SR^{cc}$, —P(═O)$(OR^{cc})_2$, —P(═O)$(R^{aa})_2$, —P(═O)$(N(R^{cc})_2)_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein.

In certain embodiments, the substituent present on the nitrogen atom is a nitrogen protecting group (also referred to herein as an “amino protecting group”). Nitrogen protecting groups include, but are not limited to, —OH, —$OR^{aa}$, —$N(R^{cc})_2$, —C(═O)$R^{aa}$, —C(═O)$N(R^{cc})_2$, —$CO_2R^{aa}$, —$SO_2R^{aa}$, —C(═$NR^{cc}$)$R^{aa}$, —C(═$NR^{cc}$)$OR^{aa}$, —C(═$NR^{cc}$)$N(R^{cc})_2$, —$SO_2N(R^{cc})_2$, —$SO_2R^{cc}$, —$SO_2OR^{cc}$, —$SOR^{aa}$, —C(═S)$N(R^{cc})_2$, —C(═O)$SR^{cc}$, —C(═S)$SR^{cc}$, $C_{1-10}$ alkyl (e.g., aralkyl, heteroaralkyl), $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(═O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(═O)$OR^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(═O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys). In certain embodiments, a nitrogen protecting group is benzyl (Bn), tert-butyloxycarbonyl (BOC), carbobenzyloxy (Cbz), 9-fluorenylmethyloxycarbonyl (Fmoc), trifluoroacetyl, triphenylmethyl, acetyl (Ac), benzoyl (Bz), p-methoxybenzyl (PMB), 3,4-dimethoxybenzyl (DMPM), p-methoxyphenyl (PMP), 2,2,2-trichloroethyloxycarbonyl (Troc), triphenylmethyl (Tr), tosyl (Ts), brosyl (Bs), nosyl (Ns), mesyl (Ms), triflyl (Tf), or dansyl (Ds).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(═O)SR$^{aa}$, —C(═O)R$^{aa}$, —CO$_2$R$^{aa}$, —C(═O)N(R$^{bb}$)$_2$, —C(═NR$^{bb}$)R$^{aa}$, —C(═NR$^{bb}$)OR$^{aa}$, —C(═NR$^{bb}$)N(R$^{bb}$)$_2$, —S(═O)R$^{aa}$, —SO$_2$R$^{aa}$, —Si(R$^{aa}$)$_3$, —P(R$^{cc}$)$_2$, —P(R$^{cc}$)$_3^+$X$^-$, —P(OR$^{cc}$)$_2$, —P(OR$^{cc}$)$_3^+$X$^-$, —P(═O)(R$^{aa}$)$_2$, —P(═O)(OR$^{cc}$)$_2$, and —P(═O)(N(R$^{bb}$)$_2$)$_2$, wherein X$^-$, R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). In certain embodiments, an oxygen protecting group is silyl. In certain embodiments, an oxygen protecting group is t-butyldiphenylsilyl (TBDPS), t-butyldimethylsilyl (TBDMS), triisoproylsilyl (TIPS), triphenylsilyl (TPS), triethylsilyl (TES), trimethylsilyl (TMS), triisopropylsiloxymethyl (TOM), acetyl (Ac), benzoyl (Bz), allyl carbonate, 2,2,2-trichloroethyl carbonate (Troc), 2-trimethylsilylethyl carbonate, methoxymethyl (MOM), 1-ethoxyethyl (EE), 2-methyoxy-2-propyl (MOP), 2,2,2-trichloroethoxyethyl, 2-methoxyethoxymethyl (MEM), 2-trimethylsilylethoxymethyl (SEM), methylthiomethyl (MTM), tetrahydropyranyl (THP), tetrahydrofuranyl (THF), p-methoxyphenyl (PMP), triphenylmethyl (Tr), methoxytrityl (MMT), dimethoxytrityl (DMT), allyl, p-methoxybenzyl (PMB), t-butyl, benzyl (Bn), allyl, or pivaloyl (Piv).

In certain embodiments, the substituent present on a sulfur atom is a sulfur protecting group (also referred to as a "thiol protecting group"). Sulfur protecting groups include, but are not limited to, $—R^{aa}$, $—N(R^{bb})_2$, $—C(=O)SR^{aa}$, $—C(=O)R^{aa}$, $—CO_2R^{aa}$, $—C(=O)N(R^{bb})_2$, $—C(=NR^{bb})R^{aa}$, $—C(=NR^{bb})OR^{aa}$, $—C(=NR^{bb})N(R^{bb})_2$, $—S(=O)R^{aa}$, $—SO_2R^{aa}$, $—Si(R^{aa})_3$, $—P(R^{cc})_2$, $—P(R^{cc})_3^+X^−$, $—P(OR^{cc})_2$, $—P(OR^{cc})_3^+X^−$, $—P(=O)(R^{aa})_2$, $—P(=O)(OR^{cc})_2$, and $—P(=O)(N(R^{bb})_2)_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3rd edition, John Wiley & Sons, 1999, incorporated herein by reference. In certain embodiments, a sulfur protecting group is acetamidomethyl, t-Bu, 3-nitro-2-pyridine sulfenyl, 2-pyridine-sulfenyl, or triphenylmethyl.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^−$, $Cl^−$, $Br^−$, $I^−$), $NO_3^−$, $ClO_4^−$, $OH^−$, $H_2PO_4^−$, $HCO_3^−$, $HSO_4^−$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^−$, $PF_4^−$, $PF_6^−$, $AsF_6^−$, $SbF_6^−$, $B[3,5\text{-}(CF_3)_2C_6H_3]_4]^−$, $B(C_6F_5)_4^−$, $BPh_4^−$, $Al(OC(CF_3)_3)_4^−$, and carborane anions (e.g., $CB_{11}H_{12}^−$ or $(HCB_{11}Me_5Br_6)^−$). Exemplary counterions which may be multivalent include $CO_3^{2−}$, $HPO_4^{2−}$, $PO_4^{3−}$, $B_4O_7^{2−}$, $SO_4^{2−}$, $S_2O_3^{2−}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

These and other exemplary substituents are described in more detail in the Detailed Description, Examples, and Claims. The invention is not intended to be limited in any manner by the above exemplary listing of substituents.

Other Definitions

The following definitions are more general terms used throughout the present application.

As used herein, the term "salt" refers to any and all salts, and encompasses pharmaceutically acceptable salts.

The term "pharmaceutically acceptable salt" refers to those salts which are, within the scope of sound medical judgment, suitable for use in contact with the tissues of humans and/or animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences,* 1977, 66, 1-19, incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}\ alkyl)_4^−$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water molecules. Typically, the number of the water molecules contained in a hydrate of a compound is in a definite ratio to the number of the compound molecules in the hydrate. Therefore, a hydrate of a compound may be represented, for example, by the general formula R·x $H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R·0.5 $H_2O$)), and polyhydrates (x is a number greater than 1, e.g., dihydrates (R·2 $H_2O$) and hexahydrates (R·6 $H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorph" refers to a crystalline form of a compound (or a salt, hydrate, or solvate thereof). Many compounds can adopt a variety of different crystal forms (i.e., different polymorphs). Typically, such different crystalline forms have different X-ray diffraction patterns, infrared spectra, and/or can vary in some or all properties such as melting points, density, hardness, crystal shape, optical and electrical properties, stability, solubility, and bioavailability. Recrystallization solvent, rate of crystallization, storage temperature, and other factors may cause one crystal form to dominate a given preparation. Various polymorphs of a compound can be prepared by crystallization under different conditions.

The term "co-crystal" refers to a crystalline structure composed of at least two components. In certain embodiments, a co-crystal contains a compound of the present disclosure and one or more other component(s), including, but not limited to, atoms, ions, molecules, or solvent molecules. In certain embodiments, a co-crystal contains a compound of the present disclosure and one or more solvent molecules. In certain embodiments, a co-crystal contains a compound of the present disclosure and one or more acid or base. In certain embodiments, a co-crystal contains a compound of the present disclosure and one or more components related to said compound, including, but not limited to, an isomer, tautomer, salt, solvate, hydrate, synthetic precursor, synthetic derivative, fragment, or impurity of said compound.

The term "prodrugs" refers to compounds that have cleavable groups that are removed, by solvolysis or under physiological conditions, to provide the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_{1-8}$ alkyl, $C_{2-8}$ alkenyl, $C_{2-8}$ alkynyl, aryl, $C_{7-12}$ substituted aryl, and $C_{7-12}$ arylalkyl esters of the compounds described herein may be preferred.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. The term "patient" refers to a human subject in need of treatment of a disease. The subject may also be a plant. In certain embodiments, the plant is a land plant. In certain embodiments, the plant is a non-vascular land plant. In certain embodiments, the plant is a vascular land plant. In certain embodiments, the plant is a seed plant. In certain embodiments, the plant is a cultivated plant. In certain embodiments, the plant is a dicot. In certain embodiments, the plant is a monocot. In certain embodiments, the plant is a flowering plant. In some embodiments, the plant is a cereal plant, e.g., maize, corn, wheat, rice, oat, barley, rye, or millet. In some embodiments, the plant is a legume, e.g., a bean plant, e.g., soybean plant. In some embodiments, the plant is a tree or shrub.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms). Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. For example, in treating cancer, an effective amount of an inventive composition may prevent tumor regrowth, reduce the tumor burden, or stop the growth or spread of a tumor. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent. In certain embodiments, a therapeutically effective amount is an amount sufficient for HDAC6 inhibition (e.g., at least 5%, at least 10%, at least 20%, at least 30%, at least 40%, at least 50%, at least 60%, at least 70%, at least 80%, at least 90%, at least 95%, or at least 99% inhibition of the activity of HDAC6). In certain embodiments, a therapeutically effective amount is an amount sufficient for treating a disease or disorder (e.g., neurological disorder, cancer). In certain embodiments, a therapeutically effective amount is an amount sufficient for HDAC6 inhibition and treating a disease or disorder (e.g., neurological disorder, cancer).

A "prophylactically effective amount" of a compound described herein is an amount sufficient to prevent a condition, or one or more signs or symptoms associated with the condition, or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent. In certain embodiments, a prophylactically effective amount is an amount sufficient for HDAC6 inhibition. In certain embodiments, a prophylactically effective amount is an amount sufficient for treating a disease or disorder (e.g., neurological disorder, cancer). In certain embodiments, a prophylactically effective amount is an amount sufficient for HDAC6 inhibition and treating a disease or disorder (e.g., neurological disorder, cancer).

As used herein, the term "inhibit" or "inhibition" in the context of enzymes, for example, in the context of HDAC6, refers to a reduction in the activity of the enzyme. In some embodiments, the term refers to a reduction of the level of enzyme activity, e.g., HDAC6 activity, to a level that is statistically significantly lower than an initial level, which may, for example, be a baseline level of enzyme activity. In some embodiments, the term refers to a reduction of the level of enzyme activity, e.g., HDAC6 activity, to a level that is less than 75%, less than 50%, less than 40%, less than 30%, less than 25%, less than 20%, less than 10%, less than 9%, less than 8%, less than 7%, less than 6%, less than 5%, less than 4%, less than 3%, less than 2%, less than 1%, less than 0.5%, less than 0.1%, less than 0.01%, less than 0.001%, or less than 0.0001% of an initial level, which may, for example, be a baseline level of enzyme activity.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as matrix metalloproteinases (e.g., collagenases, gelatinases, and elastases); or 4) pathological angiogenesis as in proliferative retinopathy and tumor metastasis. Exemplary proliferative diseases include cancers (i.e., "malignant neoplasms"), benign neoplasms, angiogenesis or diseases associated with angiogenesis, inflammatory diseases, autoinflammatory diseases, and autoimmune diseases.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An example of a pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites.

The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a malignant neoplasm (*Stedman's Medical Dictionary,* 25th ed.; Hensyl ed.; Williams & Wilkins: Philadelphia, 1990). Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematological cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic adenocarcinoma, intraductal papillary mucinous neoplasm (IPMN), Islet cell tumors); penile cancer (e.g., Pagive the's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Pagive the's disease of the vulva).

The term "immunotherapy" refers to a therapeutic agent that promotes the treatment of disease by inducing, enhancing, or suppressing an immune response. Immunotherapies designed to elicit or amplify an immune response are classified as activation immunotherapies, while immunotherapies that reduce or suppress are classified as suppression immunotherapies. Immunotherapies are typically, but not always, biotherapeutic agents. Numerous immunotherapies are used to treat cancer. These include, but are not limited to, monoclonal antibodies, adoptive cell transfer, cytokines, chemokines, vaccines, and small molecule inhibitors.

The terms "biologic," "biologic drug," and "biological product" refer to a wide range of products such as vaccines, blood and blood components, allergenics, somatic cells, gene therapy, tissues, nucleic acids, and proteins. Biologics may include sugars, proteins, or nucleic acids, or complex combinations of these substances, or may be living entities, such as cells and tissues. Biologics may be isolated from a variety of natural sources (e.g., human, animal, microorganism) and may be produced by biotechnological methods and other technologies.

The term "small molecule" or "small molecule therapeutic" refers to molecules, whether naturally occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than about 1,000 g/mol, not more than about 900 g/mol, not more than about 800 g/mol, not more than about 700 g/mol, not more than about 600 g/mol, not more than about 500 g/mol, not more than about 400 g/mol, not more than about 300 g/mol, not more than about 200 g/mol, or not more than about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and not more than about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention.

The term "therapeutic agent" refers to any substance having therapeutic properties that produce a desired, usually beneficial, effect. For example, therapeutic agents may treat, ameliorate, and/or prevent disease. Therapeutic agents, as disclosed herein, may be biologics or small molecule therapeutics, or combinations thereof.

The term "chemotherapeutic agent" refers to a therapeutic agent known to be of use in chemotherapy for cancer.

A "hematological cancer" includes a cancer which affects a hematopoietic cell or tissue. Hematological cancers include cancers associated with aberrant hematological content and/or function. Examples of hematological cancers include, but are nor limited to, leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), chronic lymphocytic leukemia (CLL) (e.g., B-cell CLL, T-cell CLL)), lymphoma such as Hodgkin's lymphoma (HL) (e.g., B-cell HL, T-cell HL), non-Hodgkin's lymphoma (NHL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma, primary central nervous system (CNS) lymphoma, T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma), a mixture of one or more leukemia/lymphoma as described above, multiple myeloma, heavy chain disease (e.g., alpha chain disease, gamma chain disease, mu chain disease) acute non-lymphocytic leukemia (ANLL), acute promyelocytic leukemia (APL), acute myelomonocytic leukemia (AMMoL), polycythemia vera, Wilm's tumor, and Ewing's sarcoma.

The term "heteroimmune disease" refers to a state in which an immune response to an exogenous antigen (e.g., drug, pathogen) results in immunopathological changes. The immune response is triggered by an antigen from a different species (heteroimmune), thus it differs from an infectious disease because the emphasis is on the immune response, not the foreign species (infectious pathogen) causing the disease.

DETAILED DESCRIPTION OF CERTAIN EMBODIMENTS

Provided herein are compounds that are HDAC inhibitors (e.g., HDAC6 inhibitors). The compounds described herein possess advantageous properties, such as selective inhibition of HDAC6 and/or the ability to cross the blood-brain-barrier, that allow the compounds to be useful as therapeutic agents. In one aspect, the provided HDAC6 inhibitors are compounds of Formula (I), and pharmaceutically acceptable salts, solvates, hydrates, polymorphs, co-crystals, tautomers, stereoisomers, isotopically labeled derivatives, prodrugs, and pharmaceutical compositions thereof. Accordingly, the compounds are useful for the treatment and/or prevention of diseases and disorders associated with HDAC6 activity (e.g., neurological disorder or disease, or peripheral disease or disorder) in a subject in need thereof.

The compounds described herein interact with HDAC6. As described herein, the therapeutic effect may be a result of inhibition, modulation, binding, and/or modification of HDAC6 by the compounds described herein. The compounds may be provided for use in any composition, kit, or method described herein as a pharmaceutically acceptable salt, co-crystal, tautomer, stereoisomer, solvate, hydrate, polymorph, isotopically enriched derivative, or prodrug thereof.

Compounds of Formula (I)

In one aspect, disclosed is a compound of Formula (I):

(I)

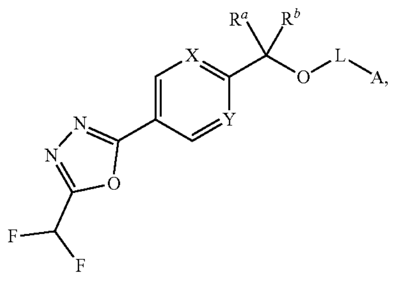

or a pharmaceutically acceptable salt, co-crystal, tautomer, stereoisomer, solvate, hydrate, polymorph, isotopically enriched derivative, or prodrug thereof, wherein:

X is $CR^1$ or N, and Y is $CR^1$ or N, provided that at least one of X and Y is N;

$R^a$ and $R^b$ are each independently hydrogen or halogen;

L is a bond or $C_{1-4}$ alkylene optionally substituted with one or more halogen;

A is aryl, heteroaryl, carbocyclyl, or heterocyclyl, wherein A is optionally substituted with one or more substituents $R^2$;

$R^1$ is hydrogen or halogen;

each occurrence of $R^2$ is independently halogen, substituted or unsubstituted amino, substituted or unsubstituted amido, cyano, substituted or unsubstituted acyl, substituted or unsubstituted alkyl, substituted or unsubstituted alkenyl, substituted or unsubstituted alkynyl, substituted or unsubstituted heteroaliphatic, substituted or unsubstituted carbocyclyl, substituted or unsubstituted heterocyclyl, substituted or unsubstituted aryl, or substituted or unsubstituted heteroaryl; or two occurrences of $R^2$ are joined with their intervening atoms to form substituted or unsubstituted carbocyclyl, substituted or unsubstituted heterocyclyl, substituted or unsubstituted aryl, or substituted or unsubstituted heteroaryl.

In one aspect, disclosed is a compound of Formula (I):

(I)

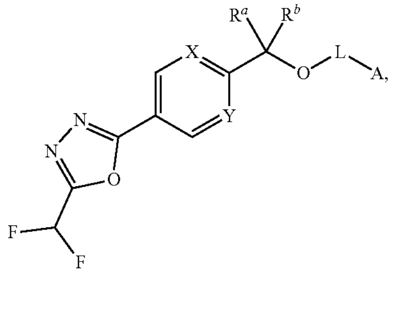

or a pharmaceutically acceptable salt, co-crystal, tautomer, stereoisomer, solvate, hydrate, polymorph, isotopically enriched derivative, or prodrug thereof, wherein:

X is $CR^1$ or N, and Y is $CR^1$ or N, provided that at least one of X and Y is N;

$R^a$ and $R^b$ are each independently hydrogen or halogen;

L is a bond or $C_{1-4}$ alkylene optionally substituted with one or more halogen;

A is aryl, heteroaryl, carbocyclyl, or heterocyclyl, wherein A is optionally substituted with one or more substituents $R^2$;

$R^1$ is hydrogen or halogen;

each occurrence of $R^2$ is independently halogen, amido, cyano, substituted or unsubstituted acyl, substituted or unsubstituted alkyl, substituted or unsubstituted alkenyl, substituted or unsubstituted alkynyl, substituted or unsubstituted heteroaliphatic, substituted or unsubstituted carbocyclyl, substituted or unsubstituted heterocyclyl, substituted or unsubstituted aryl, or substituted or unsubstituted heteroaryl; or two occurrences of $R^2$ are joined with their intervening atoms to form substituted or unsubstituted carbocyclyl, substituted or unsubstituted heterocyclyl, substituted or unsubstituted aryl, or substituted or unsubstituted heteroaryl.

In certain embodiments, compounds of Formula (I) are compounds wherein X is $CR^1$ or N, and Y is $CR^1$ or N, provided that at least one of X and Y is N; and L is a bond or $—(CH_2)—$.

In certain embodiments, compounds of Formula (I) are compounds wherein X is $CR^1$ or N and Y is $CR^1$ or N, provided that at least one of X and Y is N; L is a bond or $—(CH_2)—$; and $R^a$ and $R^b$ are each independently hydrogen or fluorine.

In certain embodiments, compounds of Formula (I) are compounds wherein X is $CR^1$ or N and Y is $CR^1$ or N, provided that at least one of X and Y is N; L is a bond or $—(CH_2)—$; $R^a$ and $R^b$ are each independently hydrogen or fluorine; and A is a $C_6$ monocyclic aryl, a bicyclic ring comprising a $C_6$ aryl or 6-membered heteroaryl fused with a $C_6$ carbocyclyl or 6-membered heterocyclyl comprising a nitrogen, oxygen or sulfur heteroatom, a $C_{10}$ bicyclic aryl, a 5-6 membered monocyclic heteroaryl comprising one or more heteroatoms selected from nitrogen, oxygen and sulfur, a 9-10 membered bicyclic heteroaryl comprising one or more nitrogen or oxygen heteroatoms (e.g., a 5,6-bicyclic heteroaryl group or a 6,6-bicyclic heteroaryl group), a $C_{4-10}$ carbocyclyl (e.g., $C_{4-7}$ monocyclic carbocyclyl or $C_{4-7}$ bridged polycyclic ring system), or a 6-10 membered heterocyclyl (e.g., 6-7 membered monocyclic heterocyclyl ring having one or more nitrogen, oxygen or sulfur heteroatoms, or a fused or bridged 7-10 membered polycyclic ring system), wherein A is optionally substituted with one or more substituents $R^2$; and each $R^2$ is independently chlorine, fluorine, —CN, $—CH_2CN$, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom. 6,6-bicyclic aryl (or ring system or group), 5,6-bicyclic heteroaryl (or ring system or group), and 6,6-bicyclic heteroaryl (or ring system or group) refer to fused ring systems (e.g., 5,6 means a 5-membered ring fused to a 6-membered ring).

In certain embodiments, the compounds of Formula (I) are compounds wherein: $R^a$ and $R^b$ are each independently hydrogen; L is a bond; $R^1$ is hydrogen or fluorine; A is a $C_6$ monocyclic aryl substituted with one or more substituents $R^2$; and each $R^2$ is independently chlorine, fluorine, —CN, —$CH_2CN$, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom.

X and Y

As described herein, X is $CR^1$ or N, and Y is $CR^1$ or N, provided that at least one of X and Y is N; and $R^1$ is hydrogen or halogen.

In certain embodiments, X is N. In certain embodiments, X is $CR^1$. In certain embodiments, X is $CR^1$; and $R^1$ is hydrogen or halogen. In certain embodiments, X is $CR^1$; and $R^1$ is hydrogen or fluoro. In certain embodiments, X is CH or CF. In certain embodiments, X is CH. In certain embodiments, X is CF.

In certain embodiments, Y is N. In certain embodiments, Y is $CR^1$. In certain embodiments, Y is $CR^1$; and $R^1$ is hydrogen or halogen. In certain embodiments, Y is $CR^1$; and $R^1$ is hydrogen or fluoro. In certain embodiments, Y is CH or CF. In certain embodiments, Y is CH. In certain embodiments, Y is CF.

In certain embodiments, at least one of X and Y is N. In certain embodiments, one of X and Y is N. In certain embodiments, X is N, and Y is $CR^1$. In certain embodiments, X is N, and Y is CH. In certain embodiments, X is N, and Y is CF. In certain embodiments, X is N, and Y is N.

In certain embodiments, Y is N, and X is $CR^1$. In certain embodiments, Y is N, and X is CH. In certain embodiments, Y is N, and X is CF. In certain embodiments, Y is N, and X is N.

$R^1$

As described herein, $R^1$ is hydrogen or halogen. In certain embodiments, $R^1$ is hydrogen or fluoro. In certain embodiments, $R^1$ is hydrogen. In certain embodiments, $R^1$ is fluoro.

$R^a$ and $R^b$

As described herein, $R^a$ and $R^b$ are each independently hydrogen or halogen. In certain embodiments, $R^a$ and $R^b$ are each independently halogen. In certain embodiments, $R^a$ and $R^b$ are each independently hydrogen or fluoro. In certain embodiments, $R^a$ and $R^b$ are each hydrogen. In certain embodiments, $R^a$ and $R^b$ are each fluoro.

In certain embodiments, $R^a$ is hydrogen or halogen, and $R^b$ is halogen. In certain embodiments, $R^a$ is hydrogen or halogen, and $R^b$ is hydrogen. In certain embodiments, $R^a$ is hydrogen, and $R^b$ is halogen. In certain embodiments, $R^a$ is hydrogen, and $R^b$ is hydrogen or halogen. In certain embodiments, $R^a$ is halogen, and $R^b$ is hydrogen or halogen. In certain embodiments, $R^a$ is halogen, and $R^b$ is hydrogen.

In certain embodiments, $R^a$ is hydrogen or fluoro, and $R^b$ is fluoro. In certain embodiments, $R^a$ is hydrogen or fluoro, and $R^b$ is hydrogen. In certain embodiments, $R^a$ is hydrogen, and $R^b$ is hydrogen or fluoro. In certain embodiments, $R^a$ is fluoro, and $R^b$ is hydrogen or fluoro.

In certain embodiments, $R^a$ is hydrogen, and $R^b$ is fluoro. In certain embodiments, $R^a$ is fluoro, and $R^b$ is hydrogen. In certain embodiments, $R^a$ is fluoro, and $R^b$ is hydrogen.

L

As described herein, L is a bond or $C_{1-4}$ alkylene optionally substituted with one or more halogen. In certain embodiments, L is a bond or $C_{1-3}$ alkylene optionally substituted with one or more halogen. In certain embodiments, L is a bond or $C_{1-2}$ alkylene optionally substituted with one or more halogen. In certain embodiments, L is a bond. In certain embodiments, L is unsubstituted methylene. In certain embodiments, L is methylene optionally substituted with one or more halogen. In certain embodiments, L is ethylene optionally substituted with one or more halogen. In certain embodiments, L is ethylene optionally substituted with one or more halogen. In certain embodiments, L is n-propylene optionally substituted with one or more halogen. In certain embodiments, L is a bond or $C_{1-2}$ alkylene optionally substituted with one or more fluoro. In certain embodiments, L is a bond or unsubstituted $C_{1-3}$ alkylene. In certain embodiments, L is a bond or unsubstituted $C_{1-2}$ alkylene. In certain embodiments, L is a bond or —$CH_2$—. In certain embodiments, L is —$CH_2$—. In certain embodiments, L is a bond when A is substituted or unsubstituted aryl or heteroaryl. In certain embodiments, L is unsubstituted methylene when A is substituted or unsubstituted carbocyclyl or heterocyclyl.

A

As described herein, A is aryl, heteroaryl, carbocyclyl, or heterocyclyl, wherein A is optionally substituted with one or more substituents $R^2$.

In certain embodiments, A is $C_{6-14}$ aryl, 5-11 membered heteroaryl, $C_{3-10}$ cycloalkyl, or 4-11 membered heterocyclyl, wherein A is optionally substituted with 1-3 independent substituents $R^2$.

In certain embodiments, A is phenyl, $C_{9-14}$ fused bicyclic aryl, 5-6 membered heteroaryl, or 9-14 membered fused bicyclic heteroaryl, wherein A is optionally substituted with 1-3 independent substituents $R^2$.

In certain embodiments, A is phenyl fused to a 5-6 membered heteroaryl, a 4-6 membered heterocyclyl, or a $C_{4-6}$ carbocyclyl ring, or A is a 5-6 membered heteroaryl fused to a phenyl, a 4-6 membered heterocyclyl, or a $C_{4-6}$ carbocyclic ring, wherein A is optionally substituted with 1-3 independent substituents $R^2$. In certain embodiments, A is phenyl fused to a 4-6 membered heterocyclyl or a $C_{4-6}$ carbocyclic ring, or A is a 5-6 membered heteroaryl fused to a 4-6 membered heterocyclyl or a $C_{4-6}$ carbocyclic ring, wherein A is optionally substituted with 1-3 independent substituents $R^2$.

In certain embodiments, A is aryl optionally substituted with 1-3 independent substituents $R^2$. In certain embodiments, A is $C_{6-14}$ aryl optionally substituted with 1-3 independent substituents $R^2$. In certain embodiments, A is phenyl or $C_{9-14}$ fused bicyclic aryl, wherein A is optionally substituted with 1-3 independent substituents $R^2$. In certain embodiments, A is phenyl or naphthyl, wherein A is optionally substituted with 1-3 independent substituents $R^2$. In certain embodiments, A is phenyl optionally substituted with 1-3 independent substituents $R^2$. In certain embodiments, A is unsubstituted phenyl. In certain embodiments, A is phenyl substituted with 1-3 independent substituents $R^2$.

In certain embodiments, A is phenyl substituted with 1-3 independent substituents $R^2$, wherein each occurrence of $R^2$ is, independently, fluoro, chloro, cyano, cyclopropyl, $C_{2-4}$ alkynyl, or $C_{1-4}$ alkyl optionally substituted with one or more fluoro, cyano, or alkynyl. In certain embodiments, A is phenyl substituted with 1-3 independent substituents $R^2$, wherein each occurrence of $R^2$ is, independently, fluoro, chloro, cyano, methyl optionally substituted with one or more fluoro, or methyl optionally substituted with a cyano. In certain embodiments, A is phenyl substituted with 1-3 independent substituents $R^2$, wherein each occurrence of $R^2$ is, independently, fluoro, chloro, cyano, methyl optionally substituted with one or more fluoro, or methyl optionally substituted with a cyano.

In certain embodiments, A is phenyl substituted with 1-2 independent substituents $R^2$, wherein each occurrence of $R^2$ is, independently, fluoro, chloro, cyano, cyclopropyl, $C_{2-4}$ alkynyl, or $C_{1-4}$ alkyl optionally substituted with one or more fluoro, cyano, or alkynyl. In certain embodiments, A is phenyl substituted with 1-2 independent substituents $R^2$, wherein each occurrence of $R^2$ is, independently, fluoro, chloro, cyano, methyl optionally substituted with one or more fluoro, or methyl optionally substituted with a cyano. In certain embodiments, A is phenyl substituted with 1-2 independent substituents $R^2$, wherein each occurrence of $R^2$ is, independently, fluoro, chloro, cyano, methyl optionally substituted with one or more fluoro, or methyl optionally substituted with a cyano.

In certain embodiments, A is

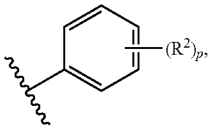

wherein p is 0, 1, 2, or 3. In certain embodiments, A is

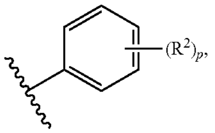

wherein p is 1, 2, or 3. In certain embodiments, A is

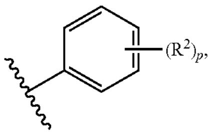

wherein p is 1 or 2. In certain embodiments, A is

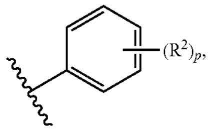

wherein p is 1. In certain embodiments, A is

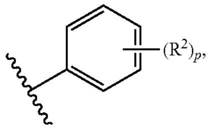

wherein p is 2. In certain embodiments, A is

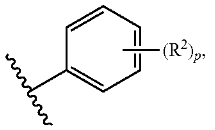

wherein p is 3.

In certain embodiments, A is

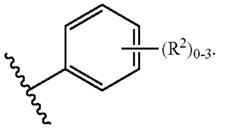

In certain embodiments, A is

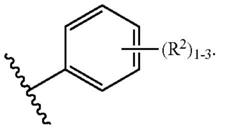

In certain embodiments, A is

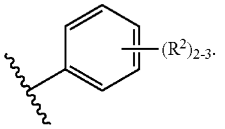

In certain embodiments, A is

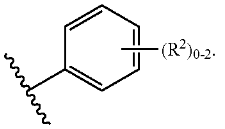

In certain embodiments, A is

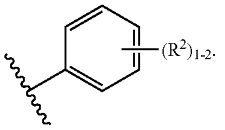

In certain embodiments, A is

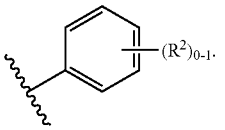

In certain embodiments, A is

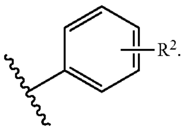

In certain embodiments, A is
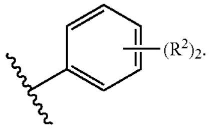
In certain embodiments, A is
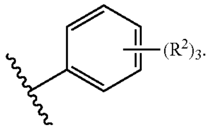
In certain embodiments, A is
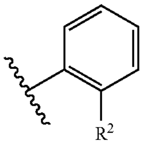
,
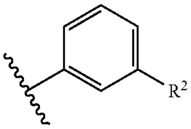
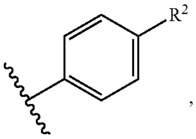
,
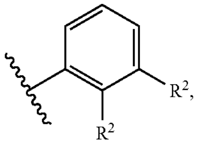
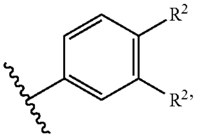
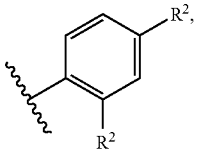
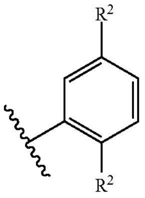
,
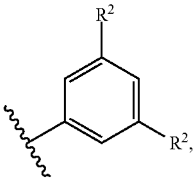
or
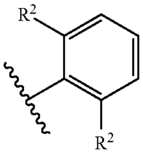
.
In certain embodiments, A is
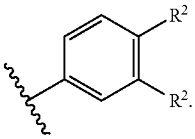
In certain embodiments, A is
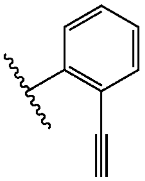
,
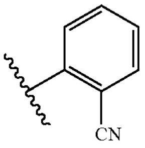
,
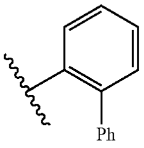
,
-continued
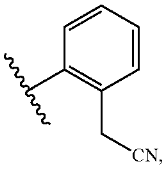
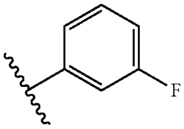
,
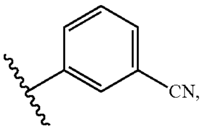
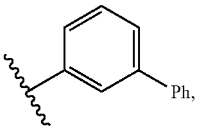
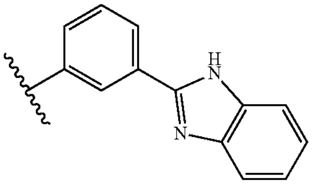
,
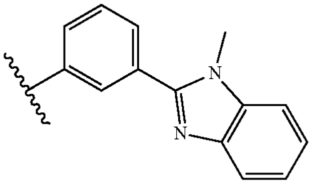
,
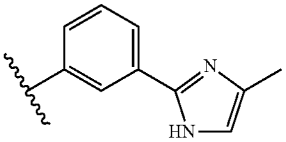
,
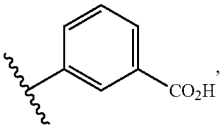
,
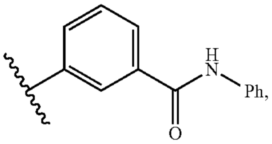
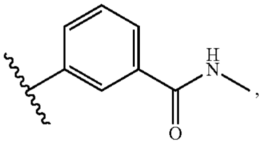
,
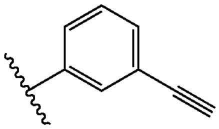
,
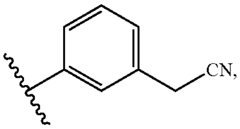
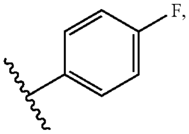
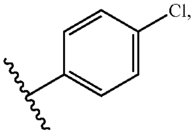
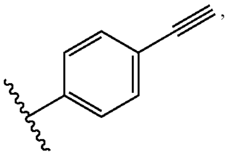
,
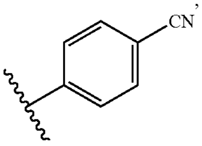
,
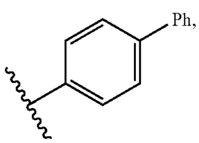
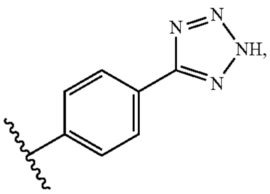

-continued
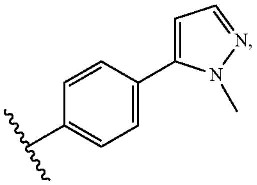
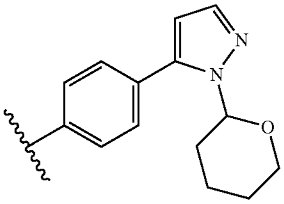
,
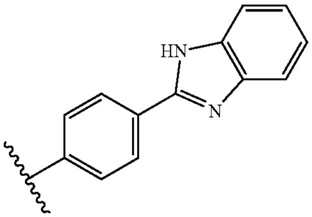
,
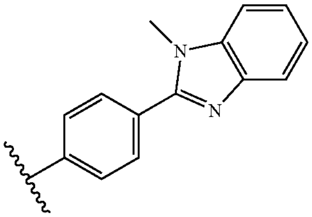
,
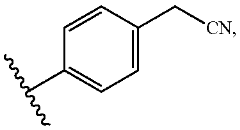
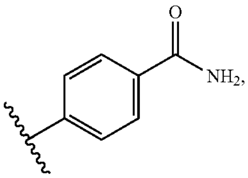
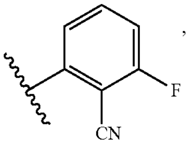
,
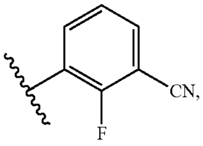
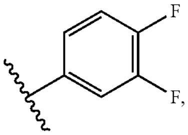
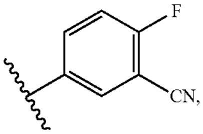
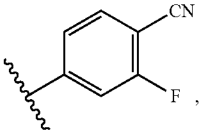
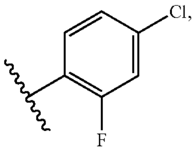
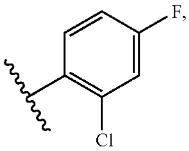
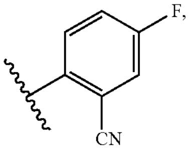
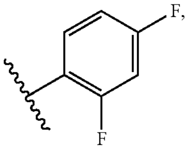
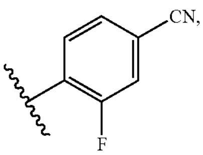
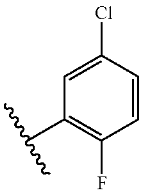
,
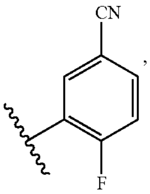
,
-continued
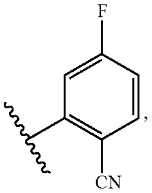
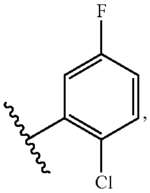
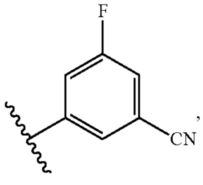
, or
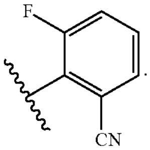
.
In certain embodiments, A is
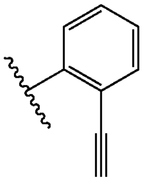
,
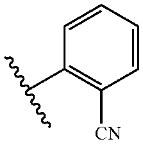
,
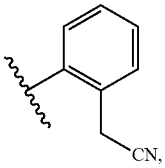
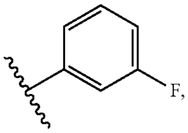
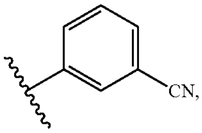
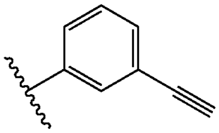
,
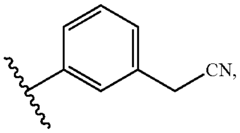
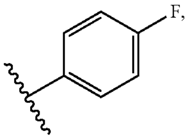
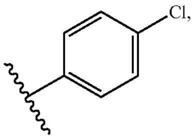
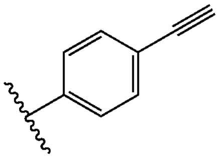
,
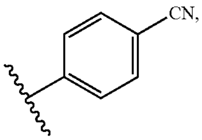
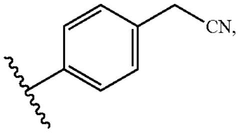
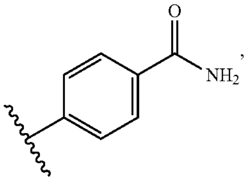
,
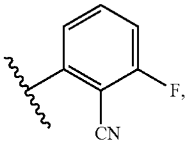
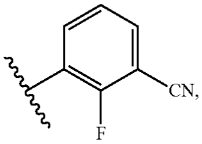
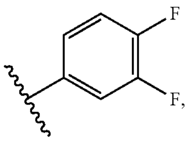
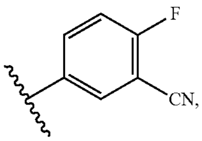

-continued

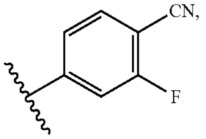
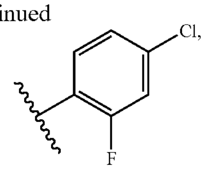
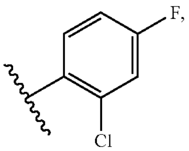
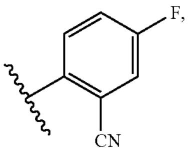
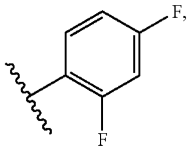
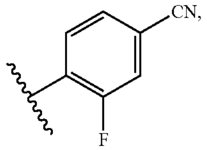
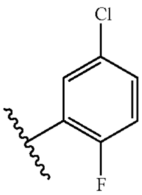
,
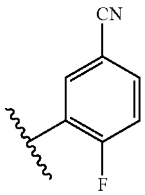
,
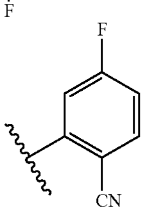
,
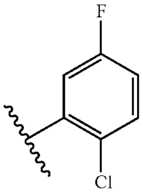
,
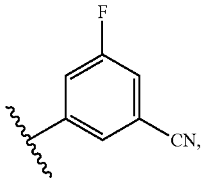
or
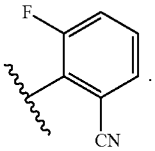

In certain embodiments, A is

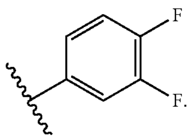 [SMILES: *c1ccc(F)c(F)c1]

In certain embodiments, A is

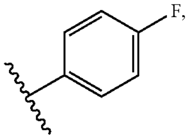
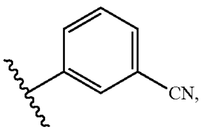
or
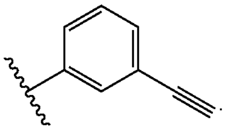

In certain embodiments, A is

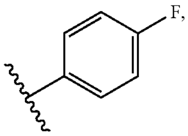
or
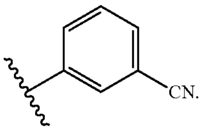

In certain embodiments, A is

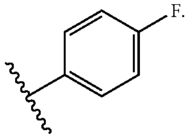 [SMILES: *c1ccc(F)cc1]

In certain embodiments, A is

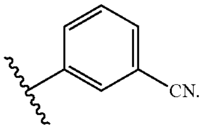

In certain embodiments, A is

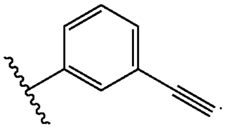 [SMILES: *c1cccc(C#C)c1]

In certain embodiments, A is $C_{9-14}$ fused bicyclic aryl, wherein A is optionally substituted with 1-3 independent substituents $R^2$. In certain embodiments, A is

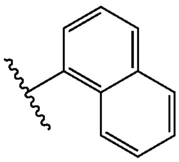
or
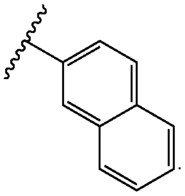

In certain embodiments, A is

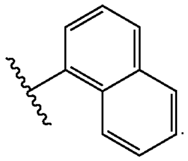 [SMILES: *c1cccc2ccccc12]

In certain embodiments, A is

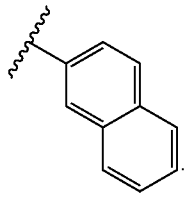 [SMILES: *c1ccc2ccccc2c1]

In certain embodiments, A is heteroaryl optionally substituted with 1-3 independent substituents $R^2$. In certain embodiments, A is 5-11 membered heteroaryl optionally substituted with 1-3 independent substituents $R^2$. In certain embodiments, A is 5-6 membered heteroaryl optionally substituted with 1-3 independent substituents $R^2$. In certain embodiments, A is monocyclic or bicyclic heteroaryl, wherein A is optionally substituted with 1-3 independent substituents $R^2$. In certain embodiments, A is bicyclic heteroaryl optionally substituted with 1-3 independent substituents $R^2$. In certain embodiments, A is 5-membered monocyclic heteroaryl optionally substituted with 1-3 independent substituents $R^2$ fused with another 5-membered monocyclic heteroaryl optionally substituted with 1-3 independent substituents $R^2$. In certain embodiments, A is 5-membered monocyclic heteroaryl optionally substituted with 1-3 independent substituents $R^2$ fused with 6-membered monocyclic heteroaryl optionally substituted with 1-3 independent substituents $R^2$, wherein the attachment point is on the 5-membered monocyclic heteroaryl. In certain embodiments, A is 6-membered monocyclic heteroaryl optionally substituted with 1-3 independent substituents $R^2$ fused with 5-membered monocyclic heteroaryl optionally substituted with 1-3 independent substituents $R^2$, wherein the attachment point is on the 6-membered monocyclic heteroaryl. In certain embodiments, A is 6-membered monocyclic heteroaryl optionally substituted with 1-3 independent substituents $R^2$ fused with another 6-membered monocyclic heteroaryl optionally substituted with 1-3 independent substituents $R^2$.

In certain embodiments, A is monocyclic heteroaryl optionally substituted with 1-3 independent substituents $R^2$. In certain embodiments, A is 5-6 membered monocyclic heteroaryl optionally substituted with 1-3 independent substituents $R^2$. In certain embodiments, A is 5-membered monocyclic heteroaryl optionally substituted with 1-3 independent substituents $R^2$. In certain embodiments, A is 6-membered monocyclic heteroaryl optionally substituted with 1-3 independent substituents $R^2$. In certain embodiments, A is pyridyl, pyrimidinyl, pyrazolyl, imidazolyl, pyrrolyl, thiophenyl, oxazolyl, thiazolyl, isoxazolyl, pyrazinyl, pyridazinyl, or oxadiazolyl, wherein A is optionally substituted with 1-3 independent substituents $R^2$. In certain embodiments, A is pyridyl, pyrimidinyl, pyrazinyl, or pyridazinyl, wherein A is optionally substituted with 1-3 independent substituents $R^2$. In certain embodiments, A is pyridyl or pyrimidinyl, wherein A is optionally substituted with 1-3 independent substituents $R^2$. In certain embodiments, A is pyridyl optionally substituted with 1-3 independent substituents $R^2$. In certain embodiments, A is 2-pyridyl, 3-pyridyl, or 4-pyridyl, wherein A is optionally substituted with 1-3 independent substituents $R^2$. In certain embodiments, A is 2-pyridyl or 3-pyridyl substituted with 1-3 independent substituents $R^2$.

In certain embodiments, A is

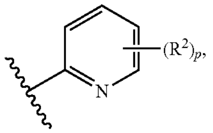

wherein p is 0, 1, 2, or 3. In certain embodiments, A is

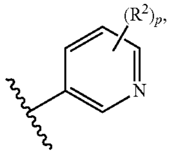

wherein p is 0, 1, 2, or 3. In certain embodiments, A is

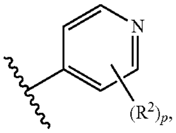

wherein p is 0, 1, 2, or 3. In certain embodiments, A is

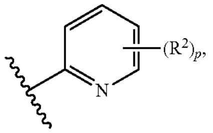

wherein p is 0 or 1. In certain embodiments, A is

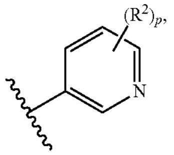

wherein p is 0 or 1. In certain embodiments, A is

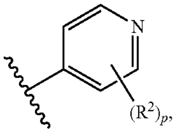

wherein p is 0 or 1.

In certain embodiments, A is pyrimidinyl optionally substituted with 1-3 independent substituents $R^2$. In certain embodiments, A is pyrimidinyl optionally substituted with 1-2 independent substituents $R^2$. In certain embodiments, A is pyrimidinyl optionally substituted with 1 substituent $R^2$.

In certain embodiments, A is
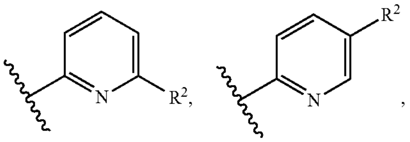
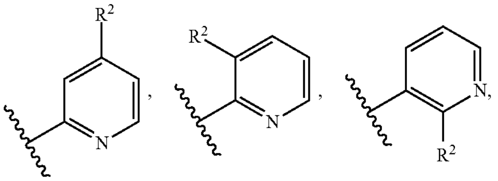
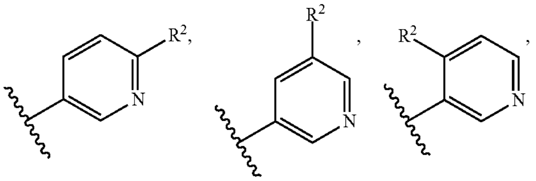
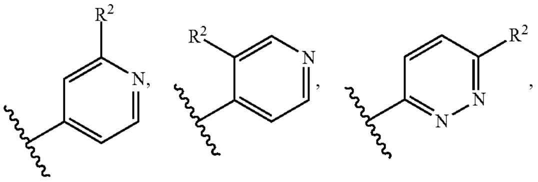
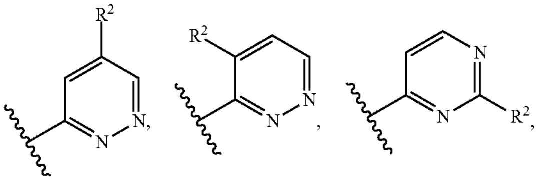
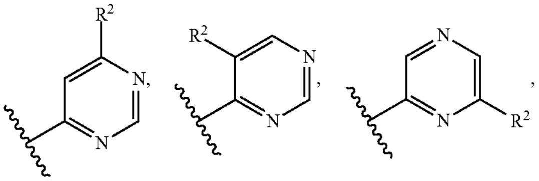
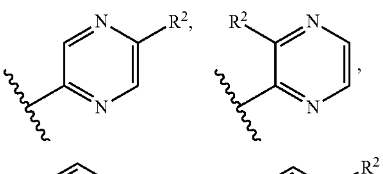
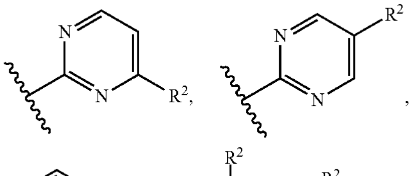
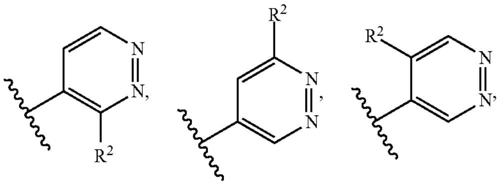
-continued
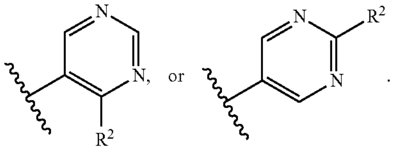
In certain embodiments, A is
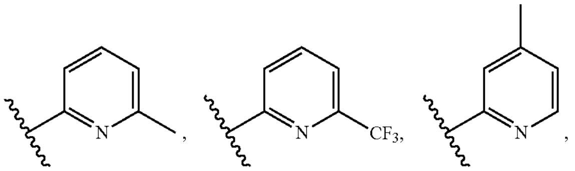
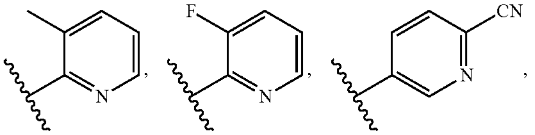
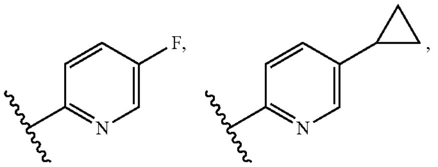
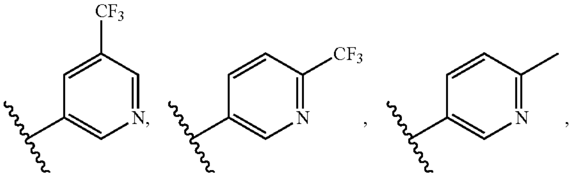
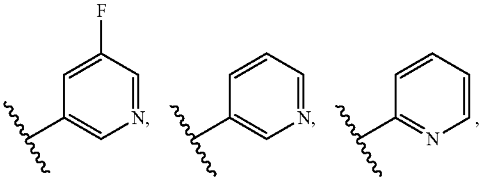
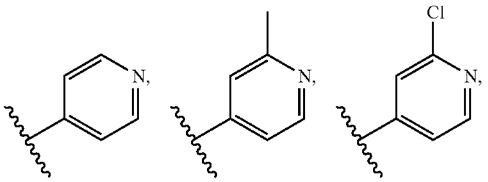
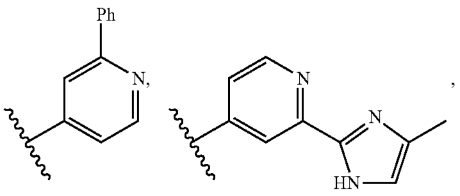
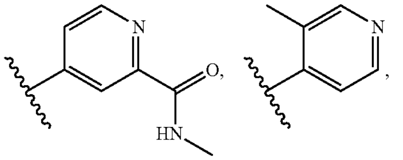

-continued
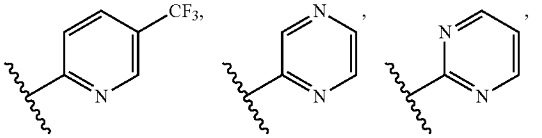
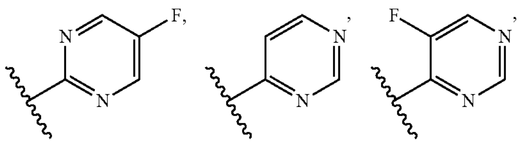
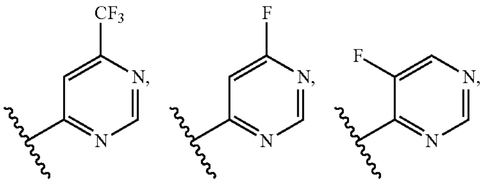
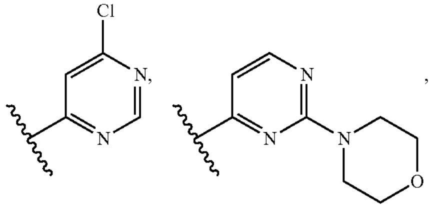
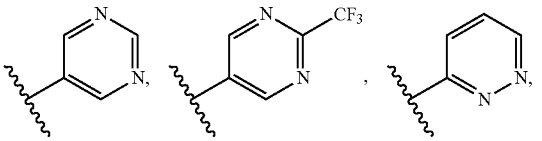
or
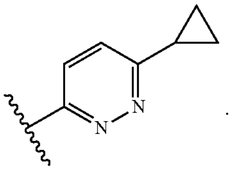
In certain embodiments, A is
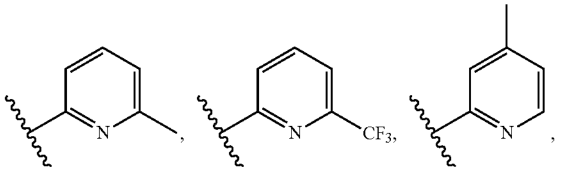
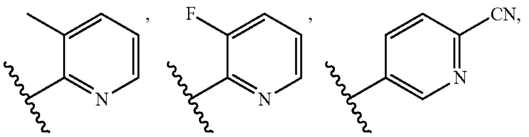
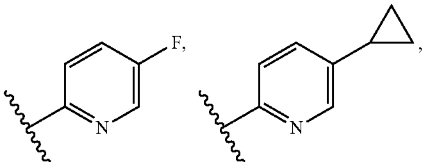
-continued
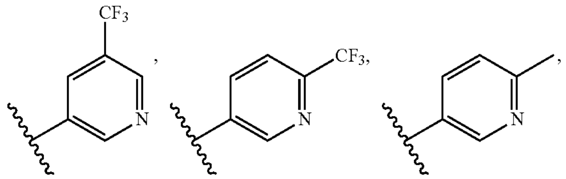
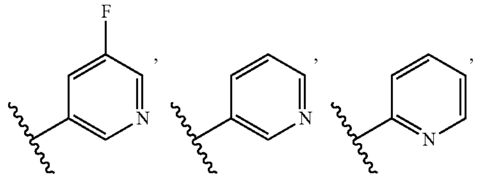
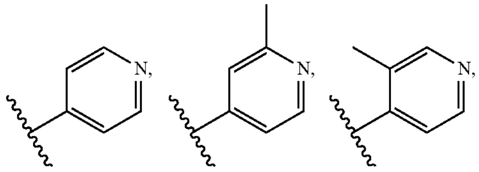
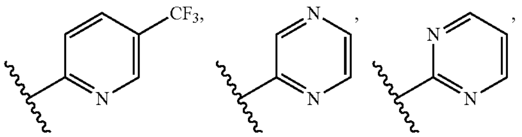
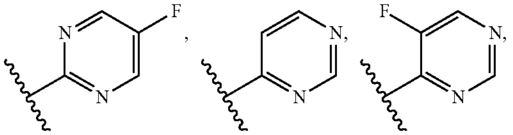
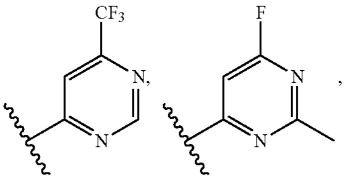
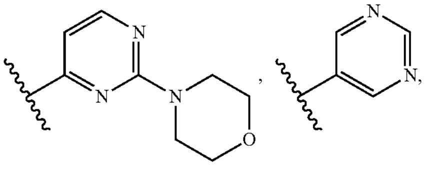
or
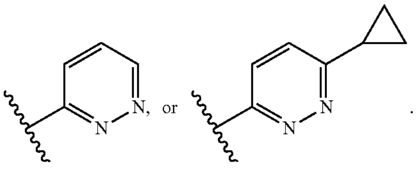
In certain embodiments, A is pyrazolyl, imidazolyl, oxazolyl, isoxazolyl, thiophenyl, or oxadiazolyl optionally substituted with 1-3 independent substituents $R^2$. In certain embodiments, A is
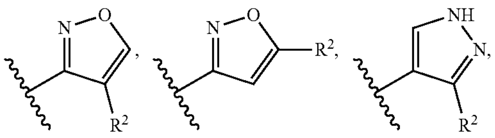

-continued

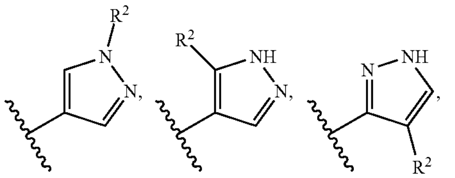

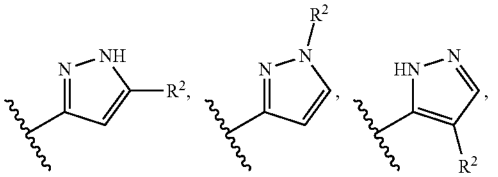

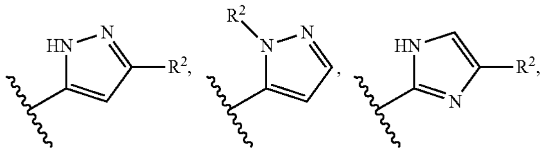

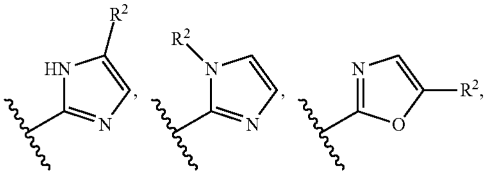

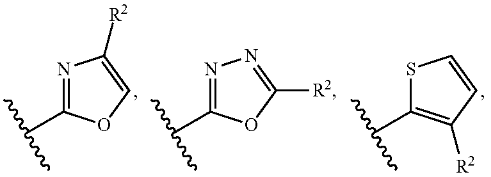

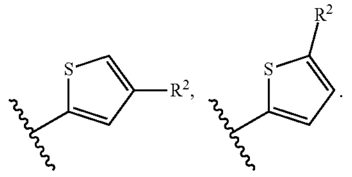

In certain embodiments, A is

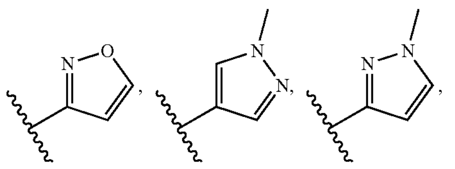

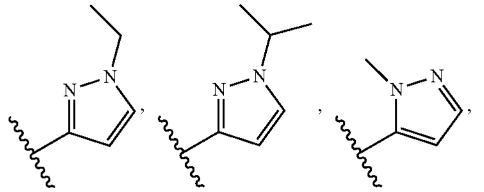

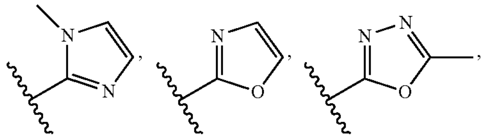

, or

-continued

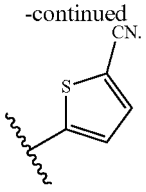

In certain embodiments, A is 9-14 membered fused bicyclic heteroaryl optionally substituted with 1-3 independent substituents $R^2$.

In certain embodiments, A is phenyl fused to a 5-6 membered heteroaryl, a 4-6 membered heterocyclyl, or a $C_{4-6}$ carbocyclyl ring, or A is a 5-6 membered heteroaryl fused to a phenyl, a 5-6 membered heteroaryl, a 4-6 membered heterocyclyl, or a $C_{4-6}$ carbocyclyl ring, wherein A is optionally substituted with 1-3 independent substituents $R^2$. In certain embodiments, A is phenyl fused to a 5-6 membered heteroaryl, a 4-6 membered heterocyclyl, or a $C_{4-6}$ carbocyclyl ring, or A is a 5-6 membered heteroaryl fused to a phenyl, a 4-6 membered heterocyclyl, or a $C_{4-6}$ carbocyclyl ring, wherein A is optionally substituted with 1-3 independent substituents $R^2$. In certain embodiments, A is phenyl fused to a 4-6 membered heterocyclyl or a $C_{4-6}$ carbocyclyl ring, or A is a 5-6 membered heteroaryl fused to a 4-6 membered heterocyclyl or a $C_{4-6}$ carbocyclic ring, wherein A is optionally substituted with 1-3 independent substituents $R^2$. In certain embodiments, A is phenyl fused to a 5-6 membered heteroaryl, wherein A is optionally substituted with 1-3 independent substituents $R^2$. In certain embodiments, A is phenyl fused to a 4-6 membered heterocyclyl, wherein A is optionally substituted with 1-3 independent substituents $R^2$. In certain embodiments, A is phenyl fused to a $C_{4-6}$ carbocyclic ring, wherein A is optionally substituted with 1-3 independent substituents $R^2$. In certain embodiments, A is a 5-6 membered heteroaryl fused to a phenyl, wherein A is optionally substituted with 1-3 independent substituents $R^2$. In certain embodiments, A is a 5-6 membered heteroaryl fused to a 4-6 membered heterocyclyl, wherein A is optionally substituted with 1-3 independent substituents $R^2$. In certain embodiments, A is a 5-6 membered heteroaryl fused to a $C_{4-6}$ carbocyclic ring, wherein A is optionally substituted with 1-3 independent substituents $R^2$.

In certain embodiments, A is benzoxazolyl, indazolyl, isoquinolinyl, tetrahydroisoquinolinyl, tetrahydroisoxazolo[4,5-c]pyridinyl, tetrahydroisoxazolo[5,4-c]pyridinyl, quinazolinyl, triazolo[4,3-a]pyridinyl, imidazo[1,2-a]pyrazinyl, imidazo[1,2-a]pyridinyl, pyrazolo[1,5-a]pyrimidinyl, [1,2,4]triazolo[4,3-a]pyridinyl, quinolinyl, benzoisoxazolyl, benzoimidazolyl, benzopyrazolyl, benzotriazolyl, indolyl, or quinoxalinyl, wherein A is optionally substituted with 1-3 independent substituents $R^2$. In certain embodiments, A is benzoxazolyl, indazolyl, isoquinolinyl, tetrahydroisoquinolinyl, quinazolinyl, triazolo[4,3-a]pyridinyl, imidazo[1,2-a]pyrazinyl, imidazo[1,2-a]pyridinyl, quinolinyl, benzoisoxazolyl, benzoimidazolyl, or quinoxalinyl, wherein A is optionally substituted with 1-3 independent substituents $R^2$. In certain embodiments, A is quinazolinyl, imidazo[1,2-a]pyrazinyl, benzoisoxazolyl, or benzopyrazolyl, wherein A is optionally substituted with 1-3 independent substituents $R^2$. In certain embodiments, A is phenyl, quinazolinyl, imidazo[1,2-a]pyrazinyl, benzoisoxazolyl, or benzopyrazolyl, wherein A is optionally substituted with 1-3 independent substituents $R^2$. In certain embodiments, A is quinazolinyl, imidazo[1,2-a]pyrazinyl, benzoisoxazolyl, or benzopyrazolyl, wherein A is optionally substituted with 1-3 independent substituents $R^2$. In certain embodiments, A is quinazolinyl, wherein A is optionally substituted with 1-3 independent substituents $R^2$. In certain embodiments, A is imidazo[1,2-a]pyrazinyl, wherein A is optionally substituted with 1-3 independent substituents $R^2$. In certain embodiments, A is benzoisoxazolyl, wherein A is optionally substituted with 1-3 independent substituents $R^2$. In certain embodiments, A is benzopyrazolyl, wherein A is optionally substituted with 1-3 independent substituents $R^2$.

In certain embodiments, A is

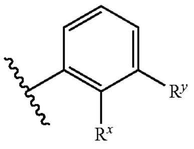 or 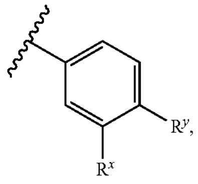, wherein $R^x$ and $R^y$ join to form a 5-6 membered heteroaryl, a 4-6 membered heterocyclyl, or a $C_{4-6}$ carbocyclyl ring, wherein A is optionally substituted with 1-3 independent substituents $R^2$. In certain embodiments, $R^2$ may be attached to the phenyl ring of A or to the 5-6 membered heteroaryl, 4-6 membered heterocyclyl, or $C_{4-6}$ carbocyclyl ring formed by joining $R^x$ and $R^y$.

In certain embodiments, A is

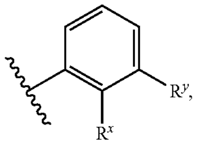, wherein $R^x$ and $R^y$ join to form a 5-6 membered heteroaryl, a 4-6 membered heterocyclyl, or a $C_{4-6}$ carbocyclyl ring, wherein A is optionally substituted with 1-3 independent substituents $R^2$. In certain embodiments, A is

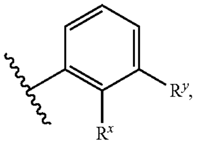, wherein $R^x$ and $R^y$ join to form a 5-6 membered heteroaryl ring, wherein A is optionally substituted with 1-3 independent substituents $R^2$. In certain embodiments, A is

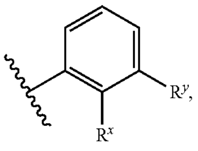, wherein $R^x$ and $R^y$ join to form a 4-6 membered heterocyclyl ring, wherein A is optionally substituted with 1-3 independent substituents $R^2$. In certain embodiments, A is

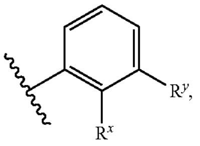, wherein $R^x$ and $R^y$ join to form a $C_{4-6}$ carbocyclyl ring, wherein A is optionally substituted with 1-3 independent substituents $R^2$.

In certain embodiments, A is

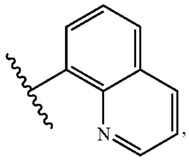, 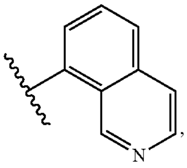, 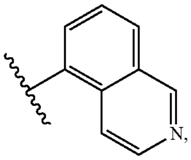, 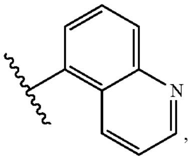, 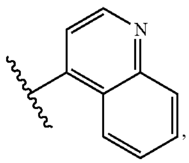, 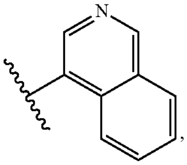, 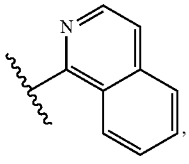, 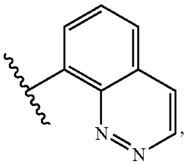, 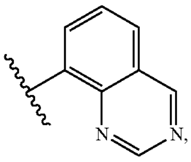, 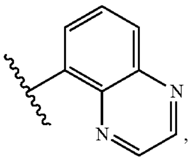, 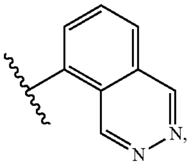, 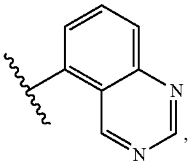, 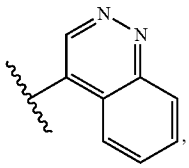, 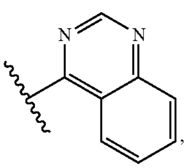, 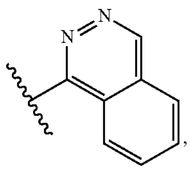, 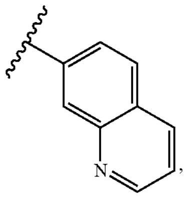, -continued
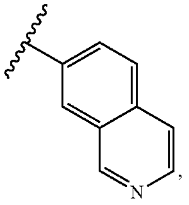 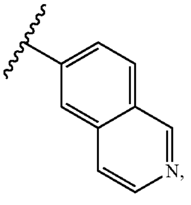
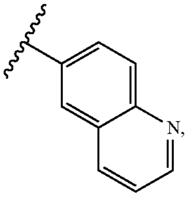 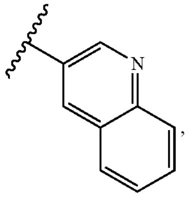
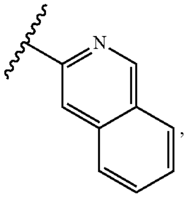 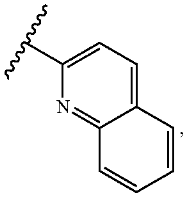
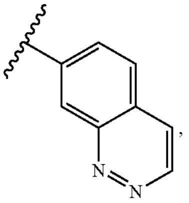 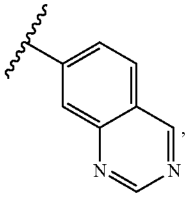
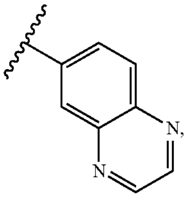 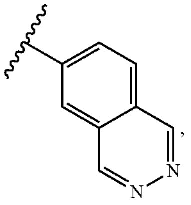
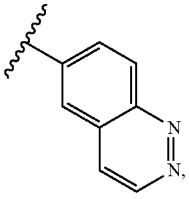 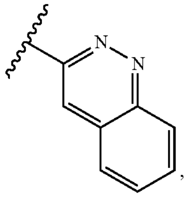
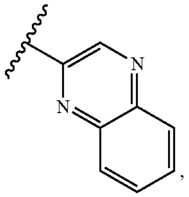 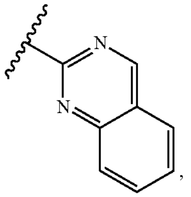
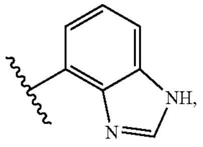 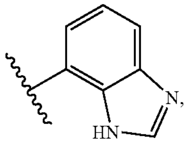
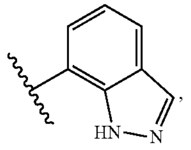 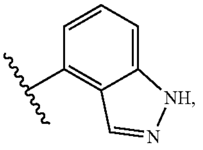
-continued
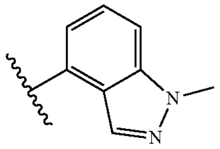 , 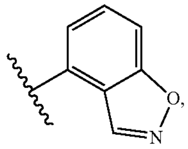
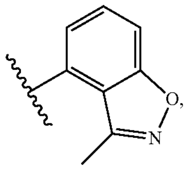 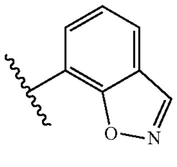 , 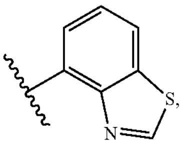
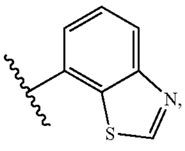 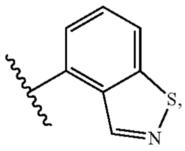 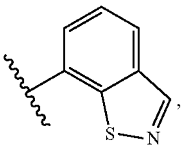
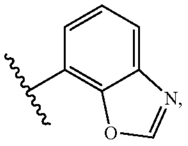 or 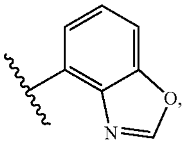
wherein A is optionally substituted with 1-3 independent substituents $R^2$.
In certain embodiments, A is
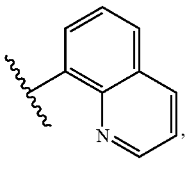 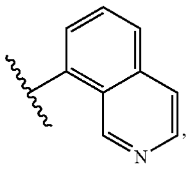
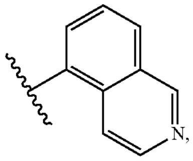 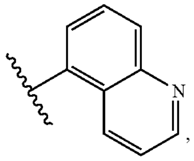
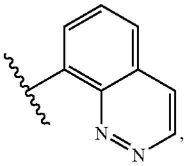 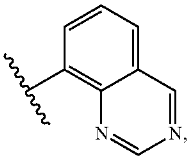
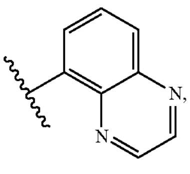 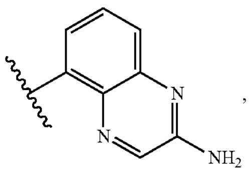
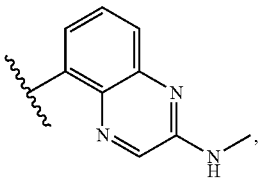 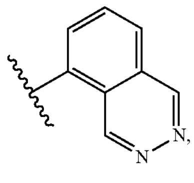

-continued

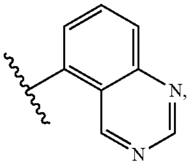, 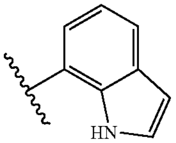, 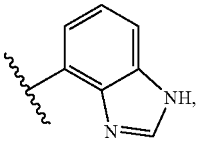, 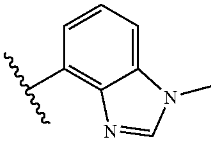, 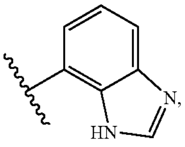, 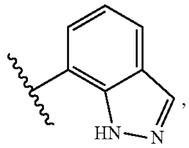, 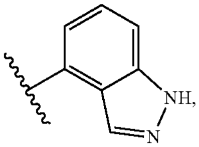, 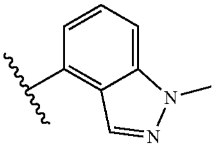, 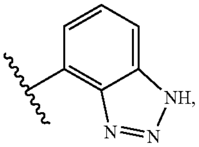, 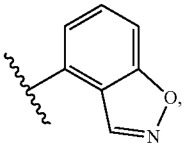, 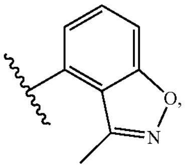, 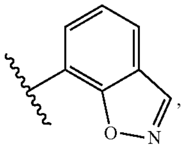, 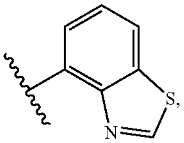, 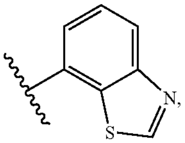, 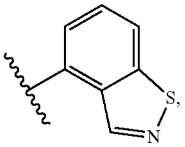, 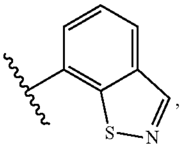, 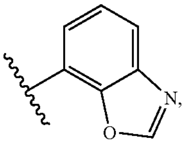, or 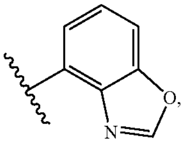, wherein A is optionally substituted with 1-3 independent substituents $R^2$. In certain embodiments, A is

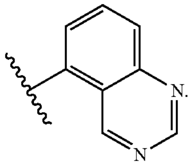 [SMILES: *c1cccc2ncncc12].

In certain embodiments, A is

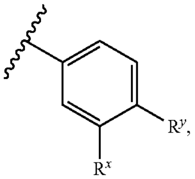, wherein $R^x$ and $R^y$ join to form a 5-6 membered heteroaryl, a 4-6 membered heterocyclyl, or a $C_{4-6}$ carbocyclyl ring, wherein A is optionally substituted with 1-3 independent substituents $R^2$. In certain embodiments, A is

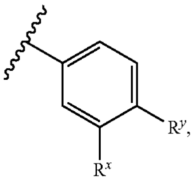, wherein $R^x$ and $R^y$ join to form a 5-6 membered heteroaryl ring, wherein A is optionally substituted with 1-3 independent substituents $R^2$. In certain embodiments, A is

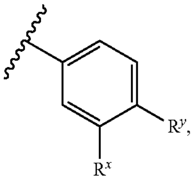, wherein $R^x$ and $R^y$ join to form a 4-6 membered heterocyclyl ring, wherein A is optionally substituted with 1-3 independent substituents $R^2$. In certain embodiments, A is

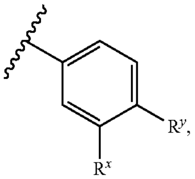, wherein $R^x$ and $R^y$ join to form a $C_{4-6}$ carbocyclyl ring, wherein A is optionally substituted with 1-3 independent substituents $R^2$. In certain embodiments, A is

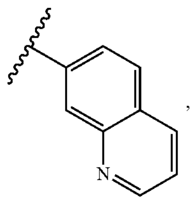, 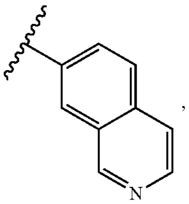,

-continued
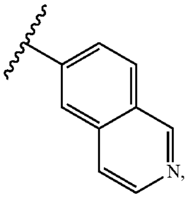
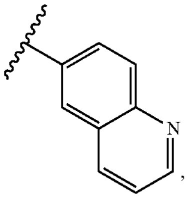
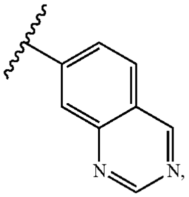
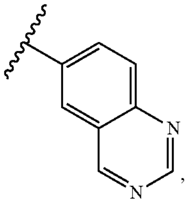
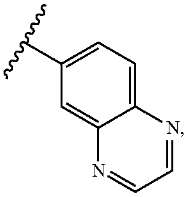
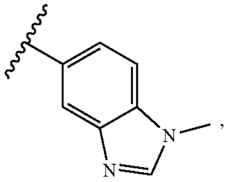
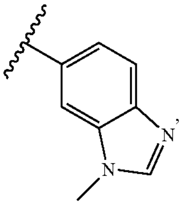
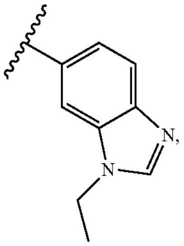
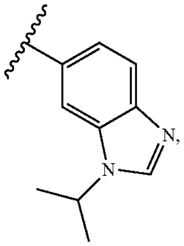
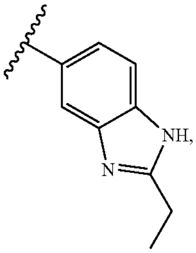
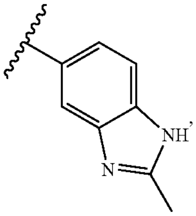
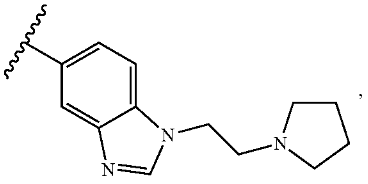
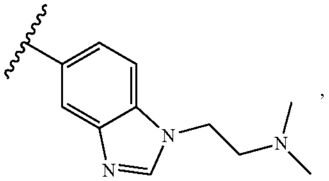
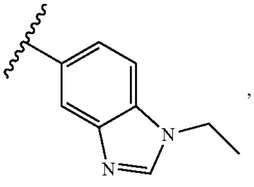
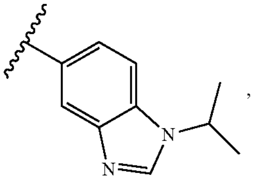
-continued
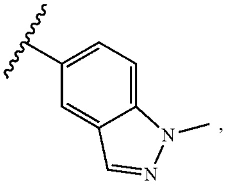
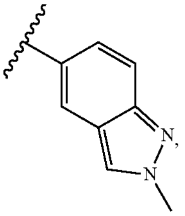
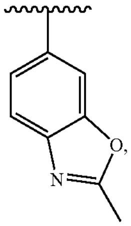
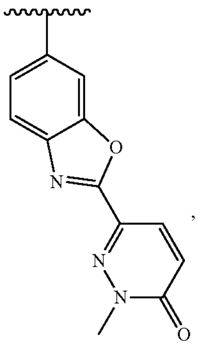
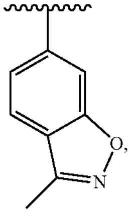
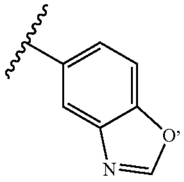
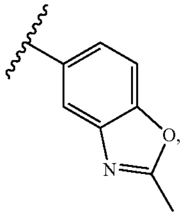
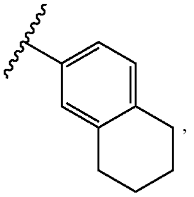
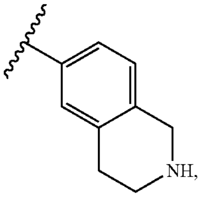
or
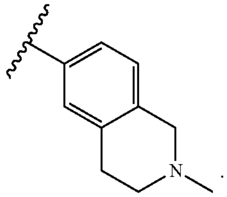
In certain embodiments, A is
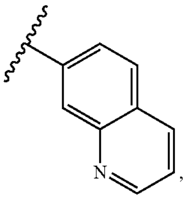
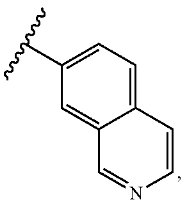
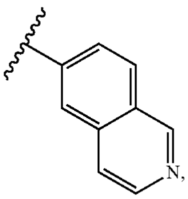
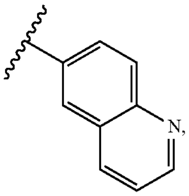
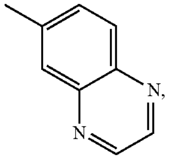
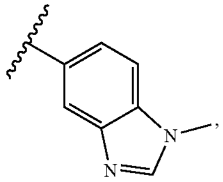
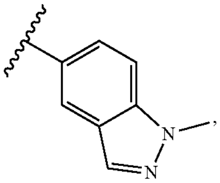

-continued
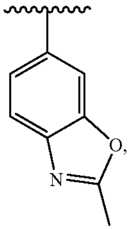
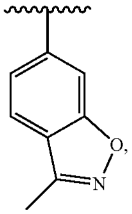
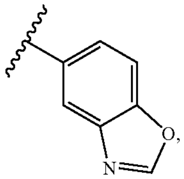
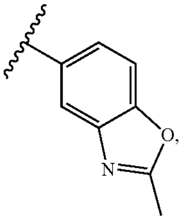
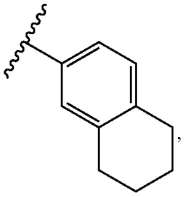
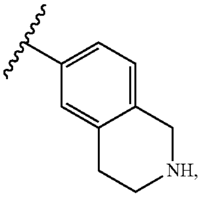
or
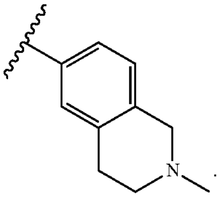
In certain embodiments, A is
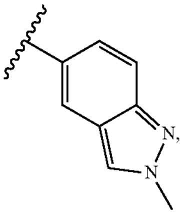 [SMILES: *c1ccc2nn(C)cc2c1]
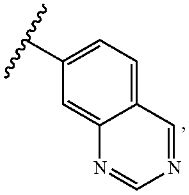
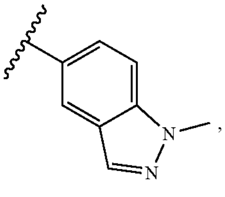
or
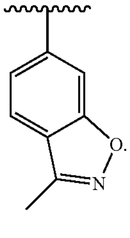
In certain embodiments, A is
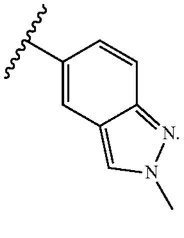
In certain embodiments, A is
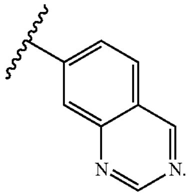 [SMILES: *c1ccc2cncnc2c1]
In certain embodiments, A is
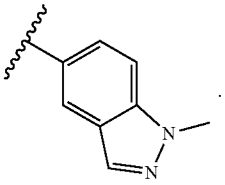 [SMILES: *c1ccc2c(cnn2C)c1]
In certain embodiments, A is
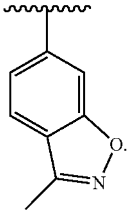
In certain embodiments, A is
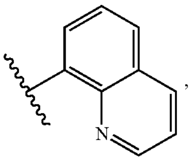
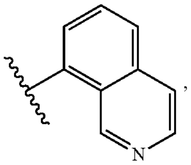
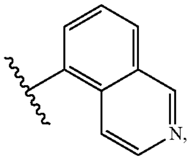
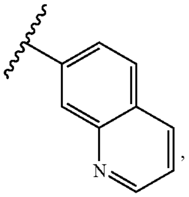
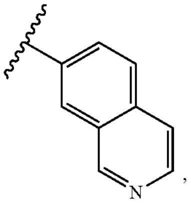
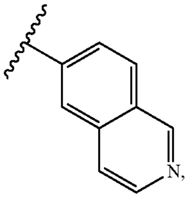
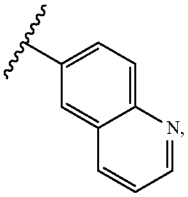
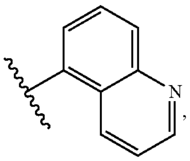

-continued
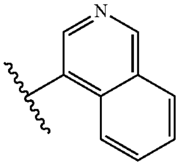, 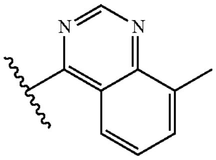,
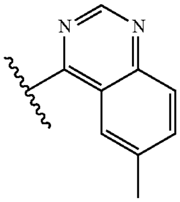, 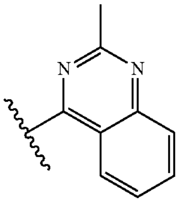,
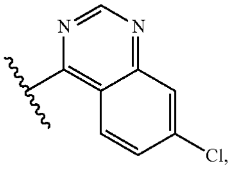, 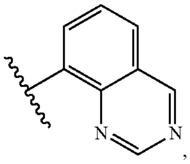,
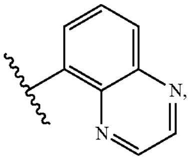, 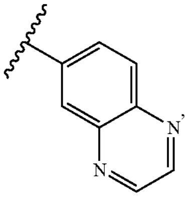,
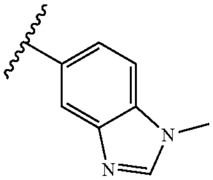, 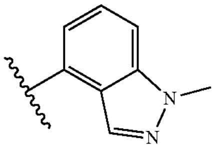,
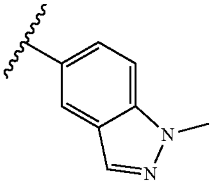, 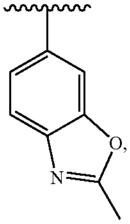, 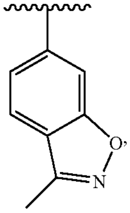 [SMILES: *c1ccc2c(C)noc2c1],
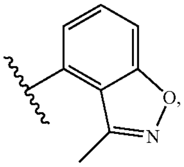, 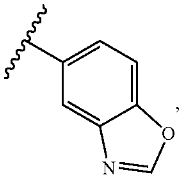,
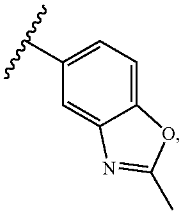, 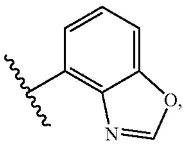,
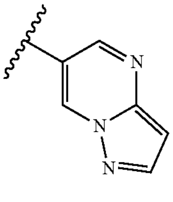, 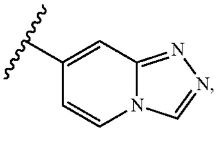,
-continued
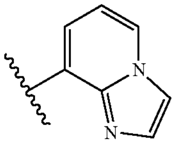, 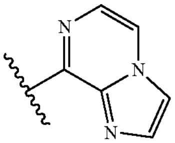,
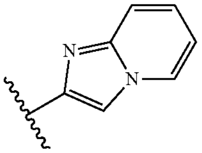, 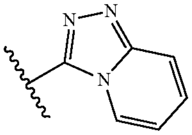,
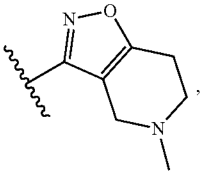, 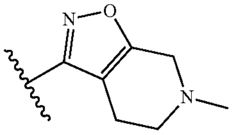,
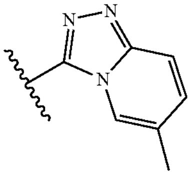, 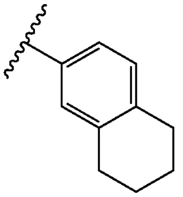,
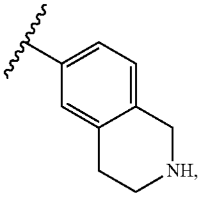 or 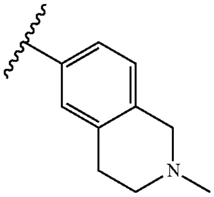.
In certain embodiments, A is
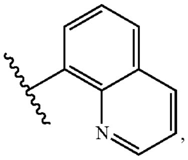, 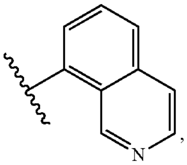, 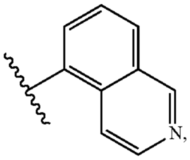,
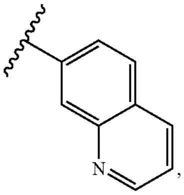, 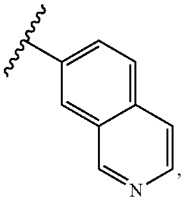, 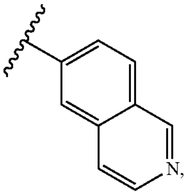,
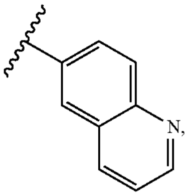, 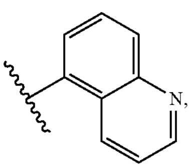, 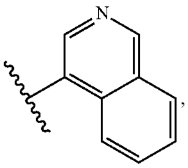, -continued
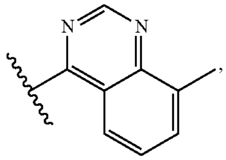,
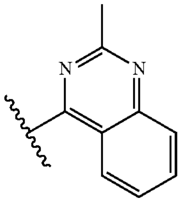,
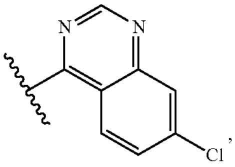
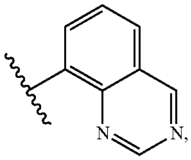
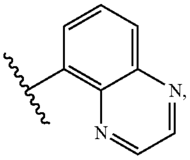
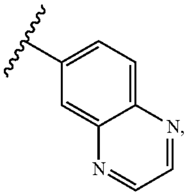
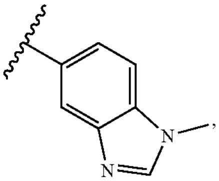
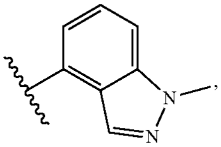
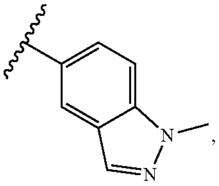
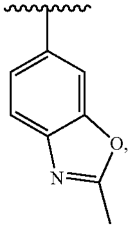
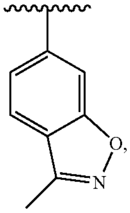
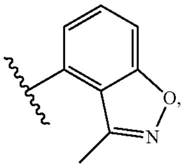
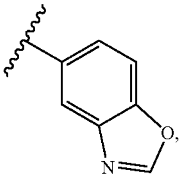
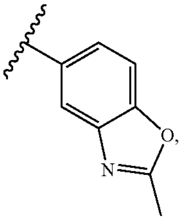
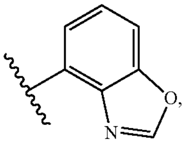
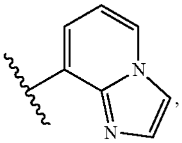
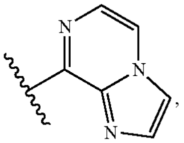
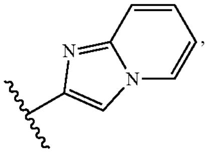,
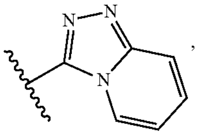,
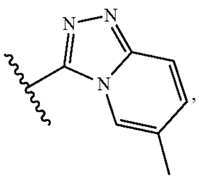
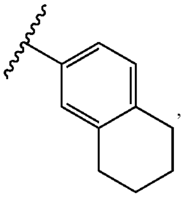,
-continued
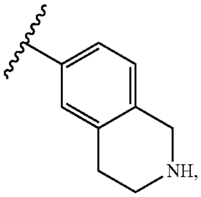
or
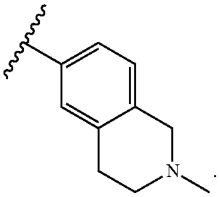.
In certain embodiments, A is
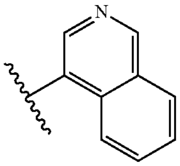,
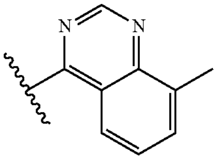,
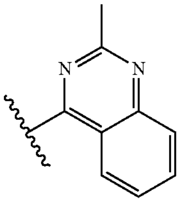
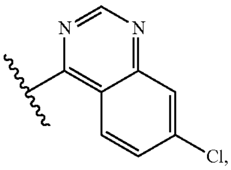
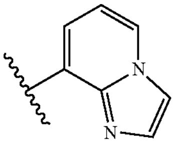,
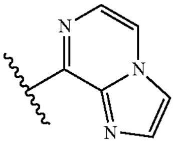,
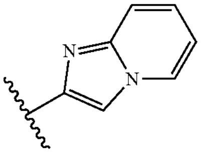,
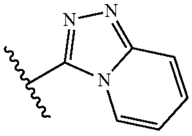,
or
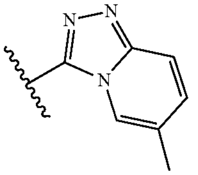.
In certain embodiments, A is
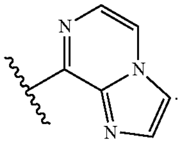 [SMILES: *c1nccn2ccnc12].
In certain embodiments, A is
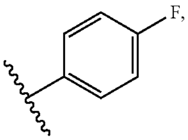
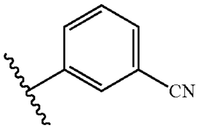, -continued

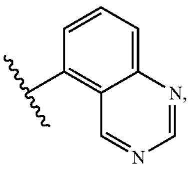

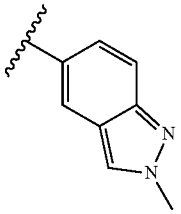
,

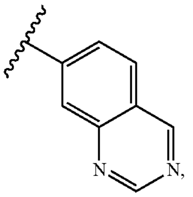

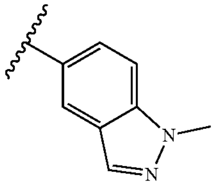
,

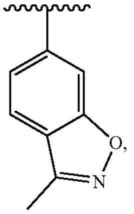
or
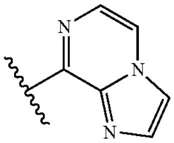
.

In certain embodiments, A is carbocyclyl or heterocyclyl, wherein A is optionally substituted with one or more substituents $R^2$. In certain embodiments, A is $C_{3-10}$ cycloalkyl or 4-11 membered heterocyclyl, wherein A is optionally substituted with 1-3 independent substituents $R^2$.

In certain embodiments, A is cycloalkyl optionally substituted with one or more substituents $R^2$. In certain embodiments, A is $C_{3-10}$ cycloalkyl optionally substituted with one or more substituents $R^2$. In certain embodiments, A is $C_{5-10}$ bridged cycloalkyl, $C_{5-10}$ spirocyclic cycloalkyl, or $C_{3-8}$ monocyclic cycloalkyl, wherein A is optionally substituted with one or more substituents $R^2$. In certain embodiments, A is $C_{5-10}$ bridged cycloalkyl or $C_{3-8}$ monocyclic cycloalkyl, wherein A is optionally substituted with one or more substituents $R^2$. In certain embodiments, A is $C_{5-10}$ bridged cycloalkyl optionally substituted with one or more substituents $R^2$. In certain embodiments, A is $C_{5-10}$ spirocyclic cycloalkyl optionally substituted with one or more substituents $R^2$. In certain embodiments, A is $C_{8-10}$ spirocyclic cycloalkyl optionally substituted with one or more substituents $R^2$. In certain embodiments, A is $C_{3-8}$ monocyclic cycloalkyl optionally substituted with one or more substituents $R^2$. In certain embodiments, A is $C_{3-6}$ monocyclic cycloalkyl optionally substituted with one or more substituents $R^2$.

In certain embodiments, A is bicyclo[1.1.1]pentan-1-yl, tetrahydronaphthalenyl, or adamantyl, wherein A is optionally substituted with 1-3 independent substituents $R^2$. In certain embodiments, A is adamantyl or bicyclo[1.1.1]pentan-1-yl, wherein A is optionally substituted with 1-3 independent substituents $R^2$.

In certain embodiments, A is

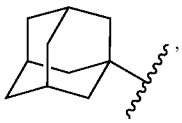
,
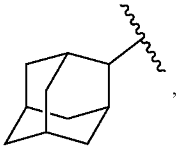
, or

-continued

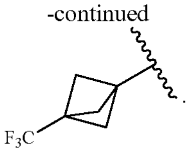
.

In certain embodiments, A is heterocyclyl optionally substituted with 1-3 independent substituents $R^2$. In certain embodiments, A is 4-11 membered heterocyclyl optionally substituted with 1-3 independent substituents $R^2$. In certain embodiments, A is 4-10 membered heterocyclyl optionally substituted with 1-3 independent substituents $R^2$. In certain embodiments, A is monocyclic 4-7 membered heterocyclyl, 5-10 membered bridged heterocyclyl, or 7-11 membered heterocyclic spiro ring system, wherein A is optionally substituted with 1-3 independent substituents $R^2$. In certain embodiments, A is monocyclic 4-7 membered heterocyclyl or 5-10 membered bridged heterocyclyl, wherein A is optionally substituted with 1-3 independent substituents $R^2$. In certain embodiments, A is monocyclic 4-7 membered heterocyclyl optionally substituted with 1-3 independent substituents $R^2$. In certain embodiments, A is monocyclic 4-6 membered heterocyclyl optionally substituted with 1-3 independent substituents $R^2$. In certain embodiments, A is monocyclic 4-5 membered heterocyclyl optionally substituted with 1-3 independent substituents $R^2$. In certain embodiments, A is monocyclic 5-6 membered heterocyclyl optionally substituted with 1-3 independent substituents $R^2$. In certain embodiments, A is 5-10 membered bridged heterocyclyl optionally substituted with 1-3 independent substituents $R^2$. In certain embodiments, A is 6-10 membered bridged heterocyclyl optionally substituted with 1-3 independent substituents $R^2$. In certain embodiments, A is 8-10 membered bridged heterocyclyl optionally substituted with 1-3 independent substituents $R^2$. In certain embodiments, A is 10-membered bridged heterocyclyl optionally substituted with 1-3 independent substituents $R^2$. In certain embodiments, A is a 7-11 membered heterocyclic spiro ring system optionally substituted with 1-3 independent substituents $R^2$. In certain embodiments, A is a 7-9 membered heterocyclic spiro ring system optionally substituted with 1-3 independent substituents $R^2$. In certain embodiments, A is a 9-11 membered heterocyclic spiro ring system optionally substituted with 1-3 independent substituents $R^2$. In certain embodiments, A is a 8-10 membered heterocyclic spiro ring system optionally substituted with 1-3 independent substituents $R^2$. In certain embodiments, A is a 9-membered heterocyclic spiro ring system optionally substituted with 1-3 independent substituents $R^2$.

In certain embodiments, A is azabicyclo[3.2.1]octanyl, 2-oxa-5-azabicyclo[2.2.1]heptanyl, 8-oxabicyclo[3.2.1]octanyl, 3-oxabicyclo[3.2.1]octanyl, quinuclidinyl, morpholinyl, or oxaadamantanyl, wherein A is optionally substituted with 1-3 independent substituents $R^2$. In certain embodiments, A is (1r,3r,5r,7r)-2-oxaadamantanyl.

In certain embodiments, A is

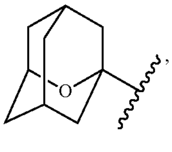
,
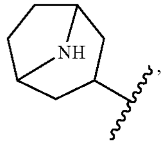
,
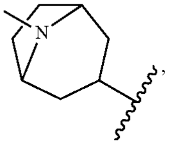
,

-continued
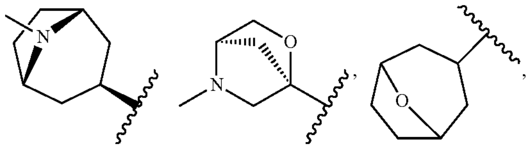
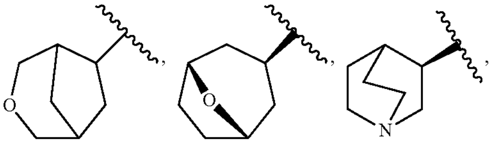
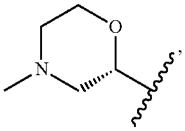
or
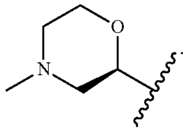
In certain embodiments, A is phenyl, pyridinyl, quinolinyl, or naphthalenyl, wherein A is optionally substituted with 1-3 independent substituents $R^2$.
In certain embodiments, A is
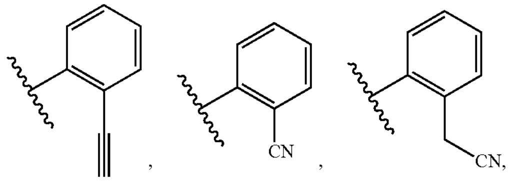
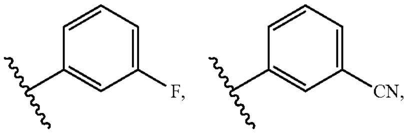
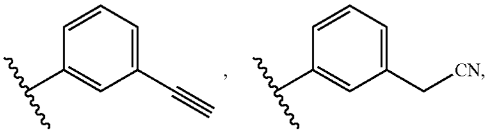
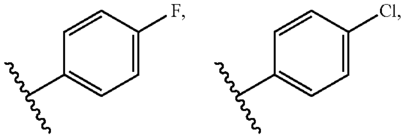
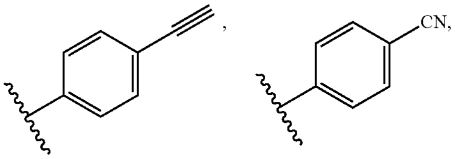
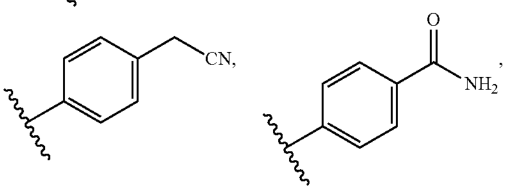
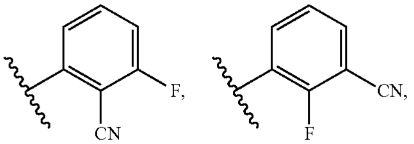
-continued
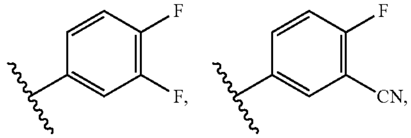
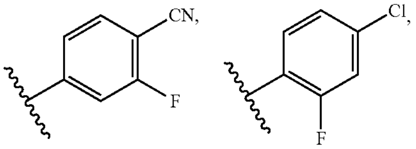
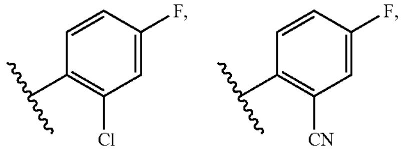
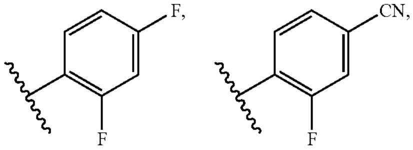
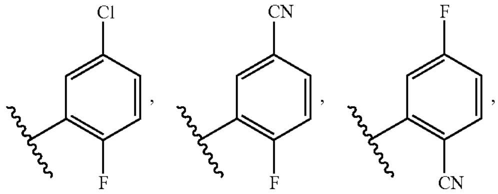
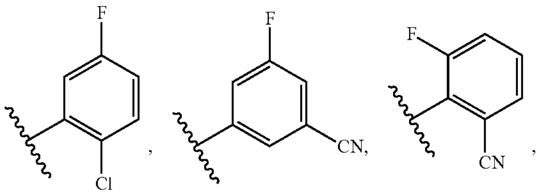
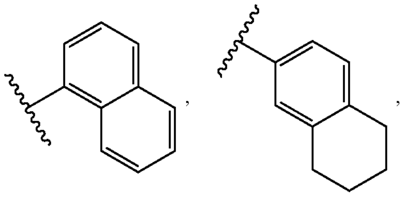
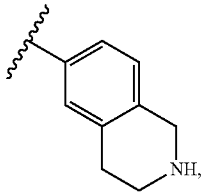
or
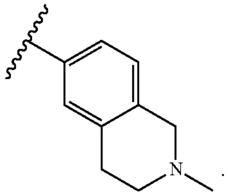
In certain embodiments, A is
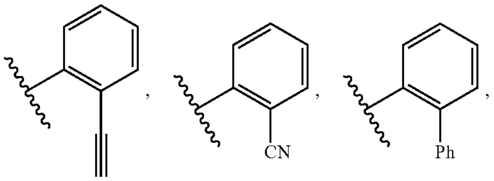

-continued
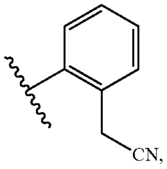
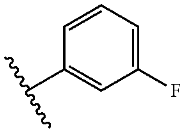
,
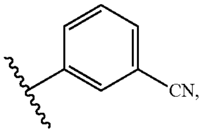
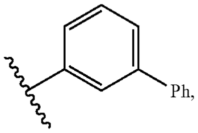
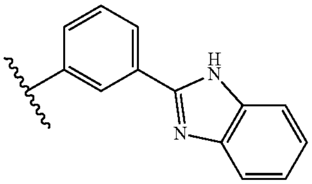
,
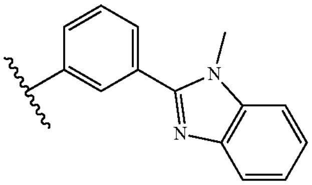
,
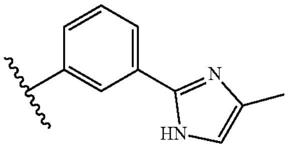
,
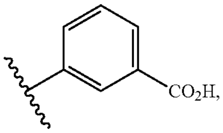
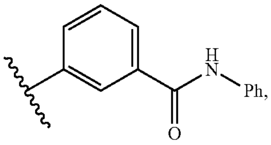
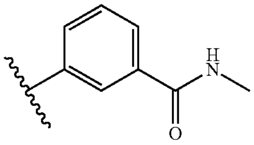
,
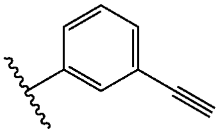
,
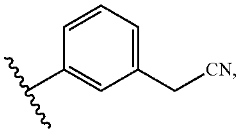
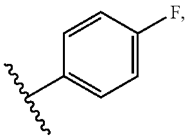
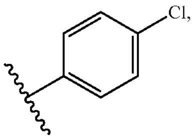
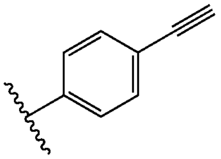
,
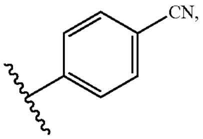
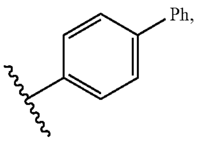
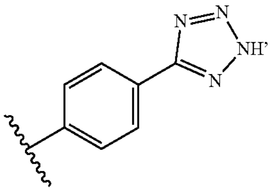
-continued
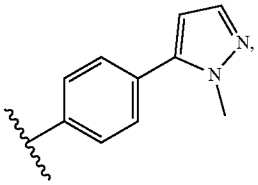
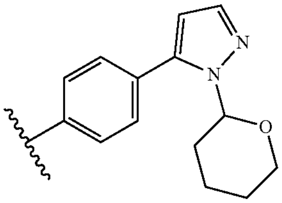
,
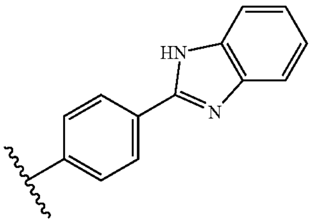
,
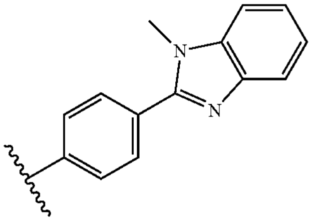
,
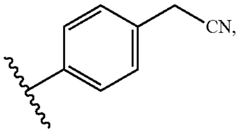
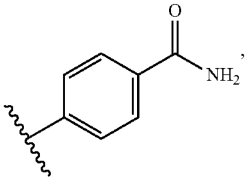
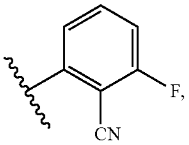
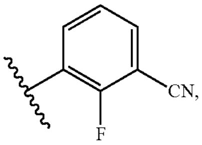
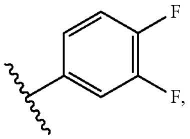
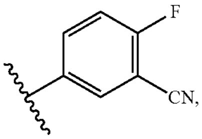
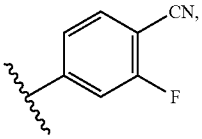
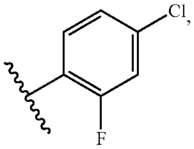
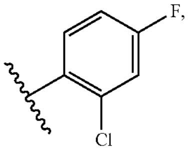
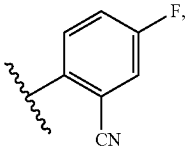
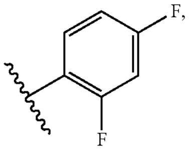
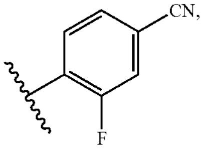

-continued
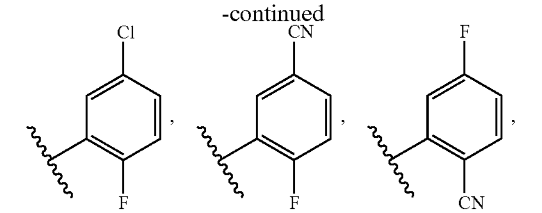
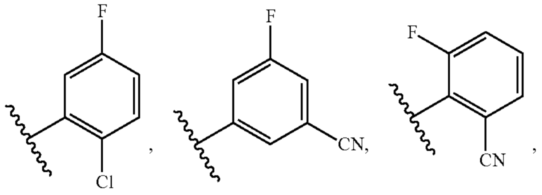
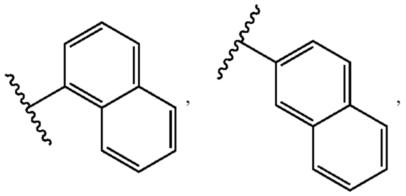
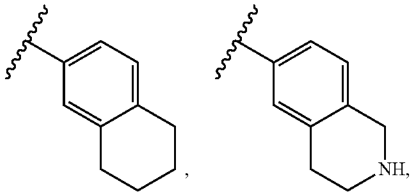
or
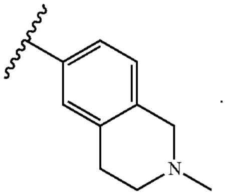
In certain embodiments, A is
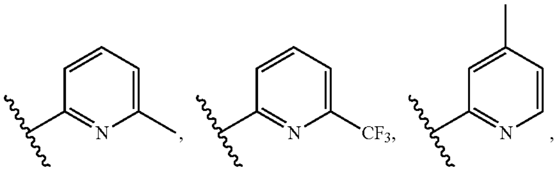
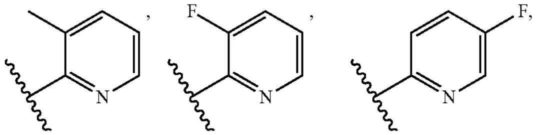
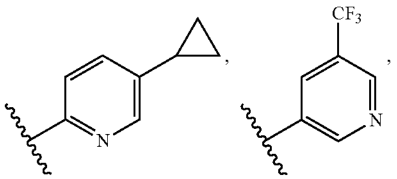
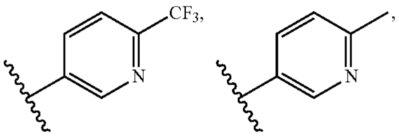
-continued
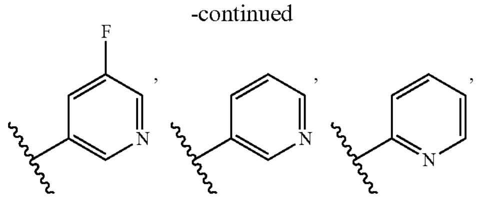
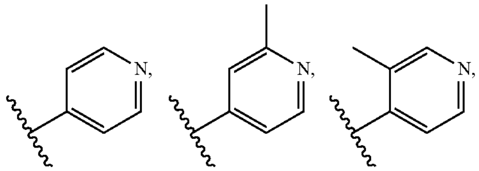
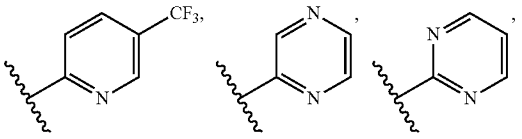
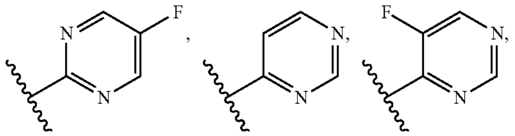
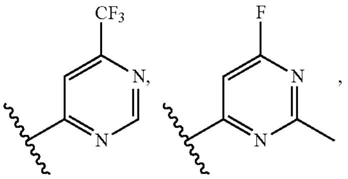
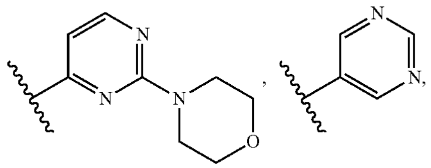
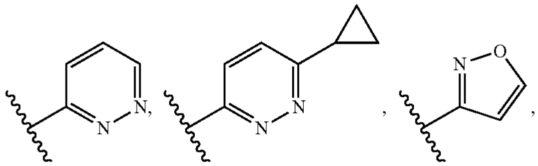
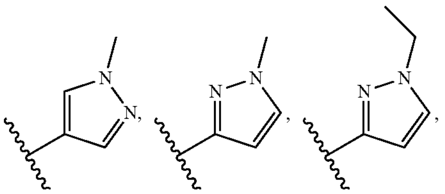
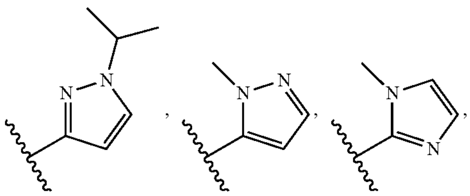
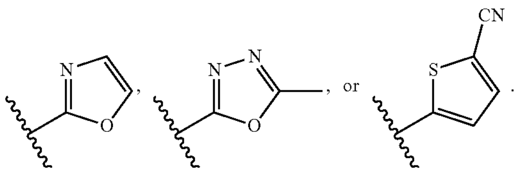
or In certain embodiments, A is
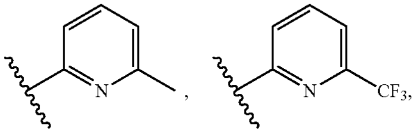
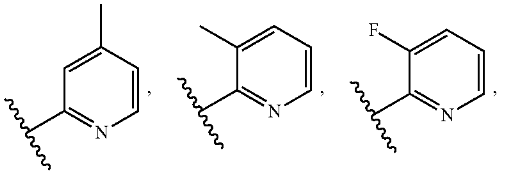
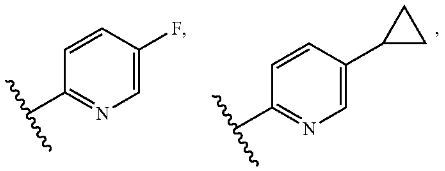
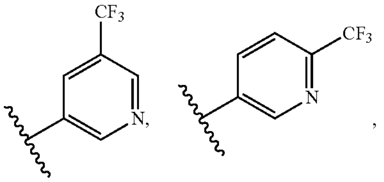
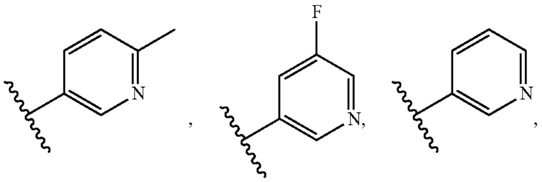
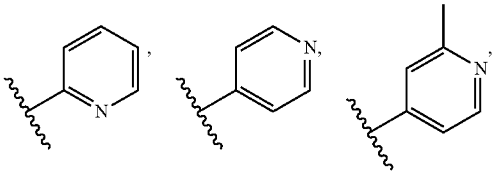
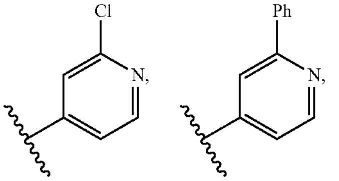
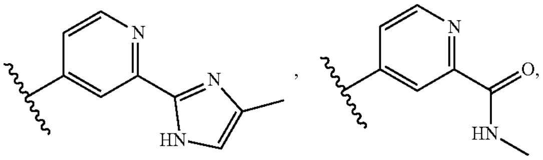
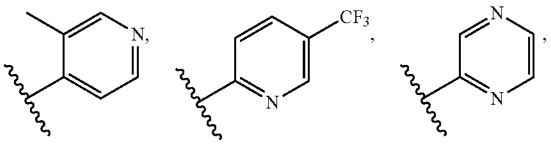
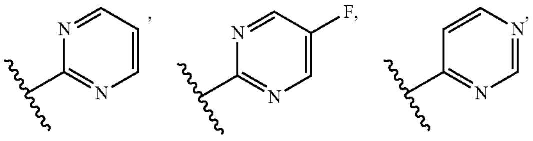
-continued
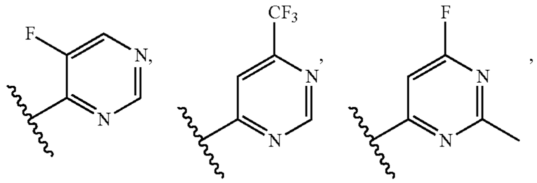
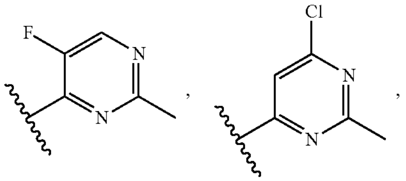
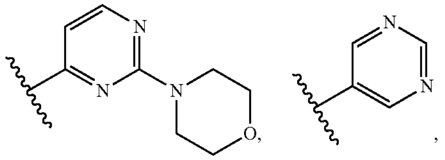
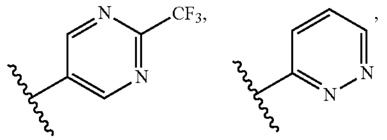
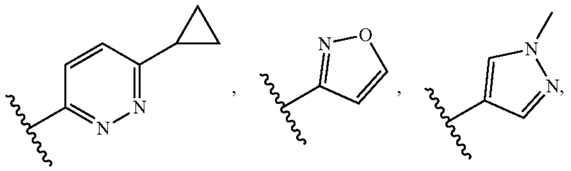
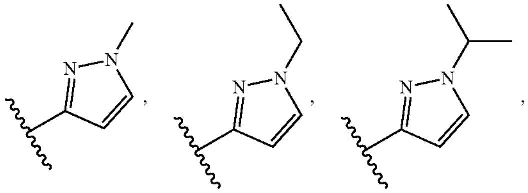
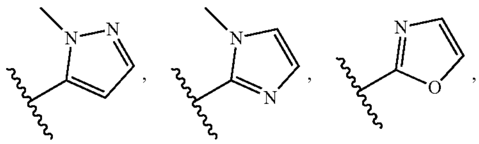
, or
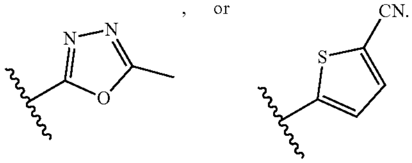
In some embodiments, A is
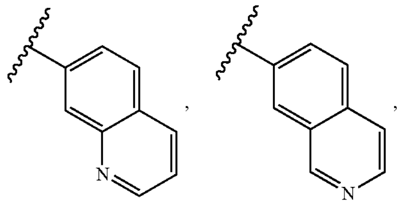

-continued
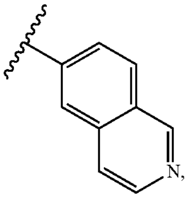, 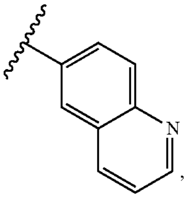,
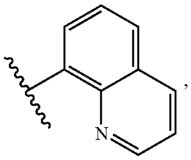, 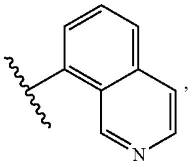,
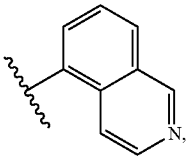, 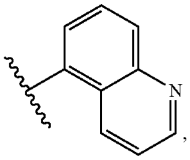,
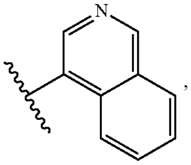, 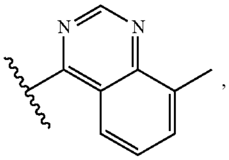,
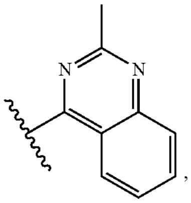, 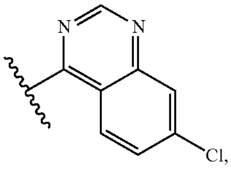,
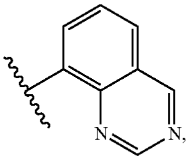, 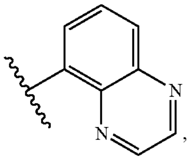,
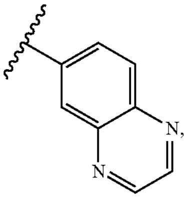, 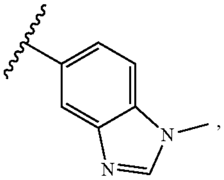,
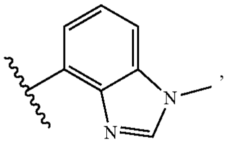, 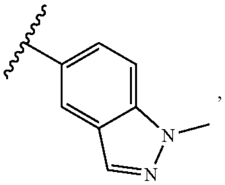,
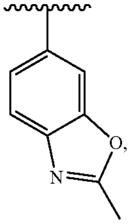, 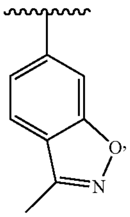, 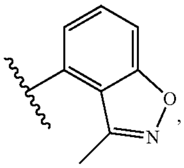,
-continued
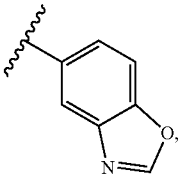, 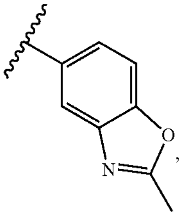, 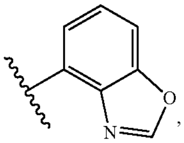,
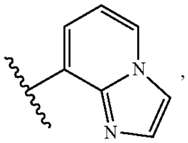, 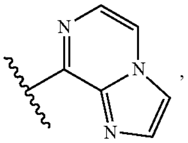,
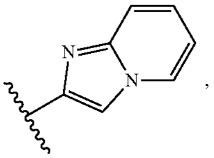, 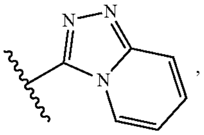, or
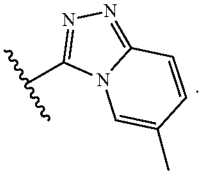.
In some embodiments, A is
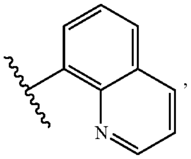, 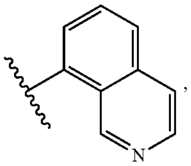,
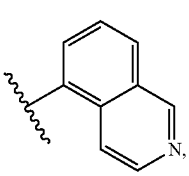, 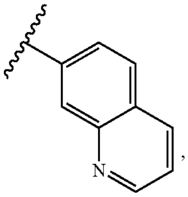,
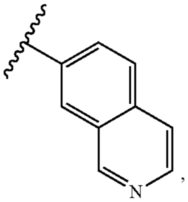, 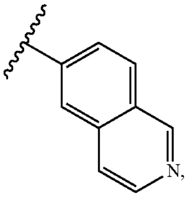,
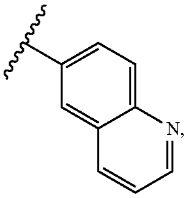, 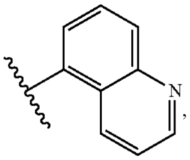, -continued
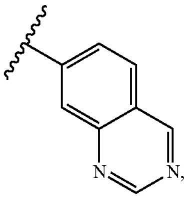
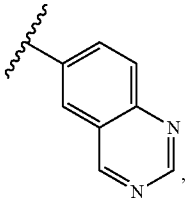
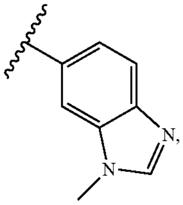
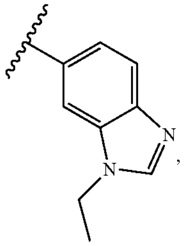
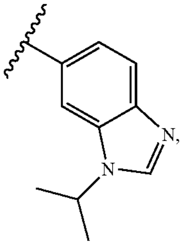
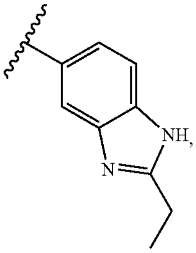
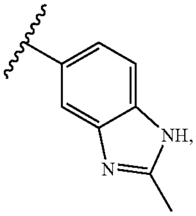
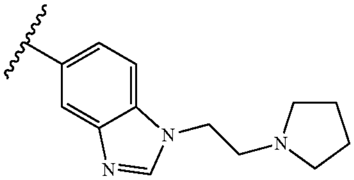
,
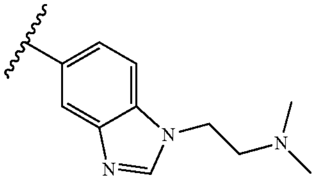
,
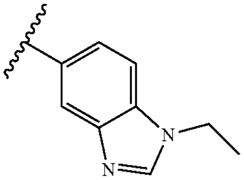
,
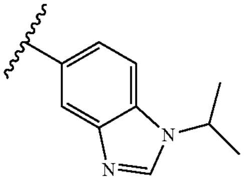
,
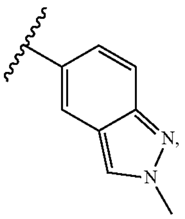
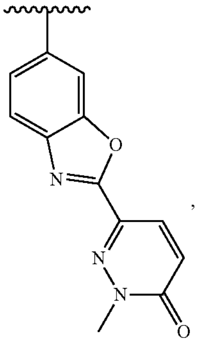
,
-continued
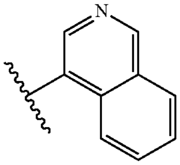
,
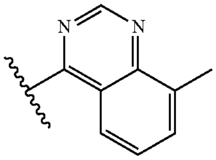
,
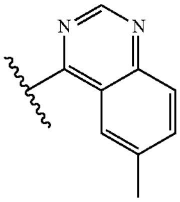
,
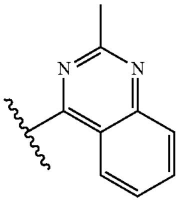
,
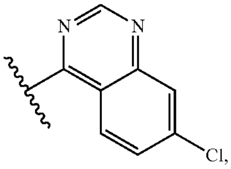
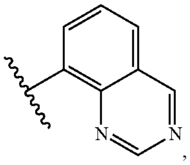
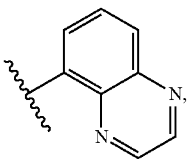
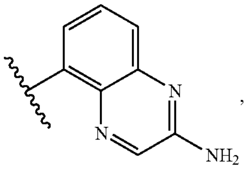
,
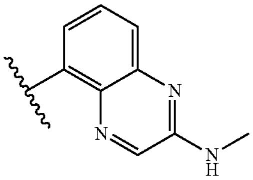
,
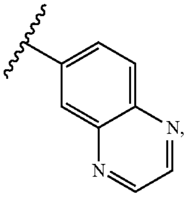
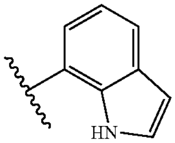
,
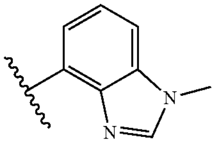
,
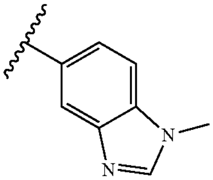
,
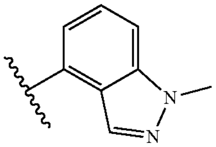
,
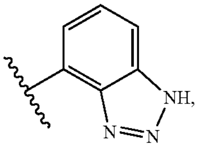
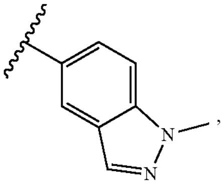
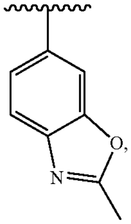
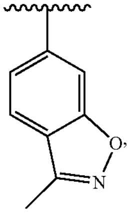
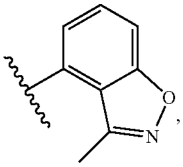

-continued

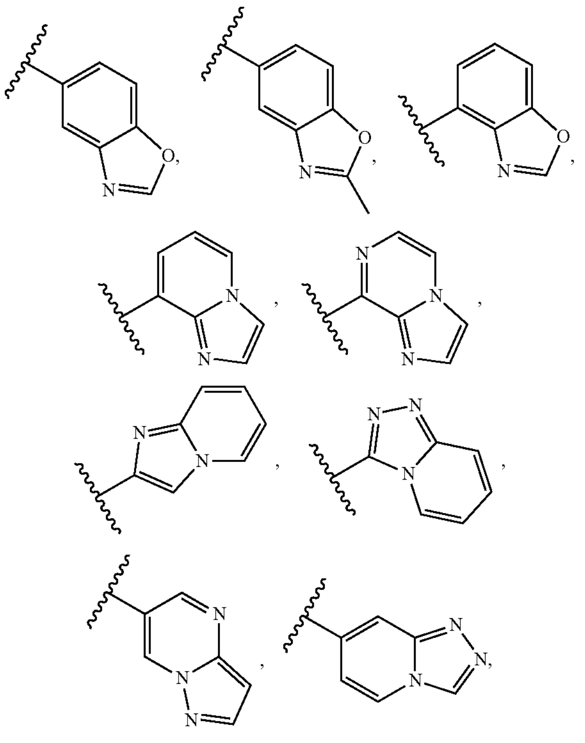

or

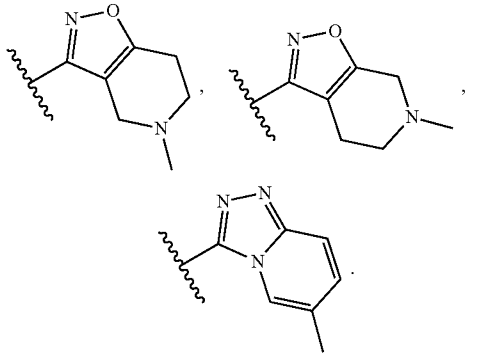

In some embodiments, A is

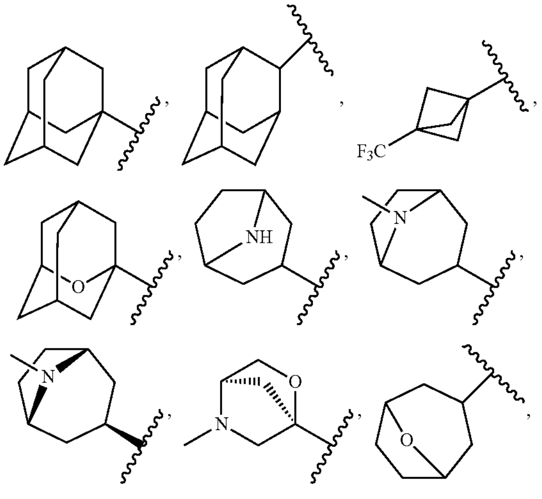

-continued

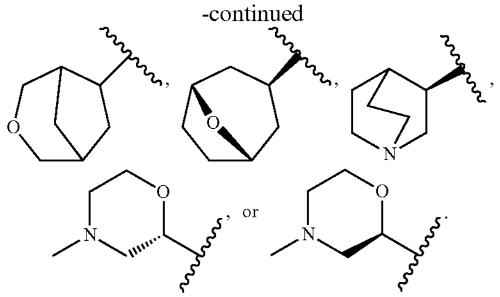

or

R$^2$

As described herein, each occurrence of R$^2$ is independently halogen, substituted or unsubstituted amino, substituted or unsubstituted amido, cyano, substituted or unsubstituted acyl, substituted or unsubstituted alkyl, substituted or unsubstituted alkenyl, substituted or unsubstituted alkynyl, substituted or unsubstituted heteroaliphatic, substituted or unsubstituted carbocyclyl, substituted or unsubstituted heterocyclyl, substituted or unsubstituted aryl, or substituted or unsubstituted heteroaryl; or two occurrences of R$^2$ are joined with their intervening atoms to form substituted or unsubstituted carbocyclyl, substituted or unsubstituted heterocyclyl, substituted or unsubstituted aryl, or substituted or unsubstituted heteroaryl. In certain embodiments, each occurrence of R$^2$ is independently halogen, amido, cyano, substituted or unsubstituted acyl, substituted or unsubstituted alkyl, substituted or unsubstituted alkenyl, substituted or unsubstituted alkynyl, substituted or unsubstituted heteroaliphatic, substituted or unsubstituted carbocyclyl, substituted or unsubstituted heterocyclyl, substituted or unsubstituted aryl, or substituted or unsubstituted heteroaryl; or two occurrences of R$^2$ are joined with their intervening atoms to form substituted or unsubstituted carbocyclyl, substituted or unsubstituted heterocyclyl, substituted or unsubstituted aryl, or substituted or unsubstituted heteroaryl. In certain embodiments, each occurrence of R$^2$ is independently halogen, amido, cyano, substituted or unsubstituted acyl, substituted or unsubstituted alkyl, substituted or unsubstituted alkenyl, substituted or unsubstituted alkynyl, substituted or unsubstituted heteroaliphatic, substituted or unsubstituted carbocyclyl, substituted or unsubstituted heterocyclyl, substituted or unsubstituted aryl, or substituted or unsubstituted heteroaryl. In certain embodiments, each occurrence of R$^2$ is independently halogen, amido, cyano, substituted or unsubstituted acyl, substituted or unsubstituted alkyl, substituted or unsubstituted alkenyl, substituted or unsubstituted alkynyl, substituted or unsubstituted heteroaliphatic, substituted or unsubstituted carbocyclyl, or substituted or unsubstituted heterocyclyl.

In certain embodiments, R$^2$ is substituted or unsubstituted aminoalkyl, substituted or unsubstituted amidoalkyl, amino optionally substituted with $C_{1-4}$ alkyl, or amido optionally substituted with $C_{1-4}$ alkyl. In certain embodiments, R$^2$ is amino or amido optionally substituted with substituted or unsubstituted $C_{1-4}$ alkyl. In certain embodiments, R$^2$ is amino or amido optionally substituted with $C_{1-4}$ alkyl.

In certain embodiments, each occurrence of R$^2$ is independently halogen, cyano, —$NH_2$, —$NHCH_3$, —(C═O)OH, —(C═O)$NH_2$, —(C═O)$NHCH_3$, —(C═O)NHPh, substituted or unsubstituted $C_{1-6}$ alkyl, substituted or unsubstituted aminoalkyl, 4-6 membered substituted or unsubstituted heterocyclylalkyl, substituted or unsubstituted phenyl, substituted or unsubstituted $C_{3-6}$ cycloalkyl, substituted or unsubstituted 4-6 membered heterocyclyl, substituted or unsubstituted 5-6 membered heteroaryl, substituted or unsubstituted $C_{2-6}$ alkenyl, or substituted or unsubstituted $C_{2-6}$ alkynyl. In certain embodiments, each occurrence of $R^2$ is independently halogen, cyano, —$NH_2$, —$NHCH_3$, —(C═O)OH, —(C═O)$NH_2$, —(C═O)$NHCH_3$, —(C═O)NHPh, $C_{1-6}$ alkyl, aminoalkyl, 4-6 membered heterocyclylalkyl, substituted or unsubstituted phenyl, $C_{3-6}$ cycloalkyl, 4-6 membered heterocyclyl, 5-6 membered substituted or unsubstituted heteroaryl, $C_{2-6}$ alkenyl, or $C_{2-6}$ alkynyl, wherein each $C_{1-6}$ alkyl, $C_{3-6}$ cycloalkyl, $C_{2-6}$ alkenyl, or $C_{2-6}$ alkynyl is optionally substituted with one or more halogen or cyano. In certain embodiments, each occurrence of $R^2$ is independently halogen, cyano, —(C═O)$NH_2$, $C_{1-6}$ alkyl, $C_{3-6}$ cycloalkyl, 4-6 membered heterocyclyl, $C_{2-6}$ alkenyl, or $C_{2-6}$ alkynyl, wherein each $C_{1-6}$ alkyl, $C_{3-6}$ cycloalkyl, $C_{2-6}$ alkenyl, or $C_{2-6}$ alkynyl is optionally substituted with one or more halogen or cyano.

In certain embodiments, each occurrence of $R^2$ is independently fluoro, chloro, methyl, ethyl, isopropyl, trifluoromethyl, cyclopropyl, —(C═O)$NH_2$, cyano, cyanomethyl, ethynyl, or morpholinyl. In certain embodiments, each occurrence of $R^2$ is independently fluoro. In certain embodiments, each occurrence of $R^2$ is independently chloro. In certain embodiments, each occurrence of $R^2$ is independently methyl. In certain embodiments, each occurrence of $R^2$ is independently ethyl. In certain embodiments, each occurrence of $R^2$ is independently isopropyl. In certain embodiments, each occurrence of $R^2$ is independently trifluoromethyl. In certain embodiments, each occurrence of $R^2$ is independently cyclopropyl. In certain embodiments, each occurrence of $R^2$ is independently —(C═O)$NH_2$. In certain embodiments, each occurrence of $R^2$ is independently cyano. In certain embodiments, each occurrence of $R^2$ is independently cyanomethyl. In certain embodiments, each occurrence of $R^2$ is independently ethynyl. In certain embodiments, each occurrence of $R^2$ is independently morpholinyl.

In certain embodiments, each occurrence of $R^2$ is independently halogen. In certain embodiments, each occurrence of $R^2$ is independently fluoro or chloro. In certain embodiments, each occurrence of $R^2$ is fluoro.

In certain embodiments, each occurrence of $R^2$ is independently halogen, cyano, or substituted or unsubstituted $C_{1-6}$ alkyl. In certain embodiments, each occurrence of $R^2$ is independently halogen, cyano, or unsubstituted $C_{1-6}$ alkyl. In certain embodiments, each occurrence of $R^2$ is independently fluoro, cyano, or methyl.

In certain embodiments, A is substituted with 1 or 2 $R^2$ groups, wherein each occurrence of $R^2$ is independently halogen, cyano, —(C═O)$NH_2$, $C_{1-6}$ alkyl, $C_{3-6}$ cycloalkyl, 4-6 membered heterocyclyl, $C_{2-6}$ alkenyl, or $C_{2-6}$ alkynyl, wherein each $C_{1-6}$ alkyl, $C_{3-6}$ cycloalkyl, $C_{2-6}$ alkenyl, or $C_{2-6}$ alkynyl is optionally substituted with one or more halogen or cyano.

In certain embodiments, A is substituted with 1 or 2 $R^2$ groups, wherein each occurrence of $R^2$ is independently fluoro, chloro, methyl, ethyl, isopropyl, trifluoromethyl, cyclopropyl, —(C═O)$NH_2$, cyano, cyanomethyl, ethynyl, or morpholinyl.

In certain embodiments, A is substituted with 1 or 2 $R^2$ groups, wherein each occurrence of $R^2$ is independently fluoro, chloro, cyano, cyclopropyl, $C_{2-4}$ alkynyl, or $C_{1-4}$ alkyl optionally substituted with one or more fluoro, cyano, or alkynyl.

In certain embodiments, A is substituted with 1 or 2 $R^2$ groups, wherein each occurrence of $R^2$ is independently halogen. In certain embodiments, A is substituted with 1 or 2 $R^2$ groups, wherein each occurrence of $R^2$ is independently fluoro or chloro. In certain embodiments, A is substituted with 1 or 2 $R^2$ groups, wherein each occurrence of $R^2$ is fluoro.

In certain embodiments, A is $C_{6-14}$ aryl, 5-11 membered heteroaryl, $C_{3-10}$ cycloalkyl, or 4-11 membered heterocyclyl, wherein A is optionally substituted with 1-3 independent substituents $R^2$; each occurrence of $R^1$ is independently hydrogen, halogen, or $C_{1-6}$ alkyl optionally substituted with one or more halogen or alkoxy; and each occurrence of $R^2$ is independently halogen, cyano, $C_{1-6}$ alkyl, $C_{3-6}$ cycloalkyl, $C_{2-6}$ alkenyl, or $C_{2-6}$ alkynyl, wherein each $C_{1-6}$ alkyl, $C_{3-6}$ cycloalkyl, $C_{2-6}$ alkenyl, or $C_{2-6}$ alkynyl is optionally substituted with one or more halogen or cyano.

In certain embodiments, each occurrence of $R^1$ is independently hydrogen, halogen, or methyl optionally substituted with one or more halogen or alkoxy; and each occurrence of $R^2$ is independently halogen, cyano, methyl, cyclopropyl, $C_{2-3}$ alkenyl, or $C_{2-3}$ alkynyl, wherein each methyl, cyclopropyl, $C_{2-3}$ alkenyl, or $C_{2-3}$ alkynyl is optionally substituted with one or more halogen or cyano.

In certain embodiments, each halogen in $R^1$, $R^2$, $R^a$ and $R^b$ is fluoro or chloro. In certain embodiments, each halogen in $R^1$, $R^2$, $R^a$ and $R^b$ is fluoro.

CERTAIN EMBODIMENTS

In certain embodiments, the compound of Formula (I) is of Formula (I-a):

(I-a)

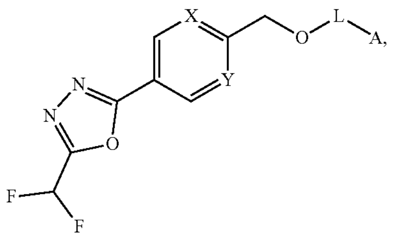

or a pharmaceutically acceptable salt thereof; wherein A, X, Y, L, and A are as defined herein.

In certain embodiments of Formula (I-a), at least one of X and Y is N. In certain embodiments of Formula (I-a), one of X and Y is N. In certain embodiments of Formula (I-a), A is phenyl, pyridinyl or pyrimidinyl, and A is optionally substituted with 1 or 2 $R^2$ groups, wherein each occurrence of $R^2$ is independently fluoro, chloro, cyano, methyl optionally substituted with one or more fluoro, or methyl optionally substituted with a cyano. In certain embodiments of Formula (I-a), A is phenyl, quinazolinyl, imidazo[1,2-a]pyrazinyl, benzoisoxazolyl, or benzopyrazolyl, and A is optionally substituted with 1 or 2 $R^2$ groups, wherein each occurrence of $R^2$ is independently fluoro, cyano, or substituted or unsubstituted $C_{1-6}$ alkyl.

In certain embodiments of Formula (I-a), A is a bicyclic fused heteroaryl comprising at least two heteroatoms (e.g., S, N, O), and A is optionally substituted with 1 or 2 $R^2$ groups, wherein each occurrence of $R^2$ is independently fluoro, cyano, or substituted or unsubstituted $C_{1-6}$ alkyl. In certain embodiments of Formula (I-a), A is a 5,6 bicyclic fused heteroaryl comprising at least two heteroatoms (e.g., S, N, O), and A is optionally substituted with 1 or 2 $R^2$ groups, wherein each occurrence of $R^2$ is independently fluoro, cyano, or substituted or unsubstituted $C_{1-6}$ alkyl. In certain embodiments of Formula (I-a), A is a 5,6 bicyclic fused heteroaryl comprising at least two heteroatoms (e.g., S, N, O), and A is optionally substituted with 1 or 2 $R^2$ groups, wherein each occurrence of $R^2$ is independently fluoro, cyano, or substituted or unsubstituted $C_{1-6}$ alkyl. In certain embodiments of Formula (I-a), A is quinazolinyl, imidazo[1,2-a]pyrazinyl, benzoisoxazolyl, or benzopyrazolyl, and A is optionally substituted with 1 or 2 $R^2$ groups, wherein each occurrence of $R^2$ is independently fluoro, cyano, or substituted or unsubstituted $C_{1-6}$ alkyl. In certain embodiments of Formula (I-a), A is imidazo[1,2-a]pyrazinyl, and A is optionally substituted with 1 or 2 $R^2$ groups, wherein each occurrence of $R^2$ is independently fluoro, cyano, or substituted or unsubstituted $C_{1-6}$ alkyl. In certain embodiments of Formula (I-a), A is an unsubstituted 5,6 bicyclic heteroaryl. In certain embodiments of Formula (I-a), A is unsubstituted imidazo[1,2-a]pyrazinyl.

In certain embodiments, the compound of Formula (I) is of Formula (I-b):

(I-b)

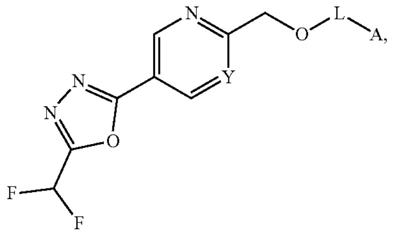

or a pharmaceutically acceptable salt thereof; where A, Y, L, and A are as defined herein.

In certain embodiments of Formula (I-b), A is phenyl, pyridinyl or pyrimidinyl, and A is optionally substituted with 1 or 2 $R^2$ groups, wherein each occurrence of $R^2$ is independently fluoro, chloro, cyano, methyl optionally substituted with one or more fluoro, or methyl optionally substituted with a cyano. In certain embodiments of Formula (I-b), A is phenyl, quinazolinyl, imidazo[1,2-a]pyrazinyl, benzoisoxazolyl, or benzopyrazolyl, and A is optionally substituted with 1 or 2 $R^2$ groups, wherein each occurrence of $R^2$ is independently fluoro, cyano, or substituted or unsubstituted $C_{1-6}$ alkyl.

In certain embodiments of Formula (I-b), A is a bicyclic fused heteroaryl comprising at least two heteroatoms (e.g., S, N, O), and A is optionally substituted with 1 or 2 $R^2$ groups, wherein each occurrence of $R^2$ is independently fluoro, cyano, or substituted or unsubstituted $C_{1-6}$ alkyl. In certain embodiments of Formula (I-b), A is a 5,6 bicyclic fused heteroaryl comprising at least two heteroatoms (e.g., S, N, O), and A is optionally substituted with 1 or 2 $R^2$ groups, wherein each occurrence of $R^2$ is independently fluoro, cyano, or substituted or unsubstituted $C_{1-6}$ alkyl. In certain embodiments of Formula (I-b), A is quinazolinyl, imidazo[1,2-a]pyrazinyl, benzoisoxazolyl, or benzopyrazolyl, and A is optionally substituted with 1 or 2 $R^2$ groups, wherein each occurrence of $R^2$ is independently fluoro, cyano, or substituted or unsubstituted $C_{1-6}$ alkyl. In certain embodiments of Formula (I-b), A is imidazo[1,2-a]pyrazinyl, and A is optionally substituted with 1 or 2 $R^2$ groups, wherein each occurrence of $R^2$ is independently fluoro, cyano, or substituted or unsubstituted $C_{1-6}$ alkyl. In certain embodiments of Formula (I-b), A is an unsubstituted 5,6 bicyclic heteroaryl. In certain embodiments of Formula (I-b), A is unsubstituted imidazo[1,2-a]pyrazinyl.

In certain embodiments, the compound of Formula (I) is of Formula (I-c):

(I-c)

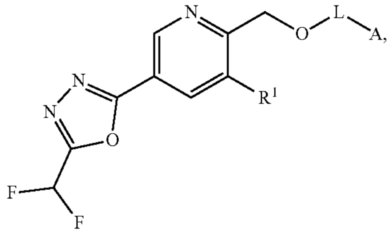

or a pharmaceutically acceptable salt thereof; wherein A, $R^1$, and L are as defined herein.

In certain embodiments of Formula (I-c), $R^1$ is hydrogen or fluoro, L is a bond or —$CH_2$—, A is phenyl, pyridinyl or pyrimidinyl, and A is optionally substituted with 1 or 2 $R^2$ groups, wherein each occurrence of $R^2$ is independently fluoro, chloro, cyano, methyl optionally substituted with one or more fluoro, or methyl optionally substituted with a cyano.

In certain embodiments of Formula (I-c), L is a bond or —$CH_2$—; $R^1$ is hydrogen or fluoro; A is a phenyl, a 6-membered heteroaryl, a $C_6$ aryl ring fused to a 6-membered carbocyclyl, a 6,6 bicyclic aryl ring system, a 5,6 bicyclic heteroaryl ring system, or a 6,6 bicyclic heteroaryl ring system, and wherein A is optionally substituted with one or more substituents $R^2$; and each $R^2$ is independently chlorine, fluorine, —CN, —$CH_2$CN, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-c), L is a bond or —$CH_2$—; $R^1$ is hydrogen or fluoro; A is a phenyl or a 6-membered heteroaryl, and wherein A is optionally substituted with one or more substituents $R^2$; and each $R^2$ is independently chlorine, fluorine, —CN, —$CH_2$CN, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-c), L is a bond or —$CH_2$—; $R^1$ is hydrogen or fluoro; A is a $C_6$ aryl ring fused to a 6-membered carbocyclyl and wherein A is optionally substituted with one or more substituents $R^2$; and each $R^2$ is independently chlorine, fluorine, —CN, —$CH_2$CN, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-c), L is a bond or —$CH_2$—; $R^1$ is hydrogen or fluoro; A is a 5,6 bicyclic heteroaryl ring system, or a 6,6 bicyclic heteroaryl ring system, and wherein A is optionally substituted with one or more substituents $R^2$; and each $R^2$ is independently chlorine, fluorine, —CN, —$CH_2$CN, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-c), L is a bond or —$CH_2$—; $R^1$ is hydrogen or fluoro; A is a 6,6 bicyclic aryl ring system and wherein A is optionally substituted with one or more substituents $R^2$; and each $R^2$ is independently chlorine, fluorine, —CN, —$CH_2$CN, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-c), A is a bicyclic fused heteroaryl comprising at least two heteroatoms (e.g., S, N, O), and A is optionally substituted with 1 or 2 $R^2$ groups, wherein each occurrence of $R^2$ is independently fluoro, cyano, or substituted or unsubstituted $C_{1-6}$ alkyl. In certain embodiments of Formula (I-c), A is a 5,6 bicyclic fused heteroaryl comprising at least two heteroatoms (e.g., S, N, O), and A is optionally substituted with 1 or 2 $R^2$ groups, wherein each occurrence of $R^2$ is independently fluoro, cyano, or substituted or unsubstituted $C_{1-6}$ alkyl. In certain embodiments of Formula (I-c), A is quinazolinyl, imidazo[1,2-a]pyrazinyl, benzoisoxazolyl, or benzopyrazolyl, and A is optionally substituted with 1 or 2 $R^2$ groups, wherein each occurrence of $R^2$ is independently fluoro, cyano, or substituted or unsubstituted $C_{1-6}$ alkyl. In certain embodiments of Formula (I-c), A is imidazo[1,2-a]pyrazinyl, and A is optionally substituted with 1 or 2 $R^2$ groups, wherein each occurrence of $R^2$ is independently fluoro, cyano, or substituted or unsubstituted $C_{1-6}$ alkyl. In certain embodiments of Formula (I-c), A is an unsubstituted 5,6 bicyclic heteroaryl. In certain embodiments of Formula (I-c), A is unsubstituted imidazo[1,2-a]pyrazinyl.

In certain embodiments of Formula (I-c), L is a bond; $R^1$ is hydrogen or fluoro; A is a bicyclic fused heteroaryl comprising at least two heteroatoms (e.g., S, N, O), and A is optionally substituted with 1 or 2 $R^2$ groups, wherein each occurrence of $R^2$ is independently substituted or unsubstituted $C_{1-6}$ alkyl. In certain embodiments of Formula (I-c), L is a bond; A is a 5,6 bicyclic fused heteroaryl comprising at least two heteroatoms (e.g., S, N, O), and A is optionally substituted with 1 or 2 $R^2$ groups, wherein each occurrence of $R^2$ is independently fluoro, cyano, or substituted or unsubstituted $C_{1-6}$ alkyl. In certain embodiments of Formula (I-c), L is a bond; $R^1$ is hydrogen or fluoro; A is quinazolinyl, imidazo[1,2-a]pyrazinyl, benzoisoxazolyl, or benzopyrazolyl, and A is optionally substituted with 1 or 2 $R^2$ groups, wherein each occurrence of $R^2$ is independently substituted or unsubstituted $C_{1-6}$ alkyl. In certain embodiments of Formula (I-c), L is a bond; $R^1$ is hydrogen or fluoro; A is imidazo[1,2-a]pyrazinyl, and A is optionally substituted with 1 or 2 $R^2$ groups, wherein each occurrence of $R^2$ is independently fluoro, cyano, or substituted or unsubstituted $C_{1-6}$ alkyl. In certain embodiments of Formula (I-c), L is a bond; A is an unsubstituted 5,6 bicyclic heteroaryl. In certain embodiments of Formula (I-c), L is a bond; A is unsubstituted imidazo[1,2-a]pyrazinyl.

In certain embodiments, the compound of Formula (I) is of Formula (I-c-1):

(I-c-1)

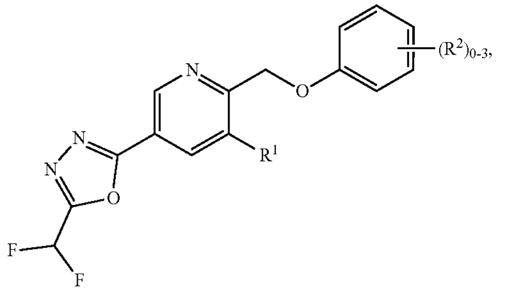

or a pharmaceutically acceptable salt thereof; wherein $R^1$ and $R^2$ are as defined herein.

In certain embodiments of Formula (I-c-1), $R^1$ is hydrogen or fluorine; and each $R^2$ is independently chlorine, fluorine, —CN, —$CH_2CN$, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-c-1), $R^1$ is hydrogen or fluorine; and each $R^2$ is independently chlorine or fluorine.

In certain embodiments of Formula (I-c-1), $R^1$ is hydrogen or fluorine; and each $R^2$ is fluorine. In certain embodiments of Formula (I-c-1), $R^1$ is hydrogen or fluorine; and each $R^2$ is fluorine or cyano.

In certain embodiments, the compound of Formula (I) is of Formula (I-c-2):

(I-c-2)

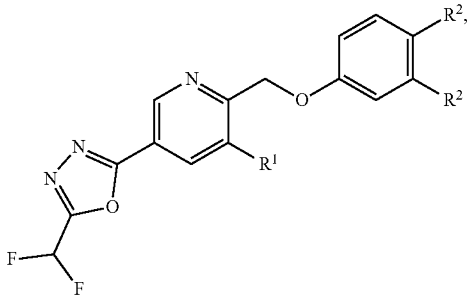

or a pharmaceutically acceptable salt thereof; wherein $R^1$ and $R^2$ are as defined herein.

In certain embodiments of Formula (I-c-2), $R^1$ is hydrogen or fluorine and each $R^2$ is independently chlorine, fluorine, —CN, —$CH_2CN$, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-c-2), $R^1$ is hydrogen or fluorine and each $R^2$ is independently chlorine or fluorine.

In certain embodiments of Formula (I-c-2), $R^1$ is hydrogen or fluorine and each $R^2$ is fluorine.

In certain embodiments, the compound of Formula (I) is of Formula (I-c-3):

(I-c-3)

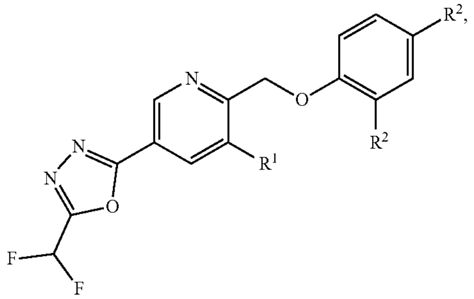

or a pharmaceutically acceptable salt thereof; wherein $R^1$ and $R^2$ are as defined herein.

In certain embodiments of Formula (I-c-3), $R^1$ is hydrogen or fluorine and each $R^2$ is independently chlorine, fluorine, —CN, —$CH_2CN$, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-c-3), $R^1$ is hydrogen or fluorine and each $R^2$ is independently chlorine or fluorine.

In certain embodiments of Formula (I-c-3), $R^1$ is hydrogen or fluorine and each $R^2$ is fluorine.

In certain embodiments, the compound of Formula (I) is of Formula (I-c-4):

(I-c-4)

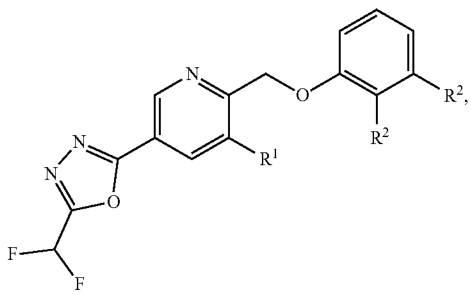

or a pharmaceutically acceptable salt thereof; wherein $R^1$ and $R^2$ are as defined herein.

In certain embodiments of Formula (I-c-4), $R^1$ is hydrogen or fluorine and each $R^2$ is independently chlorine, fluorine, —CN, —$CH_2CN$, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-c-4), $R^1$ is hydrogen or fluorine and each $R^2$ is independently chlorine or fluorine.

In certain embodiments of Formula (I-c-4), $R^1$ is hydrogen or fluorine and each $R^2$ is fluorine.

In certain embodiments, the compound of Formula (I) is of Formula (I-d):

(I-d)

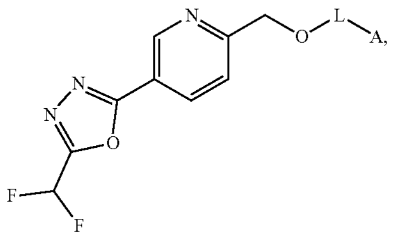

or a pharmaceutically acceptable salt thereof; wherein L and A are as defined herein.

In certain embodiments of Formula (I-d), L is a bond or —$CH_2$—; A is a phenyl, a 6-membered heteroaryl, a $C_6$ aryl ring fused to a 6-membered carbocyclyl, a 6,6 bicyclic aryl ring system, a 5,6 bicyclic heteroaryl ring system, or a 6,6 bicyclic heteroaryl ring system, and wherein A is optionally substituted with one or more substituents $R^2$; and each $R^2$ is independently chlorine, fluorine, —CN, —$CH_2CN$, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-d), L is a bond or —$CH_2$—; A is a phenyl or a 6-membered heteroaryl, and wherein A is optionally substituted with one or more substituents $R^2$; and each $R^2$ is independently chlorine, fluorine, —CN, —$CH_2CN$, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-d), L is a bond or —$CH_2$—; A is a $C_6$ aryl ring fused to a 6-membered carbocyclyl and wherein A is optionally substituted with one or more substituents $R^2$; and each $R^2$ is independently chlorine, fluorine, —CN, —$CH_2CN$, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-d), L is a bond or —$CH_2$—; A is a 5,6 bicyclic heteroaryl ring system, or a 6,6 bicyclic heteroaryl ring system, and wherein A is optionally substituted with one or more substituents $R^2$; and each $R^2$ is independently chlorine, fluorine, —CN, —$CH_2CN$, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-d), L is a bond or —$CH_2$—; A is a 6,6 bicyclic aryl ring system and wherein A is optionally substituted with one or more substituents $R^2$; and each $R^2$ is independently chlorine, fluorine, —CN, —$CH_2CN$, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-d), A is phenyl, pyridinyl or pyrimidinyl, and A is optionally substituted with 1 or 2 $R^2$ groups, wherein each occurrence of $R^2$ is independently fluoro, chloro, cyano, methyl optionally substituted with one or more fluoro, or methyl optionally substituted with a cyano.

In certain embodiments of Formula (I-d), A is a bicyclic fused heteroaryl comprising at least two heteroatoms (e.g., S, N, O), and A is optionally substituted with 1 or 2 $R^2$ groups, wherein each occurrence of $R^2$ is independently fluoro, cyano, or substituted or unsubstituted $C_{1-6}$ alkyl. In certain embodiments of Formula (I-d), A is a 5,6 bicyclic fused heteroaryl comprising at least two heteroatoms (e.g., S, N, O), and A is optionally substituted with 1 or 2 $R^2$ groups, wherein each occurrence of $R^2$ is independently fluoro, cyano, or substituted or unsubstituted $C_{1-6}$ alkyl. In certain embodiments of Formula (I-d), A is quinazolinyl, imidazo[1,2-a]pyrazinyl, benzoisoxazolyl, or benzopyrazolyl, and A is optionally substituted with 1 or 2 $R^2$ groups, wherein each occurrence of $R^2$ is independently fluoro, cyano, or substituted or unsubstituted $C_{1-6}$ alkyl. In certain embodiments of Formula (I-d), A is imidazo[1,2-a]pyrazinyl, and A is optionally substituted with 1 or 2 $R^2$ groups, wherein each occurrence of $R^2$ is independently fluoro, cyano, or substituted or unsubstituted $C_{1-6}$ alkyl. In certain embodiments of Formula (I-d), A is an unsubstituted 5,6 bicyclic heteroaryl. In certain embodiments of Formula (I-d), A is unsubstituted imidazo[1,2-a]pyrazinyl.

In certain embodiments of Formula (I-d), L is a bond; and A is a bicyclic fused heteroaryl comprising at least two heteroatoms (e.g., S, N, O), and A is optionally substituted with 1 or 2 $R^2$ groups, wherein each occurrence of $R^2$ is independently fluoro, cyano, or substituted or unsubstituted $C_{1-6}$ alkyl. In certain embodiments of Formula (I-d), L is a bond; A is a 5,6 bicyclic fused heteroaryl comprising at least two heteroatoms (e.g., S, N, O), and A is optionally substituted with 1 or 2 $R^2$ groups, wherein each occurrence of $R^2$ is independently fluoro, cyano, or substituted or unsubstituted $C_{1-6}$ alkyl. In certain embodiments of Formula (I-d), L is a bond; and A is quinazolinyl, imidazo[1,2-a]pyrazinyl, benzoisoxazolyl, or benzopyrazolyl, and A is optionally substituted with 1 or 2 $R^2$ groups, wherein each occurrence of $R^2$ is independently fluoro, cyano, or substituted or unsubstituted $C_{1-6}$ alkyl. In certain embodiments of Formula (I-d), L is a bond; and A is imidazo[1,2-a]pyrazinyl, and A is optionally substituted with 1 or 2 $R^2$ groups, wherein each occurrence of $R^2$ is independently fluoro, cyano, or substituted or unsubstituted $C_{1-6}$ alkyl. In certain embodiments of Formula (I-d), L is a bond; A is an unsubstituted 5,6 bicyclic heteroaryl. In certain embodiments of Formula (I-d), L is a bond; and A is unsubstituted imidazo[1,2-a]pyrazinyl.

In certain embodiments, the compound of Formula (I) is of Formula (I-d-1):

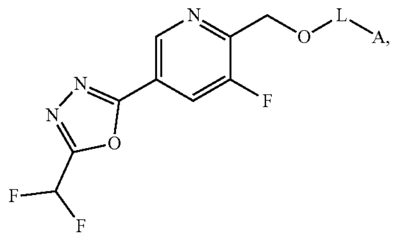

(I-d-1)

or a pharmaceutically acceptable salt thereof; wherein L and A are as defined herein.

In certain embodiments of Formula (I-d-1), L is a bond or —$CH_2$—; A is a phenyl, a 6-membered heteroaryl, a $C_6$ aryl ring fused to a 6-membered carbocyclyl, a 6,6 bicyclic aryl ring system, a 5,6 bicyclic heteroaryl ring system, or a 6,6 bicyclic heteroaryl ring system, and wherein A is optionally substituted with one or more substituents $R^2$; and each $R^2$ is independently chlorine, fluorine, —CN, —$CH_2$CN, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-d-1), L is a bond or —$CH_2$—; A is a phenyl or a 6-membered heteroaryl, and wherein A is optionally substituted with one or more substituents $R^2$; and each $R^2$ is independently chlorine, fluorine, —CN, —$CH_2$CN, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-d-1), L is a bond or —$CH_2$—; A is a $C_6$ aryl ring fused to a 6-membered carbocyclyl and wherein A is optionally substituted with one or more substituents $R^2$; and each $R^2$ is independently chlorine, fluorine, —CN, —$CH_2$CN, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-d-1), L is a bond or —$CH_2$—; A is a 5,6 bicyclic heteroaryl ring system, or a 6,6 bicyclic heteroaryl ring system, and wherein A is optionally substituted with one or more substituents $R^2$; and each $R^2$ is independently chlorine, fluorine, —CN, —$CH_2$CN, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-d-1), L is a bond or —$CH_2$—; A is a 6,6 bicyclic aryl ring system and wherein A is optionally substituted with one or more substituents $R^2$; and each $R^2$ is independently chlorine, fluorine, —CN, —$CH_2$CN, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-d-1), A is phenyl, pyridinyl or pyrimidinyl, and A is optionally substituted with 1 or 2 $R^2$ groups, wherein each occurrence of $R^2$ is independently fluoro, chloro, cyano, methyl optionally substituted with one or more fluoro, or methyl optionally substituted with a cyano.

In certain embodiments of Formula (I-d-1), L is a bond; A is quinazolinyl, benzoisoxazolyl, or benzopyrazolyl, and A is optionally substituted with 1 or 2 $R^2$ groups, wherein each occurrence of $R^2$ is independently fluoro, cyano, or substituted or unsubstituted $C_{1-6}$ alkyl.

In certain embodiments, the compound of Formula (I) is of Formula (I-d-2):

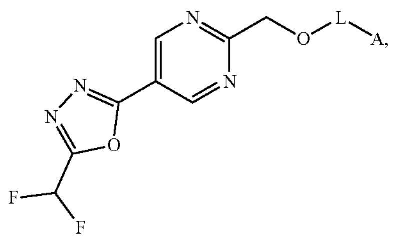

(I-d-2)

or a pharmaceutically acceptable salt thereof; wherein A, $R^1$, and L are as defined herein.

In certain embodiments of Formula (I-d-2), L is a bond or —$CH_2$—; A is a phenyl, a 6-membered heteroaryl, a $C_6$ aryl ring fused to a 6-membered carbocyclyl, a 6,6 bicyclic aryl ring system, a 5,6 bicyclic heteroaryl ring system, or a 6,6 bicyclic heteroaryl ring system, and wherein A is optionally substituted with one or more substituents $R^2$; and each $R^2$ is independently chlorine, fluorine, —CN, —$CH_2$CN, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-d-2), L is a bond or —$CH_2$—; A is a phenyl or a 6-membered heteroaryl, and wherein A is optionally substituted with one or more substituents $R^2$; and each $R^2$ is independently chlorine, fluorine, —CN, —$CH_2$CN, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-d-2), L is a bond or —$CH_2$—; A is a $C_6$ aryl ring fused to a 6-membered carbocyclyl and wherein A is optionally substituted with one or more substituents $R^2$; and each $R^2$ is independently chlorine, fluorine, —CN, —$CH_2$CN, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-d-2), L is a bond or —$CH_2$—; A is a 5,6 bicyclic heteroaryl ring system, or a 6,6 bicyclic heteroaryl ring system, and wherein A is optionally substituted with one or more substituents $R^2$; and each $R^2$ is independently chlorine, fluorine, —CN, —$CH_2$CN, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-d-2), L is a bond or —$CH_2$—; A is a 6,6 bicyclic aryl ring system and wherein A is optionally substituted with one or more substituents $R^2$; and each $R^2$ is independently chlorine, fluorine, —CN, —$CH_2CN$, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-d-2), A is phenyl, pyridinyl or pyrimidinyl, and A is optionally substituted with 1 or 2 $R^2$ groups, wherein each occurrence of $R^2$ is independently fluoro, chloro, cyano, methyl optionally substituted with one or more fluoro, or methyl optionally substituted with a cyano.

In certain embodiments of Formula (I-d-2), A is phenyl, and A is optionally substituted with 1 or 2 $R^2$ groups, wherein each occurrence of $R^2$ is independently fluoro or cyano.

In certain embodiments, the compound of Formula (I) is of Formula (I-e):

(I-e)

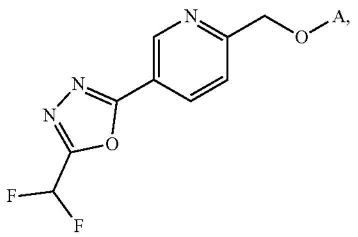

or a pharmaceutically acceptable salt thereof; wherein A is as defined herein.

In certain embodiments of Formula (I-e), A is a phenyl, a 6-membered heteroaryl, a $C_6$ aryl ring fused to a 6-membered carbocyclyl, a 6,6 bicyclic aryl ring system, a 5,6 bicyclic heteroaryl ring system, or a 6,6 bicyclic heteroaryl ring system, and wherein A is optionally substituted with one or more substituents $R^2$; and each $R^2$ is independently chlorine, fluorine, —CN, —$CH_2CN$, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-e), A is a phenyl or a 6-membered heteroaryl, and wherein A is optionally substituted with one or more substituents $R^2$; and each $R^2$ is independently chlorine, fluorine, —CN, —$CH_2CN$, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-e), A is a $C_6$ aryl ring fused to a 6-membered carbocyclyl and wherein A is optionally substituted with one or more substituents $R^2$; and each $R^2$ is independently chlorine, fluorine, —CN, —$CH_2CN$, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-e), A is a 5,6 bicyclic heteroaryl ring system, or a 6,6 bicyclic heteroaryl ring system, and wherein A is optionally substituted with one or more substituents $R^2$; and each $R^2$ is independently chlorine, fluorine, —CN, —$CH_2CN$, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-e), A is a 6,6 bicyclic aryl ring system and wherein A is optionally substituted with one or more substituents $R^2$; and each $R^2$ is independently chlorine, fluorine, —CN, —$CH_2CN$, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-e), A is phenyl, pyridinyl or pyrimidinyl, and A is optionally substituted with 1 or 2 $R^2$ groups, wherein each occurrence of $R^2$ is independently fluoro, chloro, cyano, methyl optionally substituted with one or more fluoro, or methyl optionally substituted with a cyano.

In certain embodiments of Formula (I-e), A is a bicyclic fused heteroaryl comprising at least two heteroatoms (e.g., S, N, O), and A is optionally substituted with 1 or 2 $R^2$ groups, wherein each occurrence of $R^2$ is independently fluoro, cyano, or substituted or unsubstituted $C_{1-6}$ alkyl. In certain embodiments of Formula (I-e), A is a 5,6 bicyclic fused heteroaryl comprising at least two heteroatoms (e.g., S, N, O), and A is optionally substituted with 1 or 2 $R^2$ groups, wherein each occurrence of $R^2$ is independently fluoro, cyano, or substituted or unsubstituted $C_{1-6}$ alkyl. In certain embodiments of Formula (I-e), A is quinazolinyl, imidazo[1,2-a]pyrazinyl, benzoisoxazolyl, or benzopyrazolyl, and A is optionally substituted with 1 or 2 $R^2$ groups, wherein each occurrence of $R^2$ is independently fluoro, cyano, or substituted or unsubstituted $C_{1-6}$ alkyl. In certain embodiments of Formula (I-e), A is imidazo[1,2-a]pyrazinyl, and A is optionally substituted with 1 or 2 $R^2$ groups, wherein each occurrence of $R^2$ is independently fluoro, cyano, or substituted or unsubstituted $C_{1-6}$ alkyl. In certain embodiments of Formula (I-e), A is an unsubstituted 5,6 bicyclic heteroaryl. In certain embodiments of Formula (I-e), A is unsubstituted imidazo[1,2-a]pyrazinyl.

In certain embodiments, the compound of Formula (I) is of Formula (I-e-1):

(I-e-1)

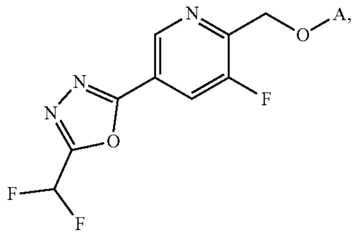

or a pharmaceutically acceptable salt thereof; wherein A is as defined herein.

In certain embodiments of Formula (I-e-1), A is a phenyl, a 6-membered heteroaryl, a $C_6$ aryl ring fused to a 6-membered carbocyclyl, a 6,6 bicyclic aryl ring system, a 5,6 bicyclic heteroaryl ring system, or a 6,6 bicyclic heteroaryl ring system, and wherein A is optionally substituted with one or more substituents $R^2$; and each $R^2$ is independently chlorine, fluorine, —CN, —$CH_2CN$, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-e-1), A is a phenyl or a 6-membered heteroaryl, and wherein A is optionally substituted with one or more substituents $R^2$; and each $R^2$ is independently chlorine, fluorine, —CN, —$CH_2CN$, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-e-1), L is a bond or —$CH_2$—; A is a $C_6$ aryl ring fused to a 6-membered carbocyclyl and wherein A is optionally substituted with one or more substituents $R^2$; and each $R^2$ is independently chlorine, fluorine, —CN, —$CH_2$CN, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-e-1), A is a 5,6 bicyclic heteroaryl ring system, or a 6,6 bicyclic heteroaryl ring system, and wherein A is optionally substituted with one or more substituents $R^2$; and each $R^2$ is independently chlorine, fluorine, —CN, —$CH_2$CN, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-e-1), A is a 6,6 bicyclic aryl ring system and wherein A is optionally substituted with one or more substituents $R^2$; and each $R^2$ is independently chlorine, fluorine, —CN, —$CH_2$CN, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-e-1), A is phenyl, pyridinyl or pyrimidinyl, and A is optionally substituted with 1 or 2 $R^2$ groups, wherein each occurrence of $R^2$ is independently fluoro, chloro, cyano, methyl optionally substituted with one or more fluoro, or methyl optionally substituted with a cyano.

In certain embodiments of Formula (I-e-1), A is quinazolinyl, benzoisoxazolyl, or benzopyrazolyl, and A is optionally substituted with 1 or 2 $R^2$ groups, wherein each occurrence of $R^2$ is independently substituted or unsubstituted $C_{1-6}$ alkyl.

In certain embodiments, the compound of Formula (I) is of Formula (I-e-2):

(I-e-2)

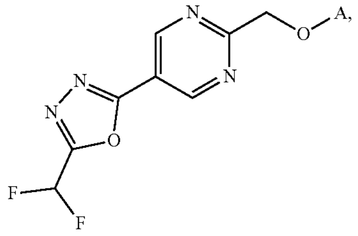

or a pharmaceutically acceptable salt thereof; wherein A is as defined herein.

In certain embodiments of Formula (I-e-2), A is a phenyl, a 6-membered heteroaryl, a $C_6$ aryl ring fused to a 6-membered carbocyclyl, a 6,6 bicyclic aryl ring system, a 5,6 bicyclic heteroaryl ring system, or a 6,6 bicyclic heteroaryl ring system, and wherein A is optionally substituted with one or more substituents $R^2$; and each $R^2$ is independently chlorine, fluorine, —CN, —$CH_2$CN, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-e-2), A is a phenyl or a 6-membered heteroaryl, and wherein A is optionally substituted with one or more substituents $R^2$; and each $R^2$ is independently chlorine, fluorine, —CN, —$CH_2$CN, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-e-2), L is a bond or —$CH_2$—; A is a $C_6$ aryl ring fused to a 6-membered carbocyclyl and wherein A is optionally substituted with one or more substituents $R^2$; and each $R^2$ is independently chlorine, fluorine, —CN, —$CH_2$CN, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-e-2), A is a 5,6 bicyclic heteroaryl ring system, or a 6,6 bicyclic heteroaryl ring system, and wherein A is optionally substituted with one or more substituents $R^2$; and each $R^2$ is independently chlorine, fluorine, —CN, —$CH_2$CN, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-e-2), A is a 6,6 bicyclic aryl ring system and wherein A is optionally substituted with one or more substituents $R^2$; and each $R^2$ is independently chlorine, fluorine, —CN, —$CH_2$CN, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-e-2), A is phenyl, pyridinyl or pyrimidinyl, and A is optionally substituted with 1 or 2 $R^2$ groups, wherein each occurrence of $R^2$ is independently fluoro, chloro, cyano, methyl optionally substituted with one or more fluoro, or methyl optionally substituted with a cyano.

In certain embodiments of Formula (I-e-2), A is phenyl, and A is optionally substituted with 1 or 2 $R^2$ groups, wherein each occurrence of $R^2$ is independently fluoro or cyano.

In certain embodiments, the compound of Formula (I) is of Formula (I-f):

(I-f)

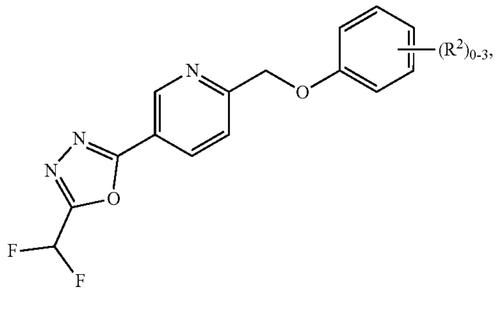

or a pharmaceutically acceptable salt thereof; wherein $R^2$ is as defined herein.

In certain embodiments of Formula (I-f), each $R^2$ is independently chlorine, fluorine, —CN, —$CH_2$CN, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-f), each $R^2$ is independently chlorine or fluorine.

In certain embodiments of Formula (I-f), each $R^2$ is fluorine.

In certain embodiments of Formula (I-f), each occurrence of $R^2$ is independently fluoro, chloro, cyano, methyl optionally substituted with one or more fluoro, or methyl optionally substituted with a cyano.

In certain embodiments, the compound of Formula (I) is of Formula (I-f-1):

(I-f-1)

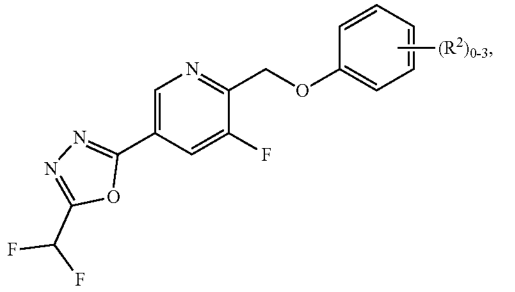

or a pharmaceutically acceptable salt thereof; wherein $R^2$ is as defined herein.

In certain embodiments of Formula (I-f-1), each $R^2$ is independently chlorine, fluorine, —CN, —$CH_2CN$, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-f-1), each $R^2$ is independently chlorine or fluorine.

In certain embodiments of Formula (I-f-1), each $R^2$ is fluorine.

In certain embodiments of Formula (I-f-1), each occurrence of $R^2$ is independently fluoro, chloro, cyano, methyl optionally substituted with one or more fluoro, or methyl optionally substituted with a cyano.

In certain embodiments, the compound of Formula (I) is of Formula (I-f-2):

(I-f-2)

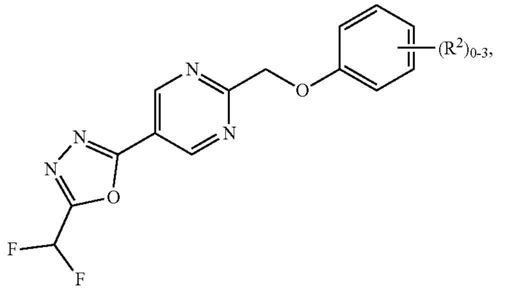

or a pharmaceutically acceptable salt thereof; wherein $R^2$ is as defined herein.

In certain embodiments of Formula (I-f-2), each $R^2$ is independently chlorine, fluorine, —CN, —$CH_2CN$, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-f-2), each $R^2$ is independently chlorine or fluorine.

In certain embodiments of Formula (I-f-2), each $R^2$ is fluorine.

In certain embodiments of Formula (I-f-2), each occurrence of $R^2$ is independently fluoro, chloro, cyano, methyl optionally substituted with one or more fluoro, or methyl optionally substituted with a cyano.

In certain embodiments, the compound of Formula (I) is of Formula (I-g):

(I-g)

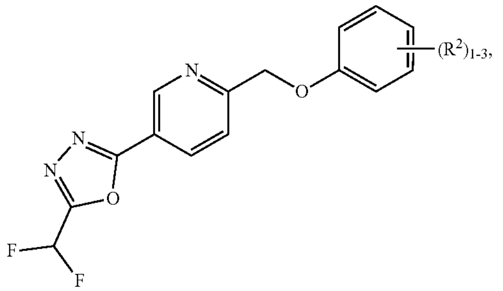

or a pharmaceutically acceptable salt thereof; wherein $R^2$ is as defined herein.

In certain embodiments of Formula (I-g), each $R^2$ is independently chlorine, fluorine, —CN, —$CH_2CN$, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-g), each $R^2$ is independently chlorine or fluorine.

In certain embodiments of Formula (I-g), each $R^2$ is fluorine.

In certain embodiments of Formula (I-g), each occurrence of $R^2$ is independently fluoro, chloro, cyano, methyl optionally substituted with one or more fluoro, or methyl optionally substituted with a cyano.

In certain embodiments, the compound of Formula (I) is of Formula (I-g-1):

(I-g-1)

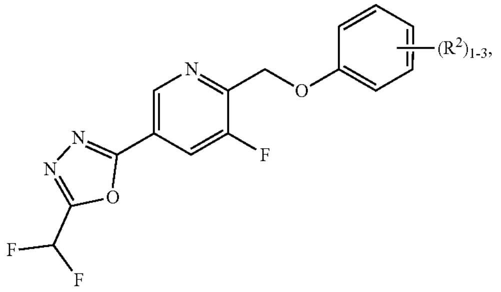

or a pharmaceutically acceptable salt thereof; wherein $R^2$ is as defined herein.

In certain embodiments of Formula (I-g-1), each $R^2$ is independently chlorine, fluorine, —CN, —$CH_2CN$, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-g-1), each $R^2$ is independently chlorine or fluorine.

In certain embodiments of Formula (I-g-1), each $R^2$ is fluorine.

In certain embodiments of Formula (I-g-1), each occurrence of $R^2$ is independently fluoro, chloro, cyano, methyl optionally substituted with one or more fluoro, or methyl optionally substituted with a cyano.

In certain embodiments, the compound of Formula (I) is of Formula (I-g-2):

(I-g-2)

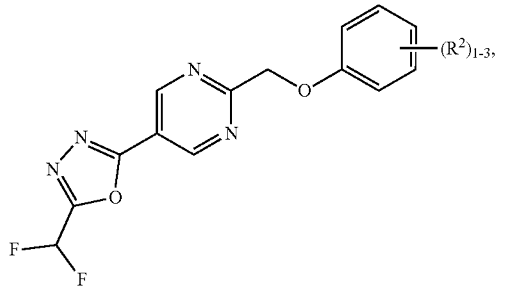

or a pharmaceutically acceptable salt thereof; wherein $R^2$ is as defined herein.

In certain embodiments of Formula (I-g-2), each $R^2$ is independently chlorine, fluorine, —CN, —$CH_2CN$, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-g-2), each $R^2$ is independently chlorine or fluorine.

In certain embodiments of Formula (I-g-2), each $R^2$ is fluorine.

In certain embodiments of Formula (I-g-2), each occurrence of $R^2$ is independently fluoro, chloro, cyano, methyl optionally substituted with one or more fluoro, or methyl optionally substituted with a cyano.

In certain embodiments of Formula (I-g-2), each $R^2$ is independently fluorine or cyano.

In certain embodiments, the compound of Formula (I) is of Formula (I-h):

(I-h)

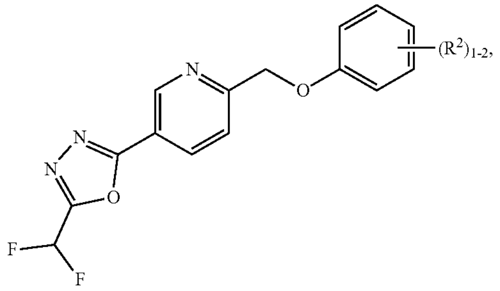

or a pharmaceutically acceptable salt thereof; wherein $R^2$ is as defined herein.

In certain embodiments of Formula (I-h), each $R^2$ is independently chlorine, fluorine, —CN, —$CH_2CN$, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-h), each $R^2$ is independently chlorine or fluorine.

In certain embodiments of Formula (I-h), each $R^2$ is fluorine.

In certain embodiments of Formula (I-h), each occurrence of $R^2$ is independently fluoro, chloro, cyano, methyl optionally substituted with one or more fluoro, or methyl optionally substituted with a cyano.

In certain embodiments, the compound of Formula (I) is of Formula (I-h-1):

(I-h-1)

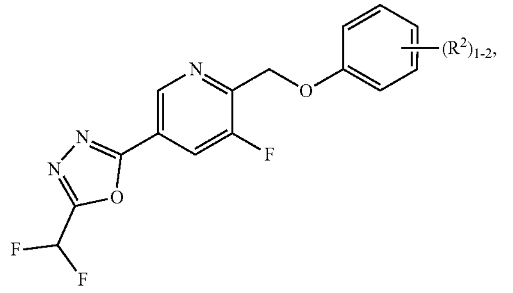

or a pharmaceutically acceptable salt thereof; wherein $R^2$ is as defined herein.

In certain embodiments of Formula (I-h-1), each $R^2$ is independently chlorine, fluorine, —CN, —$CH_2CN$, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-h-1), each $R^2$ is independently chlorine or fluorine.

In certain embodiments of Formula (I-h-1), each $R^2$ is fluorine.

In certain embodiments of Formula (I-h-1), each occurrence of $R^2$ is independently fluoro, chloro, cyano, methyl optionally substituted with one or more fluoro, or methyl optionally substituted with a cyano.

In certain embodiments, the compound of Formula (I) is of Formula (I-h-2):

(I-h-2)

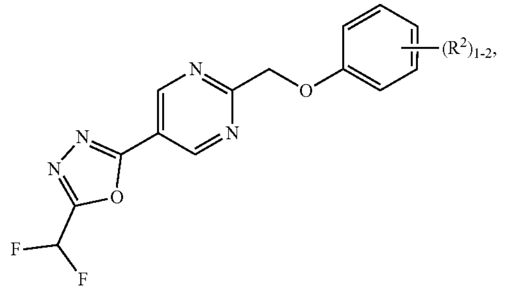

or a pharmaceutically acceptable salt thereof; wherein $R^2$ is as defined herein.

In certain embodiments of Formula (I-h-2), each $R^2$ is independently chlorine, fluorine, —CN, —$CH_2CN$, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-h-2), each $R^2$ is independently chlorine or fluorine.

In certain embodiments of Formula (I-h-2), each $R^2$ is fluorine.

In certain embodiments of Formula (I-h-2), each occurrence of $R^2$ is independently fluoro, chloro, cyano, methyl optionally substituted with one or more fluoro, or methyl optionally substituted with a cyano.

In certain embodiments, the compound of Formula (I) is of Formula (I-i):

(I-i)

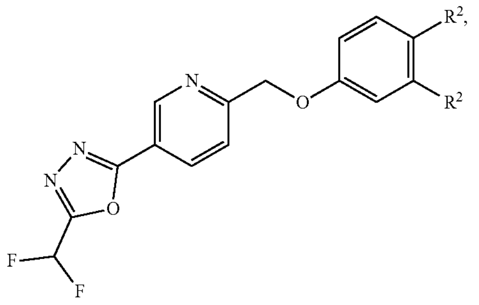

or a pharmaceutically acceptable salt thereof; wherein $R^2$ is as defined herein.

In certain embodiments of Formula (I-i), each $R^2$ is independently chlorine, fluorine, —CN, —$CH_2CN$, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-i), each $R^2$ is independently chlorine or fluorine.

In certain embodiments of Formula (I-i), each $R^2$ is fluorine.

In certain embodiments of Formula (I-i), each occurrence of $R^2$ is independently fluoro, chloro, cyano, methyl optionally substituted with one or more fluoro, or methyl optionally substituted with a cyano.

In certain embodiments, the compound of Formula (I) is of Formula (I-i-1):

(I-i-1)

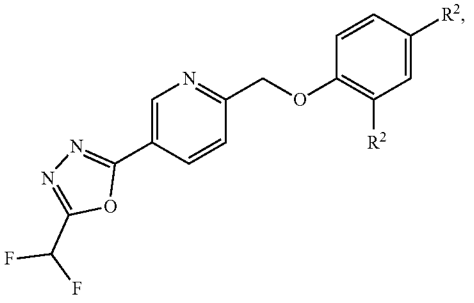

or a pharmaceutically acceptable salt thereof; wherein $R^2$ is as defined herein.

In certain embodiments of Formula (I-i-1), each $R^2$ is independently chlorine, fluorine, —CN, —$CH_2CN$, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-i-1), $R^2$ is independently chlorine or fluorine.

In certain embodiments of Formula (I-i-1), each $R^2$ is fluorine.

In certain embodiments, the compound of Formula (I) is of Formula (I-i-2):

(I-i-2)

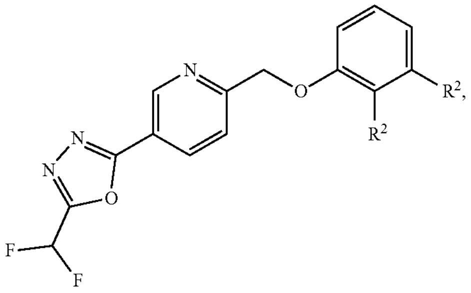

or a pharmaceutically acceptable salt thereof; wherein $R^2$ is as defined herein.

In certain embodiments of Formula (I-i-2), each $R^2$ is independently chlorine, fluorine, —CN, —$CH_2CN$, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-i-2), $R^2$ is independently chlorine or fluorine.

In certain embodiments of Formula (I-i-2), each $R^2$ is fluorine.

In certain embodiments, the compound of Formula (I) is of Formula (I-i-3):

(I-i-3)

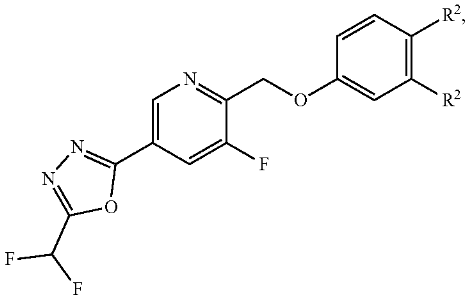

or a pharmaceutically acceptable salt thereof; wherein $R^2$ is as defined herein.

In certain embodiments of Formula (I-i-3), each $R^2$ is independently chlorine, fluorine, —CN, —$CH_2CN$, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-i-3), each $R^2$ is independently chlorine or fluorine.

In certain embodiments of Formula (I-i-3), each $R^2$ is fluorine.

In certain embodiments of Formula (I-i-3), each occurrence of $R^2$ is independently fluoro, chloro, cyano, methyl optionally substituted with one or more fluoro, or methyl optionally substituted with a cyano.

In certain embodiments, the compound of Formula (I) is of Formula (I-i-4):

(I-i-4)

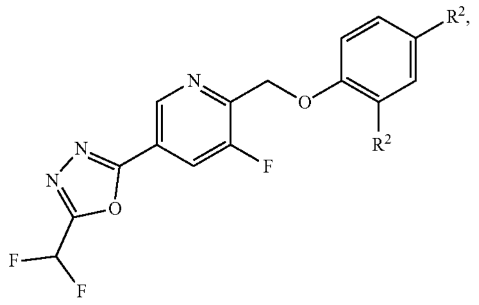

or a pharmaceutically acceptable salt thereof; wherein $R^2$ is as defined herein.

In certain embodiments of Formula (I-i-4), each $R^2$ is independently chlorine, fluorine, —CN, —$CH_2CN$, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-i-4), each $R^2$ is independently chlorine or fluorine.

In certain embodiments of Formula (I-i-4), each $R^2$ is fluorine.

In certain embodiments, the compound of Formula (I) is of Formula (I-i-5):

(I-i-5)

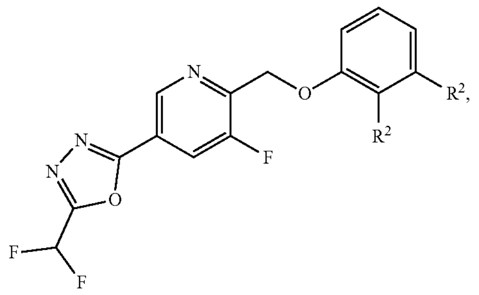

or a pharmaceutically acceptable salt thereof; wherein $R^2$ is as defined herein.

In certain embodiments of Formula (I-i-5), each $R^2$ is independently chlorine, fluorine, —CN, —$CH_2CN$, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-i-5), each $R^2$ is independently chlorine or fluorine.

In certain embodiments of Formula (I-i-5), each $R^2$ is fluorine.

In certain embodiments, the compound of Formula (I) is of Formula (I-i-6):

(I-i-6)

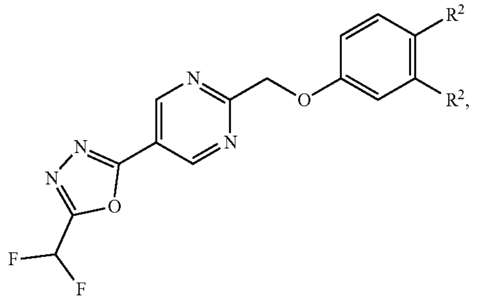

or a pharmaceutically acceptable salt thereof; wherein $R^2$ is as defined herein.

In certain embodiments of Formula (I-i-6), each $R^2$ is independently chlorine, fluorine, —CN, —$CH_2CN$, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-i-6), each $R^2$ is independently chlorine or fluorine.

In certain embodiments of Formula (I-i-6), each $R^2$ is fluorine.

In certain embodiments of Formula (I-i-6), each occurrence of $R^2$ is independently fluoro, chloro, cyano, methyl optionally substituted with one or more fluoro, or methyl optionally substituted with a cyano.

In certain embodiments, the compound of Formula (I) is of Formula (I-i-7):

(I-i-7)

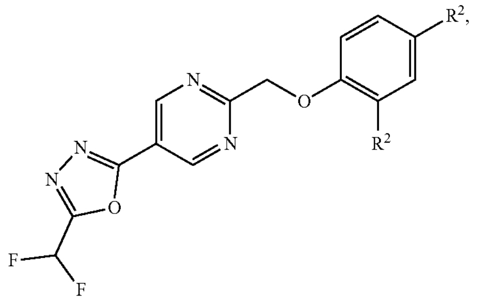

or a pharmaceutically acceptable salt thereof; wherein $R^2$ is as defined herein.

In certain embodiments of Formula (I-i-7), each $R^2$ is independently chlorine, fluorine, —CN, —$CH_2CN$, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-i-7), each $R^2$ is independently chlorine or fluorine.

In certain embodiments of Formula (I-i-7), each $R^2$ is fluorine.

In certain embodiments, the compound of Formula (I) is of Formula (I-i-8):

(I-i-8)

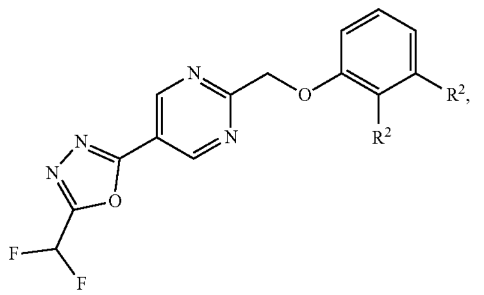

or a pharmaceutically acceptable salt thereof; wherein $R^2$ is as defined herein.

In certain embodiments of Formula (I-i-8), each $R^2$ is independently chlorine, fluorine, —CN, —$CH_2CN$, $C_{1-4}$ alkyl, $C_{3-6}$ cycloalkyl, $C_{1-4}$ haloalkyl, acyl, amide, or 5-6 membered heterocyclyl comprising one or more nitrogen, oxygen or sulfur heteroatom(s).

In certain embodiments of Formula (I-i-8), each $R^2$ is independently chlorine or fluorine.

In certain embodiments of Formula (I-i-8), each $R^2$ is fluorine.

In certain embodiments, the compound of Formula (I) is of Formula (I-j):

(I-j)

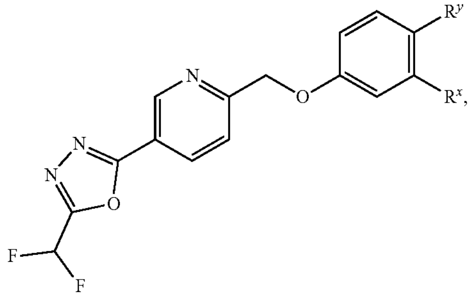

or a pharmaceutically acceptable salt thereof; wherein $R^x$ and $R^y$ join to form a 5-6 membered heteroaryl, a 4-6 membered heterocyclyl, or a $C_{4-6}$ carbocyclyl ring, wherein the resulting fused bicyclic ring is optionally substituted with 1-3 independent substituents $R^2$.

In certain embodiments of Formula (I-j), $R^x$ and $R^y$ join to form a 5-6 membered heteroaryl ring, wherein the resulting fused bicyclic ring is optionally substituted with 1-3 independent substituents $R^2$.

In certain embodiments of Formula (I-j), $R^x$ and $R^y$ join to form a 4-6 membered heterocyclyl ring, wherein the resulting fused bicyclic ring is optionally substituted with 1-3 independent substituents $R^2$.

In certain embodiments of Formula (I-j), $R^x$ and $R^y$ join to form a $C_{4-6}$ carbocyclyl ring, wherein the resulting fused bicyclic ring is optionally substituted with 1-3 independent substituents $R^2$.

In certain embodiments of Formula (I-j), each occurrence of $R^2$ is independently fluoro, chloro, cyano, methyl optionally substituted with one or more fluoro, or methyl optionally substituted with a cyano.

In certain embodiments of Formula (I-j), each occurrence of $R^2$ is independently methyl, ethyl, isopropyl, n-propyl, fluoro or chloro.

In certain embodiments of Formula (I-j), each occurrence of $R^2$ is methyl.

In certain embodiments, the compound of Formula (I) is of Formula (I-j-1):

(I-j-1)

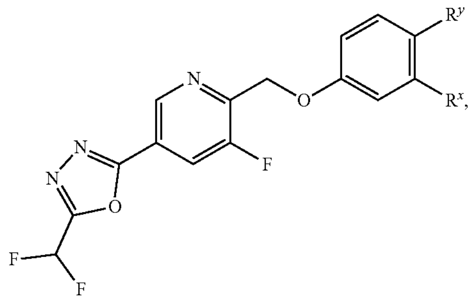

or a pharmaceutically acceptable salt thereof; wherein $R^x$ and $R^y$ join to form a 5-6 membered heteroaryl, a 4-6 membered heterocyclyl, or a $C_{4-6}$ carbocyclyl ring, wherein the resulting fused bicyclic ring is optionally substituted with 1-3 independent substituents $R^2$.

In certain embodiments of Formula (I-j-1), $R^x$ and $R^y$ join to form a 5-6 membered heteroaryl ring, wherein the resulting fused bicyclic ring is optionally substituted with 1-3 independent substituents $R^2$.

In certain embodiments of Formula (I-j-1), $R^x$ and $R^y$ join to form a 4-6 membered heterocyclyl ring, wherein the resulting fused bicyclic ring is optionally substituted with 1-3 independent substituents $R^2$.

In certain embodiments of Formula (I-j-1), $R^x$ and $R^y$ join to form a $C_{4-6}$ carbocyclyl ring, wherein the resulting fused bicyclic ring is optionally substituted with 1-3 independent substituents $R^2$.

In certain embodiments of Formula (I-j-1), each occurrence of $R^2$ is independently fluoro, chloro, cyano, methyl optionally substituted with one or more fluoro, or methyl optionally substituted with a cyano.

In certain embodiments of Formula (I-j-1), each occurrence of $R^2$ is independently methyl, ethyl, isopropyl, n-propyl, fluoro or chloro.

In certain embodiments of Formula (I-j-1), each occurrence of $R^2$ is methyl.

In certain embodiments of Formula (I-j-1), $R^x$ and $R^y$ join to form a 5-6 membered heteroaryl ring, wherein the resulting fused bicyclic ring is optionally substituted with 1-3 independent substituents $R^2$, and each occurrence of $R^2$ is independently substituted or unsubstituted $C_{1-6}$ alkyl.

In certain embodiments of Formula (I-j-1), $R^x$ and $R^y$ join to form a pyrazolyl, pyrimidinyl, or isoxazolyl, wherein the resulting fused bicyclic ring is optionally substituted with 1-3 independent substituents $R^2$, and each occurrence of $R^2$ is independently substituted or unsubstituted $C_{1-6}$ alkyl.

In certain embodiments of Formula (I-j-1), $R^x$ and $R^y$ join to form a pyrazolyl, pyrimidinyl, or isoxazolyl, wherein the resulting fused bicyclic ring is optionally substituted with 1-3 independent substituents $R^2$, and each occurrence of $R^2$ is independently unsubstituted $C_{1-6}$ alkyl.

In certain embodiments of Formula (I-j-1), $R^x$ and $R^y$ join to form a pyrazolyl, pyrimidinyl, or isoxazolyl, wherein the resulting fused bicyclic ring is optionally substituted with 1-3 independent substituents $R^2$, and each occurrence of $R^2$ is methyl.

In certain embodiments, the compound of Formula (I) is of Formula (I-j-2):

(I-j-2)

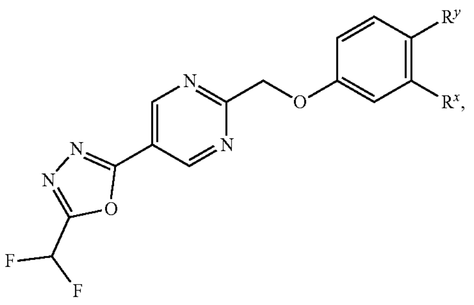

or a pharmaceutically acceptable salt thereof; wherein $R^x$ and $R^y$ join to form a 5-6 membered heteroaryl, a 4-6 membered heterocyclyl, or a $C_{4-6}$ carbocyclyl ring, wherein the resulting fused bicyclic ring is optionally substituted with 1-3 independent substituents $R^2$.

In certain embodiments of Formula (I-j-2), $R^x$ and $R^y$ join to form a 5-6 membered heteroaryl ring, wherein the resulting fused bicyclic ring is optionally substituted with 1-3 independent substituents $R^2$.

In certain embodiments of Formula (I-j-2), $R^x$ and $R^y$ join to form a 4-6 membered heterocyclyl ring, wherein the resulting fused bicyclic ring is optionally substituted with 1-3 independent substituents $R^2$.

In certain embodiments of Formula (I-j-2), $R^x$ and $R^y$ join to form a $C_{4-6}$ carbocyclyl ring, wherein the resulting fused bicyclic ring is optionally substituted with 1-3 independent substituents $R^2$.

In certain embodiments of Formula (I-j-2), each occurrence of $R^2$ is independently fluoro, chloro, cyano, methyl optionally substituted with one or more fluoro, or methyl optionally substituted with a cyano.

In certain embodiments of Formula (I-j-2), each occurrence of $R^2$ is independently methyl, ethyl, isopropyl, n-propyl, fluoro or chloro.

In certain embodiments of Formula (I-j-2), each occurrence of $R^2$ is methyl.

In certain embodiments, the compound of Formula (I) is of Formula (I-k):

(I-k)

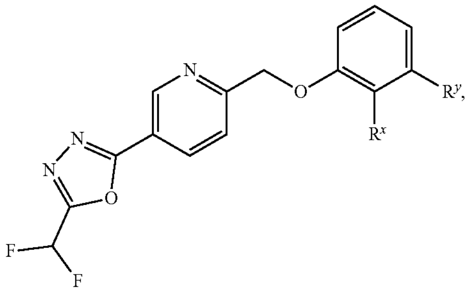

or a pharmaceutically acceptable salt thereof; wherein $R^x$ and $R^y$ join to form a 5-6 membered heteroaryl, a 4-6 membered heterocyclyl, or a $C_{4-6}$ carbocyclyl ring, wherein the resulting fused bicyclic ring is optionally substituted with 1-3 independent substituents $R^2$.

In certain embodiments of Formula (I-k), $R^x$ and $R^y$ join to form a 5-6 membered heteroaryl ring, wherein the resulting fused bicyclic ring is optionally substituted with 1-3 independent substituents $R^2$.

In certain embodiments of Formula (I-k), $R^x$ and $R^y$ join to form a 4-6 membered heterocyclyl ring, wherein the resulting fused bicyclic ring is optionally substituted with 1-3 independent substituents $R^2$.

In certain embodiments of Formula (I-k), $R^x$ and $R^y$ join to form a $C_{4-6}$ carbocyclyl ring, wherein the resulting fused bicyclic ring is optionally substituted with 1-3 independent substituents $R^2$.

In certain embodiments of Formula (I-k), each occurrence of $R^2$ is independently fluoro, chloro, cyano, methyl optionally substituted with one or more fluoro, or methyl optionally substituted with a cyano.

In certain embodiments of Formula (I-k), each occurrence of $R^2$ is independently methyl, ethyl, isopropyl, n-propyl, fluoro or chloro.

In certain embodiments of Formula (I-k), each occurrence of $R^2$ is methyl.

In certain embodiments of Formula (I-k), $R^x$ and $R^y$ join to form a 6 membered heteroaryl ring, wherein the resulting fused bicyclic ring is optionally substituted with 1-3 independent substituents $R^2$.

In certain embodiments of Formula (I-k), $R^x$ and $R^y$ join to form a pyrimidinyl, wherein the resulting fused bicyclic ring is optionally substituted with 1-3 independent substituents $R^2$.

In certain embodiments of Formula (I-k), $R^x$ and $R^y$ join to form an unsubstituted pyrimidinyl.

In certain embodiments, the compound of Formula (I) is of Formula (I-k-1):

(I-k-1)

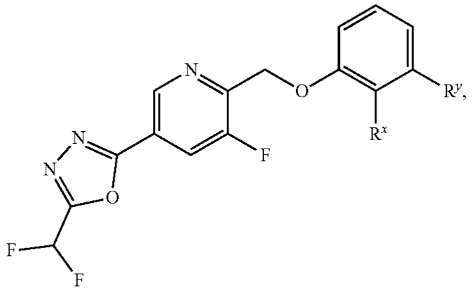

or a pharmaceutically acceptable salt thereof; wherein $R^x$ and $R^y$ join to form a 5-6 membered heteroaryl, a 4-6 membered heterocyclyl, or a $C_{4-6}$ carbocyclyl ring, wherein the resulting fused bicyclic ring is optionally substituted with 1-3 independent substituents $R^2$.

In certain embodiments of Formula (I-k-1), $R^x$ and $R^y$ join to form a 5-6 membered heteroaryl ring, wherein the resulting fused bicyclic ring is optionally substituted with 1-3 independent substituents $R^2$.

In certain embodiments of Formula (I-k-1), $R^x$ and $R^y$ join to form a 4-6 membered heterocyclyl ring, wherein the resulting fused bicyclic ring is optionally substituted with 1-3 independent substituents $R^2$.

In certain embodiments of Formula (I-k-1), $R^x$ and $R^y$ join to form a $C_{4-6}$ carbocyclyl ring, wherein the resulting fused bicyclic ring is optionally substituted with 1-3 independent substituents $R^2$.

In certain embodiments of Formula (I-k-1), each occurrence of $R^2$ is independently fluoro, chloro, cyano, methyl optionally substituted with one or more fluoro, or methyl optionally substituted with a cyano.

In certain embodiments of Formula (I-k-1), each occurrence of $R^2$ is independently methyl, ethyl, isopropyl, n-propyl, fluoro or chloro.

In certain embodiments of Formula (I-k-1), each occurrence of $R^2$ is methyl.

In certain embodiments of Formula (I-k-1), $R^x$ and $R^y$ join to form a 6 membered heteroaryl ring, wherein the resulting fused bicyclic ring is optionally substituted with 1-3 independent substituents $R^2$.

In certain embodiments of Formula (I-k-1), $R^x$ and $R^y$ join to form a pyrimidinyl, wherein the resulting fused bicyclic ring is optionally substituted with 1-3 independent substituents $R^2$.

In certain embodiments of Formula (I-k-1), $R^x$ and $R^y$ join to form an unsubstituted pyrimidinyl.

In certain embodiments, the compound of Formula (I) is of Formula (I-k-2):

(I-k-2)

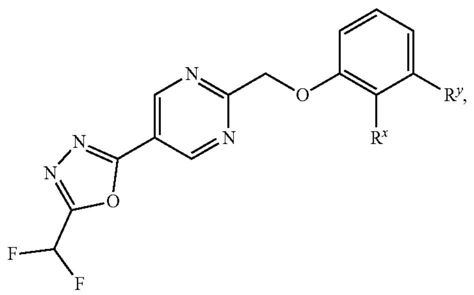

or a pharmaceutically acceptable salt thereof; wherein $R^x$ and $R^y$ join to form a 5-6 membered heteroaryl, a 4-6 membered heterocyclyl, or a $C_{4-6}$ carbocyclyl ring, wherein the resulting fused bicyclic ring is optionally substituted with 1-3 independent substituents $R^2$.

In certain embodiments of Formula (I-k-2), $R^x$ and $R^y$ join to form a 5-6 membered heteroaryl ring, wherein the resulting fused bicyclic ring is optionally substituted with 1-3 independent substituents $R^2$.

In certain embodiments of Formula (I-k-2), $R^x$ and $R^y$ join to form a 4-6 membered heterocyclyl ring, wherein the resulting fused bicyclic ring is optionally substituted with 1-3 independent substituents $R^2$.

In certain embodiments of Formula (I-k-2), $R^x$ and $R^y$ join to form a $C_{4-6}$ carbocyclyl ring, wherein the resulting fused bicyclic ring is optionally substituted with 1-3 independent substituents $R^2$.

In certain embodiments of Formula (I-k-2), each occurrence of $R^2$ is independently fluoro, chloro, cyano, methyl optionally substituted with one or more fluoro, or methyl optionally substituted with a cyano.

In certain embodiments of Formula (I-k-2), each occurrence of $R^2$ is independently methyl, ethyl, isopropyl, n-propyl, fluoro or chloro.

In certain embodiments of Formula (I-k-2), each occurrence of $R^2$ is methyl.

In certain embodiments, the compound of Formula (I) is of Formula (I-l):

(I-l)

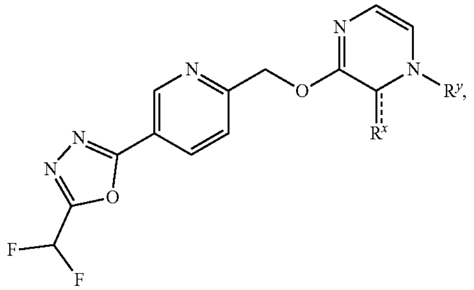

or a pharmaceutically acceptable salt thereof; wherein $R^x$ and $R^y$ join to form a 5-6 membered heteroaryl, wherein the resulting fused bicyclic ring is optionally substituted with 1-3 independent substituents $R^2$; and ⎓ is a double or single bond.

In certain embodiments of Formula (I-l), $R^x$ and $R^y$ join to form a bicyclic fused heteroaryl comprising at least two heteroatoms (e.g., S, N, O), and the resulting fused bicyclic ring is optionally substituted with 1 or 2 $R^2$ groups, wherein each occurrence of $R^2$ is independently fluoro, cyano, or substituted or unsubstituted $C_{1-6}$ alkyl.

In certain embodiments of Formula (I-l), $R^x$ and $R^y$ join to form a 5,6 bicyclic fused heteroaryl comprising at least two heteroatoms (e.g., S, N, O), and A is optionally substituted with 1 or 2 $R^2$ groups, wherein each occurrence of $R^2$ is independently fluoro, cyano, or substituted or unsubstituted $C_{1-6}$ alkyl.

In certain embodiments of Formula (I-l), $R^x$ and $R^y$ join to form an imidazo[1,2-a]pyrazinyl ring system, and A is optionally substituted with 1 or 2 $R^2$ groups, wherein each occurrence of $R^2$ is independently fluoro, cyano, or substituted or unsubstituted $C_{1-6}$ alkyl.

In certain embodiments of Formula (I-l), $R^x$ and $R^y$ join to form an unsubstituted 5,6 bicyclic heteroaryl. In certain embodiments of Formula (I-l), $R^x$ and $R^y$ join to form unsubstituted imidazo[1,2-a]pyrazinyl.

In certain embodiments, the compound of Formula (I) is of Formula (I-l-1):

(I-l-1)

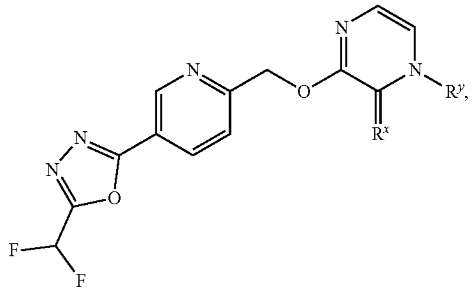

or a pharmaceutically acceptable salt thereof; wherein $R^x$ and $R^y$ join to form a 5-6 membered heteroaryl, wherein the resulting fused bicyclic ring is optionally substituted with 1-3 independent substituents $R^2$.

In certain embodiments of Formula (I-i-1), $R^x$ and $R^y$ join to form a bicyclic fused heteroaryl comprising at least two heteroatoms (e.g., S, N, O), and the resulting fused bicyclic ring is optionally substituted with 1 or 2 $R^2$ groups, wherein each occurrence of $R^2$ is independently fluoro, cyano, or substituted or unsubstituted $C_{1-6}$ alkyl.

In certain embodiments of Formula (I-i-1), $R^x$ and $R^y$ join to form a 5,6 bicyclic fused heteroaryl comprising at least two heteroatoms (e.g., S, N, O), and A is optionally substituted with 1 or 2 $R^2$ groups, wherein each occurrence of $R^2$ is independently fluoro, cyano, or substituted or unsubstituted $C_{1-6}$ alkyl.

In certain embodiments of Formula (I-i-1), $R^x$ and $R^y$ join to form an imidazo[1,2-a]pyrazinyl ring system, and A is optionally substituted with 1 or 2 $R^2$ groups, wherein each occurrence of $R^2$ is independently fluoro, cyano, or substituted or unsubstituted $C_{1-6}$ alkyl.

In certain embodiments of Formula (I-i-1), $R^x$ and $R^y$ join to form an unsubstituted 5,6 bicyclic heteroaryl. In certain embodiments of Formula (I-i-1), $R^x$ and $R^y$ join to form unsubstituted imidazo[1,2-a]pyrazinyl.

In certain embodiments, the compound of Formula (I) is one of the following compounds, or a pharmaceutically acceptable salt thereof:

1

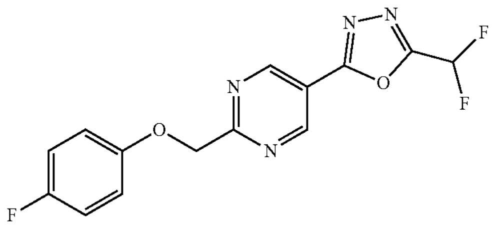

2

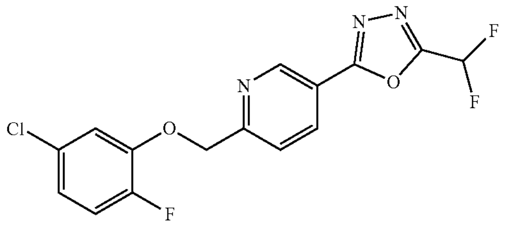

3

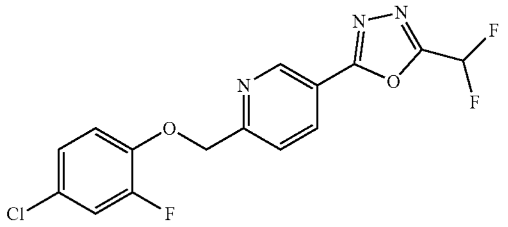

4

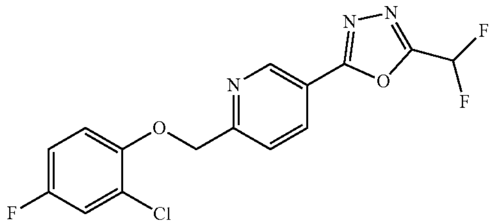

-continued

5

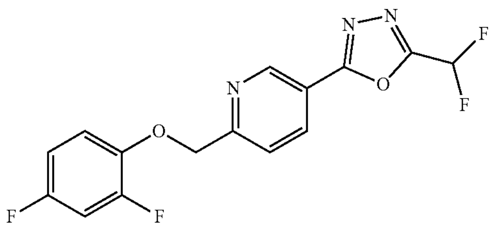

6

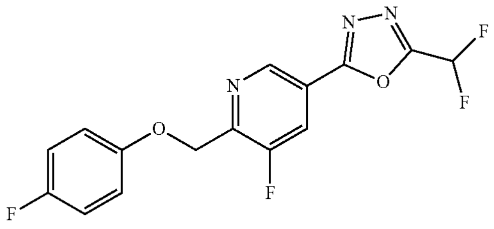

7

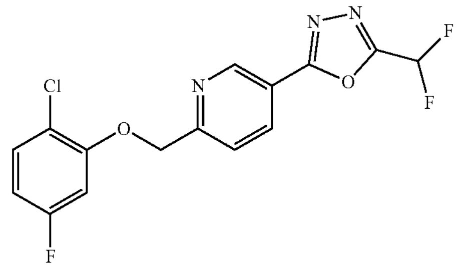

8

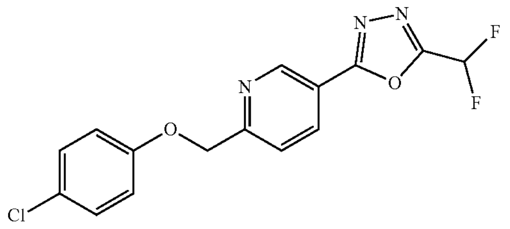

9

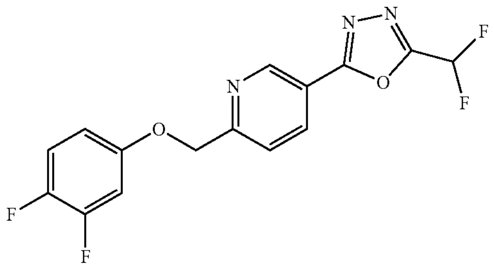

10

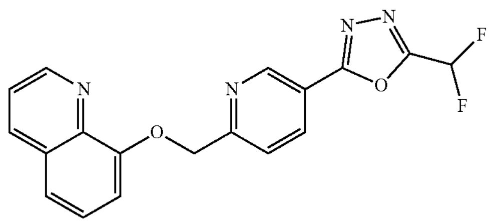

-continued
11
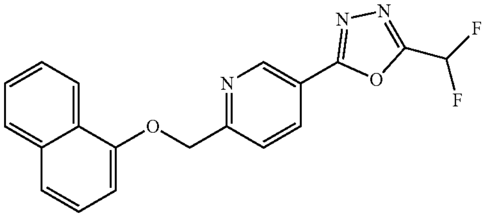
12
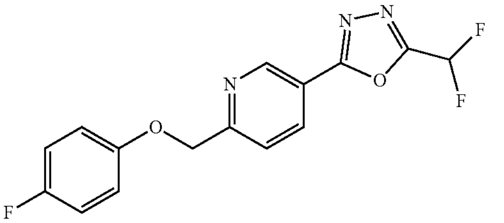
13
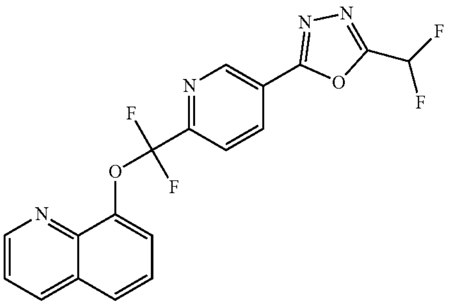
14
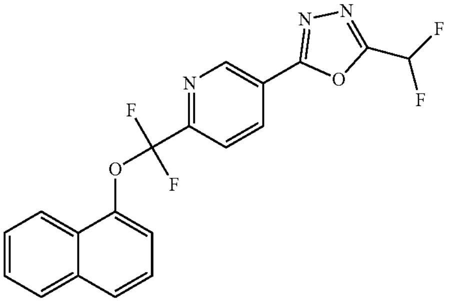
15
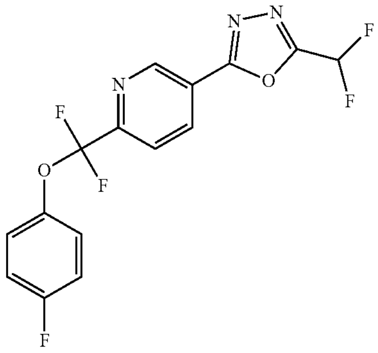
-continued
16
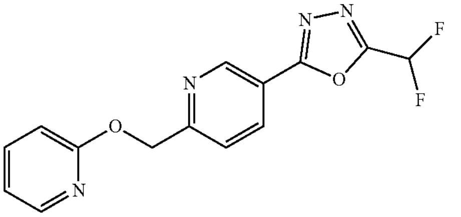
17
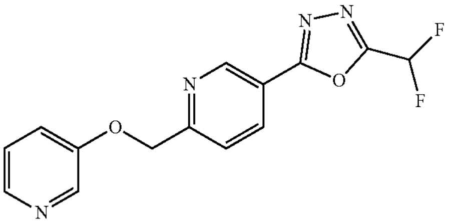
18
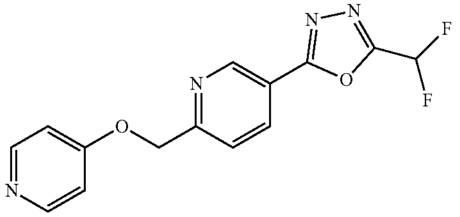
19
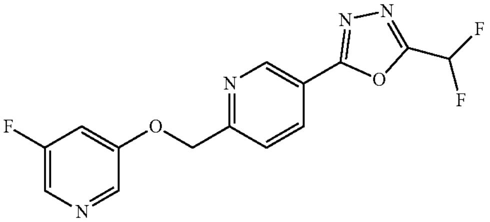
20
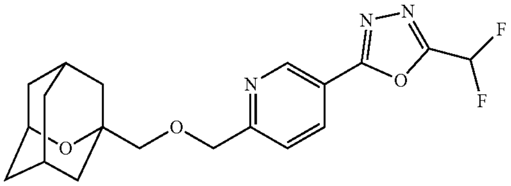
21
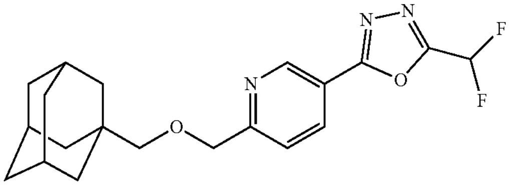
22
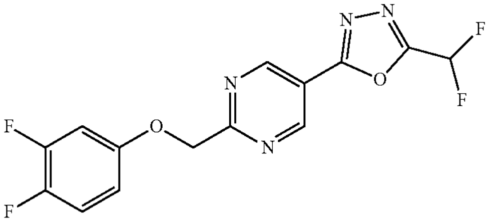

-continued
23
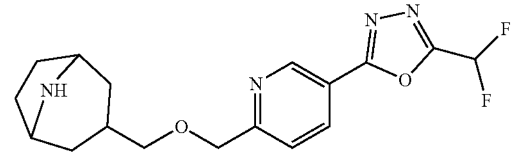
24
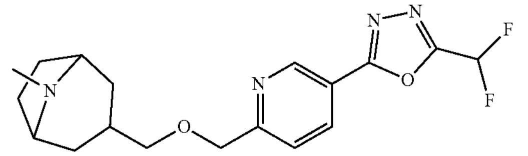
25
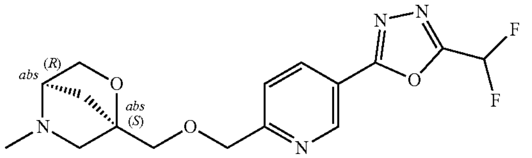
26
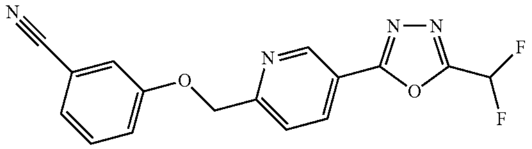
27
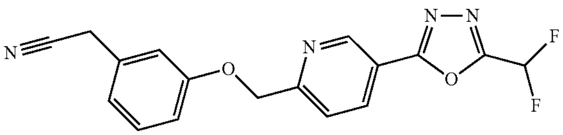
28
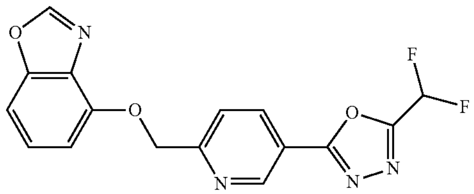
29
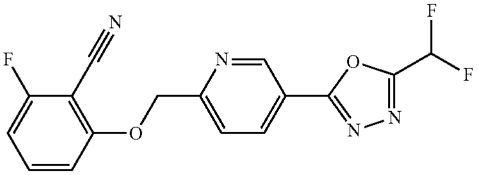
30
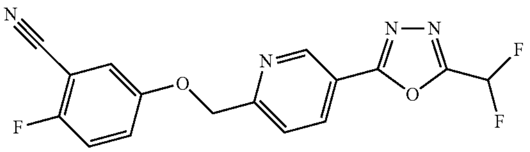
31
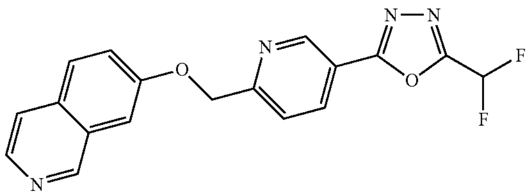
-continued
32
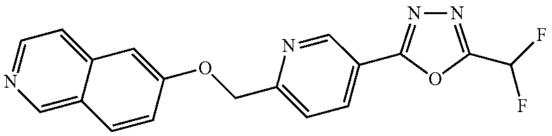
33
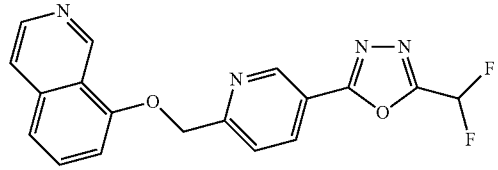
34
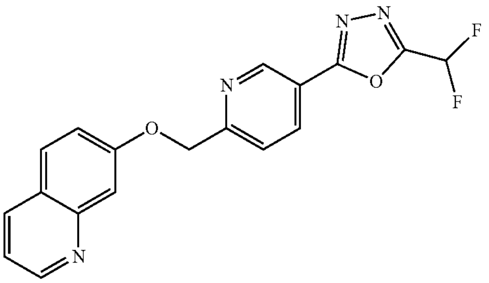
35
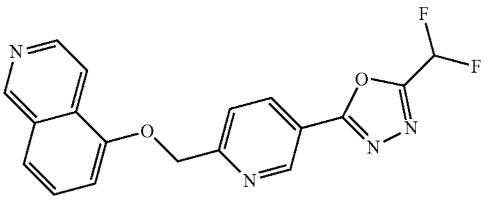
36
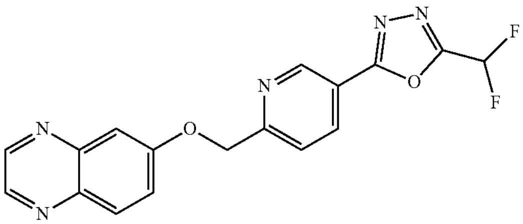
37
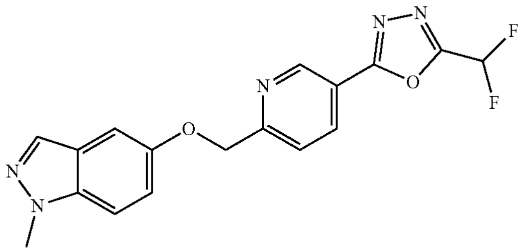
38
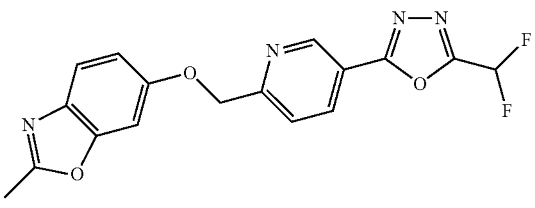

-continued
39
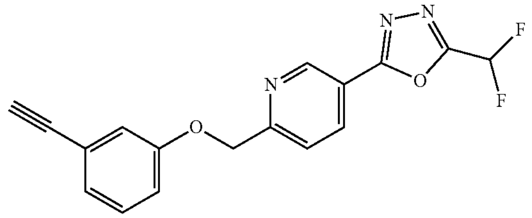
40
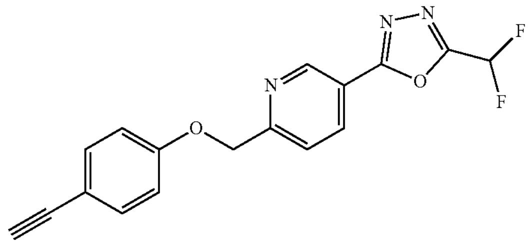
41
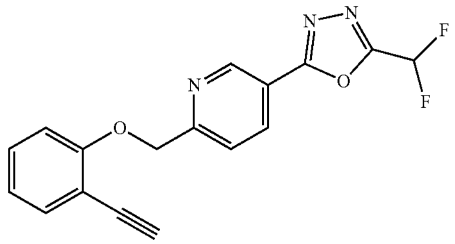
42
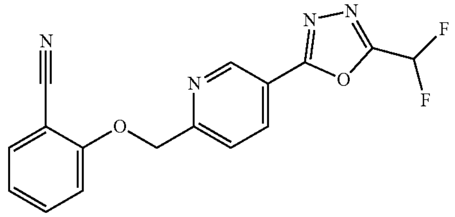
43
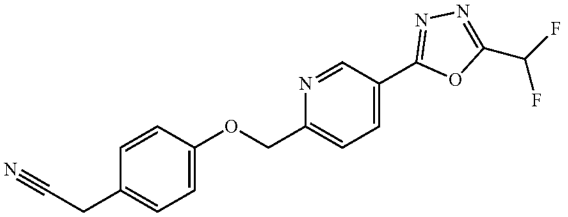
44
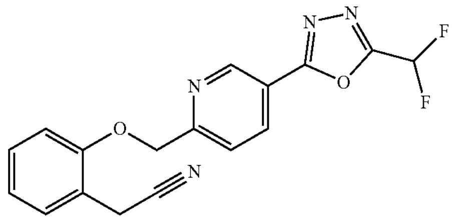
-continued
45
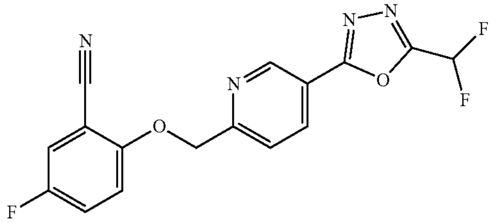
46
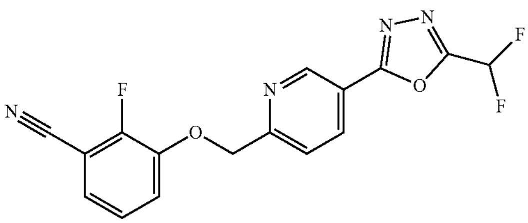
47
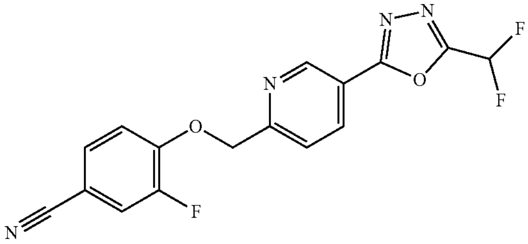
48
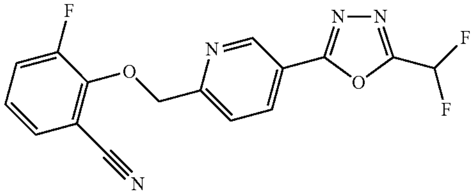
49
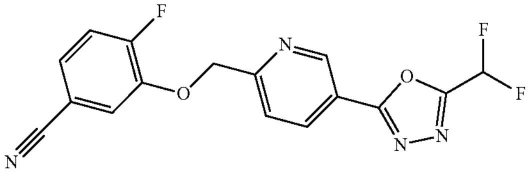
50
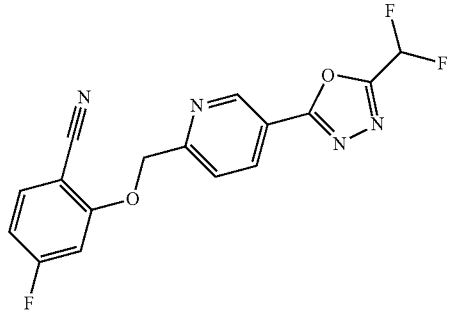

-continued
51
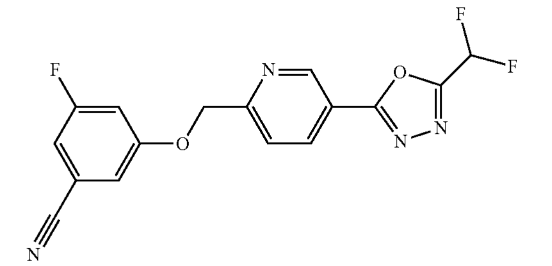
52
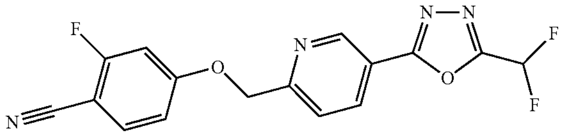
53
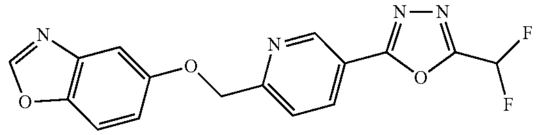
54
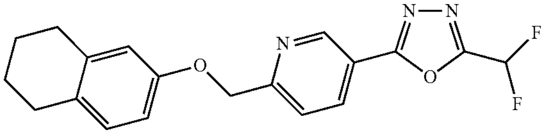
55
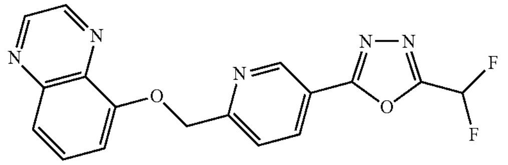
56
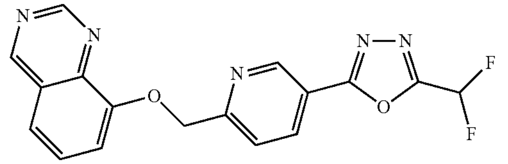
57
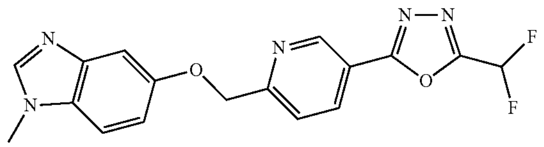
58
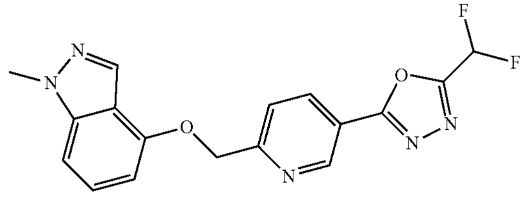
-continued
59
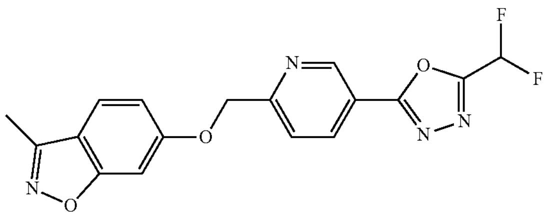
60
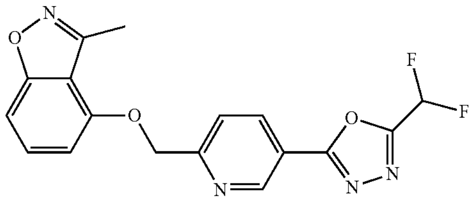
61
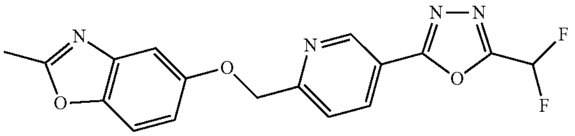
62
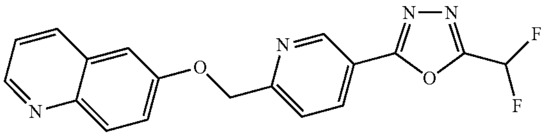
63
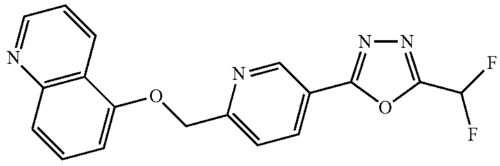
64
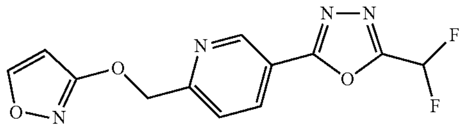
65
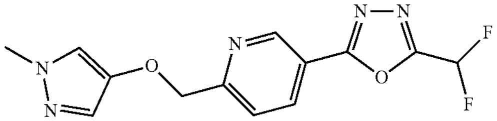
66
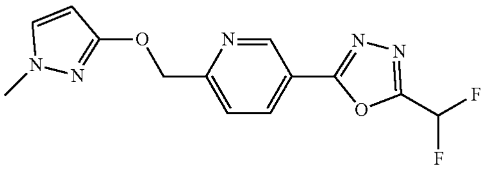
67
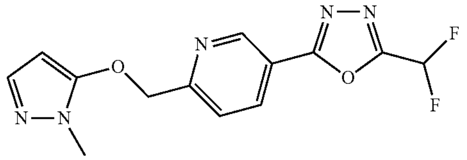

-continued
68
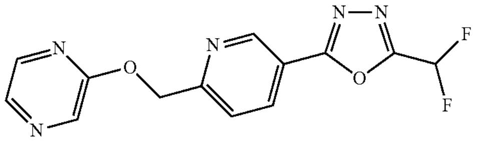
69
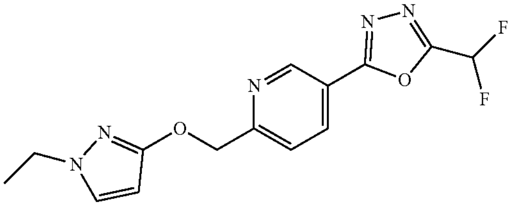
70
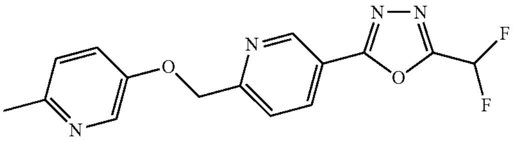
71
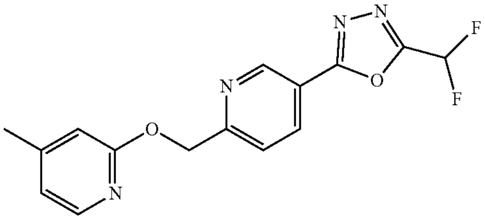
72
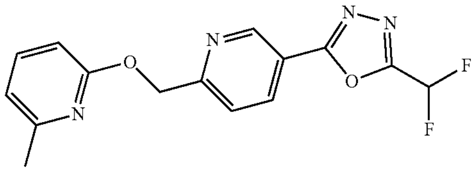
73
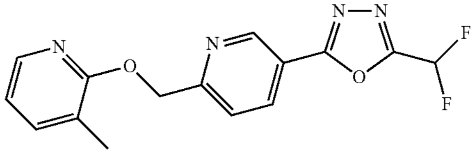
74
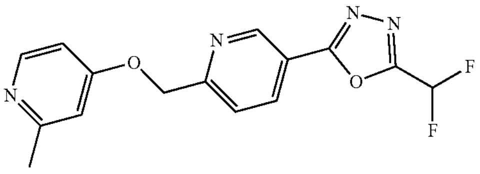
75
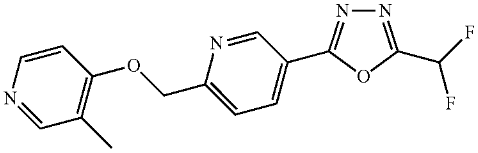
76
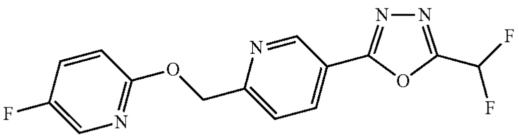
-continued
77
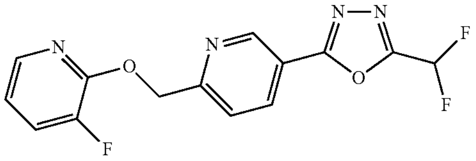
78
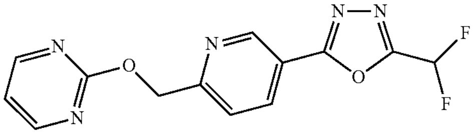
79
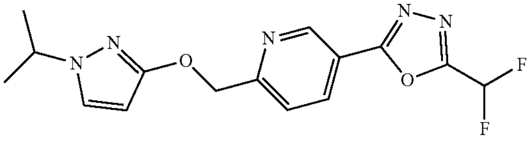
80
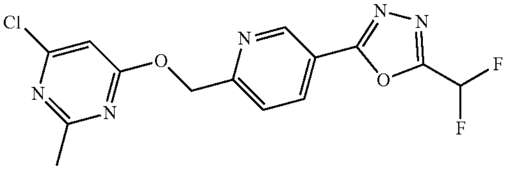
81
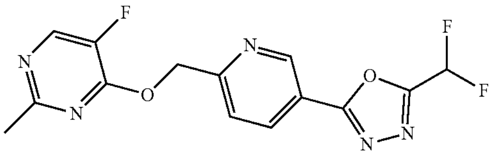
82
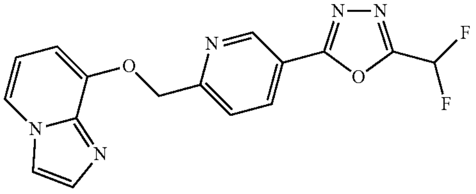
83
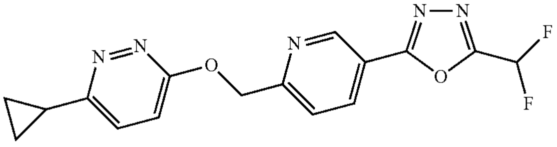
84
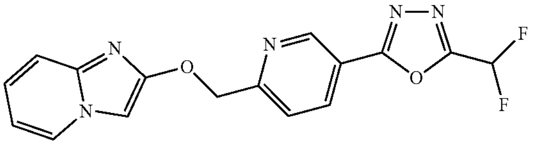
85
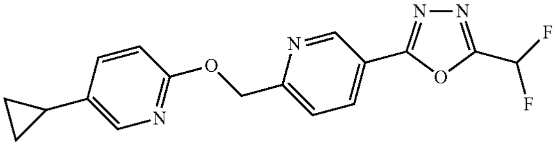

-continued
86
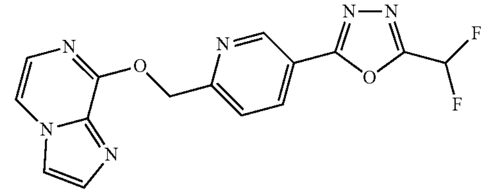
87
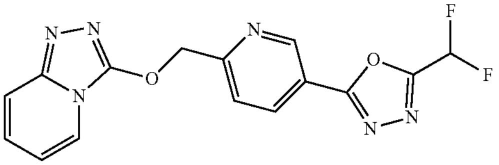
88
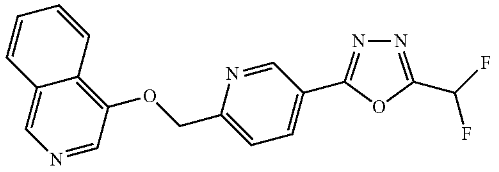
89
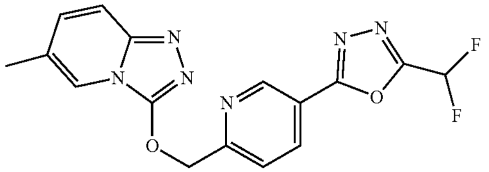
90
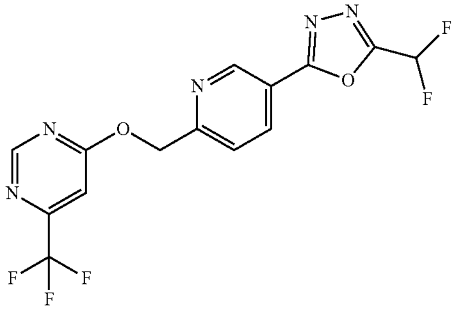
91
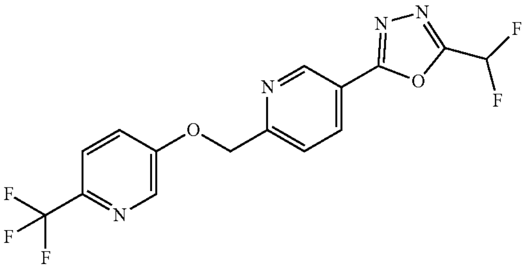
92
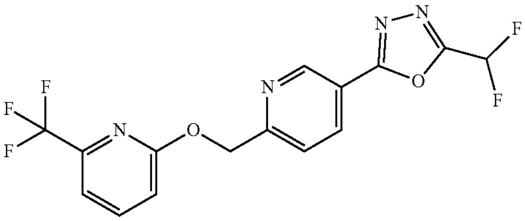
-continued
93
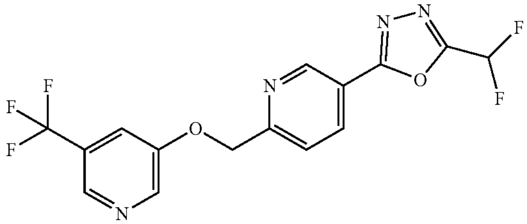
94
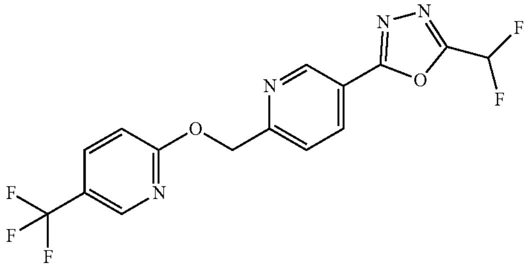
95
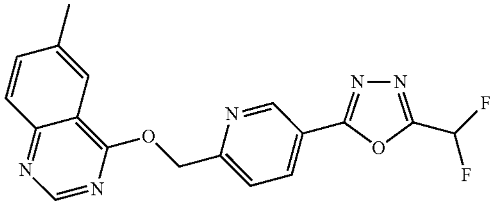
96
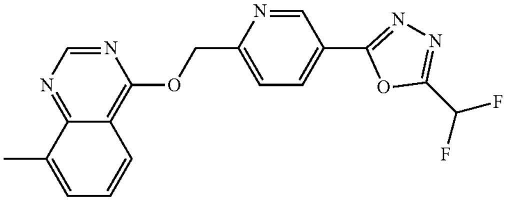
97
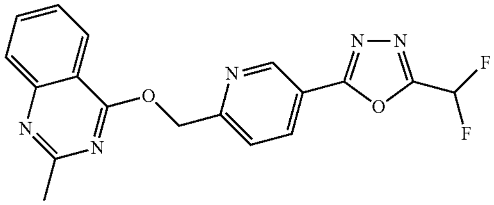
98
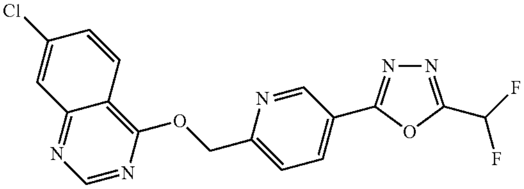

99
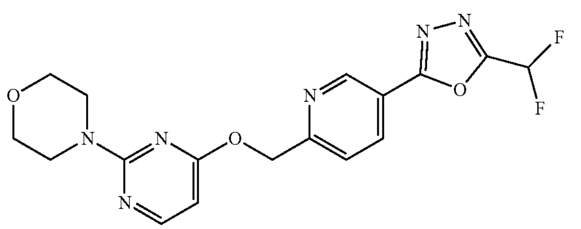
100
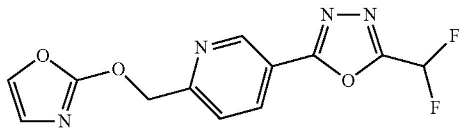
101
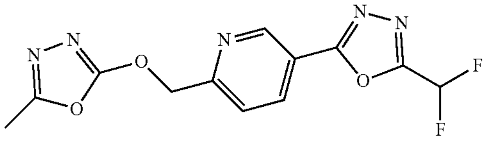
102
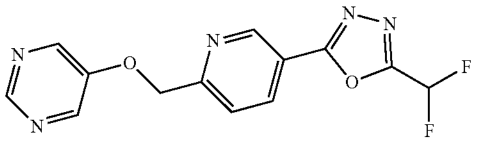
103
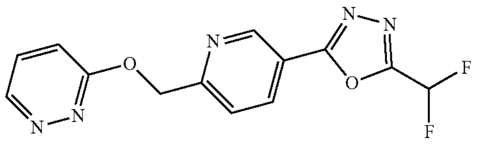
104
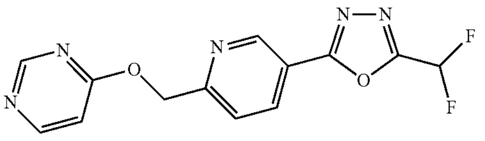
105
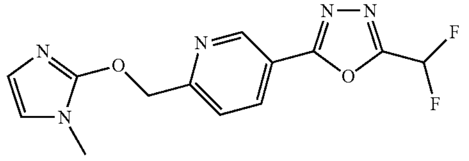
106
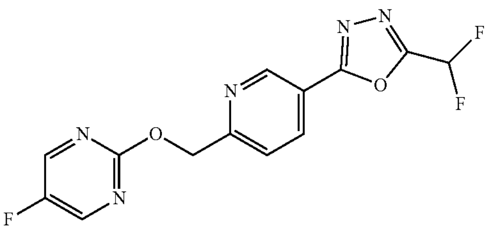
107
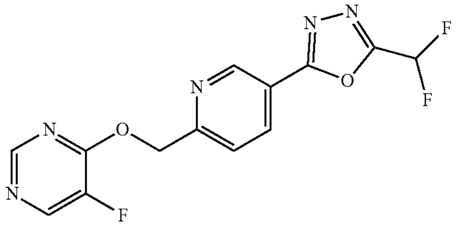
108
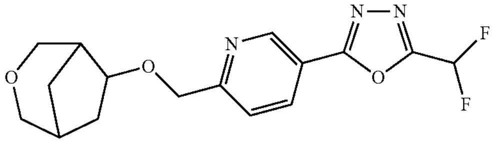
109
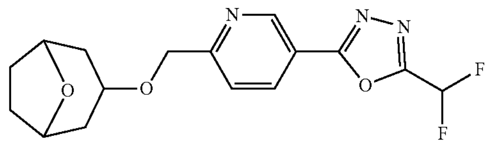
110
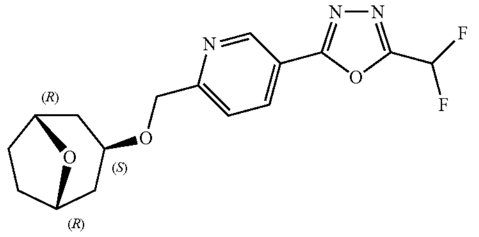
111
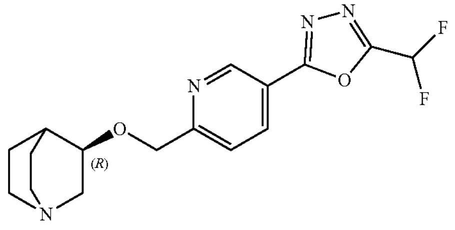
112
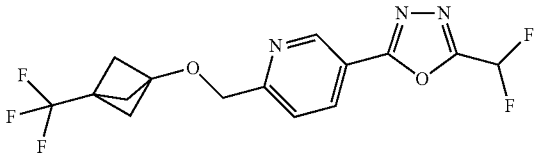
113
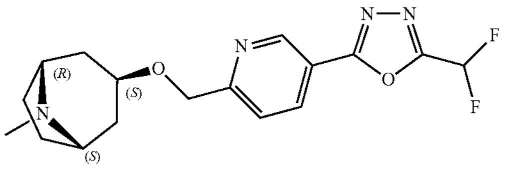
114
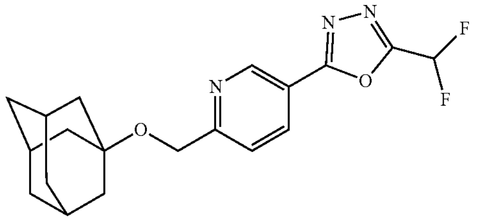

-continued
115
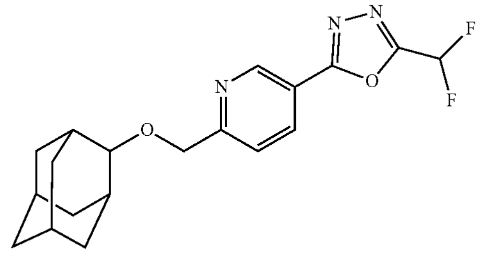
116
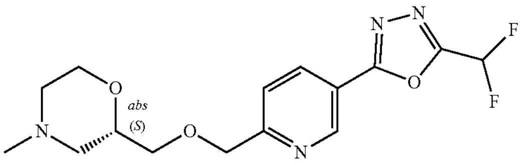
117
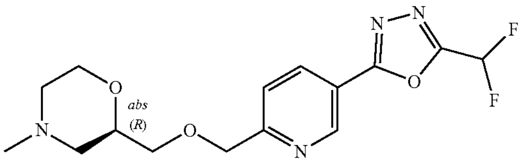
118
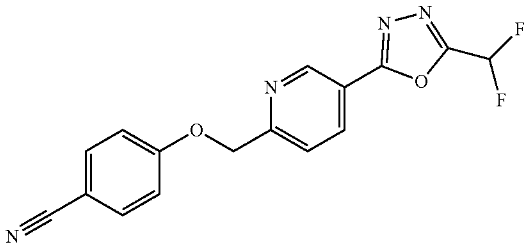
119
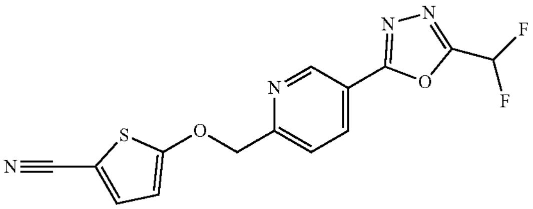
120
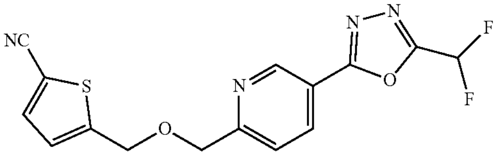
121
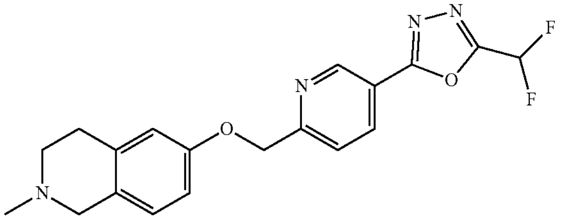
-continued
122
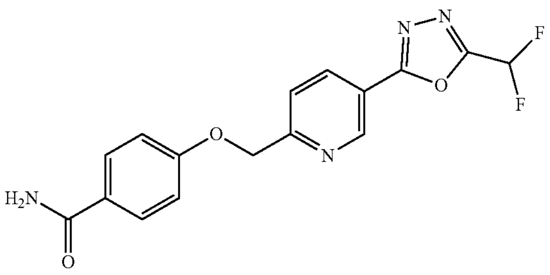
123
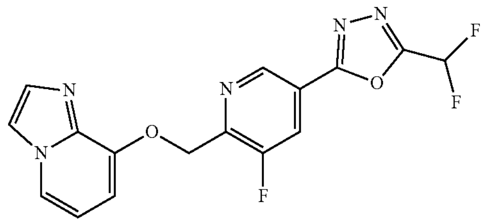
124
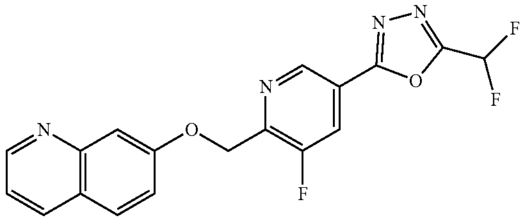
125
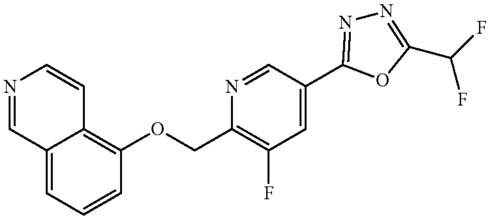
126
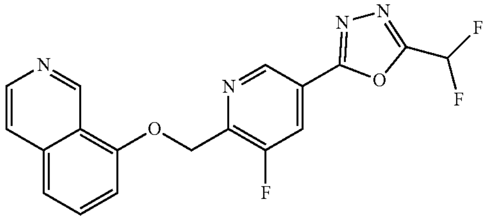
127
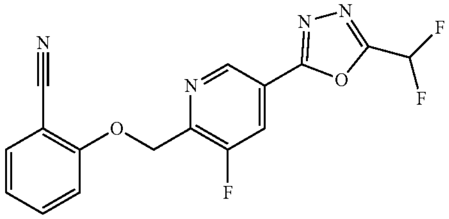

-continued
128
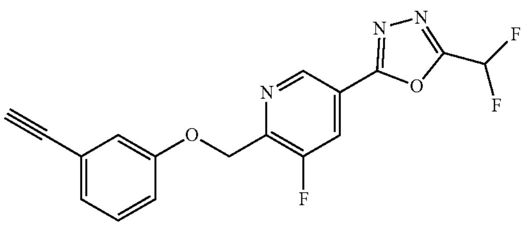
129
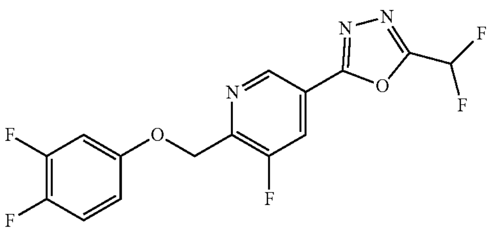
130
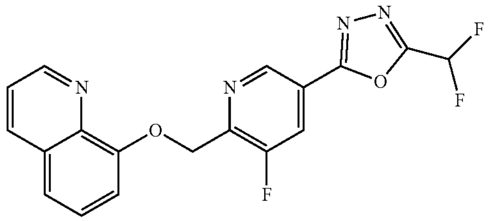
131
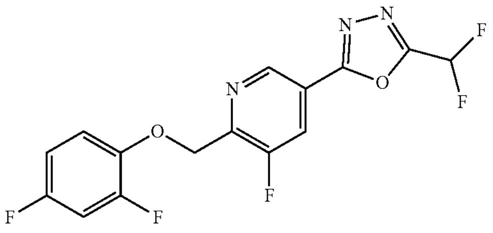
132
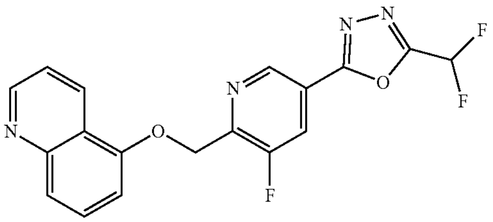
133
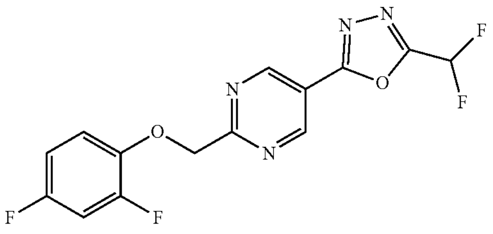
-continued
134
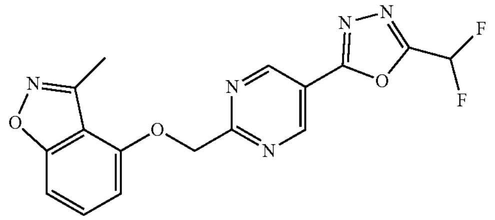
135
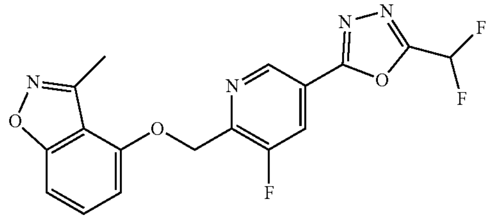
136
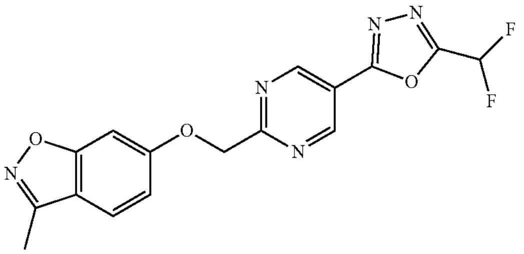
137
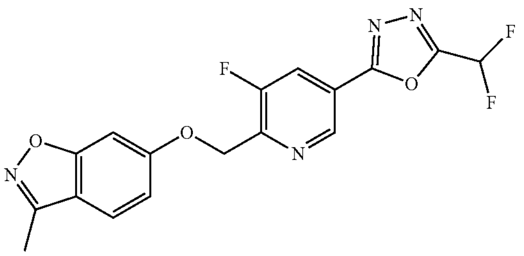
138
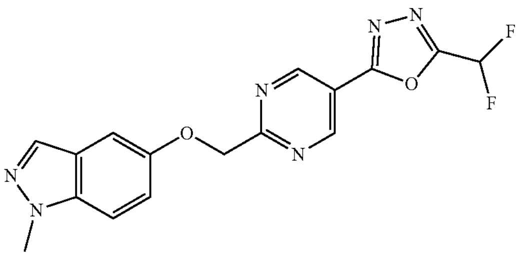
139
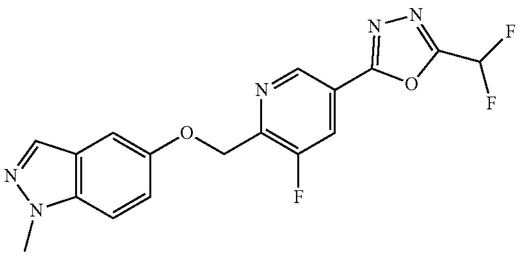

140
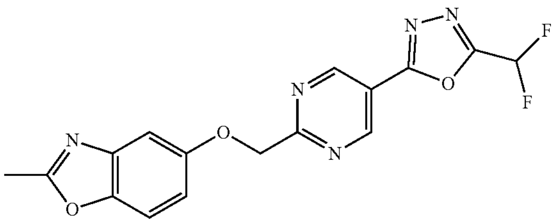
141
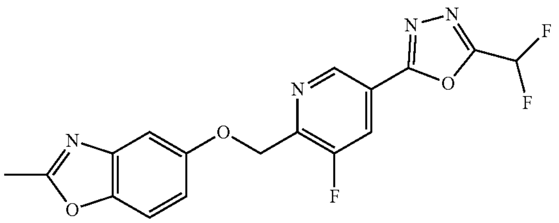
142
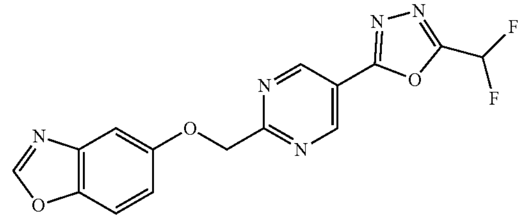
143
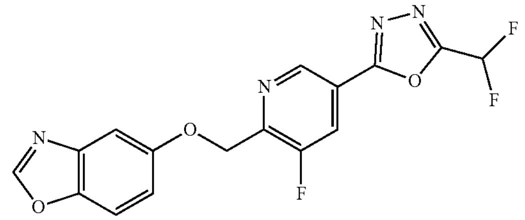
144
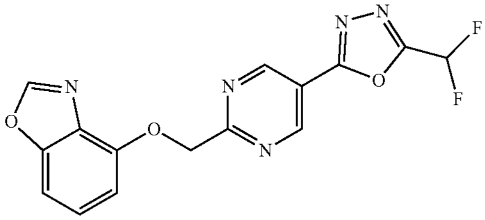
145
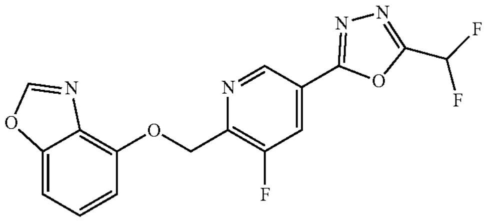
146
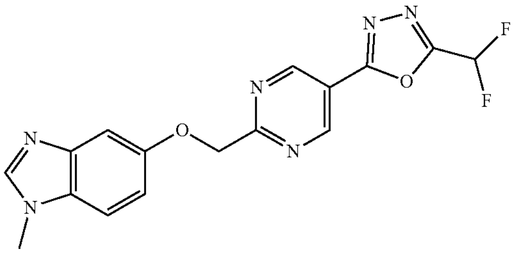
147
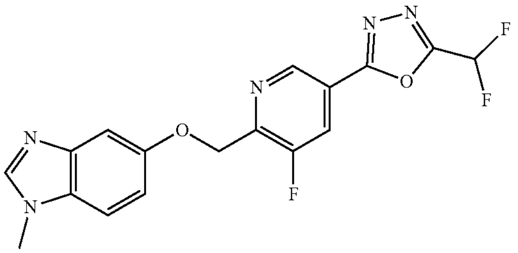
148
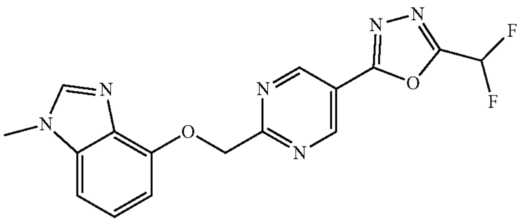
149
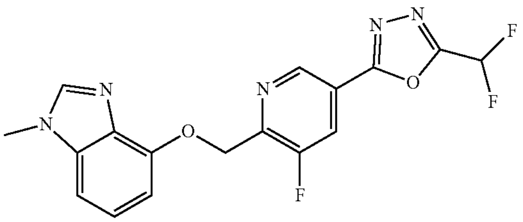
150
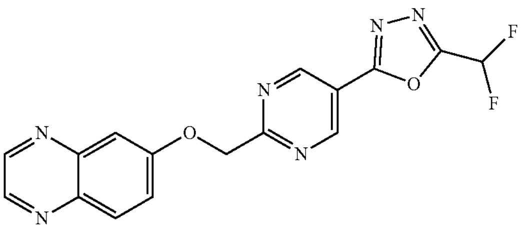
151
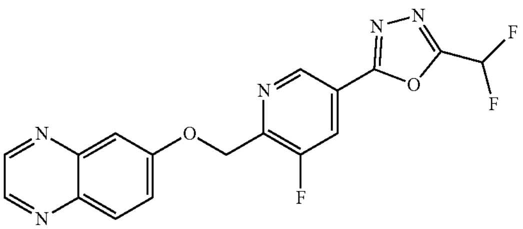

-continued
152
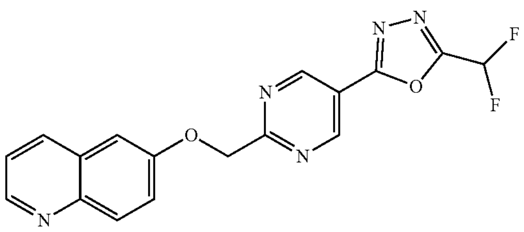
153
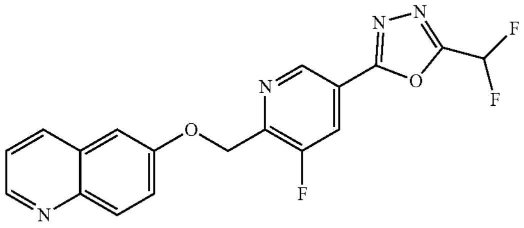
154
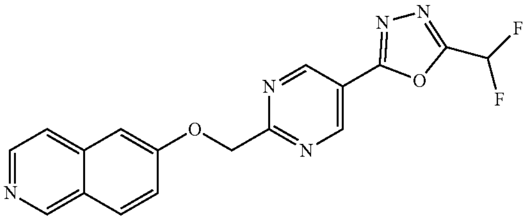
155
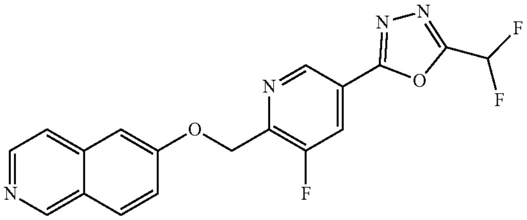
156
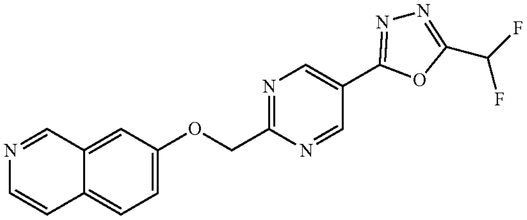
157
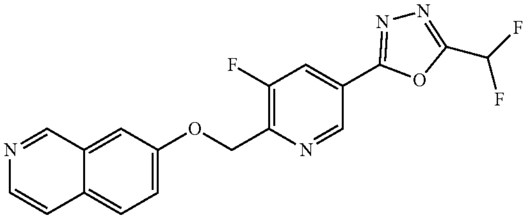
-continued
158
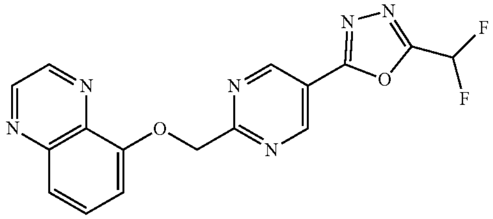
159
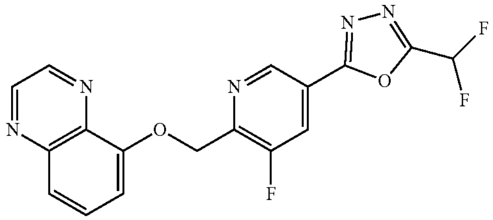
160
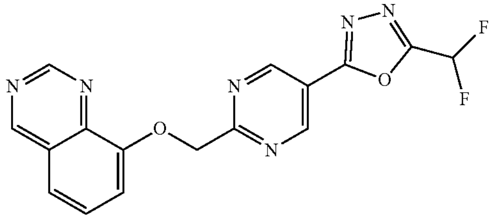
161
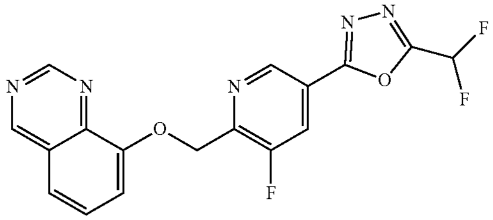
162
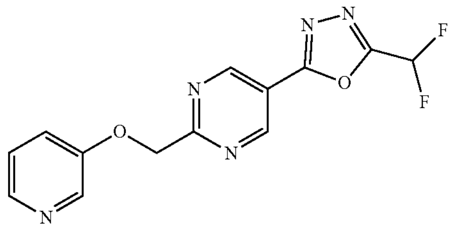
163
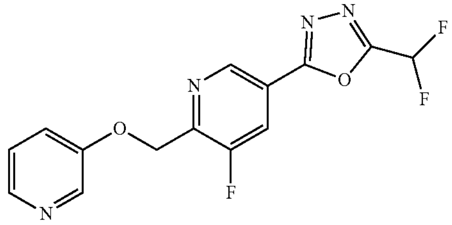

-continued
164
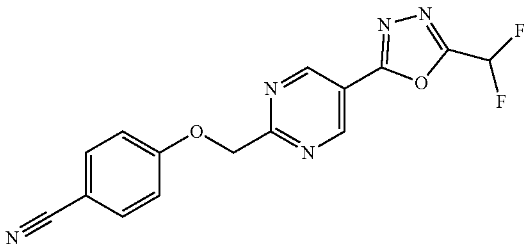
165
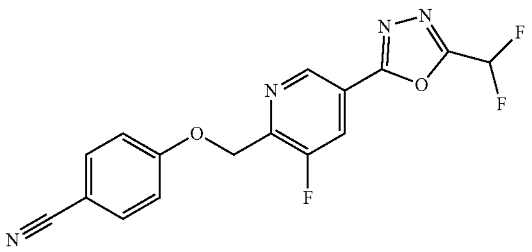
166
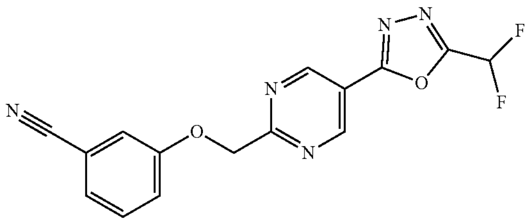
167
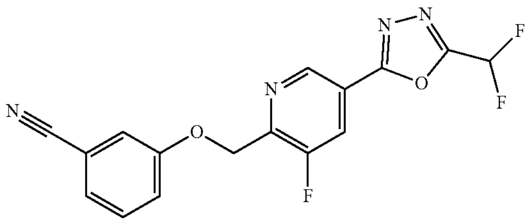
168
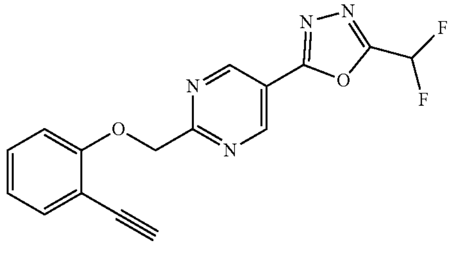
169
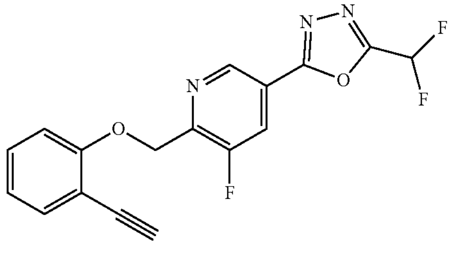
-continued
170
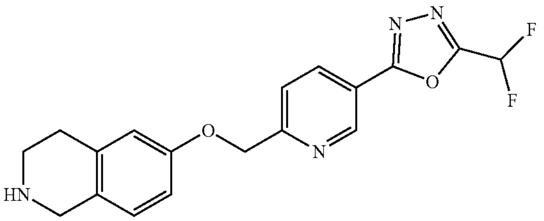
171
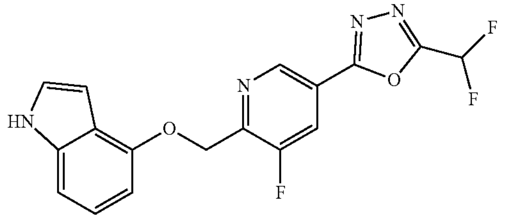
172
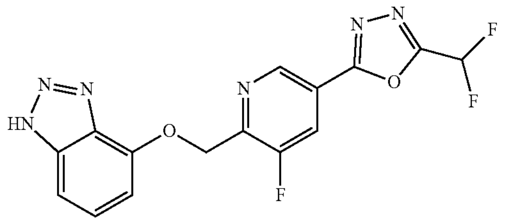
173
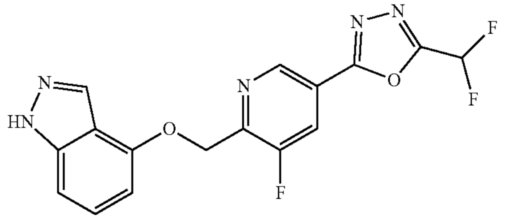
174
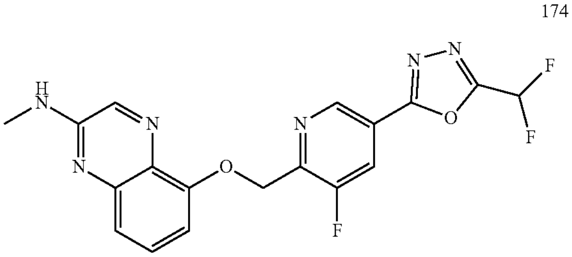
175
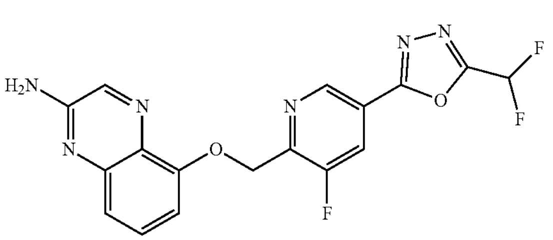

176
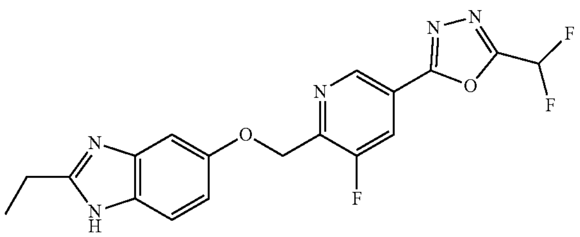
177
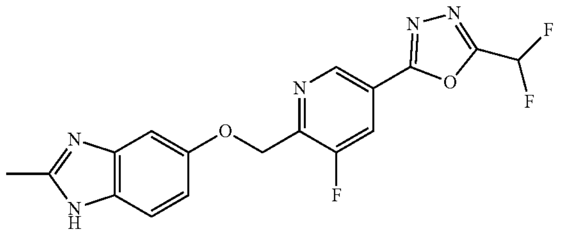
178
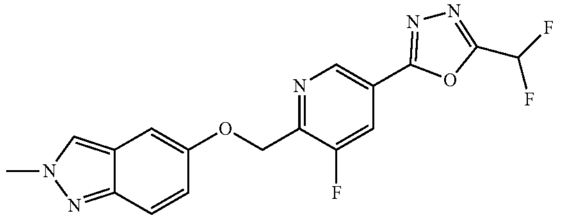
179
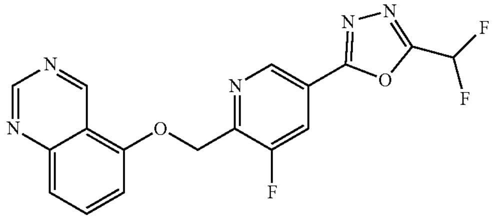
180
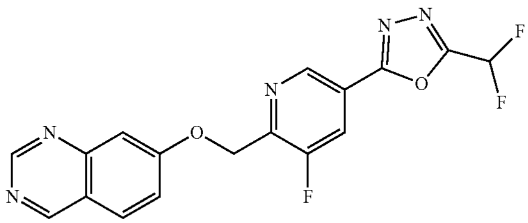
181
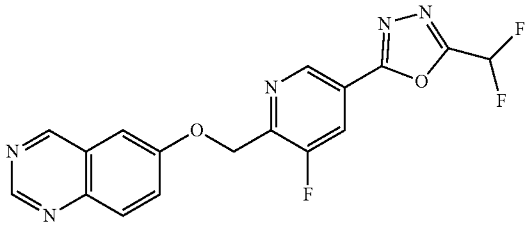
182
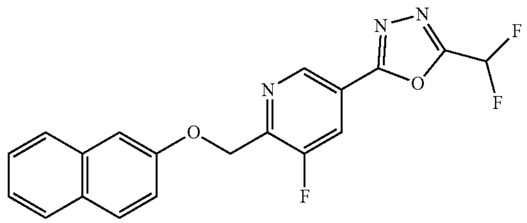
183
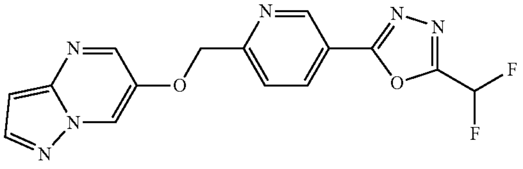
184
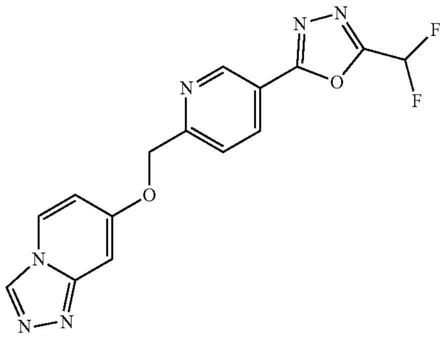
185
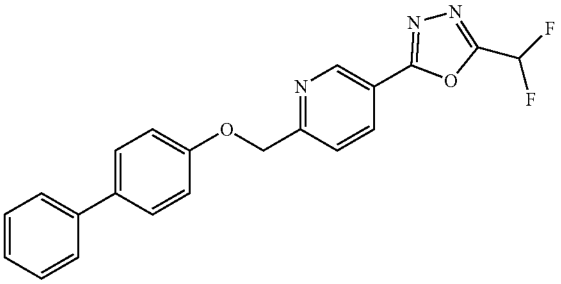
186
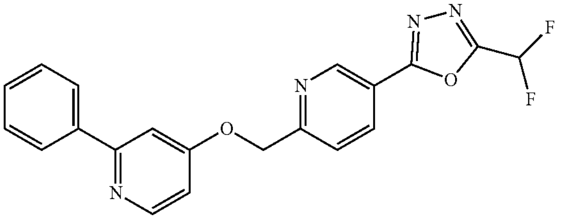
187
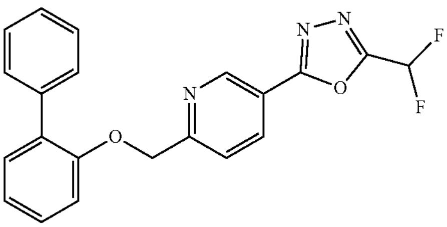

-continued
188
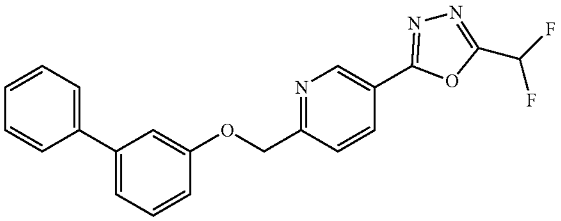
189
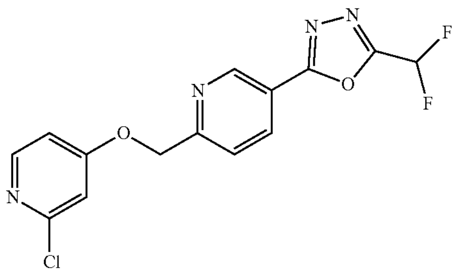
190
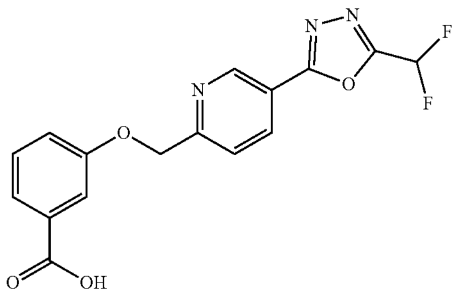
191
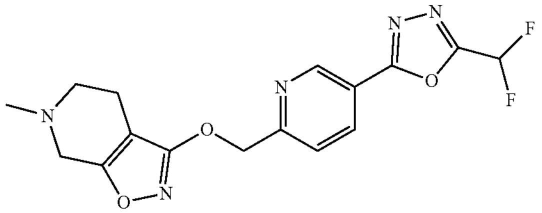
192
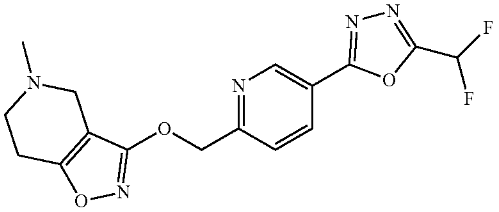
-continued
193
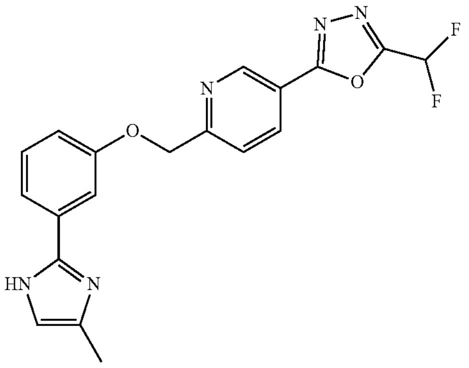
194
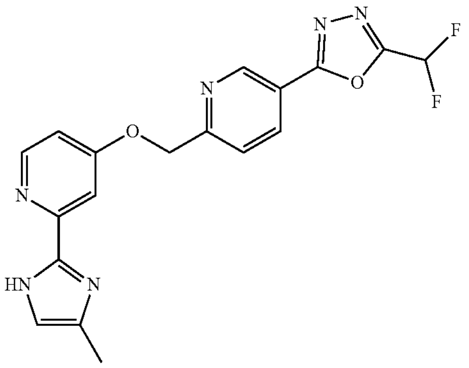
195
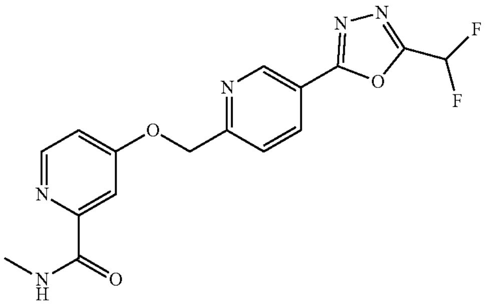
196
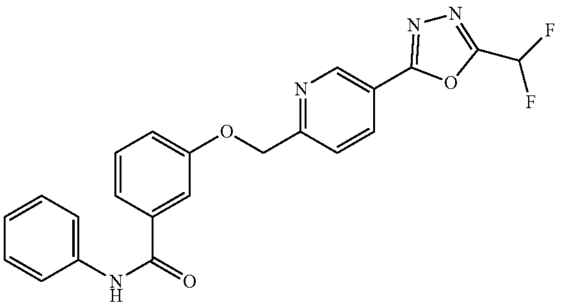

-continued
197
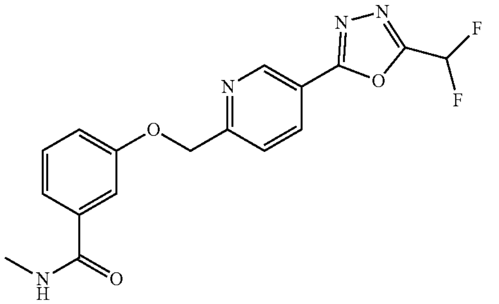
198
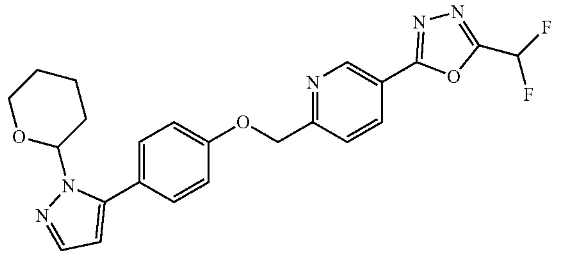
199
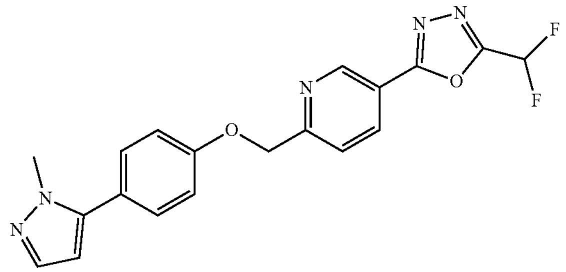
200
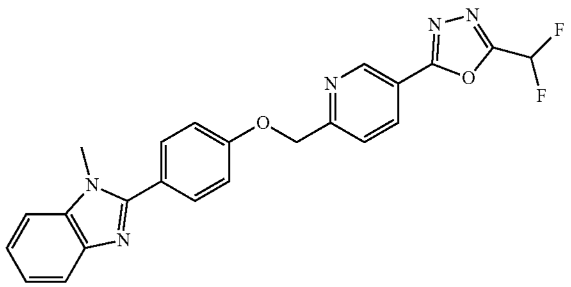
201
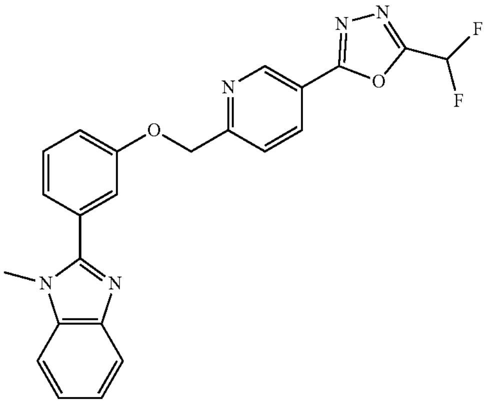
-continued
202
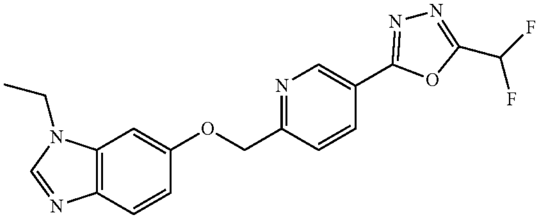
203
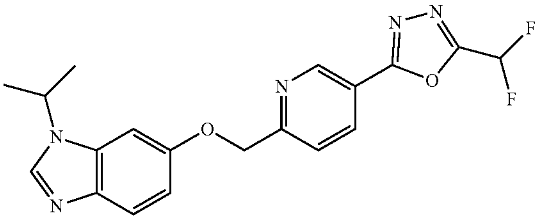
204
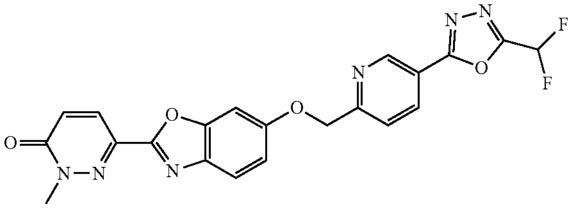
205
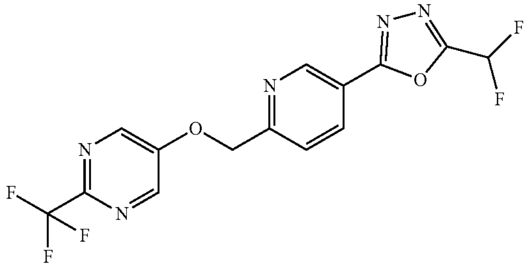
206
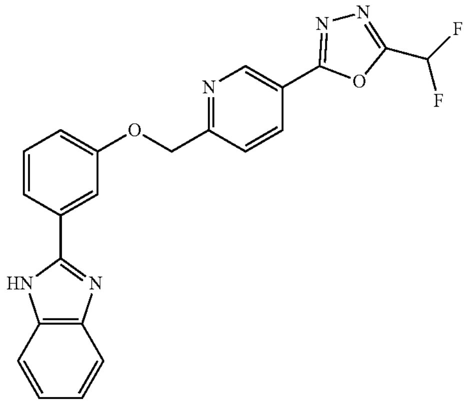

-continued
207
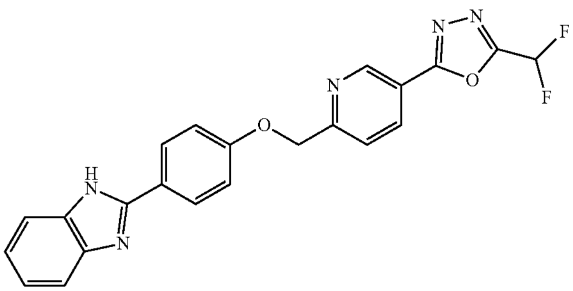
208
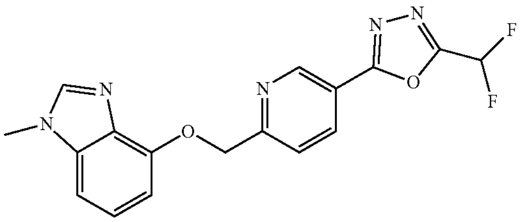
209
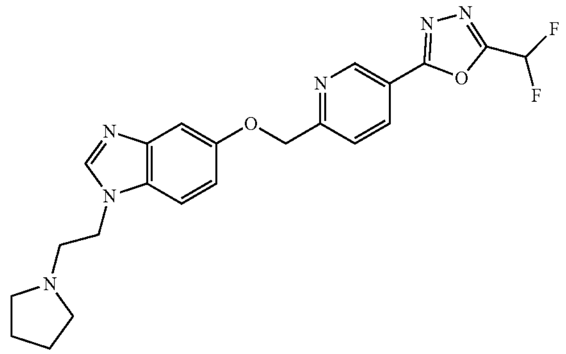
210
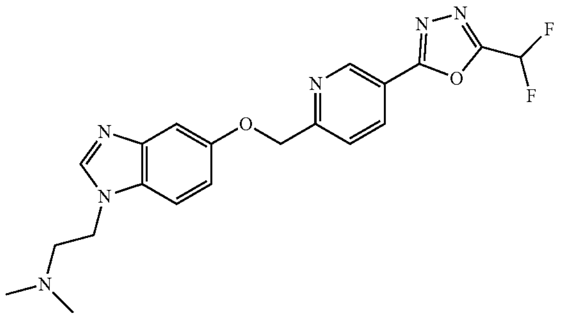
211
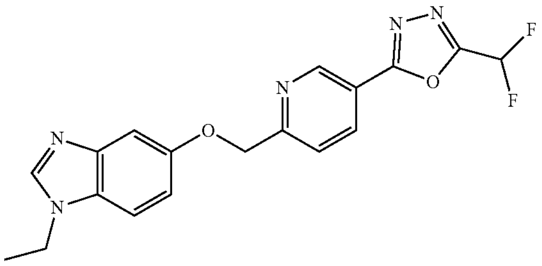
-continued
212
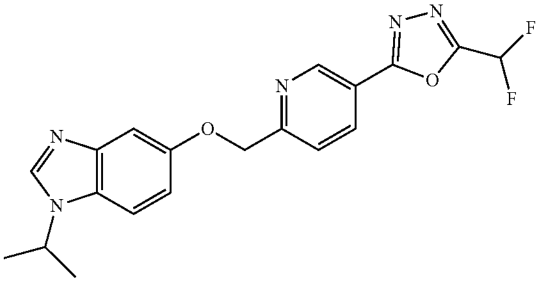
213
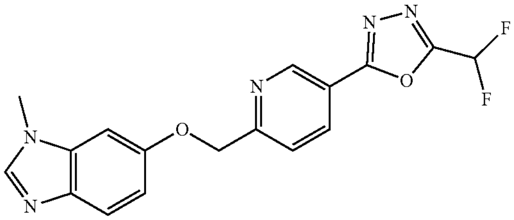
214
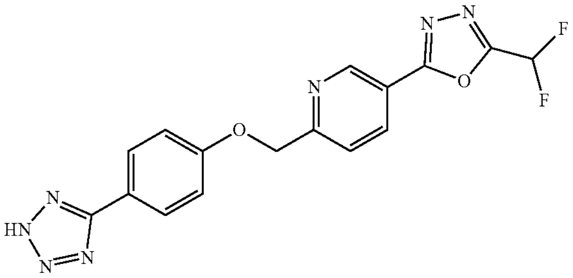
In certain embodiments, the compound of Formula (I) is one of the following compounds, or a pharmaceutically acceptable salt thereof:
(1)
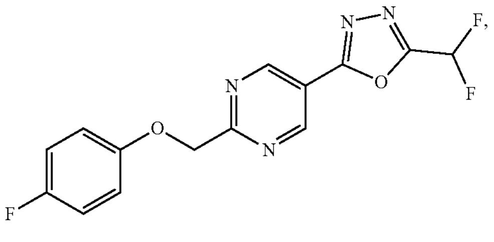
(2)
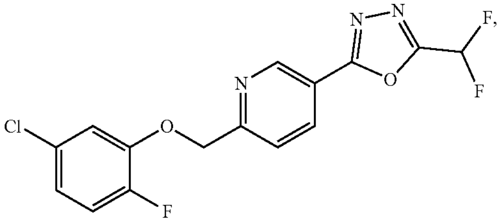

-continued
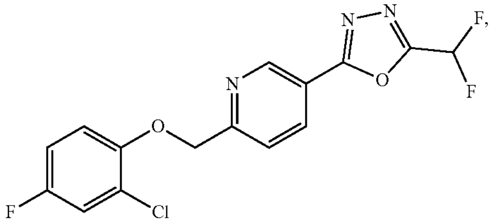
(4)
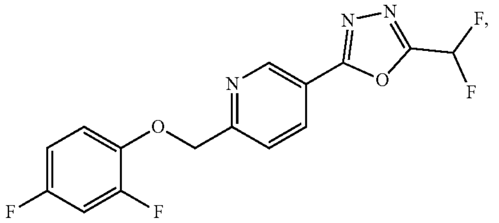
(5)
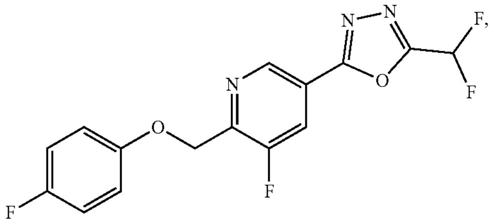
(6)
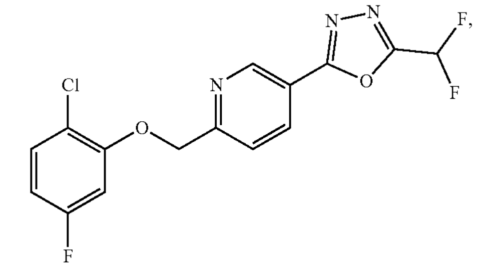
(7)
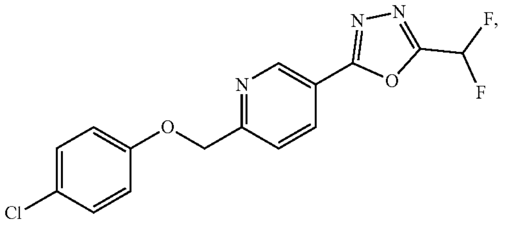
(8)
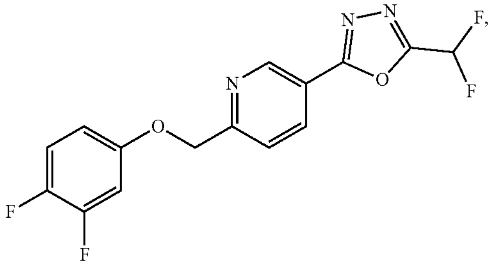
(9)
-continued
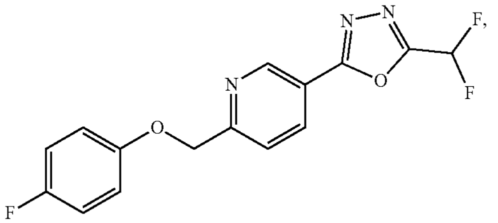
(12)
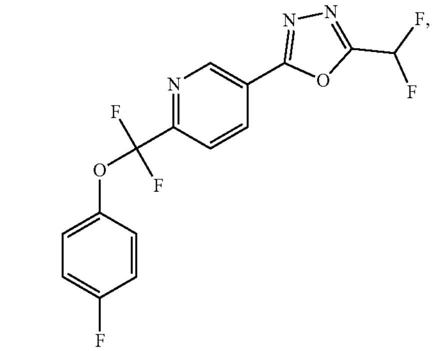
(15)
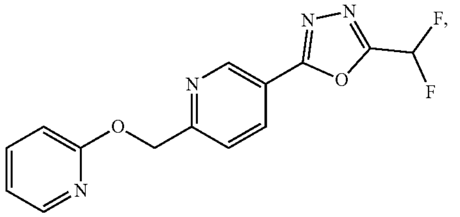
(16)
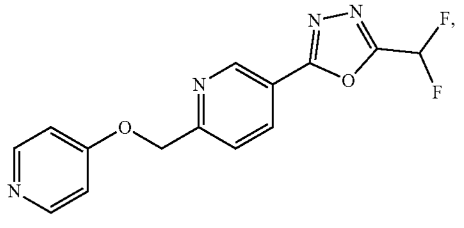
(18)
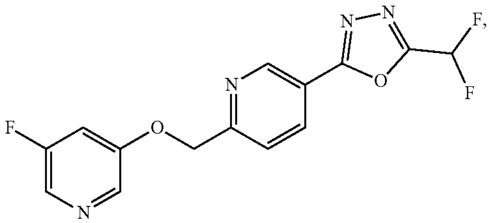
(19)
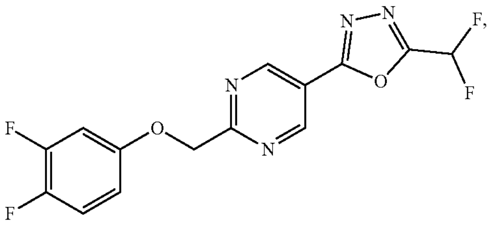
(22)

-continued
(26)
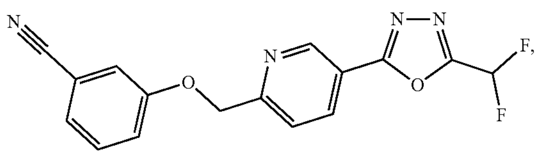
(27)
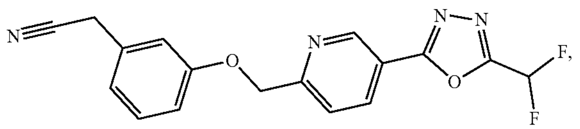
(29)
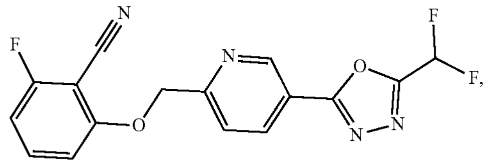
(30)
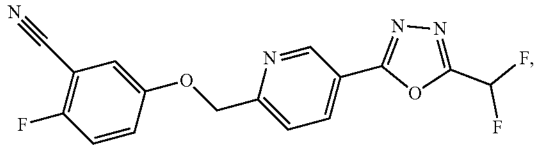
(39)
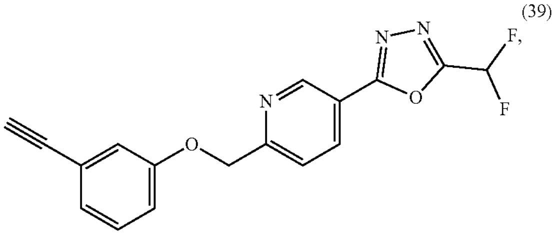
(40)
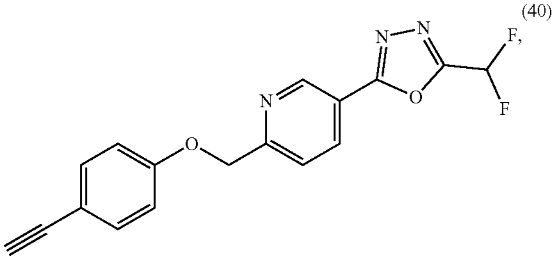
(41)
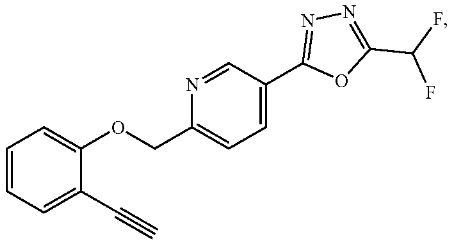
(42)
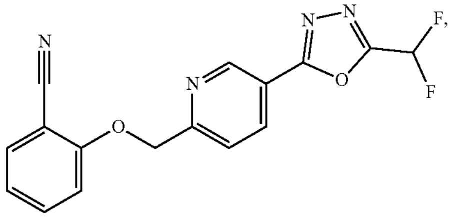
-continued
(43)
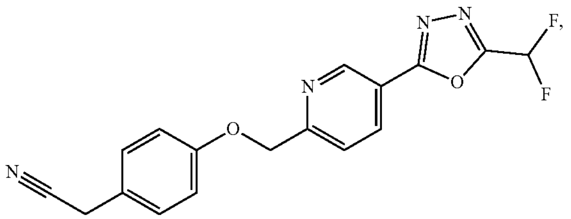
(44)
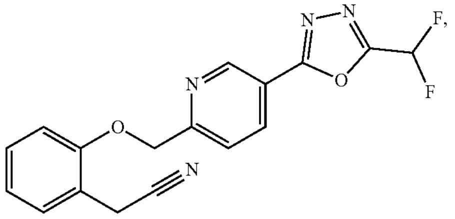
(45)
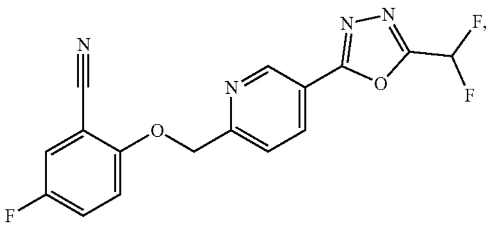
(46)
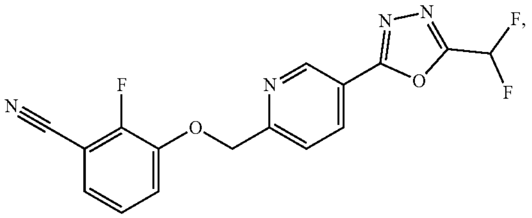
(47)
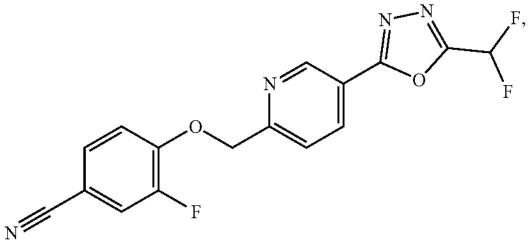
(48)
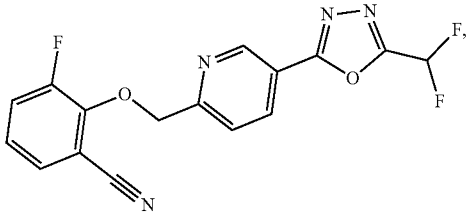

-continued
(49)
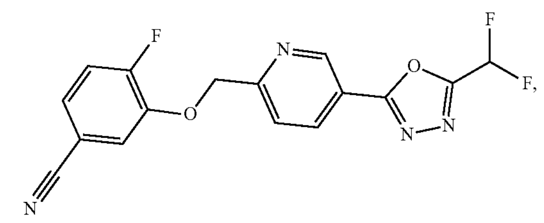
(50)
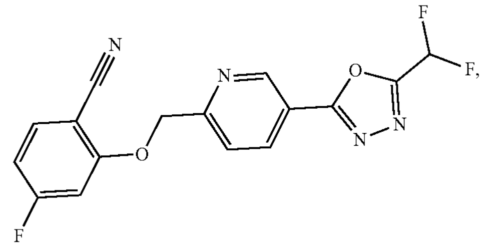
(51)
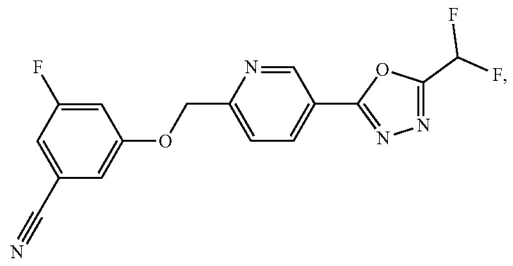
(52)
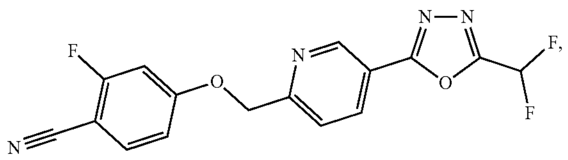
(68)
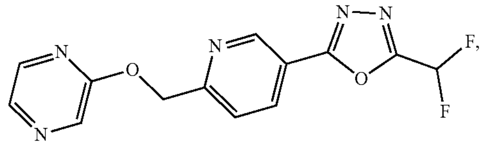
(70)
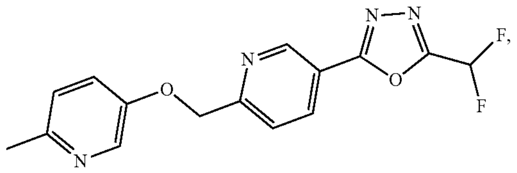
(71)
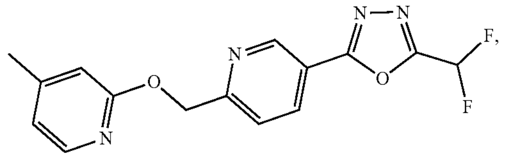
(72)
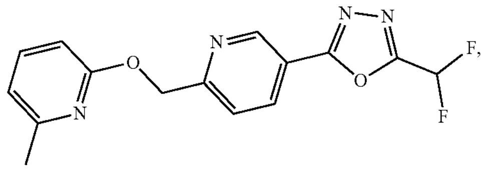
-continued
(73)
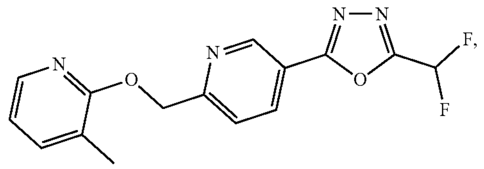
(74)
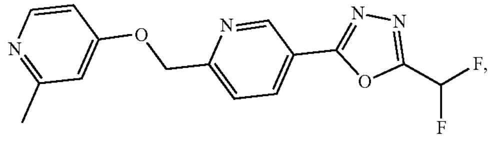
(75)
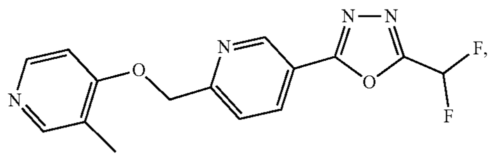
(76)
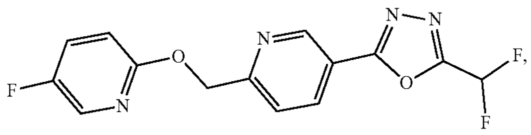
(77)
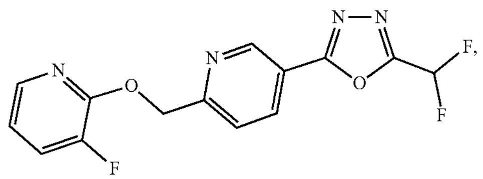
(78)
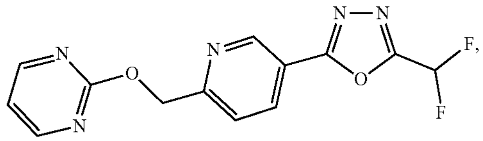
(80)
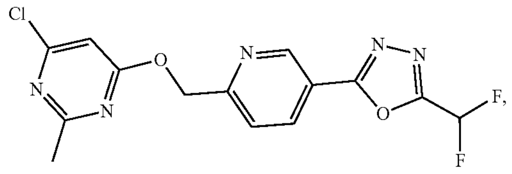
(81)
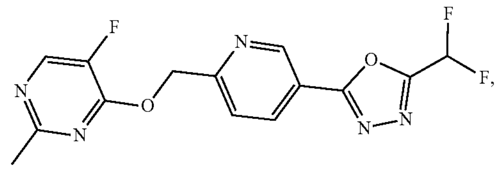
(83)
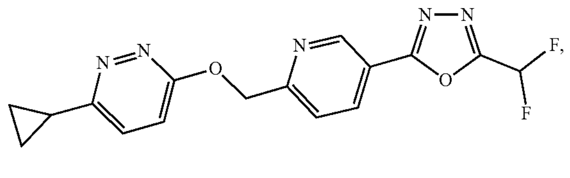

-continued
(85)
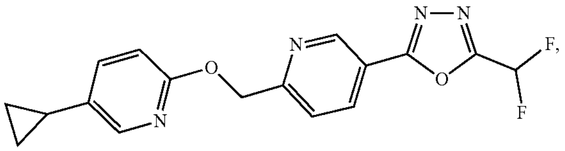
(90)
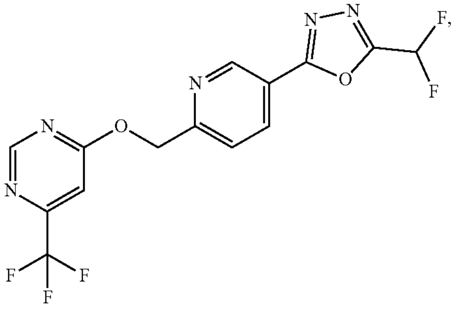
(91)
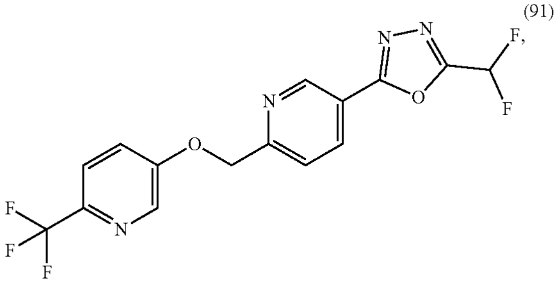
(92)
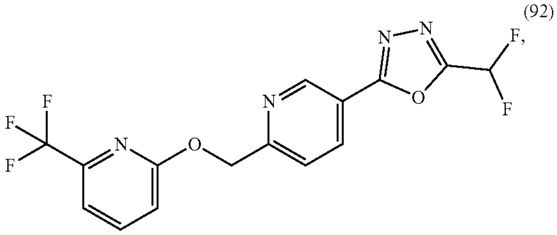
(93)
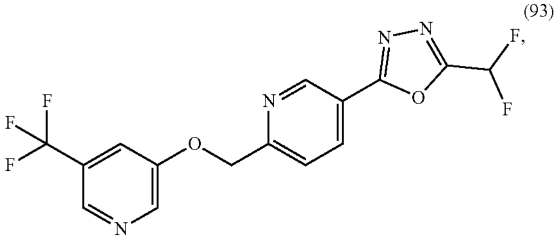
(94)
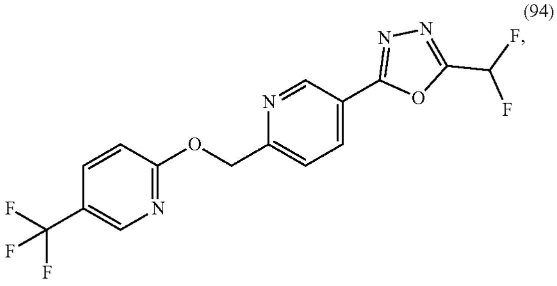
(102)
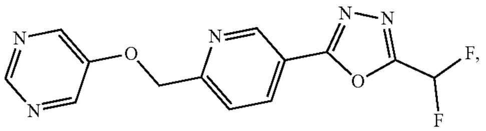
-continued
(103)
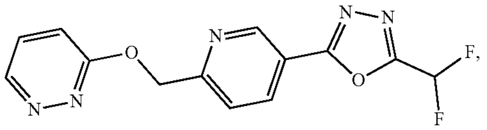
(104)
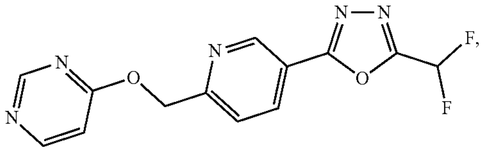
(106)
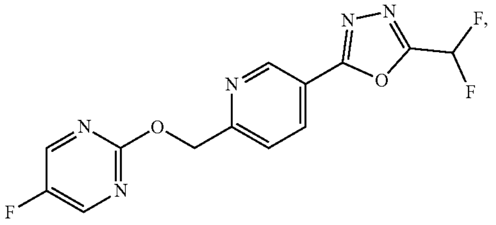
(107)
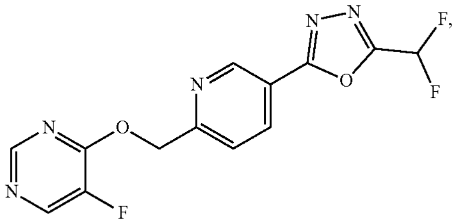
(118)
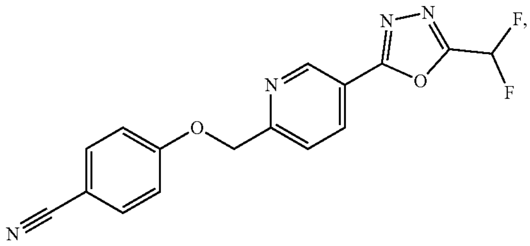
or
(122)
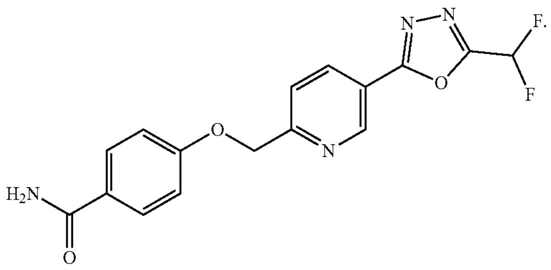
In certain embodiments, the compound of Formula (I) is one of the following compounds, or a pharmaceutically acceptable salt thereof:

(1)
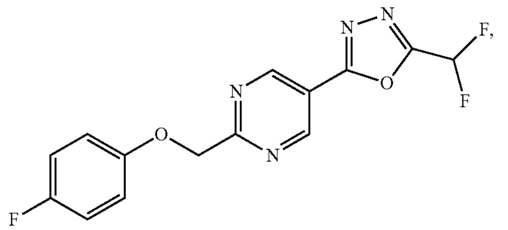
(2)
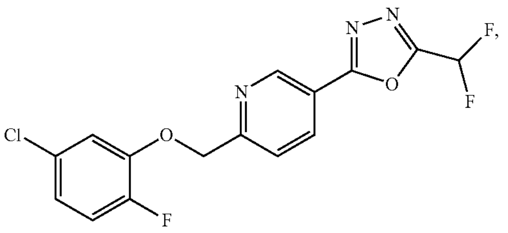
(3)
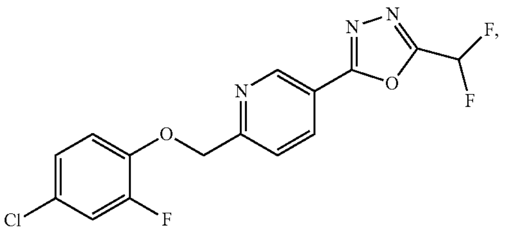
(4)
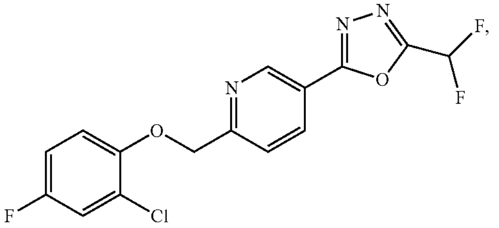
(5)
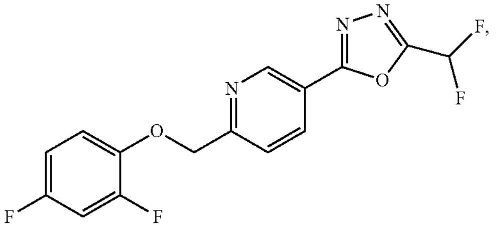
(6)
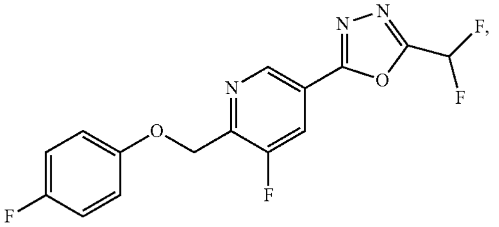
-continued
(7)
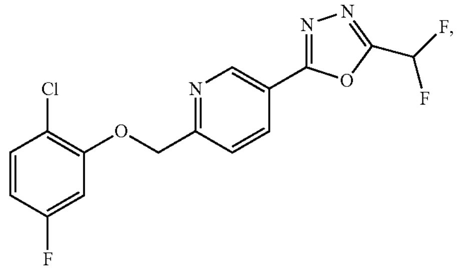
(8)
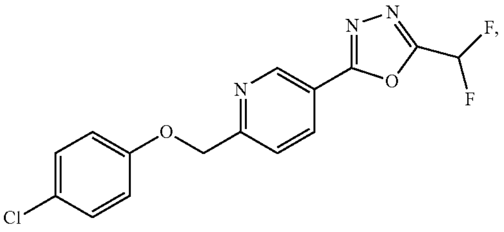
(9)
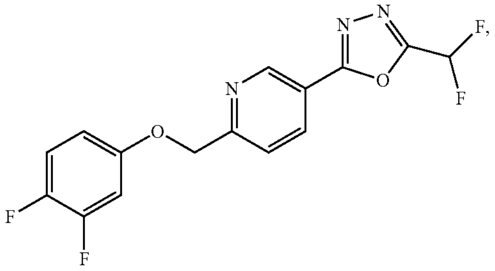
(12)
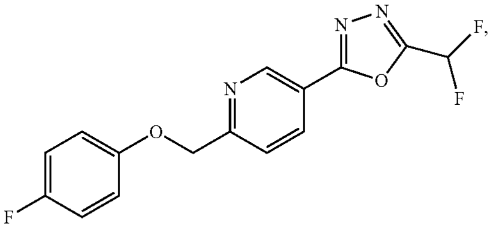
(15)
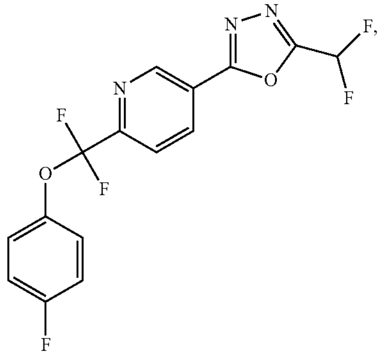
(22)
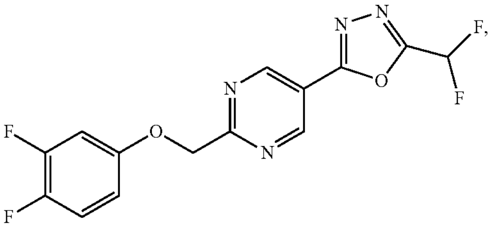

-continued
(26)
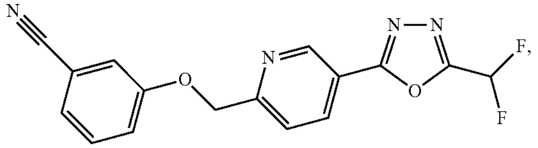
(27)
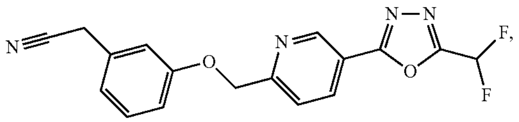
(29)
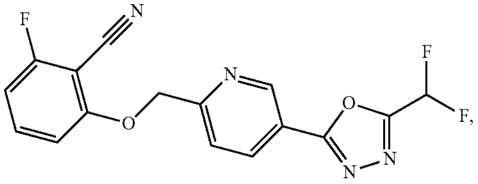
(30)
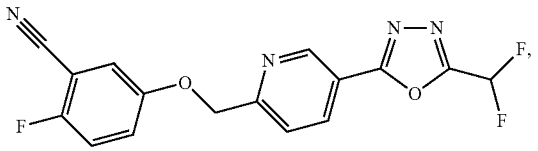
(39)
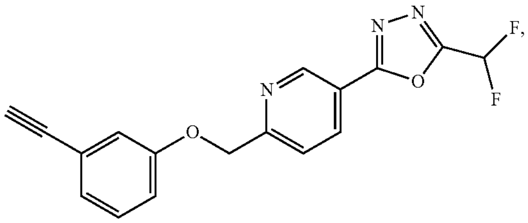
(40)
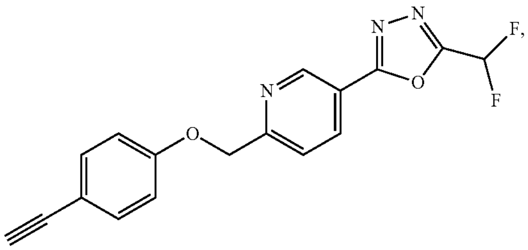
(41)
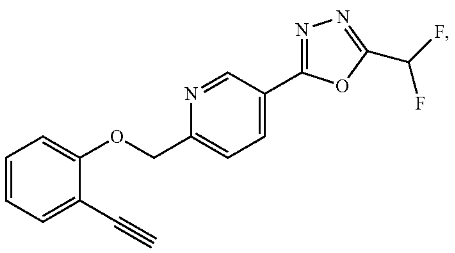
-continued
(42)
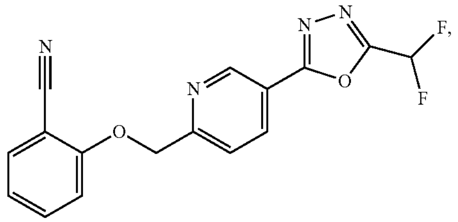
(43)
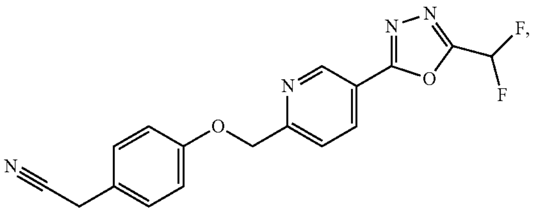
(44)
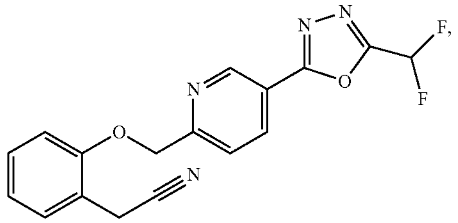
(45)
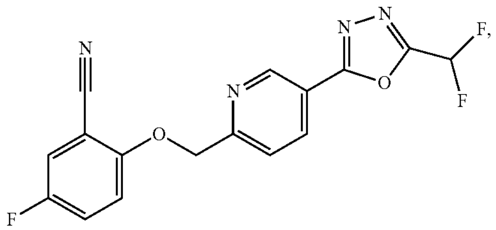
(46)
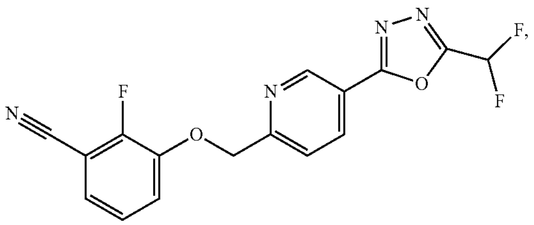
(47)
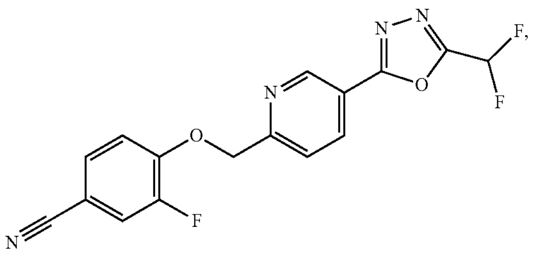

-continued
(48)
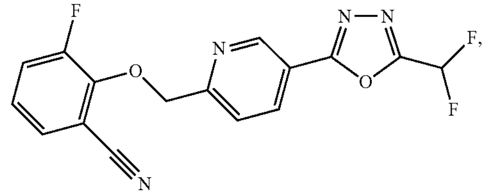
(49)
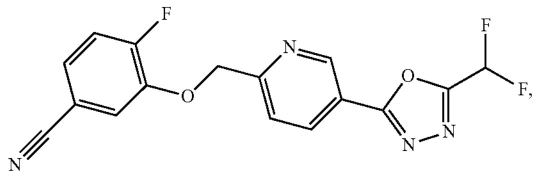
(50)
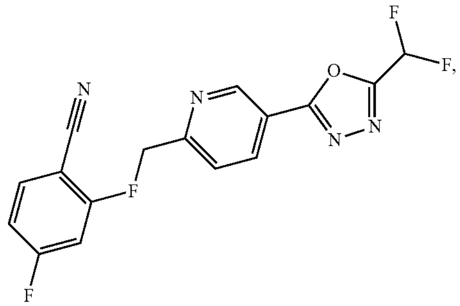
(51)
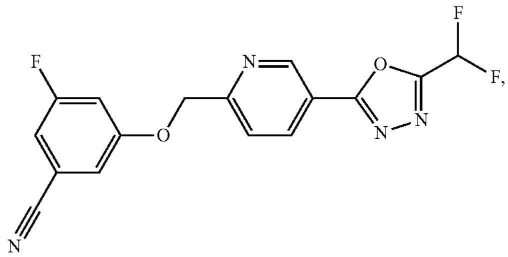
(52)
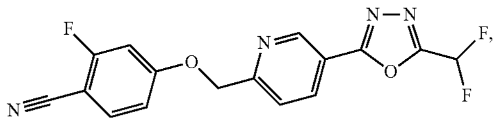
or
(122)
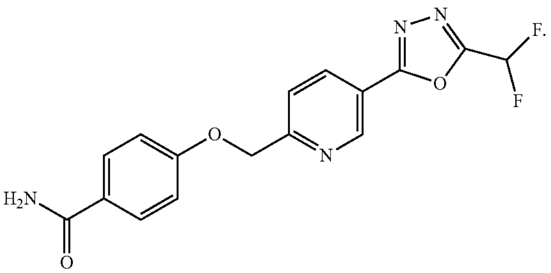
In certain embodiments, the compound of Formula (I) is one of the following compounds, or a pharmaceutically acceptable salt thereof:
(16)
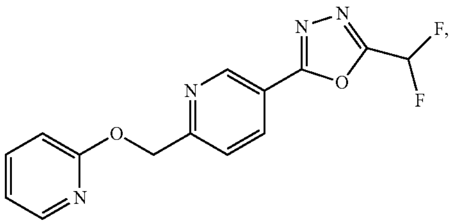
(18)
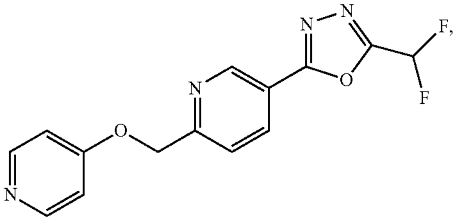
(19)
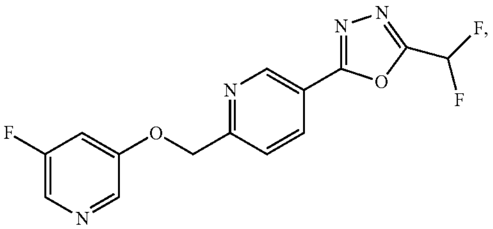
(70)
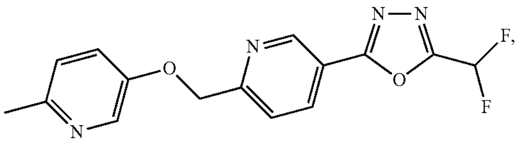
(71)
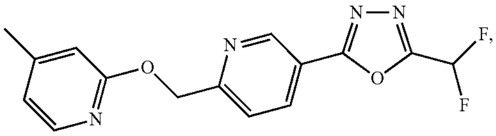
(72)
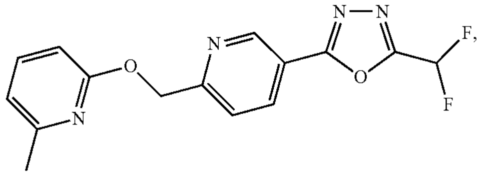
(73)
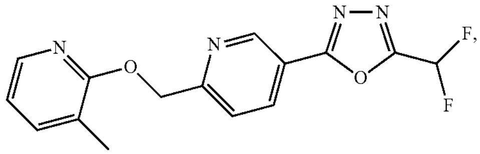
(74)
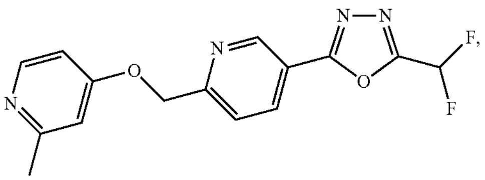

-continued
(75)
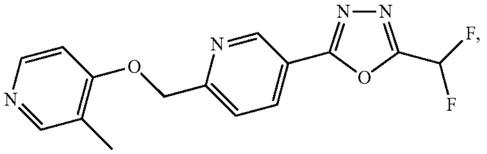
(76)
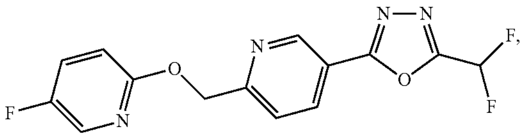
(77)
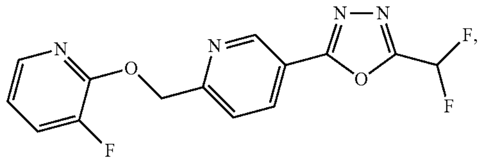
(85)
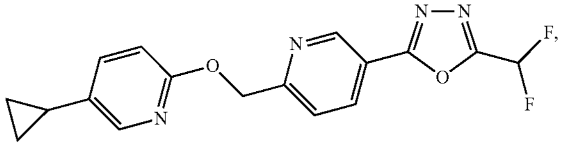
(91)
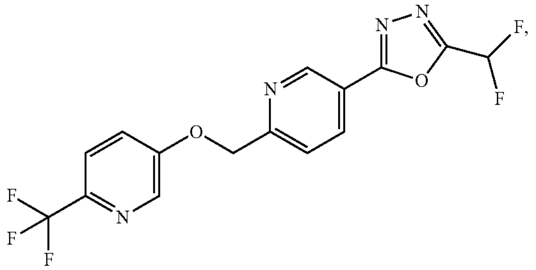
(92)
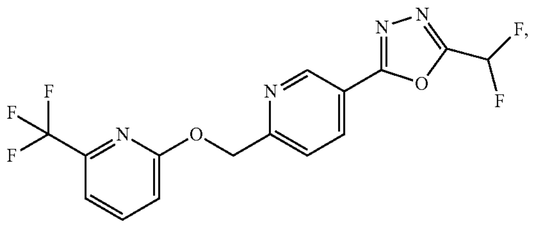
(93)
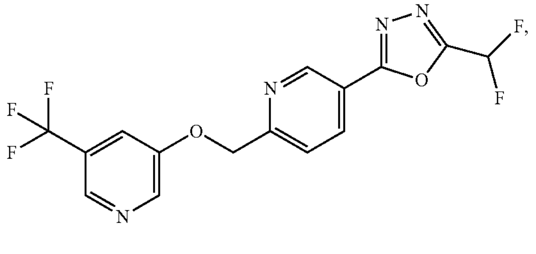
-continued
(94)
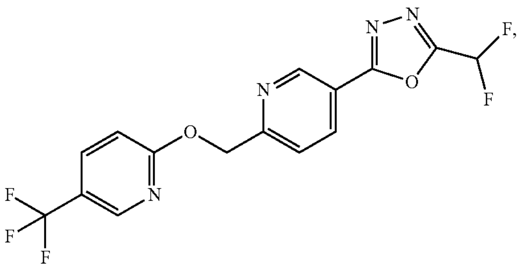
or
(102)
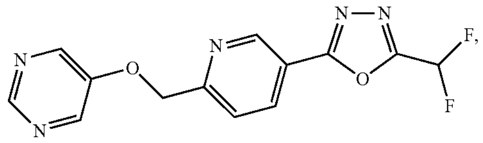
In certain embodiments, the compound of Formula (I) is one of the following compounds, or a pharmaceutically acceptable salt thereof:
(78)
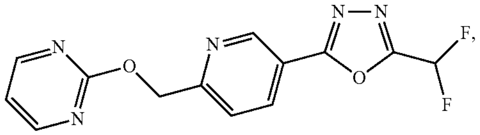
(80)
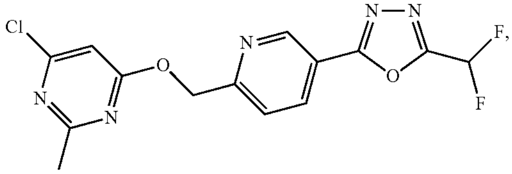
(81)
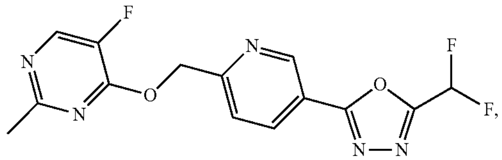
(83)
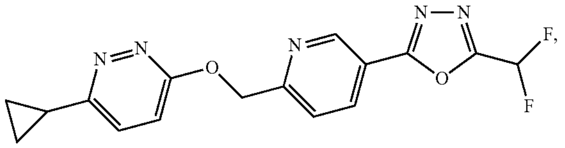
(90)
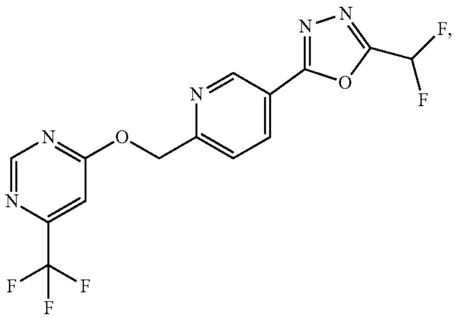

-continued
(102)
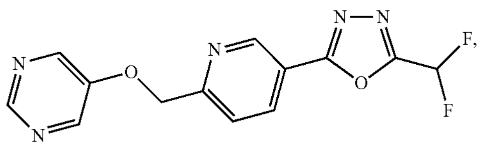
(103)
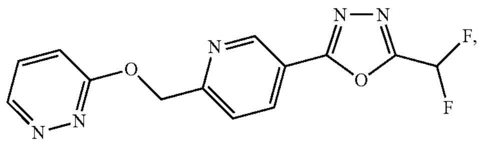
(104)
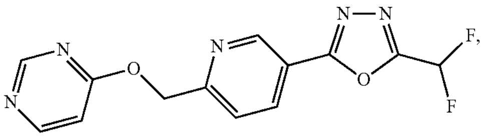
(106)
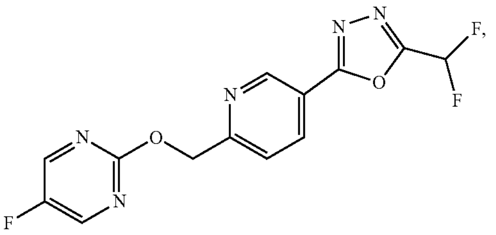
(107)
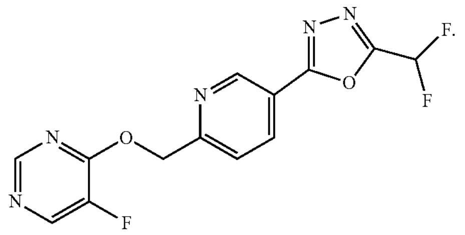
In certain embodiments, the compound of Formula (I) is one of the following compounds, or a pharmaceutically acceptable salt thereof:
(1)
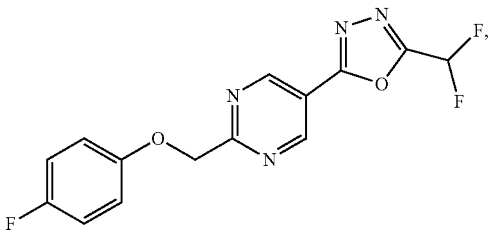
(2)
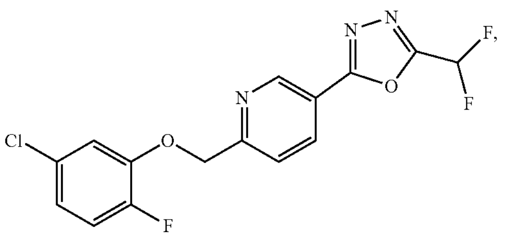
-continued
(3)
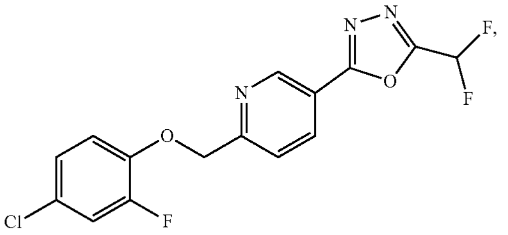
(4)
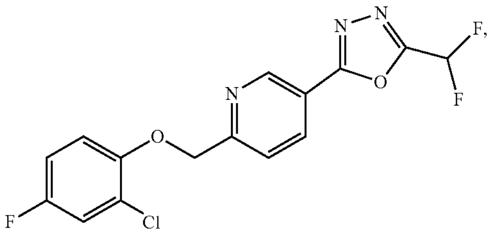
(5)
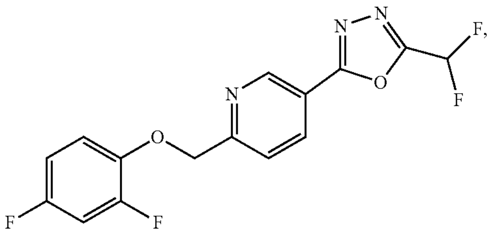
(7)
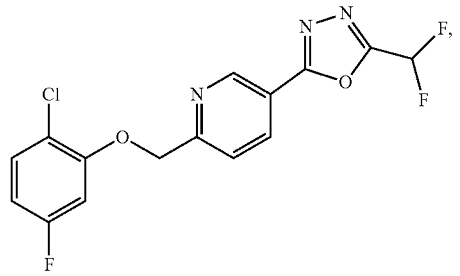
(8)
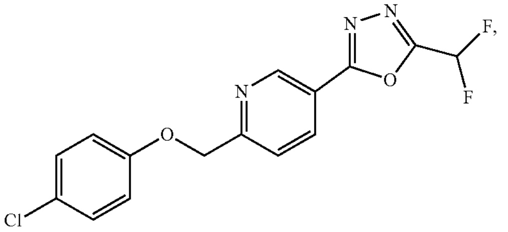
(9)
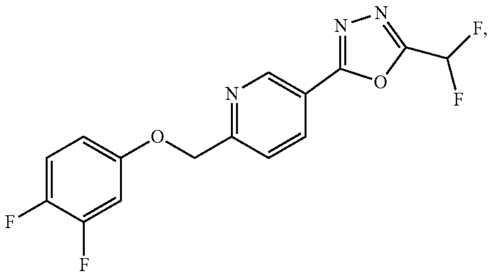

-continued
(12)
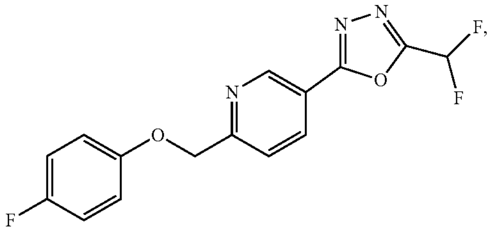
(15)
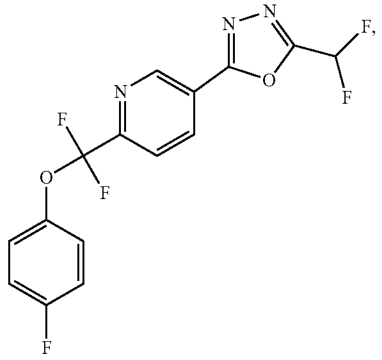
or
(22)
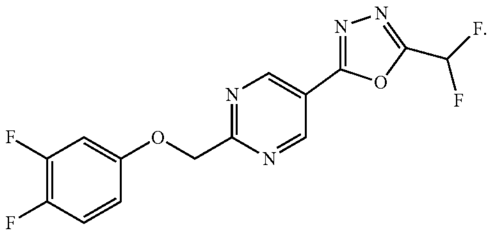
In certain embodiments, the compound of Formula (I) is one of the following compounds, or a pharmaceutically acceptable salt thereof:
(26)
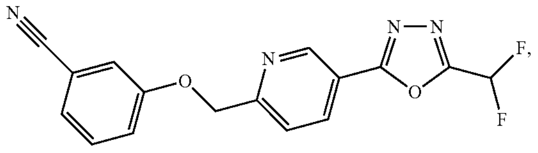
(27)
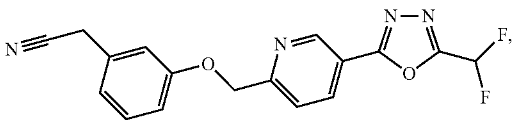
(29)
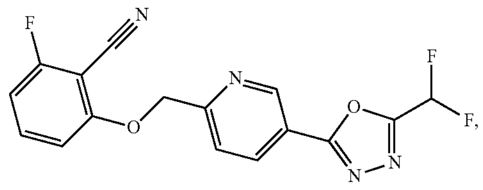
-continued
(30)
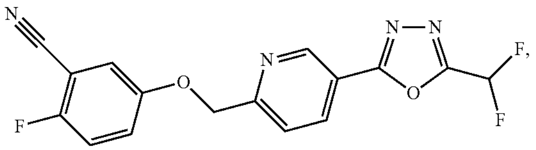
(42)
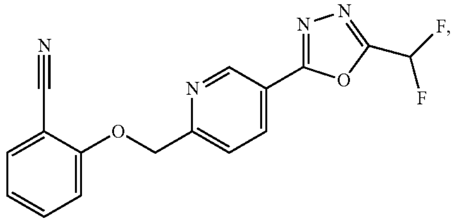
(43)
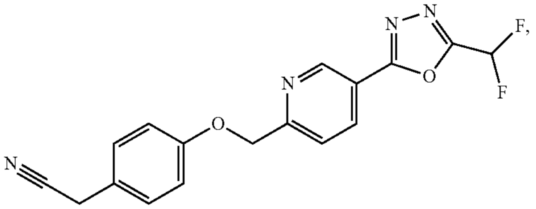
(44)
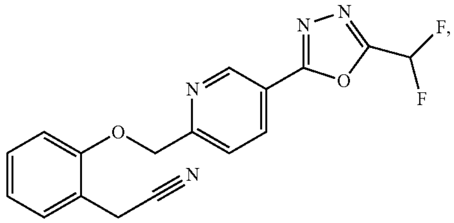
(45)
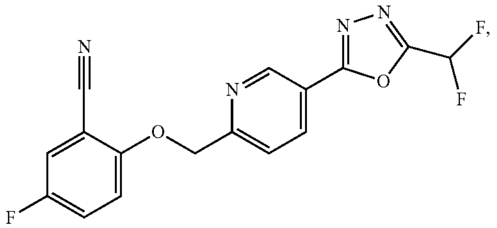
(46)
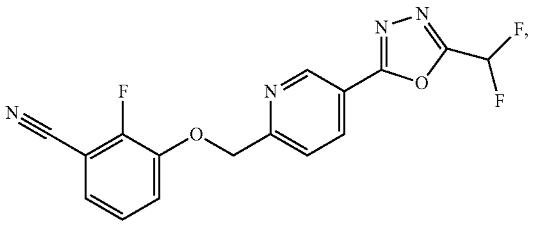
(47)
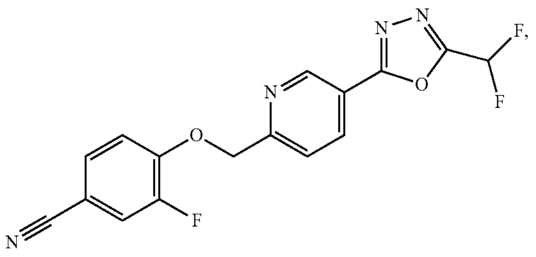

(48)

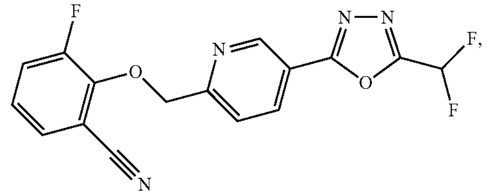

(49)

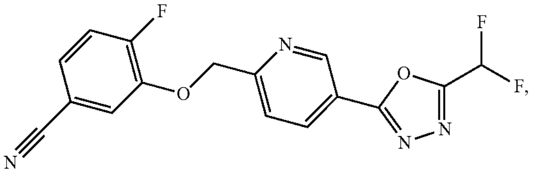

(50)

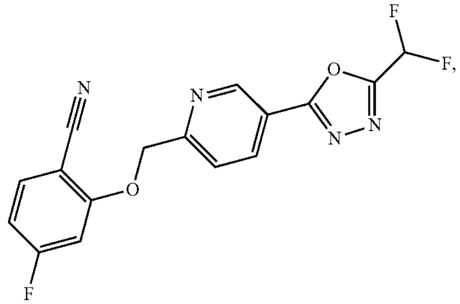

(51)

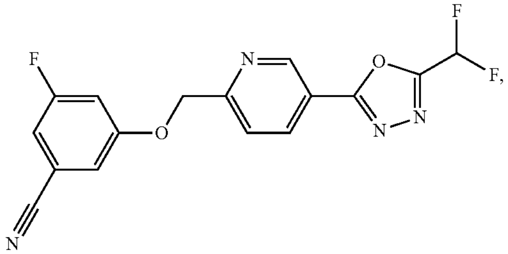

or (52)

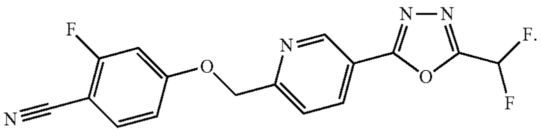

In certain embodiments, the compound of Formula (I) is one of the following compounds, or a pharmaceutically acceptable salt thereof:

(68)

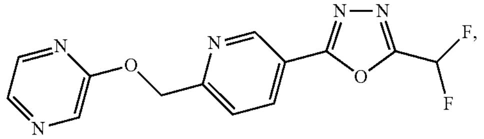

(78)

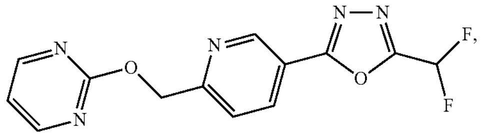

(102)

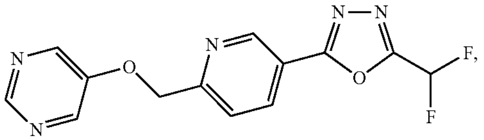

(103)

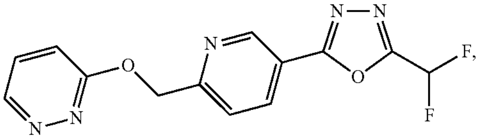

or (104)

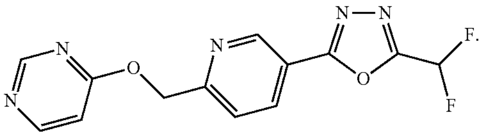

In certain embodiments, the compound of Formula (I) is one of the following compounds, or a pharmaceutically acceptable salt thereof:

(73)

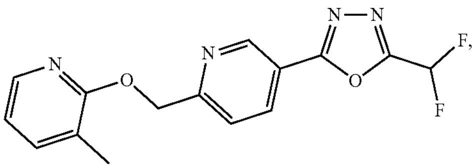

(74)

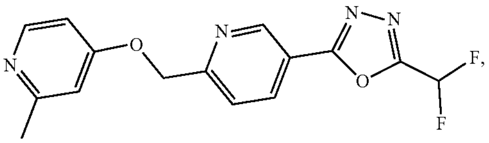

or (75)

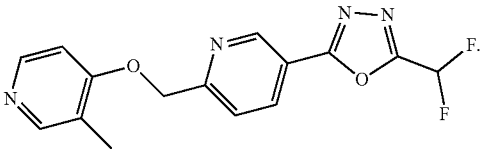

In certain embodiments, the compound of Formula (I) is one of the following compounds, or a pharmaceutically acceptable salt thereof:

(76)

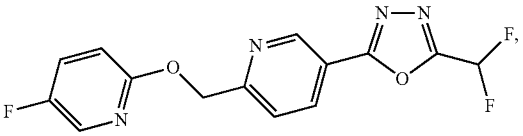

-continued
(77)
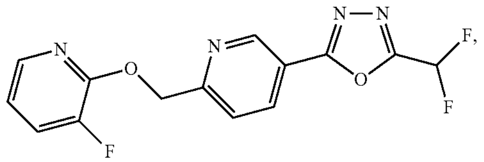
(80)
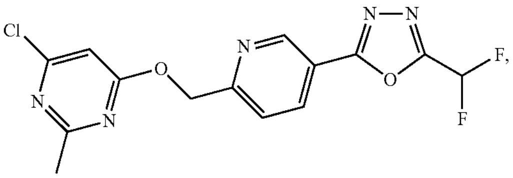
(81)
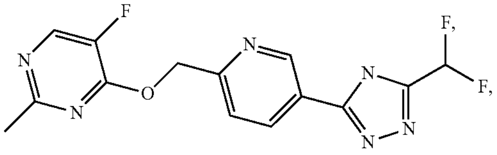
(90)
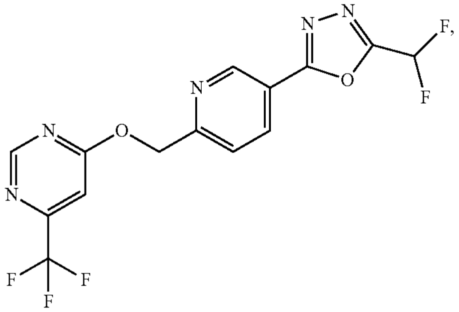
(91)
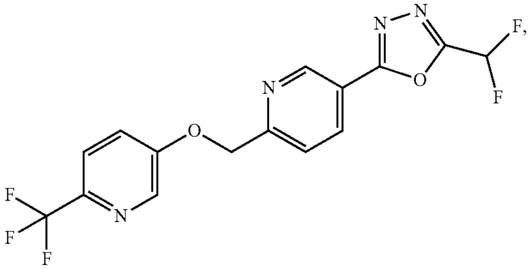
(92)
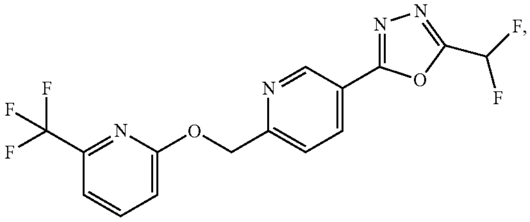
-continued
(93)
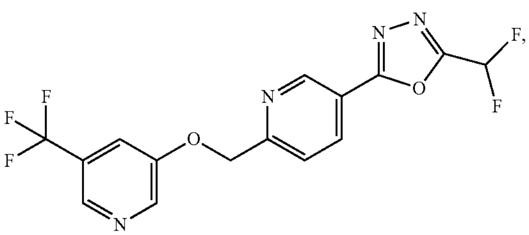
(94)
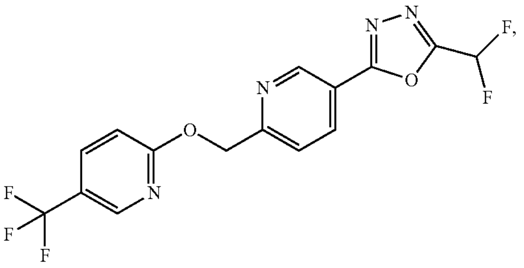
(106)
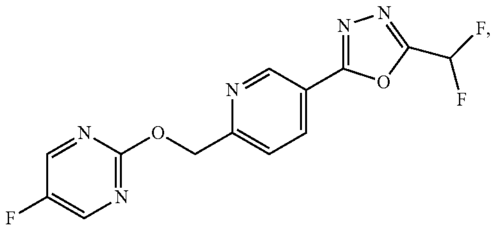
or
(107)
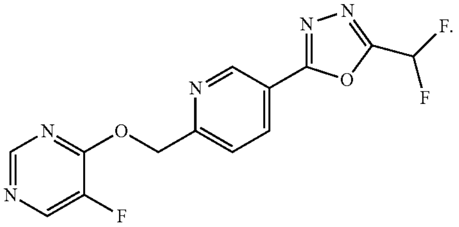
In certain embodiments, the compound of Formula (I) is one of the following compounds, or a pharmaceutically acceptable salt thereof:
(1)
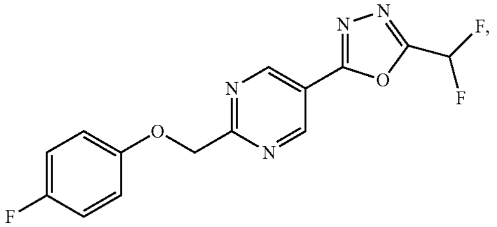

-continued
(2)
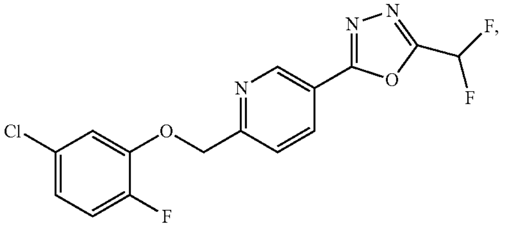
(3)
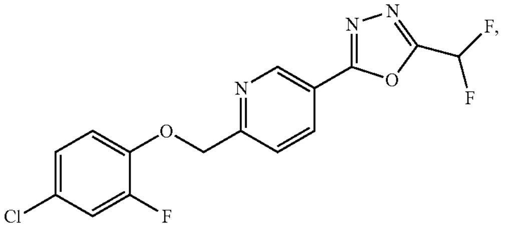
(4)
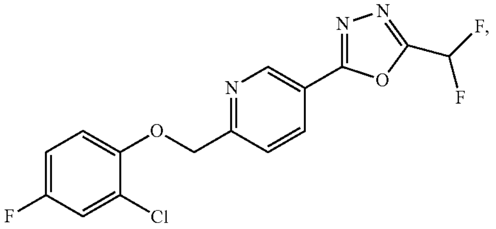
(5)
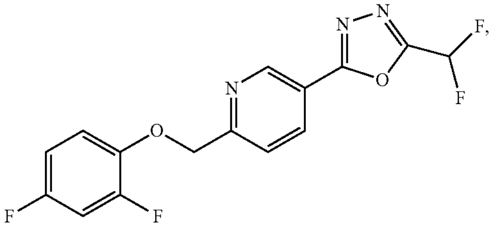
(6)
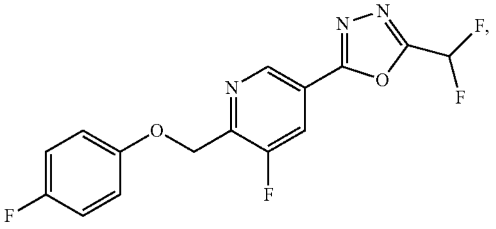
(7)
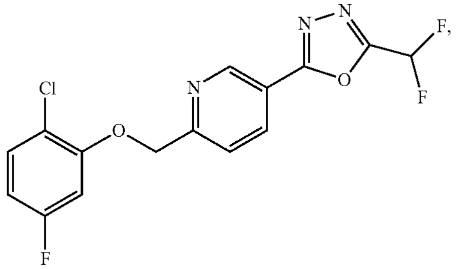
-continued
(9)
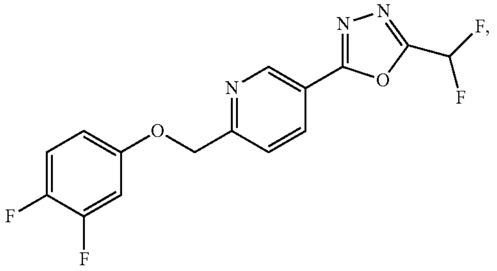
(10)
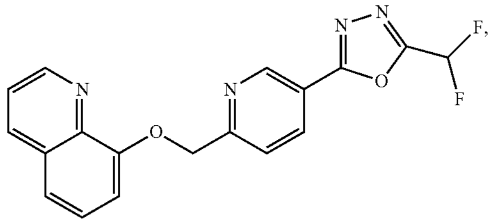
(11)
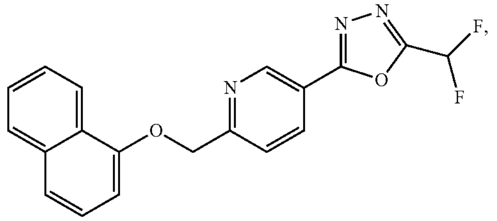
(12)
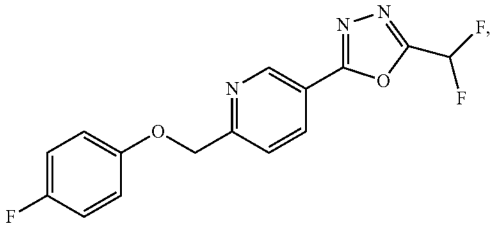
(36)
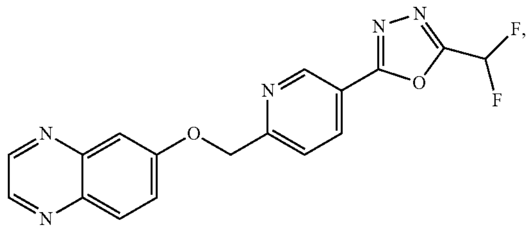
(58)
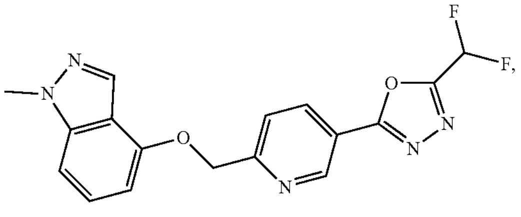
or -continued
(59)
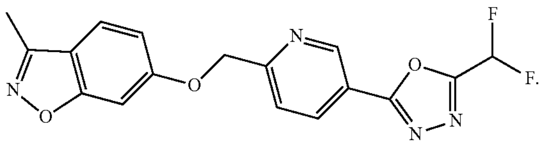
In certain embodiments, the compound of Formula (I) is one of the following compounds, or a pharmaceutically acceptable salt thereof:
(1)
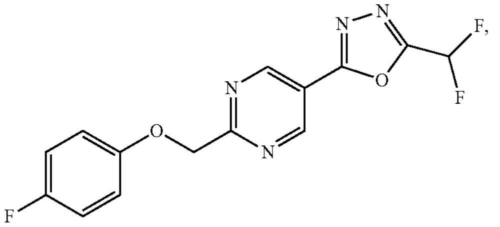
(2)
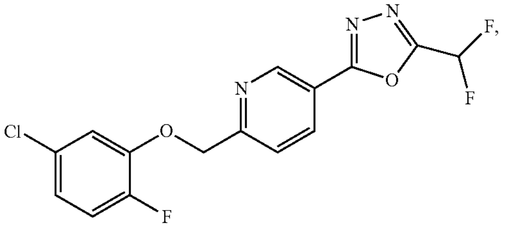
(3)
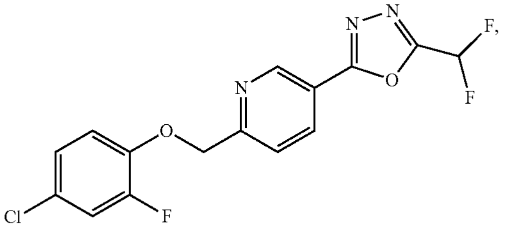
(4)
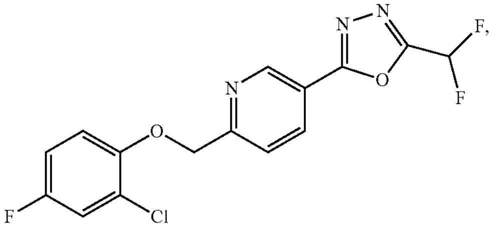
(5)
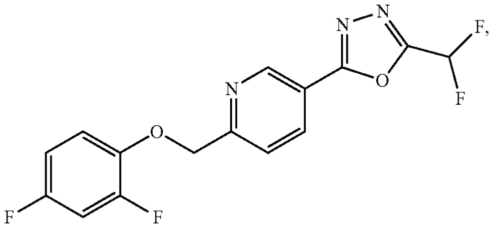
-continued
(6)
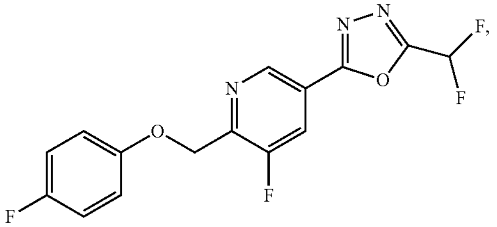
(7)
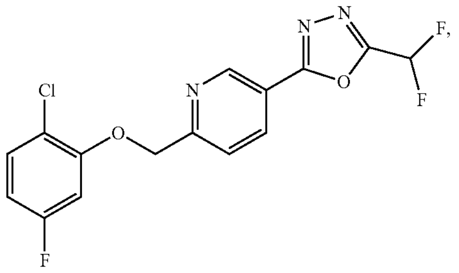
(9)
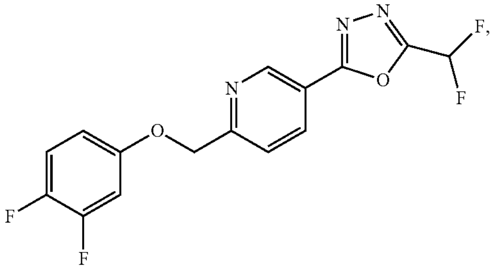
or
(12)
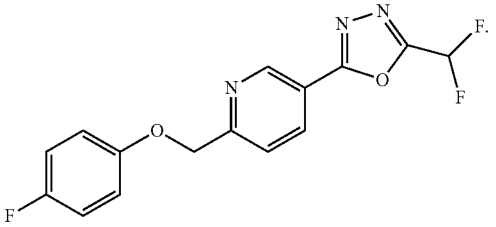
In certain embodiments, the compound of Formula (I) is of formula:
(1)
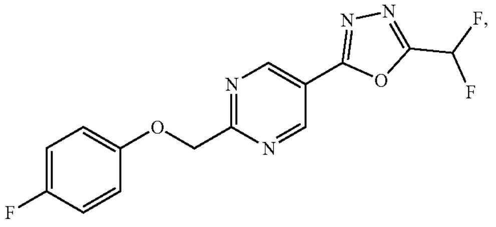
or a pharmaceutically acceptable salt thereof.
In certain embodiments, the compound of Formula (I) is of formula:

(2)

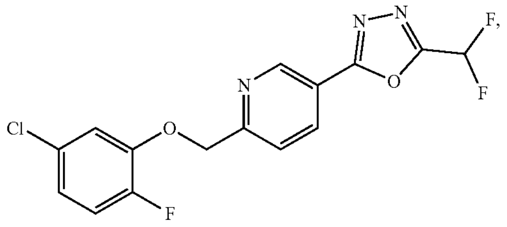

or a pharmaceutically acceptable salt thereof.

In certain embodiments, the compound of Formula (I) is of formula:

(3)

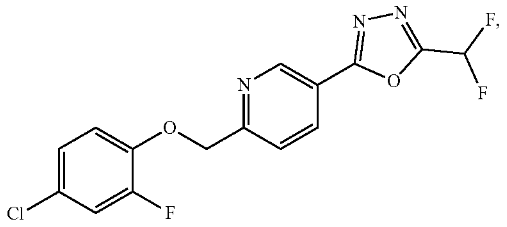

or a pharmaceutically acceptable salt thereof.

In certain embodiments, the compound of Formula (I) is of formula:

(4)

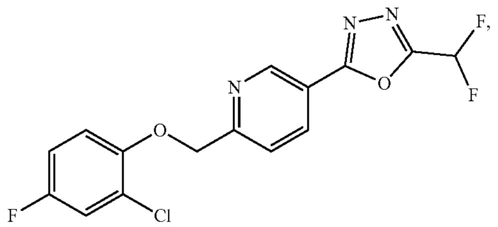

or a pharmaceutically acceptable salt thereof.

In certain embodiments, the compound of Formula (I) is of formula:

(5)

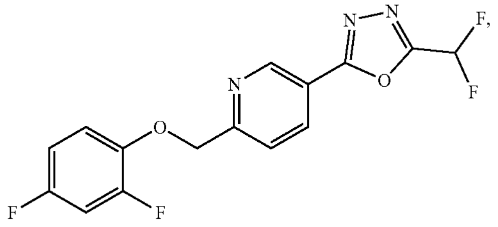

or a pharmaceutically acceptable salt thereof.

In certain embodiments, the compound of Formula (I) is of formula:

(6)

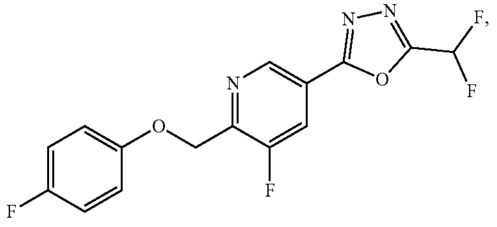

or a pharmaceutically acceptable salt thereof.

In certain embodiments, the compound of Formula (I) is of formula:

(7)

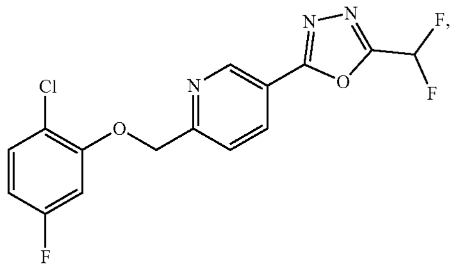

or a pharmaceutically acceptable salt thereof.

In certain embodiments, the compound of Formula (I) is of formula:

(9)

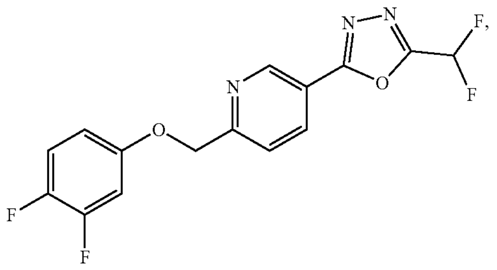

or a pharmaceutically acceptable salt thereof.

In certain embodiments, the compound of Formula (I) is of formula:

(12)

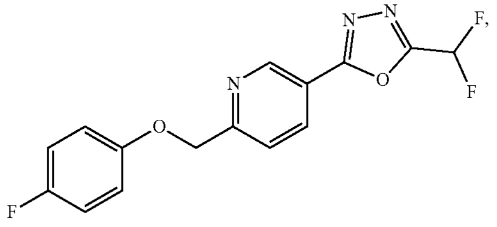

or a pharmaceutically acceptable salt thereof.

In certain embodiments, the compound of Formula (I) is one of the following compounds, or a pharmaceutically acceptable salt thereof:

(10)

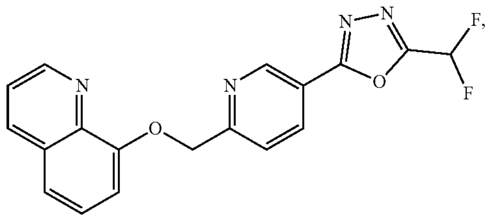

(11)

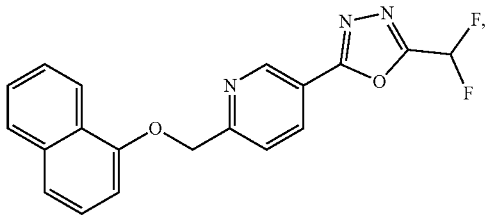

(36)

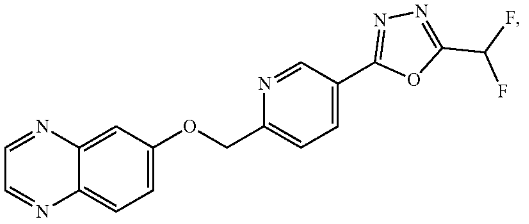

(58)

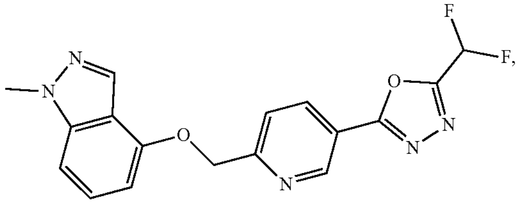

(59)

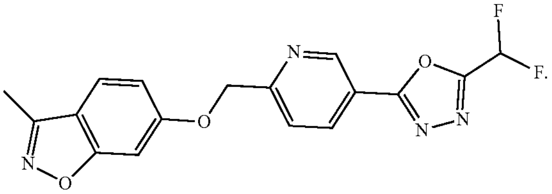

In certain embodiments, the compound of Formula (I) is of formula:

(10)

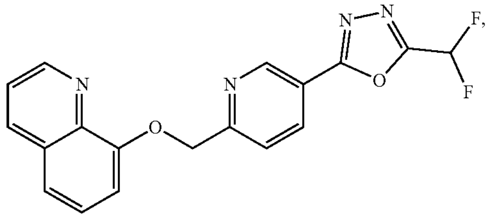

or a pharmaceutically acceptable salt thereof.

In certain embodiments, the compound of Formula (I) is of formula:

(11)

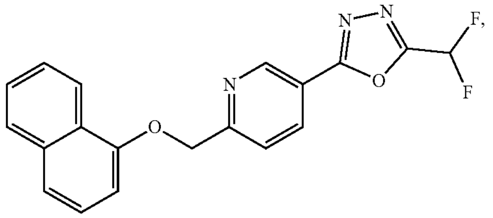

or a pharmaceutically acceptable salt thereof.

In certain embodiments, the compound of Formula (I) is of formula:

(36)

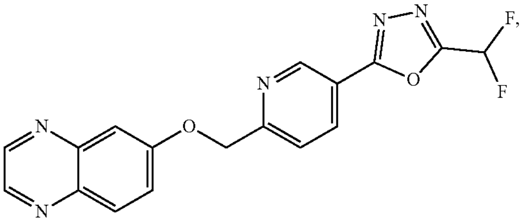

or a pharmaceutically acceptable salt thereof.

In certain embodiments, the compound of Formula (I) is of formula:

(58)

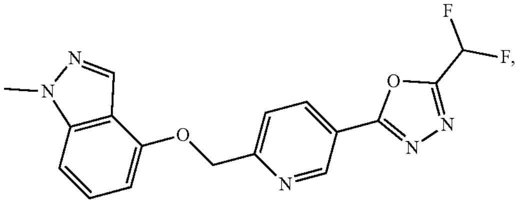

or a pharmaceutically acceptable salt thereof.

In certain embodiments, the compound of Formula (I) is of formula:

(59)

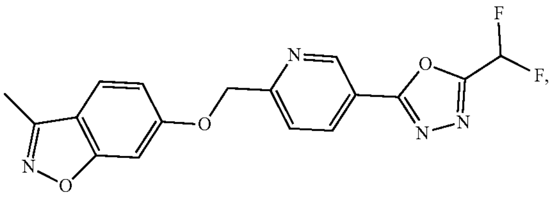

or a pharmaceutically acceptable salt thereof.

In certain embodiments, the compound of Formula (I) is one of the following compounds, or a pharmaceutically acceptable salt thereof:

(1)
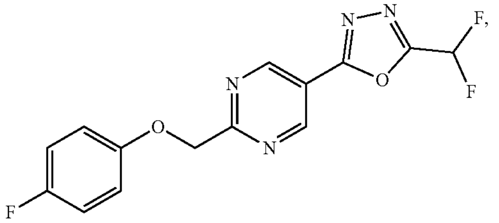
(86)
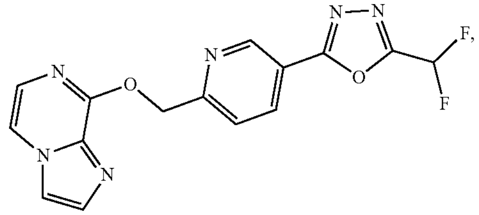
(137)
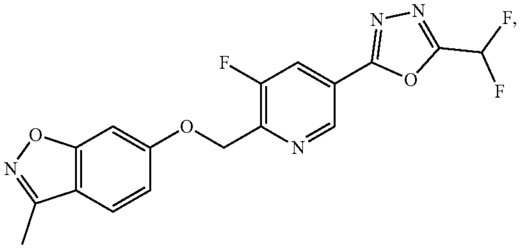
(139)
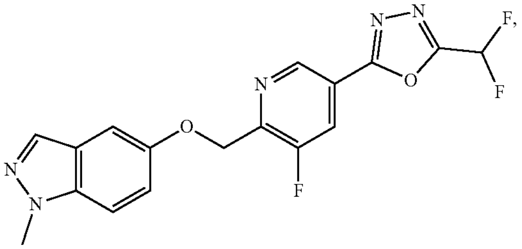
(166)
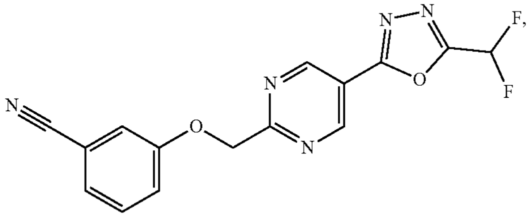
(178)
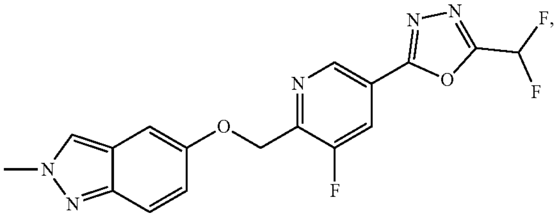
-continued
(179)
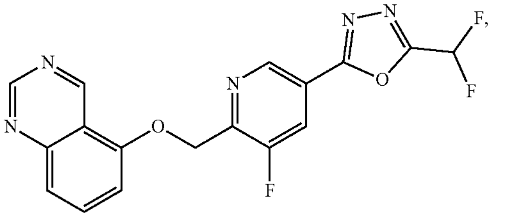
(180)
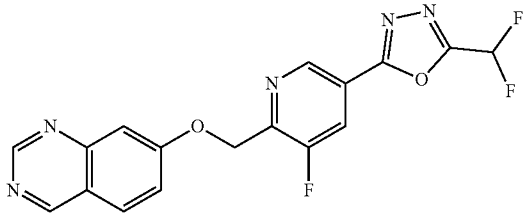
(181)
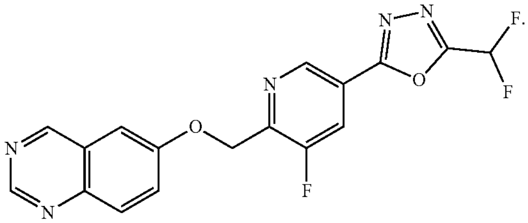
In certain embodiments, the compound of Formula (I) is of formula:
(86)
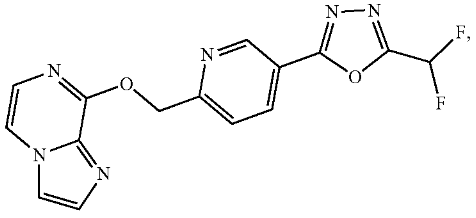
or a pharmaceutically acceptable salt thereof.
In certain embodiments, the compound of Formula (I) is of formula:
(137)
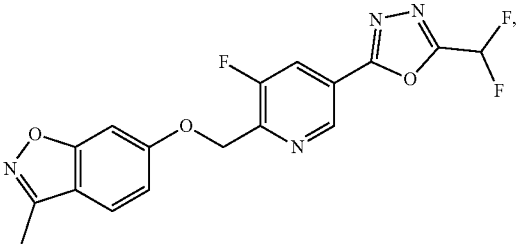
or a pharmaceutically acceptable salt thereof.
In certain embodiments, the compound of Formula (I) is of formula:

(139)

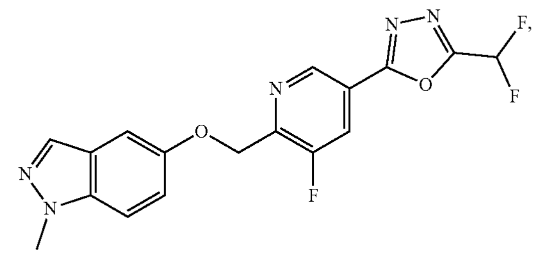

or a pharmaceutically acceptable salt thereof.

In certain embodiments, the compound of Formula (I) is of formula:

(166)

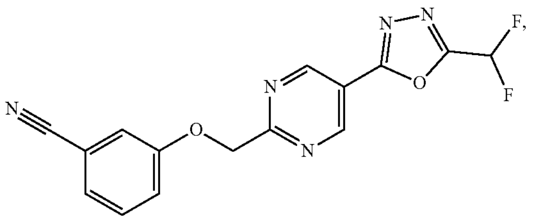

or a pharmaceutically acceptable salt thereof.

In certain embodiments, the compound of Formula (I) is of formula:

(178)

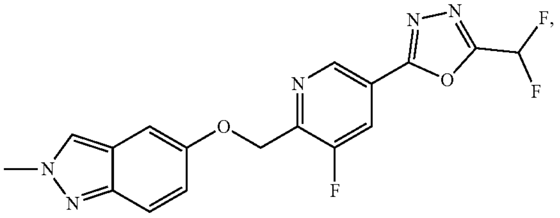

or a pharmaceutically acceptable salt thereof.

In certain embodiments, the compound of Formula (I) is of formula:

(179)

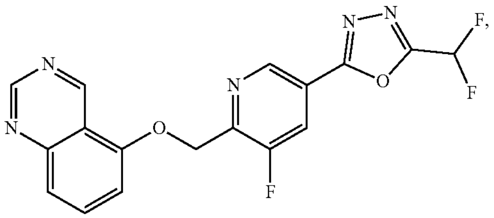

or a pharmaceutically acceptable salt thereof.

In certain embodiments, the compound of Formula (I) is of formula:

(180)

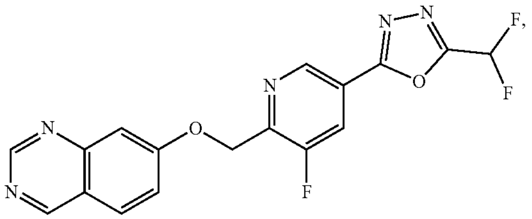

or a pharmaceutically acceptable salt thereof.

In certain embodiments, the compound of Formula (I) is of formula:

(181)

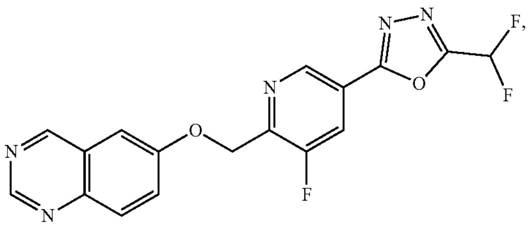

or a pharmaceutically acceptable salt thereof.

In certain embodiments, a compound is a compound of Formula (I) or a pharmaceutically acceptable salt thereof, wherein:

$R^a$ and $R^b$ are each independently hydrogen or fluoro;

Y is $CR^1$ or N;

$R^1$ is hydrogen or fluoro;

A is a monocyclic or bicyclic aryl or heteroaryl, wherein A is optionally substituted with one or more substituents $R^2$;

each occurrence of $R^2$ is independently fluoro, chloro, cyano, alkyl optionally substituted with cyano, halogen, amido, cyano, substituted or unsubstituted acyl, substituted or unsubstituted alkyl, substituted or unsubstituted alkenyl, substituted or unsubstituted alkynyl, substituted or unsubstituted heteroaliphatic, substituted or unsubstituted carbocyclyl, or substituted or unsubstituted heterocyclyl.

In certain embodiments, a compound is a compound of Formula (I) or a pharmaceutically acceptable salt thereof, wherein: $R^a$ and $R^b$ are each independently hydrogen or fluoro; Y is $CR^1$ or N; $R^1$ is hydrogen or fluoro; and A in Formula (I) or Formula (I-1) is (a) a $C_6$ aryl ring optionally fused with a $C_{5-6}$ carbocyclyl or a 5-6 membered heterocyclyl, (b) a 5-6-membered heteroaryl comprising one or more heteroatoms selected from the group consisting of nitrogen, oxygen and sulfur, and optionally fused with a $C_{5-6}$ carbocyclyl or a 5-6 membered heterocyclyl, or (c) an 8-10 membered bicyclic aryl or heteroaryl ring system; and A is optionally substituted with one or two $R^2$ that may be the same or different, wherein $R^2$ is selected from fluoro, chloro, $C_{1-4}$ alkyl optionally substituted with one or more fluoro, —CN, —$CH_2CN$, 3-6 membered cycloalkyl or heterocycloalkyl, or amido.

In certain embodiments, a compound is a compound of Formula (I) or a pharmaceutically acceptable salt thereof, wherein: $R^a$ and $R^b$ are each independently hydrogen or fluoro; and $R^1$ is hydrogen in Formula (I) or Formula (I-1).

In certain embodiments, $R^a$ and $R^b$ are each independently hydrogen or fluoro; Y is $CR^1$ or N; $R^1$ is hydrogen or fluoro; and A in Formula (I) or Formula (I-1) is a $C_6$ aryl ring optionally substituted with one or two $R^2$ that may be the same or different, wherein each $R^2$ is independently selected from fluoro, chloro, $C_{1-4}$ alkyl optionally substituted with one or two fluoro or chloro, —CN, —$CH_2$CN, and —C(O)$NH_2$. In certain embodiments, $R^a$ and $R^b$ are each independently hydrogen; Y is $CR^1$ or N; $R^1$ is hydrogen or fluoro; and A in Formula (I) or Formula (I-1) is a $C_6$ aryl ring optionally substituted with one or two fluoro. In certain embodiments, $R^a$ and $R^b$ are each independently hydrogen; Y is $CR^1$ or N; $R^1$ is hydrogen or fluoro; and A in Formula (I) or Formula (I-1) is a $C_6$ aryl ring substituted with one or two fluoro.

In certain embodiments, a compound is a compound of Formula (I) or a pharmaceutically acceptable salt thereof, wherein: $R^a$ and $R^b$ are each independently hydrogen; Y is $CR^1$; $R^1$ is hydrogen; A in Formula (I) or Formula (I-1) is a 5- or 6-membered heteroaryl comprising one or more heteroatoms selected from the group consisting of nitrogen, oxygen and sulfur, and optionally substituted with one or two $R^2$ that may be the same or different, wherein each $R^2$ is independently selected from fluoro, methyl optionally substituted with one or two fluoro, chloro, methyl optionally substituted with one, two or three fluoro, —CN, ethyl, propyl, cyclopropyl, and morpholinyl. In certain embodiments, $R^a$ and $R^b$ are each independently hydrogen; Y is $CR^1$; $R^1$ is hydrogen; A in Formula (I) or Formula (I-1) is pyrimidinyl, pyrazinyl, isoxazolyl, pyrazolyl, oxadiazolyl, imidazolyl, or thiophenyl; and A is optionally substituted with one or two fluoro, chloro, methyl, —$CF_3$, —CN, ethyl, propyl, cyclopropyl, and morpholinyl.

In certain embodiments, a compound is a compound of Formula (I) or a pharmaceutically acceptable salt thereof, wherein: $R^a$ and $R^b$ are each independently hydrogen or fluoro; Y is $CR^1$ or N; $R^1$ is hydrogen; A in Formula (I) or Formula (I-1) is a $C_6$ aryl ring fused with a $C_{5-6}$ carbocyclyl or a 5-6 membered heterocyclyl, and A is optionally substituted with one or two $R^2$ that may be the same or different, wherein $R^2$ is selected from fluoro and chloro. In certain embodiments, $R^a$ and $R^b$ are each independently hydrogen or fluoro; Y is $CR^1$ or N; $R^1$ is hydrogen; A in Formula (I) or Formula (I-1) is a tetrahydroisoquinolinyl, or tetrahydronaphthalenyl, and A is substituted with one or two methyl.

In certain embodiments, a compound is a compound of Formula (I) or a pharmaceutically acceptable salt thereof, wherein: $R^a$ and $R^b$ are each independently hydrogen or fluoro; Y is $CR^1$ or N; $R^1$ is hydrogen or fluoro; and A in Formula (I) or Formula (I-1) is an 8-10 membered bicyclic aryl or heteroaryl ring system comprising one or more heteroatoms selected from nitrogen, oxygen and sulfur; and A is optionally substituted with one or two $R^2$ that may be the same or different, wherein $R^2$ is selected from chloro, fluoro, and methyl. In certain embodiments, $R^a$ and $R^b$ are each independently hydrogen or fluoro; Y is $CR^1$ or N; $R^1$ is hydrogen, fluoro, or methyl; and A in Formula (I) or Formula (I-1) is a 5,6-bicyclic aryl or a 5,6-bicyclic heteroaryl ring system comprising one or more heteroatoms selected from nitrogen, oxygen and sulfur; and A is optionally substituted with one or two $R^2$ that may be the same or different, wherein $R^2$ is selected from chloro, fluoro, or methyl. In certain embodiments, $R^a$ and $R^b$ are each hydrogen; Y is $CR^1$ or N; $R^1$ is hydrogen or fluoro; and A in Formula (I) or Formula (I-1) is quinolinyl, naphthalenyl, isoquinolinyl, tetrahydroisoquinolinyl quinazolinyl, quinoxalinyl, naphthalenyl, benzimidazolyl, benzoxazolyl, indazolyl, indozazinyl, or imidazopyridinyl; and A is optionally substituted with methyl.

In certain embodiments, a compound is a compound of Formula (I) or a pharmaceutically acceptable salt thereof, wherein: $R^a$ and $R^b$ are each independently hydrogen or fluoro; Y is $CR^1$ or N; $R^1$ is hydrogen; A in Formula (I) or Formula (I-1) is (a) a $C_6$ aryl ring optionally fused with a $C_{5-6}$ carbocyclyl or a 5-6 membered heterocyclyl, (b) a 5- or 6-membered heteroaryl ring comprising one or more heteroatoms selected from the group consisting of nitrogen, oxygen and sulfur, and optionally fused with a $C_{5-6}$ carbocyclyl or a 5-6 membered heterocyclyl, or (c) an 8-10 membered bicyclic aryl or heteroaryl ring system; and A is optionally substituted with one or two $R^2$ that may be the same or different, wherein $R^2$ is selected from fluoro, chloro, $C_{1-4}$ alkyl optionally substituted with one or more fluoro, —CN, —$CH_2$CN, 3-6 membered cycloalkyl or heterocycloalkyl, or amido.

In certain embodiments, the compound of Formula (I) is not one or more of the following compounds: 2-(difluoromethyl)-5-(2-((4-fluorophenoxy)methyl)pyrimidin-5-yl)-1,3,4-oxadiazole (1); 2-(6-((5-chloro-2-fluorophenoxy)methyl)pyridin-3-yl)-5-(difluoromethyl)-1,3,4-oxadiazole (2); 2-(6-((4-chloro-2-fluorophenoxy)methyl)pyridin-3-yl)-5-(difluoromethyl)-1,3,4-oxadiazole (3); 2-(6-((2-chloro-4-fluorophenoxy)methyl)pyridin-3-yl)-5-(difluoromethyl)-1,3,4-oxadiazole (4); 2-(difluoromethyl)-5-(6-((2,4-difluorophenoxy)methyl)pyridin-3-yl)-1,3,4-oxadiazole (5); 2-(difluoromethyl)-5-(5-fluoro-6-((4-fluorophenoxy)methyl)pyridin-3-yl)-1,3,4-oxadiazole (6); 2-(6-((2-chloro-5-fluorophenoxy)methyl)pyridin-3-yl)-5-(difluoromethyl)-1,3,4-oxadiazole (7); 2-(6-((4-chlorophenoxy)methyl)pyridin-3-yl)-5-(difluoromethyl)-1,3,4-oxadiazole (8); 2-(difluoromethyl)-5-(6-((3,4-difluorophenoxy)methyl)pyridin-3-yl)-1,3,4-oxadiazole (9); 2-(difluoromethyl)-5-(6-((quinolin-8-yloxy)methyl)pyridin-3-yl)-1,3,4-oxadiazole (10); 2-(difluoromethyl)-5-(6-((naphthalen-1-yloxy)methyl)pyridin-3-yl)-1,3,4-oxadiazole (11); 2-(difluoromethyl)-5-(6-((4-fluorophenoxy)methyl)pyridin-3-yl)-1,3,4-oxadiazole (12); 2-(6-(difluoro(quinolin-8-yloxy)methyl)pyridin-3-yl)-5-(difluoromethyl)-1,3,4-oxadiazole (13); 2-(6-(difluoro(naphthalen-1-yloxy)methyl)pyridin-3-yl)-5-(difluoromethyl)-1,3,4-oxadiazole (14); and 2-(6-(difluoro(4-fluorophenoxy)methyl)pyridin-3-yl)-5-(difluoromethyl)-1,3,4-oxadiazole (15).

In certain embodiments, the provided compounds (e.g., compounds of Formula (I)) inhibit HDAC6 with an $IC_{50}$ of less than 100,000 nM, less than 50,000 nM, less than 20,000 nM, less than 10,000 nM, less than 5,000 nM, less than 2,500 nM, less than 1,000 nM, less than 900 nM, less than 800 nM, less than 700 nM, less than 600 nM, less than 500 nM, less than 400 nM, less than 300 nM, less than 200 nM, less than 100 nM, less than 90 nM, less than 80 nM, less than 70 nM, less than 60 nM, less than 50 nM, less than 40 nM, less than 30 nM, less than 20 nM, less than 10 nM, less than 5 nM, less than 4 nM, less than 3 nM, less than 2 nM, or less than 1 nM.

In certain embodiments, the provided compounds (e.g., compounds of Formula (I)) selectively inhibit HDAC6 over any of HDAC1, HDAC2, HDAC3, HDAC4, HDAC5, HDAC7, HDAC8, HDAC9, HDAC10, and HDAC11. In certain embodiments, the compounds selectively inhibit HDAC6 over each of HDAC1, HDAC2, HDAC3, HDAC4, HDAC5, HDAC7, HDAC8, HDAC9, HDAC10, and HDAC11. In certain embodiments, the compounds are 5-fold, 10-fold, 20-fold, 30-fold, 40-fold, 50-fold, 60-fold, 70-fold, 80-fold, 90-fold, 100-fold, 1,000-fold, or 10,000-fold, more selective inhibitors of HDAC6 over any of HDAC1, HDAC2, HDAC3, HDAC4, HDAC5, HDAC7, HDAC8, HDAC9, HDAC10, and HDAC11. In certain embodiments, the compounds are 5-fold, 10-fold, 20-fold, 30-fold, 40-fold, 50-fold, 60-fold, 70-fold, 80-fold, 90-fold, 100-fold, 1,000-fold, or 10,000-fold, more selective inhibitors of HDAC6 over each of HDAC1, HDAC2, HDAC3, HDAC4, HDAC5, HDAC7, HDAC8, HDAC9, HDAC10, and HDAC11. In certain embodiments, the compounds are 5-fold, 10-fold, 20-fold, 30-fold, 40-fold, 50-fold, 60-fold, 70-fold, 80-fold, 90-fold, 100-fold, 1,000-fold, or 10,000-fold, more selective inhibitors of HDAC6 over HDAC8.

Pharmaceutical Compositions, Kits, and Administration

The present disclosure provides pharmaceutical compositions comprising a disclosed compound (e.g., a compound of Formula (I)), or a pharmaceutically acceptable salt, co-crystal, tautomer, stereoisomer, solvate, hydrate, polymorph, isotopically enriched derivative, or prodrug thereof, and optionally a pharmaceutically acceptable excipient. In certain embodiments, the pharmaceutical composition described herein comprises a compound of Formula (I), or a pharmaceutically acceptable salt thereof, and a pharmaceutically acceptable excipient.

In certain embodiments, the compound of Formula (I) is provided in an effective amount in the pharmaceutical composition. In certain embodiments, the effective amount is a therapeutically effective amount. In certain embodiments, the effective amount is a prophylactically effective amount. In certain embodiments, the effective amount is an amount effective for treating a proliferative disease in a subject in need thereof. In certain embodiments, the effective amount is an amount effective for treating cancer in a subject in need thereof. In certain embodiments, the effective amount is an amount effective for preventing cancer in a subject in need thereof. In certain embodiments, the effective amount is an amount effective for treating a hematological cancer in a subject in need thereof. In certain embodiments, the effective amount is an amount effective for treating a cancer comprising a solid tumor in a subject in need thereof. In certain embodiments, the effective amount is an amount effective for treating inflammatory disease in a subject in need thereof. In certain embodiments, the effective amount is an amount effective for preventing inflammatory disease in a subject in need thereof. In certain embodiments, the effective amount is an amount effective for treating an infectious disease in a subject in need thereof. In certain embodiments, the effective amount is an amount effective for preventing an infectious disease in a subject in need thereof. In certain embodiments, the effective amount is an amount effective for treating a cardiovascular disease in a subject in need thereof. In certain embodiments, the effective amount is an amount effective for treating a neurological disorder in a subject in need thereof. In certain embodiments, the effective amount is an amount effective for preventing a neurological disorder in a subject in need thereof. In certain embodiments, the effective amount is an amount effective for treating a neurodegenerative, neurodevelopmental, neuropsychiatric, or neuropathy disease in a subject in need thereof. In certain embodiments, the effective amount is an amount effective for preventing a neurodegenerative, neurodevelopmental, neuropsychiatric, or neuropathy disease in a subject in need thereof.

In certain embodiments, the effective amount is an amount effective for reducing the risk of developing a disease (e.g., proliferative disease, inflammatory disease, infectious disease, a neurological disorder, peripheral disease, or cardiovascular disease) in a subject in need thereof.

In certain embodiments, the effective amount is an amount effective for inhibiting the activity (e.g., aberrant activity, such as increased activity) of HDAC6 in a subject, tissue, biological sample, or cell.

In certain embodiments, the subject being treated or administered a compound described herein is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs). In certain embodiments, the subject is a fish or reptile.

In certain embodiments, the effective amount is an amount effective for inhibiting the activity of HDAC6 by at least about 10%, at least about 20%, at least about 30%, at least about 40%, at least about 50%, at least about 60%, at least about 70%, at least about 80%, at least about 90%, at least about 95%, at least about 98%, or at least about 99%. In certain embodiments, the effective amount is an amount effective for inhibiting the activity of HDAC6 by a range between a percentage described in this paragraph and another percentage described in this paragraph, inclusive.

The present disclosure provides pharmaceutical compositions comprising a compound that interacts with (e.g., inhibits) HDAC6 for use in treating a HDAC6-related disease or disorder in a subject in need thereof. The present disclosure provides pharmaceutical compositions comprising a compound that interacts with (e.g., inhibits) HDAC6 for use in treating a disease or disorder associated with aberrant activity of HDAC6 in a subject in need thereof. The present disclosure provides pharmaceutical compositions comprising a compound that interacts with (e.g., inhibits) HDAC6 for use in treating a disease or disorder associated with increased activity of HDAC6 in a subject in need thereof.

In certain embodiments, the composition is for use in treating a proliferative disease in a subject in need thereof. In certain embodiments, the composition is for use in treating cancer in a subject in need thereof. In certain embodiments, the composition is for use in treating a hematological cancer. In certain embodiments, the composition is for use in treating a leukemia, T-cell lymphoma, Hodgkin's Disease, non-Hodgkin's lymphoma, or multiple myeloma. In certain embodiments, the composition is for use in treating a cancer comprising a solid tumor. In certain embodiments, the composition is for use in treating glioma, glioblastoma, non-small cell lung cancer, brain tumor, neuroblastoma, bone tumor, soft-tissue sarcoma, head and neck cancer, genitourinary cancer, lung cancer, breast cancer, pancreatic cancer, melanoma, stomach cancer, brain cancer, liver cancer, thyroid cancer, clear cell carcinoma, uterine cancer, or ovarian cancer.

In certain embodiments, the composition is for use in treating an inflammatory disease. In certain embodiments, the composition is for use in treating osteoarthritis, rheumatoid arthritis, lupus, inflammatory bowel disease, Crohn's Disease, ulcerative colitis, anemia, leukocytosis, asthma, chronic obstructive pulmonary disease, appendicitis, bronchitis, bursitis, conjunctivitis, dermatitis, encephalitis, myelitis myocarditis, sinusitis, dermatitis, psoriasis, eczema, or acne.

In certain embodiments, the composition is for use in treating an infectious disease. In certain embodiments, the composition is for use in treating bacterial, fungal, or protozoal infections.

In certain embodiments, the composition is for use in treating autoimmune disease. In certain embodiments, the composition is for use in treating diabetes, thyroiditis, Graves' disease, Guillain-Barre syndrome, Addison's disease, scleroderma, primary biliary cirrhosis, Reiter's syndrome, psoriasis, chronic fatigue, or endometriosis.

In certain embodiments, the composition is for use in treating heteroimmune disease. In certain embodiments, the composition is for use in treating graft versus host disease, transplantation, transfusion, anaphylaxis, allergic conjunctivitis, or allergic rhinitis.

In certain embodiments, the composition is for use in treating a neurological disease or disorder. In certain embodiments, the composition is for use in treating a neurodegenerative, neurodevelopmental, neuropsychiatric, or neuropathy disease or disorder. In certain embodiments, the composition is for use in treating Fragile-X syndrome, Charcot-Marie-Tooth disease, Alzheimer's disease, Parkinson's diseases, Huntington's disease, multiple sclerosis, amyotrophic lateral sclerosis, Creutzfeldt-Jakob disease, Lewy body dementia, vascular dementia, muscular atrophy, seizure induced memory loss, schizophrenia, Rubinstein Taybi syndrome, Rett Syndrome, attention deficit hyperactivity disorder, dyslexia, bipolar disorder, social, cognitive and learning disorders associated with autism, attention deficit disorder, schizophrenia, major depressive disorder, peripheral neuropathy, diabetic retinopathy, diabetic peripheral neuropathy, chemotherapy-induced peripheral neuropathy, chemotherapy-induced cognitive dysfunction, traumatic brain injury (TBI), chronic traumatic encephalopathy (CTE), or a tauopathy. In certain embodiments, the composition is for use in treating primary age-related tauopathy (PART)/neurofibrillary tangle-predominant senile dementia, chronic traumatic encephalopathy, dementia pugilistica, progressive supranuclear palsy, corticobasal degeneration, Pick's disease, frontotemporal dementia, frontotemporal dementia and parkinsonism linked to chromosome 17, Lytico-Bodig disease, ganglioglioma, gangliocytoma, meningioangiomatosis, postencephalitic parkinsonism, subacute sclerosing panencephalitis, lead encephalopathy, tuberous sclerosis, lipofuscinosis, Alzheimer's disease, or argyrophilic grain disease.

In certain embodiments, the composition is for use in treating a neurological or peripheral disorder. In certain embodiments, the composition is for use in treating a neurodegenerative, neurodevelopmental, neuropsychiatric, or neuropathy disease or disorder.

In certain embodiments, the composition is for use in treating Alzheimer's disease, Fragile-X syndrome, Charcot-Marie-Tooth disease, Parkinson's disease, Huntington's disease, multiple sclerosis, amyotrophic lateral sclerosis, Rett Syndrome, major depressive disorder, chemotherapy-induced cognitive dysfunction, traumatic brain injury (TBI), chronic traumatic encephalopathy (CTE), brain cancer, or a tauopathy such as frontotemporal dementia, progressive supranuclear palsy, or corticobasal degeneration.

In certain embodiments, the composition is for use in treating chemotherapy-induced peripheral neuropathy, diabetic peripheral neuropathy, peripheral neuropathy, diabetic retinopathy, obesity, autosomal dominant polycystic kidney disease, cardiomyopathy, an auto-immune disease such as systemic lupus erythematosus (SLE), or cancer.

In certain embodiments, the composition is for use in treating a disease or disorder mediated by or linked to T-cell dysregulation. In certain embodiments, the composition is for use in treating arthritis, colitis, allograft rejection, lupus, asthma, psoriasis, inflammation, allergy, allergic encephalomyelitis, autoimmune lymphoproliferative disorder, autoimmune polyglandular syndrome type II, type I diabetes, lymphoma, Wiskott-Aldrich syndrome, or myasthenia gravis.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, and/or in reducing the risk to develop a disease in a subject in need thereof), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a pharmaceutical composition described herein including a compound described herein and an additional pharmaceutical agent exhibit a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease, hematological cancer, chemo-induced neuropathy, neurological disorder, peripheral disease, autoimmune disease, and/or inflammatory disease). Each additional pharmaceutical agent may be administered at a dose and/or on a time schedule determined for that pharmaceutical agent. The additional pharmaceutical agents may also be administered to give theher with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, anti-proliferative agents, anti-cancer agents, anti-angiogenesis agents, anti-inflammatory agents, and immunosuppressants. In certain embodiments, the additional pharmaceutical agent is an anti-inflammatory agent. In certain embodiments, the additional pharmaceutical agent is an immunotherapy. In certain embodiments, the additional pharmaceutical agent is an anti-proliferative agent. In certain embodiments, the additional pharmaceutical agent is an anti-cancer agent. In certain embodiments, the anti-cancer agents include, but are not limited to, epigenetic or transcriptional modulators (e.g., DNA methyltransferase inhibitors, HDAC inhibitors, lysine methyltransferase inhibitors), antimitotic drugs (e.g., taxanes and vinca alkaloids), cell signaling pathway inhibitors (e.g., tyrosine protein kinase inhibitors), modulators of protein stability (e.g., proteasome inhibitors), Hsp90 inhibitors, glucocorticoids, all-trans retinoic acids, anti-estrogens (e.g., tamoxifen, raloxifene, and megestrol), LHRH agonists (e.g., goscrclin and leuprolide), anti-androgens (e.g. flutamide and bicalutamide), photodynamic therapies (e.g., vertoporfin (BPD-MA), phthalocyanine, photosensitizer Pc4, and demethoxy-hypocrellin A (2BA-2-DMHA)), nitrogen mustards (e.g., cyclophosphamide, ifosfamide, trofosfamide, chlorambucil, estramustine, and melphalan), nitrosoureas (e.g., carmustine (BCNU) and lomustine (CCNU)), alkylsulphonates (e.g., busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent such as nanoparticle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), antimetabolites, DHFR inhibitors (e.g., methotrexate, dichloromethotrexate, trimetrexate, edatrexate), IMP dehydrogenase inhibitors (e.g., mycophenolic acid, tiazofurin, ribavirin, and EICAR), ribonuclotide reductase inhibitors (e.g., hydroxyurea and deferoxamine), uracil analogs (e.g., 5-fluorouracil (5-FU), floxuridine, doxifluridine, ratitrexed, tegafur-uracil, capecitabine), cytosine analogs (e.g., cytarabine (ara C), cytosine arabinoside, and fludarabine), purine analogs (e.g., mercaptopurine and Thioguanine), Vitamin D3 analogs (e.g., EB 1089, CB 1093, and KH 1060), isoprenylation inhibitors (e.g., lovastatin), dopaminergic neurotoxins (e.g., 1-methyl-4-phenylpyridinium ion), cell cycle inhibitors (e.g., staurosporine), actinomycin (e.g., actinomycin D, dactinomycin), bleomycin (e.g., bleomycin A2, bleomycin B2, peplomycin), anthracycline (e.g., daunorubicin, doxorubicin, pegylated liposomal doxorubicin, idarubicin, epirubicin, pirarubicin, zorubicin, mitoxantrone), MDR inhibitors (e.g., verapamil), $Ca^{2+}$ ATPase inhibitors (e.g., thapsigargin), thalidomide, lenalidomide, pomalidomide, tyrosine kinase inhibitors (e.g., axitinib, bosutinib, cediranib (RECENTIN™), dasatinib (SPRYCEL®), erlotinib (TARCEVA®), gefitinib (IRESSA®), imatinib (Gleevec®), lapatinib (TYKERB®, TYVERB®), lestaurtinib, neratinib, nilotinib (TASIGNA®), semaxanib, sunitinib (SUTENT®), toceranib (PALLADIA®), vandetanib (ZACTIMA®, ZD6474), vatalanib (PTK787), nilotinib (TASIGNA®), sorafenib (NEXAVAR®), everolimus (AFINITOR®), gemtuzumab ozogamicin (MYLOTARG®), temsirolimus (TORISEL®), ENMD-2076, PCI-32765, AC220, dovitinib lactate (TK1258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine. In certain embodiments, the additional pharmaceutical agent is cisplatin. In certain embodiments, the additional pharmaceutical agent is paclitaxel. In certain embodiments, the additional pharmaceutical agent is vincristine.

In certain embodiments, the additional pharmaceutical agent is an immunotherapy. In certain embodiments, the immunotherapy is useful in the treatment of a cancer. Exemplary immunotherapies include, but are not limited to, T-cell therapies, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies. In certain embodiments, the immunotherapy is a T-cell therapy. In certain embodiments, the T-cell therapy is chimeric antigen receptor T cells (CAR-T). In certain embodiments, the immunotherapy is an antibody. In certain embodiments, the antibody is an anti-PD-1 antibody, an anti-PD-L1 antibody, an anti-CTLA-4 antibody, an anti-TIM3 antibody, an anti-OX40 antibody, an anti-GITR antibody, an anti-LAG-3 antibody, an anti-CD137 antibody, an anti-CD27 antibody, an anti-CD28 antibody, an anti-CD28H antibody, an anti-CD30 antibody, an anti-CD39 antibody, an anti-CD40 antibody, an anti-CD47 antibody, an anti-CD48 antibody, an anti-CD70 antibody, an anti-CD73 antibody, an anti-CD96 antibody, an anti-CD160 antibody, an anti-CD200 antibody, an anti-CD244 antibody, an anti-ICOS antibody, an anti-TNFRSF25 antibody, an anti-TMIGD2 antibody, an anti-DNAM1 antibody, an anti-BTLA antibody, an anti-LIGHT antibody, an anti-TIGIT antibody, an anti-VISTA antibody, an anti-HVEM antibody, an anti-Siglec antibody, an anti-GAL1 antibody, an anti-GAL3 antibody, an anti-GAL9 antibody, an anti-BTNL2 (butrophylins) antibody, an anti-B7-H3 antibody, an anti-B7-H4 antibody, an anti-B7-H5 antibody, an anti-B7-H6 antibody, an anti-KIR antibody, an anti-LIR antibody, an anti-ILT antibody, an anti-MICA antibody, an anti-MICB antibody, an anti-NKG2D antibody, an anti-NKG2A antibody, an anti-TGFβ antibody, an anti-TGFβR antibody, an anti-CXCR4 antibody, an anti-CXCL12 antibody, an anti-CCL2 antibody, an anti-IL-10 antibody, an anti-IL-13 antibody, an anti-IL-23 antibody, an anti-phosphatidylserine antibody, an anti-neuropilin antibody, an anti-GalCer antibody, an anti-HER2 antibody, an anti-VEGFA antibody, an anti-VEGFR antibody, an anti-EGFR antibody, or an anti-Tie2 antibody. In certain embodiments, the antibody is pembrolizumab, nivolumab, pidilizumab, ipilimumab, tremelimumab, durvalumab, atezolizumab, avelumab, PF-06801591, utomilumab, PDR001, PBF-509, MGB453, LAG525, AMP-224, INCSHR1210, INCAGN1876, INCAGN1949, samalizumab, PF-05082566, urelumab, lirilumab, lulizumab, BMS-936559, BMS-936561, BMS-986004, BMS-986012, BMS-986016, BMS-986178, IMP321, IPH2101, IPH2201, varilumab, ulocuplumab, monalizumab, MEDI0562, MEDIO680, MEDI1873, MEDI6383, MEDI6469, MEDI9447, AMG228, AMG820, CC-90002, CDX-1127, CGEN15001T, CGEN15022, CGEN15029, CGEN15049, CGEN15027, CGEN15052, CGEN15092, CX-072, CX-2009, CP-870893, lucatumumab, dacetuzumab, Chi Lob 7/4, RG6058, RG7686, RG7876, RG7888, TRX518, MK-4166, MGA271, IMC-CS4, emactuzumab, pertuzumab, obinutuzumab, cabiralizumab, margive theuximab, enoblituzumab, mogamulizumab, carlumab, bevacizumab, trastuzumab (HERCEPTIN®), bevacizumab (AVASTIN®), rituximab (RITUXAN®), cetuximab (ERBITUX®), panitumumab (VECTIBIX®), alemtuzumab (CAMPATH®), or ranibizumab (Lucentis®).

In certain embodiments, the additional pharmaceutical agent is a symptomatic drug, such as cholinesterase inhibitors (e.g., ARICEPT®, EXELON®, RAZADYNE®, donepezil, rivastigmine, and galantamine) and glutamate regulators (e.g., NAMENDA®, memantine). In certain embodiments, the additional pharmaceutical agent is riluzole. In certain embodiments, the additional pharmaceutical agent is edaravone. In certain embodiments, the additional pharmaceutical agent is an anti-amyloid or anti-tau antibody. In certain embodiments, the additional pharmaceutical agent is any agent useful in the treatment of Alzheimer's disease (e.g., small molecule, antibody, polypeptide, antisense oligo, RNA).

In certain embodiments, the compounds or pharmaceutical compositions described herein can be administered in combination with an anti-cancer therapy including, but not limited to, surgery, radiation therapy, and transplantation (e.g., stem cell transplantation, bone marrow transplantation).

In certain embodiments, the compound or pharmaceutical composition is a solid. In certain embodiments, the compound or pharmaceutical composition is a powder. In certain embodiments, the compound or pharmaceutical composition can be dissolved in a liquid to make a solution. In certain embodiments, the compound or pharmaceutical composition is dissolved in water to make an aqueous solution. In certain embodiments, the pharmaceutical composition is a liquid for parental injection. In certain embodiments, the pharmaceutical composition is a liquid for oral administration (e.g., ingestion). In certain embodiments, the pharmaceutical composition is a liquid (e.g., aqueous solution) for intravenous injection. In certain embodiments, the pharmaceutical composition is a liquid (e.g., aqueous solution) for subcutaneous injection.

After formulation with an appropriate pharmaceutically acceptable excipient in a desired dosage, the pharmaceutical compositions of the present disclosure can be administered to humans and other animals orally, parenterally, intracisternally, intraperitoneally, topically, bucally, or the like, depending on the disease or condition being treated.

In certain embodiments, a pharmaceutical composition comprising a compound of Formula (I) is administered, orally or parenterally, at dosage levels of each pharmaceutical composition sufficient to deliver from about 0.001 mg/kg to about 200 mg/kg in one or more dose administrations for one or several days (depending on the mode of administration). In certain embodiments, the effective amount per dose varies from about 0.001 mg/kg to about 200 mg/kg, about 0.001 mg/kg to about 100 mg/kg, about 0.01 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, of subject body weight per day, one or more times a day, to obtain the desired therapeutic and/or prophylactic effect. In certain embodiments, the compounds described herein may be at dosage levels sufficient to deliver from about 0.001 mg/kg to about 200 mg/kg, from about 0.001 mg/kg to about 100 mg/kg, from about 0.01 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic and/or prophylactic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations). In certain embodiments, the composition described herein is administered at a dose that is below the dose at which the agent causes non-specific effects.

In certain embodiments, the pharmaceutical composition is administered at a dose of about 0.001 mg to about 1000 mg per unit dose. In certain embodiments, the pharmaceutical composition is administered at a dose of about 0.01 mg to about 200 mg per unit dose. In certain embodiments, the pharmaceutical composition is administered at a dose of about 0.01 mg to about 100 mg per unit dose. In certain embodiments, pharmaceutical composition is administered at a dose of about 0.01 mg to about 50 mg per unit dose. In certain embodiments, the pharmaceutical composition is administered at a dose of about 0.01 mg to about 10 mg per unit dose. In certain embodiments, the pharmaceutical composition is administered at a dose of about 0.1 mg to about 10 mg per unit dose.

Pharmaceutical compositions described herein can be prepared by any method known in the art of pharmacology. In general, such preparatory methods include the steps of bringing the composition comprising a compound of Formula (I) into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite (aluminum silicate) and Veegum (magnesium aluminum silicate)), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g. polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g. Cremophor™) polyoxyethylene ethers, (e.g. polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F-68, Poloxamer-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazelnut, hyssop, isopropyl myristate, jojoba, kukui nut, lavandin, lavender, lemon, *Litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include, but are not limited to, pharmaceutically acceptable emulsions, microemulsions, solutions, suspensions, syrups, and elixirs. In addition to the active agents, the liquid dosage forms may contain inert diluents commonly used in the art such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can also include adjuvants such as wetting agents, emulsifying and suspending agents, sweetening, flavoring, and perfuming agents. In certain embodiments for parenteral administration, agents of the invention are mixed with solubilizing agents such CREMOPHOR EL® (polyethoxylated castor oil), alcohols, oils, modified oils, glycols, polysorbates, cyclodextrins, polymers, and combinations thereof.

Injectable preparations, for example, sterile injectable aqueous or oleaginous suspensions, may be formulated according to the known art using suitable dispersing or wetting agents and suspending agents. Sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Solid dosage forms for oral administration include capsules, tablets, pills, powders, and granules. In such solid dosage forms, the active agent is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner.

Examples of embedding compositions which can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active agents can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active agent may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets, and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Formulations suitable for topical administration include liquid or semi-liquid preparations such as liniments, lotions, gels, applicants, oil-in-water or water-in-oil emulsions such as creams, ointments, or pastes; or solutions or suspensions such as drops. Formulations for topical administration to the skin surface can be prepared by dispersing the drug with a dermatologically acceptable carrier such as a lotion, cream, ointment, or soap. Useful carriers are capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used. Ophthalmic formulation, ear drops, and eye drops are also contemplated as being within the scope of this invention. Additionally, the present disclosure contemplates the use of transdermal patches, which have the added advantage of providing controlled delivery of an agent to the body. Such dosage forms can be made by dissolving or dispensing the agent in the proper medium. Absorption enhancers can also be used to increase the flux of the agent across the skin. The rate can be controlled by either providing a rate controlling membrane or by dispersing the agent in a polymer matrix or gel.

Additionally, the carrier for a topical formulation can be in the form of a hydroalcoholic system (e.g., liquids and gels), an anhydrous oil or silicone based system, or an emulsion system, including, but not limited to, oil-in-water, water-in-oil, water-in-oil-in-water, and oil-in-water-in-silicone emulsions. The emulsions can cover a broad range of consistencies including thin lotions (which can also be suitable for spray or aerosol delivery), creamy lotions, light creams, heavy creams, and the like. The emulsions can also include microemulsion systems. Other suitable topical carriers include anhydrous solids and semisolids (such as gels and sticks); and aqueous based mousse systems.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound or pharmaceutical composition described herein. In certain embodiments, the kits are useful for treating a disease (e.g., proliferative disease, inflammatory disease, infectious disease, autoimmune disease, heteroimmune disease, neurological disorder, metabolic disease, cystic fibrosis, polycystic kidney disease, pulmonary hypertension, cardiac dysfunction, or disease or disorder mediated by or linked to T-cell dysregulation) in a subject in need thereof. In certain embodiments, the kits are useful for preventing a disease (e.g., proliferative disease, inflammatory disease, infectious disease, autoimmune disease, heteroimmune disease, neurological disorder, metabolic disease, cystic fibrosis, polycystic kidney disease, pulmonary hypertension, cardiac dysfunction, or disease or disorder mediated by or linked to T-cell dysregulation) in a subject in need thereof. In certain embodiments, the kits are useful for reducing the risk of developing a disease (e.g., proliferative disease, inflammatory disease, infectious disease, autoimmune disease, heteroimmune disease, neurological disorder, metabolic disease, cystic fibrosis, polycystic kidney disease, pulmonary hypertension, cardiac dysfunction, or disease or disorder mediated by or linked to T-cell dysregulation) in a subject in need thereof. In certain embodiments, the kits are useful for inhibiting the activity (e.g., aberrant activity, such as increased activity) of HDAC6 in a subject or cell.

In certain embodiments, a kit described herein further includes instructions for using the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease (e.g., proliferative disease, inflammatory disease, infectious disease, autoimmune disease, heteroimmune disease, neurological disorder, metabolic disease, cystic fibrosis, polycystic kidney disease, pulmonary hypertension, cardiac dysfunction, or disease or disorder mediated by or linked to T-cell dysregulation) in a subject in need thereof. In certain embodiments, the kits and instructions provide for preventing a disease (e.g., proliferative disease, inflammatory disease, infectious disease, autoimmune disease, heteroimmune disease, neurological disorder, metabolic disease, cystic fibrosis, polycystic kidney disease, pulmonary hypertension, cardiac dysfunction, or disease or disorder mediated by or linked to T-cell dysregulation) in a subject in need thereof. In certain embodiments, the kits and instructions provide for reducing the risk of developing a disease (e.g., proliferative disease, inflammatory disease, infectious disease, autoimmune disease, heteroimmune disease, neurological disorder, metabolic disease, cystic fibrosis, polycystic kidney disease, pulmonary hypertension, cardiac dysfunction, or disease or disorder mediated by or linked to T-cell dysregulation) in a subject in need thereof. In certain embodiments, the kits and instructions provide for inhibiting the activity (e.g., aberrant activity, such as increased activity) of HDAC6 in a subject or cell. A kit described herein may include one or more additional pharmaceutical agents described herein as a separate composition.

Methods of Treatment

HDAC6 is unique in structure and function among all HDAC paralogs. In particular, it possesses two catalytic (deacetylase) domains and a zinc finger ubiquitin-binding domain. HDAC6 does not deacetylate histones, yet interacts with multiple substrates that affect disease-relevant pathways including microtubule stability, axonal and mitochondrial transport, protein aggregation, and autophagy. For example, HDAC6's direct substrates (e.g., tau, tubulin, and HSP90) engage key mechanisms in Alzheimer's disease. As a result of its unique structure and function, selectively targeting and inhibiting HDAC6 activity may avoid the side effects that are typical of existing FDA-approved HDAC inhibitors that result in clinical toxicity due to broad inhibition of multiple HDAC paralogs an/or inhibition of HDACs 1 and/or 2 (which has been shown to cause thrombocytopenia, a dose-limiting toxicity of most FDA-approved pan-HDAC inhibitors). Thus, treatment of HDAC6-related diseases with HDAC6-selective inhibitors may be particularly effective.

The present disclosure provides methods for treating HDAC6-related diseases and disorders. In certain embodiments, the application provides a method of treating a proliferative disease, inflammatory disease, infectious disease, autoimmune disease, heteroimmune disease, neurological disorder, peripheral disease or disorder, metabolic disease, cystic fibrosis, polycystic kidney disease, pulmonary hypertension, cardiac dysfunction, or disease or disorder mediated by or linked to T-cell dysregulation. In certain embodiments, the application provides a method of treating a proliferative disease. In certain embodiments, the application provides a method of treating cancer. In certain embodiments, the application provides a method of treating a hematological cancer. In certain embodiments, the application provides a method of treating leukemia, T-cell lymphoma, Hodgkin's Disease, non-Hodgkin's lymphoma, or multiple myeloma. In certain embodiments, the application provides a method of treating a cancer comprising a solid tumor. In certain embodiments, the application provides a method of treating glioma, glioblastoma, non-small cell lung cancer, brain tumor, neuroblastoma, bone tumor, soft-tissue sarcoma, head and neck cancer, genitourinary cancer, lung cancer, breast cancer, pancreatic cancer, melanoma, stomach cancer, brain cancer, liver cancer, thyroid cancer, clear cell carcinoma, uterine cancer, or ovarian cancer.

In certain embodiments, the application provides a method of treating an inflammatory disease. In certain embodiments, the application provides a method of treating osteoarthritis, rheumatoid arthritis, lupus, inflammatory bowel disease, Crohn's Disease, ulcerative colitis, anemia, leukocytosis, asthma, chronic obstructive pulmonary disease, appendicitis, bronchitis, bursitis, conjunctivitis, dermatitis, encephalitis, myelitis myocarditis, sinusitis, dermatitis, psoriasis, eczema, or acne.

In certain embodiments, the application provides a method of treating an infectious disease. In certain embodiments, the application provides a method of treating bacterial, fungal, or protozoal infections.

In certain embodiments, the application provides a method of treating an autoimmune disease. In certain embodiments, the application provides a method of treating diabetes, thyroiditis, Graves' disease, Guillain-Barre syndrome, Addison's disease, scleroderma, primary biliary cirrhosis, Reiter's syndrome, psoriasis, chronic fatigue, or endometriosis.

In certain embodiments, the application provides a method of treating a heteroimmune disease. In certain embodiments, the application provides a method of treating graft versus host disease, transplantation, transfusion, anaphylaxis, allergic conjunctivitis, or allergic rhinitis.

In certain embodiments, the application provides a method of treating a neurological disease or disorder. In certain embodiments, the application provides a method of treating a neurodegenerative, neurodevelopmental, neuropsychiatric, or neuropathy disease or disorder. In certain embodiments, the application provides a method of treating Fragile-X syndrome, Charcot-Marie-Tooth disease, Alzheimer's disease, Parkinson's diseases, Huntington's disease, multiple sclerosis, amyotrophic lateral sclerosis, Creutzfeldt-Jakob disease, Lewy body dementia, vascular dementia, muscular atrophy, seizure induced memory loss, schizophrenia, Rubinstein Taybi syndrome, Rett Syndrome, attention deficit hyperactivity disorder, dyslexia, bipolar disorder, social, cognitive and learning disorders associated with autism, attention deficit disorder, schizophrenia, major depressive disorder, peripheral neuropathy, diabetic retinopathy, diabetic peripheral neuropathy, chemotherapy-induced peripheral neuropathy, chemotherapy-induced cognitive dysfunction, traumatic brain injury (TBI), chronic traumatic encephalopathy (CTE), or a tauopathy. In certain embodiments, the application provides a method of treating primary age-related tauopathy (PART)/neurofibrillary tangle-predominant senile dementia, chronic traumatic encephalopathy, dementia pugilistica, progressive supranuclear palsy, corticobasal degeneration, Pick's disease, frontotemporal dementia, frontotemporal dementia and parkinsonism linked to chromosome 17, Lytico-Bodig disease, ganglioglioma, gangliocytoma, meningioangiomatosis, postencephalitic parkinsonism, subacute sclerosing panencephalitis, lead encephalopathy, tuberous sclerosis, lipofuscinosis, Alzheimer's disease, or argyrophilic grain disease. In certain embodiments, the application provides a method of treating Alzheimer's disease.

In certain embodiments, the application provides a method of treating a neurological or peripheral disease or disorder.

In certain embodiments, the application provides a method of treating a neurodegenerative, neurodevelopmental, neuropsychiatric, or neuropathy disease or disorder.

In certain embodiments, the application provides a method of treating a neurological disease or disorder, such as Alzheimer's disease, Fragile-X syndrome, Charcot-Marie-Tooth disease, Parkinson's disease, Huntington's disease, multiple sclerosis, amyotrophic lateral sclerosis, Rett Syndrome, major depressive disorder, chemotherapy-induced cognitive dysfunction, traumatic brain injury (TBI), chronic traumatic encephalopathy (CTE), brain cancer, or a tauopathy such as frontotemporal dementia, progressive supranuclear palsy, or corticobasal degeneration.

In certain embodiments, the application provides a method of treating a peripheral disease or disorder such as chemotherapy-induced peripheral neuropathy, diabetic peripheral neuropathy, peripheral neuropathy, diabetic retinopathy, obesity, autosomal dominant polycystic kidney disease, cardiomyopathy, an auto-immune disease such as systemic lupus erythematosus (SLE), or cancer.

In certain embodiments, the application provides a method of treating cystic fibrosis.

In certain embodiments, the application provides a method of treating polycystic kidney disease.

In certain embodiments, the application provides a method of treating pulmonary hypertension.

In certain embodiments, the application provides a method of treating cardiac dysfunction.

The present disclosure provides methods of inhibiting the activity of HDAC. In certain embodiments, the application provides a method of inhibiting the activity of HDAC6. In certain embodiments, the application provides a method of inhibiting the activity of HDAC6 in vitro. In certain embodiments, the application provides a method of inhibiting the activity of HDAC6 in vivo. In certain embodiments, the application provides a method of inhibiting the activity of HDAC6 in a cell. In certain embodiments, the application provides a method of inhibiting the activity of HDAC6 in a human cell.

In certain embodiments, the methods comprise administering to a subject in need thereof (e.g., a subject with a neurological disorder) a compound that interacts with HDAC6, for example, a compound that is an inhibitor of HDAC6, a modulator of HDAC6, a binder of HDAC6, or a compound that modifies HDAC6. In certain embodiments, the methods comprise administering a compound of the disclosure (e.g., a compound of Formula (I)), or a pharmaceutically acceptable salt, co-crystal, tautomer, stereoisomer, solvate, hydrate, polymorph, isotopically enriched derivative, or prodrug, or composition thereof, to a subject in need thereof. In some embodiments, the method comprises administering a pharmaceutical composition comprising a compound of the disclosure (e.g., a compound of Formula (I)), or a pharmaceutically acceptable salt, co-crystal, tautomer, stereoisomer, solvate, hydrate, polymorph, isotopically enriched derivative, or prodrug, or composition thereof, to a subject in need thereof.

In certain embodiments, the methods comprise administering an additional therapeutic agent.

EXAMPLES @

In order that the invention described herein may be more fully understood, the following examples are set forth. The examples described in this application are offered to illustrate the compounds, pharmaceutical compositions, and methods provided herein and are not to be construed in any way as limiting their scope.

Synthetic Methods

Compounds of Formula (I) were prepared following the synthetic schemes and procedures described in detail below. The examples described in this application are offered to illustrate the compounds, pharmaceutical compositions, and methods provided herein and are not to be construed in any way as limiting their scope. Compounds of the disclosure that are not explicitly described in the following procedures may be prepared by analogous methods. Those having ordinary skill in the art would understand how to make such compounds from the disclosure provided herein and by means known in the art of organic synthesis. For example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995) and subsequent editions thereof are representative and instructive. Methods for optimizing reaction conditions, if necessary minimizing competing by products, are known in the art.

General details. All oxygen and/or moisture-sensitive reactions were carried out under nitrogen ($N_2$) atmosphere in glassware that had been flame-dried under vacuum (approximately 0.5 mm Hg) and purged with $N_2$ prior to use. All reagents and solvents were purchased from commercial vendors and used as received or synthesized according to methods already reported. NMR spectra were recorded on a Bruker 300 (300 MHz $^1$H, 75 MHz $^{13}$C) or Varian UNITY INOVA 500 (500 MHz $^1$H, 125 MHz $^{13}$C) spectrometer. Proton and carbon chemical shifts are reported in ppm (δ) referenced to the NMR solvent. Data are reported as follows: chemical shifts, multiplicity (br=broad, s=singlet, d=doublet, t=triplet, q=quartet, m=multiplet; coupling constant(s) in Hz). Unless otherwise indicated, NMR data were collected at 25° C. Flash chromatography was performed using 40-60 μm Silica Gel (60 Å mesh) on a Teledyne Isco Combiflash Rf. Tandem Liquid Chromatography/Mass Spectrometry (LC/MS) was performed on a Waters 2795 separations module and 3100 mass detector. Analytical thin layer chromatography (TLC) was performed on EM Reagent 0.25 mm silica gel 60-F plates.

LCMS_Condition_01: Column: X-Bridge BEH C-18 (3.0×50 mm, 2.5 μm), Mobile Phase: A-0.025% FA in Water, Mobile Phase: B-ACN, Flow Rate: 1.2 mL/min (Gradient).

LCMS Condition_02: Column: X-Select CSH C-18 (150×4.6 mm, 3.5 μm), Mobile Phase: A-0.025% Aq FORMIC ACID, Mobile Phase: B-ACN, Flow Rate: 1.0 mL/min (Gradient).

HPCL_Condition_01: Column: XSELECT CSH C18 (150×4.6 mm, 3.5μ), Mobile Phase-A: 0.05% TFA: ACETONITRILE (95:05), Mobile Phase-B: ACETONITRILE: 0.05% TFA (95:05), Flow: 1.0 mL/min, Diluent: ACN: Water.

HPLC_Condition_02: Column: XSELECT CSH C18 (150×4.6 mm, 3.5μ), Mobile Phase-A: 5 mM Ammonium acetate, Mobile Phase-ACN, Flow: 1.0 mL/min, Diluent: ACN:Water.

Reverse phase PREP Purification methods: Preparative Column X-SELECT (250*30 mm), 5u Mobile Phase A 10 mm ABC in Water Mobile Phase B ACN Flow rate 25 mL, Instrument ID Prep-14 Gradient (Time/% B) 0/10, 3/10, 10/25, 20/40, 30/55, 40/60, 50/75, 60/95.

Compounds of Formula (I) were prepared following the synthetic schemes and procedures are described in detail below.

General Scheme - Formula (I)

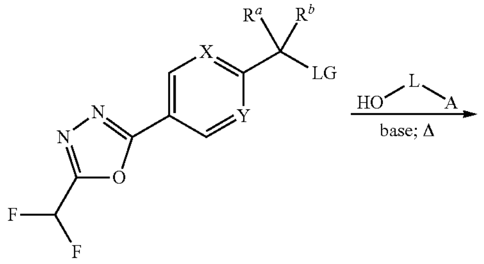

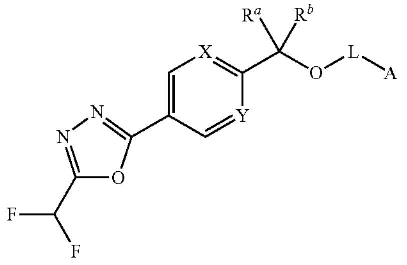

In general, compounds of Formula (I) can be prepared via nucleophilic displacement of a leaving group (LG) in the presence of a base (e.g., $K_2CO_3$ or $Ag_2CO_3$) at a temperature above room temperature. Other synthetic strategies may be employed according to the syntheses described below. Synthesis of the disclosed compounds employ reaction methods known to one of ordinary skill in the art.

2-(Difluoromethyl)-5-(2-((4-fluorophenoxy)methyl) pyrimidin-5-yl)-1,3,4-oxadiazole (1)

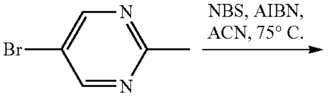

-continued

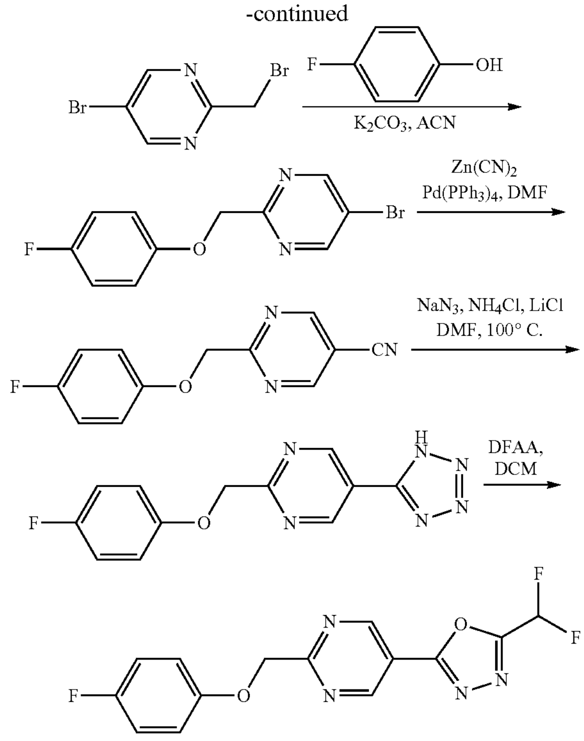

1

Step-1: 5-Bromo-2-(bromomethyl)pyrimidine: To a stirred solution of 5-bromo-2-methylpyrimidine (5.0 g, 2.89 mmol) in ACN (500 mL) was added portion wise NBS (6.4 g, 3.61 mmol) for 15-20 mins at 0° C., followed by AIBN (0.76 g, 0.29 mmol) at room temperature. The reaction mixture was stirred at same temperature for 30 mins, then heated at 75° C. for 48 h. After completion of reaction (monitored by TLC), the reaction mixture was quenched with water (100 mL) and extracted with DCM (200 mL). The organic layer was dried over sodium sulphate and concentrated under reduced pressure to give a light brown thick crude product. The crude product was purified by using 100-200 mesh silica gel column chromatography by eluting with 0-50% DCM in hexane to give the product (1.5 g, 20% yield) as light brown solid.

Step-2: 5-Bromo-2-((4-fluorophenoxy)methyl)pyrimidine: To a stirred solution of 5-bromo-2-(bromomethyl) pyrimidine (0.7 g, 2.78 mmol) and 4-fluorophenol (0.374 g, 3.34 mmol) in acetonitrile (10 mL) was added $K_2CO_3$ (1.15 g, 8.34 mmol) and the reaction mixture was stirred at 80° C. for 12 hours. After completion of reaction (monitored by TLC), the reaction mixture was concentrated under reduced pressure to give the crude product. The crude product was purified by using 100-200 mesh silica gel column chromatography by eluting with 0-30% ethyl acetate in hexane to give the product (0.7 g, 89% yield) as an off white solid.

Step-3: 2-((4-Fluorophenoxy)methyl)pyrimidine-5-carbonitrile: To a stirred solution of 5-bromo-2-((4-fluorophenoxy)methyl)pyrimidine (0.5 g, 1.77 mmol) in DMF (20 mL), was added $Zn(CN)_2$ (0.622 g, 5.31 mmol) at RT, the reaction mixture was purged with argon for 30 mins and was added $Pd(PPh_3)_4$ (0.2 g, 0.177 mmol) and again it was purged with argon for 10 mins. The reaction mixture was stirred at 100° C. for 12 h. After completion of reaction (monitored by TLC), the reaction mixture was filtered through celite and the filtrate was concentrated to give the crude product. The crude product was purified by using 230-400 mesh silica gel column chromatography by eluting with 0-20% ethyl acetate in hexane to give the product (0.25 g, 61.75% yield) as an off white solid. LC-MS: m/z 248.8 $[M-H]^-$.

Step-4: 2-((4-Fluorophenoxy)methyl)-5-(1H-tetrazol-5-yl)pyrimidine: To a stirred solution of 2-((4-fluorophenoxy) methyl)pyrimidine-5-carbonitrile (0.25 g, 1.09 mmol) in DMF (20 mL) was added sodium azide (0.212 g, 3.27 mmol), $NH_4Cl$ (0.176 g, 3.27 mmol) and LiCl (0.045 g, 1.09 mmol) at room temperature and the reaction mixture was stirred at 100° C. for 12 h. After completion of reaction (monitored by TLC), the reaction mixture was concentrated under reduced pressure and was acidified with 6N HCl and the precipitated solid was filtered and dried to give the product (0.25 g, 84.45% yield) as an off white solid. LC-MS: m/z 273.0 $[M+H]^+$.

Step-5: 2-(Difluoromethyl)-5-(2-((4-fluorophenoxy) methyl)pyrimidin-5-yl)-1,3,4-oxadiazole (1): To a stirred solution of 2-((4-fluorophenoxy)methyl)-5-(1H-tetrazol-5-yl)pyrimidine (0.25 g, 0.92 mmol) in DCM (25 mL) was added difluoro acetic anhydride (0.4 mL, 3.67 mmol) at 0° C. and the reaction mixture was stirred at RT for 12 h. After completion of reaction (monitored by TLC), the reaction mixture was quenched with water (20 mL) and extracted with DCM (100 mL). The organic layer was dried over sodium sulphate and concentrated under reduced pressure to give the crude product. The crude product was purified by using 230-400 mesh silica gel column chromatography by eluting with 30% ethyl acetate in hexane to give the product (0.11 g, 37.28% yield) as an off white solid. $^1H$ NMR (400 MHz, DMSO-$d_6$) δ 9.44 (s, 2H), 7.77-7.43 (m, 1H), 7.16-7.07 (m, 2H), 7.07-6.98 (m, 2H), 5.42 (s, 2H); $^{19}F$ NMR (400 MHz, DMSO-$d_6$): −120, −123. LC-MS: m/z 323.00 $[M+H]^+$ 2-(6-((5-Chloro-2-fluorophenoxy)methyl)pyridin-3-yl)-5-(difluoromethyl)-1,3,4-oxadiazole (2)

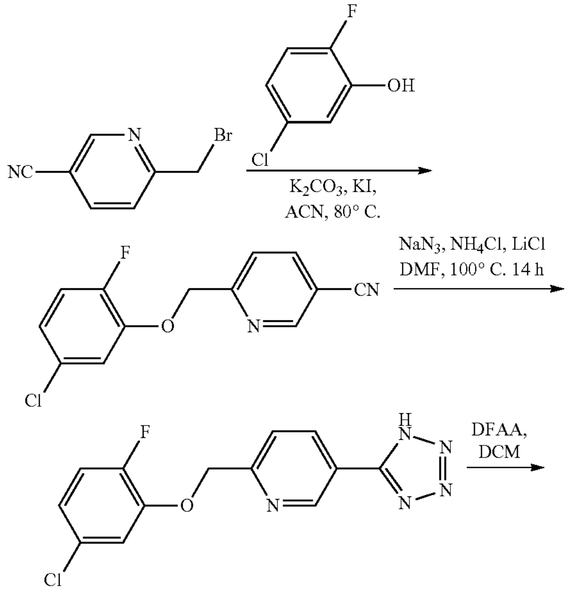

-continued

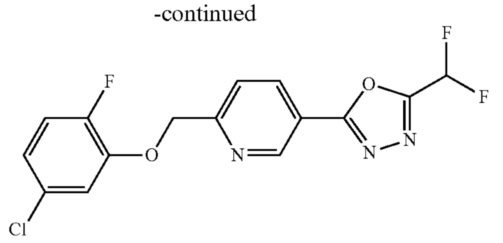

2

Step-1: 6-((5-Chloro-2-fluorophenoxy)methyl)nicotinonitrile: To a stirred solution of 6-(bromomethyl)nicotinonitrile (0.5 g, 2.55 mmol) and 2-fluoro-5-chlorophenol (0.521 g, 3.57 mmol) in acetonitrile (10 mL), $K_2CO_3$ (0.528 g, 3.72 mmol) and KI (0.083 g, 0.51 mmol) were added and the reaction mixture was stirred at 80° C. for 12 hours. After completion of reaction (monitored by TLC), the reaction mixture was filtered through celite bed and filtrate was concentrated under reduced pressure to give the crude product. The crude product was purified by using 100-200 mesh silica gel column chromatography by eluting with 0-10% ethyl acetate in hexane to give the product (0.600 g, 89.82% yield) as an off white solid. LC-MS: m/z 263.00 $[M+H]^+$.

Step-2: 2-((5-Chloro-2-fluorophenoxy)methyl)-5-(1H-tetrazol-5-yl)pyridine: To a stirred solution of 6-((5-chloro-2-fluorophenoxy)methyl)nicotinonitrile (0.6 g, 2.29 mmol) in DMF (10 mL), sodium azide (0.744 g, 11.4 mmol), $NH_4Cl$ (0.6 g, 11.4 mmol) and LiCl (0.060 g) were added and the reaction mixture was stirred at 100° C. for 16 h. After completion of reaction (monitored by TLC), the reaction mixture was concentrated under reduced pressure and was acidified with 6N HCl, extracted with ethyl acetate (2×50 mL). The organic layer was dried over sodium sulphate and concentrated to give the crude product. The crude product was washed with hexane (2×10 mL) to give the product (0.65 g, 92.85% yield) as an off white solid. LC-MS: m/z 306.00 $[M+H]^+$.

Step-3: 2-(6-((5-Chloro-2-fluorophenoxy)methyl)pyridin-3-yl)-5-(difluoromethyl)-1,3,4-oxadiazole (2): To a stirred solution of 2-((5-chloro-2-fluorophenoxy)methyl)-5-(1H-tetrazol-5-yl)pyridine (0.350 g, 1.14 mmol) in DCM (15 mL) at 0° C., difluoroacetic anhydride (0.4 mL, 3.42 mmol) was added and the reaction mixture was stirred at RT for 16 hours. After completion of reaction (monitored by TLC), the reaction mixture was diluted with DCM (20 mL) and basified with saturated sodium bicarbonate solution and extracted with DCM (50 mL). The organic layer was dried over sodium sulphate and concentrated under reduced pressure to give the crude product. The crude product was purified by using 100-200 mesh silica gel column chromatography by eluting with 0-10% ethyl acetate in hexane to give the product (0.170 g, 41.76% yield) as an off white solid. $^1H$ NMR (400 MHz, DMSO-$d_6$) δ 9.24 (d, J=2.0 Hz, 1H), 8.56-8.49 (m, 1H), 7.79 (d, J=8.3 Hz, 1H), 7.74-7.45 (m, 2H), 7.45-7.39 (m, 1H), 7.10-7.02 (m, 1H), 5.44 (s, 2H); $^{19}F$ NMR (400 MHz, DMSO-$d_6$) δ −121, −138; LC-MS: m/z 356.00 $[M+H]^+$ 2-(6-((4-Chloro-2-fluorophenoxy)methyl)pyridin-3-yl)-5-(difluoromethyl)-1,3,4-oxadiazole (3)

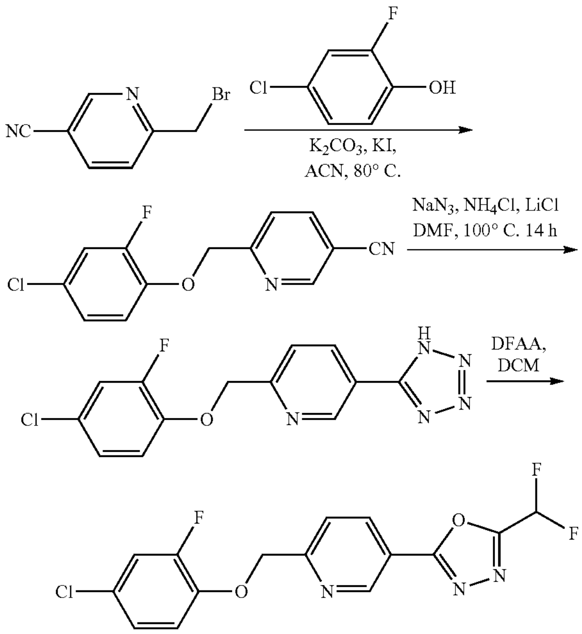

3

Step-1: 6-((4-Chloro-2-fluorophenoxy)methyl)nicotinonitrile: To a stirred solution of 6-(bromomethyl)nicotinonitrile (0.5 g, 2.55 mmol) and 2-fluoro-4-chlorophenol (0.521 g, 3.57 mmol) in acetonitrile (10 mL), $K_2CO_3$ (0.528 g, 3.82 mmol) and KI (0.084 g, 0.51 mmol) were added and the reaction mixture was stirred at 80° C. for 12 hours. After completion of reaction (monitored by TLC), the reaction mixture was filtered through celite bed and filtrate was concentrated under reduced pressure to give the crude product. The crude product was purified by using 100-200 mesh silica gel column chromatography by eluting with 0-10% ethyl acetate in hexane to give the product (0.400 g, 59.88% yield) as an off white solid. LC-MS: m/z 262.8 $[M+H]^+$.

Step-2: 2-((4-chloro-2-fluorophenoxy)methyl)-5-(1H-tetrazol-5-yl)pyridine: To a stirred solution of 6-((4-chloro-2-fluorophenoxy)methyl)nicotinonitrile (0.4 g, 1.52 mmol) in DMF (10 mL), sodium azide (0.297 g, 4.58 mmol), $NH_4Cl$ (0.247 g, 4.58 mmol) and LiCl (0.064 g, 1.52 mmol) were added, and the reaction mixture was stirred at 100° C. for 16 h. After completion of reaction (monitored by TLC), the reaction mixture was concentrated under reduced pressure and was acidified with 6N HCl, extracted with ethyl acetate (2×50 mL). The organic layer was dried over sodium sulphate and concentrated to give the crude product. The crude product was washed with hexane (2×10 mL) to give the product (0.300 g, 64.51% yield) as light brown liquid. LC-MS: m/z 306.05 $[M+H]^+$.

Step-3: 2-(6-((4-chloro-2-fluorophenoxy)methyl)pyridin-3-yl)-5-(difluoromethyl)-1,3,4-oxadiazole (3): To a stirred solution of 2-((4-chloro-2-fluorophenoxy)methyl)-5-(1H-tetrazol-5-yl)pyridine (0.300 g, 0.98 mmol) in DCM (10 mL) at 0° C., difluoro acetic anhydride (0.342 g, 1.96 mmol) was added and the reaction mixture was stirred at RT for 15 hours. After completion of reaction (monitored by TLC), the reaction mixture was diluted with DCM (20 mL) and basified with saturated sodium bicarbonate solution and extracted with ethyl acetate (50 mL). The organic layer was dried over sodium sulphate and concentrated under reduced pressure to give the crude product. The crude product was purified by using 100-200 mesh silica gel column chromatography by eluting with 0-20% ethyl acetate in hexane to give the product (0.120 g, 34.38% yield) as an off white solid. $^{1}$H NMR (400 MHz, DMSO-$d_6$) δ 9.23 (d, J=2.0 Hz, 1H), 8.51 (dd, J=2.4, 8.3 Hz, 1H), 7.78 (d, J=8.3 Hz, 1H), 7.73-7.44 (m, 2H), 7.30 (t, J=9.0 Hz, 1H), 7.26-7.20 (m, 1H), 5.41 (s, 2H); LC-MS: m/z 355.9 [M+H]+

2-(6-((2-Chloro-4-fluorophenoxy)methyl)pyridin-3-yl)-5-(difluoromethyl)-1,3,4-oxadiazole (4)

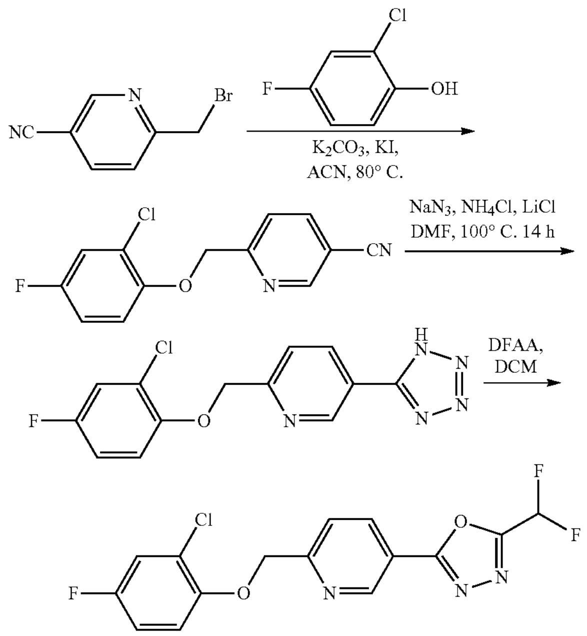

4

Step-1: 6-((2-Chloro-4-fluorophenoxy)methyl)nicotinonitrile: To a stirred solution of 6-(bromomethyl)nicotinonitrile (0.5 g, 2.55 mmol) and 2-chloro-4-fluorophenol (0.524 g, 3.57 mmol) in acetonitrile (10 mL), $K_2CO_3$ (0.520 g, 3.72 mmol) and KI (0.083 g, 0.51 mmol) were added, and the reaction mixture was stirred at 80° C. for 12 hours. After completion of reaction (monitored by TLC), the reaction mixture was filtered through celite bed and filtrate was concentrated under reduced pressure to give the crude product. The crude product was purified by using 100-200 mesh silica gel column chromatography by eluting with 0-10% ethyl acetate in hexane to give the product (0.35 g, 52.39% yield) as an off white solid. LC-MS: m/z 262.9 $[M+H]^+$ Step-2: 2-((2-Chloro-4-fluorophenoxy)methyl)-5-(1H-tetrazol-5-yl)pyridine: To a stirred solution of 6-((2-chloro-4-fluorophenoxy)methyl)nicotinonitrile (0.35 g, 1.33 mmol) in DMF (10 mL), sodium azide (0.434 g, 6.67 mmol), $NH_4Cl$ (0.35 g, 6.67 mmol) and LiCl (0.035 g, 1.33 mmol) were added, and the reaction mixture was stirred at 100° C. for 16 h. After completion of reaction (monitored by TLC), the reaction mixture was concentrated under reduced pressure and was acidified with 6N HCl, solid precipitated out was filtered and was dried to give the product (0.370 g, 90.68% yield) as an off white solid. LC-MS: m/z 306.05 $[M+H]^+$ Step-3: 2-(6-((2-Chloro-4-fluorophenoxy)methyl)pyridin-3-yl)-5-(difluoromethyl)-1,3,4-oxadiazole (4): To a stirred solution of 2-((2-chloro-4-fluorophenoxy)methyl)-5-(1H-tetrazol-5-yl)pyridine (0.37 g, 1.21 mmol) in DCM (10 mL) at 0° C., difluoro acetic anhydride (0.43 mL, 3.63 mmol) was added and the reaction mixture was stirred at RT for 15 hours. After completion of reaction (monitored by TLC), the reaction mixture was diluted with DCM (20 mL) and washed with water (20 mL). The organic layer was dried over sodium sulphate and concentrated under reduced pressure to give the crude product. The crude product was purified by using 100-200 mesh silica gel column chromatography by eluting with 0-20% ethyl acetate in hexane to give the product (0.160 g, 37.20% yield) as an off white solid. $^{1}$H NMR (400 MHz, DMSO-$d_6$) δ 9.23 (d, J=2.0 Hz, 1H), 8.63-8.44 (m, 1H), 7.82 (d, J=7.8 Hz, 1H), 7.73-7.44 (m, 2H), 7.33-7.25 (m, 1H), 7.21 (dt, J=2.9, 8.6 Hz, 1H), 5.41 (s, 2H). $^{19}$F NMR (400 MHz, DMSO-$d_6$) δ −121. LC-MS: m/z 356.05 $[M+H]^+$ 2-(Difluoromethyl)-5-(6-((2,4-difluorophenoxy)methyl)pyridin-3-yl)-1,3,4-oxadiazole (5)

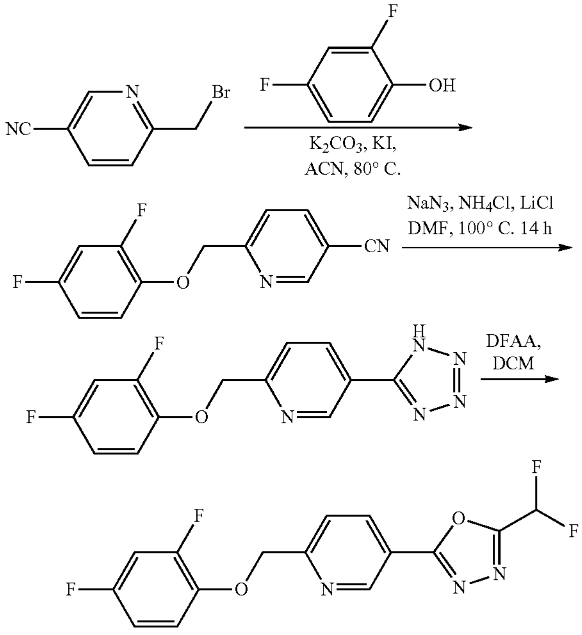

5

Step-1: 6-((2,4-Difluorophenoxy)methyl)nicotinonitrile: To a stirred solution of 6-(bromomethyl)nicotinonitrile (0.5 g, 2.55 mmol) and 2,4-difluorophenol (0.455 g, 3.57 mmol) in acetonitrile (10 mL), $K_2CO_3$ (0.520 g, 3.72 mmol) and KI (0.083 g, 0.51 mmol) were added, and the reaction mixture was stirred at 80° C. for 12 hours. After completion of reaction (monitored by TLC), the reaction mixture was filtered through celite bed and filtrate was concentrated under reduced pressure to give the crude product. The crude product was purified by using 230-400 mesh silica gel column chromatography by eluting with 0-30% ethyl acetate in hexane to give the product (0.474 g, 76.82% yield) as an off white solid. LC-MS: m/z 246.9 $[M+H]^+$.

Step-2: 2-((2,4-Difluorophenoxy)methyl)-5-(1H-tetrazol-5-yl)pyridine: To a stirred solution of 6-((2,4-difluorophenoxy)methyl)nicotinonitrile (0.4 g, 1.65 mmol) in DMF (10 mL), sodium azide (0.573 g, 8.26 mmol), $NH_4Cl$ (0.438 g, 8.26 mmol) and LiCl (0.040 g, 1.65 mmol) were added and the reaction mixture was stirred at 100° C. for 16 h. After completion of reaction (monitored by TLC), the reaction mixture was concentrated under reduced pressure and was acidified with 6N HCl, solid precipitated out was filtered and was dried to give the product (0.429 g, 89.93% yield) as an off white solid. LC-MS: m/z 289.9 $[M+H]^+$.

Step-3: 2-(Difluoromethyl)-5-(6-((2,4-difluorophenoxy)methyl)pyridin-3-yl)-1,3,4-oxadiazole (5): To a stirred solution of 2-((2,4-difluorophenoxy)methyl)-5-(1H-tetrazol-5-yl)pyridine (0.4 g, 1.38 mmol) in DCM (10 mL) at 0° C., difluoro acetic anhydride (0.484 g, 2.76 mmol) was added and the reaction mixture was stirred at RT for 14 hours. After completion of reaction (monitored by TLC), the reaction mixture was diluted with DCM (20 mL) and washed with water (20 mL). The organic layer was dried over sodium sulphate and concentrated under reduced pressure to give the crude product. The crude product was purified by using 230-400 mesh silica gel column chromatography by eluting with 0-30% ethyl acetate in hexane to give the product (0.100 g, 21.32% yield) as an off white solid. $^1H$ NMR (400 MHz, DMSO-$d_6$) δ 9.23 (d, J=2.0 Hz, 1H), 8.51 (dd, J=2.2, 8.1 Hz, 1H), 7.82-7.74 (m, 1H), 7.72-7.43 (m, 1H), 7.42-7.24 (m, 2H), 7.10-6.97 (m, 1H), 5.38 (s, 2H); $^{19}F$ NMR (400 MHz, DMSO-$d_6$) δ: −119, −121, −130. LC-MS: m/z 340.00 $[M+H]^+$ 2-(Difluoromethyl)-5-(5-fluoro-6-((4-fluorophenoxy)methyl)pyridin-3-yl)-1,3,4-oxadiazole (6)

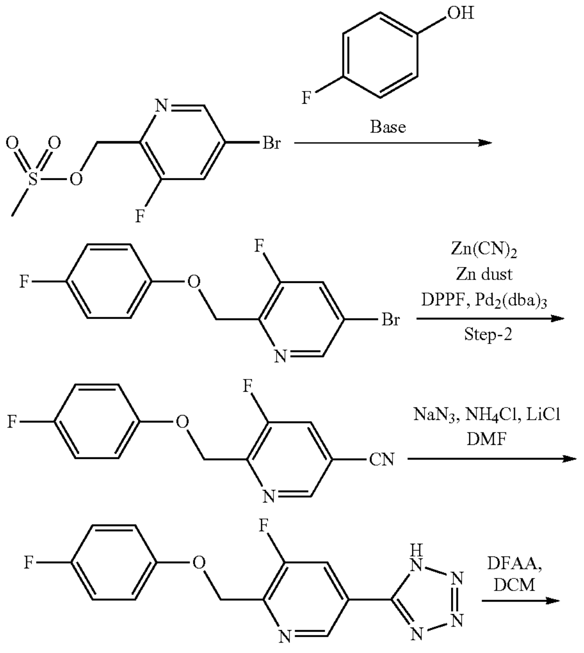

-continued

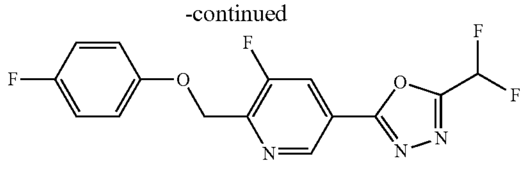

6

Step-1: 5-Bromo-3-fluoro-2-((4-fluorophenoxy)methyl)pyridine: To a stirred solution of (5-bromo-3-fluoropyridin-2-yl)methyl methanesulfonate (0.5 g, 1.76 mmol) in DMF (7 mL), was added NaH (0.063 g, 2.64 mmol) at 0° C., then stirred it for 5 min at 0° C. 4-Fluorophenol (0.197 g, 1.76 mmol) dissolved in DMF (2 mL) was slowly added at 0° C. Then the reaction mixture was stirred at room temperature for 45 mins. After completion of reaction (monitored by TLC), the reaction mixture was quenched with water (100 mL) and extracted with ethyl acetate (150 mL). The organic layer was dried over sodium sulphate and concentrated under reduced pressure to give the crude product. The crude product was purified by using 100-200 mesh silica gel column chromatography by eluting with 0-10% ethyl acetate in hexane to give the product (0.4 g, 76.05% yield) as an off white solid. LC-MS: m/z 299.8 $[M+H]^+$.

Step-2: 5-fluoro-6-((4-fluorophenoxy)methyl)nicotinonitrile: To a stirred solution of 5-bromo-3-fluoro-2-((4-fluorophenoxy)methyl)pyridine (0.4 g, 1.36 mmol) in DMA (10 mL), was added $Zn(CN)_2$ (0.393 g, 3.40 mmol) and Zn dust (0.061 g, 0.95 mmol) at RT, the reaction mixture was purged with argon for 45 mins and the $Pd_2(dba)_3$ (0.138 g, 0.13 mmol) and dppf (0.222 g, 0.40 mmol) was added and again it was purged with argon for 20 mins. The reaction mixture was stirred at 100° C. for 16 h. After completion of reaction (monitored by TLC), the reaction mixture was filtered through celite and the filtrated was diluted with ethyl acetate (100 mL) and washed with water (2×50 mL). The organic layer was dried over sodium sulphate and concentrated under reduced pressure to give the crude product. The crude product was purified by using 100-200 mesh silica gel column chromatography by eluting with 0-25% ethyl acetate in hexane to give the product (0.2 g, 60.79% yield) as a brown sticky solid. LC-MS: m/z 246.8 $[M+H]^+$.

Step-3: 3-fluoro-2-((4-fluorophenoxy)methyl)-5-(1H-tetrazol-5-yl)pyridine: To a stirred solution of 5-fluoro-6-((4-fluorophenoxy)methyl)nicotinonitrile (0.2 g, 0.81 mmol) in DMF (10 mL), sodium azide (0.264 g, 4.06 mmol), $NH_4Cl$ (0.22 g, 4.06 mmol) and LiCl (0.060 g, 0.81 mmol) were added and the reaction mixture was stirred at 100° C. for 16 h. After completion of reaction (monitored by TLC), the reaction mixture was concentrated under reduced pressure and was acidified with 6N HCl and extracted with ethyl acetate (2×50 mL). The organic layer was dried over sodium sulphate and concentrated under reduced pressure to give the product (0.21 g, 89.36% yield) as a brown sticky solid which was used as such for further step.

Step-4: 2-(difluoromethyl)-5-(5-fluoro-6-((4-fluorophenoxy)methyl)pyridin-3-yl)-1,3,4-oxadiazole (6): To a stirred solution of 3-fluoro-2-((4-fluorophenoxy)methyl)-5-(1H-tetrazol-5-yl)pyridine (0.21 g, 0.73 mmol) in DCM (10 mL) was added difluoro acetic anhydride (0.253 g, 1.5 mmol) at 0° C. The reaction mixture was stirred at RT for 16 h. After completion of reaction (monitored by TLC), the reaction mixture was quenched with water (20 mL) and extracted with DCM (100 mL). The organic layer was dried over sodium sulphate and concentrated under reduced pressure to give the crude product. The crude product was purified by using 100-200 mesh silica gel column chromatography by eluting with 30% ethyl acetate in hexane to give the product (60 mg, 24.39% yield) as light brown solid. $^1$H NMR (400 MHz, DMSO-$d_6$): δ 9.09 (s, 1H), 8.46 (dd, J=1.5, 10.3 Hz, 1H), 7.77-7.41 (m, 1H), 7.17-7.11 (m, 2H), 7.11-7.05 (m, 2H), 5.33 (s, 2H); $^{19}$F NMR (400 MHz, DMSO-$d_6$): δ −122. LC-MS: m/z 340.05 $[M+H]^+$ 2-(6-((2-Chloro-5-fluorophenoxy)methyl)pyridin-3-yl)-5-(difluoromethyl)-1,3,4-oxadiazole (7)

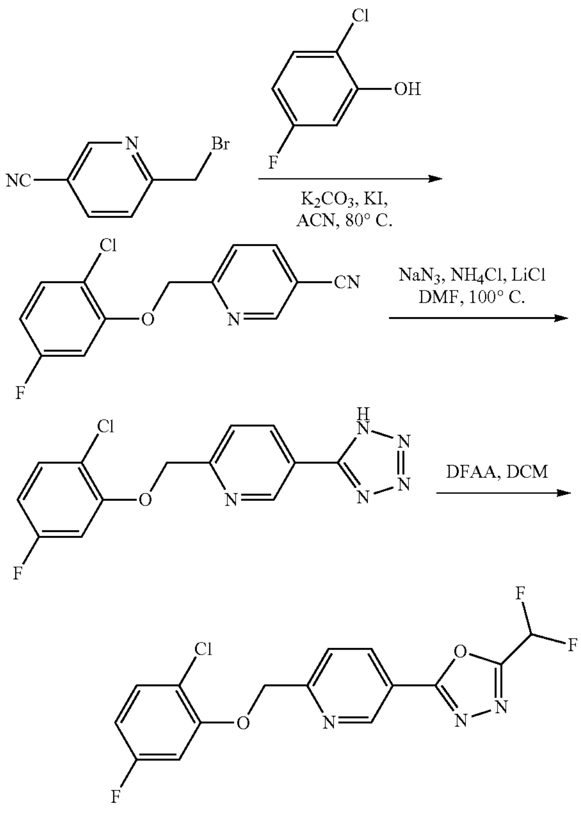

7

Step-1: 6-((2-Chloro-5-fluorophenoxy)methyl)nicotinonitrile: To a stirred solution of 6-(bromomethyl)nicotinonitrile (0.5 g, 2.55 mmol) and 2-chloro-5-fluorophenol (0.521 g, 3.57 mmol) in acetonitrile (10 mL), $K_2CO_3$ (0.528 g, 3.72 mmol) and KI (0.083 g, 0.51 mmol) were added, and the reaction mixture was stirred at 80° C. for 16 hours. After completion of reaction (monitored by TLC), the reaction mixture was quenched with ice cold water (50 mL) and extracted with ethyl acetate (2×50 mL). The organic layer was dried over sodium sulphate and concentrated under reduced pressure to give the crude product. The crude product was purified by using 100-200 mesh silica gel column chromatography by eluting with 0-10% ethyl acetate in hexane to give the product (0.5 g, 74.85% yield) as an off white solid. LC-MS: m/z 263.05 $[M+H]^+$.

Step-2: 2-((2-Chloro-5-fluorophenoxy)methyl)-5-(1H-tetrazol-5-yl)pyridine: To a stirred solution of 6-((2-chloro-5-fluorophenoxy)methyl)nicotinonitrile (0.9 g, 1.91 mmol) in DMF (15 mL), sodium azide (0.62 g, 9.59 mmol), $NH_4Cl$ (0.513 g, 9.59 mmol) and LiCl (0.050 g) were added, and the reaction mixture was stirred at 100° C. for 16 h. After completion of reaction (monitored by TLC), the reaction mixture was concentrated under reduced pressure and was acidified with 6N HCl, the precipitated solid was filtered and washed with ice cold water and hexane. The product was dried under reduced pressure to give the product (0.45 g, 77.18% yield) as an off white solid. LC-MS: m/z 306.0 $[M+H]^+$.

Step-3: 2-(6-((2-Chloro-5-fluorophenoxy)methyl)pyridin-3-yl)-5-(difluoromethyl)-1,3,4-oxadiazole (7): To a stirred solution of 2-((2-chloro-5-fluorophenoxy)methyl)-5-(1H-tetrazol-5-yl)pyridine (0.3 g, 0.98 mmol) in DCM (9 mL) at 0° C., difluoro acetic anhydride (0.34 mL, 2.94 mmol) was added and the reaction mixture was stirred at RT for 16 h. After completion of reaction (monitored by TLC), the reaction mixture was quenched with ice cold water (20 mL) and extracted with DCM (50 mL). The organic layer was dried over sodium sulphate and concentrated under reduced pressure to give the crude product. The crude product was purified by using 100-200 mesh silica gel column chromatography by eluting with 0-30% ethyl acetate in hexane to give the product (0.160 g, 45.84% yield) as an off white solid. $^1$H NMR (400 MHz, DMSO-$d_6$) δ 9.24 (d, J=2.0 Hz, 1H), 8.54 (dd, J=2.0, 8.3 Hz, 1H), 7.83 (d, J=8.3 Hz, 1H), 7.73-7.43 (m, 2H), 7.36-7.17 (m, 1H), 6.89 (dt, J=2.9, 8.6 Hz, 1H), 5.44 (s, 2H); $^{19}$F NMR (400 MHz, DMSO-$d_6$) δ −112, −120; LC-MS: m/z 355.9 $[M+H]^+$ 2-(6-((4-Chlorophenoxy)methyl)pyridin-3-yl)-5-(difluoromethyl)-1,3,4-oxadiazole (8)

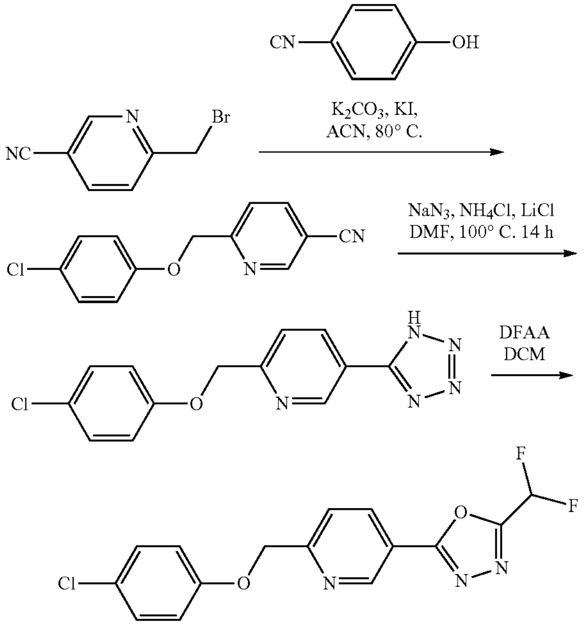

8

Step-1: 6-((4-Chlorophenoxy)methyl)nicotinonitrile: To a stirred solution of 6-(bromomethyl)nicotinonitrile (0.5 g, 2.55 mmol) and 4-chlorophenol (0.393 g, 3.06 mmol) in acetonitrile (20 mL), $K_2CO_3$ (0.528 g, 3.82 mmol) and KI (0.084 g, 0.51 mmol) were added, and the reaction mixture was stirred at 80° C. for 12 hours. After completion of reaction (monitored by TLC), the reaction mixture was filtered through celite bed and filtrate was concentrated under reduced pressure to give the crude product. The crude product was purified by using 230-400 mesh silica gel column chromatography by eluting with 0-30% ethyl acetate in hexane to give the product (0.4 g, 64.3% yield) as an off white solid. LC-MS: m/z 244.9[M+H]$^+$.

Step-2: 2-((4-Chlorophenoxy)methyl)-5-(1H-tetrazol-5-yl)pyridine: To a stirred solution of 6-((4-chlorophenoxy)methyl)nicotinonitrile (0.4 g, 1.63 mmol) in DMF (20 mL), sodium azide (0.319 g, 4.91 mmol), $NH_4Cl$ (0.265 g, 4.91 mmol) and LiCl (0.068 g, 1.63 mmol) were added and the reaction mixture was stirred at 100° C. for 12 h. After completion of reaction (monitored by TLC), the reaction mixture was concentrated under reduced pressure and was acidified with 6N HCl, solid precipitated out was filtered and was dried to give the product (0.3 g, 63.82% yield) as an off white solid. LC-MS: m/z 287.95 [M+H]$^+$.

Step-3: 2-(6-((4-Chlorophenoxy)methyl)pyridin-3-yl)-5-(difluoromethyl)-1,3,4-oxadiazole (8): To a stirred solution of 2-((4-chlorophenoxy)methyl)-5-(1H-tetrazol-5-yl)pyridine (0.3 g, 1.04 mmol) in DCM (20 mL) at 0° C., difluoro acetic anhydride (0.45 mL, 4.18 mmol) was added and the reaction mixture was stirred at RT for 12 hours. After completion of reaction (monitored by TLC), the reaction mixture was diluted with DCM (20 mL) and washed with water (20 mL). The organic layer was dried over sodium sulphate and concentrated under reduced pressure to give the crude product. The crude product was purified by using 230-400 mesh silica gel column chromatography by eluting with 0-30% ethyl acetate in hexane to give the product (0.070 g, 19.88% yield) as an off white solid. $^1$H NMR (400 MHz, DMSO-$d_6$) δ 9.30-9.14 (m, 1H), 8.48 (dd, J=2.2, 8.1 Hz, 1H), 7.77 (br d, J=7.8 Hz, 1H), 7.73-7.43 (m, 1H), 7.43-7.29 (m, 2H), 7.09 (br d, J=8.8 Hz, 2H), 5.32 (s, 2H); $^{19}$F NMR (400 MHz, DMSO-$d_6$) δ −122; LC-MS: m/z 338.05 [M+H]$^+$ 2-(Difluoromethyl)-5-(6-((naphthalen-1-yloxy)methyl)pyridin-3-yl)-1,3,4-oxadiazole (11)

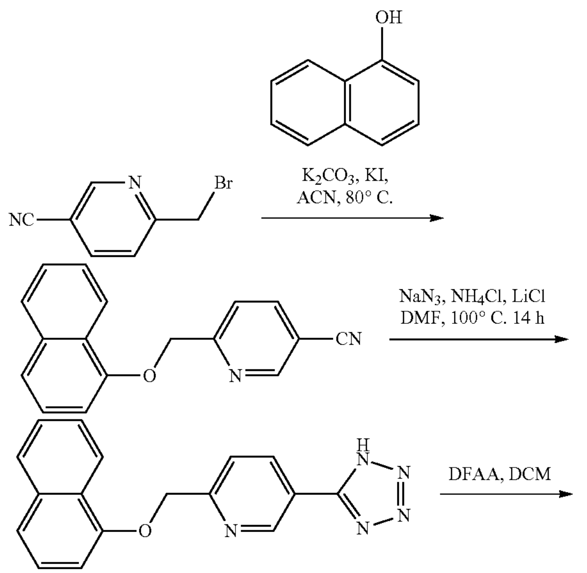

-continued

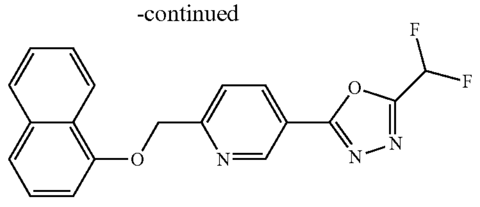

11

Step-1: 6-((Naphthalen-1-yloxy)methyl)nicotinonitrile: To a stirred solution of 6-(bromomethyl)nicotinonitrile (0.5 g, 2.55 mmol) and naphthalen-1-ol (0.477 g, 3.31 mmol) in acetonitrile (20 mL), was added $K_2CO_3$ (0.528 g, 3.82 mmol) and KI (0.084 g, 0.51 mmol) and the reaction mixture was stirred at 80° C. for 12 hours. After completion of reaction (monitored by TLC), the reaction mixture was filtered through celite bed and filtrate was concentrated under reduced pressure to give the crude product. The crude product was purified by using 230-400 mesh silica gel column chromatography by eluting with 0-15% ethyl acetate in hexane to give the product (0.35 g, 52.79% yield) as a light yellow solid. LC-MS: m/z 260.95[M+H]$^+$.

Step-2: 2-((Naphthalen-1-yloxy)methyl)-5-(1H-tetrazol-5-yl)pyridine: To a stirred solution of 6-((naphthalen-1-yloxy)methyl)nicotinonitrile (0.35 g, 1.34 mmol) in DMF (10 mL) was added sodium azide (0.262 g, 4.03 mmol), $NH_4Cl$ (0.218 g, 4.03 mmol) and LiCl (0.056 g, 1.34 mmol) and the reaction mixture was stirred at 100° C. for 12 h. After completion of reaction (monitored by TLC), the reaction mixture was concentrated under reduced pressure and was acidified with 6N HCl, solid precipitated out was filtered and was dried to give the product (0.3 g, 73.71% yield) as an off white solid. LC-MS: m/z 303.9 [M+H]$^+$.

Step-3: 2-(Difluoromethyl)-5-(6-((naphthalen-1-yloxy)methyl)pyridin-3-yl)-1,3,4-oxadiazole (11): To a stirred solution of 2-((naphthalen-1-yloxy)methyl)-5-(1H-tetrazol-5-yl)pyridine (0.3 g, 0.99 mmol) in DCM (20 mL) was added difluoroacetic anhydride (0.34 mL, 1.98 mmol) at 0° C. and the reaction mixture was stirred at RT for 12 hours. After completion of reaction (monitored by TLC), the reaction mixture was diluted with DCM (20 mL) and washed with water (20 mL). The organic layer was dried over sodium sulphate and concentrated under reduced pressure to give the crude product. The crude product was purified by using 230-400 mesh silica gel column chromatography by eluting with 0-40% ethyl acetate in hexane to give the product (0.11 g, 31.51% yield) as an off white solid. $^1$H NMR (400 MHz, DMSO-$d_6$): δ $^1$H NMR (400 MHz, DMSO-$d_6$) δ 9.26 (s, 1H), 8.59-8.45 (m, 1H), 8.41-8.24 (m, 1H), 8.03-7.82 (m, 2H), 7.76-7.68 (m, 1H), 7.63-7.50 (m, 3H), 7.50-7.38 (m, 1H), 7.08 (br d, J=7.3 Hz, 1H), 5.53 (s, 2H); $^{19}$F NMR (400 MHz, DMSO-$d_6$) δ −122. LC-MS: m/z 354.05 [M+H]$^+$ 2-(Difluoromethyl)-5-(6-((4-fluorophenoxy)methyl)pyridin-3-yl)-1,3,4-oxadiazole (12)

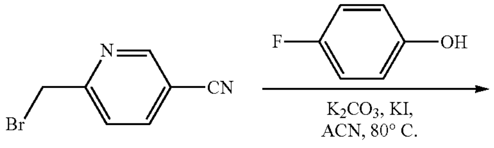

-continued

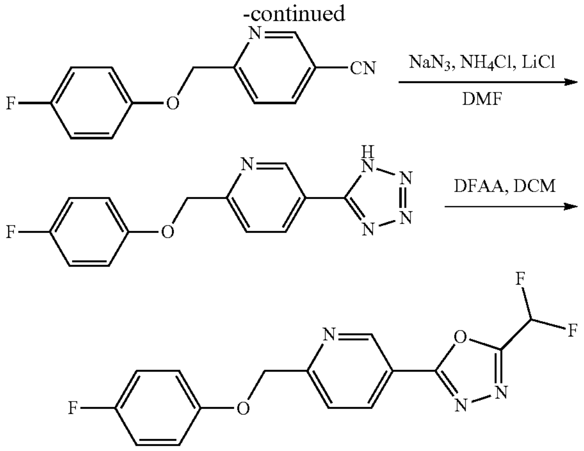

12

Step-1: 6-((4-Fluorophenoxy)methyl)nicotinonitrile: To a stirred solution of 6-(bromomethyl)nicotinonitrile (0.3 g, 1.53 mmol) and 4-fluorophenol (0.222 g, 1.98 mmol) in acetonitrile (10 mL), $K_2CO_3$ (0.316 g, 2.29 mmol) and KI (0.050 g, 0.306 mmol) were added, and the reaction mixture was stirred at 80° C. for 12 hours. After completion of reaction (monitored by TLC), the reaction mixture was quenched with ice cold water (50 mL) and extracted with DCM (2×50 mL). The organic layer was dried over sodium sulphate and concentrated under reduced pressure to give the crude product. The crude product was purified by using 230-400 mesh silica gel column chromatography by eluting with 0-30% ethyl acetate in hexane to give the product (0.25 g, 71.83% yield) as a white solid. LC-MS: m/z 228.90 $[M+H]^+$.

Step-2: 2-((4-Fluorophenoxy)methyl)-5-(1H-tetrazol-5-yl)pyridine: To a stirred solution of 6-((4-fluorophenoxy)methyl)nicotinonitrile (0.25 g, 1.09 mmol) in DMF (10 mL), sodium azide (0.213 g, 3.28 mmol), $NH_4Cl$ (0.177 g, 3.28 mmol) and LiCl (0.046 g) were added and the reaction mixture was stirred at 100° C. for 12 h. After completion of reaction (monitored by TLC), the reaction mixture was concentrated under reduced pressure and was acidified with 6N HCl, the precipitated solid was filtered and washed with ice cold water and hexane. The product was dried under reduced pressure to give the product (0.2 g, 67.34% yield) as an off-white solid which was used as such for further step. LC-MS: m/z 272.05 $[M+H]^+$.

Step-3: 2-(Difluoromethyl)-5-(6-((4-fluorophenoxy)methyl)pyridin-3-yl)-1,3,4-oxadiazole (12): To a stirred solution of 2-((4-fluorophenoxy)methyl)-5-(1H-tetrazol-5-yl)pyridine (0.2 g, 0.74 mmol) in DCM (20 mL) at 0° C., difluoro acetic anhydride (0.16 mL, 1.47 mmol) was added and the reaction mixture was stirred at RT for 12 h. After completion of reaction (monitored by TLC), the reaction mixture was quenched with ice cold water (20 mL) and extracted with DCM (50 mL). The organic layer was dried over sodium sulphate and concentrated under reduced pressure to give the crude product. The crude product was purified by using 230-400 mesh silica gel column chromatography by eluting with 0-30% ethyl acetate in hexane to give the product (0.110 g, 46.61% yield) as an off white solid. $^1H$ NMR (400 MHz, DMSO-$d_6$): δ 9.22 (d, J=2.0 Hz, 1H), 8.48 (dd, J=2.0, 8.3 Hz, 1H), 7.77 (d, J=8.3 Hz, 1H), 7.71-7.45 (m, 1H), 7.17-7.06 (m, 4H), 5.30 (s, 2H); $^{19}F$ NMR (400 MHz, DMSO-$d_6$): δ −120, −123. LC-MS: m/z 322.05 $[M+H]^+$ 2-(6-(Difluoro(quinolin-8-yloxy)methyl)pyridin-3-yl)-5-(difluoromethyl)-1,3,4-oxadiazole (13)

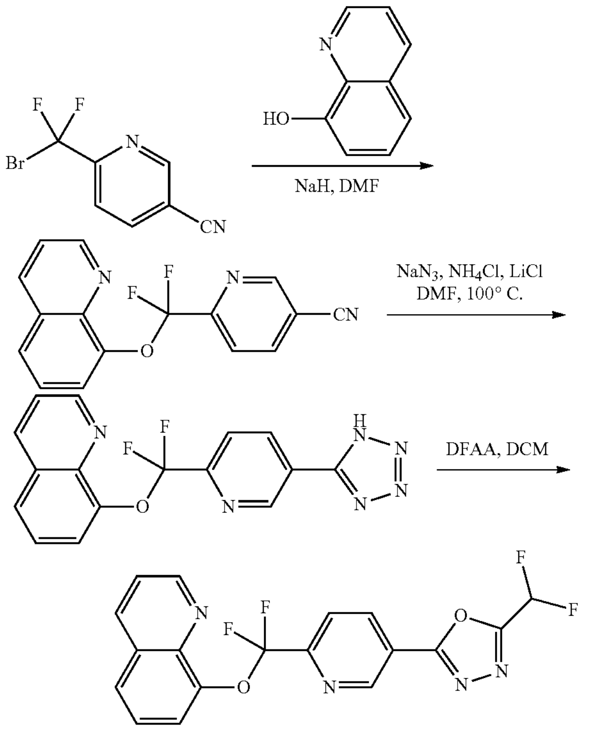

13

Step-1: 6-(Difluoro(quinolin-8-yloxy)methyl)nicotinonitrile: To a stirred solution of 6-(bromodifluoromethyl)nicotinonitrile (0.48 g, 2.06 mmol) in DMF (5 mL), was added NaH (60%, 0.099 g, 2.48 mmol) at 0° C., then stirred it for 5 min at 0° C. Quinolin-8-ol (0.3 g, 2.06 mmol) dissolved in DMF (2 mL) was slowly added at 0° C. Then the reaction mixture was stirred at room temperature for 30 mins. After completion of reaction (monitored by TLC), the reaction mixture was quenched with water (50 mL) and extracted with ethyl acetate (100 mL). The organic layer was dried over sodium sulphate and concentrated under reduced pressure to give the crude product. The crude product was purified by using 100-200 mesh silica gel column chromatography by eluting with 0-10% ethyl acetate in hexane to give the product (0.22 g, 35.83% yield) as an off white solid. LC-MS: m/z 298.1 $[M+H]^+$.

Step-2: 8-((5-(1H-Tetrazol-5-yl)pyridin-2-yl)difluoromethoxy)quinoline: To a stirred solution of 6-(difluoro(quinolin-8-yloxy)methyl)nicotinonitrile (0.22 g, 0.74 mmol) in DMF (7 mL), sodium azide (0.144 g, 2.22 mmol), $NH_4Cl$ (0.124 g, 2.22 mmol) and LiCl (0.030 g) were added, and the reaction mixture was stirred at 100° C. for 8 h. After completion of reaction (monitored by TLC), the reaction mixture was concentrated under reduced pressure and was acidified with 6N HCl, extracted with ethyl acetate (2×50 mL). The organic layer was dried over sodium sulphate and concentrated to give the product (0.220 g, 87.64%) as an off white solid which was used as such for further step.

Step-3: 2-(6-(Difluoro(quinolin-8-yloxy)methyl)pyridin-3-yl)-5-(difluoromethyl)-1,3,4-oxadiazole (13): To a stirred solution of 8-((5-(1H-tetrazol-5-yl)pyridin-2-yl)difluoromethoxy)quinoline (0.220 g, 0.64 mmol) in DCM (10 mL) at 0° C., difluoro acetic anhydride (0.225 g, 1.29 mmol) was added and the reaction mixture was stirred at RT for 16 hours. After completion of reaction (monitored by TLC), the reaction mixture was diluted with water (20 mL) and extracted with DCM (50 mL). The organic layer was dried over sodium sulphate and concentrated under reduced pressure to give the crude product. The crude product was purified by using 100-200 mesh silica gel column chromatography by eluting with 0-10% ethyl acetate in hexane to give the product (0.080 g, 31.74% yield) as an off white solid. $^1$H NMR (400 MHz, DMSO-$d_6$) δ 9.39 (s, 1H), 9.09-8.89 (m, 1H), 8.86-8.64 (m, 1H), 8.48 (s, 1H), 8.44-8.35 (m, 1H), 7.98 (d, J=8.5 Hz, 1H), 7.82 (br d, J=7.5 Hz, 1H), 7.77-7.47 (m, 3H); $^{19}$F NMR (400 MHz, DMSO-$d_6$) δ −78, −121. LC-MS: m/z 391.20 [M+H]$^+$ 2-(6-(Difluoro(4-fluorophenoxy)methyl)pyridin-3-yl)-5-(difluoromethyl)-1,3,4-oxadiazole (15)

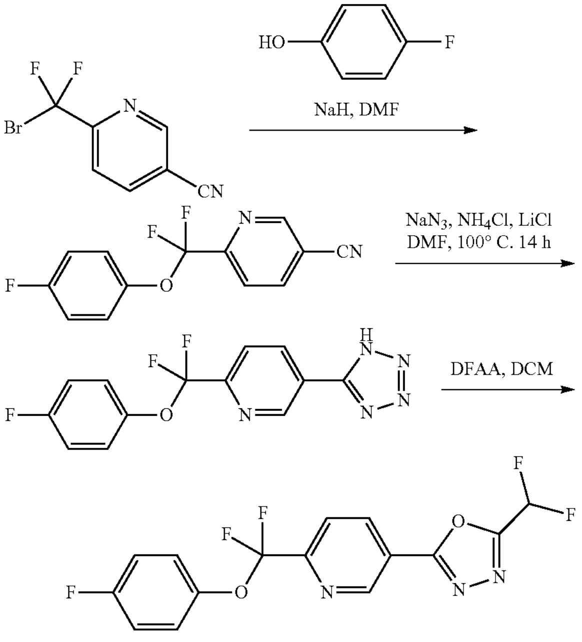

15

Step-1: 6-(Difluoro(4-fluorophenoxy)methyl)nicotinonitrile: To a stirred solution of 6-(bromodifluoromethyl)nicotinonitrile (0.3 g, 1.28 mmol) in DMF (5 mL), was added NaH (60%, 0.062 g, 1.54 mmol) at 0° C., then stirred it for 5 min at 0° C. 4-fluorophenol (0.144 g, 1.28 mmol) dissolved in DMF (2 mL) was slowly added at 0° C. Then the reaction mixture was stirred at room temperature for 45 mins. After completion of reaction (monitored by TLC), the reaction mixture was quenched with water (50 mL) and extracted with ethyl acetate (100 mL). The organic layer was dried over sodium sulphate and concentrated under reduced pressure to give the crude product. The crude product was purified by using 100-200 mesh silica gel column chromatography by eluting with 0-10% ethyl acetate in hexane to give the product (0.2 g, 58.8% yield) as an off white solid. LC-MS: m/z 265.20 [M+H]$^+$.

Step-2: 2-(Difluoro(4-fluorophenoxy)methyl)-5-(1H-tetrazol-5-yl)pyridine: To a stirred solution of 6-(difluoro(4-fluorophenoxy)methyl)nicotinonitrile (0.2 g, 0.75 mmol) in DMF (5 mL), sodium azide (0.148 g, 2.27 mmol), $NH_4Cl$ (0.127 g, 2.27 mmol) and LiCl (0.020 g) were added and the reaction mixture was stirred at 100° C. for 16 h. After completion of reaction (monitored by TLC), the reaction mixture was concentrated under reduced pressure and was acidified with 6N HCl, extracted with ethyl acetate (2×50 mL). The organic layer was dried over sodium sulphate and concentrated to give the crude product. The crude product was washed with hexane (2×10 mL) to give the product (0.2 g of crude product) as an off white solid which was used as such for further step.

Step-3: 2-(6-(Difluoro(4-fluorophenoxy)methyl)pyridin-3-yl)-5-(difluoromethyl)-1,3,4-oxadiazole (15): To a stirred solution of 2-(difluoro(4-fluorophenoxy)methyl)-5-(1H-tetrazol-5-yl)pyridine (0.200 g, 0.65 mmol) in DCM (10 mL) at 0° C., difluoro acetic anhydride (1.2 mL, 6.5 mmol) was added and the reaction mixture was stirred at RT for 16 hours. After completion of reaction (monitored by TLC), the reaction mixture was diluted with DCM (20 mL) and basified with saturated sodium bicarbonate solution and extracted with DCM (50 mL). The organic layer was dried over sodium sulphate and concentrated under reduced pressure to give the crude product. The crude product was purified by using 100-200 mesh silica gel column chromatography by eluting with 0-10% ethyl acetate in hexane to give the product (0.120 g, 51.72% yield) as an off white solid. $^1$H NMR (400 MHz, DMSO-$d_6$) δ 9.38 (d, J=1.5 Hz, 1H), 8.69 (dd, J=2.0, 8.3 Hz, 1H), 8.17 (d, J=8.3 Hz, 1H), 7.76-7.47 (m, 1H), 7.43-7.35 (m, 2H), 7.35-7.26 (m, 2H); $^{19}$F NMR (400 MHz, DMSO-$d_6$) δ −70, −116, −121; LC-MS: m/z 358.15 [M+H]+

2-(Difluoromethyl)-5-(6-(((5-fluoropyridin-3-yl)oxy)methyl)pyridin-3-yl)-1,3,4-oxadiazole (19)

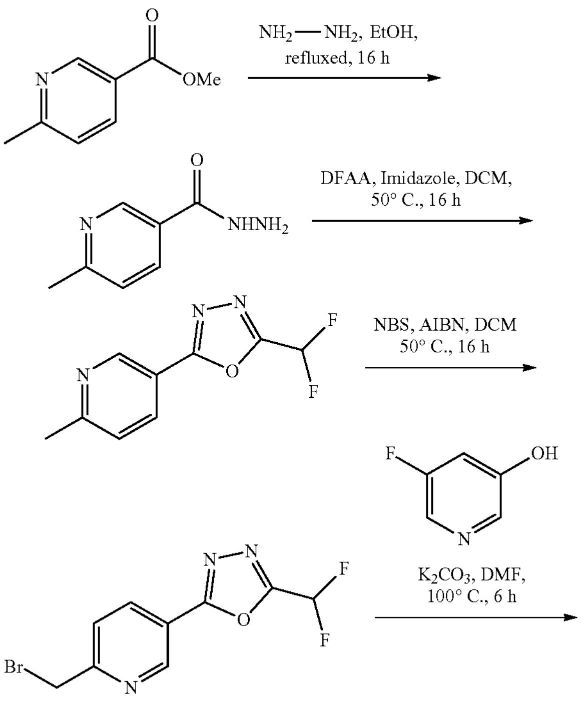

-continued

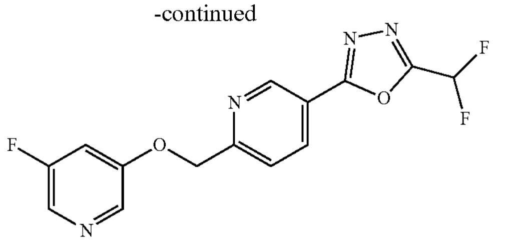

19

Step-1: Synthesis of 6-methylnicotinohydrazide: To a stirred solution of methyl 6-methylnicotinate (3.0 g, 19.867 mmol, 1.0 equiv.) in EtOH (15 mL) were added hydrazine hydride (4.0 g, 79.47 mmol, 4.0 equiv.) at room temperature and stirred for 5 min. The reaction mixture was refluxed for 16 h and progress of reaction was monitored by TLC. After completion of reaction, reaction mixture was cooled to room temperature and concentrated under reduced pressure to obtain crude product. The obtained crude product was triturated with diethyl ether (50 mL) to afford desired product (2.0 g, 93%) as a white solid. LC-MS: m/z 151.00 (M+1).

Step-2: Synthesis of 2-(difluoromethyl)-5-(6-methylpyridin-3-yl)-1,3,4-oxadiazole: To a solution of 6-methylnicotinohydrazide (2, 2.8 g, 18.543 mmol, 1.0 equiv.) in DCM (20 mL) were added imidazole (3.70 g, 55.62 mmol, 3.0 equiv.), and DFAA (9.64 g, 55.62 mmol, 3.0 equiv.) at room temperature and stirred for 5 min. The resulting reaction mixture was heated at 50° C. and stirred for 16 h. The progress of reaction was monitored by TLC. After completion of the reaction, the reaction mixture was quenched with sat. aq. $NaHCO_3$ (10 mL) and aq. layer was extracted with DCM (30 mL×2). The organic layer was washed with brine, dried over anhydrous $Na_2SO_4$ and concentrated under reduced pressure to obtain the crude product (2.40 g) as a sticky solid. The crude product was purified by CombiFlash column chromatography using an eluent ethyl acetate: n-heptane (15%) to afford desired product (1.80 g, 47%) as a white solid. LC-MS: m/z 212.00 (M+1).

Step-3: Synthesis of 2-(6-(bromomethyl)pyridin-3-yl)-5-(difluoromethyl)-1,3,4-oxadiazole: To a solution of 2-(difluoromethyl)-5-(6-methylpyridin-3-yl)-1,3,4-oxadiazole (1.80 g, 8.53 mmol, 1.0 equiv.) in DCM (15 mL) were added NBS (2.30 g, 12.79 mmol, 1.5 equiv.) followed by AIBN (420 mg, 2.55 mmol, 0.3 equiv.) at RT. Reaction mixture was stirred at 50° C. for 16 h. The progress of reaction was monitored by TLC and TLC showed new spot of product along with unreacted starting material. After completion of reaction, the reaction mixture was cooled to RT and concentrated under reduced pressure to obtain crude product. The crude product was purified by CombiFlash column chromatography using an eluent ethyl acetate: n-heptane (10%) to provide the product (950 mg, 39%). LCMS: m/z 292.00 (M+1).

Step-4: Synthesis of 2-(difluoromethyl)-5-(6-(((5-fluoropyridin-3-yl)oxy)methyl)pyridin-3-yl)-1,3,4-oxadiazole (19): To a stirred solution of 5-fluoropyridin-3-ol (46.0 mg, 0.4136 mmol, 1.2 equiv.) in DMF (2 mL) was added $K_2CO_3$ (142 mg, 1.034 mmol, 3.0 equiv) at room temperature and stirred for 15 min. To the resulting reaction mixture was added 2-(6-(bromomethyl)pyridin-3-yl)-5-(difluoromethyl)-1,3,4-oxadiazole (100 mg, 0.3447 mmol, 1.0 equiv.) at room temperature. The reaction mixture was heated at 100° C. for further 6 h. The progress of reaction was monitored by TLC. After completion of reaction, reaction mixture was quenched with saturated $NH_4Cl$ solution (5 mL) and aq. layer was extracted with ethyl acetate (10 mL×2). The organic layer was washed with water (10 mL) followed by brine (10 mL), dried over anhydrous $Na_2SO_4$ and concentrated under reduced pressure to obtain crude product. The crude product was purified by CombiFlash chromatography eluted with ethyl acetate: n-heptane (40%) to afford desired product (19, 30 mg, 27%) as a pale yellow solid. $^1H$ NMR (400 MHz, DMSO-$d_6$) δ ppm 5.43 (s, 2H) 7.45-7.71 (m, 2H) 7.83 (d, J=8.4 Hz, 1H) 8.14-8.24 (m, 1H), 8.34 (br. s, 1H), 8.52 (dd, J=2.4 Hz, J=10.4 Hz, 1H), 9.20-9.30 (m, 1H). $^{19}F$-NMR (400 MHz, DMSO-$d_6$): δ −120.70, 126.28. LC-MS: m/z 322.85 [M+H].

The following compounds were prepared in a manner analogous to that used for preparing compound (19).

| Compound | Structure/Name | Characterization |
|---|---|---|
| 213 | 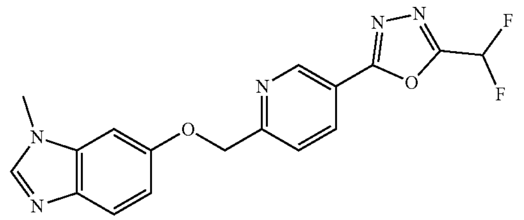 [SMILES: Cn1cnc2ccc(OCc3ccc(-c4nnc(C(F)F)o4)cn3)cc21] | $^1$HNMR (400 MHz, METHANOL-d4) δ ppm 9.32 (s, 1H) 9.20 (s, 1H) 8.58 (dd, J = 8.26, 2.00 Hz, 1H) 7.94 (d, J = 8.13 Hz, 1H) 7.79 (d, J = 9.01 Hz, 1H) 7.60 (d, J = 2.00 Hz, 1H) 7.41-7.48 (m, 1H) 7.13-7.40 (m, 1H) 5.48 (s, 2H) 4.12 (s, 3H); MS (ESI): 358[M + H]$^+$ |
| 208 | 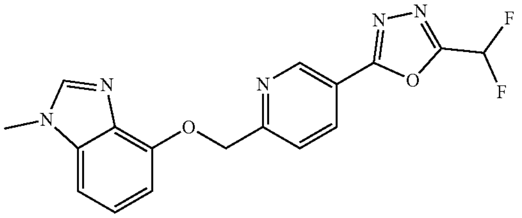 [SMILES: Cn1cnc2c(OCc3ccc(-c4nnc(C(F)F)o4)cn3)cccc21] | $^1$HNMR (400 MHz, METHANOL-d4) δ ppm 9.28 (d, J = 1.75 Hz, 1H) 8.54 (dd, J = 8.32, 2.19 Hz, 1H) 8.11 (t, J = 3.94 Hz, 2H) 7.13-7.43 (m, 3H) 6.89 (d, J = 7.13 Hz, 1H) 5.53 (s, 2H) 3.92 (s, 3H); MS (ESI): 358.2 [M + H]$^+$ |

-continued

| Compound | Structure/Name | Characterization |
|---|---|---|
| 204 | 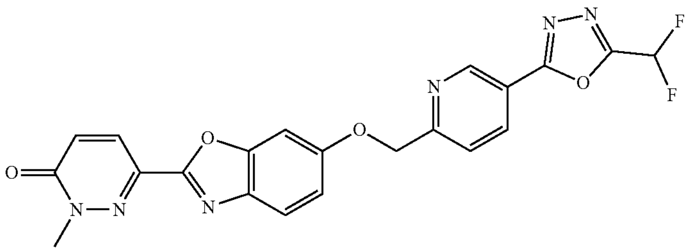 [SMILES: Cn1nc(-c2nc3ccc(OCc4ccc(-c5nnc(C(F)F)o5)cn4)cc3o2)ccc1=O] | $^1$HNMR (400 MHz, DMSO-d6) δ ppm 9.25 (d, J = 1.00 Hz, 1H) 8.52 (dd, J = 8.07, 1.94 Hz, 1H) 8.13 (d, J = 9.63 Hz, 1H) 7.85 (d, J = 8.00 Hz, 1H) 7.80 (d, J = 8.76 Hz, 1H) 7.46-7.72 (m, 2H) 7.22 (dd, J = 8.82, 2.19 Hz, 1H) 7.14 (d, J = 9.76 Hz, 1H) 5.44 (s, 2H) 3.80 (s, 3H) MS (ESI): 453.2 $[M + H]^+$ |
| 150 | 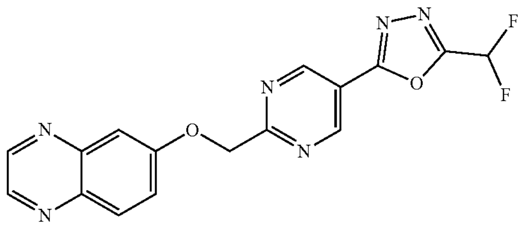 [SMILES: FC(F)c1nnc(-c2cnc(COc3ccc4nccnc4c3)nc2)o1] | $^1$HNMR (400 MHz, METHANOL-d4) δ = 9.49 (s, 2H), 8.80 (d, J = 1.9 Hz, 1H), 8.75 (d, J = 2.0 Hz, 1H), 8.06 (d, J = 9.3 Hz, 1H), 7.71-7.68 (m, 1H), 7.50 (d, J = 2.9 Hz, 2H), 7.42-7.15 (m, 1H), 5.67 (s, 2H) $^{19}$F NMR (377 MHz, METHANOL-d4) δ = −122.69 (s, 2F) MS (ESI): 357.0 $[M + H]^+$ |
| 156 | 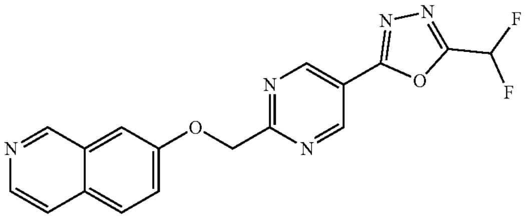 [SMILES: FC(F)c1nnc(-c2cnc(COc3ccc4ccncc4c3)nc2)o1] | MS(ESI): 356.0 $[M + H]^+$ $^1$HNMR (400 MHz, DMSO-d6) δ = 9.47 (s, 2H), 9.15 (s, 1H), 8.38 (d, J = 5.6 Hz, 1H), 7.96-7.93 (m, 1H), 7.78-7.75 (m, 1H), 7.62-7.56 (m, 3H), 5.64 (s, 2H) $^{19}$F NMR (377 MHz, DMSO-d6) δ = −120.69 (s, 2F) |
| 158 | 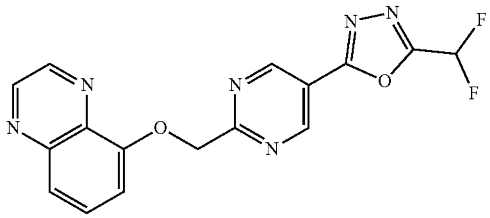 [SMILES: FC(F)c1nnc(-c2cnc(COc3cccc4nccnc34)nc2)o1] | MS(ESI): 357.0 $[M + H]^+$ $^1$HNMR (400 MHz, METHANOL-d4) δ = 9.46 (s, 2H), 8.95 (d, J = 1.3 Hz, 1H), 8.89 (s, 1H), 7.76-7.71 (m, 2H), 7.41-7.15 (m, 2H), 5.76 (s, 2H) $^{19}$F NMR (377 MHz, METHANOL-d4) δ = −122.37-−122.52 (m, 2F) |
| 164 | 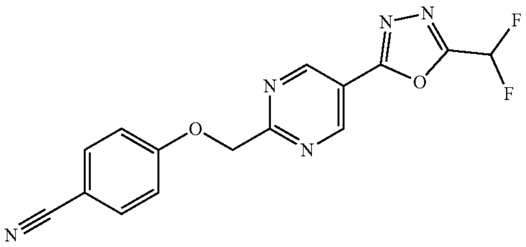 [SMILES: N#Cc1ccc(OCc2ncc(-c3nnc(C(F)F)o3)cn2)cc1] | MS(ESI): 330.0 $[M + H]^+$ $^1$HNMR (400 MHz, DMSO-d6) δ = 9.44 (s, 2H), 7.78 (d, J = 8.8 Hz, 2H), 7.73-7.47 (m, 1H), 7.19 (d, J = 8.9 Hz, 2H), 5.58 (s, 2H) $^{19}$F NMR (376 MHz, DMSO-d6) δ = −120.70 (s, 2F) |
| 154 | 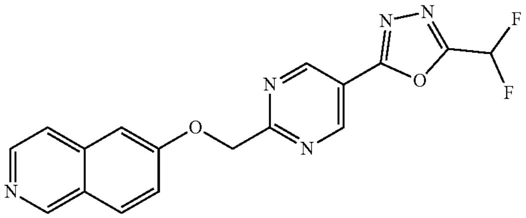 [SMILES: FC(F)c1nnc(-c2cnc(COc3ccc4cnccc4c3)nc2)o1] | MS(ESI): 356.0 $[M + H]^+$ $^1$HNMR (400 MHz, DMSO-d6) δ = 9.47 (s, 2H), 9.17 (s, 1H), 8.39 (d, J = 5.8 Hz, 1H), 8.07 (d, J = 8.9 Hz, 1H), 7.74-7.61 (m, 2H), 7.45-7.39 (m, 2H), 5.64 (s, 2H) $^{19}$F NMR (377 MHz, DMSO-d6) δ = −119.99-−121.36 (m, 2F) |

-continued

| Compound | Structure/Name | Characterization |
| --- | --- | --- |
| 142 | 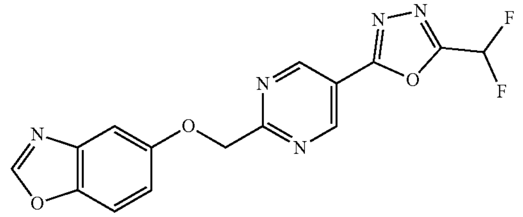 [SMILES: FC(F)c1nnc(-c2cnc(COc3ccc4ocnc4c3)nc2)o1] | MS(ESI): 346.0 [M + H]+ $^1$HNMR (400 MHz, DMSO-d6) δ = 9.46 (s, 2H), 8.69 (s, 1H), 7.69 (d, J = 8.9 Hz, 1H), 7.63-7.45 (m, 1H), 7.41 (d, J = 2.6 Hz, 1H), 7.14 (dd, J = 2.6, 8.9 Hz, 1H), 5.51 (s, 2H) $^{19}$F NMR (377 MHz, DMSO-d6) δ = −120.68 (s, 2F) |
| 168 | 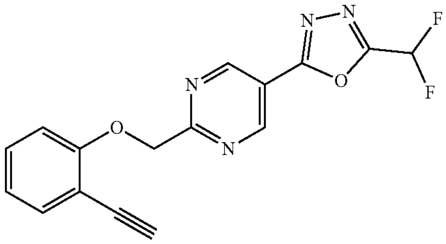 [SMILES: C#Cc1ccccc1OCc1ncc(-c2nnc(C(F)F)o2)cn1] | MS(ESI): 329.0 [M + H]+ $^1$HNMR (400 MHz, DMSO-d6) δ = 9.45 (s, 2H), 7.74-7.48 (m, 1H), 7.45 (d, J = 6.8 Hz, 1H), 7.30 (t, J = 7.9 Hz, 1H), 6.97 (dd, J = 5.1, 7.8 Hz, 2H), 5.54 (s, 2H), 4.25 (s, 1H) $^{19}$F NMR (376 MHz, DMSO-d6) δ = −120.70 (s, 2F) |
| 146 | 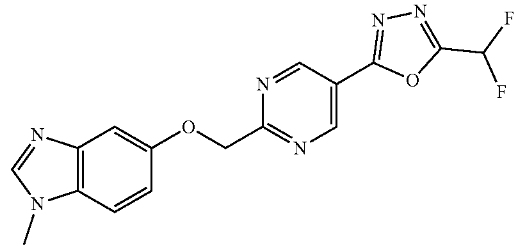 [SMILES: Cn1cnc2cc(OCc3ncc(-c4nnc(C(F)F)o4)cn3)ccc21] | MS(ESI): 359.0 [M + H]+ $^1$HNMR (400 MHz, DMSO-d6) δ = 9.45 (s, 2H), 8.10 (br s, 1H), 7.84-7.57 (m, 1H), 7.50-7.45 (m, 1H), 7.21 (br s, 1H), 7.02 (dd, J = 1.6, 8.7 Hz, 1H), 5.45 (s, 2H), 3.80 (s, 3H) $^{19}$F NMR (377 MHz, DMSO-d6) δ = −120.52-−120.89 (m, 2F) |
| 205 | 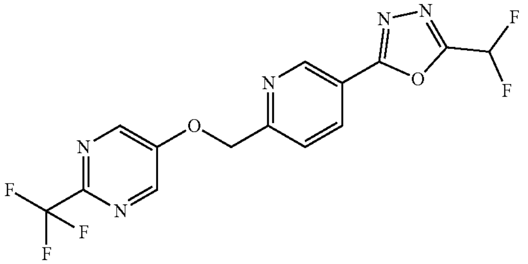 [SMILES: FC(F)c1nnc(-c2ccc(COc3cnc(C(F)(F)F)nc3)nc2)o1] | MS(ESI): 374.0 [M + H]+ $^1$HNMR (400 MHz, DMSO-d6) δ = 9.33-9.16 (m, 1H), 8.93 (s, 2H), 8.54 (dd, J = 2.0, 8.3 Hz, 1H), 7.87 (d, J = 8.3 Hz, 1H), 7.60 (t, J = 51.2 Hz, 1H), 5.63 (s, 2H) $^{19}$F NMR (377 MHz, DMSO-d6) δ = −67.75 (s, 1F), −120.27-−121.21 (m, 1F) |
| 207 | 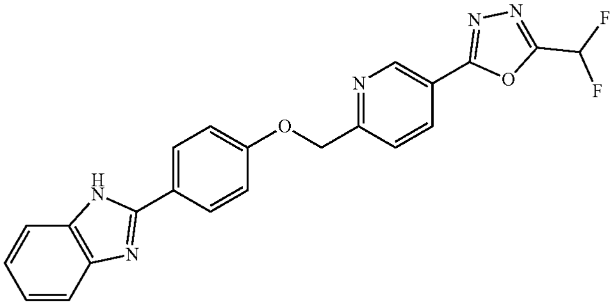 [SMILES: FC(F)c1nnc(-c2ccc(COc3ccc(-c4nc5ccccc5[nH]4)cc3)nc2)o1] | MS(ESI): 420.0 [M + H]+ $^1$HNMR (400 MHz, DMSO-d6) δ = 12.76 (br s, 1H), 9.26 (d, J = 1.5 Hz, 1H), 8.52 (dd, J = 1.8, 8.2 Hz, 1H), 8.14 (d, J = 8.6 Hz, 2H), 7.83 (d, J = 8.3 Hz, 1H), 7.73-7.58 (m, 2H), 7.50 (br d, J = 5.4 Hz, 1H), 7.25 (d, J = 8.6 Hz, 2H), 7.18 (br d, J = 4.3 Hz, 2H), 5.43 (s, 2H) $^{19}$F NMR (376 MHz, DMSO-d6) δ = −120.70 (s, 2F) |

-continued

| Compound | Structure/Name | Characterization |
|---|---|---|
| 206 | 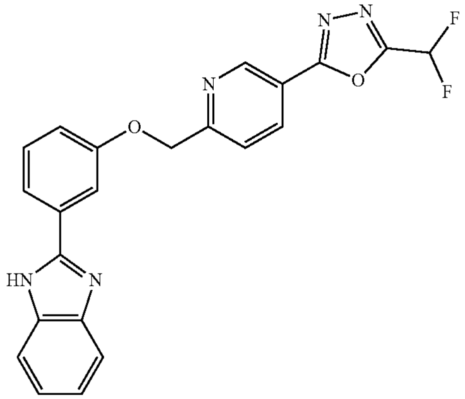 [SMILES: FC(F)c1nnc(-c2ccc(COc3cccc(-c4nc5ccccc5[nH]4)c3)nc2)o1] | MS(ESI): 420.0 [M + H]$^+$ $^1$HNMR (400 MHz, DMSO-d6) δ = 12.92 (br s, 1H), 9.26 (d, J = 1.8 Hz, 1H), 8.52 (dd, J = 2.0, 8.3 Hz, 1H), 7.90 (s, 1H), 7.83 (t, J = 8.7 Hz, 2H), 7.72-7.55 (m, 3H), 7.54-7.53 (m, 1H), 7.51 (t, J = 7.9 Hz, 1H), 7.23-7.19 (m, 3H), 5.45 (s, 2H) $^{19}$F NMR (376 MHz, DMSO-d6) δ = −120.70 (s, 2F) |
| 200 | 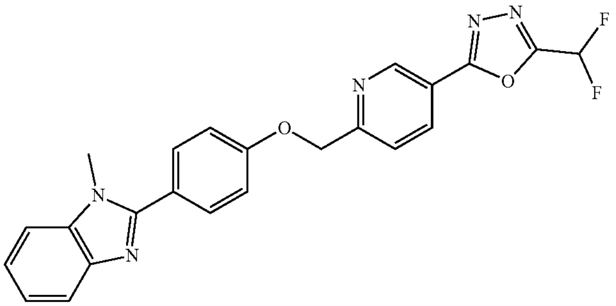 [SMILES: Cn1c(-c2ccc(OCc3ccc(-c4nnc(C(F)F)o4)cn3)cc2)nc2ccccc21] | MS(ESI): 434.0 [M + H]$^+$ $^1$HNMR (400 MHz, DMSO-d6) δ = 9.26 (d, J = 1.9 Hz, 1H), 8.53 (dd, J = 2.2, 8.2 Hz, 1H), 7.84 (dd, J = 3.1, 8.5 Hz, 3H), 7.73-7.46 (m, 3H), 7.31-7.21 (m, 4H), 5.45 (s, 2H), 3.87 (s, 3H) $^{19}$F NMR (376 MHz, DMSO-d6) δ = −120.70 (br s, 2F) |
| 201 | 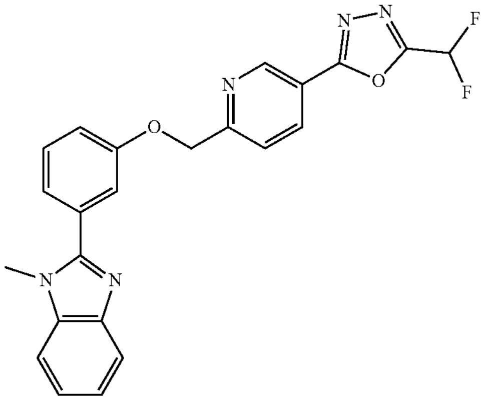 [SMILES: Cn1c(-c2cccc(OCc3ccc(-c4nnc(C(F)F)o4)cn3)c2)nc2ccccc21] | MS(ESI): 434.0 [M + H]$^+$ $^1$HNMR (400 MHz, DMSO-d6) δ = 9.25 (d, J = 1.3 Hz, 1H), 8.51 (dd, J = 2.1, 8.2 Hz, 1H), 7.85 (d, J = 8.3 Hz, 1H), 7.72-7.67 (m, 1H), 7.60 (br d, J = 9.0 Hz, 1H), 7.58-7.36 (m, 4H), 7.34-7.24 (m, 3H), 5.45 (s, 2H), 3.87 (s, 3H) $^{19}$F NMR (377 MHz, DMSO-d6) δ = −120.57-−120.89 (m, 2F) |
| 203 | 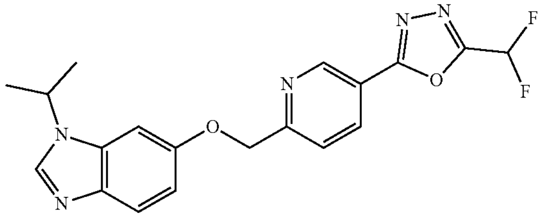 [SMILES: CC(C)n1cnc2ccc(OCc3ccc(-c4nnc(C(F)F)o4)cn3)cc21] | $^1$HNMR (400 MHz, DMSO-d6) δ = 9.24 (d, J = 1.5 Hz, 1H), 8.50 (dd, J = 2.2, 8.2 Hz, 1H), 8.22 (s, 1H), 7.85 (d, J = 8.1 Hz, 1H), 7.71-7.48 (m, 2H), 7.33 (d, J = 2.3 Hz, 1H), 6.97 (dd, J = 2.4, 8.8 Hz, 1H), 5.39 (s, 2H), 4.76-4.67 (m, 1H), 1.51 (d, J = 6.8 Hz, 6H) $^{19}$F NMR (377 MHz, DMSO-d6) δ = −120.08-−121.05 (m, 2F) |

-continued

| Compound | Structure/Name | Characterization |
| --- | --- | --- |
| 212 | 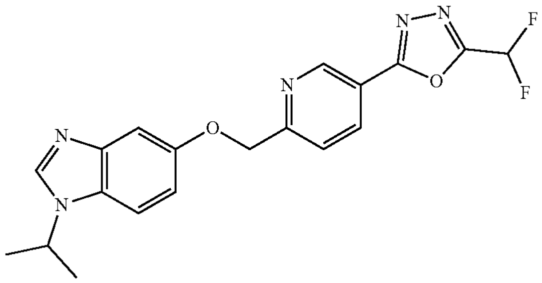 [SMILES: CC(C)n1cnc2cc(OCc3ccc(-c4nnc(C(F)F)o4)cn3)ccc21] | MS(ESI): 386.0 [M + H]+ 1HNMR (400 MHz, DMSO-d6) δ = 9.23 (s, 1H), 8.48 (dd, J = 1.9, 8.2 Hz, 1H), 8.26 (s, 1H), 7.81 (d, J = 8.3 Hz, 1H), 7.65-7.44 (m, 2H), 7.28 (d, J = 2.0 Hz, 1H), 7.04 (dd, J = 2.1, 8.8 Hz, 1H), 5.36 (s, 2H), 4.71 (td, J = 6.6, 13.4 Hz, 1H), 1.52 (d, J = 6.8 Hz, 6H) 19F NMR (377 MHz, DMSO-d6) δ = −120.02-−121.17 (m, 2F) |
| 209 | 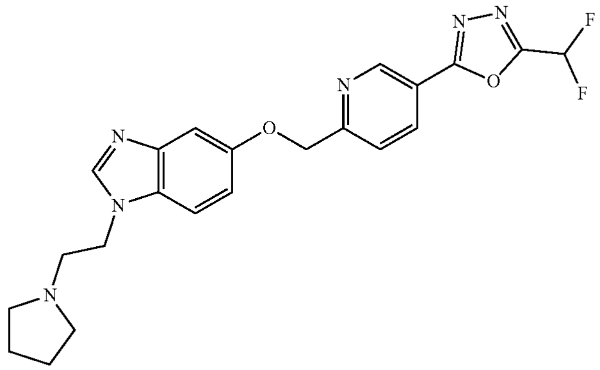 [SMILES: FC(F)c1nnc(-c2ccc(COc3ccc4c(c3)ncn4CCN3CCCC3)nc2)o1] | MS(ESI): 441.0 [M + H]+ 1HNMR (400 MHz, METHANOL-d4) δ = 9.46-9.36 (m, 1H), 9.27 (br d, J = 1.3 Hz, 1H), 8.61 (dd, J = 2.2, 8.1 Hz, 1H), 7.89 (br d, J = 8.1 Hz, 2H), 7.44-7.14 (m, 3H), 5.31 (br t, J = 7.4 Hz, 2H), 4.97 (s, 2H), 4.19-4.12 (m, 2H), 4.01-3.93 (m, 2H), 3.85-3.76 (m, 2H), 2.44-2.35 (m, 4H) 19F NMR (376 MHz, METHANOL-d4) δ = −76.92 (br s, 3F), −122.37 (s, 2F) |
| 152 | 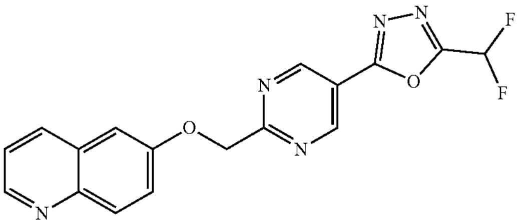 [SMILES: FC(F)c1nnc(-c2cnc(COc3ccc4ncccc4c3)nc2)o1] | MS(ESI): 356.2[M + H]+ 1HNMR (400 MHz, DMSO-d6) δ = 9.47 (s, 2H), 8.75 (dd, J = 1.6, 4.2 Hz, 1H), 8.21 (d, J = 8.5 Hz, 1H), 7.96 (d, J = 9.1 Hz, 1H), 7.75-7.52 (m, 2H), 7.49-7.45 (m, 1H), 7.43 (d, J = 2.9 Hz, 1H), 5.61 (s, 2H) 19F NMR (377 MHz, DMSO-d6) δ = −120.69 (s, 2F) |
| 162 | 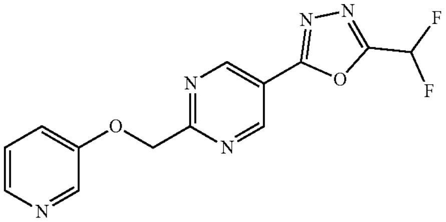 [SMILES: FC(F)c1nnc(-c2cnc(COc3cccnc3)nc2)o1] | MS(ESI): 306.1[M + H]+ 1HNMR (400 MHz, DMSO-d6) δ = 9.46 (s, 2H), 8.38 (d, J = 2.9 Hz, 1H), 8.20 (dd, J = 1.2, 4.6 Hz, 1H), 7.62 (t, J = 51.1 Hz, 1H), 7.45 (ddd, J = 1.3, 3.0, 8.5 Hz, 1H), 7.33 (dd, J = 4.5, 8.4 Hz, 1H), 5.55 (s, 2H) 19F NMR (377 MHz, DMSO-d6) δ = −120.70 (s, 2F) |
| 144 | 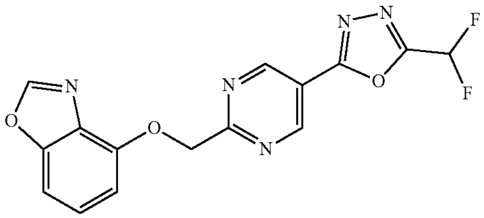 [SMILES: FC(F)c1nnc(-c2cnc(COc3cccc4ocnc34)nc2)o1] | MS(ESI): 346.2[M + H]+ 1HNMR (400 MHz, METHANOL-d4) δ = 9.45 (s, 2H), 8.36 (s, 1H), 7.41-7.15 (m, 3H), 7.00 (d, J = 7.9 Hz, 1H), 5.78 (s, 2H) 19F NMR (376 MHz, METHANOL-d4) δ = −122.44 (s, 2F) |
| 134 | 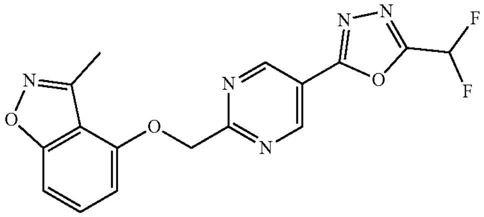 [SMILES: Cc1noc2cccc(OCc3ncc(-c4nnc(C(F)F)o4)cn3)c12] | MS(ESI): 360.2[M + H]+ 1HNMR (400 MHz, METHANOL-d4) δ = 9.48 (s, 2H), 7.47 (t, J = 8.3 Hz, 1H), 7.42-7.15 (m, 2H), 6.81 (d, J = 8.1 Hz, 1H), 5.63 (s, 2H), 2.73 (s, 3H) 19F NMR (376 MHz, METHANOL-d4) δ = −122.43 (s, 2F) |

-continued

| Compound | Structure/Name | Characterization |
|---|---|---|
| 160 | 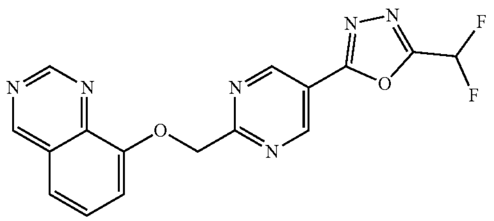 [SMILES: FC(F)c1nnc(-c2cnc(COc3cccc4cncnc34)nc2)o1] | MS(ESI): 357.2[M + H]$^+$<br>$^1$HNMR (400 MHz, METHANOL-d4) δ = 9.55 (s, 1H), 9.45 (s, 2H), 9.27 (s, 1H), 7.75-7.72 (m, 1H), 7.69-7.64 (m, 1H), 7.52 (d, J = 7.8 Hz, 1H), 7.28 (t, J = 51.6 Hz, 1H), 5.77 (s, 2H)<br>$^{19}$F NMR (376 MHz, METHANOL-d4) δ = −122.44 (s, 2F) |
| 210 | 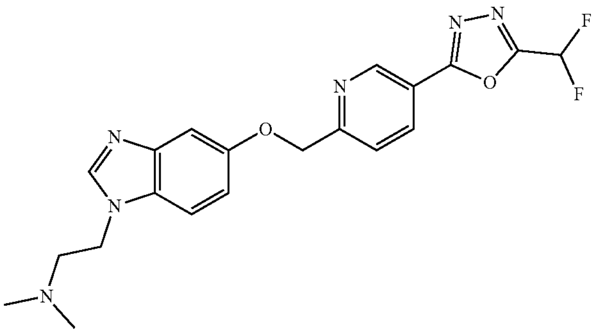 [SMILES: CN(C)CCn1cnc2cc(OCc3ccc(-c4nnc(C(F)F)o4)cn3)ccc21] | MS(ESI): 415.3[M + H]$^+$<br>$^1$HNMR (400 MHz, DMSO-d6) δ = 9.36 (d, J = 2.0 Hz, 1H), 9.04 (s, 1H), 8.63 (dd, J = 2.3, 8.0 Hz, 1H), 7.94 (d, J = 8.1 Hz, 1H), 7.80 (d, J = 8.9 Hz, 1H), 7.62 (t, J = 51.3 Hz, 1H), 7.12 (d, J = 2.0 Hz, 1H), 7.05 (dd, J = 2.0, 8.9 Hz, 1H), 5.05 (br t, J = 7.4 Hz, 2H), 4.92 (s, 2H), 3.96-3.91 (m, 2H), 3.28 (s, 6H)<br>$^{19}$F NMR (376 MHz, DMSO-d6) δ = −73.92 (s, 3F), −120.79 (s, 2F) |
| 202 | 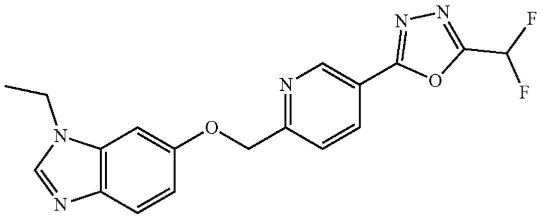 [SMILES: CCn1cnc2ccc(OCc3ccc(-c4nnc(C(F)F)o4)cn3)cc21] | MS(ESI): 372.2[M + H]$^+$<br>$^1$HNMR (400 MHz, DMSO-d6) δ = 9.24 (d, J = 2.0 Hz, 1H), 8.50 (dd, J = 2.3, 8.3 Hz, 1H), 8.13 (s, 1H), 7.84 (d, J = 8.3 Hz, 1H), 7.72-7.46 (m, 2H), 7.33 (d, J = 2.3 Hz, 1H), 6.97 (dd, J = 2.3, 8.8 Hz, 1H), 5.39 (s, 2H), 4.23 (q, J = 7.2 Hz, 2H), 1.39 (t, J = 7.3 Hz, 3H)<br>$^{19}$F NMR (376 MHz, DMSO-d6) δ = −120.70 (s, 2F) |
| 211 | 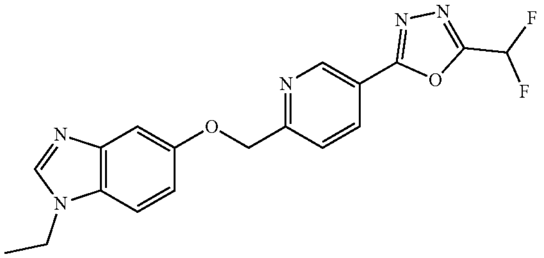 [SMILES: CCn1cnc2cc(OCc3ccc(-c4nnc(C(F)F)o4)cn3)ccc21] | MS(ESI): 372.2[M + H]$^+$<br>$^1$HNMR (400 MHz, DMSO-d6) δ = 9.24 (d, J = 1.5 Hz, 1H), 8.48 (dd, J = 2.1, 8.2 Hz, 1H), 8.18 (s, 1H), 7.81 (d, J = 8.3 Hz, 1H), 7.71-7.45 (m, 2H), 7.28 (d, J = 2.1 Hz, 1H), 7.05 (dd, J = 2.1, 8.8 Hz, 1H), 5.36 (s, 2H), 4.24 (q, J = 7.2 Hz, 2H), 1.40 (t, J = 7.3 Hz, 3H)<br>$^{19}$F NMR (376 MHz, DMSO-d6) δ = −120.70 (s, 2F) |
| 121 | 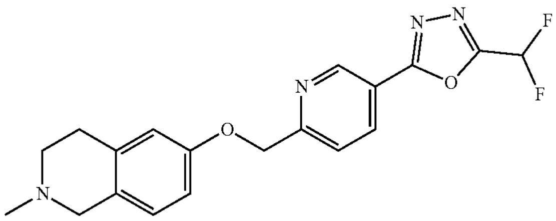 [SMILES: CN1CCc2cc(OCc3ccc(-c4nnc(C(F)F)o4)cn3)ccc2C1] | $^1$HNMR (400 MHz, CDCl3) δ ppm 9.30 (m, 1H), 8.41 (dd, J = 2.0 Hz, 8.0 Hz 1H), 7.57 (dd, 0.8 Hz, 8.4 Hz, 1H), 6.81-7.06 (m, 2H), 6.69-6.79 (m, 2H), 5.26 (s, 2H), 3.51 (s, 2H), 2.90 (t, J = 12.0 Hz, 2H), 2.67 (t, J = 12.0 Hz, 2H), 2.44 s, 3H). LC-MS: m/z 373.35 [M + H]. |
| 136 | 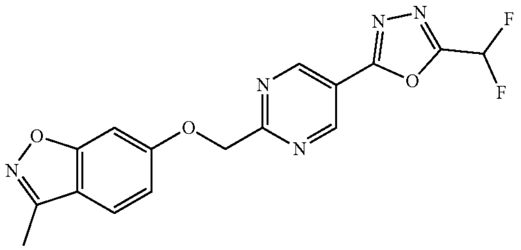 [SMILES: Cc1noc2cc(OCc3ncc(-c4nnc(C(F)F)o4)cn3)ccc12] | $^1$HNMR (400 MHz, CDCl3) δ ppm 9.46 (s, 2H), 7.52 (d, J = 8.68 Hz, 1H), 6.83-7.10 (m, 3H), 5.50 (s, 2H), 2.53 (s, 3H). LC-MS: m/z 360.1 [M + H]. |

-continued

| Compound | Structure/Name | Characterization |
| --- | --- | --- |
| 138 | 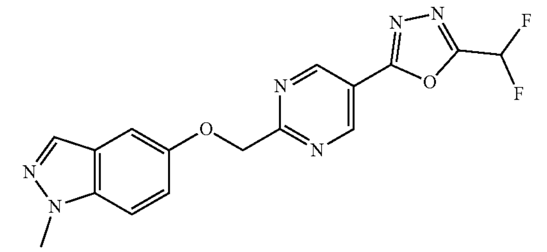 [SMILES: Cn1ncc2cc(OCc3ncc(-c4nnc(C(F)F)o4)cn3)ccc21] | $^1$HNMR (400 MHz, DMSO-d6) δ ppm 9.45 (s, 2H), 7.87 (s, 1H), 7.47-7.74 (m, 2H), 7.21 (d, J = 2.25 Hz, 1H), 7.17 (dd, J = 8.94, 2.31 Hz, 1H), 5.45 (s, 2H), 4.00 (s, 3H). LC-MS: m/z 359.0 [M + H]. |
| 140 | 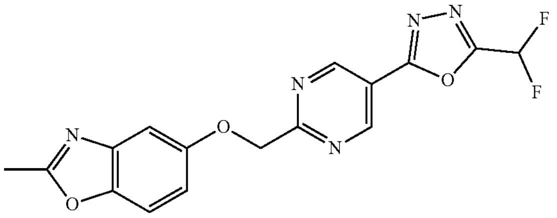 [SMILES: Cc1nc2cc(OCc3ncc(-c4nnc(C(F)F)o4)cn3)ccc2o1] | $^1$HNMR (400 MHz, DMSO-d6) δ ppm 9.45 (s, 2H), 7.45-7.76 (m, 2H), 7.27 (d, J = 2.63 Hz, 1H), 7.02 (dd, J = 8.82, 2.56 Hz, 1H), 5.48 (s, 2H), 2.57 (s, 3H). LC-MS: m/z 359.92 [M + H]. |
| 141 | 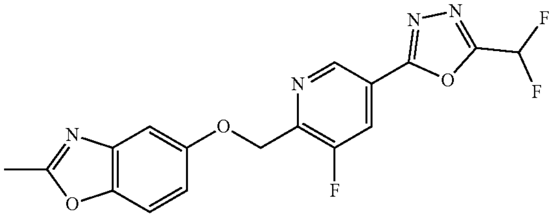 [SMILES: Cc1nc2cc(OCc3ncc(-c4nnc(C(F)F)o4)cc3F)ccc2o1] | $^1$HNMR (400 MHz, DMSO-d6) δ ppm 9.10 (d, J = 1.00 Hz, 1H), 8.43-8.48 (m, 1H), 7.44-7.74 (m, 2H), 7.37 (d, J = 2.50 Hz, 1H), 6.97-7.04 (m, 1H), 5.39 (d, J = 1.63 Hz, 2H), 2.40-2.50 (m, 3H). LC-MS: m/z 377.2 [M + H]. |
| 147 | 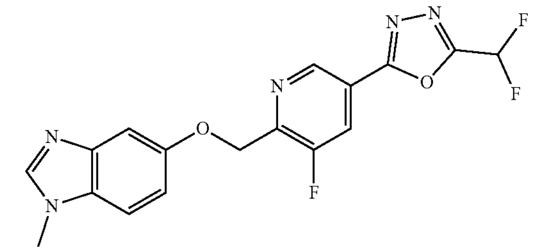 [SMILES: Cn1cnc2cc(OCc3ncc(-c4nnc(C(F)F)o4)cc3F)ccc21] | $^1$HNMR (400 MHz, DMSO-d6) δ ppm 9.08-9.13 (m, 1H), 8.42-8.48 (m, 1H), 8.09-8.12 (m, 1H), 7.43-7.74 (m, 2H), 7.34 (d, J = 2.25 Hz, 1H), 6.96-7.02 (m, 1H), 5.38 (d, J = 1.38 Hz, 2H), 3.81 (s, 3H). LC-MS: m/z 376.2 [M + H]. |
| 151 | 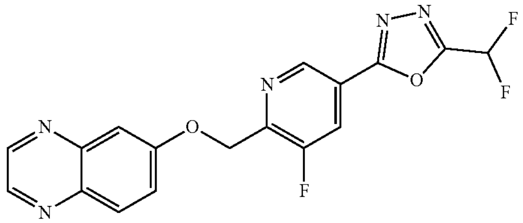 [SMILES: Fc1cc(-c2nnc(C(F)F)o2)cnc1COc1ccc2nccnc2c1] | $^1$HNMR (400 MHz, DMSO-d6) δ ppm 9.12 (s, 1H), 8.95 (d, J = 1.75 Hz, 1H), 8.89 (d, J = 1.75 Hz, 1H), 8.50 (dd, J = 9.76, 1.63 Hz, 1H), 7.76-7.82 (m, 1H), 7.67-7.74 (m, 1H), 7.60 (s, 1H), 7.46-7.52 (m, 1H), 5.60 (d, J = 1.50 Hz, 2H). LC-MS: m/z 373.91 [M + H]. |
| 153 | 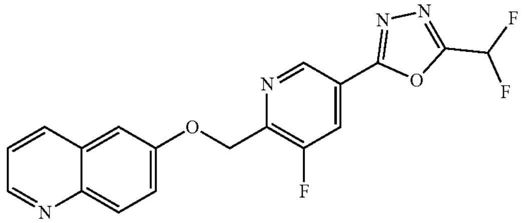 [SMILES: Fc1cc(-c2nnc(C(F)F)o2)cnc1COc1ccc2ncccc2c1] | $^1$HNMR (400 MHz, DMSO-d6) δ ppm 9.58 (br. s, 1H), 9.25 (s, 1H), 9.11 (s, 1H), 8.51 (dd, J = 1.6 Hz, J = 11.2 Hz, 1H), 8.26 (d, J = 7.2 Hz, 1H), 7.47-7.75 (m, 4H), 5.60 (br. s, 2H). LC-MS: m/z 373.2 [M + H]. |

-continued

| Compound | Structure/Name | Characterization |
|---|---|---|
| 155 | 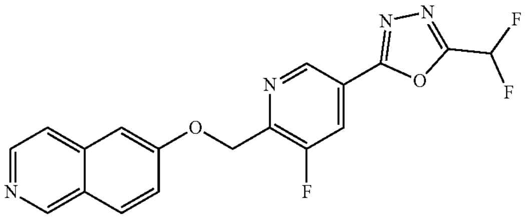 [SMILES: Fc1cc(-c2nnc(C(F)F)o2)cnc1COc1ccc2cnccc2c1] | $^1$HNMR (400 MHz, DMSO-d6) δ ppm 9.08-9.21 (m, 2H), 8.36-8.53 (m, 2H), 8.06 (d, J = 9.01 Hz, 1H), 7.68-7.75 (m, 1H), 7.50-7.61 (m, 2H), 7.31-7.47 (m, 1H), 5.49-5.59 (m, 2H). LC-MS: m/z 373.2 [M + H]. |
| 157 | 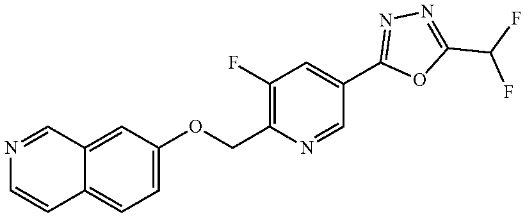 [SMILES: Fc1cc(-c2nnc(C(F)F)o2)cnc1COc1ccc2ccncc2c1] | $^1$HNMR (400 MHz, DMSO-d6) δ ppm 9.21-9.21 (m, 1H), 9.12 (s, 1H), 8.49 (dd, J = 9.82, 1.69 Hz, 1H), 8.39 (d, J = 5.63 Hz, 1H), 7.93 (d, J = 9.01 Hz, 1H), 7.77 (d, J = 5.63 Hz, 1H), 7.69-7.72 (m, 1H), 7.60 (s, 1H), 7.46-7.54 (m, 1H), 5.54 (d, J = 1.50 Hz, 2H). LC-MS: m/z: 373.2 $[M + H]^+$ |
| 159 | 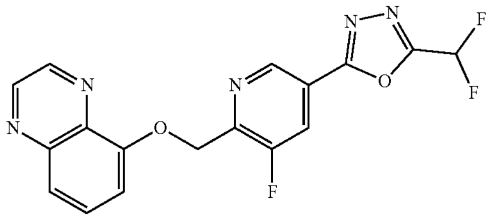 [SMILES: Fc1cc(-c2nnc(C(F)F)o2)cnc1COc1cccc2nccnc12] | $^1$HNMR (400 MHz, DMSO-d6) δ ppm 9.12 (s, 1H), 8.95 (d, J = 1.75 Hz, 1H), 8.89 (d, J = 1.75 Hz, 1H), 8.50 (dd, J = 9.76, 1.75 Hz, 1H), 7.76-7.82 (m, 1H), 7.67-7.74 (m, 1H), 7.43-7.62 (m, 2H), 5.60 (d, J = 1.63 Hz, 2H). LC-MS: m/z 374.2 [M + H]. |
| 161 | 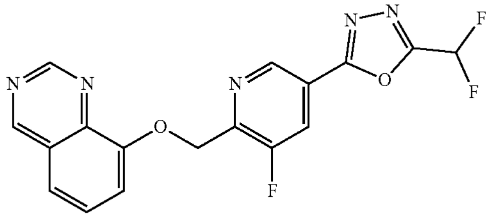 [SMILES: Fc1cc(-c2nnc(C(F)F)o2)cnc1COc1cccc2cncnc12] | $^1$HNMR (400 MHz, DMSO-d6) δ ppm 9.59 (s, 1H), 9.25 (s, 1H), 9.12 (s, 1H), 8.50 (dd, J = 9.76, 1.63 Hz, 1H), 7.65-7.76 (m, 4H), 5.57-5.64 (m, 2H). LC-MS: m/z 373.88 [M + H]. |
| 165 | 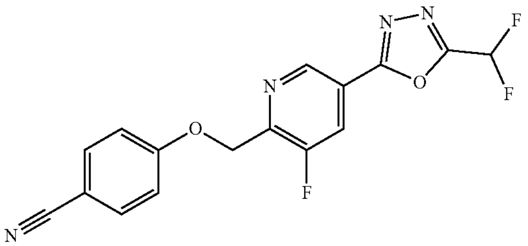 [SMILES: N#Cc1ccc(OCc2ncc(-c3nnc(C(F)F)o3)cc2F)cc1] | $^1$HNMR (400 MHz, CDCl3) δ ppm 9.18 (br. s, 1H), 8.18 (d, J = 7.99 Hz, 1H), 7.61 (d, J = 9.29 Hz, 2H), 7.11 (m, 3H), 5.39 (br. s, 2H). LC-MS: m/z 347.0 [M + H]. |
| 167 | 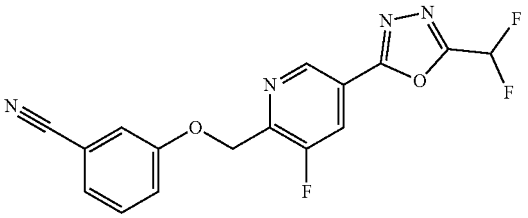 [SMILES: N#Cc1cccc(OCc2ncc(-c3nnc(C(F)F)o3)cc2F)c1] | $^1$HNMR (400 MHz, CDCl3) δ ppm 9.18 (br. s, 1H), 8.19 (d, J = 9.29 Hz, 1H), 7.36-7.44 (m, 1H), 7.29 (br. s, 3H), 6.79-7.12 (m, 1H), 5.37 (br. s, 2H). LC-MS: m/z 347.1 [M + H]. |

-continued

| Compound | Structure/Name | Characterization |
|---|---|---|
| 170 | 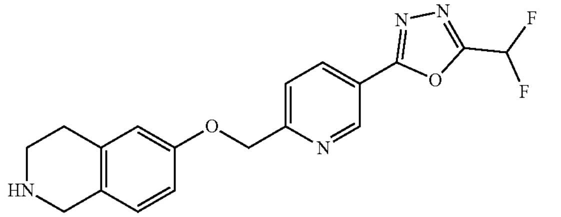 [SMILES: FC(F)c1nnc(-c2ccc(COc3ccc4c(c3)CCNC4)nc2)o1] | $^1$HNMR (400 MHz, DMSO-d6) δ ppm 9.22 (d, J = 1.50 Hz, 1H), 9.00 (br. s, 2H), 8.48 (dd, J = 8.19, 2.19 Hz, 1H), 7.68-7.78 (m, 1H), 7.43-7.61 (m, 1H), 7.16 (d, J = 8.13 Hz, 1H), 6.91-6.99 (m, 2H), 5.32 (s, 2H), 4.20 (br. s, 2H), 3.31-3.40 (m, 2H), 2.96 (t, J = 6.19 Hz, 2H). LC-MS: m/z 359.2 [M + H]. |
| 171 | 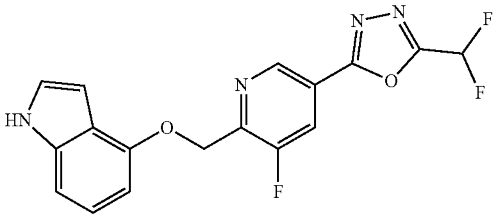 [SMILES: Fc1cc(-c2nnc(C(F)F)o2)cnc1COc1cccc2[nH]ccc12] | $^1$HNMR (400 MHz, DMSO-d6) δ ppm 11.10 (br. s, 1H), 9.08-9.12 (m, 1H), 8.46 (dd, J = 9.78, 1.71 Hz, 1H), 7.74 (t, J = 51.2 Hz, 1H), 7.18-7.24 (m, 1H), 7.02-7.05 (m, 1H), 6.95-7.01 (m, 1H), 6.64 (dd, J = 7.46, 0.73 Hz, 1H), 6.37-6.41 (m, 1H), 5.41-5.46 (m, 2H). LC-MS: m/z 361.35 [M + H]. |
| 177 | 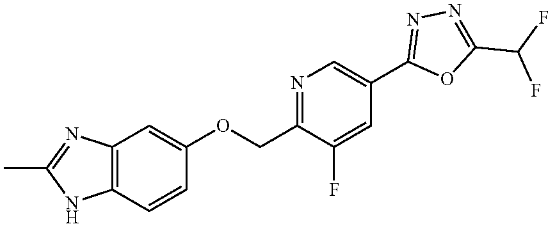 [SMILES: Cc1nc2cc(OCc3ncc(-c4nnc(C(F)F)o4)cc3F)ccc2[nH]1] | $^1$HNMR (400 MHz, DMSO-d6) δ ppm 14.26 (bs, 1H), 9.10 (d, J = 0.98 Hz, 1H), 8.48 (dd, J = 9.78, 1.71 Hz, 1H), 7.57-7.74 (m, 2H), 7.34-7.49 (m, 1H), 7.13-7.19 (m, 1H), 5.46 (d, J = 1.47 Hz, 2H) 2.70 (s, 3H). LC-MS: m/z 376.3 [M + H]. |

2-[6-(Bromomethyl)-3-pyridyl]-5-(difluoromethyl)-1,3,4-oxadiazole (A)

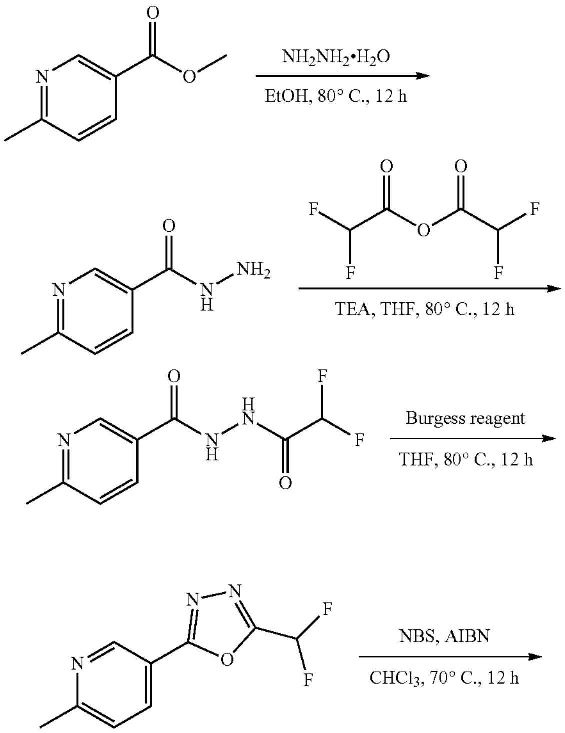

-continued

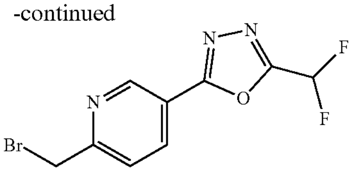

A

Step 1: 6-methylpyridine-3-carbohydrazide: To a solution of methyl 6-methylpyridine-3-carboxylate (30 g, 198.46 mmol, 1 eq) in EtOH (300 mL) was added $NH_2NH_2 \cdot H_2O$ (39.74 g, 793.85 mmol, 38.58 mL, 4 eq). Then the mixture was stirred at 80° C. under an $N_2$ atmosphere for 12 hr. The reaction mixture was concentrated under reduced pressure. The residue was purified by re-crystallization from EtOAc (200 mL) at 30° C. to obtain 6-methylpyridine-3-carbohydrazide (29 g, 189.92 mmol, 95.70% yield, 99% purity) as a yellow solid. 1H NMR (400 MHz, DMSO-d6) δ ppm 9.86 (br s, 1H) 8.84 (d, J=2.00 Hz, 1H) 8.04 (dd, J=8.07, 2.31 Hz, 1H) 7.32 (dd, J=8.00, 2.25 Hz, 1H) 4.51 (br s, 2H) 2.50 (s, 3H) LCMS: MS(ESI): 152.2 [M+H]+

Step 2: N'-(2,2-difluoroacetyl)-6-methyl-pyridine-3-carbohydrazide: A mixture of 6-methylpyridine-3-carbohydrazide (13 g, 86.00 mmol, 1 eq) and TEA (13.05 g, 129.00 mmol, 17.95 mL, 1.5 eq) in THF (130 mL) was degassed and purged trice with N2 at 25° C. 2,2-difluoroacetic anhydride (22.45 g, 129.00 mmol, 1.5 eq) was added dropwise at 25° C. The mixture was stirred at 80° C. for 12 hr under an $N_2$ atmosphere. The reaction mixture was concentrated under reduced pressure. The residue was extracted with DCM (120 mL×3). The combined organic layer was washed with $H_2O$ (80 mL×2), dried over $Na_2SO_4$, filtered and concentrated under reduced pressure. The crude product was purified by column chromatography ($SiO_2$) to obtain N'-(2,2-difluoroacetyl)-6-methyl-pyridine-3-carbohydrazide (14 g, 59.25 mmol, 68.90% yield, 97% purity) as a white solid. $^1H$ NMR (400 MHz, DMSO-$d_6$) δ=11.12-10.94 (m, 1H), 10.87-10.74 (m, 1H), 8.92 (d, J=1.8 Hz, 1H), 8.12 (dd, J=2.3, 8.1 Hz, 1H), 7.54-7.33 (m, 1H), 6.63-6.37 (m, 1H), 2.55 (s, 3H) LCMS(ESI): 230.0 [M+H]+

Step 3: 2-(difluoromethyl)-5-(6-methyl-3-pyridyl)-1,3,4-oxadiazole: A mixture of N'-(2,2-difluoroacetyl)-6-methyl-pyridine-3-carbohydrazide (11 g, 46.56 mmol, 97% purity, 1 eq), methoxycarbonyl-(triethylammonio)sulfonyl-azanide (16.64 g, 69.83 mmol, 1.5 eq) in THF (120 mL) was degassed and purged with $N_2$ for 3 times, and then the mixture was stirred at 80° C. for 12 hr under $N_2$ atmosphere. The reaction mixture was concentrated under reduced pressure and purified by column chromatography ($SiO_2$) to obtain 2-(difluoromethyl)-5-(6-methyl-3-pyridyl)-1,3,4-oxadiazole (7.3 g, 34.54 mmol, 74.18% yield, 99.9% purity) as a yellow solid. MS(ESI): 212.0 [M+H]+

Step 4: 2-[6-(bromomethyl)-3-pyridyl]-5-(difluoromethyl)-1,3,4-oxadiazole (A): To a solution of 2-(difluoromethyl)-5-(6-methyl-3-pyridyl)-1,3,4-oxadiazole (7.2 g, 34.10 mmol, 1 eq) in $CHCl_3$ (150 mL) was added NBS (8.50 g, 47.73 mmol, 1.4 eq) and AIBN (559.89 mg, 3.41 mmol, 0.1 eq) at 25° C. Then the mixture was stirred at 70° C. for 12 hr. The reaction mixture was concentrated under reduced pressure. The residue was extracted with DCM (120 mL×2). The combined organic layers were washed with H2O (80 mL×2), dried over $Na_2SO_4$, filtered and concentrated under reduced pressure. The crude product was purified by column chromatography ($SiO_2$) to obtain 2-[6-(bromomethyl)-3-pyridyl]-5-(difluoromethyl)-1,3,4-oxadiazole (5.1 g, 16.20 mmol, 49.52% yield, 97% purity) as a red solid. $^1H$ NMR (400 MHz, DMSO-$d_6$) δ=9.20 (d, J=1.8 Hz, 1H), 8.47 (dd, J=2.3, 8.1 Hz, 1H), 7.82 (d, J=8.1 Hz, 1H), 7.72-7.45 (m, 1H), 4.81 (s, 2H). MS(ESI): 289.9[M+H]$^+$.

2-(Difluoromethyl)-5-[6-[(3,4-difluorophenoxy)methyl]-3-pyridyl]-1,3,4-oxadiazole (9)

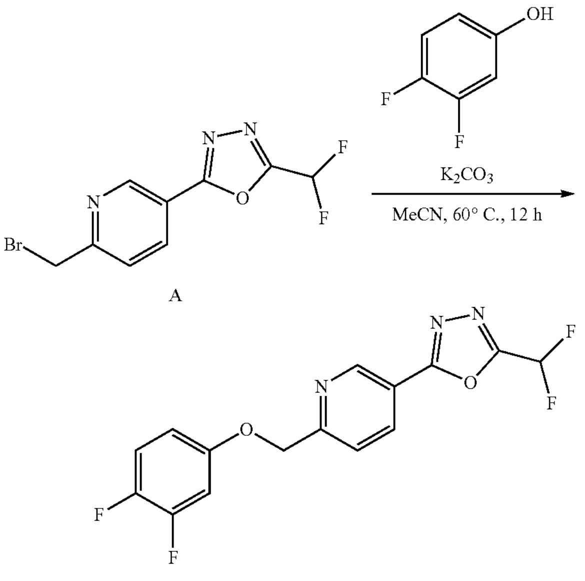

A

9

To a solution of 2-[6-(bromomethyl)-3-pyridyl]-5-(difluoromethyl)-1,3,4-oxadiazole (500 mg, 1.72 mmol, 1 eq) and 3,4-difluorophenol (224.25 mg, 1.72 mmol, 1 eq) in MeCN (8 mL) was added $K_2CO_3$ (476.47 mg, 3.45 mmol, 2 eq) at 25° C. The mixture was stirred at 60° C. for 12 hr. The mixture was concentrated under reduced pressure. The residue was purified by prep-HPLC (neutral) to obtain 2-(difluoromethyl)-5-[6-[(3,4-difluorophenoxy)methyl]-3-pyridyl]-1,3,4-oxadiazole (165.39 mg, 486.50 umol, 28.22% yield, 99.8% purity) as an off-white solid. $^1H$ NMR (400 MHz, METHANOL-$d_4$) δ=9.28 (d, J=1.8 Hz, 1H), 8.55 (dd, J=2.3, 8.3 Hz, 1H), 7.85 (d, J=8.3 Hz, 1H), 7.28-7.14 (m, 2H), 7.04 (ddd, J=3.1, 6.6, 12.2 Hz, 1H), 6.89-6.84 (m, 1H), 5.30 (s, 2H). MS(ESI): 319.2[M+H]$^+$.

2-(Difluoromethyl)-5-[6-(8-quinolyloxymethyl)-3-pyridyl]-1,3,4-oxadiazole (10)

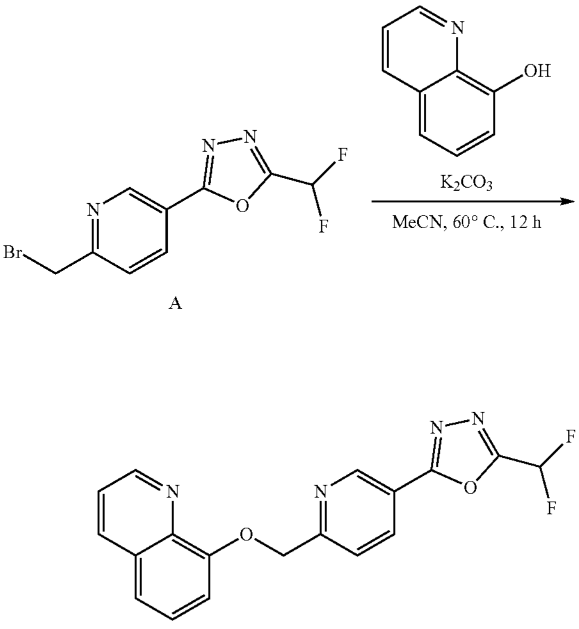

A

10

To a solution of 2-[6-(bromomethyl)-3-pyridyl]-5-(difluoromethyl)-1,3,4-oxadiazole (150 mg, 517.13 umol, 1 eq) and quinolin-8-ol (75.07 mg, 517.13 umol, 89.36 μL, 1 eq) in MeCN (4 mL) was added $K_2CO_3$ (142.94 mg, 1.03 mmol, 2 eq) at 25° C. Then the mixture was stirred at 60° C. for 12 hr. The mixture was concentrated under reduced pressure. The residue was purified by prep-HPLC (neutral) to obtain 2-(difluoromethyl)-5-[6-(8-quinolyloxymethyl)-3-pyridyl]-1,3,4-oxadiazole (18.0 mg, 50.24 umol, 9.72% yield, 98.9% purity) as a white solid. $^1H$ NMR (400 MHz, METHANOL-$d_4$) δ=9.31 (d, J=1.6 Hz, 1H), 8.90 (dd, J=1.6, 4.3 Hz, 1H), 8.52 (dd, J=2.1, 8.3 Hz, 1H), 8.38 (dd, J=1.6, 8.3 Hz, 1H), 8.04 (d, J=8.3 Hz, 1H), 7.62 (dd, J=4.3, 8.4 Hz, 1H), 7.58-7.55 (m, 1H), 7.54-7.50 (m, 1H), 7.40-7.13 (m, 2H), 5.62 (s, 2H). MS(ESI): 355.0 [M+H]+

2-(Difluoromethyl)-5-[6-[(3-fluoro-2-pyridyl)oxymethyl]-3-pyridyl]-1,3,4-oxadiazole (77)

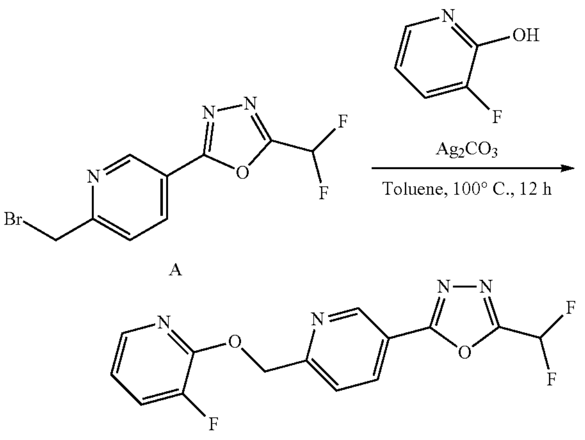

77

To a solution of 2-[6-(bromomethyl)-3-pyridyl]-5-(difluoromethyl)-1,3,4-oxadiazole (150 mg, 517.13 umol, 1 eq), and 3-fluoropyridin-2-ol (58.48 mg, 517.13 umol, 1 eq) in toluene (3 mL) was added $Ag_2CO_3$ (285.19 mg, 1.03 mmol, 46.91 µL, 2 eq) at 25° C. Then the mixture was stirred at 100° C. for 12 hr. The reaction mixture was concentrated under reduced pressure and purified by prep-HPLC (neutral) to obtain 2-(difluoromethyl)-5-[6-[(3-fluoro-2-pyridyl) oxymethyl]-3-pyridyl]-1,3,4-oxadiazole (80.12 mg, 248.38 umol, 48.03% yield, 99.9% purity) as an off-White solid. 1H NMR (400 MHz, METHANOL-d4) δ=9.26 (d, J=1.8 Hz, 1H), 8.53 (d, J=2.3, 8.3 Hz, 1H), 7.92 (d, J=1.4, 5.0 Hz, 1H), 7.80 (d, J=8.3 Hz, 1H), 7.57 (d, J=1.5, 8.0, 10.5 Hz, 1H), 7.27 (t, J=51.7 Hz, 1H), 7.02 (d, J=3.3, 4.8, 7.9 Hz, 1H), 5.68 (s, 2H). MS (ESI): 323.2 [M+H]+. The HSQC showed that chemical shift of C9 was 66 ppm.

2-[6-[(5-cyclopropyl-2-pyridyl)oxymethyl]-3-pyridyl]-5-(difluoromethyl)-1,3,4-oxadiazole (85)

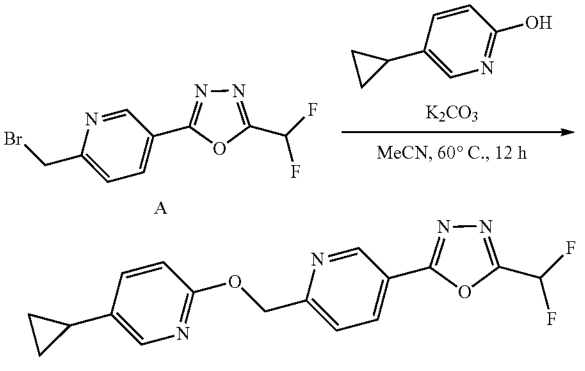

85

To a solution of 2-[6-(bromomethyl)-3-pyridyl]-5-(difluoromethyl)-1,3,4-oxadiazole (150 mg, 517.13 umol, 1 eq) in MeCN (3 mL) was added $K_2CO_3$ (142.94 mg, 1.03 mmol, 2 eq) and 5-cyclopropylpyridin-2-ol (69.90 mg, 517.13 umol, 1 eq) at 25° C. The mixture was stirred at 60° C. for 12 hr. The LCMS showed the reaction was complete and the two peaks (59% and 14%) with desired mass were detected. The reaction mixture was concentrated under reduced pressure and purified by prep-HPLC(neutral) to obtain 5-cyclopropyl-1-[[5-[5-(difluoromethyl)-1,3,4-oxadiazol-2-yl]-2-pyridyl]methyl]pyridin-2-one (80.56 mg, 232.80 umol, 45.02% yield, 99.5% purity) as a white solid, $^1H$ NMR (400 MHz, METHANOL-$d_4$) δ ppm 9.21 (d, J=2.13, 0.63 Hz, 1H) 8.46 (d, J=8.19, 2.19 Hz, 1H) 7.64 (d, J=2.63 Hz, 1H) 7.53 (d, J=8.25 Hz, 1H) 7.42 (d, J=9.32, 2.56 Hz, 1H) 7.25 (t, J=51.59 Hz, 1H) 6.55 (d, J=9.26 Hz, 1H) 5.37 (s, 2H) 1.77-1.86 (m, 1H) 0.89-0.95 (m, 2H) 0.61-0.68 (m, 2H). MS(ESI): 345.1 $[M+H]^+$. The HSQC showed that chemical shift of C25 was 54 ppm.

2-[6-[(5-cyclopropyl-2-pyridyl)oxymethyl]-3-pyridyl]-5-(difluoromethyl)-1,3,4-oxadiazole (85) (15.41 mg, 44.62 umol, 8.63% yield, 99.7% purity) was obtained as a white solid. $^1H$ NMR (400 MHz, METHANOL-$d_4$) δ ppm 9.25 (d, J=1.63 Hz, 1H) 8.50 (d, J=8.32, 2.19 Hz, 1H) 7.94 (d, J=2.50 Hz, 1H) 7.76 (d, J=8.25 Hz, 1H) 7.43 (d, J=8.57, 2.44 Hz, 1H) 7.10-7.38 (m, 1H) 6.89 (d, J=8.63 Hz, 1H) 5.55 (s, 2H) 1.86-1.94 (m, 1H) 0.95-1.00 (m, 2H) 0.64-0.69 (m, 2H). MS(ESI): 345.1 $[M+H]^+$. The HSQC showed that chemical shift of C25 was 66 ppm.

Synthesis of 2-(6-(((2-oxaadamantan-1-yl)methoxy) methyl)pyridin-3-yl)-5-(difluoromethyl)-1,3,4-oxadiazole (20)

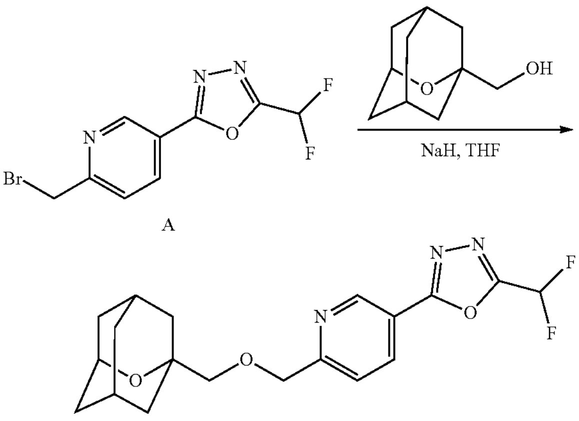

20

To a solution of (2-oxaadamantan-1-yl)methanol (100 mg, 594.42 umol, 1 eq) in THF (3 mL) was added NaH (30.91 mg, 772.74 umol, 60% purity, 1.3 eq) at 0° C. The mixture was stirred at 60° C. for 1 h. And then 2-(6-(bromomethyl)pyridin-3-yl)-5-(difluoromethyl)-1,3,4-oxadiazole (224.14 mg, 772.74 umol, 1.3 eq) was added. The mixture was stirred at 25° C. for 11 hr. LCMS showed 28% desired mass was detected. The reaction mixture was quenched by addition MeOH (5 mL) at 25° C., and then diluted with $H_2O$ (10 mL). The mixture was extracted with EtOAc (20 mL*2). The combined organic layers were washed with $H_2O$ (10 mL), dried over $Na_2SO_4$, filtered and concentrated under reduced pressure. The residue was purified by prep-HPLC (column: Phenomenex C18 150×25 mm×10 µm; mobile phase: [water (ammonia hydroxide v/v)-ACN]; B %: 33%-63%, 8 min) to give the desired compound (9.35 mg, 23.04 umol, 3.88% yield, 93% purity)

as a white solid. $^1$H NMR (400 MHz, METHANOL-d4) δ ppm 9.21 (d, J=1.88 Hz, 1H) 8.53 (dd, J=8.19, 2.19 Hz, 1H) 7.83 (d, J=8.25 Hz, 1H) 7.27 (t, J=51.65 Hz, 1H) 4.77 (s, 2H) 3.41 (s, 2H) 2.20 (br d, J=3.00 Hz, 2H) 1.92-2.01 (m, 6H) 1.68-1.76 (m, 5H). MS (ESI): 378.2 [M+H]$^+$ 2-(difluoromethyl)-5-(6-((pyridin-2-yloxy)methyl)pyridin-3-yl)-1,3,4-oxadiazole (16)

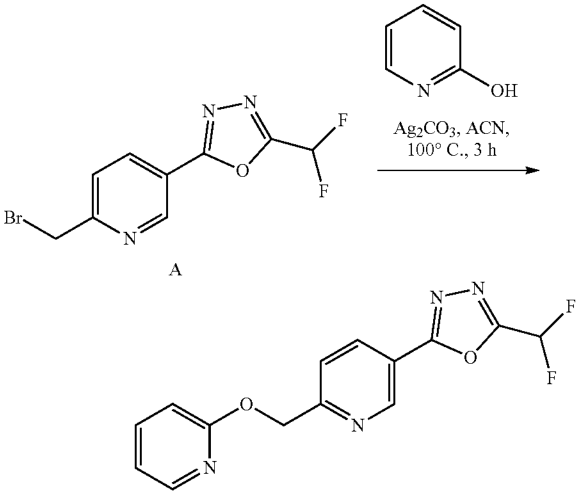

A

16

To a stirred solution of 2-(6-(bromomethyl)pyridin-3-yl)-5-(difluoromethyl)-1,3,4-oxadiazole (A, 100 mg, 0.344 mmol, 1.0 eq) in toluene (1 mL) was added pyridin-2-ol (33 mg, 0.344 mmol, 0.344 eq) followed by $Ag_2CO_3$ (0.286 g, 1.034 mmol, 3.0 eq) at room temperature and stirred for 10 min. The reaction mixture was heated at 100° C. and stirred for 3 h. The progress of reaction was monitored by TLC. After completion of reaction, reaction mixture was cooled to room temperature and filtered through a pad of Celite® bed. The obtained filtrate was concentrated under reduced pressure to obtain crude product. Crude product was purified by CombiFlash column chromatography using an eluent ethyl acetate: n-heptane (30%) to afford (16) (55.0 mg, 52.3%) as yellow liquid. $^1$H NMR (400 MHz, DMSO-$d_6$) δ ppm 5.55 (s, 2H), 6.99-7.10 (m, 2H), 7.44-7.70 (m, 2H), 7.75-7.85 (m, 1H), 8.10-8.20 (m, 1H), 8.45 (dd, J=2.4 Hz, J=10.4 Hz, 1H), 9.19 (s, 1H). $^{19}$F NMR (400 MHz, DMSO-$d_6$): δ ppm −120.69. LC-MS: m/z 304.95. [M+H]$^+$ HPLC: 99.30% at 6.930 min.

2-(difluoromethyl)-5-(6-((pyridin-3-yloxy)methyl)pyridin-3-yl)-1,3,4-oxadiazole (17)

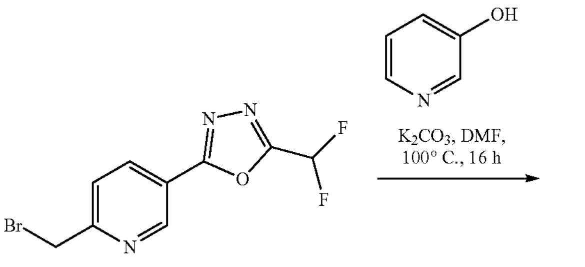

A

-continued

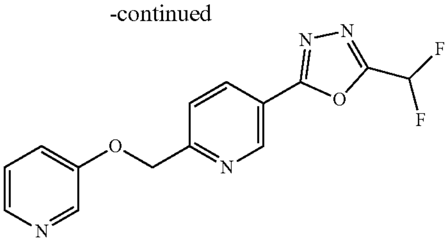

17

To a stirred solution of pyridin-3-ol (73.0 mg, 0.775 mmol, 1.5 eq) in DMF (3 mL) was added $K_2CO_3$ (214 mg, 1.551 mmol) at room temperature and stirred for 15 min. To the resulting reaction mixture was added 2-(6-(bromomethyl)pyridin-3-yl)-5-(difluoromethyl)-1,3,4-oxadiazole (A, 150 mg, 0.5171 mmol, 1.0 eq) at room temperature and reaction mixture was heated at 100° C. for 16 h. The progress of reaction was monitored by TLC. After completion of reaction, the reaction mixture was diluted with ice cold water (10 mL) and extracted with ethyl acetate (3×10 mL). The organic layer was washed with water (5 mL), brine (5 mL), dried over anhydrous $Na_2SO_4$ and concentrated under reduced pressure to obtain crude product. Crude product was purified by Prep HPLC to afford (17) (20 mg, 13%) as an off-white solid. $^1$H NMR (400 MHz, DMSO-$d_6$) δ ppm 5.41 (s, 2H), 7.30-7.40 (m, 2H), 7.45-7.70 (m, 2H), 7.78-7.88 (m, 1H), 8.05-8.15 (m, 1H), 8.51 (dd, J=2.4 Hz, J=10.4 Hz, 1H), 9.23 (s, 1H). $^{19}$F NMR (400 MHz, DMSO-$d_6$): δ ppm −120.70. LC-MS: m/z 305.30 [M+H]$^+$ 2-(difluoromethyl)-5-(6-((pyridin-4-yloxy)methyl)pyridin-3-yl)-1,3,4-oxadiazole (18)

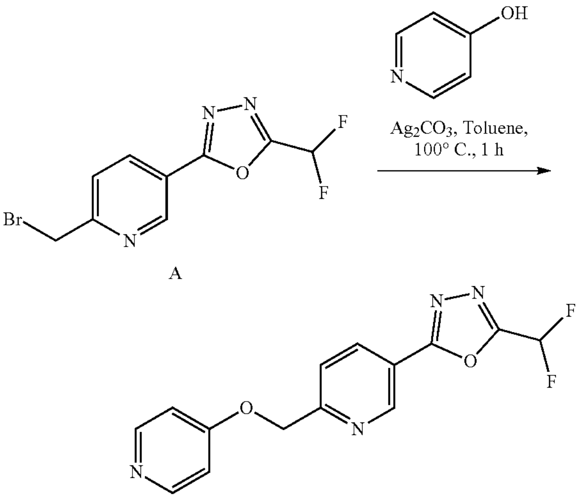

A

18

To a stirred solution of 2-(6-(bromomethyl)pyridin-3-yl)-5-(difluoromethyl)-1,3,4-oxadiazole (A, 200 mg, 0.689 mmol, 1.0 eq) in toluene (2 mL) was added pyridin-4-ol (65.6 mg, 0.0.689 mmol, 1.0 eq) followed by $Ag_2CO_3$ (0.570 g, 1.034 mmol, 3.0 eq) at room temperature and stirred for 10 min. The reaction mixture was heated at 100° C. and stirred for 1 h. The progress of reaction was monitored by TLC. After completion of the reaction, reaction mixture was cooled to room temperature and filtered through a pad of Celite® bed. The obtained filtrate was concentrated under reduced pressure to obtain crude product. Crude product was purified by CombiFlash column chromatography using an eluent ethyl acetate:n-heptane (60%) to afford (18) (55.0 mg, 26.3%) as an off-white solid. $^1$H NMR (400 MHz, DMSO-d6) δ ppm 5.42 (s, 2H), 7.0-7.15 (m, 2H), 7.45-7.79 (m, 2H), 8.10-8.20 (m, 2H), 8.45 (dd, J=2.4 Hz, J=10.4 Hz, 1H), 9.19 (s, 1H). $^{19}$F NMR (400 MHz, DMSO-$d_6$): δ ppm −115.904. LC-MS: m/z 305.00 [M+H]$^+$. HPLC: 97.66% at 5.072 min.

4-((5-(5-(difluoromethyl)-1,3,4-oxadiazol-2-yl)pyridin-2-yl)methoxy)benzonitrile (118)

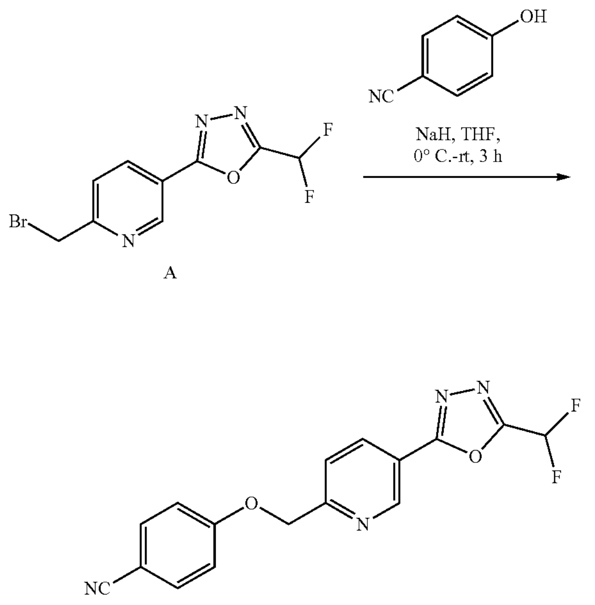

A

118

To a stirred solution of 4-hydroxybenzonitrile (61 mg, 0.5171 mmol) in THF (2 mL) was added NaH (34.4 mg, 0.8617 mmol, 60% dispersion in oil) at 0° C. and stirred for 30 min. To the resulting reaction mixture was added 2-(6-(bromomethyl)pyridin-3-yl)-5-(difluoromethyl)-1,3,4-oxadiazole (A, 100 mg, 0.3447 mmol, 1.0 eq) at room temperature. The reaction mixture was allowed to attain room temperature and stirred for 3 h. The progress of reaction was monitored by TLC. After completion of reaction, reaction mixture was diluted with ice cold water (10 mL) and extracted with ethyl acetate (3×10 mL). The organic layer was washed with water (5 mL), brine (5 mL), dried over anhydrous $Na_2SO_4$ and concentrated under reduced pressure to obtain crude product. Crude product was purified by Prep HPLC to afford (118) (15 mg, 13%) as off-white solid. $^1$H NMR (400 MHz, DMSO-$d_6$) δ ppm 5.42 (s, 2H), 7.20-7.30 (m, 2H), 7.71 (t, J=102.4 Hz, 1H), 7.75-7.85 (m, 3H), 8.51 (dd, J=2.4 Hz, J=10.4 Hz, 1H), 9.20 (t, J=1.6 Hz, 1H). $^{19}$F NMR (400 MHz, DMSO-$d_6$): δ ppm −120.70. LC-MS: m/z 329.2 [M+H]$^+$. HPLC: 99.52% at 5.562 min.

4-((5-(5-(difluoromethyl)-1,3,4-oxadiazol-2-yl)pyridin-2-yl)methoxy)benzamide (122)

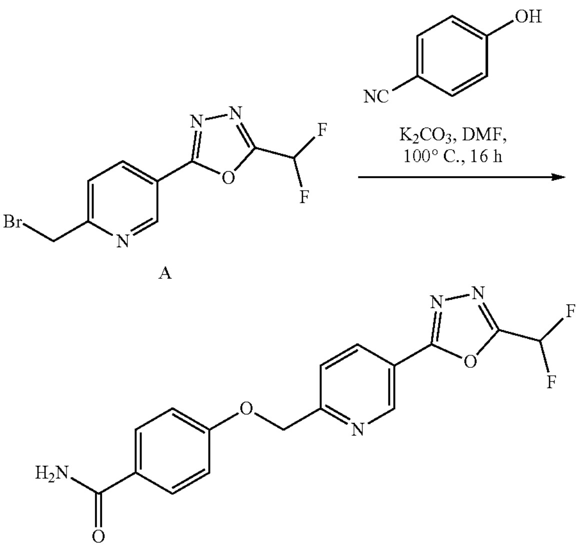

A

122

To a stirred solution of 2-(6-(bromomethyl)pyridin-3-yl)-5-(difluoromethyl)-1,3,4-oxadiazole (A, 100 mg, 0.344 mmol, 1.0 eq) in DMF (2 mL) was added $K_2CO_3$ (95.3 mg, 0.689 mmol) at room temperature and stirred for 15 min. To the resulting reaction mixture was added 4-hydroxybenzonitrile (53.4 mg, 0.448 mmol, 1.3 eq) at room temperature and the reaction mixture was heated at 100° C. for 16 h. The progress of reaction was monitored by TLC. After completion of reaction, reaction mixture was diluted with ice cold water (5 mL) and extracted with ethyl acetate (3×5 mL). The organic layer was washed with water (5 mL), brine (5 mL), dried over anhydrous $Na_2SO_4$ and concentrated under reduced pressure to obtain crude product. Crude product was purified by Prep HPLC followed by lyophilisation to afford (122) (20 mg, 13%) as an off-white solid. $^1$H NMR (400 MHz, DMSO-$d_6$) δ ppm 5.38 (s, 2H), 6.59 (t, J=106.4 Hz, 1H), 7.23 (d, J=9.20 Hz, 2H), 7.69 (d, J=8.0 Hz, 1H), 7.81 (d, J=9.6 Hz, 2H), 8.29 (dd, J=2.4 Hz, J=10.4 Hz, 1H), 9.02 (s, 1H), 10.97 (br. s, 2H). $^{19}$F NMR (400 MHz, DMSO-d6): δ ppm −126.383, −126.525. LC-MS: m/z 345.15 [M+H]$^+$.

2-(Difluoromethyl)-5-(6-(1-(4-fluorophenoxy)ethyl)pyridin-3-yl)-1,3,4-oxadiazole (AAA)

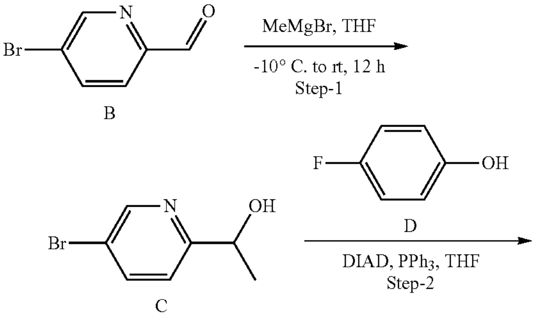

-continued

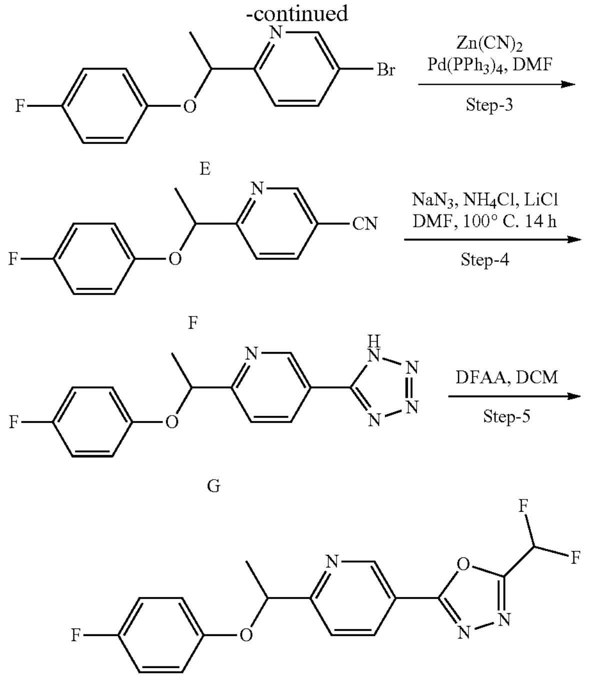

E

F

G

AAA

Step-1: Synthesis of 1-(5-Bromopyridin-2-yl)ethan-1-ol (C): To a stirred solution of compound B (0.5 g, 2.68 mmol) in dry THF (10 mL), methyl magnesium bromide (1.79 mL, 5.37 mmol) was added at −10° C., and then reaction mixture was stirred at room temperature for 12 h. After completion of reaction (monitored by TLC), the reaction mixture was quenched with aq. ammonium chloride (50 mL) and extracted with ethyl acetate (100 mL). The organic layer was dried over sodium sulphate and concentrated under reduced pressure to give the crude product. The crude product was purified by using 100-200 mesh silica gel column chromatography to give the product C (0.3 g, 55.24% yield) as colourless thick oil. LC-MS: m/z 203.90 $[M+H]^+$.

Step-2: Synthesis of 5-Bromo-2-(1-(4-fluorophenoxy)ethyl)pyridine (E): To a stirred solution of compound C (0.3 g, 1.48 mmol) in THF (5 mL), compound D (0.299 g, 2.67 mmol), $PPh_3$ (0.544 g, 2.07 mmol) were added under cooling, reaction mixture was stirred for 15 mins, then added DIAD (0.419 g, 2.07 mmol) at 0° C., then stirred at RT for 2 h. After completion of reaction (monitored by TLC), the reaction mixture was diluted with water (20 mL) and extracted with ethyl acetate (2×30 mL). The organic layer was dried over sodium sulphate and concentrated under reduced pressure to give crude product. The crude product was purified by using 100-200 mesh silica gel column chromatography to give the product E (0.2 g, 45.66% yield) as light brown liquid. LC-MS: m/z 296.00 $[M+H]^+$.

Step-3: Synthesis of 6-(1-(4-Fluorophenoxy)ethyl)nicotinonitrile (F): To a stirred solution of compound E (0.2 g, 0.677 mmol) in DMA (5 mL), were added $Zn(CN)_2$ (0.198 g, 1.69 mmol) and Zn dust (0.030 g, 0.474 mmol) at RT, the reaction mixture was purged with argon for 30 mins and the $Pd_2(dba)_3$ (0.070 g, 0.067 mmol) and dppf (0.112 g, 0.203 mmol) were added and again it was purged with argon for 15 mins. The reaction mixture was stirred at 100° C. for 12 h. After completion of reaction (monitored by TLC), the reaction mixture was filtered through Celite® and washed with ethyl acetate. The organic layer was dried over sodium sulphate and concentrated under reduced pressure to give the crude product. The crude product was purified by using 100-200 mesh silica gel column chromatography by eluting with 0-20% ethyl acetate in hexane to give the product F (0.110 g, 67.07% yield) as an off-white solid. LC-MS: m/z 243.05 $[M+H]^+$.

Step-4: Synthesis of 2-(1-(4-fluorophenoxy)ethyl)-5-(1H-tetrazol-5-yl)pyridine (G): To a stirred solution of compound F (0.11 g, 0.454 mmol) in DMF (10 mL), sodium azide (0.088 g, 1.36 mmol), $NH_4Cl$ (0.073 g, 1.36 mmol) and LiCl (0.019 g, 0.454 mmol) were added and the reaction mixture was stirred at 100° C. for 12 h. After completion of reaction (monitored by TLC), the reaction mixture was concentrated under reduced pressure and was acidified with 6N HCl and the precipitated solid was filtered and dried to give product G (0.100 g, 77.51% yield) as light brown solid. LC-MS: m/z 286.05 $[M+H]^+$.

Step-5: Synthesis of 2-(Difluoromethyl)-5-(6-(1-(4-fluorophenoxy)ethyl)pyridin-3-yl)-1,3,4-oxadiazole (AAA): To a stirred solution of compound G (0.1 g, 0.35 mmol) in DCM (5 mL) at 0° C., difluoroacetic anhydride (0.122 g, 0.701 mmol) was added and the reaction mixture was stirred at RT for 12 h. After completion of reaction (monitored by TLC), the reaction mixture was quenched with water (20 mL) and basified with saturated sodium bicarbonate solution (20 mL), extracted with 5% methanol in DCM (50 mL). The organic layer was dried over sodium sulphate and concentrated under reduced pressure to give crude product. The crude product was purified by using 230-400 mesh silica gel column chromatography by eluting with 30% ethyl acetate in hexane to give the product (AAA) (0.060 g, 51.28% yield) as an off-white solid. $^1H$ NMR (400 MHz, DMSO-$d_6$) δ=9.20 (s, 1H), 8.43 (dd, J=2.0, 8.3 Hz, 1H), 7.78-7.38 (m, 2H), 7.13-7.01 (m, 2H), 7.00-6.89 (m, 2H), 5.56 (q, J=6.4 Hz, 1H), 1.62 (d, J=6.4 Hz, 3H). $^{19}F$ NMR (376 MHz, DMSO-$d_6$) δ ppm=−120.70 (s, 1F), −120.83 (s, 1F), −123.28 (td, J=4.2, 8.2 Hz, 1F). LC-MS: m/z 336.05 $[M+H]^+$.

2-(6-(difluoro(naphthalen-1-yloxy)methyl)pyridin-3-yl)-5-(difluoromethyl)-1,3,4-oxadiazole (14)

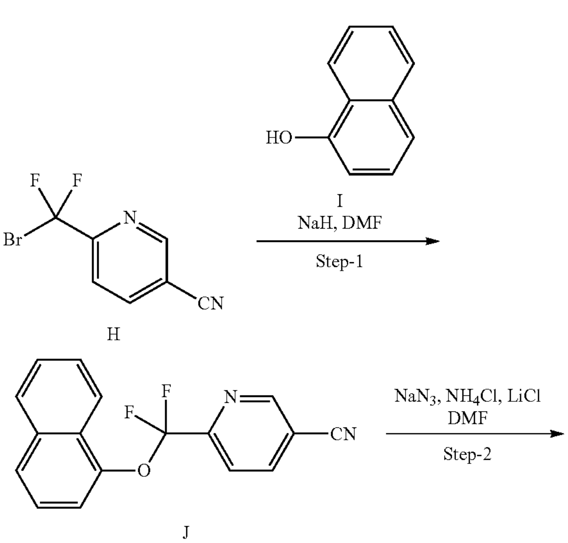

I

H

J

-continued

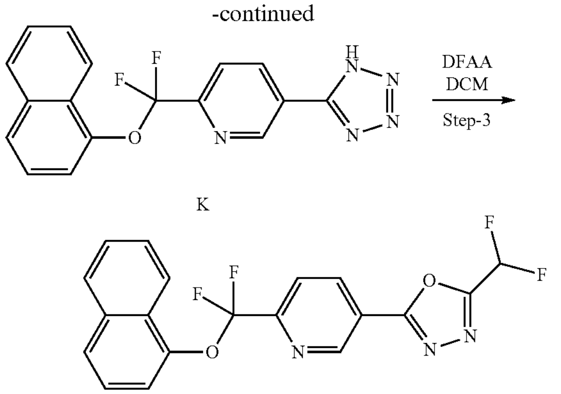

K

14

Step-1: 6-(difluoro(naphthalen-1-yloxy)methyl)nicotinonitrile (J): To a stirred solution of compound I (0.19 g, 1.30 mmol) in DMF (2 mL) was added NaH (60%, 0.08 g, 2.00 mmol) at 0° C. and the reaction mixture was stirred for 20 min at the same temperature. To the resulting reaction mixture, Compound H (0.3 g, 1.30 mmol) dissolved in DMF (1 mL) was slowly added at 0° C. and the reaction mixture was stirred at room temperature for 12 h. After completion of reaction (monitored by TLC), the reaction mixture was quenched with cold water (50 mL) and extracted with ethyl acetate (100 mL). The organic layer was dried over sodium sulphate and concentrated under reduced pressure to give the crude product. The crude product was purified by 100-200 mesh silica gel column chromatography by eluting with 0-10% ethyl acetate in hexane to give the compound J (0.32 g, 84.0%) as brown liquid. LC-MS: m/z 296.9 $[M+H]^+$.

Step-2: 2-(difluoro(naphthalen-1-yloxy)methyl)-5-(1H-tetrazol-5-yl)pyridine (K): To a stirred solution of compound J (0.32 g, 1.00 mmol) in DMF (5 mL), sodium azide (0.35 g, 5.40 mmol) was added followed by $NH_4Cl$ (0.27 g, 5.40 mmol) and LiCl (0.03 g) and the reaction mixture was stirred at 100° C. for 5 h. After completion of the reaction (monitored by TLC), the reaction mixture was concentrated under reduced pressure and was acidified with 6N HCl. Product was extracted with ethyl acetate (2×50 mL). The organic layer was dried over anhydrous sodium sulphate and concentrated under reduced pressure to afford compound K (0.30 g, 82.0%) as light brown thick liquid which was used as such for the next reaction. LC-MS: m/z 339.9 $[M+H]^+$.

Step-3: 2-(6-(difluoro(naphthalen-1-yloxy)methyl)pyridin-3-yl)-5-(difluoromethyl)-1,3,4-oxadiazole (14): To a stirred solution of compound K (0.30 g, 0.88 mmol) in DCM (6 mL), difluoroacetic anhydride (0.5 mL, 4.40 mmol) was added at 0° C. and the reaction mixture was stirred at RT for 16 h. After completion of reaction (monitored by TLC), the reaction mixture was diluted with cold water (20 mL) and extracted with DCM (50 mL). The organic layer was dried over anhydrous sodium sulphate and concentrated under reduced pressure. The crude compound was purified by 100-200 mesh silica gel column chromatography by eluting with 0-7% ethyl acetate in hexane to give (14) (0.10 g, 29.0% yield) as an off-white solid. $^1H$ NMR (400 MHz, DMSO-$d_6$) δ ppm 9.43 (d, J=1.48 Hz, 1H), 8.72 (dd, J=8.37, 1.97 Hz, 1H), 8.30 (s, 1H), 8.20 (d, J=7.88 Hz, 1H), 8.00-8.05 (m, 1H), 7.90-7.95 (m, 1H), 7.46-7.79 (m, 5H). $^{19}F$ NMR (400 MHz, DMSO-$d_6$) δ ppm −68 (s, 2F), −122 (s, 2F). LC-MS: m/z 390.15 $[M+H]^+$.

The following compounds were prepared in a manner analogous to that used for preparing compounds of Formula (I), above.

| Compound | Structure/Name | Characterization |
| --- | --- | --- |
| 72 | 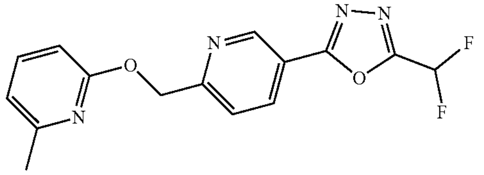 2-(difluoromethyl)-5-[6-[(6-methyl-2-pyridyl)oxymethyl]-3-pyridyl]-1,3,4-oxadiazole | $^1H$ NMR (400 MHz, METHANOL-$d_4$) δ ppm 9.19 (d, J = 1.75 Hz, 1H) 8.46 (d, J = 8.25, 2.25 Hz, 1H) 7.44-7.58 (m, 2H) 7.25 (t, J = 51.59 Hz, 1H) 6.50 (d, J = 9.01 Hz, 1H) 6.38 (d, J = 6.88 Hz, 1H) 5.57 (s, 2H) 2.48 (s, 3H). MS (ESI): 319.2 $[M + H]^+$ |
| 65 | 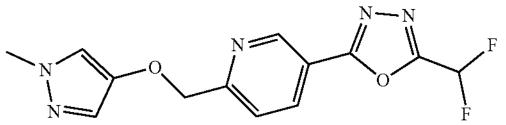 2-(difluoromethyl)-5-[6-[(1-methylpyrazol-4-yl)oxymethyl]-3-pyridyl]-1,3,4-oxadiazole | $^1H$ NMR (400 MHz, METHANOL-$d_4$) δ ppm 9.26 (d, J = 1.75 Hz, 1H) 8.46-8.65 (m, 1H) 7.83 (d, J = 8.13 Hz, 1H) 7.43 (s, 1H) 7.13-7.40 (m, 2H) 5.18 (s, 2H) 3.81 (s, 3H). MS (ESI): 308.1 $[M + H]^+$ |
| 64 | 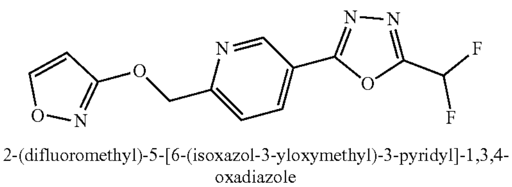 [SMILES: FC(F)c1nnc(-c2ccc(COc3ccon3)nc2)o1] 2-(difluoromethyl)-5-[6-(isoxazol-3-yloxymethyl)-3-pyridyl]-1,3,4-oxadiazole | $^1H$ NMR (400 MHz, METHANOL-$d_4$) δ ppm 9.20 (d, J = 1.73 Hz, 1H) 8.55 (dd, J = 8.19, 2.19 Hz, 1H) 8.41 (s, 1H) 7.82 (d, J = 8.13 Hz, 1H) 7.27 (t, J = 51.59 Hz, 1H) 6.27 (d, J = 1.88 Hz, 1H) 5.48 (s, 2H). MS (ESI): 295.2 $[M + H]^+$ |

-continued

| Compound | Structure/Name | Characterization |
| --- | --- | --- |
| 59 | 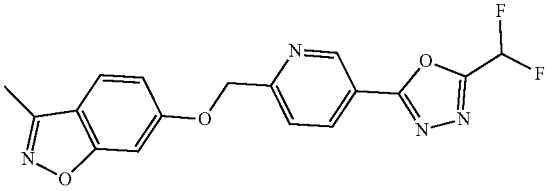 6-[[5-[5-(difluoromethyl)-1,3,4-oxadiazol-2-yl]-2-pyridyl]methoxy]-3-methyl-1,2-benzoxazole | $^1$H NMR (400 MHz, METHANOL-$d_4$) δ ppm 9.29 (d, J = 1.63 Hz, 1H) 8.55 (dd, J = 8.25, 2.13 Hz, 1H) 7.89 (d, J = 8.63 Hz, 1H) 7.54 (d, J = 8.76 Hz, 1H) 7.32 (d, J = 2.38 Hz, 1H) 7.10-7.29 (m, 2H) 5.38 (s, 2H) 2.61 (s, 3H). MS (ESI): 359.2 $[M + H]^+$ |
| 50 | 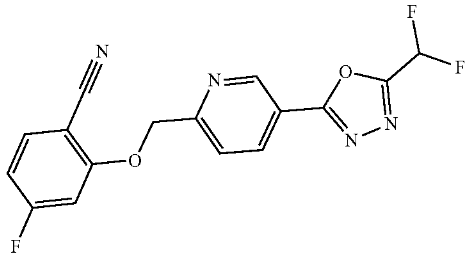 2-[[5-[5-(difluoromethyl)-1,3,4-oxadiazol-2-yl]-2-pyridyl]methoxy]-4-fluoro-benzonitrile | $^1$H NMR (400 MHz, METHANOL-$d_4$) δ ppm 9.31 (d, J = 1.75 Hz, 1H) 8.59 (dd, J = 8.25, 2.25 Hz, 1H) 7.93 (d, J = 8.25 Hz, 1H) 7.77 (dd, J = 8.63, 6.13 Hz, 1H) 7.14-7.42 (m, 2H) 6.93 (td, J = 8.41, 2.31 Hz, 1H) 5.48 (s, 2H). MS (ESI): 347.2 $[M + H]^+$ |
| 45 | 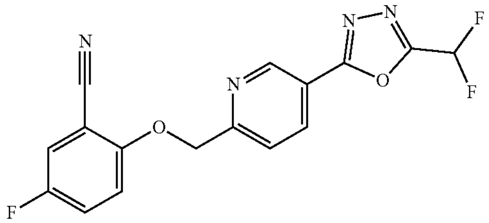 2-[[5-[5-(difluoromethyl)-1,3,4-oxadiazol-2-yl]-2-pyridyl]methoxy]-5-fluoro-benzonitrile | $^1$H NMR (400 MHz, METHANOL-$d_4$) δ ppm 9.30 (d, J = 1.50 Hz, 1H) 8.59 (dd, J = 8.25, 2.13 Hz, 1H) 7.93 (d, J = 8.25 Hz, 1H) 7.54 (dd, J = 7.75, 3.13 Hz, 1H) 7.41-7.47 (m, 1H) 7.14-7.41 (m, 2H) 5.46 (s, 2H). MS (ESI): 347.2 $[M + H]^+$ |
| 44 | 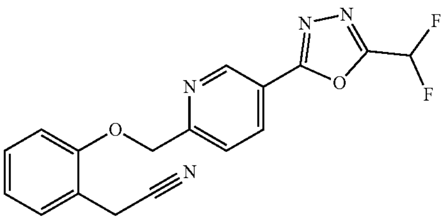 2-[2-[[5-[5-(difluoromethyl)-1,3,4-oxadiazol-2-yl]-2-pyridyl]methoxy]phenyl]acetonitrile | $^1$H NMR (400 MHz, METHANOL-$d_4$) δ ppm 9.29 (d, J = 1.50 Hz, 1H) 8.55 (dd, J = 8.19, 2.06 Hz, 1H) 7.95 (d, J = 8.13 Hz, 1H) 7.35-7.44 (m, 2H) 7.33 (s, 1H) 7.11-7.08 (m, 1H) 7.04 (t, J = 7.63 Hz, 1H) 5.42 (s, 2H) 3.95 (s, 2H). MS (ESI): 343.2 $[M + H]^+$ |
| 102 | 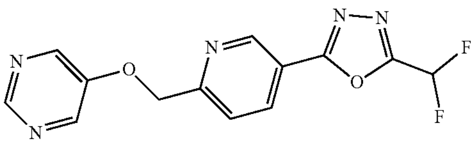 2-(difluoromethyl)-5-[6-(pyrimidin-5-yloxymethyl)-3-pyridyl]-1,3,4-oxadiazole | $^1$H NMR (400 MHz, METHANOL-$d_4$) δ = 9.31 (d, J = 2.1 Hz, 1H), 8.84 (s, 1H), 8.67 (s, 2H), 8.58 (dd, J = 2.2, 8.2 Hz, 1H), 7.90 (d, J = 8.3 Hz, 1H), 7.27 (t, J = 51.6 Hz, 1H), 5.50 (s, 2H). MS (ESI): 306.1 $[M + H]^+$ |

-continued

| Compound | Structure/Name | Characterization |
| --- | --- | --- |
| 99 | 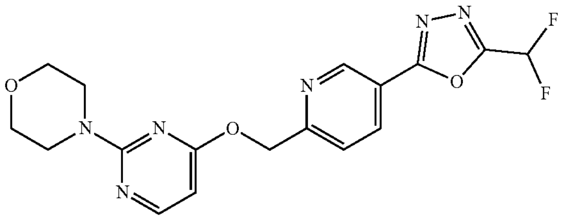 4-[4-[[5-[5-(difluoromethyl)-1,3,4-oxadiazol-2-yl]-2-pyridyl]methoxy]pyrimidin-2-yl]morpholine | $^1$H NMR (400 MHz, METHANOL-$d_4$) δ = 9.25 (d, J = 1.6 Hz, 1H), 8.51 (dd, J = 2.3, 8.3 Hz, 1H), 8.13 (d, J = 5.8 Hz, 1H), 7.73 (d, J = 8.3 Hz, 1H), 7.40-7.12 (t, J = 51.6 Hz, 1H), 6.26 (d, J = 5.6 Hz, 1H), 5.59 (s, 2H), 3.68 (s, 8H). MS (ESI): 391.0 [M + H]+ |
| 97 | 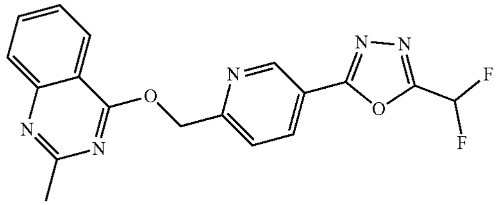 2-(difluoromethyl)-5-[6-[(2-methylquinazolin-4-yl)oxymethyl]-3-pyridyl]-1,3,4-oxadiazole | $^1$H NMR (400 MHz, METHANOL-$d_4$) δ = 9.30 (d, J = 1.6 Hz, 1H), 8.56 (dd, J = 2.3, 8.3 Hz, 1H), 8.39-8.31 (m, 1H), 7.97-7.93 (m, 1H), 7.90 (d, J = 8.3 Hz, 1H), 7.88-7.83 (m, 1H), 7.70-7.65 (m, 1H), 7.40-7.14 (t, J = 51.6 Hz, 1H), 5.90 (s, 2H), 2.69 (s, 3H). MS (ESI): 370.0 [M + H]+ |
| 93 | 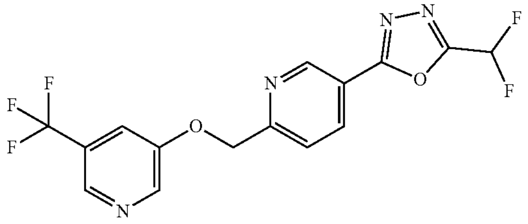 2-(difluoromethyl)-5-[6-[[5-(trifluoromethyl)-3-pyridyl]oxymethyl]-3-pyridyl]-1,3,4-oxadiazole | $^1$H NMR (400 MHz, METHANOL-$d_4$) δ = 9.31 (d, J = 1.5 Hz, 1H), 8.68 (d, J = 2.5 Hz, 1H), 8.58 (dd, J = 2.1, 8.3 Hz, 1H), 8.54 (s, 1H), 7.91 (d, J = 8.3 Hz, 1H), 7.87 (s, 1H), 7.41-7.17 (t, J = 51.6 Hz, 1H), 5.50 (s, 2H). MS (ESI): 373.0 [M + H]+ |
| 92 | 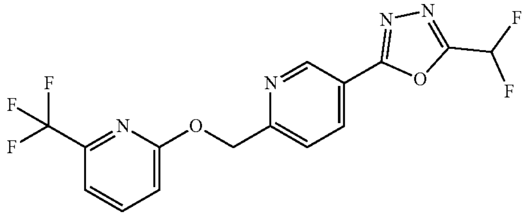 2-(difluoromethyl)-5-[6-[[6-(trifluoromethyl)-2-pyridyl]oxymethyl]-3-pyridyl]-1,3,4-oxadiazole | $^1$H NMR (400 MHz, METHANOL-$d_4$) δ = 9.26 (d, J = 1.9 Hz, 1H), 8.52 (dd, J = 2.3, 8.3 Hz, 1H), 7.96 (t, J = 7.9 Hz, 1H), 7.81 (d, J = 8.3 Hz, 1H), 7.43 (d, J = 7.3 Hz, 1H), 7.40-7.13 (m, 2H), 5.64 (s, 2H). MS (ESI): 373.0 [M + H]+ |
| 91 | 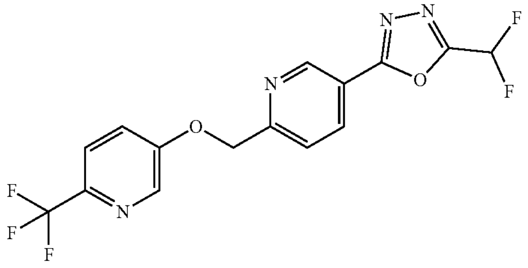 2-(difluoromethyl)-5-[6-[[6-(trifluoromethyl)-3-pyridyl]oxymethyl]-3-pyridyl]-1,3,4-oxadiazole | $^1$H NMR (400 MHz, METHANOL-$d_4$) δ = 9.31 (d, J = 1.8 Hz, 1H), 8.57 (dd, J = 2.1, 8.3 Hz, 1H), 8.54 (d, J = 2.8 Hz, 1H), 7.89 (d, J = 8.3 Hz, 1H), 7.82-7.79 (m, 1H), 7.70 (dd, J = 2.9, 8.8 Hz, 1H), 7.41-7.14 (m, 1H), 5.49 (s, 2H). MS (ESI): 373.0 [M + H]+ |

-continued

| Compound | Structure/Name | Characterization |
|---|---|---|
| 88 | 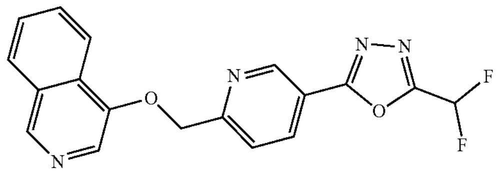 2-(difluoromethyl)-5-[6-(4-isoquinolyloxymethyl)-3-pyridyl]-1,3,4-oxadiazole | $^1$H NMR (400 MHz, METHANOL-$d_4$) δ = 9.33 (d, J = 1.8 Hz, 1H), 8.93 (s, 1H), 8.59 (dd, J = 2.1, 8.1 Hz, 1H), 8.41 (d, J = 8.3 Hz, 1H), 8.17 (s, 1H), 8.13 (d, J = 8.4 Hz, 1H), 8.01 (d, J = 8.1 Hz, 1H), 7.89-7.85 (m, 1H), 7.79-7.75 (m, 1H), 7.41-7.15 (m, 1H), 5.62 (s, 2H). MS (ESI): 355.0 [M + H]+ |
| 82 | 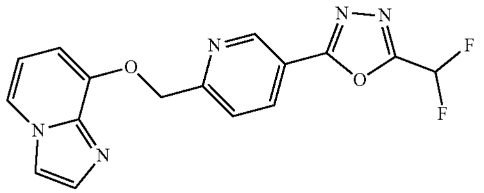 2-(difluoromethyl)-5-[6-(imidazo[1,2-a]pyridin-8-yloxymethyl)-3-pyridyl]-1,3,4-oxadiazole | $^1$H NMR (400 MHz, METHANOL-$d_4$) δ = 9.30 (d, J = 1.6 Hz, 1H), 8.57 (dd, J = 2.2, 8.2 Hz, 1H), 8.13-8.11 (m, 2H), 7.88 (d, J = 1.3 Hz, 1H), 7.59 (d, J = 1.1 Hz, 1H), 7.41-7.14 (m, 1H), 6.87-6.81 (m, 2H), 5.53 (s, 2H). MS (ESI): 344.0 [M + H]+ |
| 79 | 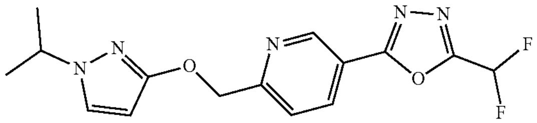 2-(difluoromethyl)-5-[6-[(1-isopropylpyrazol-3-yl)oxymethyl]-3-pyridyl]-1,3,4-oxadiazole | $^1$H NMR (400 MHz, METHANOL-$d_4$) δ = 9.26-9.24 (d, J = 1.6 Hz, 1H), 8.53 (dd, J = 2.2, 8.3 Hz, 1H), 7.83 (dd, J = 0.6, 8.3 Hz, 1H), 7.46 (d, J = 2.5 Hz, 1H), 7.40-7.14 (m, 1H), 5.76 (d, J = 2.5 Hz, 1H), 5.37 (s, 2H), 4.33 (td, J = 6.6, 13.4 Hz, 1H), 1.44 (s, 3H), 1.42 (s, 3H). MS (ESI): 336.0 [M + H]+ |
| 73 | 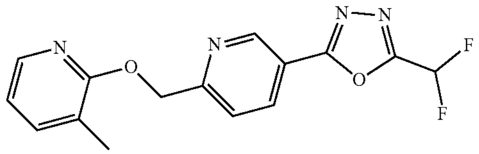 2-(difluoromethyl)-5-[6-[(3-methyl-2-pyridyl)oxymethyl]-3-pyridyl]-1,3,4-oxadiazole | $^1$H NMR (400 MHz, METHANOL-$d_4$) δ = 9.27 (d, J = 2.0 Hz, 1H), 8.53 (dd, J = 2.2, 8.2 Hz, 1H), 7.91-7.88 (m, 2H), 7.61 (d, J = 8.3 Hz, 1H), 7.40-7.13 (m, 1H), 6.48-6.44 (m, 1H), 5.41 (s, 2H), 2.06 (s, 3H). MS (ESI): 319.0 [M + H]+ |
| 70 | 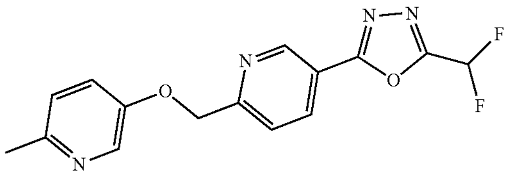 2-(difluoromethyl)-5-[6-[(6-methyl-3-pyridyl)oxymethyl]-3-pyridyl]-1,3,4-oxadiazole | $^1$H NMR (400 MHz, METHANOL-$d_4$) δ = 9.29 (d, J = 1.5 Hz, 1H), 8.56 (dd, J = 2.2, 8.2 Hz, 1H), 8.25 (d, J = 3.0 Hz, 1H), 7.87 (d, J = 8.3 Hz, 1H), 7.47 (dd, J = 3.0, 8.6 Hz, 1H), 7.40-7.14 (m, 2H), 5.38 (s, 2H), 2.49 (s, 3H). MS (ESI): 319.2 $[M + H]^+$ |
| 69 | 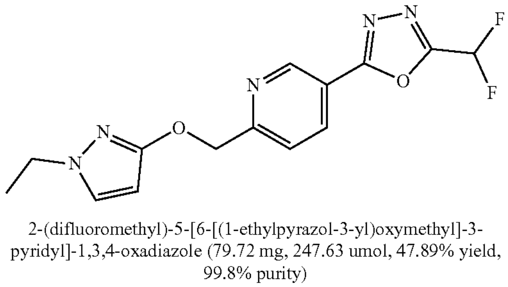 [SMILES: CCn1ccc(OCc2ccc(-c3nnc(C(F)F)o3)cn2)n1] 2-(difluoromethyl)-5-[6-[(1-ethylpyrazol-3-yl)oxymethyl]-3-pyridyl]-1,3,4-oxadiazole (79.72 mg, 247.63 umol, 47.89% yield, 99.8% purity) | $^1$H NMR (400 MHz, METHANOL-$d_4$) δ = 9.25 (d, J = 1.6 Hz, 1H), 8.53 (dd, J = 2.3, 8.3 Hz, 1H), 7.82 (d, J = 8.3 Hz, 1H), 7.44 (d, J = 2.4 Hz, 1H), 7.40-7.13 (m, 1H), 5.77 (d, J = 2.4 Hz, 1H), 5.37 (s, 2H), 4.02 (q, J = 7.3 Hz, 2H), 1.40 (t, J = 7.3 Hz, 3H). MS (ESI): 322.0 [M + H]+[1] |

-continued

| Compound | Structure/Name | Characterization |
| --- | --- | --- |
| 67 | 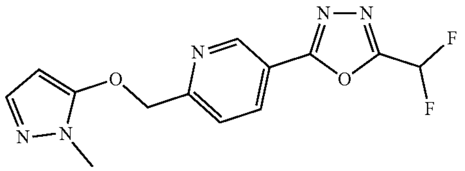<br>2-(difluoromethyl)-5-[6-[(2-methylpyrazol-3-yl)oxymethyl]-3-pyridyl]-1,3,4-oxadiazole | $^1H$ NMR (400 MHz, METHANOL-$d_4$) δ = 9.29 (d, J = 1.5 Hz, 1H), 8.56 (dd, J = 2.1, 8.3 Hz, 1H), 7.85 (d, J = 8.1 Hz, 1H), 7.41-7.13 (m, 2H), 5.72 (d, J = 2.0 Hz, 1H), 5.39 (s, 2H), 3.73 (s, 3H).<br>MS (ESI): 308.0 [M + H]+ |
| 63 | 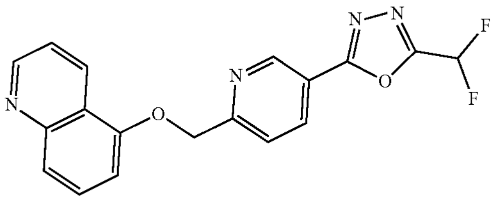<br>2-(difluoromethyl)-5-[6-(5-quinolyloxymethyl)-3-pyridyl]-1,3,4-oxadiazole | $^1H$ NMR (400 MHz, METHANOL-$d_4$) δ = 9.32 (d, J = 1.8 Hz, 1H), 8.90-8.85 (m, 2H), 8.58 (dd, J = 2.3, 8.3 Hz, 1H), 7.98 (d, J = 8.3 Hz, 1H), 7.73-7.67 (m, 2H), 7.60 (d, J = 4.4, 8.4 Hz, 1H), 7.41-7.14 (m, 2H), 5.57 (s, 2H).<br>MS (ESI): 355.1 $[M + H]^+$ |
| 62 | 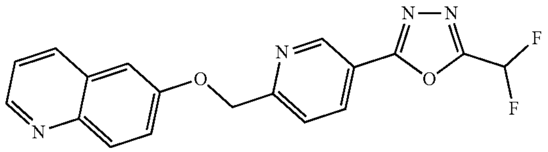<br>2-(difluoromethyl)-5-[6-(6-quinolyloxymethyl)-3-pyridyl]-1,3,4-oxadiazole | $^1H$ NMR (400 MHz, METHANOL-$d_4$) δ = 9.32 (d, J = 1.5 Hz, 1H), 8.73 (dd, J = 1.6, 4.3 Hz, 1H), 8.57 (dd, J = 2.3, 8.3 Hz, 1H), 8.30 (d, J = 8.6 Hz, 1H), 8.01 (d, J = 9.3 Hz, 1H), 7.93 (d, J = 8.3 Hz, 1H), 7.62 (dd, J = 2.8, 9.2 Hz, 1H), 7.51 (dd, J = 4.3, 8.3 Hz, 1H), 7.46 (d, J = 2.8 Hz, 1H), 7.40-7.14 (m, 1H), 5.49 (s, 2H).<br>MS (ESI): 355.0 $[M + H]^+$ |
| 61 | 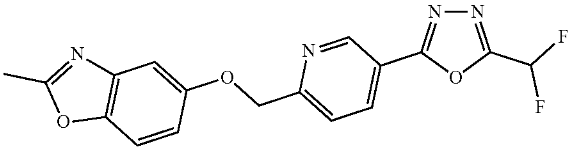<br>5-[[5-[5-(difluoromethyl)-1,3,4-oxadiazol-2-yl]-2-pyridyl]methoxy]-2-methyl-1,3-benzoxazole | $^1H$ NMR (400 MHz, METHANOL-$d_4$) δ = 9.29 (d, J = 1.9 Hz, 1H), 8.55 (dd, J = 2.1, 8.3 Hz, 1H), 7.89 (d, J = 8.4 Hz, 1H), 7.51 (d, J = 8.9 Hz, 1H), 7.40-7.27 (m, 2H), 7.14-7.11 (m, 1H), 5.37 (s, 2H), 2.63 (s, 3H).<br>MS (ESI): 359.0 [M + H]+ |
| 58 | 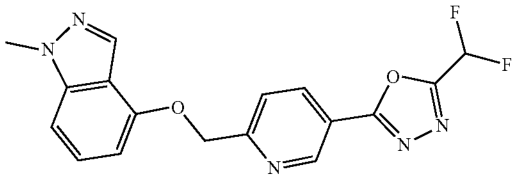<br>2-(difluoromethyl)-5-[6-[(1-methylindazol-4-yl)oxymethyl]-3-pyridyl]-1,3,4-oxadiazole | $^1H$ NMR (400 MHz, METHANOL-$d_4$) δ = 9.30 (d, J = 1.8 Hz, 1H), 8.60-8.52 (m, 1H), 8.20-8.12 (m, 1H), 7.94 (d, J = 8.3 Hz, 1H), 7.40-7.14 (m, 3H), 6.66 (d, J = 7.6 Hz, 1H), 5.49 (s, 2H), 4.07 (s, 3H).<br>MS (ESI): 358.0 [M + H]+ |
| 57 | 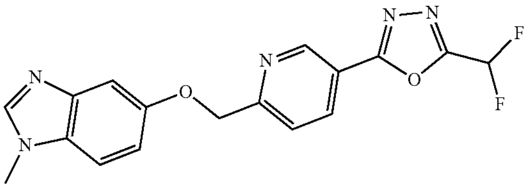<br>2-(difluoromethyl)-5-[6-[(1-methylbenzimidazol-5-yl)oxymethyl]-3-pyridyl]-1,3,4-oxadiazole | $^1H$ NMR (400 MHz, METHANOL-$d_4$) δ = 9.29 (d, J = 1.6 Hz, 1H), 8.54 (dd, J = 2.1, 8.3 Hz, 1H), 8.07 (s, 1H), 7.89 (d, J = 7.8 Hz, 1H), 7.51 (d, J = 8.9 Hz, 1H), 7.40-7.14 (m, 3H), 5.37 (s, 2H), 3.89 (s, 3H).<br>MS (ESI): 358.0 [M + H]+ |

-continued

| Compound | Structure/Name | Characterization |
|---|---|---|
| 55 | 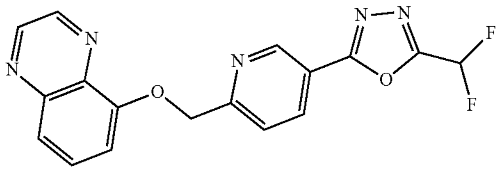 2-(difluoromethyl)-5-[6-(quinoxalin-5-yloxymethyl)-3-pyridyl]-1,3,4-oxadiazole | $^1$H NMR (400 MHz, METHANOL-$d_4$) δ = 9.31 (d, J = 2.1 Hz, 1H), 8.97 (d, J = 1.9 Hz, 1H), 8.92 (d, J = 1.8 Hz, 1H), 8.55 (dd, J = 2.1, 8.3 Hz, 1H), 8.04 (d, J = 8.5 Hz, 1H), 7.82-7.74 (m, 2H), 7.43-7.14 (m, 2H), 5.63 (s, 2H). MS (ESI): 356.0 [M + H]+ |
| 54 | 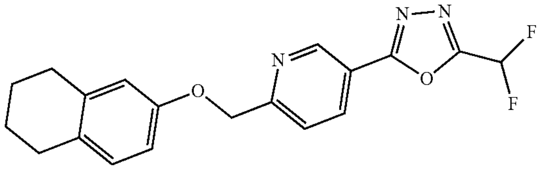 2-(difluoromethyl)-5-[6-(tetralin-6-yloxymethyl)-3-pyridyl]-1,3,4-oxadiazole | $^1$H NMR (400 MHz, METHANOL-$d_4$) δ = 9.26 (d, J = 1.5 Hz, 1H), 8.52 (dd, J = 2.3, 8.3 Hz, 1H), 7.83 (d, J = 8.3 Hz, 1H), 7.27 (t, J = 51.6 Hz, 1H), 6.97 (d, J = 8.4 Hz, 1H), 6.77 (dd, J = 2.6, 8.4 Hz, 1H), 6.73 (s, 1H), 5.26 (s, 2H), 2.74 (s, 2H), 2.70 (s, 2H), 1.79 (td, J = 3.4, 6.3 Hz, 4H). MS (ESI): 358.2 $[M + H]^+$ |
| 52 | 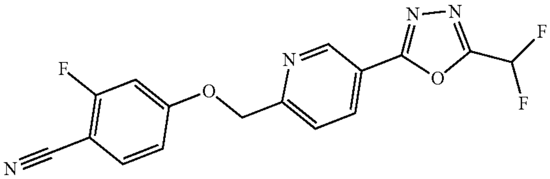 4-[[5-[5-(difluoromethyl)-1,3,4-oxadiazol-2-yl]-2-pyridyl]methoxy]-2-fluoro-benzonitrile | $^1$H NMR (400 MHz, METHANOL-$d_4$) δ = 9.30 (d, J = 1.5 Hz, 1H), 8.56 (d, J = 2.3, 8.3 Hz, 1H), 7.85 (d, J = 8.3 Hz, 1H), 7.72 (d, J = 7.7, 8.7 Hz, 1H), 7.48-7.22 (m, 1H), 7.16-7.12 (m, 1H), 7.08 (d, J = 2.3, 8.8 Hz, 1H), 5.43 (s, 2H). MS (ESI): 347.0 [M + H]+ |
| 51 | 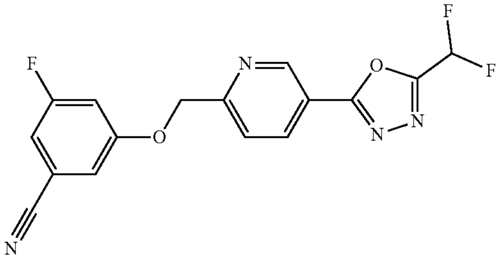 3-[[5-[5-(difluoromethyl)-1,3,4-oxadiazol-2-yl]-2-pyridyl]methoxy]-5-fluoro-benzonitrile | $^1$H NMR (400 MHz, METHANOL-$d_4$) δ = 9.30 (d, J = 2.1 Hz, 1H), 8.56 (d, J = 2.3, 8.3 Hz, 1H), 7.86 (d, J = 8.1 Hz, 1H), 7.40-7.14 (m, 4H), 5.40 (s, 2H). MS (ESI): 347.2 $[M + H]^+$ |
| 49 | 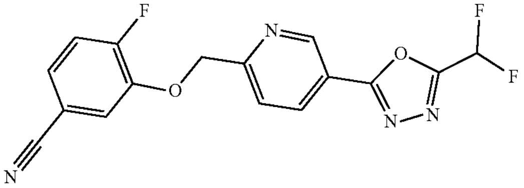 3-[[5-[5-(difluoromethyl)-1,3,4-oxadiazol-2-yl]-2-pyridyl]methoxy]-4-fluoro-benzonitrile | $^1$H NMR (400 MHz, METHANOL-$d_4$) δ = 9.31 (d, J = 1.6 Hz, 1H), 8.58 (d, J = 2.3, 8.1 Hz, 1H), 7.89 (d, J = 8.3 Hz, 1H), 7.68 (d, J = 1.9, 7.8 Hz, 1H), 7.46-7.42 (m, 1H), 7.40-7.37 (m, 1H), 7.35-7.14 (m, 1H), 5.44 (s, 2H). MS (ESI): 347.2 $[M + H]^+$ |
| 48 | 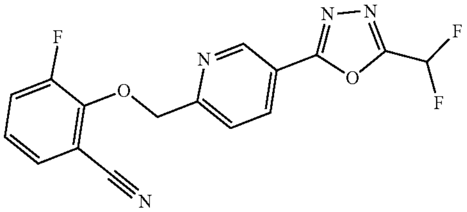 2-[[5-[5-(difluoromethyl)-1,3,4-oxadiazol-2-yl]-2-pyridyl]methoxy]-3-fluoro-benzonitrile | $^1$H NMR (400 MHz, METHANOL-$d_4$) δ = 9.27 (d, J = 2.0 Hz, 1H), 8.60 (d, J = 2.1, 8.3 Hz, 1H), 8.02 (d, J = 8.3 Hz, 1H), 7.59-7.52 (m, 2H), 7.40-7.14 (m, 2H), 5.56 (s, 2H). MS (ESI): 347.0 $[M + H]^+$ |

-continued

| Compound | Structure/Name | Characterization |
|---|---|---|
| 47 | 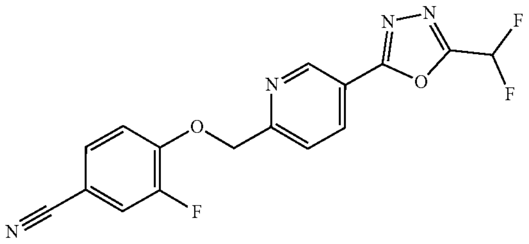 4-[[5-[5-(difluoromethyl)-1,3,4-oxadiazol-2-yl]-2-pyridyl]methoxy]-3-fluoro-benzonitrile | $^1$H NMR (400 MHz, METHANOL-$d_4$) δ = 9.30 (d, J = 1.5 Hz, 1H), 8.57 (d, J = 2.2, 8.2 Hz, 1H), 7.87 (d, J = 8.3 Hz, 1H), 7.63 (d, J = 1.9, 10.8 Hz, 1H), 7.57 (d, J = 1.6, 8.6 Hz, 1H), 7.41-7.14 (m, 2H), 5.48 (s, 2H). MS (ESI): 347.2 $[M + H]^+$ |
| 46 | 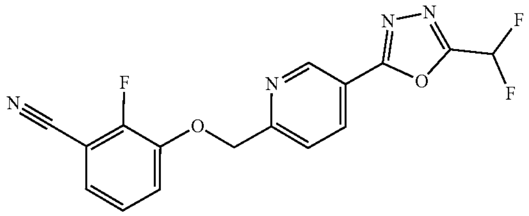 3-[[5-[5-(difluoromethyl)-1,3,4-oxadiazol-2-yl]-2-pyridyl]methoxy]-2-fluoro-benzonitrile | $^1$H NMR (400 MHz, METHANOL-$d_4$) δ = 9.30 (d, J = 1.6 Hz, 1H), 8.58 (d, J = 2.3, 8.3 Hz, 1H), 7.89 (d, J = 8.1 Hz, 1H), 7.58 (t, J = 1.8, 8.2 Hz, 1H), 7.37-7.33 (m, 1H), 7.31 (d, J = 1.0,8.0 Hz, 1H), 7.28-7.14 (m, 1H), 5.45 (s, 2H). MS (ESI): 347.0 [M + H]+ |
| 43 | 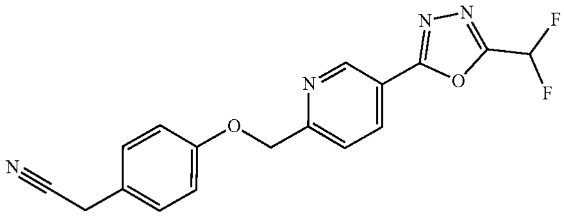 2-[4-[[5-[5-(difluoromethyl)-1,3,4-oxadiazol-2-yl]-2-pyridyl]methoxy]phenyl]acetonitrile | $^1$H NMR (400 MHz, METHANOL-$d_4$) δ = 9.28 (d, J = 1.8 Hz, 1H), 8.54 (d, J = 2.3, 8.3 Hz, 1H), 7.85 (d, J = 7.9 Hz, 1H), 7.40-7.14 (m, 3H), 7.11-7.07 (m, 2H), 5.33 (s, 2H), 3.85 (s, 2H). MS (ESI): 343.0 [M + H]+ |
| 42 | 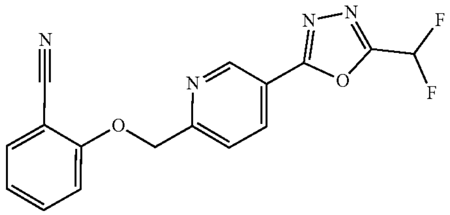 2-[[5-[5-(difluoromethyl)-1,3,4-oxadiazol-2-yl]-2-pyridyl]methoxy]benzonitrile | $^1$H NMR (400 MHz, METHANOL-$d_4$) δ = 9.30 (d, J = 2.1 Hz, 1H), 8.59 (d, J = 2.2, 8.2 Hz, 1H), 7.94 (d, J = 8.3 Hz, 1H), 7.71 (d, J = 1.6, 7.8 Hz, 1H), 7.69-7.64 (m, 1H), 7.40-7.18 (m, 2H), 7.15 (d, J = 6.4 Hz, 1H), 5.48 (s, 2H). MS (ESI): 329.1 $[M + H]^+$ |
| 41 | 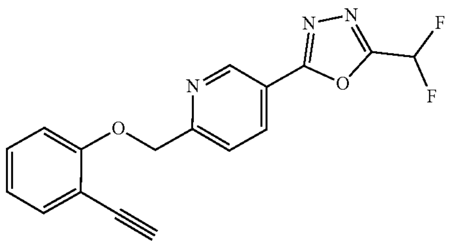 2-(difluoromethyl)-5-[6-[(2-ethynylphenoxy)methyl]-3-pyridyl]-1,3,4-oxadiazole | $^1$H NMR (400 MHz, METHANOL-$d_4$) δ = 9.28 (d, J = 1.5 Hz, 1H), 8.56 (d, J = 2.3, 8.3 Hz, 1H), 7.99 (d, J = 0.6, 8.3 Hz, 1H), 7.48 (d, J = 1.7, 7.6 Hz, 1H), 7.39-7.34 (m, 1H), 7.28-7.13 (m, 1H), 7.10 (d, J = 8.0 Hz, 1H), 7.00 (t, J = 0.9, 7.5 Hz, 1H), 5.38 (s, 2H), 3.73 (s, 1H). MS (ESI): 328.0 [M + H]+ |

-continued

| Compound | Structure/Name | Characterization |
|---|---|---|
| 39 | 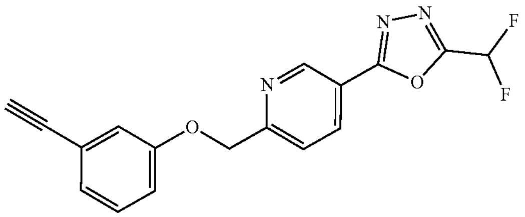<br>2-(difluoromethyl)-5-[6-[(3-ethynylphenoxy)methyl]-3-pyridyl]-1,3,4-oxadiazole | $^1$H NMR (400 MHz, METHANOL-$d_4$) δ = 9.28 (d, J = 1.9 Hz, 1H), 8.54 (d, J = 2.0, 8.3 Hz, 1H), 7.85 (d, J = 8.3 Hz, 1H), 7.40-7.26 (m, 2H), 7.15 (d, J = 1.3 Hz, 1H), 7.12-7.08 (m, 2H), 5.33 (s, 2H), 3.50 (s, 1H). MS (ESI): 328.1 $[M + H]^+$ |
| 38 | 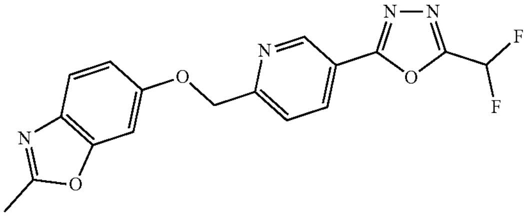<br>6-[[5-[5-(difluoromethyl)-1,3,4-oxadiazol-2-yl]-2-pyridyl]methoxy]-2-methyl-1,3-benzoxazole | $^1$H NMR (400 MHz, METHANOL-$d_4$) δ = 9.29 (d, J = 2.0 Hz, 1H), 8.55 (d, J = 2.1, 8.3 Hz, 1H), 7.88 (d, J = 8.4 Hz, 1H), 7.54 (d, J = 8.8 Hz, 1H), 7.40-7.25 (m, 2H), 7.20 (d, J = 8.8 Hz, 1H) 5.38 (s, 2H), 2.61 (s, 3H). MS (ESI): 359.1 $[M + H]^+$ |
| 37 | 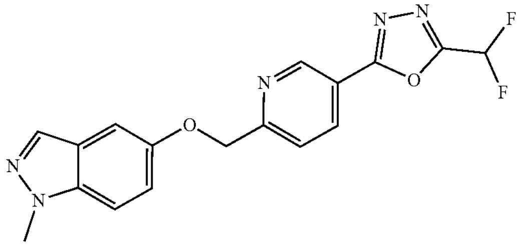<br>2-(difluoromethyl)-5-[6-[(1-methylindazol-5-yl)oxymethyl]-3-pyridyl]-1,3,4-oxadiazole | $^1$H NMR (400 MHz, METHANOL-$d_4$) δ = 9.29 (d, J = 1.9 Hz, 1H), 8.55 (d, J = 2.3, 8.3 Hz, 1H), 7.90 (t, J = 4.1 Hz, 2H), 7.55-7.52 (m, 1H), 7.40-7.27 (m, 3H), 5.36 (s, 2H), 4.06 (s, 3H). MS (ESI): 358.0 $[M + H]^+$ |
| 36 | 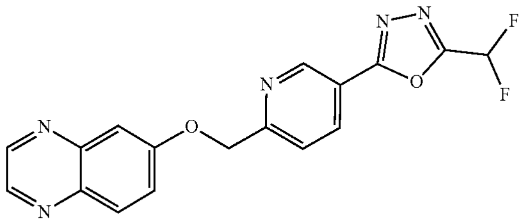<br>2-(difluoromethyl)-5-[6-(quinoxalin-6-yloxymethyl)-3-pyridyl]-1,3,4-oxadiazole | $^1$H NMR (400 MHz, METHANOL-$d_4$) δ = 9.33 (d, J = 1.6 Hz, 1H), 8.83 (d, J = 2.0 Hz, 1H), 8.77 (d, J = 1.9 Hz, 1H), 8.57 (d, J = 2.3, 8.3 Hz, 1H), 8.08 (d, J = 9.3 Hz, 1H), 7.93 (d, J = 8.3 Hz, 1H), 7.71 (d, J = 2.8, 9.3 Hz, 1H), 7.56 (d, J = 2.8 Hz, 1H), 7.27 (t, J = 51.6 Hz, 1H), 5.55 (s, 2H). MS (ESI): 356.2 $[M + H]^+$ |
| 35 | 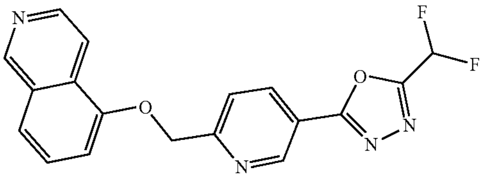<br>2-(difluoromethyl)-5-[6-(5-isoquinolyloxymethyl)-3-pyridyl]-1,3,4-oxadiazole | $^1$H NMR (400 MHz, METHANOL-$d_4$) δ = 9.33 (d, J = 2.0 Hz, 1H), 9.24 (s, 1H), 8.59 (d, J = 2.2, 8.2 Hz, 1H), 8.51 (d, J = 5.9 Hz, 1H), 8.28 (d, J = 6.0 Hz, 1H), 8.00 (d, J = 8.3 Hz, 1H), 7.74 (d, J = 8.3 Hz, 1H), 7.64 (t, J = 8.0 Hz, 1H), 7.35 (d, J = 7.8 Hz, 1H), 7.29-7.14 (m, 1H), 5.57 (s, 2H). MS (ESI): 355.1 $[M + H]^+$ |

-continued

| Compound | Structure/Name | Characterization |
|---|---|---|
| 34 | 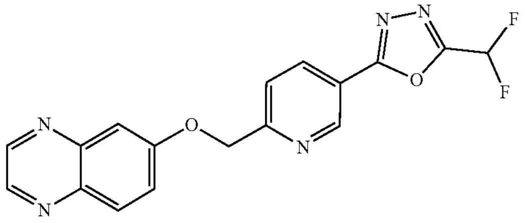 2-(difluoromethyl)-5-[6-(7-quinolyloxymethyl)-3-pyridyl]-1,3,4-oxadiazole | $^1$H NMR (400 MHz, METHANOL-$d_4$) δ = 9.32 (d, J = 1.6 Hz, 1H), 8.77 (d, J = 1.7, 4.4 Hz, 1H), 8.56 (d, J = 2.3, 8.3 Hz, 1H), 8.32 (d, J = 1.4, 8.3 Hz, 1H), 7.93 (t, J = 8.4 Hz, 2H), 7.48-7.41 (m, 3H), 7.40-7.14 (m, 1H), 5.52 (s, 2H). MS (ESI): 355.0 [M + H]+ |
| 33 | 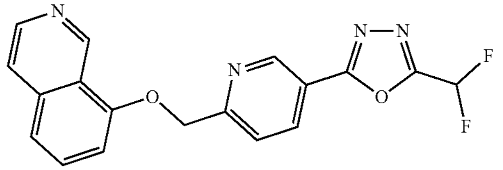 2-(difluoromethyl)-5-[6-(8-isoquinolyloxymethyl)-3-pyridyl]-1,3,4-oxadiazole | $^1$H NMR (400 MHz, METHANOL-$d_4$) δ = 9.69 (s, 1H), 9.34 (d, J = 1.6 Hz, 1H), 8.59 (d, J = 2.1, 8.3 Hz, 1H), 8.50 (d, J = 5.9 Hz, 1H), 8.00 (d, J = 8.4 Hz, 1H), 7.82 (d, J = 5.4 Hz, 1H), 7.75-7.70 (m, 1H), 7.56 (d, J = 8.1 Hz, 1H), 7.41-7.14 (m, 2H), 5.61 (s, 2H). MS (ESI): 355.0 $[M + H]^+$ |
| 32 | 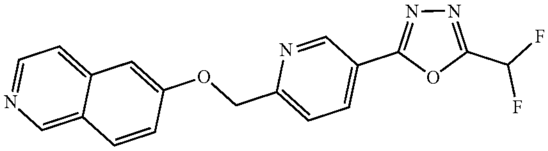 2-(difluoromethyl)-5-[6-(6-isoquinolyloxymethyl)-3-pyridyl]-1,3,4-oxadiazole | $^1$H NMR (400 MHz, METHANOL-$d_4$) δ = 9.32 (d, J = 1.8 Hz, 1H), 9.12 (s, 1H), 8.57 (d, J = 2.3, 8.3 Hz, 1H), 8.36 (d, J = 6.0 Hz, 1H), 8.09 (d, J = 9.0 Hz, 1H), 7.92 (d, J = 8.3 Hz, 1H), 7.75 (d, J = 5.9 Hz, 1H), 7.50 (d, J = 2.4, 9.0 Hz, 1H), 7.44 (d, J = 2.4 Hz, 1H), 7.40-7.14 (m, 1H), 5.52 (s, 2H). MS (ESI): 355.0 [M + H]+ |
| 29 | 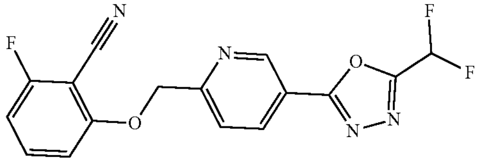 2-[[5-[5-(difluoromethyl)-1,3,4-oxadiazol-2-yl]-2-pyridyl]methoxy]-6-fluoro-benzonitrile | $^1$H NMR (400 MHz, METHANOL-$d_4$) δ = 9.31 (s, 1H), 8.62-8.56 (m, 1H), 7.92 (d, J = 8.1 Hz, 1H), 7.72-7.64 (m, 1H), 7.41-7.12 (m, 2H), 7.00 (t, J = 8.5 Hz, 1H), 5.51 (s, 2H). MS (ESI): 347.0 [M + H]+ |
| 28 | 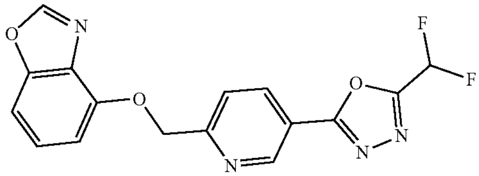 4-[[5-[5-(difluoromethyl)-1,3,4-oxadiazol-2-yl]-2-pyridyl]methoxy]-1,3-benzoxazole | $^1$H NMR (400 MHz, METHANOL-$d_4$) δ = 9.29 (d, J = 1.8 Hz, 1H), 8.56 (d, J = 2.2, 8.3 Hz, 1H), 8.45 (s, 1H), 8.01 (d, J = 8.4 Hz, 1H), 7.43-7.14 (m, 3H), 7.07 (d, J = 7.8 Hz, 1H), 5.63 (s, 2H). MS (ESI): 345.0 [M + H]+ |
| 27 | 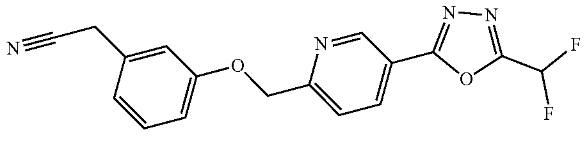 2-[3-[[5-[5-(difluoromethyl)-1,3,4-oxadiazol-2-yl]-2-pyridyl]methoxy]phenyl]acetonitrile | $^1$H NMR (400 MHz, METHANOL-$d_4$) δ = 9.28 (d, J = 2.0 Hz, 1H), 8.55 (d, J = 2.2, 8.3 Hz, 1H), 7.86 (d, J = 8.3 Hz, 1H), 7.35 (t, J = 8.0 Hz, 1H), 7.28-7.14 (m, 1H), 7.09 (s, 1H), 7.05-7.00 (m, 2H), 5.34 (s, 2H), 3.91 (s, 2H). MS (ESI): 343.0 [M + H]+ |

-continued

| Compound | Structure/Name | Characterization |
|---|---|---|
| 26 | 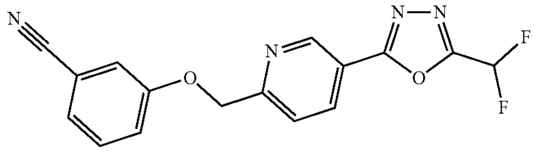 3-[[5-[5-(difluoromethyl)-1,3,4-oxadiazol-2-yl]-2-pyridyl]methoxy]benzonitrile | $^1$H NMR (400 MHz, METHANOL-$d_4$) δ = 9.30 (s, 1H), 8.56 (d, J = 8.4 Hz, 1H), 7.87 (d, J = 8.1 Hz, 1H), 7.54-7.50 (m, 1H), 7.45 (s, 1H), 7.43-7.38 (m, 2H), 7.37-7.14 (m, 1H), 5.39 (s, 2H). MS (ESI): 329.0 [M + H]$^+$ |
| 30 | 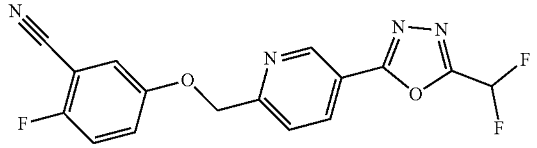 5-((5-(5-(difluoromethyl)-1,3,4-oxadiazol-2-yl)pyridin-2-yl)methoxy)-2-fluorobenzonitrile | $^1$H NMR (400 MHz, METHANOL-$d_4$) δ ppm 9.29 (d, J = 1.75 Hz, 1H) 8.56-8.45 (m, 1H) 7.86-7.71 (m, 1H) 7.12-7.51 (m, 4H) 5.36 (s, 2H) MS (ESI): 347.2 [M + H]$^+$ |
| 53 | 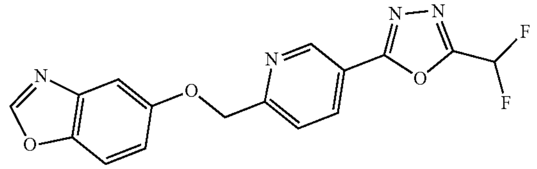 5-((5-(5-(difluoromethyl)-1,3,4-oxadiazol-2-yl)pyridin-2-yl)methoxy)benzo[d]oxazole | $^1$H NMR (400 MHz, METHANOL-$d_4$) δ ppm 9.30 (d, J = 1.75 Hz, 1H) 8.55 (d, J = 8.32, 2.19 Hz, 1H) 8.45 (s, 1H) 7.90 (d, J = 8.63 Hz, 1H) 7.63 (d, J = 9.01 Hz, 1H) 7.39-7.41 (m, 1H) 7.12-7.29 (m, 2H) 5.40 (s, 2H) MS (ESI): 345.2 [M + H]$^+$ |
| 56 | 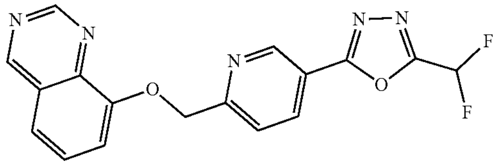 2-(difluoromethyl)-5-[6-(quinazolin-8-yloxymethyl)-3-pyridyl]-1,3,4-oxadiazole | $^1$H NMR (400 MHz, METHANOL-$d_4$) δ = 9.56 (s, 1H), 9.32-9.29 (m, 2H), 8.55 (d, J = 2.1, 8.3 Hz, 1H), 8.05 (d, J = 8.3 Hz, 1H), 7.76-7.69 (m, 2H), 7.59 (d, J = 1.4, 7.4 Hz, 1H), 7.27 (m, 1H), 5.62 (s, 2H) MS (ESI): 356.0 [M + H]$^+$ |
| 66 | 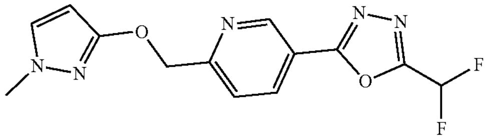 2-(difluoromethyl)-5-[6-[(1-methylpyrazol-3-yl)oxymethyl]-3-pyridyl]-1,3,4-oxadiazole | $^1$H NMR (400 MHz, METHANOL-$d_4$) δ = 9.25 (d, J = 1.6 Hz, 1H), 8.53 (d, J = 2.2, 8.3 Hz, 1H), 7.81 (d, J = 0.6,8.3 Hz, 1H), 7.40-7.14 (m, 2H), 5.77 (d, J = 2.4 Hz, 1H), 5.37 (s, 2H), 3.73 (s, 3H) MS (ESI): 308.0 [M + H]$^+$ |
| 68 | 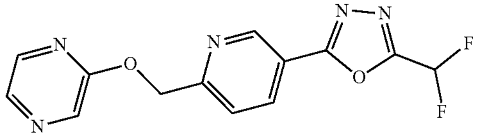 2-(difluoromethyl)-5-[6-(pyrazin-2-yloxymethyl)-3-pyridyl]-1,3,4-oxadiazole | $^1$H NMR (400 MHz, METHANOL-$d_4$) δ = 9.26 (d, J = 1.8 Hz, 1H), 8.53 (d, J = 2.1, 8.3 Hz, 1H), 8.42 (d, J = 1.3 Hz, 1H), 8.21-8.19 (m, 1H), 8.18-8.17 (m, 1H), 7.81 (d, J = 8.3 Hz, 1H), 7.27-7.17 (m, 1H), 5.66 (s, 2H) MS (ESI): 306.0 [M + H]$^+$ |
| 74 | 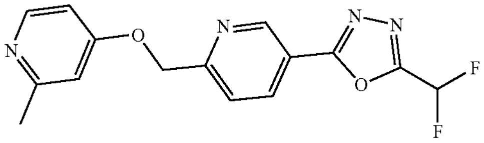 2-(difluoromethyl)-5-[6-[(2-methyl-4-pyridyl)oxymethyl]-3-pyridyl]-1,3,4-oxadiazole | $^1$H NMR (400 MHz, METHANOL-$d_4$) δ = 9.30 (d, J = 1.8 Hz, 1H), 8.56 (d, J = 2.3, 8.3 Hz, 1H), 8.27 (d, J = 6.0 Hz, 1H), 7.84 (d, J = 8.1 Hz, 1H), 7.27-7.17 (m, 1H), 7.03 (d, J = 2.4 Hz, 1H), 6.96 (d, J = 2.3, 6.1 Hz, 1H), 5.42 (s, 2H), 2.51 (s, 3H) MS (ESI): 319.0 [M + H]+ |

-continued

| Compound | Structure/Name | Characterization |
| --- | --- | --- |
| 80 | 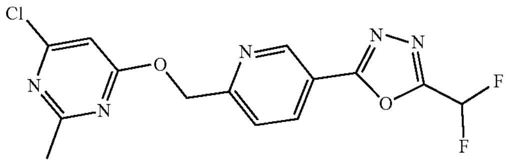 2-[6-[(6-chloro-2-methyl-pyrimidin-4-yl)oxymethyl]-3-pyridyl]-5-(difluoromethyl)-1,3,4-oxadiazole | $^1$H NMR (400 MHz, METHANOL-$d_4$) δ = 9.27 (d, J = 1.6 Hz, 1H), 8.53 (d, J = 2.3, 8.3 Hz, 1H), 7.78 (d, J = 8.3 Hz, 1H), 7.40-7.14 (m, 1H), 6.98 (s, 1H), 5.69 (s, 2H), 2.55 (s, 3H) MS (ESI): 354.0 [M + H]+ |
| 106 | 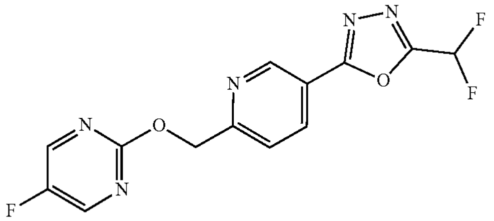 2-(difluoromethyl)-5-[6-[(5-fluoropyrimidin-2-yl)oxymethyl]-3-pyridyl]-1,3,4-oxadiazole | $^1$H NMR (400 MHz, METHANOL-$d_4$) δ = 9.26 (d, J = 1.6 Hz, 1H), 8.58 (s, 2H), 8.53 (d, J = 2.2, 8.3 Hz, 1H), 7.81 (d, J = 8.4 Hz, 1H), 7.27-7.17 (m, 1H), 5.65 (s, 2H) MS (ESI): 324.0 $[M + H]^+$ |
| 123 | 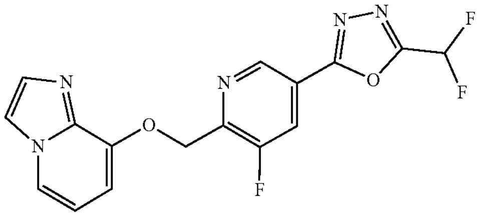 2-(difluoromethyl)-5-[5-fluoro-6-(imidazo[1,2-a]pyridin-8-yloxymethyl)-3-pyridyl]-1,3,4-oxadiazole | $^1$H NMR (400 MHz, METHANOL-$d_4$) δ = 9.03 (s, 1H), 8.26 (d, J = 1.6, 9.5 Hz, 1H), 7.98 (d, J = 6.6 Hz, 1H), 7.72 (d, J = 1.3 Hz, 1H), 7.38 (d, J = 1.3 Hz, 1H), 7.16-7.10 (m, 1H), 6.80-6.78 (m, 1H), 6.74-6.70 (m, 1H), 5.45 (d, J = 1.9 Hz, 2H) MS (ESI): 362.2 $[M + H]^+$ |
| 124 | 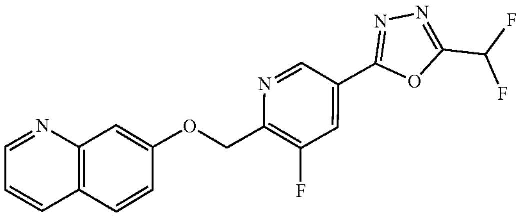 2-(difluoromethyl)-5-[5-fluoro-6-(7-quinolyloxymethyl)-3-pyridyl]-1,3,4-oxadiazole | $^1$H NMR (400 MHz, METHANOL-$d_4$) δ = 9.17 (d, J = 0.6 Hz, 1H), 8.79 (d, J = 1.7, 4.4 Hz, 1H), 8.39 (d, J = 1.8, 9.6 Hz, 1H), 8.32 (d, J = 1.0, 8.3 Hz, 1H), 7.90 (d, J = 9.0 Hz, 1H), 7.58 (d, J = 2.4 Hz, 1H), 7.45-7.15 (m, 3H), 5.57 (d, J = 1.8 Hz, 2H) MS (ESI): 373.0 [M + H]+ |
| 125 | 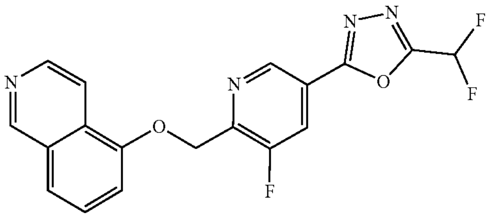 2-(difluoromethyl)-5-[5-fluoro-6-(5-isoquinolyloxymethyl)-3-pyridyl]-1,3,4-oxadiazole | $^1$H NMR (400 MHz, METHANOL-$d_4$) δ = 9.20 (s, 1H), 9.17 (s, 1H), 8.43 (d, J = 6.0 Hz, 1H), 8.40 (d, J = 1.7, 9.7 Hz, 1H), 8.10 (d, J = 5.9 Hz, 1H), 7.74-7.70 (m, 1H), 7.66-7.62 (m, 1H), 7.45 (d, J = 7.6 Hz, 1H), 7.28 (s, 1H), 5.63 (d, J = 1.6 Hz, 2H) MS (ESI): 373.0 [M + H]+ |

-continued

| Compound | Structure/Name | Characterization |
|---|---|---|
| 126 | 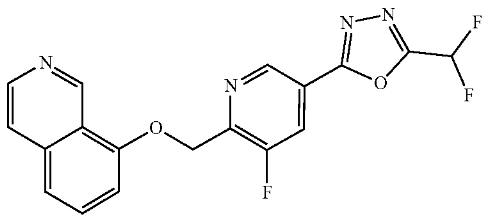 2-(difluoromethyl)-5-[5-fluoro-6-(8-isoquinolyloxymethyl)-3-pyridyl]-1,3,4-oxadiazole | $^{1}H$ NMR (400 MHz, METHANOL-$d_4$) δ = 9.52 (s, 1H), 9.19 (s, 1H), 8.46 (d, J = 5.8 Hz, 1H), 8.41 (d, J = 1.7, 9.7 Hz, 1H), 7.81-7.79 (m, 1H), 7.76-7.72 (m, 1H), 7.55 (d, J = 8.4 Hz, 1H), 7.42-7.16 (m, 2H), 5.67 (d, J = 1.8 Hz, 2H) MS (ESI): 373.0 [M + H]+ |
| 127 | 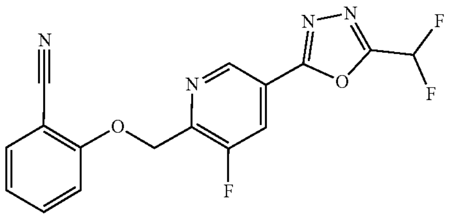 2-[[5-[5-(difluoromethyl)-1,3,4-oxadiazol-2-yl]-3-fluoro-2-pyridyl]methoxy]benzonitrile | $^{1}H$ NMR (400 MHz, METHANOL-$d_4$) δ = 9.15 (s, 1H), 8.39 (d, J = 1.8, 9.6 Hz, 1H), 7.68-7.63 (m, 2H), 7.41-7.12 (m, 3H), 5.55 (d, J = 1.9 Hz, 2H) MS (ESI): 347.2 [M + H]+ |
| 128 | 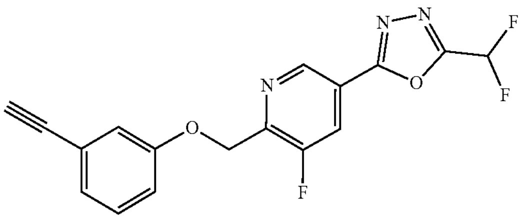 2-(difluoromethyl)-5-[6-[(3-ethynylphenoxy)methyl]-5-fluoro-3-pyridyl]-1,3,4-oxadiazole | $^{1}H$ NMR (400 MHz, METHANOL-$d_4$) δ = 9.14 (s, 1H), 8.36 (d, J = 1.8, 9.6 Hz, 1H), 7.41-7.15 (m, 3H), 7.11-7.08 (m, 2H), 5.37 (d, J = 1.9 Hz, 2H), 3.50 (s, 1H) MS (ESI): 346.1 [M + H]+ |
| 129 | 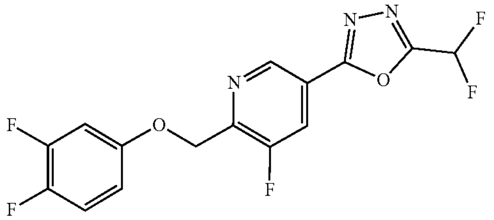 2-(difluoromethyl)-5-[6-[(3,4-difluorophenoxy)methyl]-5-fluoro-3-pyridyl]-1,3,4-oxadiazole | $^{1}H$ NMR (400 MHz, METHANOL-$d_4$) δ = 9.13 (d, J = 0.6 Hz, 1H), 8.36 (d, J = 1.8, 9.6 Hz, 1H), 7.41-7.15 (m, 2H), 7.03-6.99 (m, 1H), 6.88-6.84 (m, 1H), 5.34 (d, J = 1.8 Hz, 2H) MS (ESI): 358.0 [M + H]+ |
| 130 | 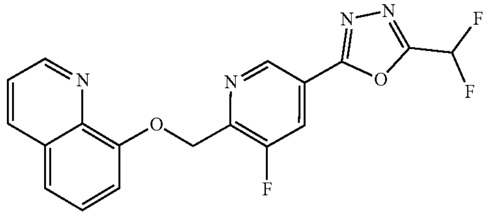 2-(difluoromethyl)-5-[5-fluoro-6-(8-quinolyloxymethyl)-3-pyridyl]-1,3,4-oxadiazole | $^{1}H$ NMR (400 MHz, METHANOL-$d_4$) δ = 9.15 (s, 1H), 8.80 (d, J = 1.5, 4.3 Hz, 1H), 8.36-8.20 (m, 2H), 7.59-7.54 (m, 3H), 7.44-7.15 (m, 2H), 5.63 (d, J = 1.4 Hz, 2H) MS (ESI): 373.0 [M + H]+ |

-continued

| Compound | Structure/Name | Characterization |
| --- | --- | --- |
| 131 | 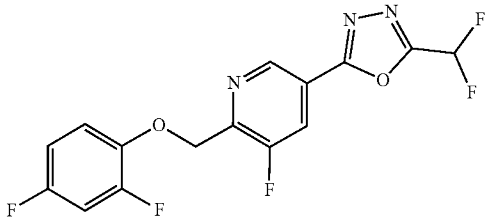 2-(difluoromethyl)-5-[6-[(2,4-difluorophenoxy)methyl]-5-fluoro-3-pyridyl]-1,3,4-oxadiazole | $^1$H NMR (400 MHz, METHANOL-$d_4$) δ = 9.14 (d, J = 0.6 Hz, 1H), 8.37 (d, J = 1.8, 9.6 Hz, 1H), 7.41-7.15 (m, 2H), 7.01-6.98 (m, 1H), 6.93-6.86 (m, 1H), 5.39 (d, J = 1.9 Hz, 2H) MS (ESI): 358.1 [M + H]+ |
| 132 | 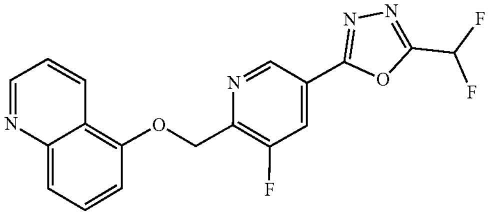 2-(difluoromethyl)-5-[5-fluoro-6-(5-quinolyloxymethyl)-3-pyridyl]-1,3,4-oxadiazole | $^1$H NMR (400 MHz, METHANOL-$d_4$) δ = 9.18 (s, 1H), 8.85 (d, J = 1.6, 4.3 Hz, 1H), 8.70 (d, J = 0.9, 8.4 Hz, 1H), 8.40 (d, J = 1.7, 9.7 Hz, 1H), 7.75-7.70 (m, 1H), 7.69-7.66 (m, 1H), 7.53 (d, J = 4.4, 8.5 Hz, 1H), 7.42-7.16 (m, 2H), 5.63 (d, J = 1.6 Hz, 2H) MS (ESI): 373.2 [M + H]+ |
| 22 | 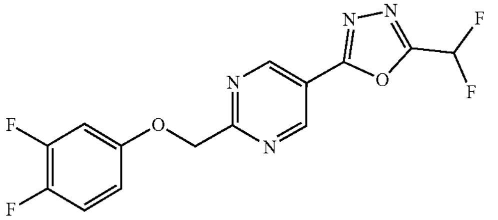 2-(difluoromethyl)-5-[2-[(3,4-difluorophenoxy)methyl]pyrimidin-5-yl]-1,3,4-oxadiazole | $^1$H NMR (400 MHz, METHANOL-$d_4$) δ = 9.47 (s, 2H), 7.44-7.14 (m, 2H), 7.01-6.98 (m, 1H), 6.86-6.80 (m, 1H), 5.42 (s, 2H) MS (ESI): 341.0 [M + H]+ |
| 31 | 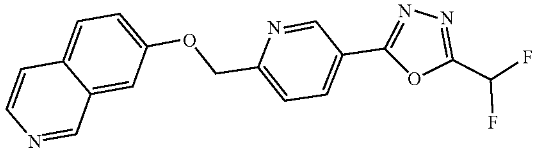 2-(difluoromethyl)-5-[6-(7-isoquinolyloxymethyl)-3-pyridyl]-1,3,4-oxadiazole | $^1$H NMR (400 MHz, METHANOL-$d_4$) δ = 9.32 (d, J = 1.5 Hz, 1H), 9.16 (s, 1H), 8.57 (d, J = 2.2, 8.3 Hz, 1H), 8.35 (d, J = 5.8 Hz, 1H), 7.94 (m, 2H), 7.80 (d, J = 5.8 Hz, 1H), 7.65-7.61 (m, 2H), 7.40-7.14 (m, 1H), 5.51 (s, 2H) MS (ESI): 355.0 [M + H]+ |
| 60 | 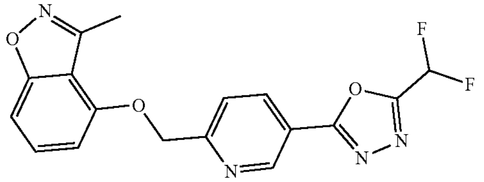 4-[[5-[5-(difluoromethyl)-1,3,4-oxadiazol-2-yl]-2-pyridyl]methoxy]-3-methyl-1,2-benzoxazole | $^1$H NMR (400 MHz, METHANOL-$d_4$) δ = 9.32 (d, J = 2.1 Hz, 1H), 8.58 (d, J = 2.1, 8.3 Hz, 1H), 7.91 (d, J = 8.3 Hz, 1H), 7.53 (m, 1H), 7.41-7.14 (m, 2H), 6.88 (d, J = 8.0 Hz, 1H), 5.51 (s, 2H), 2.74 (s, 3H) MS (ESI): 359.0 $[M + H]^+$ |
| 71 | 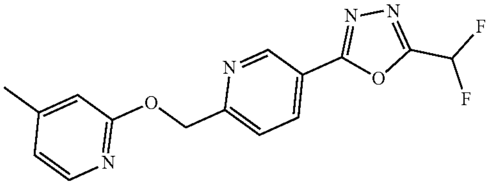 2-(difluoromethyl)-5-[6-[(4-methyl-2-pyridyl)oxymethyl]-3-pyridyl]-1,3,4-oxadiazole | $^1$H NMR (400 MHz, METHANOL-$d_4$) δ = 9.25 (s, 1H), 8.52-8.48 (m, 1H), 7.97 (d, J = 5.3 Hz, 1H), 7.77 (br d, J = 8.3 Hz, 1H), 7.26 (m, 1H), 6.86 (br d, J = 5.3 Hz, 1H), 6.83 (s, 1H), 5.56 (s, 2H), 2.37 (s, 3H) MS (ESI): 319.0 $[M + H]^+$ |

-continued

| Compound | Structure/Name | Characterization |
|---|---|---|
| 75 | 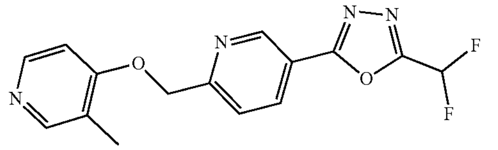 2-(difluoromethyl)-5-[6-[(3-methyl-4-pyridyl)oxymethyl]-3-pyridyl]-1,3,4-oxadiazole | $^1$H NMR (400 MHz, METHANOL-$d_4$) δ = 9.26 (d, J = 1.6 Hz, 1H), 8.51 (d, J = 2.3, 8.3 Hz, 1H), 7.94 (d, J = 1.3, 5.0 Hz, 1H), 7.77 (d, J = 0.6, 8.3 Hz, 1H), 7.59-7.55 (m, 1H), 7.40-7.13 (m, 1H), 6.91 (d, J = 5.0, 7.1 Hz, 1H), 5.62 (s, 2H), 2.34 (s, 3H) MS (ESI): 319.0 [M + H]+ |
| 76 | 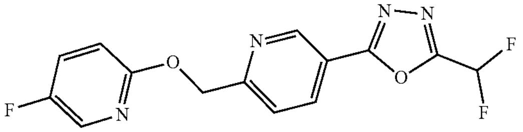 2-(difluoromethyl)-5-[6-[(5-fluoro-2-pyridyl)oxymethyl]-3-pyridyl]-1,3,4-oxadiazole | $^1$H NMR (400 MHz, METHANOL-$d_4$) δ = 9.25 (d, J = 1.9 Hz, 1H), 8.51 (d, J = 2.3, 8.3 Hz, 1H), 8.00 (d, J = 3.0 Hz, 1H), 7.77 (d, J = 8.3 Hz, 1H), 7.59 (dd, J = 3.1, 7.8, 9.0 Hz, 1H), 7.26 (m, 1H), 7.01 (d, J = 3.6, 9.1 Hz, 1H), 5.57 (s, 2H) MS (ESI): 323.0 $[M + H]^+$ |
| 78 | 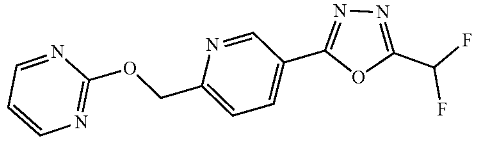 [SMILES: FC(F)c1nnc(-c2ccc(COc3ncccn3)nc2)o1] | $^1$H NMR (400 MHz, METHANOL-$d_4$) δ = 9.26 (d, J = 1.6 Hz, 1H), 8.63 (d, J = 4.9 Hz, 2H), 8.53 (dd, J = 2.3, 8.3 Hz, 1H), 7.82 (d, J = 7.8 Hz, 1H), 7.40-7.13 (m, 2H), 5.68 (s, 2H). MS (ESI): 306.2 [M + H]+ |
| 81 | 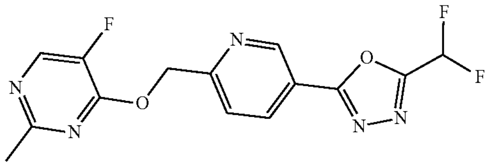 2-(difluoromethyl)-5-[6-[(5-fluoro-2-methyl-pyrimidin-4-yl)oxymethyl]-3-pyridyl]-1,3,4-oxadiazole | $^1$H NMR (400 MHz, METHANOL-$d_4$) δ = 9.28 (d, J = 1.9 Hz, 1H), 8.55 (d, J = 2.3, 8.3 Hz, 1H), 8.38 (d, J = 3.3 Hz, 1H), 7.82 (d, J = 8.3 Hz, 1H), 7.40-7.14 (m, 1H), 5.74 (s, 2H), 2.55 (d, J = 0.8 Hz, 3H) MS (ESI): 338.2 [M + H]+ |
| 83 | 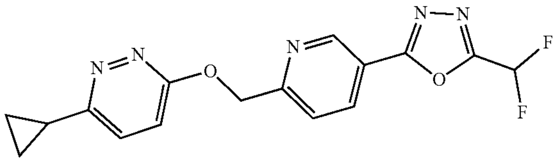 2-[6-[(6-cyclopropylpyridazin-3-yl)oxymethyl]-3-pyridyl]-5-(difluoromethyl)-1,3,4-oxadiazole | $^1$H NMR (400 MHz, METHANOL-$d_4$) δ = 9.26 (d, J = 1.5 Hz, 1H), 8.52 (d, J = 2.3, 8.3 Hz, 1H), 7.82 (d, J = 7.8 Hz, 1H), 7.45 (d, J = 9.3 Hz, 1H), 7.40-7.13 (m, 2H), 5.71 (s, 2H), 2.20 (m, 1H), 1.15-1.09 (m, 2H), 1.02-0.98 (m, 2H) MS (ESI): 346.1 [M + H]+ |
| 94 | 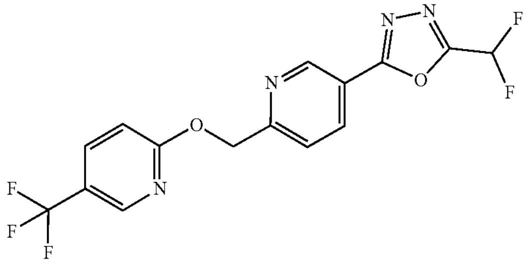 2-(difluoromethyl)-5-[6-[[5-(trifluoromethyl)-2-pyridyl]oxymethyl]-3-pyridyl]-1,3,4-oxadiazole | $^1$H NMR (400 MHz, METHANOL-$d_4$) δ = 9.26 (d, J = 1.8 Hz, 1H), 8.52 (d, J = 2.2, 8.3 Hz, 1H), 8.48 (s, 1H), 8.03 (d, J = 2.5, 8.8 Hz, 1H), 7.79 (d, J = 8.3 Hz, 1H), 7.40-7.16 (m, 1H), 7.14 (d, J = 2.0 Hz, 1H), 5.68 (s, 2H) MS (ESI): 373.2 [M + H]+ |

-continued

| Compound | Structure/Name | Characterization |
|---|---|---|
| 95 | 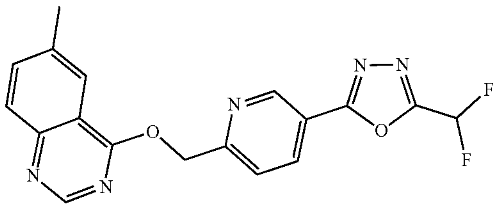 2-(difluoromethyl)-5-[6-[(6-methylquinazolin-4-yl)oxymethyl]-3-pyridyl]-1,3,4-oxadiazole | $^1$H NMR (400 MHz, METHANOL-$d_4$) δ ppm 9.30 (d, J = 1.63 Hz, 1H) 8.71 (s, 1H) 8.56 (d, J = 8.25, 2.25 Hz, 1H) 8.18 (d, J = 1.00 Hz, 1H) 7.89 (d, J = 8.25 Hz, 1H) 7.86 (d, J = 1.13 Hz, 2H) 7.27 (m, 1H) 5.91 (s, 2H) 2.61 (d, J = 0.63 Hz, 3H) MS (ESI): 370.2 [M + H]$^+$ |
| 96 | 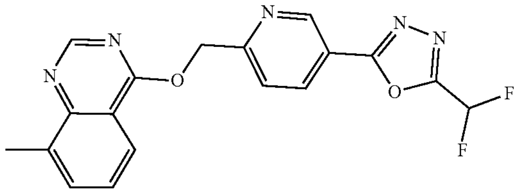 2-(difluoromethyl)-5-[6-[(8-methylquinazolin-4-yl)oxymethyl]-3-pyridyl]-1,3,4-oxadiazole | $^1$H NMR (400 MHz, METHANOL-$d_4$) δ ppm 9.30 (d, J = 1.63 Hz, 1H) 8.78 (s, 1H) 8.55 (d, J = 8.25, 2.25 Hz, 1H) 8.24 (d, J = 8.88 Hz, 1H) 7.88 (d, J = 7.88 Hz, 1H) 7.83 (d, J = 7.25 Hz, 1H) 7.58-7.66 (m, 1H) 7.27 (m, 1H) 5.90 (s, 2H) 2.74 (s, 3H) MS (ESI): 370.0 [M + H]$^+$ |
| 98 | 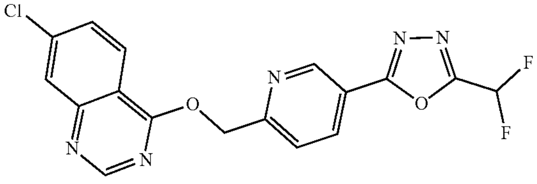 2-[6-[(7-chloroquinazolin-4-yl)oxymethyl]-3-pyridyl]-5-(difluoromethyl)-1,3,4-oxadiazole | $^1$H NMR (400 MHz, METHANOL-$d_4$) δ ppm 9.29 (d, J = 1.75 Hz, 1H) 8.79 (s, 1H) 8.56 (d, J = 8.32, 2.19 Hz, 1H) 8.40 (d, J = 8.88 Hz, 1H) 7.98 (d, J = 1.88 Hz, 1H) 7.90 (d, J = 8.25 Hz, 1H) 7.74 (d, J = 8.82, 1.94 Hz, 1H) 7.27 (t, J = 51.59 Hz, 1H) 5.92 (s, 2H) MS (ESI): 390.1 [M + H]$^+$ |
| 100 | 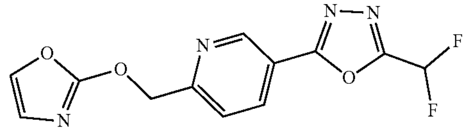 2-(difluoromethyl)-5-[6-(oxazol-2-yloxymethyl)-3-pyridyl]-1,3,4-oxadiazole | $^1$H NMR (400 MHz, METHANOL-$d_4$) δ = 9.28 (d, J = 1.5 Hz, 1H), 8.56 (d, J = 2.1, 8.3 Hz, 1H), 7.80 (d, J = 8.3 Hz, 1H), 7.51 (d, J = 1.1 Hz, 1H), 7.27 (m, 1H), 6.91 (d, J = 1.0 Hz, 1H), 5.62 (s, 2H) MS (ESI): 295.1 [M + H]+ |
| 103 | 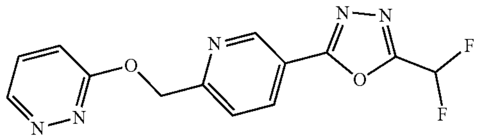 2-(difluoromethyl)-5-[6-(pyridazin-3-yloxymethyl)-3-pyridyl]-1,3,4-oxadiazole | $^1$H NMR (400 MHz, METHANOL-$d_4$) δ = 9.27 (d, J = 1.6 Hz, 1H), 8.87 (d, J = 1.3, 4.5 Hz, 1H), 8.54 (d, J = 2.3, 8.3 Hz, 1H), 7.84 (d, J = 8.0 Hz, 1H), 7.70 (d, J = 4.5, 9.0 Hz, 1H), 7.42-7.13 (m, 2H), 5.77 (s, 2H) MS (ESI): 306.0 [M + H]+ |
| 105 | 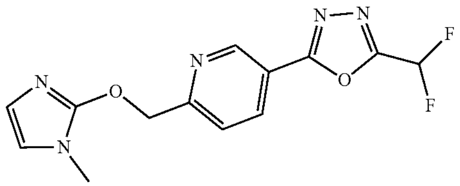 2-(difluoromethyl)-5-[6-[(1-methylimidazol-2-yl)oxymethyl]-3-pyridyl]-1,3,4-oxadiazole | $^1$H NMR (400 MHz, METHANOL-$d_4$) δ = 9.27 (d, J = 2.0 Hz, 1H), 8.54 (d, J = 2.2, 8.2 Hz, 1H), 7.80 (d, J = 8.3 Hz, 1H), 7.40-7.14 (m, 1H), 6.74 (d, J = 1.6 Hz, 1H), 6.56 (d, J = 1.6 Hz, 1H), 5.55 (s, 2H), 3.55 (s, 3H) MS (ESI): 308.2 [M + H]+ |

-continued

| Compound | Structure/Name | Characterization |
| --- | --- | --- |
| 90 | 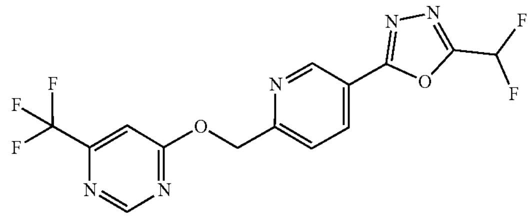 2-(difluoromethyl)-5-[6-[[6-(trifluoromethyl)pyrimidin-4-yl]oxymethyl]-3-pyridyl]-1,3,4-oxadiazole | $^1H$ NMR (400 MHz, METHANOL-$d_4$) δ = 9.27 (d, J = 1.8 Hz, 1H), 8.91 (s, 1H), 8.54 (d, J = 2.1, 8.3 Hz, 1H), 7.82 (d, J = 8.3 Hz, 1H), 7.49 (s, 1H), 7.40-7.14 (m, 1H), 5.77 (s, 2H) MS (ESI): 374.1 [M + H]+ |

2-(6-(bromomethyl)-5-fluoropyridin-3-yl)-5-(difluoromethyl)-1,3,4-oxadiazole (Int-K)

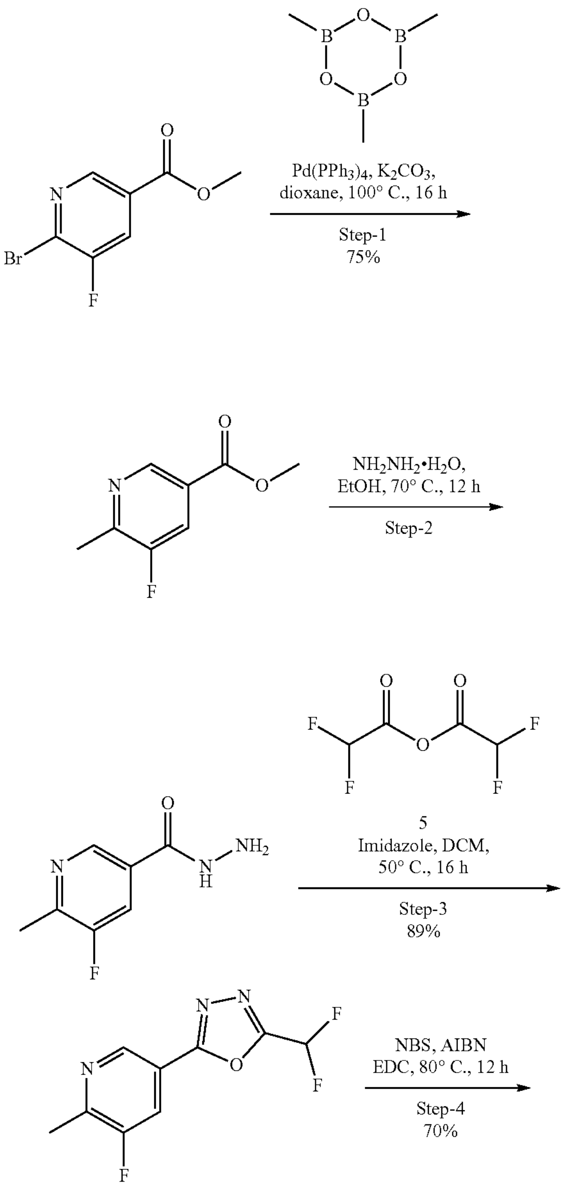

-continued

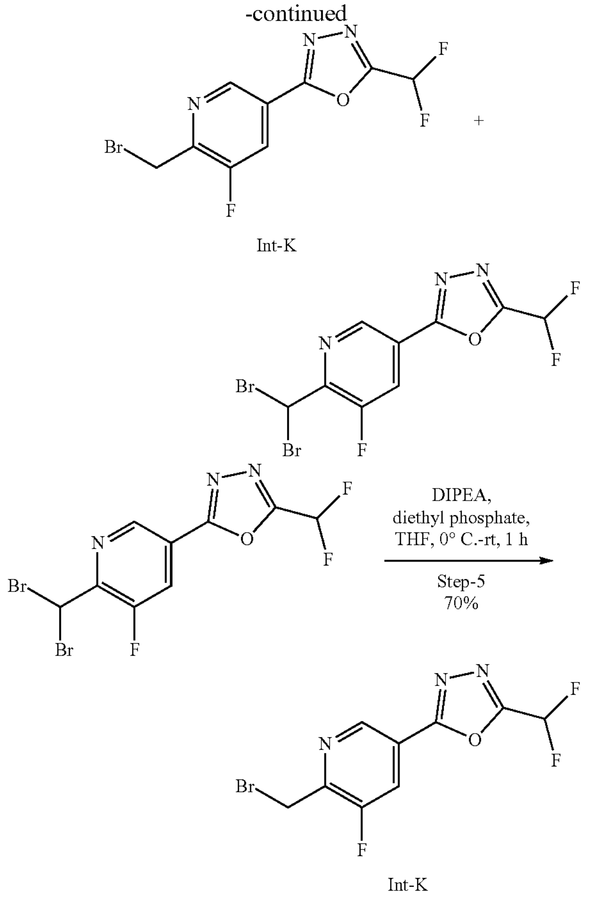

Step-1: Synthesis of methyl 5-fluoro-6-methylnicotinate: To a stirred solution of methyl 6-bromo-5-fluoronicotinate (1, 5.0 g, 21.36 mmol, 1.0 equiv.) in 1,4 dioxane (75 mL) was added 2,4,6-trimethyl-1,3,5,2,4,6-trioxatriborinane (13.41 g, 106.8 mmol, 5.0 equiv.) followed by $K_2CO_3$ (4.429 g, 32.00 mmol, 1.5 equiv.) at room temperature and degassed the reaction mixture with argon for 15 min. To the resulting reaction mixture was added $Pd(PPh_3)_4$ (2.77 g, 0.235 mmol, 0.11 eq.). The reaction mixture was heated at 100° C. and stirred for 16 h. After complete consumption of the starting material (monitored by TLC), the reaction mixture was diluted with water (100 mL) and extracted with DCM (2×100 mL). The combined organic layer was washed with brine solution (100 mL), dried over anhydrous $Na_2SO_4$ and concentrated under reduced pressure to obtain crude product. The crude product was purified by CombiFlash column chromatography using ethyl acetate: n-hexane (20%) to afford methyl 5-fluoro-6-methylnicotinate (2.70 g, 75%) as an off white solid.

Step-2: Synthesis of 5-fluoro-6-methylnicotinohydrazide: To a stirred solution of methyl 5-fluoro-6-methylnicotinate (0.740 g, 4.374 mmol, 1.0 equiv.) in EtOH (10 mL) was added hydrazine hydrate (1.402 g, 43.74 mmol, 5.0 equiv.) at room temperature. The reaction mixture was heated at 70° C. and stirred for 12 h. After complete consumption of the starting material (monitored by TLC), the reaction mixture was concentrated under reduced pressure to obtain crude product (0.740 g, crude). The crude product was as such used for next reaction without carried out further purification.

Step-3: Synthesis of 2-(difluoromethyl)-5-(5-fluoro-6-methylpyridin-3-yl)-1,3,4-oxadiazole: To a stirred solution of methyl 5-fluoro-6-methylnicotinohydrazide (0.740 g, 4.374 mmol, 1.0 equiv.) in DCM (50 mL) was added imidazole (0.893 g, 13.12 mmol, 3.0 equiv.) at room temperature for 15 min. To the resulting reaction mixture was added DFAA (2.28 g, 13.12 mmol) at 0° C. temperature. The reaction mixture was heated at 50° C. and stirred for 16 h. After complete consumption of the starting material (monitored by TLC), the reaction mixture was diluted with water (10 mL) and extracted with DCM (3×20 mL). The combined organic layer was washed with brine solution (20 mL), dried over anhydrous $Na_2SO_4$ and concentrated under reduced pressure to obtain crude product. The crude product was purified by Combi Flash column chromatography using ethyl acetate: n-heptane (30%) to afford 2-(difluoromethyl)-5-(5-fluoro-6-methylpyridin-3-yl)-1,3,4-oxadiazole (1.788 g, 89.4%, from 2 steps) as an off white solid.

Step-4: Synthesis of 2-(6-(bromomethyl)-5-fluoropyridin-3-yl)-5-(difluoromethyl)-1,3,4-oxadiazole (Int-K): To a stirred solution of methyl 5-fluoro-6-methylnicotinohydrazide 2-(difluoromethyl)-5-(5-fluoro-6-methylpyridin-3-yl)-1,3,4-oxadiazole (0.900 g, 3.927 mmol, 1.0 equiv.) in DCE (18 mL) was added NBS (2.10 g, 23.56 mmol, 6.0 equiv.) followed by AIBN (0.322 g, 1.963 mmol, 0.5 equiv.) at room temperature for 15 min. The reaction mixture was heated at 80° C. and stirred for 12 h. After complete consumption of the starting material (monitored by TLC), the reaction mixture was diluted with water (30 mL) and extracted with ethyl acetate (3×20 mL). The combined organic layer was washed with brine solution (30 mL), dried over anhydrous $Na_2SO_4$ and concentrated under reduced pressure to obtain crude product. The crude product was purified by CombiFlash column chromatography using ethyl acetate: n-heptane (30%) to afford 2-(6-(bromomethyl)-5-fluoropyridin-3-yl)-5-(difluoromethyl)-1,3,4-oxadiazole (Int-K, 0.600 g, 44%, 7, 550 mg, 35%) as an off white solid. LC-MS: m/z=309.6. $^1H$ NMR (400 MHz, $CDCl_3$) δ ppm 9.12 (s, 1H), 8.13 (br. d, J=8.80 Hz, 1H), 6.76-7.10 (m, 1H), 4.66 (s, 3H).

Step-5: Synthesis of 2-(6-(bromomethyl)-5-fluoropyridin-3-yl)-5-(difluoromethyl)-1,3,4-oxadiazole (Int-K): To a stirred solution of 2-(6-(dibromomethyl)-5-fluoropyridin-3-yl)-5-(difluoromethyl)-1,3,4-oxadiazole (0.370 g, 0.953 mmol, 1.0 equiv.) in THF (10 mL) was added DIPEA (0.246 g, 1.907 mmol, 2.0 equiv.) followed by Diethyl phosphate (263.1 g, 1.907 mmol, 1.907 equiv.) at 0° C. temperature. The resulting reaction mixture was allowed to attain room temperature and stirred for 1 h. After complete consumption of the starting material (monitored by TLC), the reaction mixture was diluted with water (10 mL) and extracted with ethyl acetate (3×15 mL). Organic layer was washed with brine solution (10 mL), dried over anhydrous $Na_2SO_4$ and concentrated under reduced pressure to obtain crude product. The crude product was purified by CombiFlash column chromatography using ethyl acetate: n-heptane (30%) to afford 2-(6-(bromomethyl)-5-fluoropyridin-3-yl)-5-(difluoromethyl)-1,3,4-oxadiazole (Int-K, 0.687 g, 72.3%) as an off white solid. LC-MS: m/z=310.11; $^1H$ NMR (400 MHz, $CDCl_3$) δ ppm 9.12 (s, 1H), 8.13 (d, J=8.80 Hz, 1H), 6.76-7.10 (m, 1H), 4.66 (s, 3H).

2-(Difluoromethyl)-5-(5-fluoro-6-((naphthalen-2-yloxy) methyl) pyridin-3-yl)-1,3,4-oxadiazole (182)

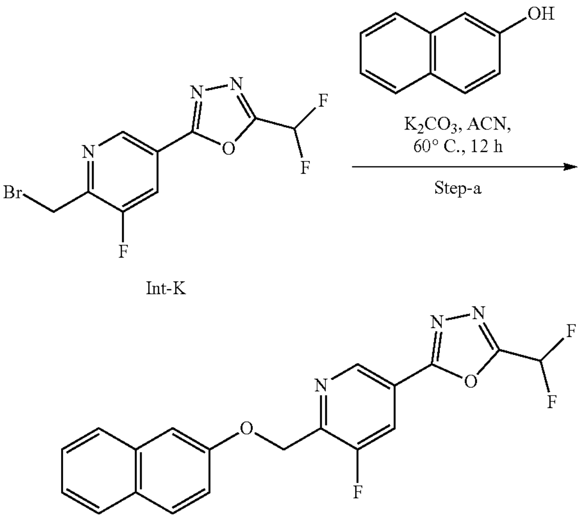

Int-K

182

2-(difluoromethyl)-5-(5-fluoro-6-((naphthalen-2-yloxy) methyl) pyridin-3-yl)-1,3,4-oxadiazole (182): To a stirred solution of naphthalen-2-ol (47 mg, 0.324 mmol, 1.0 equiv.) in acetonitrile (5 mL) was added $K_2CO_3$ (113 mg, 0.817 mmol, 2.5 equiv.) followed by 2-(difluoromethyl)-5-(5-fluoro-6-((naphthalen-2-yloxy)methyl)pyridin-3-yl)-1,3,4-oxadiazole (Int-K, 100 mg, 0.324 mmol, 1.0 equiv.) at room temperature. The reaction mixture was heated at 60° C. and stirred for 12 h. After complete consumption of the starting material (monitored by TLC), the reaction mixture was cooled to room temperature and concentrated under reduced pressure. The residue obtained was diluted with water (10 mL) and aqueous layer extracted with ethyl acetate (3×10 mL). The combined organic layer was washed with brine solution (10 mL), dried over anhydrous $Na_2SO_4$ and concentrated under reduced pressure to obtain crude product. The crude product was purified by CombiFlash column chromatography using ethyl acetate: n-hexane (30%) to afford 2-(difluoromethyl)-5-[5-fluoro-6-(2-naphthyloxymethyl)-3-pyridyl]-1,3,4-oxadiazole (182, 70.0 mg, 40%) as an off white solid. $^1H$ NMR (400 MHz, DMSO-$d_6$) δ ppm 9.12 (d, J=1.13 Hz, 1H), 8.45-8.51 (m, 1H), 7.79-7.88 (m, 3H), 7.44-7.73 (m, 3H), 7.34-7.40 (m, 1H), 7.25 (dd, J=8.80, 2.40 Hz, 1H), 5.48 (br. s, 2H). $^{19}F$ NMR (400 MHz, DMSO-$d_6$): δ −120.75; −123.29. LC-MS: m/z=371.9 [M+H]. HPLC: 99.56% at 9.207 min.

2-(Difluoromethyl)-5-(5-fluoro-6-((quinazolin-6-yloxy)methyl)pyridin-3-yl)-1,3,4-oxadiazole (181)

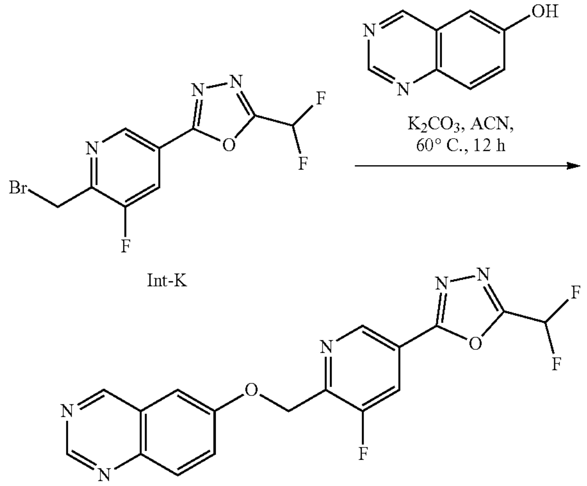

Int-K

181

Synthesis of 2-(difluoromethyl)-5-(5-fluoro-6-((quinazolin-6-yloxy)methyl)pyridin-3-yl)-1,3,4-oxadiazole (181): To a stirred solution of quinazolin-6-ol (47 mg, 0.321 mmol, 1.0 equiv.) in acetonitrile (5 mL) was added $K_2CO_3$ (112 mg, 0.400 mmol, 1.20 equiv.) followed by 2-(6-(bromomethyl)-5-fluoropyridin-3-yl)-5-(difluoromethyl)-1,3,4-oxadiazole (Int-K, 100 mg, 0.324 mmol, 1.0 equiv.) at room temperature. The reaction mixture was heated at 60° C. and stirred for 12 h. After complete consumption of the starting material (monitored by TLC), the reaction mixture was cooled to room temperature and concentrated under reduced pressure. The residue obtained was diluted with water (10 mL) and aqueous layer extracted with ethyl acetate (3x10 mL). The combined organic layer was washed with brine solution (10 mL), dried over anhydrous $Na_2SO_4$ and concentrated under reduced pressure to obtain crude product. The crude product was purified by CombiFlash column chromatography using ethyl acetate: n-hexane (30%) to afford 2-(difluoromethyl)-5-(5-fluoro-6-((quinazolin-6-yloxy)methyl)pyridin-3-yl)-1,3,4-oxadiazole (181, 57 mg, 30%) as an off white solid. $^1H$ NMR (400 MHz, DMSO-$d_6$) δ ppm 9.49 (s, 1H), 9.19 (s, 1H), 9.12 (s, 1H), 8.50 (dd, J=10.1, 2.0 Hz, 1H), 7.98 (d, J=9.01 Hz, 1H), 7.46-7.80 (m, 3H), 5.56 (d, J=1.50 Hz, 2H). $^{19}F$ NMR (400 MHz, DMSO-$d_6$): δ −120.75; −123.29. LC-MS: m/z 371.9 [M+H]. HPLC: 99.56% at 9.207 min.

2-(difluoromethyl)-5-(5-fluoro-6-((quinazolin-7-yloxy)methyl)pyridin-3-yl)-1,3,4-oxadiazole (180)

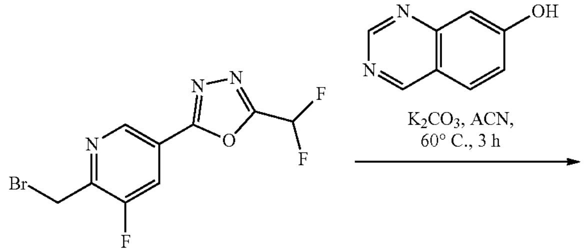

Int-K

-continued

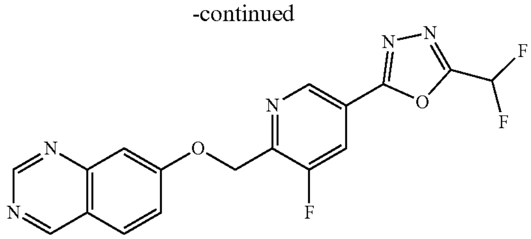

180

Synthesis of 2-(difluoromethyl)-5-(5-fluoro-6-((quinazolin-7-yloxy)methyl)pyridin-3-yl)-1,3,4-oxadiazole (180): To a stirred solution of quinazolin-7-ol (47 mg, 0.321 mmol, 1.0 equiv.) in acetonitrile (5 mL) was added $K_2CO_3$ (113 mg, 0.817 mmol, 2.5 equiv.) followed by 2-(6-(bromomethyl)-5-fluoropyridin-3-yl)-5-(difluoromethyl)-1,3,4-oxadiazole (Int-K, 100 mg, 0.324 mmol, 1.0 equiv.) at room temperature. The reaction mixture was heated at 60° C. and stirred for 12 h. After complete consumption of the starting material (monitored by TLC), the reaction mixture was cooled to room temperature and concentrated under reduced pressure. The residue obtained was diluted with water (10 mL) and aqueous layer extracted with ethyl acetate (3x10 mL). The combined organic layer was washed with brine solution (10 mL), dried over anhydrous $Na_2SO_4$ and concentrated under reduced pressure to obtain crude product. The crude product was purified by Combi Flash column chromatography using ethyl acetate: n-hexane (30%) to afford 2-(difluoromethyl)-5-(5-fluoro-6-((quinazolin-7-yloxy)methyl)pyridin-3-yl)-1,3,4-oxadiazole (180, 65 mg, 55%) as an off white solid. $^1H$ NMR (400 MHz, DMSO-$d_6$) δ ppm 9.44 (s, 1H), 9.18 (s, 1H), 9.12 (s, 1H), 8.51 (dd, J=9.82, 1.69 Hz, 1H), 8.10 (d, J=9.01 Hz, 1H), 7.55-7.75 (m, 2H), 7.40-7.50 (m, 1H), 5.62 (br. s, 2H). $^{19}F$ NMR (400 MHz, DMSO-$d_6$): δ −120.75; −123.29. LC-MS: m/z 374.4 [M+H]. HPLC: 97.51% at 9.483 min 2-(Difluoromethyl)-5-(5-fluoro-6-((quinazolin-5-yloxy)methyl)pyridin-3-yl)-1,3,4-oxadiazole (179)

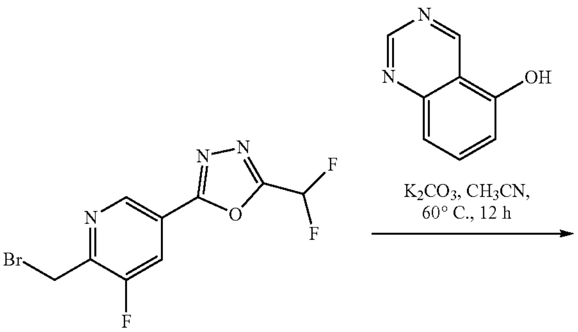

Int-K

-continued

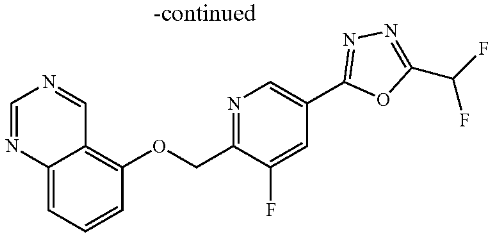

179

Synthesis of 2-(difluoromethyl)-5-(5-fluoro-6-((quinazolin-5-yloxy)methyl)pyridin-3-yl)-1,3,4-oxadiazole (179): To a stirred solution of quinazolin-5-ol (47 mg, 0.321 mmol, 1.0 equiv.) in acetonitrile (5 mL) was added $K_2CO_3$ (112 mg, 0.817 mmol, 2.5 equiv.) followed by 2-(6-(bromomethyl)-5-fluoropyridin-3-yl)-5-(difluoromethyl)-1,3,4-oxadiazole (Int-K, 100 mg, 0.324 mmol, 1.0 equiv.) at room temperature. The reaction mixture was heated at 60° C. and stirred for 12 h. After complete consumption of the starting material (monitored by TLC), the reaction mixture was cooled to room temperature and concentrated under reduced pressure. The residue obtained was diluted with water (10 mL) and aqueous layer extracted with ethyl acetate (3×10 mL). The combined organic layer was washed with brine solution (10 mL), dried over anhydrous $Na_2SO_4$ and concentrated under reduced pressure to obtain crude product. The crude product was purified by Combi Flash column chromatography using ethyl acetate: n-hexane (30%) to afford 2-(difluoromethyl)-5-(5-fluoro-6-((quinazolin-5-yloxy)methyl)pyridin-3-yl)-1,3,4-oxadiazole (179, 37 mg, 30%) as an off white solid. $^1$H NMR (400 MHz, DMSO-$d_6$) δ ppm 9.67 (s, 1H), 9.30 (s, 1H), 9.11 (s, 1H), 8.52 (t, J=32.6, 1H), 8.52 (dd, J=9.82, 1.69 Hz, 1H), 7.47-7.72 (m, 2H), 7.41 (d, J=7.6 Hz, 1H), 5.69 (br. s, 2H). $^{19}$F NMR (400 MHz, DMSO-$d_6$): δ −120.76; −123.10. LC-MS: m/z 374.4 [M+H]. HPLC: 98.83% at 5.611 min.

2-(Difluoromethyl)-5-(5-fluoro-6-(((2-methyl-2H-indazol-5-yl)oxy)methyl)pyridin-3-yl)-1,3,4-oxadiazole (178)

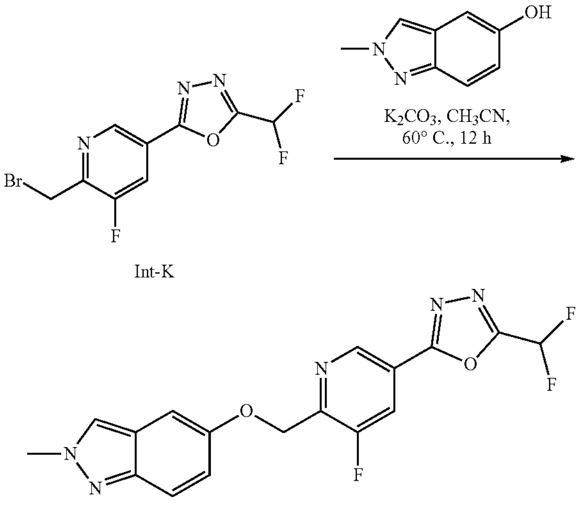

178

Synthesis of 2-(difluoromethyl)-5-(5-fluoro-6-(((2-methyl-2H-indazol-5-yl)oxy)methyl)pyridin-3-yl)-1,3,4-oxadiazole (178): To a stirred solution of 2-methyl-2H-indazol-5-ol (47.12 mg, 0.317 mmol, 1.0 equiv.) in acetonitrile (10 mL) was added $K_2CO_3$ (113 mg, 0.817 mmol, 2.5 equiv.) followed by 2-(6-(bromomethyl)-5-fluoropyridin-3-yl)-5-(difluoromethyl)-1,3,4-oxadiazole (Int-K, 100 mg, 0.324 mmol, 1.0 equiv.) at room temperature. The reaction mixture was heated at 60° C. and stirred for 12 h. After complete consumption of the starting material (monitored by TLC), the reaction mixture was cooled to room temperature and quenched with water (10 mL) and extracted with ethyl acetate (3×10 mL). The combined organic layer was washed with brine solution (10 mL), dried over anhydrous $Na_2SO_4$ and concentrated under reduced pressure to obtain crude product. The crude product was purified by Combi Flash column chromatography using ethyl acetate: n-heptane (30%) to afford 2-(difluoromethyl)-5-(5-fluoro-6-(((2-methyl-2H-indazol-5-yl)oxy)methyl)pyridin-3-yl)-1,3,4-oxadiazole (178, 25 mg, 28%) as an off white solid. $^1$H NMR (400 MHz, DMSO-$d_6$) δ ppm 9.10 (s, 1H), 8.47 (dd, J=1.6 Hz, 11.6 Hz, 1H), 8.17 (s, 1H), 7.47-7.72 (m, 2H), 7.15-7.25 (m, 1H), 6.97 (dd, J=1.0.1 Hz, 1.60 Hz, 1H), 5.69 (br. s, 2H), 4.11 (s, 3H). $^{19}$F NMR (400 MHz, DMSO-$d_6$): δ −120.75; −123.33. LC-MS: m/z 376.6 [M+H]. HPLC: 96.40% at 6.876 min.

6-((5-(5-(difluoromethyl)-1,3,4-oxadiazol-2-yl)-3-fluoropyridin-2-yl)methoxy)-3-methylbenzo[d]isoxazole (137)

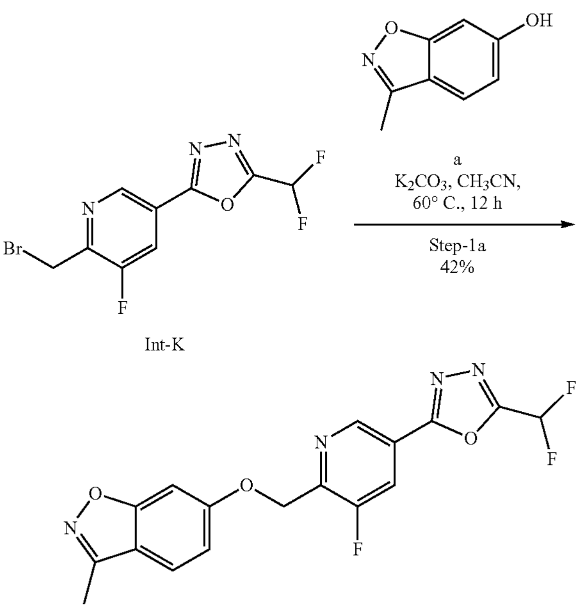

137

Synthesis of 6-((5-(5-(difluoromethyl)-1,3,4-oxadiazol-2-yl)-3-fluoropyridin-2-yl)methoxy)-3-methylbenzo[d]isoxazole (137): To a stirred solution of 3-methyl-1H-isoindol-6-ol (a, 36.4 mg, 0.244 mmol) in acetonitrile (5 mL) was added $K_2CO_3$ (101 mg, 0.733 mmol) followed by 2-[6-(bromomethyl)-5-fluoro-3-pyridyl]-5-(difluoromethyl)-1,3,4-oxadiazole (Int-K, 75 mg, 0.244 mmol) at room temperature. The reaction mixture was heated at 60° C. and stirred for 12 h.

After complete consumption of the starting material (monitored by TLC), the reaction mixture was cooled to room temperature, quenched with water (10 mL) and extracted with ethyl acetate (15 mL). Organic layer was washed with brine (15 mL), dried over anhydrous $Na_2SO_4$ and concentrated under reduced pressure to obtain crude product. The crude product was purified by Prep HPLC to afford 6-((5-(5-(difluoromethyl)-1,3,4-oxadiazol-2-yl)-3-fluoropyridin-2-yl)methoxy)-3-methylbenzo[d]isoxazole (137, 38 mg, 42%) as an off white solid. $^1$H NMR (400 MHz, $CDCl_3$) δ ppm 9.18 (s, 1H), 8.19 (dd, J=9.82, 1.69 Hz, 1H), 7.50 (d, J=8.40 Hz, 1H), 7.15 (s, 1H), 6.82-7.07 (d, J=2.13 Hz, 2H), 5.42 (br. s, 2H), 2.53 (s, 3H). LC-MS: m/z: 377.2 $[M+H]^+$. HPLC: 99.72% at 8.362 min.

2-(difluoromethyl)-5-(5-fluoro-6-(((1-methyl-1H-indazol-5-yl)oxy)methyl)pyridin-3-yl)-1,3,4-oxadiazole (139)

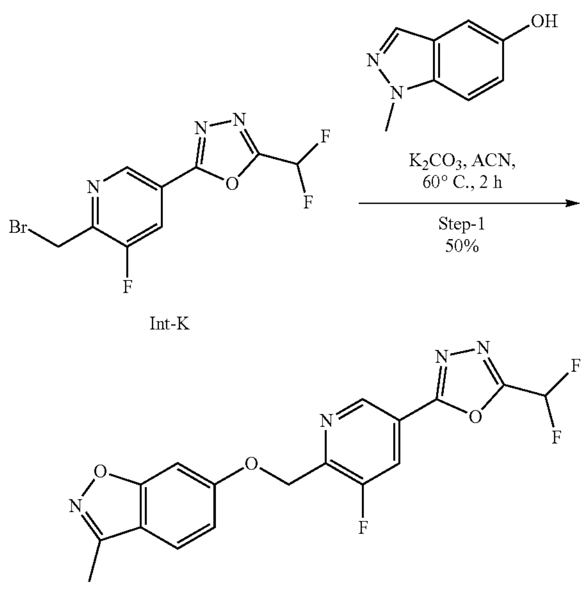

Int-K

139

Synthesis of 2-(difluoromethyl)-5-(5-fluoro-6-(((1-methyl-1H-indazol-5-yl)oxy)methyl)pyridin-3-yl)-1,3,4-oxadiazole (139): To a stirred solution of 1-methyl-1H-indazol-5-ol (36.19 mg, 0.2442 mmol) in acetonitrile (5 mL) was added $K_2CO_3$ (101.28 mg, 0.7328 mmol) followed by 2-(6-(bromomethyl)-5-fluoropyridin-3-yl)-5-(difluoromethyl)-1,3,4-oxadiazole (Int-K, 75 mg, 0.2442 mmol) at room temperature. The reaction mixture was heated at 60° C. and stirred for 2 h. After complete consumption of the starting material (monitored by TLC), the reaction mixture was cooled to room temperature and quenched with water (2 mL) and extracted with ethyl acetate (5 mL). Organic layer was washed with brine (5 mL), dried over anhydrous $Na_2SO_4$ and concentrated under reduced pressure to obtain crude product. The crude product was purified by Combi Flash column chromatography using ethyl acetate: n-heptane (30%) to afford 2-(difluoromethyl)-5-(5-fluoro-6-(((1-methyl-1H-indazol-5-yl)oxy)methyl)pyridin-3-yl)-1,3,4-oxadiazole (139, 61 mg, 50%) as an off white solid. $^1$H NMR (400 MHz, DMSO-$d_6$) δ ppm 9.10 (s, 1H), 8.45 (dd, J=9.82, 1.69 Hz, 1H), 7.92 (d, J=0.75 Hz, 1H), 7.55-7.60 (m, 2H), 7.35 (d, J=2.13 Hz, 1H), 7.13 (dd, J=9.01, 2.38 Hz, 1H), 5.37 (d, J=1.63 Hz, 2H), 4.01 (s, 3H). LC-MS: m/z: 376.44 [M+H]+. HPLC: 98.23% at 8.170 min.

2-(6-(Bromomethyl)pyridin-3-yl)-5-(difluoromethyl)-1,3,4-oxadiazole (Int-I)

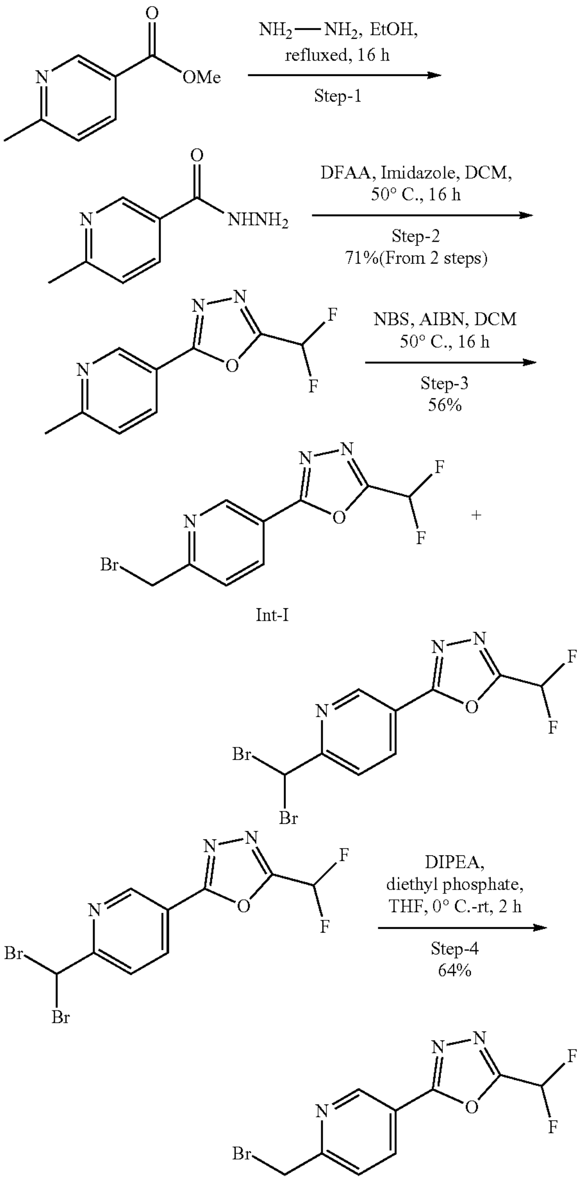

Int-I

Step-1: Synthesis of 6-methylnicotinohydrazide: To a solution of methyl 6-methylnicotinate (50 g, 331.1 mmol, 1.0 equiv.) in ethanol (500 mL) were added hydrazine hydride (53.06 g, 1655.6 mmol, 5.0 equiv.) at room temperature. The resulting reaction mixture was refluxed for 16 h and progress of reaction was monitored by TLC. After completion of reaction, reaction mixture was cooled to room temperature and concentrated under reduced pressure to obtain crude product. The crude product was triturated with diethyl ether 500 mL) to afford 6-methylnicotinohydrazide (2, 50 g, crude) as a white solid. The crude product was as such used for next reaction without carried out further purification.

Step-2: Synthesis of 2-(difluoromethyl)-5-(6-methylpyridin-3-yl)-1,3,4-oxadiazole: To a solution of 6-methylnicotinohydrazide (50 g, 331.1 mmol, 1.0 equiv.) in DCM (1000 mL) were added imidazole (67.62 g, 993.37 mmol, 3.0 equiv.), and DFAA (172.84 g, 993.37 mmol, 3.0 equiv.) at room temperature. The reaction mixture was stirred at 50° C. for 16 h and progress of reaction was monitored by TLC. Reaction mixture was quenched with sat. aq. $NaHCO_3$ solution (500 mL) and aq. layer was extracted with DCM (500 mL×2). The combined organic layer was washed with brine solution (250 mL), dried over anhydrous $Na_2SO_4$ and concentrated under reduced pressure to obtain crude compound as a sticky solid. The crude product was purified by combiFlash column chromatography using an eluent ethyl acetate: heptane (15%) to afford 2-(difluoromethyl)-5-(6-methylpyridin-3-yl)-1,3,4-oxadiazole (45 g, 71%, from 2 steps) as a white solid.

Step-3: Synthesis of 2-(6-(bromomethyl)pyridin-3-yl)-5-(difluoromethyl)-1,3,4-oxadiazole (Int-I): To a solution of 2-(difluoromethyl)-5-(6-methylpyridin-3-yl)-1,3,4-oxadiazole (45 g, 213.2 mmol, 1.0 equiv.) in DCE (450 mL) were added NBS (151.8 g, 426.54 mmol, 2.0 equiv.) followed by AIBN (17.51 mg, 106.4 mmol, 0.5 equiv.) at room temperature. The reaction mixture was stirred at 80° C. for 12 h. The progress of reaction was monitored by TLC, after completion of reaction, the reaction mixture was cooled to room temperature and quenched with water (500 mL) and extracted with DCM (3×500 mL). The combined organic layer was washed with brine solution (500 mL), dried over anhydrous $Na_2SO_4$ and concentrated under reduced pressure to obtain crude product. The crude product was purified by combiFlash column chromatography using an eluent ethyl acetate: n heptane (10%) to afford 2-(6-(bromomethyl)pyridin-3-yl)-5-(difluoromethyl)-1,3,4-oxadiazole (Int-I, 21.0 g, 34%, dibromo byproduct, 25 g, 32%) as an off white solid.

Step-4: Synthesis of 2-(6-(bromomethyl)pyridin-3-yl)-5-(difluoromethyl)-1,3,4-oxadiazole (Int-I): To a stirred solution of 2-(6-(dibromomethyl)pyridin-3-yl)-5-(difluoromethyl)-1,3,4-oxadiazole (20 g, 54.206 mmol, 1.0 equiv.) in THF (200 mL) was added DIPEA (18 mL, 108.3 mmol, 2.0 equiv.) followed by Diethyl phosphate (15 g, 108.6 mmol, 2.0 equiv.) at 0° C. temperature. The resulting reaction mixture was allowed to attain room temperature and stirred for 2 h. After complete consumption of the starting material (monitored by TLC), the reaction mixture was diluted with water (100 mL) and extracted with ethyl acetate (3×100 mL). The combined organic layer was washed with brine solution (100 mL), dried over anhydrous $Na_2SO_4$ and concentrated under reduced pressure to obtain crude product. The crude product was purified by Combi Flash column chromatography using ethyl acetate: n-heptane (30%) to afford 2-(6-(bromomethyl)pyridin-3-yl)-5-(difluoromethyl)-1,3,4-oxadiazole (Int-I, 10 g, 64%) as an off white solid. LC-MS: m/z=291.0 (M+H)+; $^1H$ NMR (400 MHz, $CDCl_3$) δ ppm 9.19 (s, 1H), 8.47 (dd, J=2.4 Hz, 8.0 Hz, 1H), 7.82 (d, J=8.80 Hz, 1H), 7.71 (t, J=47.2 Hz, 1H), 4.80 (s, 2H).

3-((5-(5-(difluoromethyl)-1,3,4-oxadiazol-2-yl)pyridin-2-yl)methoxy)-N-methylbenzamide (197)

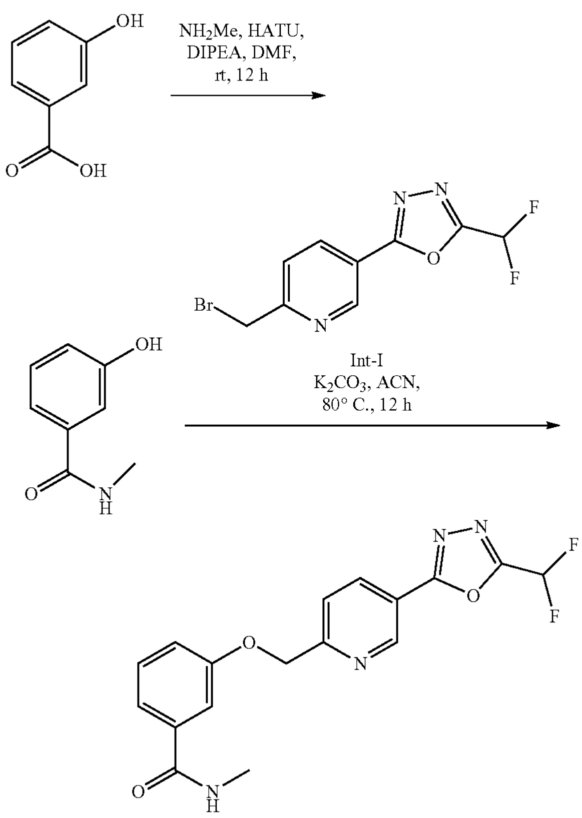

197

Synthesis of 3-hydroxy-N-methylbenzamide: To a stirred solution of 3-hydroxybenzoic acid (500 mg, 3.620 mmol, 1.0 equiv.) in DMF (5 mL) was added DIPEA (3.14 mL, 18.10 mmol, 5.0 equiv.) followed by HATU (2.06 g, 5.430 mmol, 1.5 equiv.) and methyl amine (488 mg, 7.24 mmol, 2.0 equiv.) at room temperature and stirred for 12 h. After complete consumption of the starting material (monitored by TLC), the reaction mixture was quenched with water (5 mL) and extracted with ethyl acetate (10 mL×3). The combined organic layer was washed with brine solution (10 mL), dried over anhydrous $Na_2SO_4$ and concentrated under reduced pressure to obtain crude product. The crude product was purified by Combi Flash column chromatography using ethyl acetate: n-heptane (50%) to afford 3-hydroxy-N-methylbenzamide (2, 546 mg, 98%) as a yellow solid.

Synthesis of 3-((5-(5-(difluoromethyl)-1,3,4-oxadiazol-2-yl)pyridin-2-yl)methoxy)-N-methylbenzamide (197): To a stirred solution of 3-hydroxy-N-methylbenzamide (99 mg, 0.655 mmol, 1.5 equiv.) in acetonitrile (5 mL) was added $K_2CO_3$ (180 mg, 1.310 mmol, 3.0 equiv.) followed by 2-(6-(bromomethyl)pyridin-3-yl)-5-(difluoromethyl)-1,3,4-oxadiazole (Int-I, 100 mg, 0.436 mmol, 1.0 equiv.) at room temperature. The reaction mixture was heated at 80° C. and stirred for 12 h. After complete consumption of the starting material (monitored by TLC), the reaction mixture was cooled to room temperature and quenched with water (10 mL) and extracted with ethyl acetate (3×10 mL). The combined organic layer was washed with brine solution (10 mL), dried over anhydrous $Na_2SO_4$ and concentrated under reduced pressure to obtain crude product. The crude product was purified by Combi Flash column chromatography using ethyl acetate: n-heptane (20%) to afford 3-((5-(5-(difluoromethyl)-1,3,4-oxadiazol-2-yl)pyridin-2-yl)methoxy)-N-methylbenzamide (197, 20 mg, 13%) as an off white solid. $^1H$ NMR (400 MHz, DMSO-$d_6$) δ ppm 9.23 (s, 1H), 8.40-8.52 (m, 2H), 7.70-7.81 (m, 1H), 7.36-7.60 (m, 4H), 7.21 (d, J=8.31 Hz, 1H), 5.37 (s, 2H), 2.77 (d, J=4.40 Hz, 3H). $^{19}F$ NMR (400 MHz, DMSO-$d_6$): δ −121.780; −121.917. LC-MS: m/z 360.8 [M+H]. HPLC: 95.83% at 6.995 min.

3-((5-(1,3,4-oxadiazol-2-yl)pyridin-2-yl)methoxy)-N-phenylbenzamide (196)

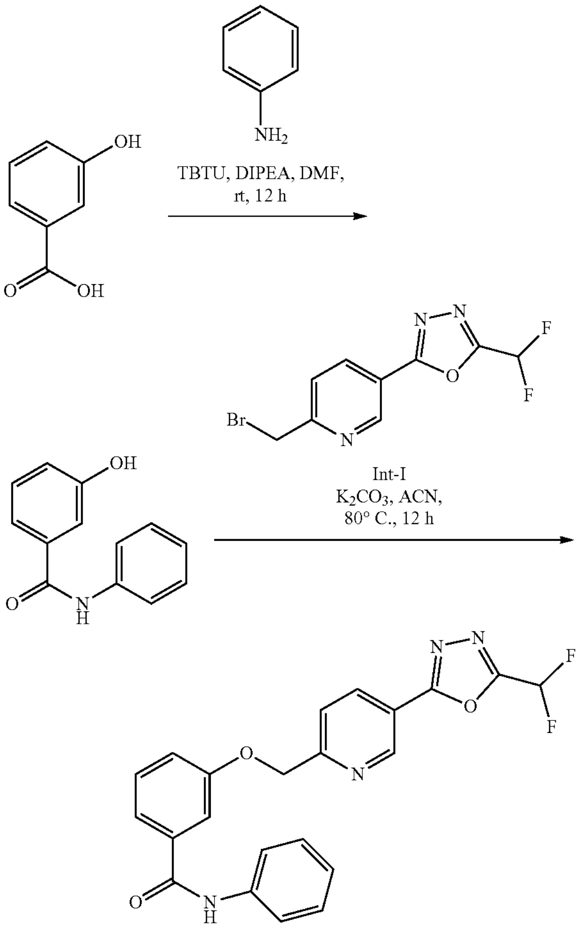

196

Synthesis of 3-hydroxy-N-phenylbenzamide: To a stirred solution of 3-hydroxybenzoic acid (1.0 g, 7.240 mmol, 1.0 equiv.) in DMF (20 mL) was added DIPEA (1.40 mL, 10.86 mmol, 1.5 equiv.) followed by TBTU (3.48 g, 10.86 mmol, 1.5 equiv.) and aniline (2, 674 g, 7.240 mmol, 1.0 equiv.) at room temperature and stirred for 12 h. After complete consumption of the starting material (monitored by TLC), the reaction mixture was quenched with water (10 mL) and extracted with ethyl acetate (3×10 mL). The combined organic layer was washed with brine solution (10 mL), dried over anhydrous $Na_2SO_4$ and concentrated under reduced pressure to afford 3-hydroxy-N-phenylbenzamide (600 mg, crude). The crude product as such used for next reaction without carried out further purification.

Synthesis of 3-((5-(1,3,4-oxadiazol-2-yl)pyridin-2-yl)methoxy)-N-phenylbenzamide (196): To a stirred solution of 3-hydroxy-N-phenylbenzamide (147 mg, 0.690 mmol, 1.0 equiv.) in acetonitrile (5 mL) was added $K_2CO_3$ (143 mg, 1.034 mmol, 1.5 equiv.) followed by 2-(6-(bromomethyl)pyridin-3-yl)-5-(difluoromethyl)-1,3,4-oxadiazole (Int-I, 200 mg, 0.690 mmol, 1.0 equiv.) at room temperature. The reaction mixture was heated at 80° C. and stirred for 12 h. After complete consumption of the starting material (monitored by TLC), the reaction mixture was cooled to room temperature and quenched with water (10 mL) and extracted with ethyl acetate (3×10 mL). The combined organic layer was washed with brine (10 mL), dried over anhydrous $Na_2SO_4$ and concentrated under reduced pressure to obtain crude product. The crude product was purified by reverse phase Prep HPLC to afford 3-((5-(1,3,4-oxadiazol-2-yl)pyridin-2-yl)methoxy)-N-phenylbenzamide (196, 30 mg, 10%) as an off white solid. $^1H$ NMR (400 MHz, DMSO-$d_6$) δ ppm 10.21 (s, 1H), 9.24 (s, 1H), 8.52 (d, J=8.4 Hz, 1H), 7.83 (d, J=8.26, 1H), 7.77 (d, J=8.0 Hz, 2H), 7.58-7.71 (m, 3H), 7.50 (t, J=17.6 Hz, 2H), 7.37 (t, J=16.0 Hz, 1H), 7.30 (d, J=8.0 Hz, 1H), 7.12 (t, J=14.4 Hz, 1H), 5.42 (s, 2H). $^{19}F$ NMR (400 MHz, DMSO-$d_6$): δ −120.653; −120.790. LC-MS: m/z 423.27 [M+H]. HPLC: 98.72% at 8.433 min.

2-(6-(((2-Chloropyridin-4-yl)oxy)methyl)pyridin-3-yl)-5-(difluoromethyl)-1,3,4-oxadiazole (189)

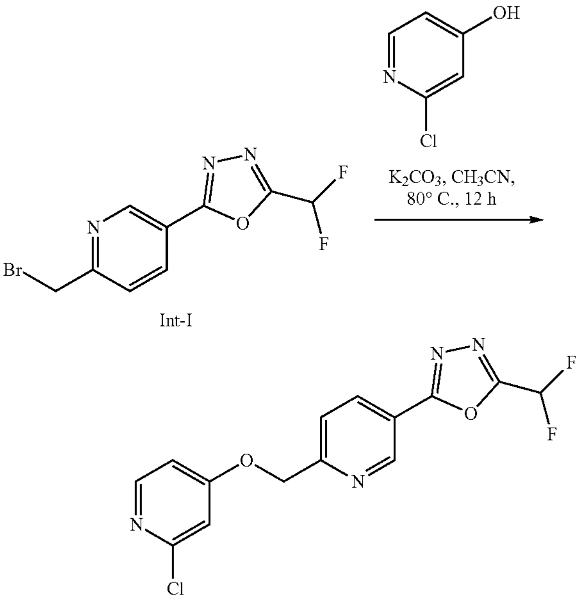

189

Synthesis of 2-(6-(((2-chloropyridin-4-yl)oxy)methyl)pyridin-3-yl)-5-(difluoromethyl)-1,3,4-oxadiazole (189): To a stirred solution of 2-chloropyridin-4-ol (29 mg, 0.218 mmol, 1.0 equiv.) in acetonitrile (5 mL) was added $K_2CO_3$ (91 mg, 0.655 mmol, 3.0 equiv.) followed by 2-(6-(bromomethyl)pyridin-3-yl)-5-(difluoromethyl)-1,3,4-oxadiazole (Int-I, 50 mg, 0.218 mmol, 1.0 equiv.) at room temperature. The reaction mixture was heated at 80° C. and stirred for 12 h. After complete consumption of the starting material (monitored by TLC), the reaction mixture was cooled to room temperature and quenched with water (10 mL) and extracted with ethyl acetate (3×10 mL). The combined organic layer was washed with brine solution (10 mL), dried over anhydrous $Na_2SO_4$ and concentrated under reduced pressure to obtain crude product. The crude product was purified by reverse phase Prep HPLC to afford 2-(6-(((2-chloropyridin-4-yl)oxy)methyl)pyridin-3-yl)-5-(difluoromethyl)-1,3,4-oxadiazole (189, 43 mg, 74%) as an off white solid. $^1$H NMR (400 MHz, DMSO-$d_6$) δ ppm 9.23 (s, 1H), 8.52 (d, J=8.4 Hz, 1H), 8.26 (d, J=8.8 Hz, 1H), 7.80 (d, J=8.0 Hz, 1H), 7.70 (t, J=52.2, 1H), 7.26 (s, 1H), 7.10-7.20 (m, 1H), 5.46 (br. s, 2H). $^{19}$F NMR (400 MHz, DMSO-$d_6$): δ −120.658; −120.795. LC-MS: m/z 339.0 [M+H]. HPLC: 99.62% at 7.864 min.

2-(6-(([1,1'-Biphenyl]-3-yloxy)methyl)pyridin-3-yl)-5-(difluoromethyl)-1,3,4-oxadiazole (188)

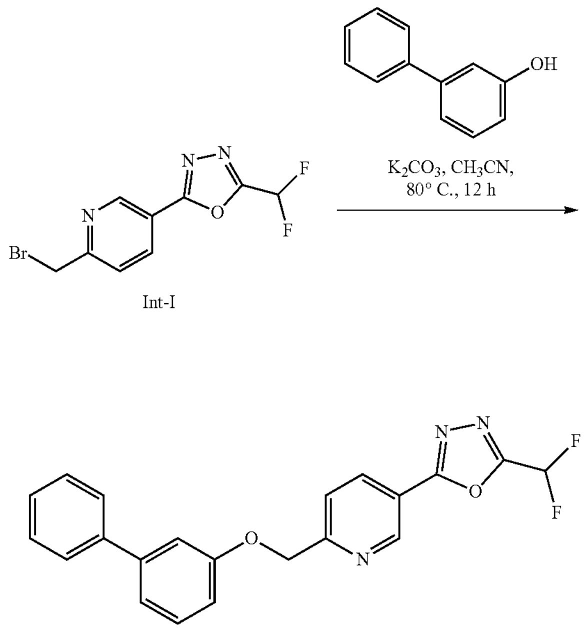

188

Synthesis of 2-(6-(([1,1'-biphenyl]-3-yloxy)methyl)pyridin-3-yl)-5-(difluoromethyl)-1,3,4-oxadiazole (188): To a stirred solution of [1,1'-biphenyl]-3-ol (118 mg, 0.692 mmol, 1.0 equiv.) in acetonitrile (5 mL) was added $K_2CO_3$ (287 mg, 2.076 mmol, 3.0 equiv.) followed by 2-(6-(bromomethyl)pyridin-3-yl)-5-(difluoromethyl)-1,3,4-oxadiazole (Int-I, 200 mg, 0.692 mmol, 1.0 equiv.) at room temperature. The reaction mixture was heated at 80° C. and stirred for 12 h. After complete consumption of the starting material (monitored by TLC), the reaction mixture was cooled to room temperature and quenched with water (10 mL) and extracted with ethyl acetate (3×10 mL). The combined organic layer was washed with brine (10 mL), dried over anhydrous $Na_2SO_4$ and concentrated under reduced pressure to obtain crude product. The crude product was purified by reverse phase Prep HPLC to afford 2-(6-(([1,1'-biphenyl]-3-yloxy)methyl)pyridin-3-yl)-5-(difluoromethyl)-1,3,4-oxadiazole (188, 132 mg, 73%) as an off white solid. $^1$H NMR (400 MHz, $CDCl_3$) δ ppm 9.33 (d, J=1.50 Hz, 1H), 8.43 (dd, J=8.25, 2.25 Hz, 1H), 7.80 (dd, J=8.25, 0.63 Hz, 1H), 7.56-7.60 (m, 2H), 7.41-7.47 (m, 2H), 7.33-7.40 (m, 2H), 7.22-7.27 (m, 2H), 6.80-7.08 (m, 2H), 5.37 (s, 2H). $^{19}$F NMR (400 MHz, DMSO-$d_6$): δ −119.14. LC-MS: m/z 380.35 [M+H]. HPLC: 98.50% at 9.384 min.

2-(6-(([1,1'-biphenyl]-2-yloxy)methyl)pyridin-3-yl)-5-(difluoromethyl)-1,3,4-oxadiazole (187)

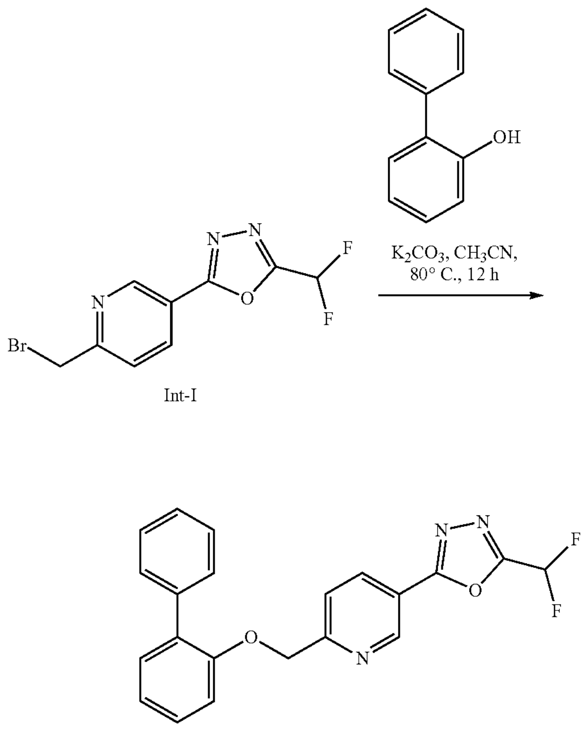

187

Synthesis of 2-(6-(([1,1'-biphenyl]-2-yloxy)methyl)pyridin-3-yl)-5-(difluoromethyl)-1,3,4-oxadiazole (187): To a stirred solution of [1,1'-biphenyl]-2-ol (29 mg, 0.170 mmol, 1.0 equiv.) in acetonitrile (5 mL) was added $K_2CO_3$ (71 mg, 0.513 mmol, 3.0 equiv.) followed by 2-(6-(bromomethyl)pyridin-3-yl)-5-(difluoromethyl)-1,3,4-oxadiazole (Int-I, 50 mg, 0.172 mmol, 1.0 equiv.) at room temperature. The reaction mixture was heated at 80° C. and stirred for 12 h. After complete consumption of the starting material (monitored by TLC), the reaction mixture was cooled to room temperature and quenched with water (10 mL) and extracted with ethyl acetate (3×10 mL). The combined organic layer was washed with brine (10 mL), dried over anhydrous $Na_2SO_4$ and concentrated under reduced pressure to obtain crude product. The crude product was purified by CombiFlash column chromatography using ethyl acetate: n-heptane (20%) to afford 2-(6-(([1,1'-biphenyl]-2-yloxy)methyl)pyridin-3-yl)-5-(difluoromethyl)-1,3,4-oxadiazole (187, 23 mg, 34%) as an off white solid. $^1$H NMR (400 MHz, DMSO-$d_6$) δ ppm 9.21 (s, 1H), 8.45 (dd, J=8.4 Hz, 2.4 Hz, 1H), 7.41-7.70 (m, 6H), 7.30-7.40 (m, 3H), 7.19 (d, J=8.04 Hz, 1H), 7.0-7.10 (m, 1H), 5.33 (s, 2H). $^{19}$F NMR (400 MHz, DMSO-$d_6$): δ −121.87. LC-MS: m/z 380.38 [M+H]. HPLC: 99.87% at 9.486 min.

2-(Difluoromethyl)-5-(6-(((2-phenylpyridin-4-yl) oxy)methyl)pyridin-3-yl)-1,3,4-oxadiazole (186)

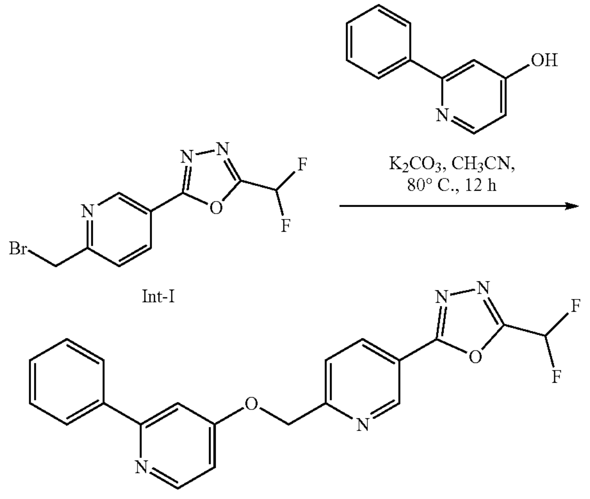

186

Synthesis of 2-(difluoromethyl)-5-(6-(((2-phenylpyridin-4-yl)oxy)methyl)pyridin-3-yl)-1,3,4-oxadiazole (186): To a stirred solution of 2-phenylpyridin-4-ol (59 mg, 0.344 mmol, 1.9 equiv.) in acetonitrile (5 mL) was added $K_2CO_3$ (71 mg, 0.513 mmol, 3.0 equiv.) followed by 2-(6-(bromomethyl)pyridin-3-yl)-5-(difluoromethyl)-1,3,4-oxadiazole (Int-I, 50 mg, 0.172 mmol, 1.0 equiv.) at room temperature. The reaction mixture was heated at 80° C. and stirred for 12 h. After complete consumption of the starting material (monitored by TLC), the reaction mixture was cooled to room temperature and quenched with water (10 mL) and extracted with ethyl acetate (3×10 mL). The combined organic layer was washed with brine solution (10 mL), dried over anhydrous $Na_2SO_4$ and concentrated under reduced pressure to obtain crude product. The crude product was purified by reverse phase Prep HPLC to afford 2-(6-(([1,1'-biphenyl]-2-yloxy)methyl)pyridin-3-yl)-5-(difluoromethyl)-1,3,4-oxadiazole (186, 22 mg, 34%) as an off white solid. $^1$H NMR (400 MHz, DMSO-$d_6$) δ ppm 9.27 (s, 1H), 8.35-8.45 (m, 2H), 8.09-8.15 (m, 2H), 7.80-7.90 (m, 1H), 7.41-7.70 (m, 5H), 7.05-7.15 (m, 1H), 5.53 (s, 2H). $^{19}$F NMR (400 MHz, DMSO-$d_6$): δ −121.85. LC-MS: m/z 381.39 [M+H]. HPLC: 99.19% at 5.578 min.

2-(6-(([1,1'-Biphenyl]-4-yloxy)methyl)pyridin-3-yl)-5-(difluoromethyl)-1,3,4-oxadiazole (185)

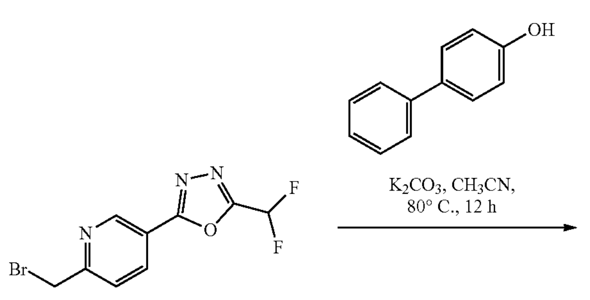

Int-I

-continued

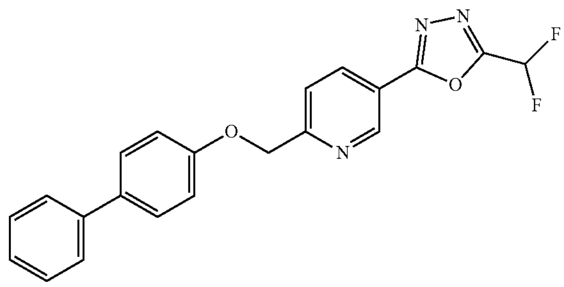

185

Synthesis of 2-(6-(([1,1'-biphenyl]-4-yloxy)methyl)pyridin-3-yl)-5-(difluoromethyl)-1,3,4-oxadiazole (185): To a stirred solution of [1,1'-biphenyl]-4-ol (29 mg, 0.170 mmol, 1.0 equiv.) in acetonitrile (5 mL) was added $K_2CO_3$ (71 mg, 0.513 mmol, 3.0 equiv.) followed by 2-(6-(bromomethyl)pyridin-3-yl)-5-(difluoromethyl)-1,3,4-oxadiazole (Int-I, 50 mg, 0.172 mmol, 1.0 equiv.) at room temperature. The reaction mixture was heated at 80° C. and stirred for 12 h. After complete consumption of the starting material (monitored by TLC), the reaction mixture was cooled to room temperature and quenched with water (5 mL) and extracted with ethyl acetate (3×10 mL). The combined organic layer was washed with brine solution (5 mL), dried over anhydrous $Na_2SO_4$ and concentrated under reduced pressure to obtain crude product. The crude product was purified by CombiFlash column chromatography using ethyl acetate: n-heptane (20%) to afford 2-(6-2-(6-(([1,1'-biphenyl]-4-yloxy)methyl)pyridin-3-yl)-5-(difluoromethyl)-1,3,4-oxadiazole (185, 23 mg, 34%) as an off white solid. $^1$H NMR (400 MHz, DMSO-$d_6$) δ ppm 9.24 (br. s, 1H), 8.51 (dd, J=9.6 Hz, 2.0 Hz, 1H), 7.78-7.88 (m, 1H), 7.58-7.70 (m, 5H), 7.40-7.50 (m, 2H), 7.28-7.38 (m, 1H), 7.10-7.20 (m, 2H), 5.37 (s, 2H). $^{19}$F NMR (400 MHz, DMSO-$d_6$): δ −120.70. LC-MS: m/z 380.2 [M+H]. HPLC: 99.46% at 9.667 min.

2-(6-(([1,2,4]triazolo[4,3-a]pyridin-7-yloxy)methyl) pyridin-3-yl)-5-(difluoromethyl)-1,3,4-oxadiazole (184)

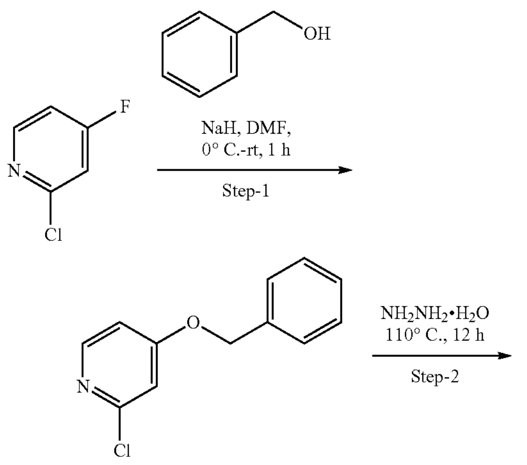

-continued

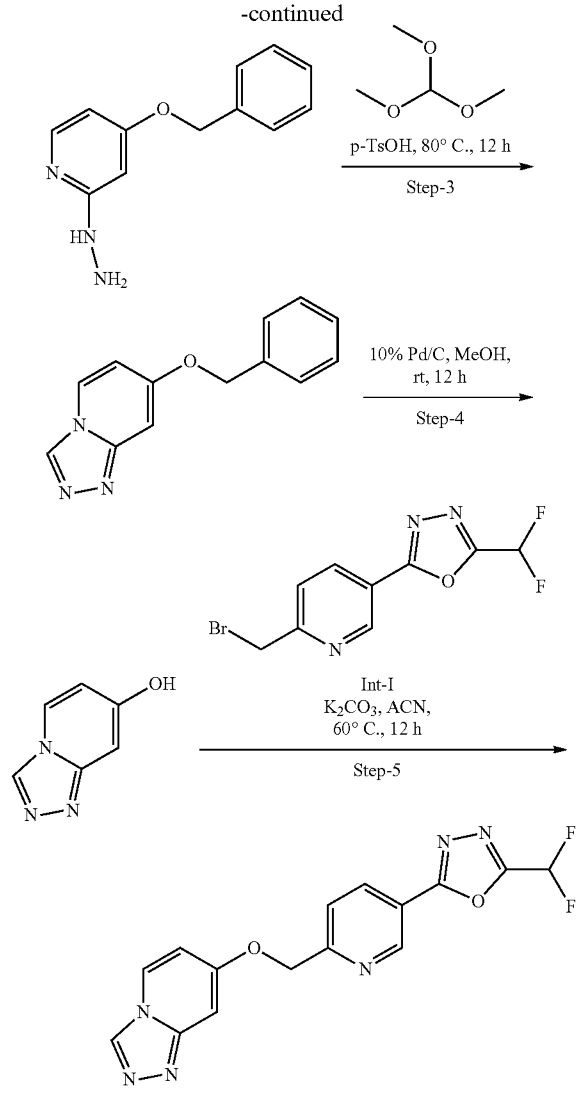

184

Step-1: Synthesis of 4-(benzyloxy)-2-chloropyridine: To a stirred solution of phenylmethanol (4 g, 40 mmol) in DMF (100 mL, 1290 mmol) was added Sodium hydride (1.3 g, 49 mmol, 1.2 eq) followed by 2-chloro-4-fluoro-pyridine (1, 5 g, 38.011 mmol, 0.95 eq) at 0° C. and stirred for 5 min. The reaction mixture was allowed to attain room temperature and stirred for 30 min. After complete consumption of the starting material (monitored by TLC), the reaction mixture quenched with water (100 mL) and extracted with ethyl acetate (3×50 mL). The combined organic layer was washed with brine solution (50 mL), dried over anhydrous $Na_2SO_4$ and concentrated under reduced pressure to obtain crude product. The crude product was purified by CombiFlash column chromatography using ethyl acetate: n-heptane (15%) to afford 4-(benzyloxy)-2-chloropyridine (4.7 g, 57%) as an off white solid.

Step-2: Synthesis of 4-(benzyloxy)-2-hydrazinylpyridine: To a stirred solution of 4-benzyloxy-2-chloro-pyridine (500 mg, 2.2761 mmol, 1 eq) in pyridine (5 mL) was added Hydrazine solution (17.7 mg, 11.38 mmol, 5 eq) at room temperature. The reaction mixture was heated at 110° C. for 24 h. After complete consumption of the starting material (monitored by TLC), the reaction mixture was concentrated under reduced pressure to afford (4-benzyloxy-2-pyridyl) hydrazine (400 mg, crude). The crude product as such used for next reaction without carried out further purification.

Step-3: Synthesis of 7-(benzyloxy)-[1,2,4] triazolo[4,3-a] pyridine: To a stirred solution of (4-benzyloxy-2-pyridyl) hydrazine (4, 400 mg, 1.858 mmol, 1 eq) in trimethoxy methane (5, 5 mL) was added P-toluene sulfonic acid (360 mg, 2.102 mmol, 1.1 eq) at room temperature and stirred for 5 min. The reaction mixture was heat 80° C. for 12 h. After complete consumption of the starting material (monitored by TLC), the reaction mixture quenched with water (20 mL) and extracted with ethyl acetate (3×20 mL). The combined organic layer was washed with brine solution (15 mL), dried over anhydrous $Na_2SO_4$ and concentrated under reduced pressure to afford 7-(benzyloxy)-[1,2,4] triazolo[4,3-a] pyridine (6, 200 mg, crude) as an off white solid. The crude product as such used for next reaction without carried out further purification.

Step-4: Synthesis of [1,2,4] triazolo[4,3-a] pyridin-7-ol: To a stirred solution of 7-benzyloxy-[1,2,4]triazolo[4,3-a] pyridine (400 mg, 1.776 mmol, 1 eq) in methanol (5 mL) were added 10% Pd/C (200 mg, 50% wt) under nitrogen at room temperature and stirred for 12 h under hydrogen pressure at 60 psi. After complete consumption of the starting material (monitored by TLC), the reaction mixture was filtered through a pad of Celite and obtained filtrate was concentrated under reduced pressure to afford [1,2,4]triazolo [4,3-a]pyridin-7-ol (200 mg, crude) as an off white solid. The crude product as such used for next reaction without carried out further purification.

Step-5: Synthesis of 2-(6-(([1,2,4]triazolo[4,3-a]pyridin-7-yloxy)methyl)pyridin-3-yl)-5-(difluoromethyl)-1,3,4-oxadiazole (184): To a stirred solution of [1,2,4]triazolo[4,3-a] pyridin-7-ol (7, 280 mg, 2.0722 mmol, 2 eq) in acetonitrile (5 mL) were added $K_2CO_3$ (429 mg, 3.10411 mmol, 3 eq) and 2-[6-(bromomethyl)-3-pyridyl]-5-(difluoromethyl)-1,3,4-oxadiazole (Int-I, 300 mg, 1.0343 mmol, 1 eq) at room temperature. Reaction mixture was heated at 80° C. for 12 h. After complete consumption of the starting material (monitored by TLC), the reaction mixture was cooled to room temperature and concentrated under reduced pressure. The residue obtained was diluted with water (20 mL) and aqueous layer extracted with ethyl acetate (3×20 mL). The combined organic layer was washed with brine solution (20 mL), dried over anhydrous $Na_2SO_4$ and concentrated under reduced pressure to obtain crude product. The crude product was purified by reverse phase Prep HPLC to afford 2-(6-(([1,2,4]triazolo[4,3-a]pyridin-7-yloxy)methyl)pyridin-3-yl)-5-(difluoromethyl)-1,3,4-oxadiazole (184, 10 mg, 3.0%) as an off white solid. $^1$H NMR (400 MHz, DMSO-$d_6$) δ ppm 9.25 (br. s, 1H), 9.06 (br. s, 1H), 8.47-8.57 (m, 2H), 7.85 (d, J=8.4 Hz, 1H), 7.71 (t, J=52.4 Hz, 1H), 7.21 (br. s, 1H), 6.86 (dd, J=2.4 Hz, 10.0 Hz, 1H), 5.44 (s, 2H). $^{19}$F NMR (400 MHz, DMSO-$d_6$): δ −120.70. LC-MS: m/z 345.4 [M+H]. HPLC: 97.99% at 5.219 min.

2-(Difluoromethyl)-5-(6-((pyrazolo[1,5-a]pyrimidin-6-yloxy)methyl)pyridin-3-yl)-1,3,4-oxadiazole (183)

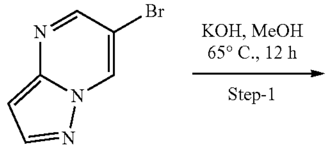

-continued

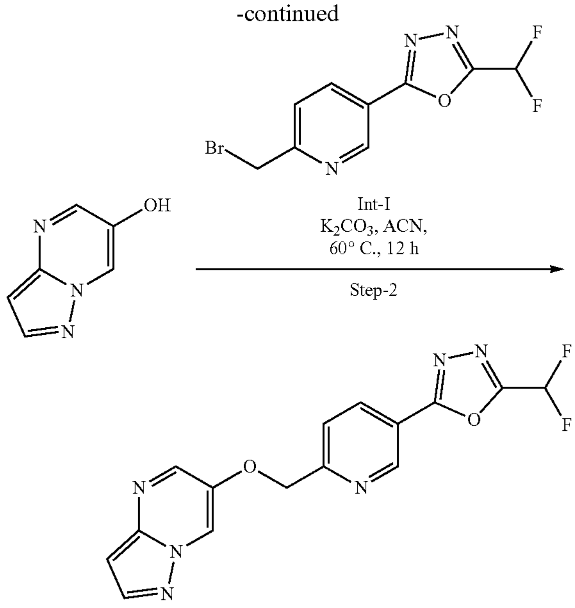

183

Step-1: Synthesis of pyrazolo[1,5-a]pyrimidin-6-ol: To a stirred solution of 6-bromopyrazolo[1,5-a]pyrimidine (150 mg, 0.7575 mmol, 1.0 equiv.) in methanol (6 mL) was added KOH (259 mg, 4.620 mmol, 6.0 equiv.) at 0° C. temperature. The reaction mixture was heated at 65° C. and stirred for 12 h. After complete consumption of the starting material (monitored by TLC), the reaction mixture was quenched with water (20 mL) and extracted with IPA:DCM (3:1, 3×20 mL). The combined organic layer was washed with brine solution (10 mL), dried over anhydrous $Na_2SO_4$ and concentrated under reduced pressure to afford pyrazolo[1,5-a]pyrimidin-6-ol (135 mg, crude). The crude product as such used for next reaction without carried out further purification.

Step-2: Synthesis of 2-(difluoromethyl)-5-(6-((pyrazolo[1,5-a]pyrimidin-6-yloxy)methyl)pyridin-3-yl)-1,3,4-oxadiazole (183): To a stirred solution of pyrazolo[1,5-a]pyrimidin-6-ol (2, 14 mg, 0.1034 mmol, 1.0 equiv.) in acetonitrile (3 mL) was added $K_2CO_3$ (42 mg, 0.3102 mmol, 3.0 equiv.) followed by 2-(6-(bromomethyl)pyridin-3-yl)-5-(difluoromethyl)-1,3,4-oxadiazole (Int-I, 30 mg, 0.1034 mmol, 1.0 equiv.) at room temperature. The reaction mixture was heated at 80° C. and stirred for 12 h. After complete consumption of the starting material (monitored by TLC), the reaction mixture was cooled to room temperature and quenched with water (10 mL) and extracted with ethyl acetate (3×10 mL). The combined organic layer was washed with brine (10 mL), dried over anhydrous $Na_2SO_4$ and concentrated under reduced pressure to obtain crude product. The crude product was purified by reverse phase Prep HPLC to afford 2-(difluoromethyl)-5-(6-((pyrazolo[1,5-a]pyrimidin-6-yloxy)methyl)pyridin-3-yl)-1,3,4-oxadiazole (183, 20 mg, 56%) as an off white solid. $^1$H NMR (400 MHz, DMSO-$d_6$) δ ppm 9.30-9.40 (m, 1H), 8.49-8.59 (m, 2H), 8.30-8.40 (m, 1H), 8.4 (s, 1H), 7.79 (dd, J=0.4 Hz, 8.8 Hz, 1H), 7.08 (t, J=51.6 Hz, 1H), 6.69 (dd, J=0.8 Hz, 2.4 Hz, 1H), 5.32 (s, 2H). $^{19}$F NMR (400 MHz, DMSO-$d_6$): δ −120.667, −120.804. LC-MS: m/z 345.3 [M+H]. HPLC: 96.29% at 6.997 min.

4-((5-(5-(Difluoromethyl)-1,3,4-oxadiazol-2-yl)pyridin-2-yl)methoxy)benzonitrile (118) & 4-((5-(5-(Difluoromethyl)-1,3,4-oxadiazol-2-yl)pyridin-2-yl)methoxy)benzonitrile (214)

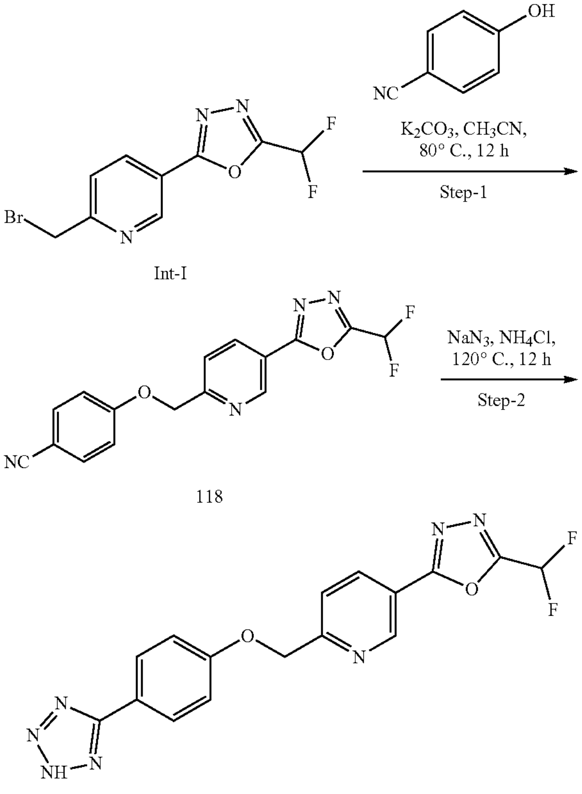

Int-I

118

214

Step-1: Synthesis of 4-((5-(5-(difluoromethyl)-1,3,4-oxadiazol-2-yl)pyridin-2-yl)methoxy)benzonitrile (118): To a stirred solution of 4-hydroxybenzonitrile (206 mg, 1.730 mmol, 1.0 equiv.) in acetonitrile (5 mL) was added $K_2CO_3$ (710 mg, 5.190 mmol, 3.0 equiv.) at room temperature and stirred for 5 min. To the resulting reaction mixture was added 2-(6-(bromomethyl)pyridin-3-yl)-5-(difluoromethyl)-1,3,4-oxadiazole (Int-I, 500 mg, 1.730 mmol, 1.0 equiv.) at room temperature. The reaction mixture was heated at 60° C. and stirred for 12 h. The progress of reaction was monitored by TLC. After completion of reaction, reaction mixture was cooled to room temperature, quenched with ice cold water (30 mL) and extracted with ethyl acetate (3×30 mL). The combined organic layer was washed with brine solution (30 mL), dried over anhydrous $Na_2SO_4$ and concentrated under reduced pressure to obtain crude product. The crude product was purified by Crude product was purified by combiflash column chromatography using 20% ethyl acetate in n heptane to afford 118 (190 mg, 34%) as off white solid.

Step-2: Synthesis of 4-((5-(5-(difluoromethyl)-1,3,4-oxadiazol-2-yl)pyridin-2-yl)methoxy)benzonitrile (214): To a solution of 4-((5-(5-(difluoromethyl)-1,3,4-oxadiazol-2-yl)pyridin-2-yl)methoxy)benzonitrile (118, 200 mg, 0.6092 mmol, 1 equiv.) in DMF (5 mL) were added $NaN_3$ (118 mg, 1.815 mmol, 3 equiv.), $NH_4Cl$ (97.84 mg, 1.829 mmol, 3 equiv.) and lithium chloride (25 mg, 0.609 mmol, 1 equiv.) at room temperature. The reaction mixture was heated at 120° C. for 12 h. After complete consumption of the starting material (monitored by TLC), the reaction mixture was cooled to room temperature and concentrated under reduced pressure to obtain crude product. The crude product was purified by reverse phase Prep HPLC to afford 4-((5-(5-(difluoromethyl)-1,3,4-oxadiazol-2-yl)pyridin-2-yl)methoxy)benzonitrile (214, 65 mg, 29%) as an off white solid. $^1$H NMR (400 MHz, DMSO-$d_6$) δ ppm 9.23 (s, 1H), 8.49 (d, J=8.31 Hz, 1H), 7.89 (d, J=8.31 Hz, 2H), 7.80 (d, J=8.31 Hz, 1H), 7.43-7.72 (m, 2H), 7.06 (d, J=8.31 Hz, 2H), 5.34 (s, 2H). $^{19}$F NMR (400 MHz, DMSO-$d_6$): δ −120.674; −120.809. LC-MS: m/z 372.24 [M+H]. HPLC: 98.17% at 6.002 min.

3-((5-(5-(Difluoromethyl)-1,3,4-oxadiazol-2-yl)pyridin-2-yl)methoxy)-6-methyl-4,5,6,7-tetrahydroisoxazolo[5,4-c]pyridine (191)

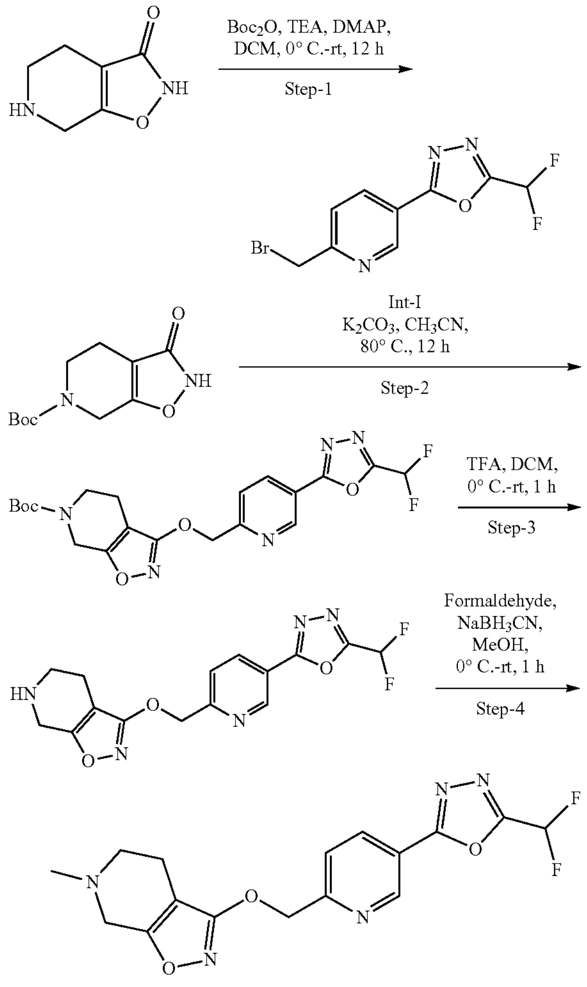

191

Step-1: Synthesis of tert-butyl 3-oxo-3,4,5,7-tetrahydroisoxazolo[5,4-c]pyridine-6(2H)-carboxylate: To a solution of 4,5,6,7-tetrahydroisoxazolo[5,4-c]pyridin-3(2H)-one (250 mg, 1.785 mmol, 1 equiv.) in DCM (10 mL) were added triethylamine (450 mg, 4.460 mmol, 2.5 equiv.), DMAP (75.6 mg, 0.178 mmol, 0.1 equiv.) at 0° C. temperature and stirred for 5 min. to the resulting reaction mixture was added Boc anhydride (427 mg, 1.96 mmol, 1.1 equiv.) at same temperature. The resulting reaction mixture was allowed to attain room temperature and stirred for 12 h. After complete consumption of the starting material (monitored by TLC), the reaction mixture was quenched with water (20 mL) and extracted with ethyl acetate (3×20 mL). The combined organic layer was washed with brine solution (20 mL), dried over anhydrous $Na_2SO_4$ and concentrated under reduced pressure to obtain crude product. The crude product was purified by combiFlash column chromatography using 20% ethyl acetate in n heptane to afford tert-butyl 3-oxo-3,4,5,7-tetrahydroisoxazolo[5,4-c]pyridine-6(2H)-carboxylate (240 mg, 56%) as an off white solid.

Step-2: Synthesis of tert-butyl 3-((5-(5-(difluoromethyl)-1,3,4-oxadiazol-2-yl)pyridin-2-yl)methoxy)-4,7-dihydroisoxazolo[5,4-c]pyridine-6(5H)-carboxylate: To a solution of tert-butyl 3-((5-(5-(difluoromethyl)-1,3,4-oxadiazol-2-yl)pyridin-2-yl)methoxy)-4,7-dihydroisoxazolo[5,4-c]pyridine-6(5H)-carboxylate (240 mg, 1.00 mmol, 1 equiv.) and 2-(6-(bromomethyl)pyridin-3-yl)-5-(difluoromethyl)-1,3,4-oxadiazole (Int-I, 290 mg, 1.00 mmol, 1 equiv.) in acetonitrile (10 mL) was added $K_2CO_3$ (414 mg, 3.00 mmol, 3 equiv.) at room temperature and stirred for 5 min. The reaction mixture was heated at 80° C. for 12 h. After complete consumption of the starting material (monitored by TLC), the reaction mixture was cooled to room temperature and quenched with water (20 mL) and extracted with ethyl acetate (3×20 mL). The combined organic layer was washed with brine solution (20 mL), dried over anhydrous $Na_2SO_4$ and concentrated under reduced pressure to obtain crude product. The crude product was purified by reverse phase Prep HPLC to afford tert-butyl 3-((5-(5-(difluoromethyl)-1,3,4-oxadiazol-2-yl)pyridin-2-yl)methoxy)-4,7-dihydroisoxazolo[5,4-c]pyridine-6(5H)-carboxylate (150 mg, 33%) as an off white solid.

Step-3: Synthesis of 3-((5-(5-(difluoromethyl)-1,3,4-oxadiazol-2-yl)pyridin-2-yl)methoxy)-4,5,6,7-tetrahydroisoxazolo[5,4-c]pyridine: To a solution of tert-butyl 3-((5-(5-(difluoromethyl)-1,3,4-oxadiazol-2-yl)pyridin-2-yl)methoxy)-4,7-dihydroisoxazolo[5,4-c]pyridine-6(5H)-carboxylate (150 mg, 0.334 mmol, 1 equiv.) in DCM (5 mL) was added TFA (0.5 mL) at 0° C. and stirred for 5 min. The resulting reaction mixture was allowed to attain room temperature and stirred for 1 h. After complete consumption of the starting material (monitored by TLC), the reaction mixture was concentrated under reduced pressure to afford 3-((5-(5-(difluoromethyl)-1,3,4-oxadiazol-2-yl)pyridin-2-yl)methoxy)-4,5,6,7tetrahydroisoxazolo[5,4-c]pyridine (120 mg, crude). The crude product was as such used for next reaction without carried out further purification.

Step-4: Synthesis of 3-((5-(5-(difluoromethyl)-1,3,4-oxadiazol-2-yl)pyridin-2-yl)methoxy)-6-methyl-4,5,6,7-tetrahydroisoxazolo[5,4-c]pyridine (191): To a stirred solution of 3-[[5-[5-(difluoromethyl)-1,3,4-oxadiazol-2-yl]-2-pyridyl]methoxy]-4,5,6,7-tetrahydroisoxazolo[5,4-c]pyridine (4, 100 mg, 0.286 mmol, 1 equiv.) in methanol (2.5 mL) was added triethylamine (57.87 mg, 0.57 mmol, 2 equiv.) at 0° C. temperature and stirred for 5 min. To the resulting reaction mixture was added formaldehyde (1 mL) and acetic acid (0.02 mL, 0.0286 mmol, 0.1 equiv.) at 0° C. stirred for 5 min. The reaction mixture was allowed to attain room temperature and stirred for 12 h. After 12 h, sodium cyanoborohydride (36 mg, 0.573 mmol, 2 equiv.) was added into the reaction mixture at 0° C. and stirred for 2 h. After complete consumption of the starting material (monitored by TLC), the reaction mixture was quenched with water (20 mL), methanol was concentrated and extracted with ethyl acetate (3×20 mL). The combined organic layer was washed with brine (20 mL), dried over anhydrous $Na_2SO_4$ and concentrated under reduced pressure to obtain crude product. The crude product was purified by reverse phase Prep HPLC to afford 3-((5-(5-(difluoromethyl)-1,3,4-oxadiazol-2-yl)pyridin-2-yl)methoxy)-6-methyl-4,5,6,7-tetrahydroisoxazolo[5,4-c]pyridine (15 mg, 0.041 mmol, 15%) as an off white solid. $^1H$ NMR (400 MHz, DMSO-$d_6$) δ ppm 9.21 (s, 1H), 8.50 (dd, J=2.0 Hz, 10.4 Hz, 1H), 7.76 (d, J=8.8 Hz, 1H), 7.71 (t, J=51.2 Hz, 1H), 5.45 (br. s, 2H), 3.45 (s, 2H), 2.60-2.70 (m, 2H), 2.39-2.49 (m, 2H), 2.35 (s, 3H). $^{19}F$ NMR (400 MHz, DMSO-$d_6$): δ −120.70. LC-MS: m/z 364.1 [M+H]. HPLC: 98.53% at 7.527 min.

2-(Difluoromethyl)-5-(6-((4-(1-methyl-1H-pyrazol-5-yl)phenoxy)methyl)pyridin-3-yl)-1,3,4-oxadiazole (199)

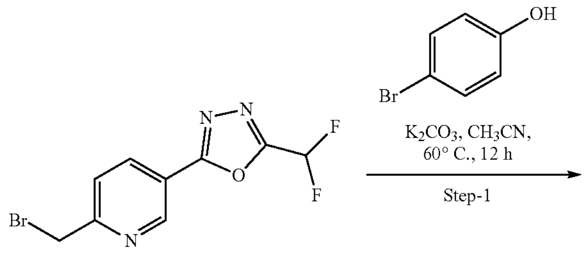

Int-I

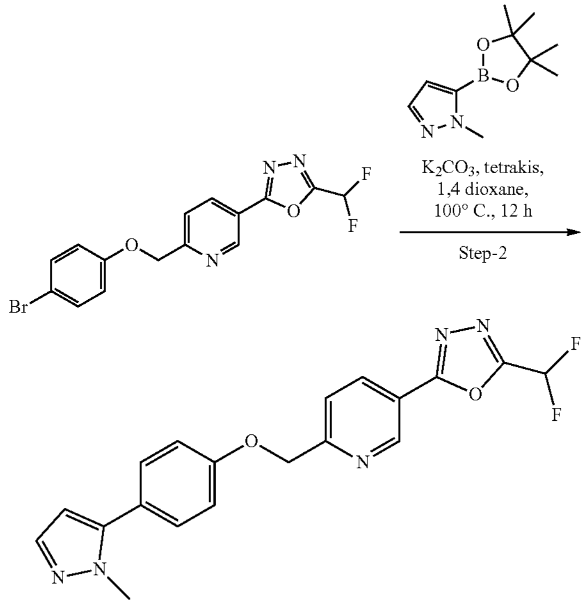

199

Step-1: Synthesis of 2-(6-((4-bromophenoxy)methyl)pyridin-3-yl)-5-(difluoromethyl)-1,3,4-oxadiazole: To a stirred solution of 4-bromophenol (149 mg, 0.8650 mmol, 1.0 equiv.) in acetonitrile (2.5 mL) was added $K_2CO_3$ (358 mg, 2.595 mmol, 3.0 equiv.) followed by 2-(6-(bromomethyl)pyridin-3-yl)-5-(difluoromethyl)-1,3,4-oxadiazole (Int-I, 250 mg, 0.8650 mmol, 1.0 equiv.) at room temperature. The reaction mixture was heated at 60° C. and stirred for 12 h. After complete consumption of the starting material (monitored by TLC), the reaction mixture was cooled to room temperature and quenched with water (20 mL) and extracted with ethyl acetate (3×20 mL). The combined organic layer was washed with brine (20 mL), dried over anhydrous $Na_2SO_4$ and concentrated under reduced pressure to obtain crude product. The crude product was purified by combiflash column chromatography using 0-30% ethyl acetate in n heptane to afford 2-(6-((4-bromophenoxy)methyl)pyridin-3-yl)-5-(difluoromethyl)-1,3,4-oxadiazole (100 mg, 40%) as an off white solid.

Step-2: Synthesis of 2-(difluoromethyl)-5-(6-((4-(1-methyl-1H-pyrazol-5-yl)phenoxy)methyl)pyridin-3-yl)-1,3,4-oxadiazole (199): To a stirred solution of 2-(6-((4-bromophenoxy)methyl)pyridin-3-yl)-5-(difluoromethyl)-1,3,4-oxadiazole (100 mg, 0.2616 mmol, 1.0 equiv.) and 1-methyl-5-(4,4,5,5-tetramethyl-1,3,2-dioxaborolan-2-yl)-1H-pyrazole (3, 65 mg, 0.3139 mmol, 1.2 equiv.) in 1,4 dioxane (10 mL) was added $K_2CO_3$ (108 mg, 0.7850 mmol, 3.0 equiv.) at room temperature and degassed the reaction mixture with argon gas for 10 min. To the resulting reaction mixture was added $Pd(PPh_3)_4$ (30 mg, 0.0261 mmol) at room temperature. The reaction mixture was heated at 100° C. and stirred for 12 h. After complete consumption of the starting material (monitored by TLC), the reaction mixture was cooled to room temperature and filtered through a pad of celite bed. The filtrate obtained was diluted with water (15 mL) and extracted with ethyl acetate (3×15 mL). The combined organic layer was washed with brine solution (15 mL), dried over anhydrous $Na_2SO_4$ and concentrated under reduced pressure to obtain crude product. The crude product was purified by reverse phase Prep HPLC to afford 2-(difluoromethyl)-5-(6-((4-(1-methyl-1H-pyrazol-5-yl)phenoxy)methyl)pyridin-3-yl)-1,3,4-oxadiazole (199, 100 mg, 40%) as an off white solid. $^1H$ NMR (400 MHz, DMSO-$d_6$) δ ppm 9.24 (s, 1H), 8.48-8.53 (m, 1H), 7.81 (d, J=8.31 Hz, 1H), 7.38-7.73 (m, 4H), 7.18 (d, J=8.80 Hz, 2H), 6.33 (s, 1H), 5.39 (s, 2H), 3.82 (s, 3H). LC-MS: m/z 383.93 [M+H]. HPLC: 95.03% at 7.959 min.

2-(difluoromethyl)-5-(6-((imidazo[1,2-a]pyrazin-8-yloxy)methyl)pyridin-3-yl)-1,3,4-oxadiazole (86)

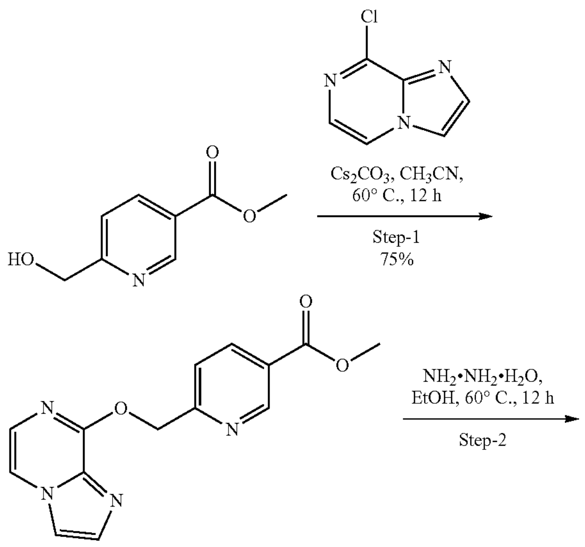

-continued

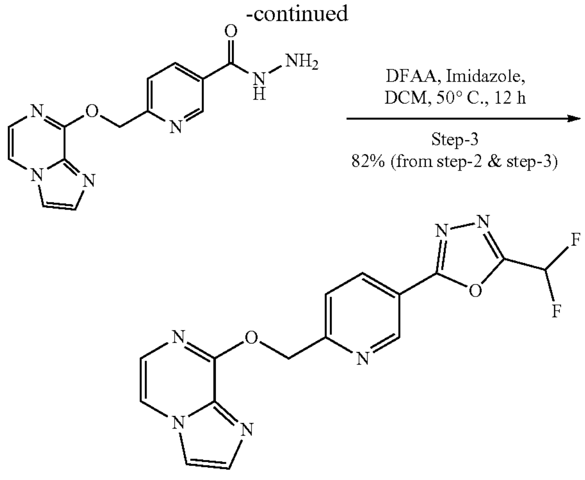

86

Step-1: Synthesis of methyl 6-((imidazo[1,2-a]pyrazin-8-yloxy)methyl)nicotinate: To a solution of (methyl 6-(hydroxymethyl)pyridine-3-carboxylate (5.0 g, 29.91 mmol) in acetonitrile (100 mL) in were added $Cs_2CO_3$ (17.0 g, 52.17 mmol) and 8-chloroimidazo[1,2-a]pyrazine (4.1 g, 27 mmol) at room temperature and stirred for 5 min. The reaction mixture was heated at 60° C. temperature and stirred for 12 h. Progress of reaction was monitored by TLC. After complete consumption of the starting material, the reaction mixture was cooled to room temperature and concentrated under reduced pressure. The residue obtained was dissolved in water (100 mL) and extracted with ethyl acetate (2×250 mL). Organic layer was washed with brine (100 mL), dried over anhydrous $Na_2SO_4$ and concentrated under reduced pressure to obtain crude product. The crude product was purified by Combi Flash column chromatography using methanol in DCM (0-10%) to afford methyl 5-fluoro-6-methylnicotinate (2.70 g, 75%) as an off-white solid. LC-MS: m/z 285.4 [M+H].

Step-2: Synthesis of 6-((imidazo[1,2-a]pyrazin-8-yloxy)methyl)nicotinohydrazide: To a solution of methyl 6-(imidazo[1,2-a]pyrazin-8-yloxymethyl)pyridine-3-carboxylate (4.2 g, 15 mmol) in ethanol (100 mL) were added hydrazine hydride (3.5 g, 110 mmol) at room temperature and stirred for 5 min. The reaction mixture was heated at 70° C. temperature and stirred for 12 h. Progress of reaction was monitored by TLC. After complete consumption of the starting material, the reaction mixture was cooled to room temperature and concentrated under reduced pressure to afford 6-((imidazo[1,2-a]pyrazin-8-yloxy)methyl)nicotinohydrazide (3.6 g, crude). The crude was as such used for next reaction without carried out further purification. LC-MS: m/z 286.0 [M+H].

Step-3: Synthesis of 2-(difluoromethyl)-5-(6-((imidazo[1,2-a]pyrazin-8-yloxy)methyl)pyridin-3-yl)-1,3,4-oxadiazole (86): To a solution of (6-(imidazo[1,2-a]pyrazin-8-yloxymethyl)pyridine-3-carbohydrazide (6.05 g, 21.3 mmol) in DCM (200 mL) were added imidazole (4.34 g, 62.5 mmol) and difluoroacetic anhydride (11.12 g, 54.31 mmol) at 0° C. temperature and stirred for 5 min. The resulting reaction mixture was heated at 50° C. temperature and stirred for 4 h. Progress of reaction was monitored by TLC. After complete consumption of the starting material, the reaction mixture was cooled to room temperature and concentrated under reduced pressure. The residue obtained was dissolved in water (100 mL) and extracted with DCM (2×250 mL). Organic layer was washed with brine (100 mL), dried over anhydrous $Na_2SO_4$ and concentrated under reduced pressure to obtain crude product. The crude product was purified by Combi Flash column chromatography using methanol in DCM (0-5%) to afford methyl 5-fluoro-6-methylnicotinate (86, 6.0 g, 82%, From 2 steps) as an off-white solid. LC-MS: m/z 344.93 [M+H]. $^1H$ NMR (400 MHz, DMSO-$d_6$) δ ppm 9.22 (d, J=1.47 Hz, 1H), 8.48 (dd, J=8.25, 2.14 Hz, 1H), 8.27 (d, J=4.65 Hz, 1H), 8.12 (d, J=0.98 Hz, 1H), 7.69-7.77 (m, 2H), 7.37-7.59 (m, 2H), 5.74 (s, 2H). HPLC=97.54%, RT=6.815 min.

The following compounds were prepared in a manner analogous to that used for preparing compound (86).

| Compound | Structure/Name | Characterization |
| --- | --- | --- |
| 25 | 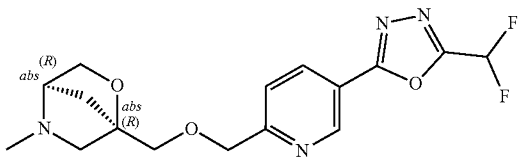 (1R,4R)-1-[[5-[5-(difluoromethyl)-1,3,4-oxadiazol-2-yl]-2-pyridyl]methoxymethyl]-5-methyl-2-oxa-5-azabicyclo[2.2.1]heptane | $^1$HNMR (400 MHz, METHANOL-d4) δ ppm 9.18-9.24 (m, 1H) 8.53 (d, J = 8.25, 2.25 Hz, 1H) 7.80 (d, J = 8.25 Hz, 1H) 7.27 (s, 1H) 4.81 (s, 2H) 4.16 (d, J = 8.63 Hz, 1H) 3.90-4.00 (m, 2H) 3.84 (d, J = 8.50, 1.75 Hz, 1H) 3.70 (s, 1H) 3.07 (d, J = 10.51 Hz, 1H) 2.92 (d, J = 10.51 Hz, 1H) 2.60 (s, 3H) 2.09 (d, J = 9.76 Hz, 1H) 1.92 (d, J = 10.51 Hz, 1H). MS (ESI): 253 $[M + H]^+$ |
| 109 | 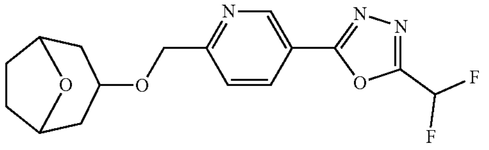 2-(difluoromethyl)-5-[6-(8-oxabicyclo[3.2.1]octan-3-yloxymethyl)-3-pyridyl]-1,3,4-oxadiazole | $^1$HNMR (400 MHz, METHANOL-d4) δ ppm 9.20 (s, 1H) 8.51 (d, J = 9.38 Hz, 1H) 7.77 (d, J = 8.13 Hz, 1H) 7.26 (t, J = 51.53 Hz, 1H) 4.75 (s, 2H) 4.47 (s, 2H) 3.96 (t, J = 10.87, 5.33 Hz, 1H) 2.09 (dd, J = 12.57, 5.57 Hz, 2H) 1.91-1.98 (m, 2H) 1.78-1.84 (m, 2H) 1.63-1.73 (m, 2H). MS (ESI): 338.2 $[M + H]^+$ |

-continued

| Compound | Structure/Name | Characterization |
|---|---|---|
| 113 | 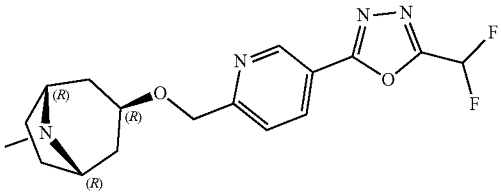<br>2-(difluoromethyl)-5-[6-[[(1S,5R)-8-methyl-8-azabicyclo[3.2.1]octan-3-yl]oxymethyl]-3-pyridyl]-1,3,4-oxadiazole | $^{1}$HNMR (400 MHz, METHANOL-d4) δ ppm 9.20 (d, J = 1.38 Hz, 1H) 8.51 (d, J = 8.32, 1.94 Hz, 1H) 7.77 (d, J = 8.25 Hz, 1H) 7.26 (t, J = 51.65 Hz, 1H) 4.74 (s, 2H) 3.86-3.96 (m, 1H) 3.40 (s, 2H) 2.42 (s, 3H) 2.06-2.16 (m, 4H) 1.71-1.81 (m, 4H). MS (ESI): 351.2 $[M + H]^+$ |
| 110 | 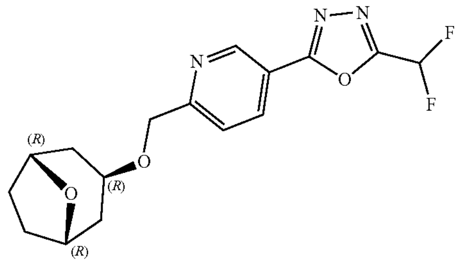<br>2-(difluoromethyl)-5-[6-[[(1S,5R)-8-oxabicyclo[3.2.1]octan-3-yl]oxymethyl]-3-pyridyl]-1,3,4-oxadiazole | $^{1}$HNMR (400 MHz, METHANOL-d4) δ ppm 9.19 (s, 1H) 8.48 (s, 1H) 7.76 (d, J = 8.38 Hz, 1H) 7.25 (t, J = 51.72 Hz, 1H) 4.73 (s, 2H) 4.46 (s, 2H) 3.94 (td, J = 10.82, 5.38 Hz, 1H) 2.08 (d, J = 12.94, 5.82 Hz, 2H) 1.89-1.95 (m, 2H) 1.76-1.82 (m, 2H) 1.62-1.69 (m, 2H). MS (ESI): 338.2 $[M + H]^+$ |
| 104 | 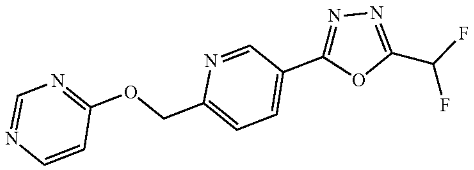 [SMILES: FC(F)c1nnc(-c2ccc(COc3ccncn3)nc2)o1] | H NMR (400 MHz, METHANOL-d4) δ ppm 9.26 (d, J = 2.00 Hz, 1H) 8.75 (s, 1H) 8.49-8.58 (m, 2H) 7.79 (d, J = 8.25 Hz, 1H) 7.26 (t, J = 51.59 Hz, 1H) 7.10 (dd, J = 5.88, 1.00 Hz, 1H) 5.70 (s, 2H) MS (ESI): 306.1 $[M + H]^+$ |
| 107 | 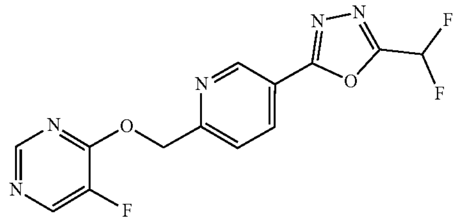 [SMILES: Fc1cncnc1OCc1ccc(-c2nnc(C(F)F)o2)cn1] | MS (ESI): 324.0 $[M + H]^+$ $^{1}$HNMR (400 MHz, METHANOL-d4) δ = 9.27 (d, J = 1.6 Hz, 1H), 8.56-8.53 (m, 3H), 7.82 (d, J = 8.3 Hz, 1H), 7.40-7.14 (m, 1H), 5.78 (s, 2H) $^{19}$F NMR (377 MHz, METHANOL-$d_4$) δ = −122.16-−122.74 (m, 2F), −153.33 (s, 1F) |
| 23 | 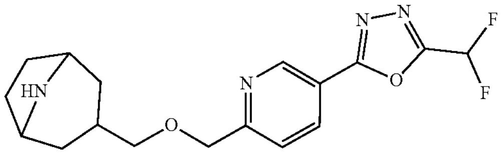 [SMILES: FC(F)c1nnc(-c2ccc(COCC3CC4CCC(C3)N4)nc2)o1] | MS (ESI): 351.1 $[M + H]^+$ $^{1}$HNMR (400 MHz, METHANOL-d4) δ = 9.23 (d, J = 1.9 Hz, 1H), 8.53 (dd, J = 2.3, 8.3 Hz, 1H), 7.78 (d, J = 8.3 Hz, 1H), 7.27 (t, J = 51.6 Hz, 1H), 4.76 (s, 2H), 3.84 (br s, 2H), 3.68 (d, J = 8.0 Hz, 2H), 2.28-2.23 (m, 1H), 2.21-2.14 (m, 2H), 2.09-2.04 (m, 2H), 1.91 (d, J = 8.3 Hz, 2H), 1.84 (br d, J = 15.0 Hz, 2H) $^{19}$F NMR (377 MHz, METHANOL-$d_4$) δ = −122.38 (s, 1F) |
| 89 | 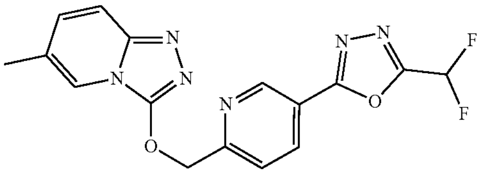 [SMILES: Cc1ccc2nnc(OCc3ccc(-c4nnc(C(F)F)o4)cn3)n2c1] | $^{1}$HNMR (400 MHz, METHANOL-d4) δ = 9.30 (d, J = 1.6 Hz, 1H), 8.57 (dd, J = 2.3, 8.3 Hz, 1H), 7.98 (d, J = 1.3 Hz, 1H), 7.94 (d, J = 8.1 Hz, 1H), 7.46 (d, J = 9.6 Hz, 1H), 7.41-7.14 (m, 2H), 5.86 (s, 2H), 2.36 (d, J = 1.0 Hz, 3H) $^{19}$F NMR (377 MHz, METHANOL-$d_4$) δ = −122.41 (s, 2F) |

-continued

| Compound | Structure/Name | Characterization |
| --- | --- | --- |
| 87 | 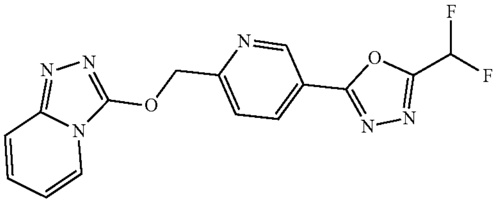 [SMILES: FC(F)c1nnc(-c2ccc(COc3nnc4ccccn34)nc2)o1] | $^1$HNMR (400 MHz, DMSO-d6) δ ppm 9.15 (s, 1H), 8.42 (dd, J = 2.4 Hz, J = 10.4 Hz, 1H), 7.91 (d, J = 7.90 Hz, 1H), 7.44-7.70 (m, 2H), 7.24 (m, 2H), 6.65 (t, 1H), 5.35 (s, 2H) LC-MS: m/z 345.12 [M + H]. |
| 120 | 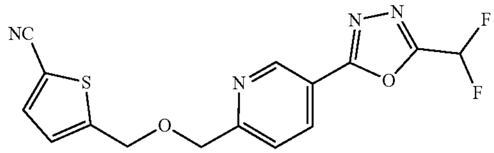 [SMILES: N#Cc1ccc(COCc2ccc(-c3nnc(C(F)F)o3)cn2)s1] | $^1$HNMR (400 MHz, DMSO-d6) δ ppm 9.17 (s, 1H), 8.48 (dd, J = 2.4 Hz, J = 10.4 Hz, 1H), 7.90 (d, J = 7.90 Hz, 1H), 7.45-7.72 (m, 2H), 7.29 (d, J = 4.00 Hz, 1H), 4.94 (s, 2H), 4.79 (s, 2H). LC-MS: m/z 348.95 [M + H]. |

2-(2-(bromomethyl)pyrimidin-5-yl)-5-(difluoromethyl)-1,3,4-oxadiazole (Int-J)

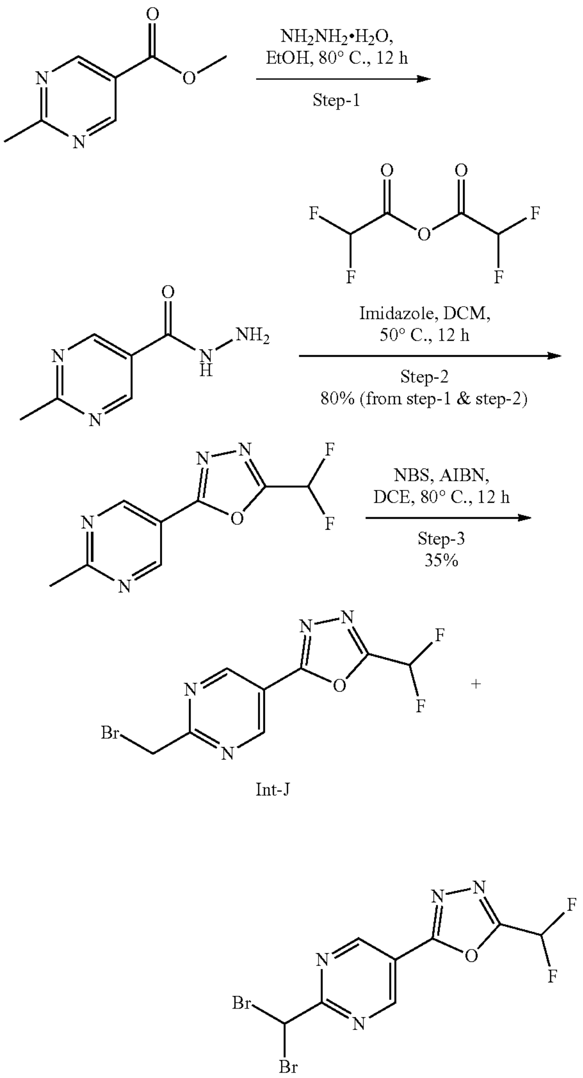

-continued

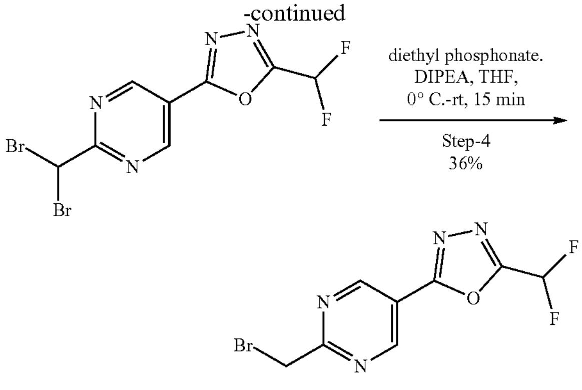

Int-J

Step-1: Synthesis of 2-methylpyrimidine-5-carbohydrazide: To a stirred solution of methyl methyl 2-methylpyrimidine-5-carboxylate (1,1 g, 6.57 mmol) in EtOH (30 mL) was added hydrazine hydrate (1.05 g, 32.86 mmol) at room temperature under $N_2$ atmosphere. The reaction mixture was heated at 80° C. and stirred for 12 h. After complete consumption of the starting material (monitored by TLC), the reaction mixture was cooled to room temperature and concentrated under reduced pressure to afford 2-methylpyrimidine-5-carbohydrazide (1.2 g, crude). The crude was as such used for next reaction without carried out further purification. LC-MS: m/z 153.1 [M+H].

Step-2: Synthesis of 2-(difluoromethyl)-5-(2-methylpyrimidin-5-yl)-1,3,4-oxadiazole: To a stirred solution of (2-methylpyrimidine-5-carbohydrazide (1.9 g, 12 mmol) in DCM (25 mL) were added imidazole (2.55 g, 37.5 mmol) followed by (2,2-difluoroacetyl) 2,2-difluoroacetate (6.52 g, 37.49 mmol) at 0° C. temperature and stirred for 5 min. The reaction mixture was heated at 50° C. for 12 h. Progress of reaction was monitored by TLC. After complete consumption of the starting material, the reaction mixture was cooled to room temperature and concentrated under reduced pressure. The residue obtained was dissolved in water (10 mL) and extracted with DCM (2x20 mL). Organic layer was washed with brine (10 mL), dried over anhydrous $Na_2SO_4$ and concentrated under reduced pressure to obtain crude product. The crude product was purified by Combi Flash column chromatography using ethyl acetate in n-heptane (0-5%) to afford 2-(difluoromethyl)-5-(2-methylpyrimidin-5-yl)-1,3,4-oxadiazole (2.0 g, 80%) as white solid. LC-MS: m/z 213.0 [M+H].

Step-4: Synthesis of 2-(2-(bromomethyl)pyrimidin-5-yl)-5-(difluoromethyl)-1,3,4-oxadiazole (Int-J): To a solution of (2-(difluoromethyl)-5-(2-methylpyrimidin-5-yl)-1,3,4-oxadiazole (100 mg, 0.471 mmol) in DCE (5.00 mL) were added NBS (503 mg, 2.82 mmol) and AIBN (38 mg, 0.226 mmol) at room temperature and stirred for 5 min. The reaction mixture was heated at 80 0° C. and stirred for 12 h. Progress of reaction was monitored by TLC. After 12 h, the reaction mixture was cooled to room temperature and concentrated under reduced pressure. The residue obtained was dissolved in water (10 mL) and extracted with DCM (2×25 mL). Organic layer was washed with brine (10 mL), dried over anhydrous $Na_2SO_4$ and concentrated under reduced pressure to obtain crude product. The crude product was purified by Combi Flash column chromatography using ethyl acetate in n-heptane 2-(2-(bromomethyl)pyrimidin-5-yl)-5-(difluoromethyl)-1,3,4-oxadiazole (Int-J, 20 mg, 30 mg, Int-5, 35%) as a yellow solid. $^1$H NMR (400 MHz, CHLOROFORM-d) δ ppm 9.41 (s, 1H), 7.71 (t, J=47.2 Hz, 1H), 4.81 (s, 2H).

Step-5: Synthesis of 2-(2-(bromomethyl)pyrimidin-5-yl)-5-(difluoromethyl)-1,3,4-oxadiazole (Int-J): To a stirred solution of 2-[2-(dibromomethyl)pyrimidin-5-yl]-5-(difluoromethyl)-1,3,4-oxadiazole (700 mg, 1.89 mmol) in THF (30 mL) were added DIPEA (492 mg, 3.84 mmol, 1-ethoxyphosphonoyloxyethane (527 mg, 3.816 mmol) at 0° C. temperature and stirred the reaction mixture under nitrogen for 5 min. The reaction mixture was allowed to attain room temperature and stirred for 15 min. Progress of reaction was monitored by TLC. After complete consumption of the starting material, the reaction mixture was quenched with water (30 mL) and extracted with ethyl acetate (2×25 mL). Organic layer was washed with brine (20 mL), dried over anhydrous $Na_2SO_4$ and concentrated under reduced pressure to obtain crude product. The crude product was purified by Combi Flash column chromatography using ethyl acetate in n-heptane (0-10%) 2-(2-(dibromomethyl)pyrimidin-5-yl)-5-(difluoromethyl)-1,3,4-oxadiazole (Int-J, 200 mg, 36%) as an off white solid. $^1$H NMR (400 MHz, CHLOROFORM-d) δ ppm 9.41 (s, 1H), 7.71 (t, J=47.2 Hz, 1H), 4.81 (s, 2H).

2-(difluoromethyl)-5-(2-((4-fluorophenoxy)methyl) pyrimidin-5-yl)-1,3,4-oxadiazole (166)

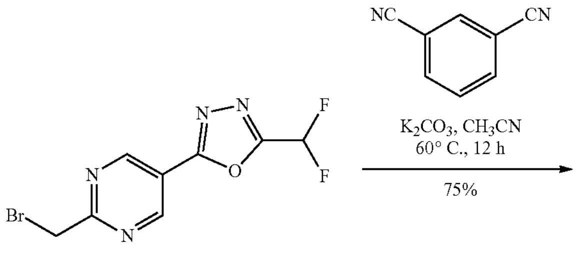

Int-J

-continued

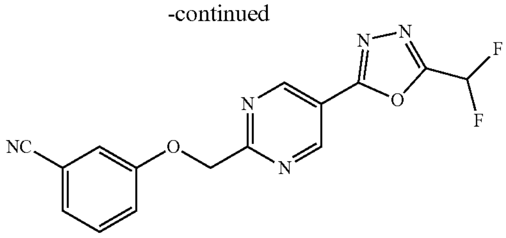

166

Synthesis of 2-(difluoromethyl)-5-(2-((4-fluorophenoxy) methyl)pyrimidin-5-yl)-1,3,4-oxadiazole (166): To a stirred solution of 3-hydroxybenzonitrile (411 mg, 3.45 mmol) in acetonitrile (20 mL, 381 mmol) were added $K_2CO_3$ (1.427 g, 10.33 mmol) and 2-[2-(bromomethyl)pyrimidin-5-yl]-5-(difluoromethyl)-1,3,4-oxadiazole (Int-J, 1.0 g, 3.43 mmol) at room temperature. The reaction mixture was heated at 60° C. and stirred for 12 h. After complete consumption of the starting material (monitored by TLC), the reaction mixture was cooled to room temperature, diluted with water (20 mL) and aqueous layer extracted with ethyl acetate (3×20 mL). The combined organic layer was washed with brine solution (20 mL), dried over anhydrous $Na_2SO_4$ and concentrated under reduced pressure to obtain crude product. The crude product was purified by CombiFlash column chromatography using ethyl acetate: n-hexane (30%) to afford 2-(difluoromethyl)-5-(2-((4-fluorophenoxy)methyl)pyrimidin-5-yl)-1,3,4-oxadiazole (166, 830 mg, 75%) as an yellow solid. LC-MS: m/z 330.15 [M+H]. $^1$H NMR (400 MHz, DMSO-$d_6$) δ ppm 9.44 (s, 2H), 7.47-7.74 (m, 3H), 7.41-7.45 (m, 1H), 7.37 (dd, J=2.8, 9.2 Hz, 1H), 5.54 (s, 2H). HPLC=98.09%, RT=7.863 min.

Biological Assay Data and Procedures

Enzymatic activity of compounds of the disclosure were determined in one of the two biochemical assays described below. Both follow the same protocol. The first relies on a caliper chip readout, while the second relies on a fluorogenic readout.

Caliper Endpoint Assay for HDAC Enzymatic Activity

HDAC reactions were assembled in 384 well plates (Greiner) in a total volume of 20 μL as follows: HDAC proteins (and their regulatory subunit, if applicable) were pre-diluted in the assay buffer comprising: 100 mM HEPES, pH 7.5, 0.1% BSA, 0.01% Triton X-100, 25 mM KCl and dispensed into a 384 well plate (10 μL per well). An example of enzyme concentrations used in each assay is listed in the table below.

| Assay | Expression Construct | Regulatory subunit | [Enzyme] nM | Substrate Peptide | Substrate Conc (μM) | Incubation Time (hr) |
|---|---|---|---|---|---|---|
| HDAC6 | Full length Human HDAC6 with C-terminal FLAG-tag, expressed in baculovirus expression system. | None | 6 | FAM-RHKK(Ac)-NH2 | 1 | 5 |

-continued

| Assay | Expression Construct | Regulatory subunit | [Enzyme] nM | Substrate Peptide | Substrate Conc (μM) | Incubation Time (hr) |
|---|---|---|---|---|---|---|
| HDAC8 | Full length Human HDAC8 with N-terminal HIS-tag, expressed in baculovirus expression system. | None | 5 | FAM-RHKK(TFAc)-NH2 | 1 | 3 |

Test compounds were serially pre-diluted in 100% DMSO using 3-fold dilution steps and added to the protein samples by acoustic dispensing (Labcyte Echo). Concentration of DMSO was equalized to 1% in all samples. Final compound concentration in assays typically ranged from 100 μM to 0.00056 μM for a 12-point concentration-response format.

Control samples (0%-inhibition in the absence of inhibitor, DMSO only) and 100%-inhibition (in the absence of enzyme) were assembled in replicates of four (for each caliper sipper) and used to calculate the %-inhibition in the presence of compounds. At this step compounds were pre-incubated with enzyme for 30 minutes at room temperature (20-23° C.). The reactions were initiated by addition of 10 μL of the FAM-labeled substrate peptide (see table above) pre-diluted in the same assay buffer. Final concentration of substrate peptide was 1 μM. The reactions were allowed to proceed at room temperature (20-23° C.). Typical incubation times for each HDAC, based on pre-determined enzyme progress curves, vary and are listed in table above.

Following incubation, the reactions were quenched by addition of 50 μL of termination buffer (100 mM HEPES, pH7.5, 0.01% Triton X-100, 0.05% SDS). Terminated plates were analyzed on a microfluidic electrophoresis instrument (Caliper LabChip® 3000, Caliper Life Sciences/Perkin Elmer) which enables electrophoretic separation of deacetylated product from acetylated substrate. A change in the relative intensity of the peptide substrate and product is the parameter measured. Activity in each test sample was determined as the product to sum ratio (PSR): P/(S+P), where P is the peak height of the product, and S is the peak height of the substrate. Percent inhibition ($P_{inh}$) is determined using the following equation: $P_{inh}=(PSR_{0\%\ inh}-PSR_{compound})/(PSR_{0\%\ inh}-PSR_{100\%\ inh})*100$, in which: $PSR_{compound}$ is the product/sum ratio in the presence of compound, $PSR_{0\%\ inh}$ is the product/sum ratio in the absence of compound and the $PSR_{100\%\ inh}$ is the product/sum ratio in the absence of the enzyme. To determine the $IC_{50}$ of compounds (50%-inhibition) the %-inh data ($P_{inh}$ versus compound concentration) were fitted by a 4 parameter sigmoid dose-response model using XLfit software (IDBS).

Nanosyn Biochemical HDAC6 Assay (Fluorogenic Format)

HDAC protein composition and respective substrate peptides are summarized in table below:

| Assay name | Expression Construct | Regulatory subunit | Substrate peptide |
|---|---|---|---|
| hHDAC6 | Full length Human HDAC6 with C-terminal FLAG-tag, expressed in baculovirus expression system. | None | LGK(Ac)-AMC |
| mHDAC6 | Full length Mouse HDAC6, a.a. 2-1149 (end) with N-terminal GST-Tag, expressed in baculovirus expression system. | None | LGK(Ac)-AMC |

The biochemical HDAC6 assay was performed using fluorescence detection (Fluor-De-Lys assay). In this assay, deacetylation of the Lysine residue in the LGK(Ac)-AMC peptide substrate, results in a cleavable bond between the fluorescent moiety of amino-methyl coumarin (AMC) and lysine. The AMC is released by the auxiliary treatment with trypsin, which is added to the termination buffer. The cleaved AMC generates strong fluorescent signal which is being detected (360 nm excitation and 460 nm emission).

HDAC reactions are assembled in black low binding 384 well plates (Corning) in a total volume of 20 mL as following:

HDAC6 protein is pre-diluted in the assay buffer comprising of: 100 mM HEPES, pH 7.5, 0.01% BSA, 0.01% Triton X-100, 25 mM KCl and dispensed into 384 well plate (10 uL per well).

Test compounds are serially pre-diluted in DMSO and added to the protein samples by acoustic dispensing (Labcyte Echo). Concentration of DMSO is equalized to 1% in all samples.

Control samples (0%-inhibition in the absence of inhibitor, DMSO only) and 100%-inhibition (in the absence of enzyme) are assembled in the same plate and used to calculate the %-inhibition in the presence of compounds.

At this step compounds are pre-incubated with enzyme for 30 min.

The reactions are initiated by addition of 10 uL of the LGK(Ac)-AMC substrate peptide pre-diluted in the same assay buffer.

Final concentration of hHDAC6 enzyme is 0.5 nM. Final concentration of mHDAC6 enzyme is 1 nM. Final concentration of substrate peptide is 1.25 uM.

The reactions are allowed to proceed at room temperature for 1 h.

Following incubation, the reactions are quenched by addition of 20 mL of termination buffer comprising of Trichostatin A (included as a termination agent) and trypsin (BPS catalog #50030). Terminated plates are read on Synergy Neo2 luminometer. A change in the relative luminescence intensity (RLUs) is the parameter measured. Percent inhibition ($P_{inh}$) is determined using the following equation:

$$P_{inh}=(RLU_{0\%\ inh}-RLU_{compound})/(RLU_{0\%\ inh}-RLU_{100\%\ inh})*100,$$

in which: $RLU_{compound}$ is the sample luminescence in the presence of compound, $RLU_{0\%\ inh}$ is the sample luminescence in the absence of compound and the $RLU_{100\%\ inh}$ is the sample luminescence in the absence of the enzyme. To determine IC50 of compounds (50%-inhibition) the %-inh data ($P_{inh}$ versus compound concentration) are fitted by a 4 parameter sigmoid dose-response model using XLfit software (IDBS)

Exemplary compounds were evaluated for inhibitory activity of a panel of HDAC paralogs. The results in Table 1 demonstrate that compounds of the disclosure have potent activity against HDAC6, and many compounds selectively inhibit HDAC6 over the Class I HDAC paralog HDAC8.

$IC_{50}$ ranges: A: 0.001-0.1 μM; B: >0.1-1 μM; C: >1-10 μM; D: >10-100 μM; E: >100 μM.

Selectivity ranges (ratio of HDAC8 $IC_{50}$/HDAC6 $IC_{50}$): I: 0.1-1; II: >1-10; III: >10-100; IV: >100-1000; V: >1000

TABLE 1

In Vitro Enzymatic $IC_{50}$ values for exemplary compounds

| Compound | HDAC6 IC50 | HDAC8 IC50 | Selectivity (6 v 8) (fold) |
|---|---|---|---|
| 1 | A | E | V |
| 2 | A | E | V |
| 3 | A | E | V |
| 4 | A | E | V |
| 5 | A | E | V |
| 6 | A | E | V |
| 7 | A | E | V |
| 8 | A | E | V |
| 9 | A | E | V |
| 10 | A | E | V |
| 11 | A | E | V |
| 12 | A | E | V |
| 13 | A | E | V |
| 14 | B | | |
| 15 | B | E | V |
| 16 | A | E | V |
| 17 | A | D | V |
| 18 | A | E | V |
| 19 | A | E | V |
| 20 | A | E | V |
| 21 | | | |
| 22 | A | | |
| 23 | B | | |
| 24 | | | |
| 25 | B | | |
| 26 | A | E | V |
| 27 | A | E | V |
| 28 | A | E | V |
| 29 | A | D | IV |
| 30 | A | E | V |
| 31 | A | C | IV |
| 32 | A | D | V |
| 33 | A | | |
| 34 | A | E | V |
| 35 | A | E | V |
| 36 | A | E | V |
| 37 | A | D | V |
| 38 | A | | |
| 39 | A | E | V |
| 40 | | | |
| 41 | A | E | V |
| 42 | A | E | V |
| 43 | A | D | IV |
| 44 | A | E | V |
| 45 | A | E | V |
| 46 | A | E | V |
| 47 | A | D | V |
| 48 | A | E | V |
| 49 | A | D | IV |
| 50 | A | E | V |
| 51 | A | E | V |
| 52 | A | E | V |
| 53 | A | E | V |
| 54 | A | E | V |
| 55 | A | E | V |
| 56 | A | E | V |
| 57 | A | D | IV |
| 58 | A | E | V |
| 59 | A | E | V |
| 60 | A | D | V |
| 61 | A | D | IV |
| 62 | A | D | V |
| 63 | A | E | V |
| 64 | B | E | V |
| 65 | B | E | V |

TABLE 1-continued

In Vitro Enzymatic $IC_{50}$ values for exemplary compounds

| Compound | HDAC6 IC50 | HDAC8 IC50 | Selectivity (6 v 8) (fold) |
|---|---|---|---|
| 66 | A | | |
| 67 | B | E | V |
| 68 | B | E | V |
| 69 | B | D | IV |
| 70 | B | E | V |
| 71 | A | E | V |
| 72 | B | E | V |
| 73 | B | E | V |
| 74 | A | E | V |
| 75 | A | D | IV |
| 76 | A | E | V |
| 77 | A | E | V |
| 78 | B | | |
| 79 | A | E | V |
| 80 | A | C | III |
| 81 | A | | |
| 82 | A | E | V |
| 83 | B | D | IV |
| 84 | | | |
| 85 | B | E | V |
| 86 | A | | |
| 87 | A | | |
| 88 | A | D | V |
| 89 | A | | |
| 90 | | | |
| 91 | A | E | V |
| 92 | A | E | V |
| 93 | A | E | V |
| 94 | B | | |
| 95 | A | | |
| 96 | A | | |
| 97 | A | E | V |
| 98 | A | | |
| 99 | B | E | V |
| 100 | B | | |
| 101 | | | |
| 102 | A | E | V |
| 103 | B | | |
| 104 | A | | |
| 105 | B | | |
| 106 | B | E | V |
| 107 | A | | |
| 108 | | | |
| 109 | B | | |
| 110 | B | | |
| 111 | | | |
| 112 | | | |
| 113 | C | | |
| 114 | | | |
| 115 | | | |
| 116 | | | |
| 117 | | | |
| 118 | A | D | V |
| 119 | | | |
| 120 | B | | |
| 121 | B | | |
| 122 | E | E | V |
| 123 | A | | |
| 124 | A | | |
| 125 | A | | |
| 126 | A | | |
| 127 | A | | |
| 128 | A | | |
| 129 | A | | |
| 130 | A | | |
| 131 | A | | |
| 132 | A | | |
| 133 | | | |
| 134 | A | | |
| 135 | | | |
| 136 | A | | |
| 137 | A | | |
| 138 | A | | |
| 139 | A | | |

TABLE 1-continued

| In Vitro Enzymatic $IC_{50}$ values for exemplary compounds | | | |
|---|---|---|---|
| Compound | HDAC6 IC50 | HDAC8 IC50 | Selectivity (6 v 8) (fold) |
| 140 | A | | |
| 141 | A | | |
| 142 | A | | |
| 143 | | | |
| 144 | A | | |
| 145 | | | |
| 146 | A | | |
| 147 | A | | |
| 148 | | | |
| 149 | | | |
| 150 | A | | |
| 151 | A | | |
| 152 | A | | |
| 153 | A | | |
| 154 | A | | |
| 155 | A | | |
| 156 | A | | |
| 157 | A | | |
| 158 | A | | |
| 159 | A | | |
| 160 | A | | |
| 161 | A | | |
| 162 | A | | |
| 163 | | | |
| 164 | A | | |
| 165 | A | | |
| 166 | A | | |
| 167 | A | | |
| 168 | A | | |
| 169 | | | |
| 170 | B | | |
| 171 | | | |
| 172 | | | |
| 173 | | | |
| 174 | | | |
| 175 | | | |
| 176 | | | |
| 177 | | | |
| 178 | A | | |
| 179 | A | | |
| 180 | A | | |
| 181 | A | | |
| 182 | A | | |
| 183 | A | | |
| 184 | B | E | IV |
| 185 | A | | |
| 186 | A | | |
| 187 | C | | |
| 188 | B | | |
| 189 | A | | |
| 190 | | | |
| 191 | B | E | IV |
| 192 | | | |
| 193 | | | |
| 194 | | | |
| 195 | | | |
| 196 | A | | |
| 197 | A | | |
| 198 | | | |
| 199 | A | | |
| 200 | A | | |
| 201 | A | | |
| 202 | B | E | IV |
| 203 | C | E | III |
| 204 | A | E | V |
| 205 | A | | |
| 206 | A | | |
| 207 | A | | |
| 208 | A | | |
| 209 | C | E | III |
| 210 | C | E | III |
| 211 | B | E | IV |
| 212 | B | E | IV |
| 213 | A | | |

TABLE 1-continued

| In Vitro Enzymatic $IC_{50}$ values for exemplary compounds | | | |
|---|---|---|---|
| Compound | HDAC6 IC50 | HDAC8 IC50 | Selectivity (6 v 8) (fold) |
| 214 | A | | |
| AAA | C | | |
| trichostatin A (TSA) | A | B | IV |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I):

(I)

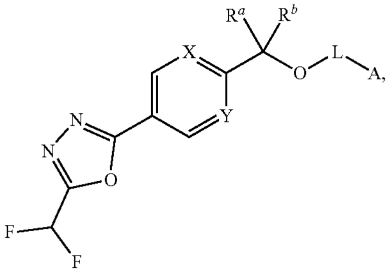

or a pharmaceutically acceptable salt thereof, wherein:

X is $CR^1$ or N; Y is $CR^1$ or N; provided that at least one of X and Y is N;

$R^1$ is hydrogen or halogen;

$R^a$ and $R^b$ are each independently hydrogen or halogen;

L is a bond;

A is a 5-membered heteroaryl, wherein A is optionally substituted with one or more substituents $R^2$; and each occurrence of $R^2$ is independently halogen, substituted or unsubstituted amin-o, substituted or unsubstituted amido, cyano, substituted or unsubstituted acyl, substituted or unsubstituted alkyl, substituted or unsubstituted alkenyl, substituted or unsubstituted alkynyl, substituted or unsubstituted heteroaliphatic, substituted or unsubstituted heterocyclyl, substituted or unsubstituted carbocyclyl, substituted or unsubstituted aryl, or substituted or unsubstituted heteroaryl.

2. The compound of claim 1, or a pharmaceutically acceptable salt thereof, wherein $R^a$ and $R^b$ are each independently hydrogen or fluoro.

3. The compound of claim 2, or a pharmaceutically acceptable salt thereof, wherein X is N and Y is CH, CF, or N.

4. The compound of claim 3, or a pharmaceutically acceptable salt thereof, wherein each occurrence of $R^2$ is independently halogen, amino, substituted amino, amido, cyano, $C_{1-4}$ alkyl, $C_{1-4}$ haloalkyl, $C_{2-4}$ alkenyl, $C_{2-4}$ alkynyl, hetero$C_{2-4}$ alkyl, hetero$C_{2-4}$ alkenyl, hetero$C_{2-4}$ alkynyl, 3-6 membered heterocyclic, $C_{3-6}$ carbocyclyl, $C_{6-14}$ aryl, or 5-10 membered heteroaryl;

wherein the amino, amido, 3-6 membered heterocyclic, $C_{3-6}$ carbocyclyl, $C_{6-14}$ aryl, or 5-10 membered heteroaryl in each $R^2$ is each optionally substituted with one or more halogen, $C_{1-4}$ alkyl, or $C_{1-4}$ haloalkyl.

5. The compound of claim 4, or a pharmaceutically acceptable salt thereof, wherein each occurrence of $R^2$ is independently halogen, amino, substituted amino, amido, cyano, $C_{1-4}$ alkyl, $C_{1-4}$ haloalkyl, $C_{2-4}$ alkenyl, $C_{2-4}$ alkynyl, hetero$C_{2-4}$ alkyl, hetero$C_{2-4}$ alkenyl, or hetero$C_{2-4}$ alkynyl; and the amino or amido in each $R^2$ is each optionally substituted with one or more halogen, $C_{1-4}$ alkyl, or $C_{1-4}$ haloalkyl.

6. The compound of claim 4, or a pharmaceutically acceptable salt thereof, wherein each occurrence of $R^2$ is independently $C_{1-4}$ alkyl, cyano, 3-6 membered heterocyclic, or $C_{3-6}$ carbocyclyl.

7. The compound of claim 6, or a pharmaceutically acceptable salt thereof, wherein A is optionally substituted with 1-3 substituents of $R^2$; and wherein A is:

a. pyrrolyl, furanyl, or thiophenyl;

b. imidazolyl, pyrazolyl, oxazolyl, isoxazolyl, thiazolyl, or isothiazolyl; or c. triazolyl, oxadiazolyl, or thiadiazolyl.

8. The compound of claim 7, or a pharmaceutically acceptable salt thereof, wherein each occurrence of $R^2$ is independently $C_{1-4}$ alkyl, $C_{1-4}$ haloalkyl, cyano, 3-6 membered heterocyclic, or $C_{3-6}$ carbocyclyl.

9. The compound of claim 8, or a pharmaceutically acceptable salt thereof, wherein A is a diazole or thiophenyl and A is optionally substituted with one $R^2$.

10. The compound of claim 9, or a pharmaceutically acceptable salt thereof, wherein each occurrence of $R^2$ is independently methyl, ethyl, cyano or tetrahydropyran.

11. The compound of claim 3, or a pharmaceutically acceptable salt thereof, wherein A is

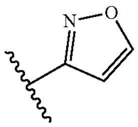 , 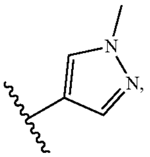 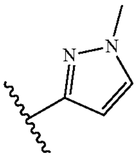 ,

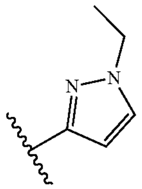 , 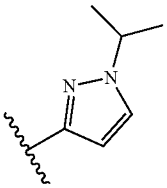 , 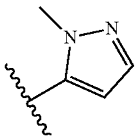 ,

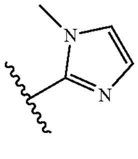 , 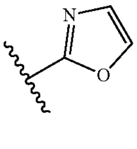 , 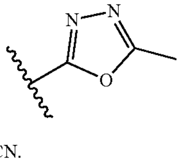 , or

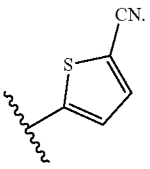

12. The compound of claim 1, wherein the compound is selected from the group consisting of:

(64)
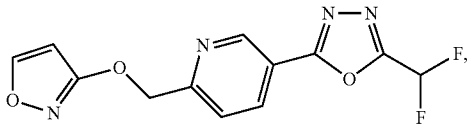
(65)
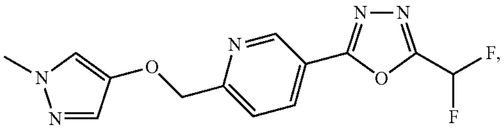
(66)
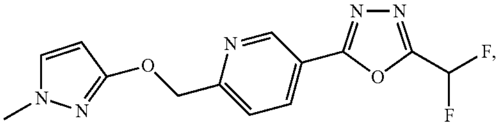
(67)
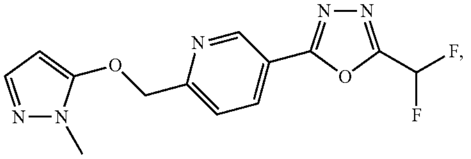
(69)
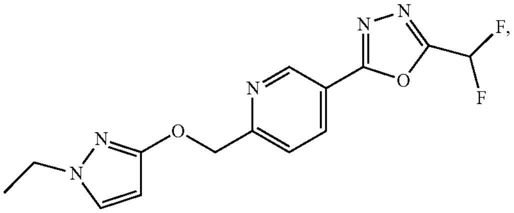
(100)
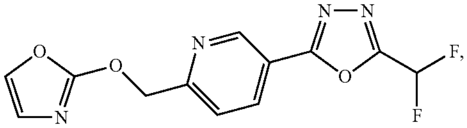
(101)
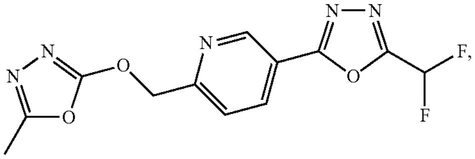
(105)
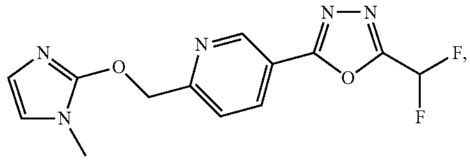
(119)
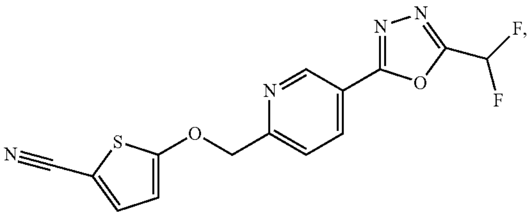
-continued
(120)
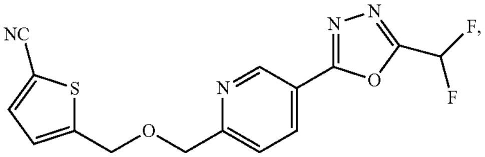
and
(198)
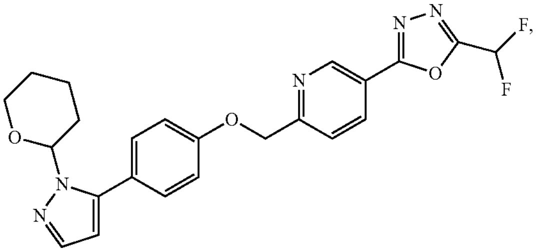
or a pharmaceutically acceptable salt thereof.
13. The compound of claim 1, wherein the compound is
(65)
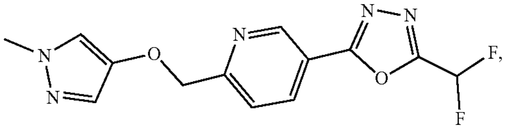
or a pharmaceutically acceptable salt thereof.
14. The compound of claim 1, wherein the compound is
(66)
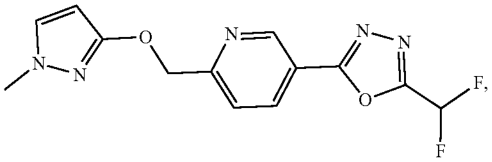
or a pharmaceutically acceptable salt thereof.
15. The compound of claim 1, wherein the compound is
(67)
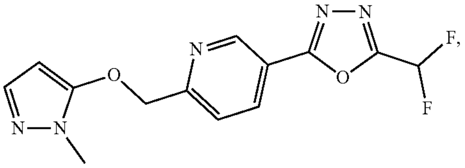
or a pharmaceutically acceptable salt thereof.

16. The compound of claim 1, wherein the compound is (69)

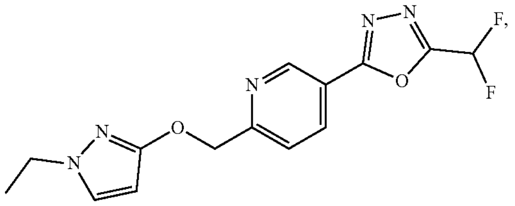

or a pharmaceutically acceptable salt thereof.

17. The compound of claim 1, wherein the compound is (120)

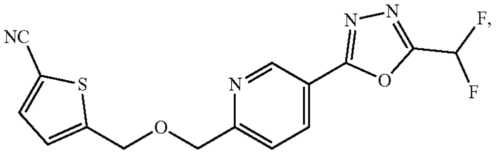

or a pharmaceutically acceptable salt thereof.

18. A compound of Formula (I):

(I)

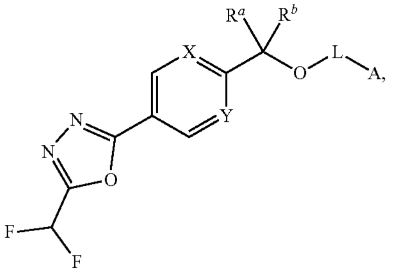

or a pharmaceutically acceptable salt thereof, wherein:

X is N; Y is CH, CF, or N;

$R^a$ and $R^b$ are each hydrogen;

L is a bond;

A is a 5-membered heteroaryl, wherein A is optionally substituted with one or more substituents $R^2$; and each occurrence of $R^2$ is independently $C_{1-4}$ alkyl, cyano, 4-6 membered heterocyclic, or $C_{3-6}$ carbocyclyl.

19. A compound of Formula (I):

(I)

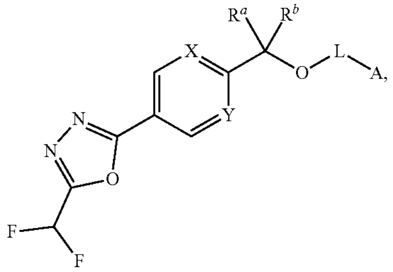

or a pharmaceutically acceptable salt thereof, wherein:

X is $CR^1$ or N; Y is $CR^1$ or N;

wherein:

$R^1$ is H or halogen;

provided that at least one of X and Y is N;

$R^a$ and $R^b$ are each independently hydrogen or halogen;

L is a bond;

A is a phenyl, pyridinyl or pyrimidinyl, wherein A is substituted with one substituent $R^2$; and wherein $R^2$ is $C_{6-14}$ aryl, or 5-10 membered heteroaryl; and wherein the $C_{6-14}$ aryl, or 5-10 membered heteroaryl as defined for $R^2$ is optionally substituted with one or more $C_{1-4}$ alkyl.

20. The compound of claim 19, wherein the compound is selected from the group consisting of:

(193)

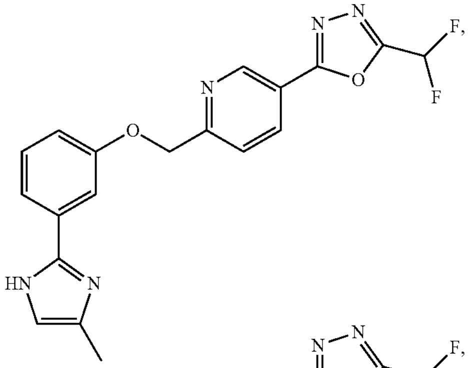

(194)

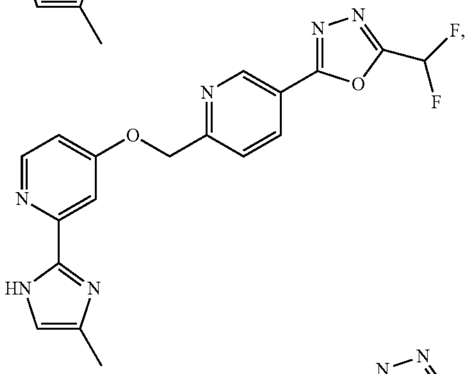

(199)

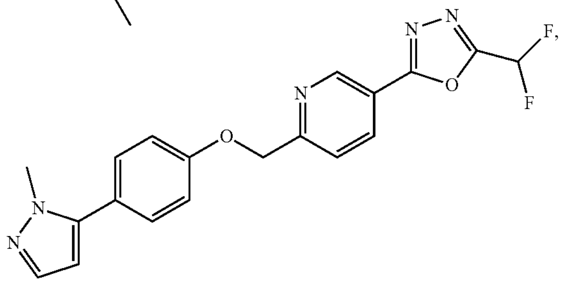

-continued
(201)
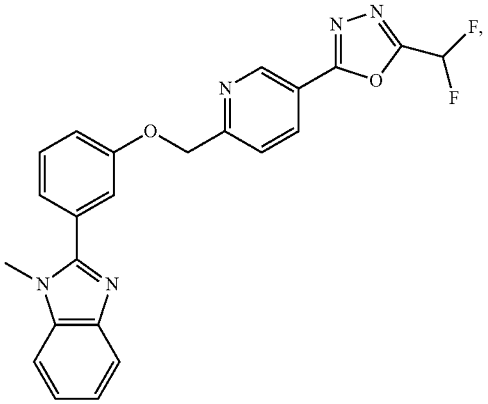
(206)
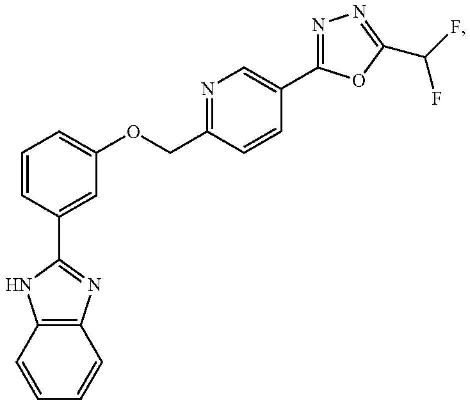
and
-continued
(207)
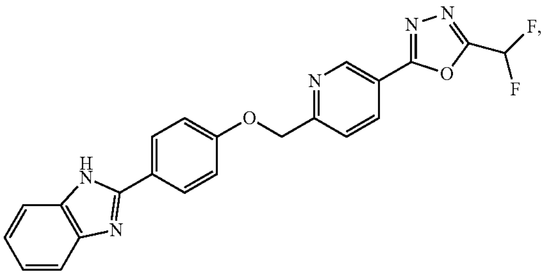
(214)
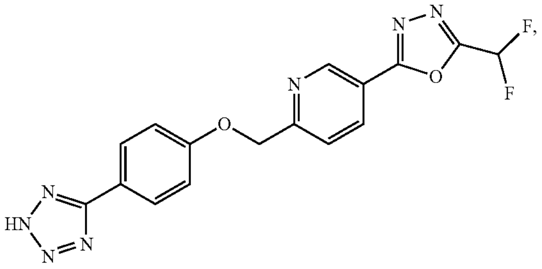
or a pharmaceutically acceptable salt thereof.
* * * * *